United States Patent
Martinborough et al.

(10) Patent No.: US 7,799,822 B2
(45) Date of Patent: Sep. 21, 2010

(54) PHENYL SULFONAMIDES AS MODULATORS OF ION CHANNELS

(75) Inventors: Esther Martinborough, San Diego, CA (US); Lev T. D. Fanning, San Marcos, CA (US); Urvi Sheth, San Diego, CA (US); Dean Wilson, Bedford, MA (US); Andreas Termin, Encinitas, CA (US); Timothy Neubert, San Diego, CA (US); Nicole Zimmermann, San Diego, CA (US); Tara Knoll, La Jolla, CA (US); Tara Whitney, San Diego, CA (US); Aarti Kawatkar, San Diego, CA (US); Danielle Lehsten, Pittsburgh, PA (US); Dean Stamos, Carlsbad, CA (US); Jinglan Zhou, San Diego, CA (US); Vijayalaksmi Arumugam, San Marco, CA (US); Corey Gutierrez, San Diego, CA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 315 days.

(21) Appl. No.: 11/643,622

(22) Filed: Dec. 21, 2006

(65) Prior Publication Data

US 2008/0027067 A1 Jan. 31, 2008

Related U.S. Application Data

(60) Provisional application No. 60/752,926, filed on Dec. 21, 2005, provisional application No. 60/791,181, filed on Apr. 11, 2006, provisional application No. 60/799,797, filed on May 12, 2006, provisional application No. 60/839,444, filed on Aug. 23, 2006.

(51) Int. Cl.
*A01N 43/36* (2006.01)
(52) U.S. Cl. .................... 514/422; 514/426; 548/577
(58) Field of Classification Search .............. 514/422, 514/426; 548/577
See application file for complete search history.

(56) References Cited

U.S. PATENT DOCUMENTS

| 3,574,194 | A | 4/1971 | Wilhelm |
| 2006/0025415 | A1 | 2/2006 | Gonzalez et al. |
| 2007/0117801 | A1 | 5/2007 | Neubert et al. |
| 2007/0203122 | A1 | 8/2007 | Martinborough et al. |
| 2007/0203130 | A1 | 8/2007 | Neubert et al. |
| 2008/0113990 | A1 | 5/2008 | Martinborough et al. |
| 2008/0119453 | A1 | 5/2008 | Termin et al. |
| 2009/0012117 | A1 | 1/2009 | Kawatkar et al. |
| 2009/0105271 | A1 | 4/2009 | Martinborough et al. |

FOREIGN PATENT DOCUMENTS

| WO | 9902502 | 1/1999 |
| WO | 2005013914 | 2/2005 |

OTHER PUBLICATIONS

International Search Report, PCT/US2006/048802.
Hassan, Hammed H.A.M., et al.; Synthesis and GC-EIMS analyses of optically pure 3-hydroxy-2-azetidinones having N-sulfonamide drugs side chain; Synthetic Communication; 30(14), 2465-2478, 2000.
Hassan, Khairy M., et al.; Synthesis and biological activity of new β-lactam and thiazolidinones containing a sulfanilamide moiety; Journal of Chemical Technology and Biotechnology (1979-1983), 32(2), 416-20; 1982.
Junasevic-Holjevac, A., et al.; N4-Acylsulphonamides. II. Derivatives of 4-(α-Methyl-α-ethylsuccinimido) and 4-(α-Ethyl-α-phenylglutaramido) Benzenesulfamide; Croatica Chemica Acta; vol. 39, 1967, pp. 49-54.
Hirapara, K.V., et al.; Synthesis of 2-azetidinones as potential antimicrobial agents; Oriental Journal of Chemistry; vol. 19, No. 2, 2003, pp. 411-416.

*Primary Examiner*—Kamal A Saeed
*Assistant Examiner*—Valerie Rodriguez-Garcia
(74) *Attorney, Agent, or Firm*—Michael J. DiVerdi

(57) ABSTRACT

The present invention relates to phenyl sulfonamides useful as inhibitors of ion channels. The invention also provides pharmaceutically acceptable compositions comprising the compounds of the invention and methods of using the compositions in the treatment of various disorders, including for example the treatment of pain.

15 Claims, No Drawings

PHENYL SULFONAMIDES AS MODULATORS OF ION CHANNELS

CROSS-REFERENCE TO RELATED APPLICATIONS

The present invention claims the benefit under 35 U.S.C. §119 of U.S. provisional application Ser. No. 60/752,926, titled "HETEROCYCLIC DERIVATIVES AS MODULATORS OF ION CHANNELS" filed Dec. 21, 2005; U.S. provisional application Ser. No. 60/791,181, titled "HETEROCYCLIC DERIVATIVES AS MODULATORS OF ION CHANNELS" filed Apr. 11, 2006; U.S. provisional application Ser. No. 60/799,797, titled "HETEROCYCLIC DERIVATIVES AS MODULATORS OF ION CHANNELS" filed May 12, 2006; and U.S. provisional application Ser. No. 60/839,444, titled "HETEROCYCLIC DERIVATIVES AS MODULATORS OF ION CHANNELS" filed Aug. 23, 2006, with the entire contents of each application being incorporated herein by reference.

TECHNICAL FIELD OF THE INVENTION

The present invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12(1): 85-91)), pain (See, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)—null mice" *J Neurosci* 22(19): 8352-6), urinary incontinence and visceral pain (See, Yoshimura, N., S. Seki, et al. (2001) "The involvement of the tetrodotoxin-resistant sodium channel Na(v) 1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). As shown in Table 1, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

TABLE 1

| Na isoform | Tissue | TTX IC50 | Indications |
| --- | --- | --- | --- |
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrhythmia, long QT |
| NaV1.6 | CNS widespread, most abundant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

(Abbreviations: CNS = central nervous system, PNS = peripheral nervous sytem, DRG = dorsal root ganglion, TG = Trigeminal ganglion):

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87(1): 7-17.) bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8.), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat Neurosci* 2(6): 541-8.). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62.). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13.). NaV1.8 protein is upregulated along uninjured C-fibers adjacent to the nerve injury. Antisense treatment prevents the redistribution of NaV1.8 along the nerve and reverses neuropathic pain. Taken together the geneknockout and antisense data support a role for NaV1.8 in the detection and transmission of inflammatory and neuropathic pain.

In neuropathic pain states there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain." *Pain* 83(3): 591-600.) The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See, Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21(16): 5952-61.). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v) 1.9 (NaN) in nociceptive primary afferent neurons." *J Neurosci* 22(17): 7425-33.). It has a slow rate of inactivation and left-shifted voltage dependence for activation (See, Dib-Hajj, S., J. A. Black, et al. (2002) "NaN/Nav1.9: a sodium channel with unique properties" *Trends Neurosci* 25(5): 253-9.). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir* (*Wien*) 144(8): 803-10; discussion 810.). NaV1.6 and NaV1.7 are also expressed in dorsal root ganglion neurons and contribute to the small TTX sensitive component seen in these cells. NaV1.7 in particular may therefore be a potential pain target in addition to it's role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14(6): 1084-90).

NaV1.1 (See, Sugawara, T., E. Mazaki-Miyazaki, et al. (2001) "Nav1.1 mutations cause febrile seizures associated with afebrile partial seizures." *Neurology* 57(4): 703-5.) and NaV1.2 (See, Sugawara, T., Y. Tsurubuchi, et al. (2001) "A missense mutation of the Na+ channel alpha II subunit gene Na(v)1.2 in a patient with febrile and afebrile seizures causes channel dysfunction" *Proc Natl Acad Sci USA* 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99(7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91.); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci USA* 96(14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human Na+ channels" *Circ Res* 79(1): 103-8, and Wang, D. W., K. Yazawa, et al. (1997) "Pharmacological targeting of long QT mutant sodium channels" *J Clin Invest* 99(7): 1714-20); neuroprotection (See, Taylor, C. P. and L. S. Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain" *Novartis Found Symp* 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48(3):382-3; femur cancer pain (see, Kohase, H., et al., Acta Anaesthesiol Scand. 2004; 48(3):382-3); non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1):11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); Neuropathic low back pain (see, Hines, R., et al., Pain Med. 2002; 3(4):361-5; Massie, J. B., et al., J Neurosci Methods. 2004; 137(2):283-9; neuropathic low back pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K A et al., Muscle Nerve. 2001; 24(1):37-46); fibromyalgia (see, Bennet & Tai, Int J Clin Pharmacol Res. 1995; 15(3):115-9); temporomandibular joint pain (see, Ime H, Ren K, Brain Res Mol Brain Res. 1999; 67(1):87-97); chronic visceral pain, including, abdominal (see, Al-Chaer, E. D., et al., Gastroenterology. 2000; 119(5):1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84); IBS pain (see, Verne, G. N., et al., Pain. 2003; 105(1-2):223-30; La J H et al., World Gastroenterol. 2003; 9(12):2791-6); chronic headache pain (see, Willimas & Stark, Cephalalgia. 2003; 23(10):963-71); migraine (see, Yamamura, H., et al., J Neurophysiol. 1999; 81(2):479-93); tension headache, including, cluster headaches (see, Costa, A., et al., Cephalalgia. 2000; 20(2):85-91); chronic neuropathic pain, including, post-herpetic neuralgia (see, Attal, N., et al., Neurology. 2004; 62(2):218-25; Kim & Chung 1992, Pain 50:355); diabetic neuropathy (see, Beidoun A et al., Clin J Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E K et al., Pain. 2004; 107(1-2):147-58; Oh, S. B., et al., J Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol. Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1):119-27); radiculopathy (see, Devers & Galer, (see, Clin J Pain. 2000; 16(3):205-8; Hayashi N et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J Pain. 2000; 16(3):205-8); central pain (Cahana, A., et al., Anesth Analg. 2004; 98(6):1581-4), spinal cord injury pain (see, Hains, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos D et al., J Pain. 2004; 5(3 Suppl 2):S1); phanton pain (see, Weber, W. E., Ned Tijdschr Geneeskd. 2001; 145(17):813-7; Levitt & Heyback, Pain. 1981; 10(1): 67-73); intractable pain (see, Yokoyama, M., et al., Can J Anaesth. 2002; 49(8):810-3); acute pain, acute post-operative pain (see, Koppert, W., et al., Anesth Analg. 2004; 98(4): 1050-5; Brennan, T. J., et al., Pain. 1996; 64(3):493-501); acute musculoskeletal pain; joint pain (see, Gotoh, S., et al., Ann Rheum Dis. 1993; 52(11):817-22); mechanical low back pain (see, Kehl, L. J., et al., Pain. 2000; 85(3):333-43); neck pain; tendonitis; injury/exercise pain (see, Sesay, M., et al., Can J Anaesth. 2002; 49(2):137-43); acute visceral pain, including, abdominal pain; pyelonephritis; appendicitis; cholecystitis; intestinal obstruction; hernias; etc (see, Giambernardino, M. A., et al., Pain. 1995; 61(3):459-69); chest pain, including, cardiac Pain (see, Vergona, R. A., et al., Life Sci. 1984; 35(18):1877-84); pelvic pain, renal colic pain, acute obstetric pain, including, labor pain (see, Segal, S., et al., Anesth Analg. 1998; 87(4):864-9); cesarean section pain; acute inflammatory, burn and trauma pain; acute intermittent pain, including, endometriosis (see, Cason, A. M., et al., Horm Behav. 2003; 44(2):123-31); acute herpes zoster pain; sickle cell anemia; acute pancreatitis (see, Toma, H; Gastroenterology. 2000; 119(5):1373-81); breakthrough pain; orofacial pain, including, sinusitis pain, dental pain (see, Nusstein, J., et al., J Endod. 1998; 24(7):487-91; Chidiac, J. J., et al., Eur J Pain. 2002; 6(1):55-67); multiple sclerosis (MS) pain (see, Sakurai & Kanazawa, J Neurol Sci. 1999; 162(2):162-8); pain in depression (see, Greene B, Curr Med Res Opin. 2003; 19(4):272-7); leprosy pain; behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130(4):429-33); Fabry's disease pain (see, Germain, D. P., J Soc Biol. 2002; 196(2):183-90); Bladder and urogenital disease, including, urinary incontinence (see, Berggren, T., et al., J Urol. 1993; 150(5 Pt 1):1540-3); hyperactivity bladder (see, Chuang, Y. C., et al., Urology. 2003; 61(3):664-70); painful bladder syndrome (see, Yoshimura, N., et al., J. Neurosci. 2001; 21(21):8690-6); interstitial cyctitis (IC) (see, Giannakopoulos & Campilomatos, Arch Ital Urol Nefrol Androl. 1992; 64(4):337-9; Boucher, M., et al., J Urol. 2000; 164(1):203-8); and prostatitis (see, Mayersak, J. S., Int Surg. 1998; 83(4):347-9; Keith, I. M., et al., J Urol. 2001; 166(1):323-8).

Unfortunately, as described above, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

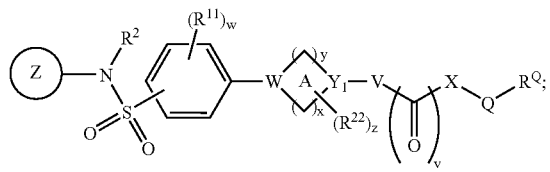

or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

In one embodiment, the present invention provides compounds of formula I:

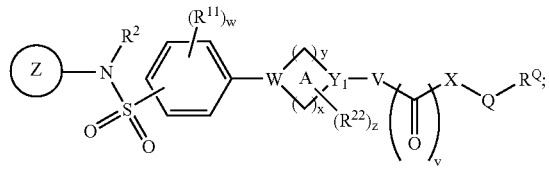

or a pharmaceutically acceptable salt thereof,
wherein:
ring Z is a 5-7 membered partially unsaturated or aromatic ring having 1-4 ring heteroatoms selected from O, S, or N, wherein Z is optionally substituted with up to q occurrences of $R^Z$ substitutents, wherein each $R^Z$ is independently selected from $R^1$, $R^2$, $R^3$, $R^4$, or $R^5$; and q is 0-4;

W and $Y_1$, each is independently CH or N, provided that at least one of W and $Y_1$ is N;

x and y each is independently 0-3; provided that x+y is 2, 3, or 4;

w is 0-4;

v is 0 or 1;

z is 0-4;

V and X each is a bond, O, $NR^2$, or $C(R^2)_2$;

Q is a bond or a C1-C6 straight or branched alkylidene chain, wherein up to two non-adjacent methylene units of Q are optionally and independently replaced by —CO—, —CS—, —COCO—, —CONR²—, —CONR²NR²—, —CO₂—, —OCO—, —NR²CO₂—, —O—, —NR²CONR²—, —OCONR²—, —NR²NR², —NR²NR²CO—, —NR²CO—, —S—, —SO, —SO₂—, —NR²—, —SO₂NR²—, NR²SO₂—, —NR²SO₂NR²—, or a spirocycloalkylene moiety;

$R^Q$ is a C1-C6 aliphatic group, a 3-8-membered saturated, partially unsaturated, or fully unsaturated monocyclic ring having 0-3 heteroatoms independently selected from O, S, N, or NH, or an 8-15 membered saturated, partially unsaturated, or fully unsaturated bicyclic ring or tricyclic fused or spirocyclic ring system having 0-5 heteroatoms independently selected from O, S, N, or NH;

wherein $R^Q$ is optionally substituted with up to 4 substituents independently selected from $R^1$, $R^2$, $R^3$, $R^4$, or $R^5$;

$R^{11}$ is $R^2$ or Y;

$R^{22}$ is $R^1$, $R^2$, or $R^4$;

wherein ring A is optionally fused to a phenyl ring, wherein said phenyl ring is optionally substituted with up to 4 substituents independently selected from $R^1$, $R^2$, or $R^4$;

$R^1$ is oxo, =NN$(R^6)_2$, =NN$(R^7)_2$, =NN$(R^6R^7)$, =N—OR⁶, =N—OR⁷, R⁶ or $(CH_2)_n$—Y;

n is 0, 1 or 2;

Y is halo, CN, NO₂, CF₃, OCF₃, OH, SR⁶, S(O)R⁶, SO₂R⁶, NH₂, NHR⁶, N(R⁶)₂, NR⁶R⁸, COOH, COOR⁶ or OR⁶; or two $R^1$ on adjacent ring atoms, taken together, form 1,2-methylenedioxy or 1,2-ethylenedioxy;

$R^2$ is hydrogen or C1-C6 aliphatic, wherein each $R^2$ is optionally substituted with up to 2 substituents independently selected from $R^1$, $R^4$, or $R^5$;

$R^3$ is a C3-C8 cycloaliphatic, C6-C10 aryl, C3-C8 heterocyclic, or C5-C10 heteroaryl ring, wherein each $R^3$ is optionally substituted with up to 3 substituents independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6C(S)N(R^6)_2$, $NR^6C(S)NR^5R^6$, $NR^6C(S)N(R^5)_2$, $NR^5C(S)N(R^6)_2$, $NR^5C(S)NR^5R^6$, $NR^5C(S)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^6)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$);

$R^5$ is a C3-C8 cycloaliphatic, C6-C10 aryl, C3-C8 heterocyclic, or C5-C10 heteroaryl ring, wherein each $R^5$ optionally substituted with up to 3 $R^1$ substituents;

$R^6$ is H or C1-C6 aliphatic, wherein $R^6$ is optionally substituted with a $R^7$ substituent;

$R^7$ is a C3-C8 cycloaliphatic, C6-C10 aryl, C3-C8 heterocyclic, or C5-C10 heteroaryl ring, and each $R^7$ is optionally substituted with up to 2 substituents independently selected from C1-C6 aliphatic, or $(CH_2)_m$-Z' wherein m is 0-2;

Z' is selected from halo, CN, $NO_2$, $C(halo)_3$, $CH(halo)_2$, $CH_2(halo)$, —$OC(halo)_3$, —$OCH(halo)_2$, —$OCH_2(halo)$, OH, S—(C1-C6) aliphatic, S(O)—(C1-C6) aliphatic, $SO_2$—(C1-C6)aliphatic, $NH_2$, NH—(C1-C6) aliphatic, N((C1-C6)aliphatic)$_2$, N((C1-C6)aliphatic)$R^8$, COOH, C(O)O—(C1-C6)aliphatic), or O—(C1-C6)aliphatic; and $R^8$ is $CH_3C(O)$—, C6-C10 aryl sulfonyl-, or C1-C6 alkyl sulfonyl-.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable (i.e., having the requisite valency available for a given substituent) position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" means a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members.

Unless otherwise specified, the term "heterocycle", "heterocyclyl", "heterocycloaliphatic", or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

The term "spirocycloalkylene" refers to a cycloaliphatic ring that has two points of attachment from the same carbon atom to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds of formula (I), wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or sodium channel blockers with improved therapeutic profile.

In one embodiment, Z is an optionally substituted ring selected from:

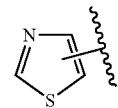

i

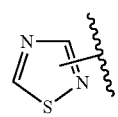

ii

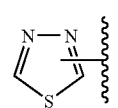

iii

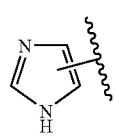

iv

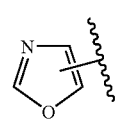

v

-continued

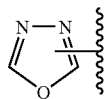

vi

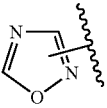

vii

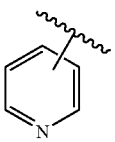

viii

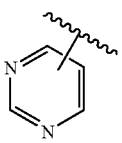

ix

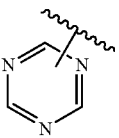

x

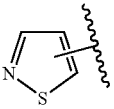

xi

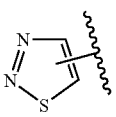

xii

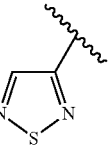

xiii

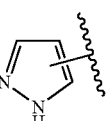

xiv

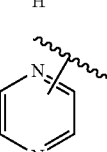

xv

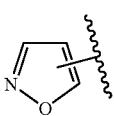

xvi

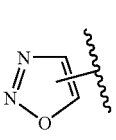

xvii

-continued
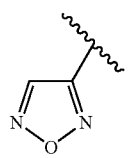 xviii
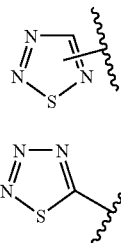 xix
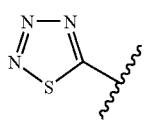 xx
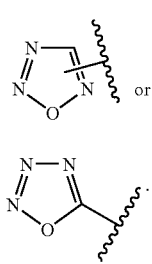 xxi or
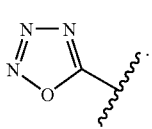 xxii.
In certain embodiments of the compounds of the present invention, Z is selected from:
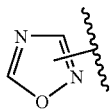 i
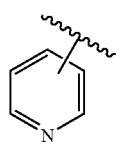 ii
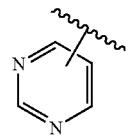 iii
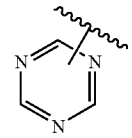 iv
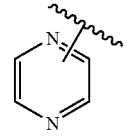 v
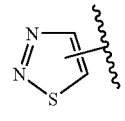 vi
-continued
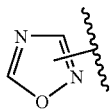 vii
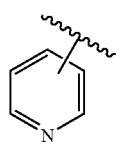 viii
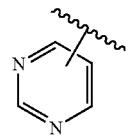 ix
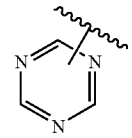 x
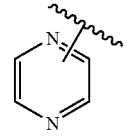 xi
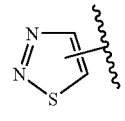 xii
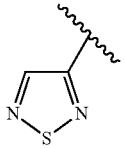 xiii
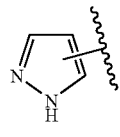 xiv
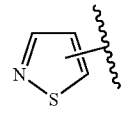 xv
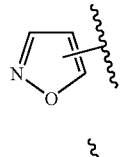 xvi
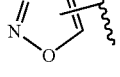 xvii -continued
xviii 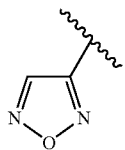
xix 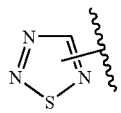
xx 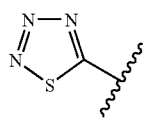
xxi 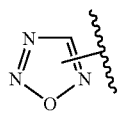
xxi 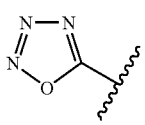
xxii 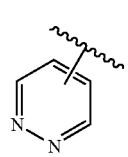
xxiii 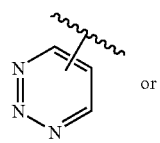 or
xxiv 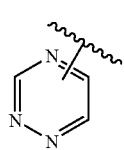
wherein Z has up to two substituents selected from $R^1$, $R^2$, or $R^5$.
In other embodiments, Z is selected from:
i-a 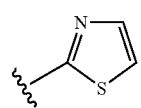
i-b 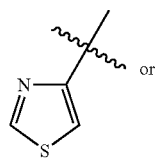 or
-continued
i-c 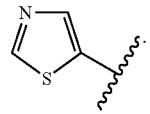
Or, Z is formula i-a.
In other embodiments, Z is selected from:
xi-a 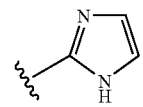
xi-b 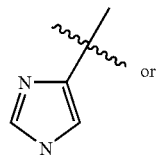 or
xi-c 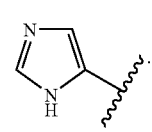
In certain embodiments of the present invention, Z is selected from:
iv-a
iv-b or
iv-c
Or, Z is selected from:
xii-a 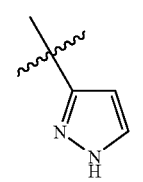

-continued
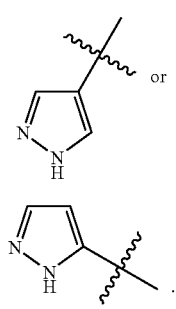 xii-b
or
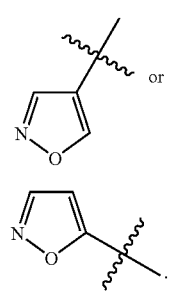 xii-c
Or, Z is selected from:
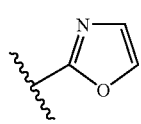 v-a
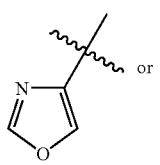 v-b
or
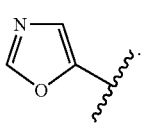 v-c
In certain embodiments, Z is selected from:
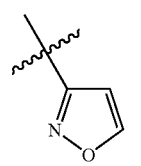 xiv-a
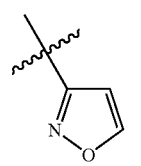 xiv-b
or
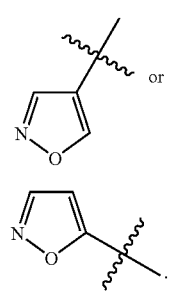 xiv-c
In certain embodiments, Z is selected from:
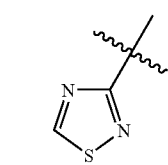 ii-a
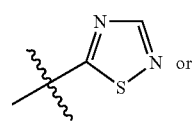 ii-b
or
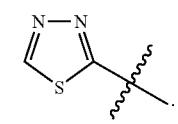 iii-a
In one embodiment Z is ii-b. Or, Z is iii-a.
In certain embodiments, Z is selected from:
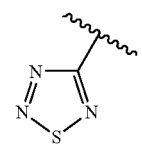 xvii
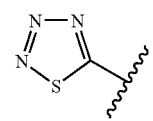 xviii
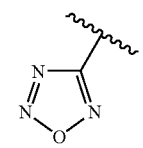 xix
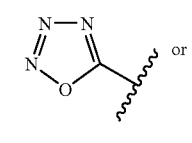 xx
or
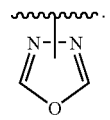 vi
In other embodiments, Z is selected from:
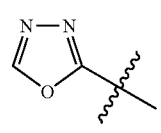 vi-a -continued
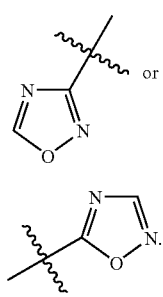 or
In other embodiments, Z is selected from:
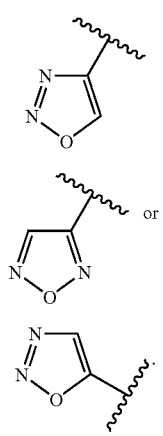
In certain embodiments, Z is selected from:
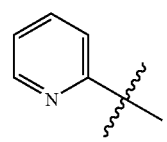
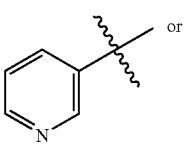 or
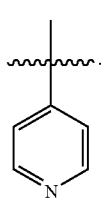
In certain embodiments, Z is selected from:
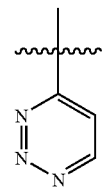
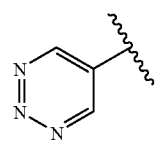
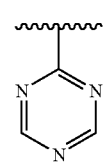
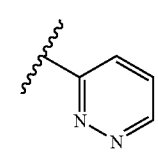
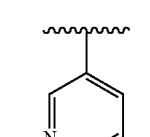
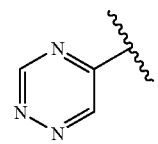
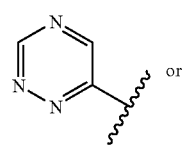 or
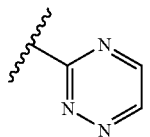
In other embodiments, Z is selected from:
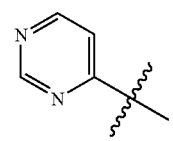
vii-a
vii-b
xv-a
xvi-a
xv-b
viii-a
viii-b
viii-c
xxii-a
xxii-b
x-a
xxi-a
xxi-b
xxii-a
xxii-b
xxii-c
ix-a

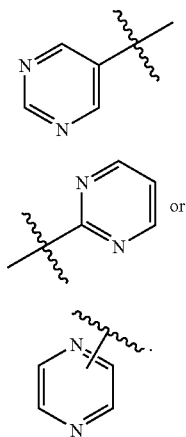

In one embodiment, Z is ix-a. Or, Z is ix-c.

In one embodiment, $R^Z$ is $R^1$. Or, $R^Z$ is $R^2$. In another embodiment, $R^Z$ is $R^4$.

In one embodiment, q is 0. Or, q is 1-2.

According to one embodiment of formula I, $R^1$ is oxo. Or $R^1$ is $=NN(R^6)_2$, $=NN(R^7)_2$, or $=NN(R^6R^7)$. According to another embodiment, $R^1$ is $R^6$.

According to one embodiment, $R^1$ is $(CH_2)_n$—Y. Or, $R^1$ is Y.

Exemplary Y includes halo, CN, $NO_2$, $CF_3$, $OCF_3$, OH, SH, S(C1-4 aliphatic), S(O)(C1-4 aliphatic), $SO_2$(C1-4 aliphatic), $NH_2$, NH(C1-4 aliphatic), N(C1-4 aliphatic)$_2$, NR(C1-4 aliphatic)$R^8$, COOH, COO(C1-4 aliphatic) or O(C1-4 aliphatic). Or, two $R^1$ on adjacent ring atoms, taken together, form 1,2-methylenedioxy or 1,2-ethylenedioxy. In another embodiment, Y is halo, OH, SH, CN, $NO_2$, $CF_3$, $OCF_3$, COOH, or C(O)O(C1-C4 alkyl). In another embodiment, $R^1$ is selected from halo, cyano, trifluoromethyl, OH, $C_{1-4}$ alkyl, $C_{2-4}$ alkenyl, $C_{1-4}$ alkoxy, trifluoromethoxy, C(O)$NH_2$, $NH_2$, NH($C_{1-4}$ alkyl), N($C_{1-4}$ alkyl)$_2$, NHC(O)$C_{1-4}$ alkyl, 1-pyrrolidinyl, 1-piperidinyl, 1-morpholinyl, or C(O)$C_{1-4}$ alkyl.

In another embodiment, $R^1$ is $(CH_2)_n$—Y. In one embodiment, n is 0 or 1. Or, n is 2. In one embodiment, Y is halo, CN, $NO_2$, $CF_3$, $OCF_3$, $OR^6$, $SR^6$, $S(O)R^6$, $SO_2R^6$, $N(R^6)_2$, $NR^6R^8$, or $COOR^6$. In another embodiment, Y is halo, OH, SH, CN, $NO_2$, $CF_3$, $OCF_3$, or C(O)O(C1-C4 alkyl).

In one embodiment, two $R^1$ on adjacent ring atoms, taken together, form 1,2-methylenedioxy or 1,2-ethylenedioxy.

According to another embodiment of formula (I), $R^2$ is a straight or branched (C1-C6) alkyl or (C2-C6)alkenyl or alkynyl, optionally substituted with up to two $R^1$ substitutions.

In one embodiment, $R^2$ is H. In another embodiment, $R^2$ is C1-C6 aliphatic. In another embodiment, $R^2$ is a C1-C6 straight or branched alkyl. In another embodiment, $R^2$ is C1-C4 alkyl. In another embodiment, $R^2$ is optionally substituted with up to 2 substituents independently selected from $R^1$ or $R^4$. Or, $R^2$ is optionally substituted with up to 2 substituents independently selected from $R^1$ or $R^5$.

In one embodiment, $R^3$ is a C3-C8 cycloaliphatic optionally substituted with up to 3 substituents independently selected from $R^1$, $R^2$, $R^4$ or $R^5$. Exemplary cycloaliphatics include cyclopropyl, cyclopentyl, cyclohexyl, or cycloheptyl. In another embodiment, $R^3$ is a C6-C10 aryl, optionally substituted with up to 3 substituents independently selected from $R^1$, $R^2$, $R^4$ or $R^5$. Exemplary aryl rings include phenyl or naphthyl. In another embodiment, $R^3$ is a C3-C8 heterocyclic, optionally substituted with up to 3 substituents independently selected from $R^1$, $R^2$, $R^4$ or $R^5$. Exemplary heterocyclic rings include azetidinyl, pyrrolidinyl, piperidinyl, piperazinyl, morpholinyl, or thiomorpholinyl. In another embodiment, $R^3$ is a C5-C10 heteroaryl ring, optionally substituted with up to 3 substituents independently selected from $R^1$, $R^2$, $R^4$ or $R^5$. Exemplary heteroaryl rings include pyridyl, pyrazinyl, triazinyl, furanyl, pyrrolyl, thiophenyl, oxazolyl, isoxazolyl, isothiazolyl, oxadiazolyl, imidazolyl, triazolyl, thiadiazolyl, pyrimidinyl, quinolinyl, isoquinolinyl, benzofuranyl, benzothiophenyl, quinolinyl, isoquinolinyl, benzofuranyl, benzothiophenyl, indolizinyl, indolyl, isoindolyl, indolinyl, indazolyl, benzimidazolyl, benzothiazolyl, purinyl, cinnolinyl, phthalazinyl, quinazolinyl, quinaoxalinyl, naphthyridinyl, or pteridinyl.

In one embodiment, $R^4$ is selected from $OR^5$ or $OR^6$. Or, $R^4$ is selected from $OC(O)R^6$ or $OC(O)R^5$. In another embodiment, $R^4$ is selected from $C(O)R^5$, $C(O)OR^5$, $C(O)R^6$, $C(O)OR^6$, $C(O)N(R^6)_2$, $C(O)N(R^5)_2$ or $C(O)N(R^5R^6)$. In yet another embodiment, $R^4$ is selected from $N(R^6)_2$, $N(R^5)_2$, or $N(R^5R^6)$. Or, $R^4$ is selected from $NR^5C(O)R^5$, $NR^6C(O)R^6$, $NR^6C(O)R^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, or $NR^5C(O)N(R^5)_2$.

In one embodiment, $R^5$ is a C3-C8 cycloaliphatic, optionally substituted with up to 3 $R^1$ substituents. Exemplary cycloaliphatics include cyclopropyl, cyclopentyl, cyclohexyl, or cycloheptyl. In another embodiment, $R^5$ is a C6-C10 aryl, optionally substituted with up to 3 $R^1$ substituents. Exemplary aryl rings include phenyl or naphthyl. In another embodiment, $R^5$ is a C3-C8 heterocyclic, optionally substituted with up to 3 $R^1$ substituents. Exemplary heterocyclic rings include azetidinyl, pyrrolidinyl, piperidinyl, piperazinyl, morpholinyl, or thiomorpholinyl. In another embodiment, $R^5$ is a C5-C10 heteroaryl ring, optionally substituted with up to 3 $R^1$ substituents. Exemplary heteroaryl rings include pyridyl, pyrazyl, triazinyl, furanyl, pyrrolyl, thiophenyl, oxazolyl, isoxazolyl, isothiazolyl, oxadiazolyl, imidazolyl, triazolyl, thiadiazolyl, pyrimidinyl, quinolinyl, isoquinolinyl, benzofuranyl, benzothiophenyl, quinolinyl, isoquinolinyl, benzofuranyl, benzothiophenyl, indolizinyl, indolyl, isoindolyl, indolinyl, indazolyl, benzimidazolyl, benzothiazolyl, purinyl, cinnolinyl, phthalazinyl, quinazolinyl, quinaoxalinyl, naphthyridinyl, or pteridinyl.

In one embodiment, $R^6$ is H. In another embodiment, $R^6$ is C1-C6 aliphatic, preferably, C1-C6 alkyl. Or, $R^6$ is C1-C6 aliphatic optionally substituted with a $R^7$ substituent.

In one embodiment, $R^7$ is a C3-C8 cycloaliphatic, optionally substituted with up to 2 substituents independently selected from C1-C6 aliphatic or $(CH_2)_m$-Z' wherein m is 0-2. Exemplary cycloaliphatics include cyclopropyl, cyclopentyl, cyclohexyl, or cycloheptyl. In another embodiment, $R^7$ is a C6-C10 aryl, optionally substituted with up to 2 substituents independently selected from C1-C6 aliphatic or $(CH_2)_m$-Z' wherein m is 0-2. Exemplary aryl rings include phenyl or naphthyl. Or, $R^7$ is a C3-C8 heterocyclic ring, optionally substituted with up to 2 substituents independently selected from C1-C6 aliphatic, or $(CH_2)_m$-Z' wherein m is 0-2. Exemplary heterocyclic rings include azetidinyl, pyrrolidinyl, piperidinyl, piperazinyl, morpholinyl, or thiomorpholinyl. Or, $R^7$ is a C5-C10 heteroaryl ring, optionally substituted with up to 2 substituents independently selected from C1-C6 aliphatic, or $(CH_2)_m$-Z' wherein m is 0-2. Exemplary heteroaryl rings include pyridyl, pyrazinyl, triazinyl, furanyl, pyrrolyl, thiophenyl, oxazolyl, isoxazolyl, isothiazolyl, oxadiazolyl, imidazolyl, triazolyl, thiadiazolyl, pyrimidinyl, quinolinyl, isoquinolinyl, benzofuranyl, benzothiophenyl, quinolinyl, isoquinolinyl, benzofuranyl, benzothiophenyl, indolizinyl, indolyl, isoindolyl, indolinyl, indazolyl, benzimidazolyl, benzothiazolyl, purinyl, cinnolinyl, phthalazinyl, quinazolinyl, quinaoxalinyl, naphthyridinyl, or pteridinyl.

In one embodiment, Z' is selected from halo, CN, $NO_2$, C(halo)$_3$, CH(halo)$_2$, CH$_2$(halo), —OC(halo)$_3$, —OCH(halo)$_2$, —OCH$_2$(halo), OH, S—(C1-C6) aliphatic, S(O)—(C1-C6) aliphatic, $SO_2$—(C1-C6)aliphatic, $NH_2$, NH—(C1-C6)aliphatic, N((C1-C6)aliphatic)$_2$, COOH, C(O)O(—(C1-C6)aliphatic), or O—(C1-C6)aliphatic.

In one embodiment, X is a bond.

In another embodiment, X is O. Or, X is C($R^2$)$_2$. Or, X is $NR^2$.

In one embodiment, X is CH$_2$. Or, X is CHMe. Or, X is C(Me)$_2$.

In another embodiment, X is NMe.

In one embodiment, Q is a bond.

In another embodiment, Q is O, S, or $NR^2$. In embodiment, Q is O. Or, Q is S. Or, Q is $NR^2$. Or, Q is NH or N(C1-C6) alkyl.

In another embodiment, Q is a C1-C6 straight or branched alkylidine chain, wherein up to one methylene unit of Q is replaced by O, S, NH, or N(C1-C4 alkyl).

In another embodiment, Q is a C1-C6 alkyl, wherein one methylene group is replaced by a spirocycloalkylene group such as spirocyclopropylene.

In another embodiment, Q is —$X_2$—($X_1$)$_p$—, wherein:
$X_2$ is C1-C6 aliphatic, optionally substituted with up to two substituents independently selected from $R^1$, $R^4$, or $R^5$; and
p is 0 or 1; and
$X_1$ is O, S, or $NR^2$.

In one embodiment, $X_2$ is C1-C6 alkyl or C2-C6 alkylidene. Or, $X_2$ is C1-C6 alkyl optionally substituted with $R^1$ or $R^4$. In one embodiment, $X_2$ is selected from —CH$_2$—, —CH$_2$—CH$_2$—, —(CH$_2$)$_3$—, —C(Me)$_2$-, —CH(Me)-, —C(Me)=CH—, —CH=CH—, —CH(Ph)-, —CH$_2$—CH(Me)-, —CH(Et)-, or —CH(i-Pr)—.

In certain embodiments, $X_1$ is NH. Or, $X_1$ is —N(C1-C4 alkyl)-.

In one embodiment, p is 0.

In another embodiment, p is 1 and $X_1$ is O.

In another embodiment, p is 1, and $X_1$ is S.

In another embodiment, p is 1, and $X_1$ is $NR^2$. Preferably, $R^2$ is hydrogen.

In one embodiment, z is 0. Or, z is 1. In another embodiment, z is 2.

In one embodiment, $R^Q$ is a C1.C6 aliphatic group, wherein $R^Q$ is optionally substituted with up to 4 substituents independently selected from $R^1$, $R^2$, $R^3$, $R^4$, or $R^5$.

In another embodiment, $R^Q$ is a 3-8-membered saturated, partially unsaturated, or aromatic monocyclic ring having 0-3 heteroatoms independently selected from O, S, N, or NH, wherein $R^Q$ is optionally substituted with up to 4 substituents selected from $R^1$, $R^2$, $R^3$, $R^4$, or $R^5$. In one embodiment, $R^Q$ is optionally substituted with up to 3 substituents selected from halo, cyano, trifluoromethyl, OH, $C_{1-4}$ alkyl, $C_{2-4}$ alkenyl, $C_{1-4}$ alkoxy, trifluoromethoxy, C(O)NH$_2$, NH$_2$, NH($C_{1-4}$ alkyl), N($C_{1-4}$ alkyl)$_2$, NHC(O)$C_{1-4}$ alkyl, or C(O)$C_{1-4}$ alkyl.

In one embodiment, $R^Q$ is optionally substituted phenyl, wherein $R^Q$ is optionally substituted with up to 4 substituents selected from $R^1$, $R^2$, $R^3$, $R^4$, or $R^5$. In one embodiment, $R^Q$ is phenyl optionally substituted with up to 3 substituents selected from halo, cyano, trifluoromethyl, OH, $C_{1-4}$ alkyl, $C_{2-4}$ alkenyl, $C_{1-4}$ alkoxy, trifluoromethoxy, C(O)NH$_2$, NH$_2$, NH($C_{1-4}$ alkyl), N($C_{1-4}$ alkyl)$_2$, NHC(O)$C_{1-4}$ alkyl, or C(O)$C_{1-4}$ alkyl. Exemplary $R^Q$ include:

| $R^Q$ |
| --- |
| 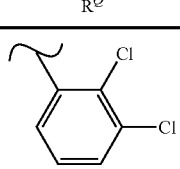 |
| 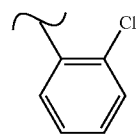 |
| 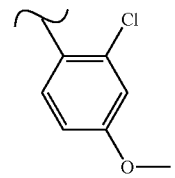 |
| 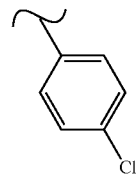 |
| 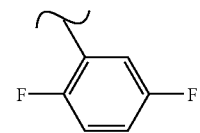 |
| 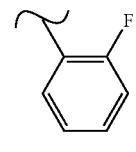 |
| 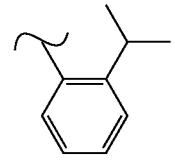 |
| 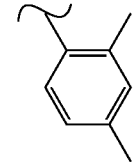 |
| 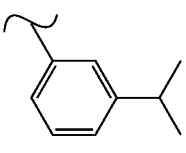 |

-continued
| $R^Q$ |
|---|
| 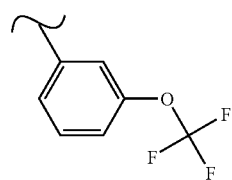 |
| 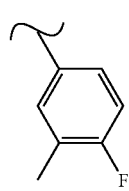 |
| 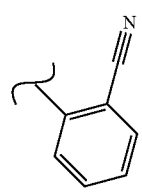 |
| 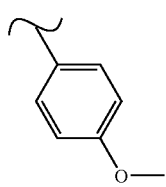 |
| 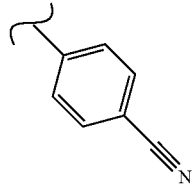 |
| 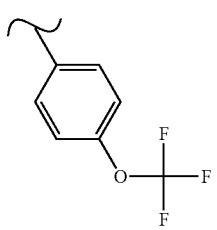 |
| 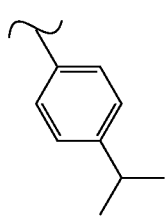 |
-continued
| $R^Q$ |
|---|
| 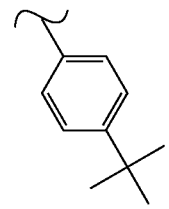 |
| 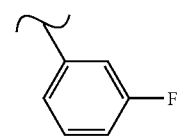 |
| 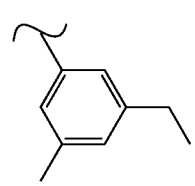 |
| 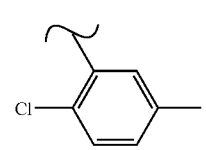 |
| 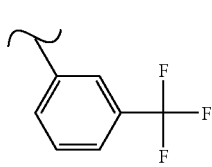 |
| 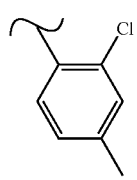 |
| 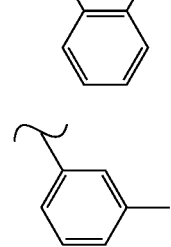 |

-continued
R^Q
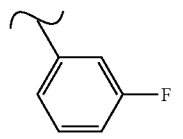
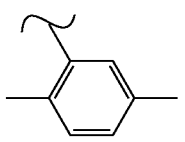
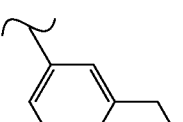
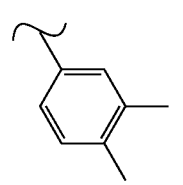
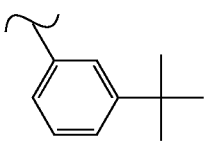
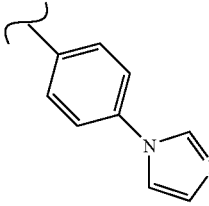
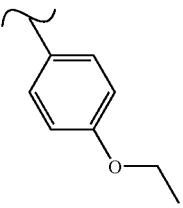
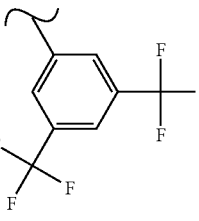
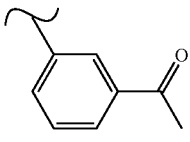
-continued
R^Q
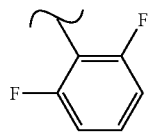
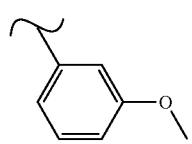
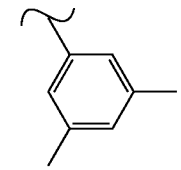
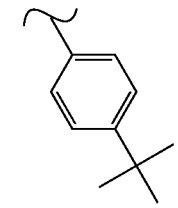
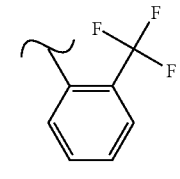
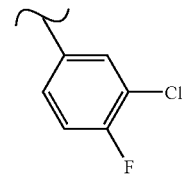
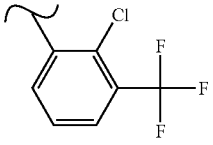

-continued
| $R^Q$ | $R^Q$ |
|---|---|
| 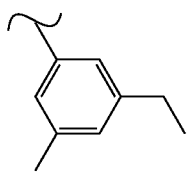 | 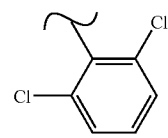 |
| 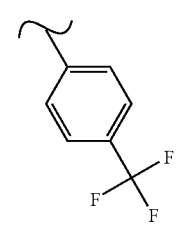 | 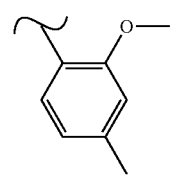 |
| 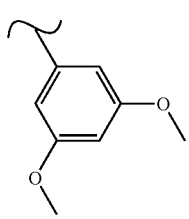 | 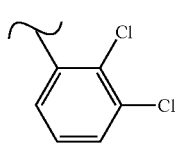 |
| 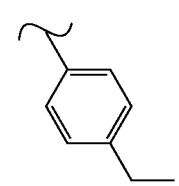 | 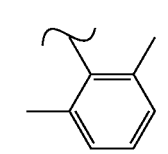 |
| 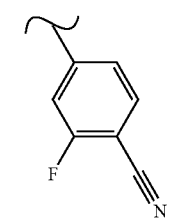 | 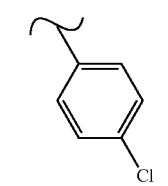 |
| 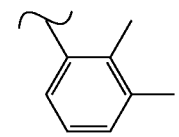 | 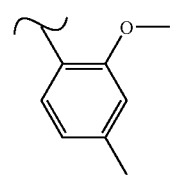 |
| 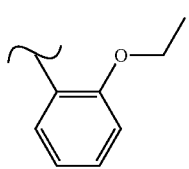 | 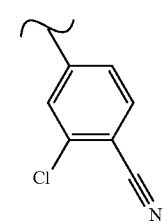 |
| | 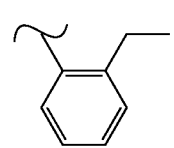 |

-continued

| $R^Q$ |
|---|
| 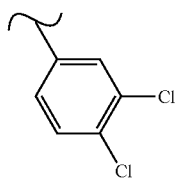 |
| 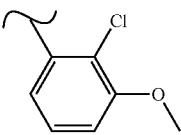 |
| 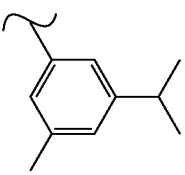 |
| 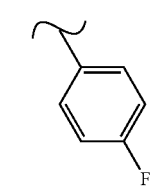 |
| 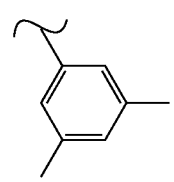 |
| 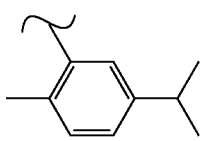 |
| 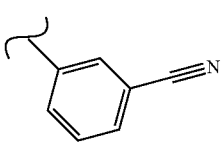 |
| 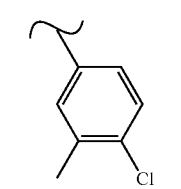 |
| 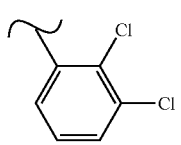 |

-continued

| $R^Q$ |
|---|
| 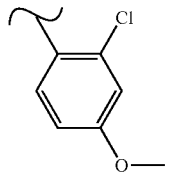 |
| 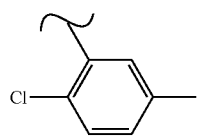 |
| 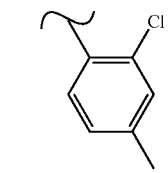 |
| 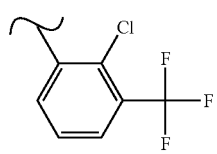 |
| 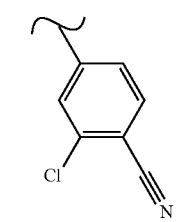 |
| 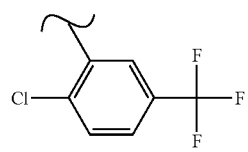 |

In one embodiment, $R^Q$ is optionally substituted naphthyl, wherein $R^Q$ is optionally substituted with up to 4 substituents selected from $R^1$, $R^2$, $R^3$, $R^4$, or $R^5$. In one embodiment, $R^Q$ is naphthyl optionally substituted with up to 5 substituents selected from halo, cyano, trifluoromethyl, OH, $C_{1-4}$ alkyl, $C_{2-4}$ alkenyl, $C_{1-4}$ alkoxy, trifluoromethoxy, $C(O)NH_2$, $NH_2$, $NH(C_{1-4}$ alkyl), $N(C_{1-4}$ alkyl$)_2$, $NHC(O)C_{1-4}$ alkyl, or $C(O)$ $C_{1-4}$ alkyl.

Or, $R^Q$ is an optionally substituted 3-8 membered cycloaliphatic ring, wherein $R^Q$ is optionally substituted with up to 4 substituents selected from $R^1$, $R^2$, $R^3$, $R^4$, or $R^5$. In one embodiment, $R^Q$ is selected from optionally substituted cyclopropyl, cyclobutyl, cyclopentyl, or cyclohexyl.

Or, $R^Q$ is an optionally substituted 5-6 membered monocyclic, unsaturated, partially saturated, or aromatic ring containing up to 3 heteroatoms independently selected from O, S, N, or NH. Or, $R^Q$ is a 3-7 membered monocyclic, heterocyclic ring.

In one embodiment, $R^Q$ is selected from an optionally substituted ring selected from:

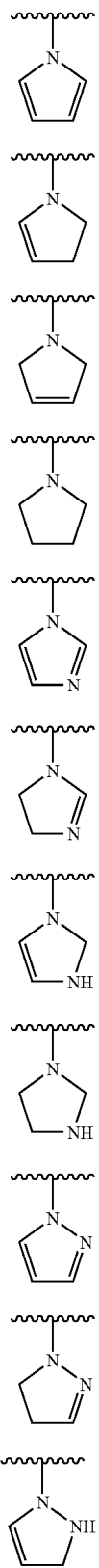

-continued

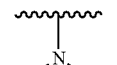
a-11

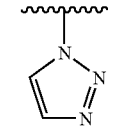
a-12

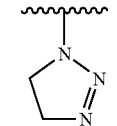
a-13

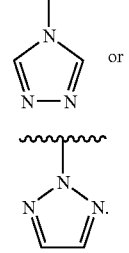
a-14 or a-15

In another embodiment, $R^Q$ is selected from any of rings a-1 to a-13 or a-15, wherein said ring is fused to an optionally substituted phenyl ring.

In another embodiment, $R^Q$ is selected from an optionally substituted ring selected from pyridyl, pyrimidinyl, pyrazinyl, pyridazinyl.

In another embodiment, $R^Q$ is an optionally substituted ring selected from:

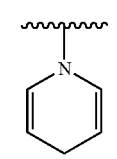
a-16

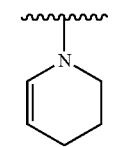
a-17

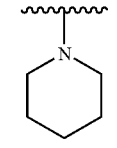
a-18

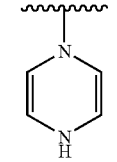
a-19

-continued

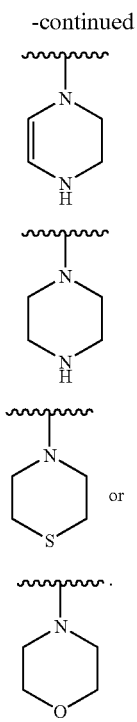

a-20 a-21 a-22 or a-23

In another embodiment, $R^Q$ is any one of the above rings a-16 to a-21, wherein said ring is fused to an optionally substituted phenyl ring.

In another embodiment $R^Q$ is ring a-18, wherein said ring is optionally substituted with a 3-6 membered monocyclic spirocyclic ring containing 0 to 3 heteroatoms independently selected from O, S, N, or NH; wherein said spirocyclic ring is optionally substituted with up to 4 substituents independently selected from $R^1$, $R^2$, $R^3$, $R^4$ or $R^5$; and wherein said spirocyclic ring is optionally fused to a phenyl ring optionally substituted with up to 4 substituents independently selected from $R^1$, $R^2$, $R^3$, $R^4$, or $R^5$.

In another embodiment, $R^Q$ is an 8-12 membered saturated, partially unsaturated, or fully unsaturated bicyclic ring system having 0-5 heteroatoms independently selected from O, S, N, or NH, wherein $R^Q$ is optionally substituted with up to 4 substituents selected from $R^1$, $R^2$, $R^3$, $R^4$, or $R^5$. In one embodiment, $R^Q$ is optionally substituted naphthyl. Or, $R^Q$ is an optionally substituted 8-10 membered, bicyclic, heteroaromatic ring. Or, $R^Q$ is an optionally substituted, 8-10 membered, bicyclic, heterocyclic ring.

In one embodiment, $R^Q$ is an optionally substituted ring selected from:

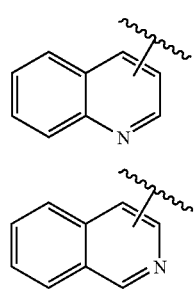

a-24 a-25

-continued

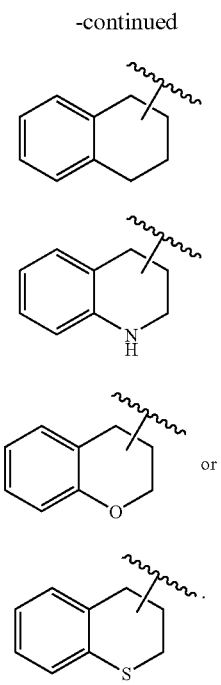

a-26 a-27 or a-28 a-29

In another embodiment, $R^Q$ is an optionally substituted ring selected from:

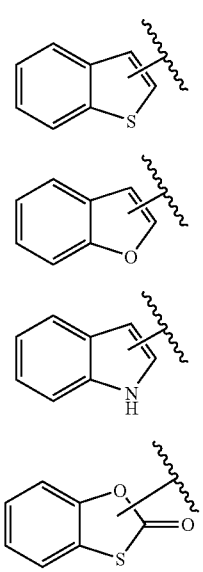

a-30 a-31 a-32 a-33 a-34 a-35

-continued
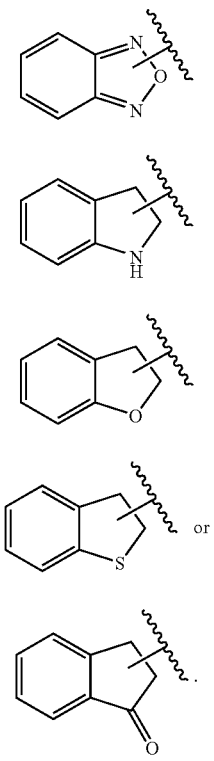
a-36
a-37
a-38
a-39 or
a-40
In another embodiment, $R^Q$ is an optionally substituted ring selected from:
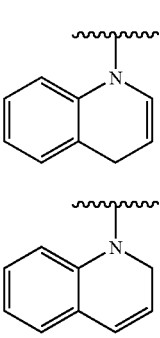
a-41
a-42
a-43
a-44
a-45
-continued
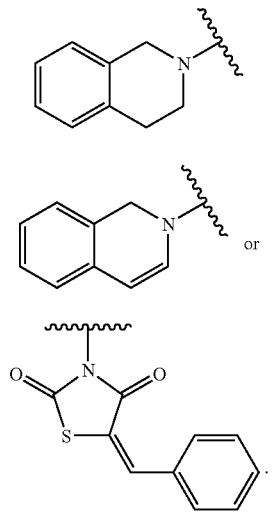
a-46
a-47
a-48
a-49 or
a-50
In another embodiment, $R^Q$ is an optionally substituted ring selected from:
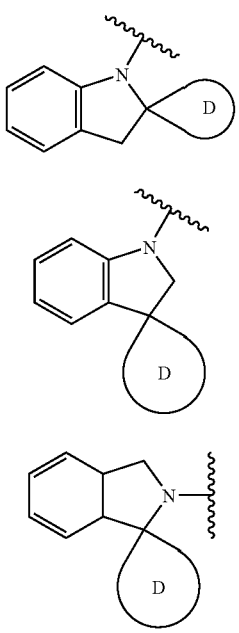
a-42-1
a-42-2
a-44-1

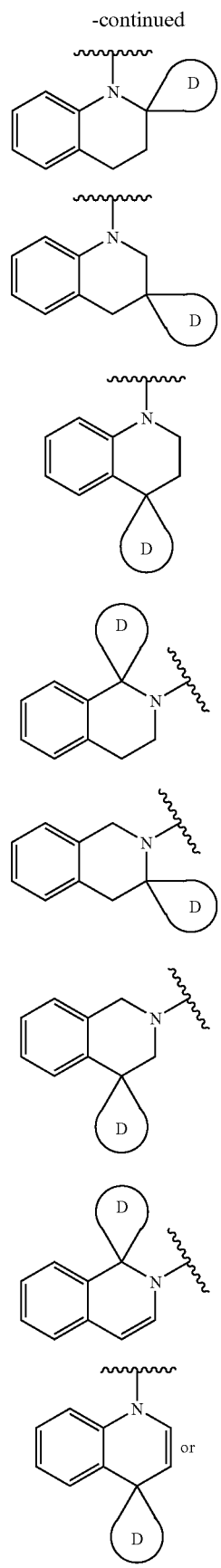

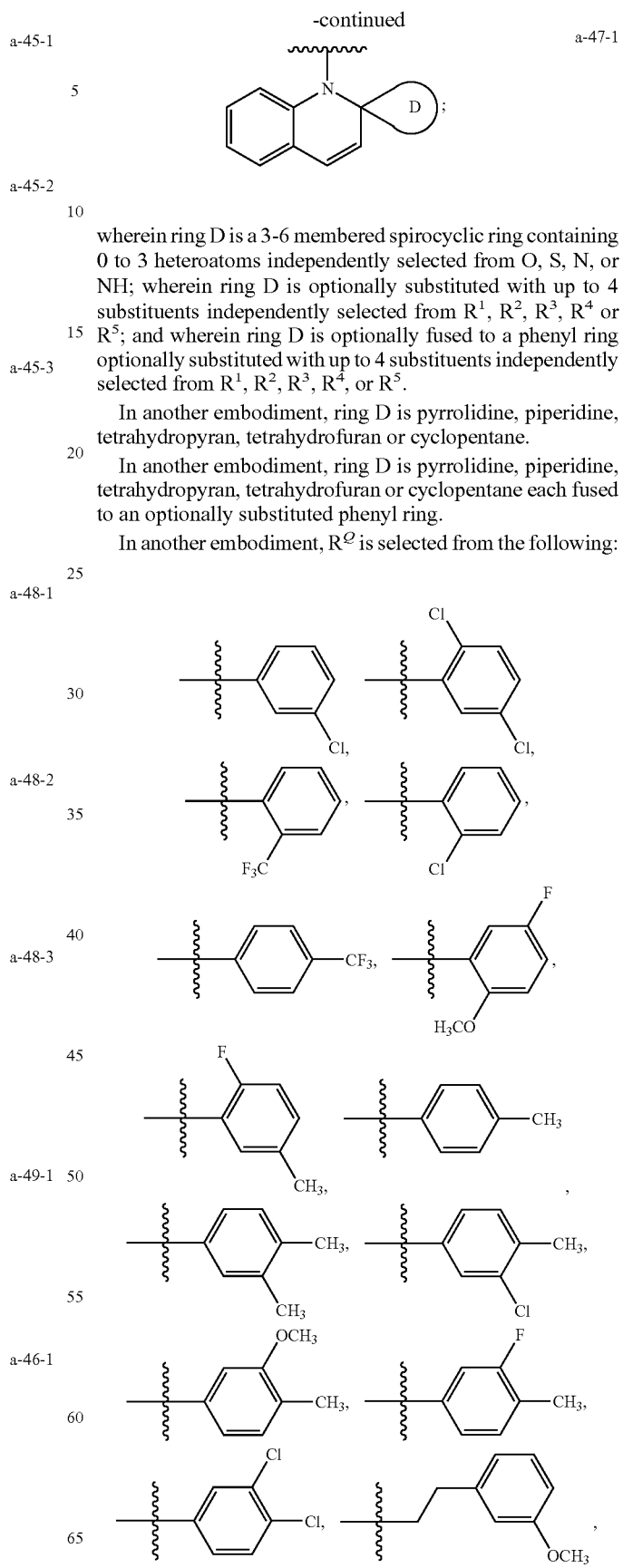

wherein ring D is a 3-6 membered spirocyclic ring containing 0 to 3 heteroatoms independently selected from O, S, N, or NH; wherein ring D is optionally substituted with up to 4 substituents independently selected from $R^1$, $R^2$, $R^3$, $R^4$ or $R^5$; and wherein ring D is optionally fused to a phenyl ring optionally substituted with up to 4 substituents independently selected from $R^1$, $R^2$, $R^3$, $R^4$, or $R^5$.

In another embodiment, ring D is pyrrolidine, piperidine, tetrahydropyran, tetrahydrofuran or cyclopentane.

In another embodiment, ring D is pyrrolidine, piperidine, tetrahydropyran, tetrahydrofuran or cyclopentane each fused to an optionally substituted phenyl ring.

In another embodiment, $R^Q$ is selected from the following:

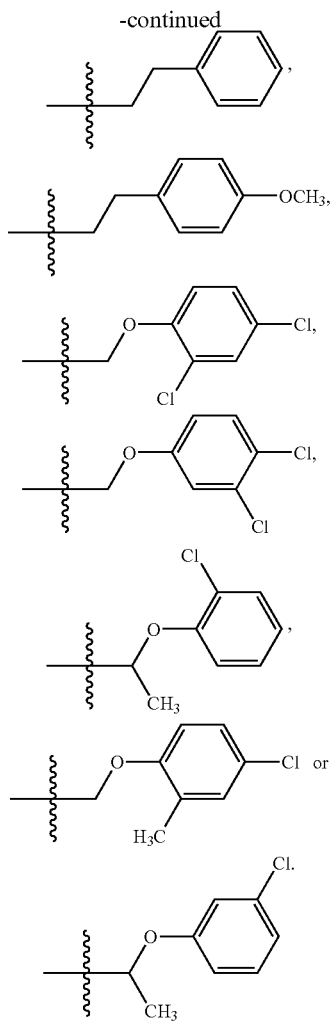

In another embodiment, $R^Q$ is selected from pyrrolidin-1-yl, 3,3-difluoropyrrolidin-1-yl, piperidin-1-yl, 3-methyl-piperidin-1-yl, 4-methyl-piperidin-1-yl, 4,4-difluoropiperidin-1-yl, 4,5-dimethyl-4-morpholin-1-yl, indol-1-yl, 5-chloro-indol-1-yl, tetrahydro-isoquinolin-2-yl, 7-chloro-tetrahydro-isoquinolin-2-yl, 7-trifluoromethyl-tetrahydro-isoquinolin-2-yl, 7-fluoro-tetrahydro-isoquinolin-2-yl, 6-methyl-tetrahydro-isoquinolin-2-yl, 6-chloro-tetrahydroquino-1-yl, 8-trifluoromethyl-quinolin-4-yl, pyridin-3-yl, or pyridin-4-yl.

In one embodiment, $R^Q$ is

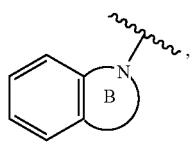

wherein ring B is a 5-7 membered heterocyclic or heteroaryl ring having a single nitrogen heteroatom; wherein $R^Q$ is optionally substituted with up to 4 substituents selected from $R^1$, $R^2$, or $R^3$.

Exemplary embodiments of $R^Q$ include:

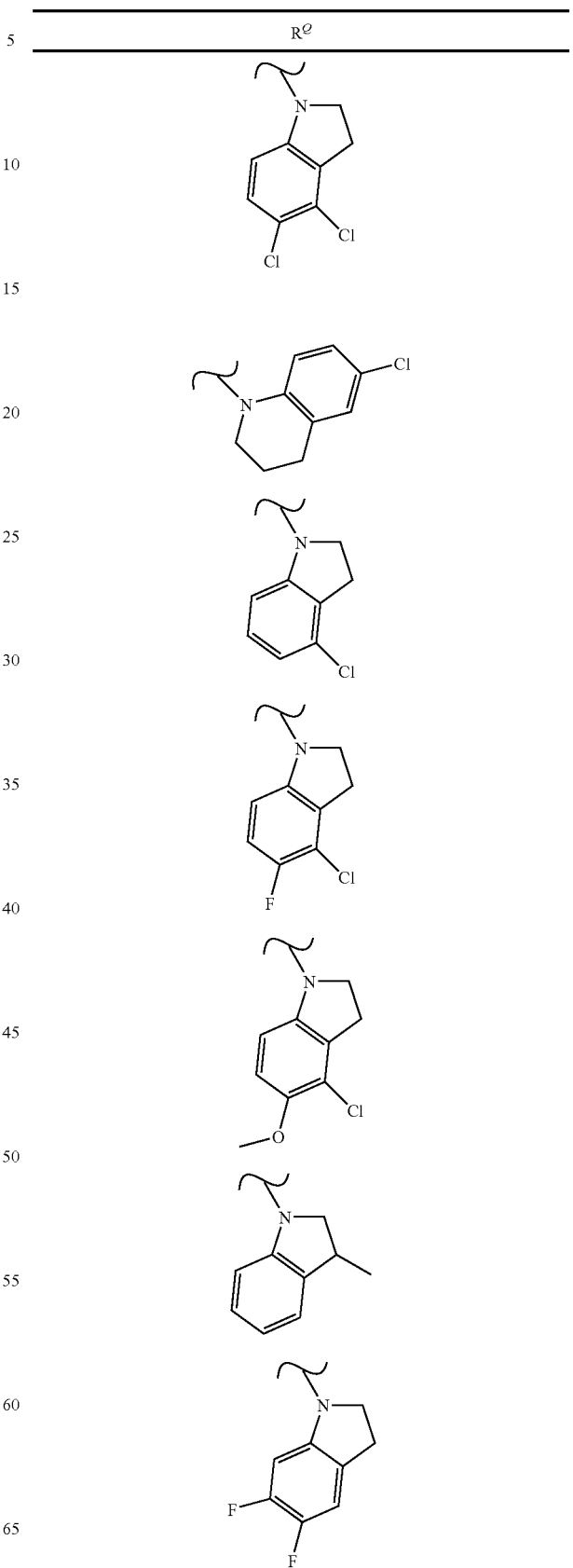

-continued
| R<sup>Q</sup> |
|---|
| 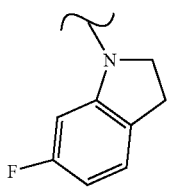 |
| 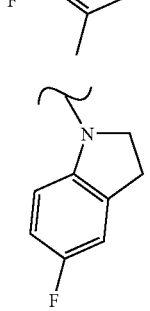 |
| 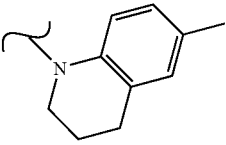 |
|  |
| 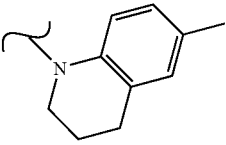 |
| 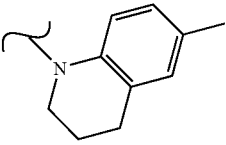 |
-continued
| R<sup>Q</sup> |
|---|
| 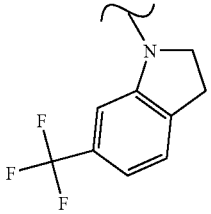 |
| 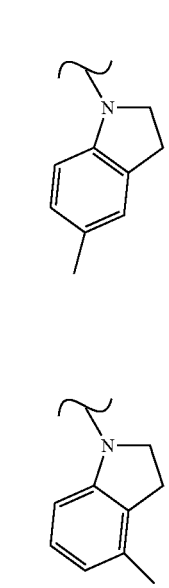 |
| 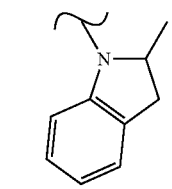 |
| 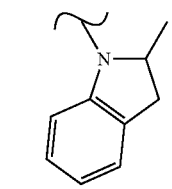 |
| 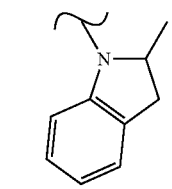 |
| 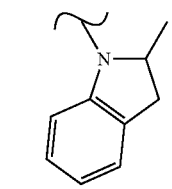 |

-continued
| $R^Q$ |
|---|
| 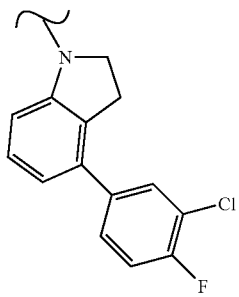 |
| 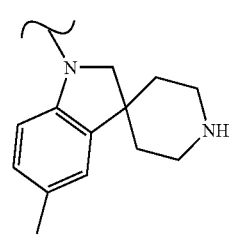 |
| 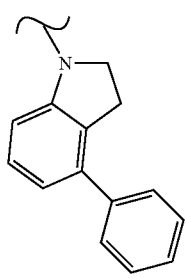 |
| 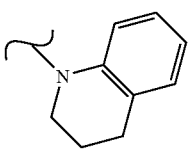 |
| 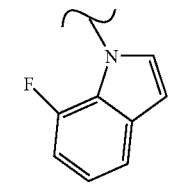 |
| 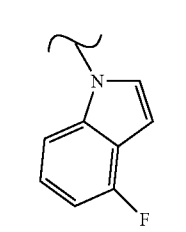 |
-continued
| $R^Q$ |
|---|
| 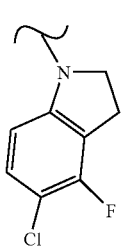 |
| 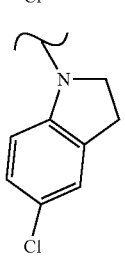 |
| 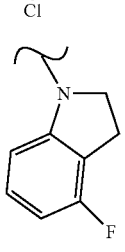 |
| 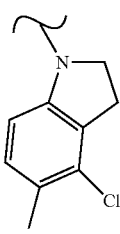 |
| 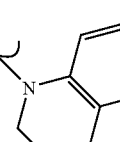 |
| 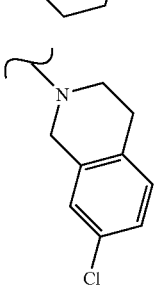 |
| 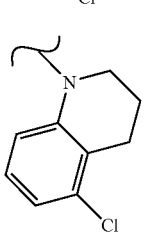 |

-continued
| $R^Q$ |
|---|
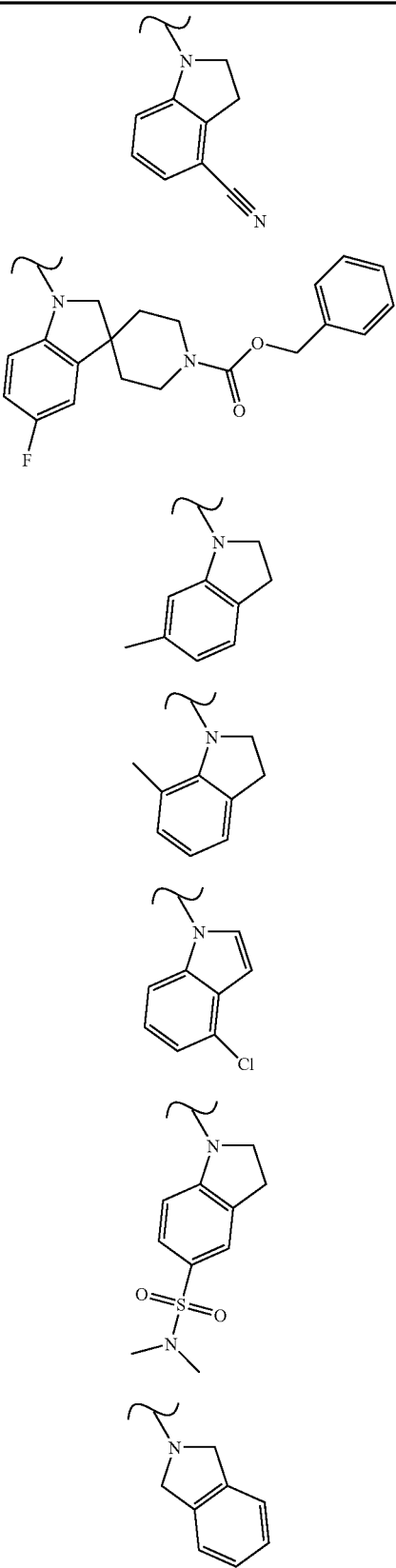
-continued
| $R^Q$ |
|---|
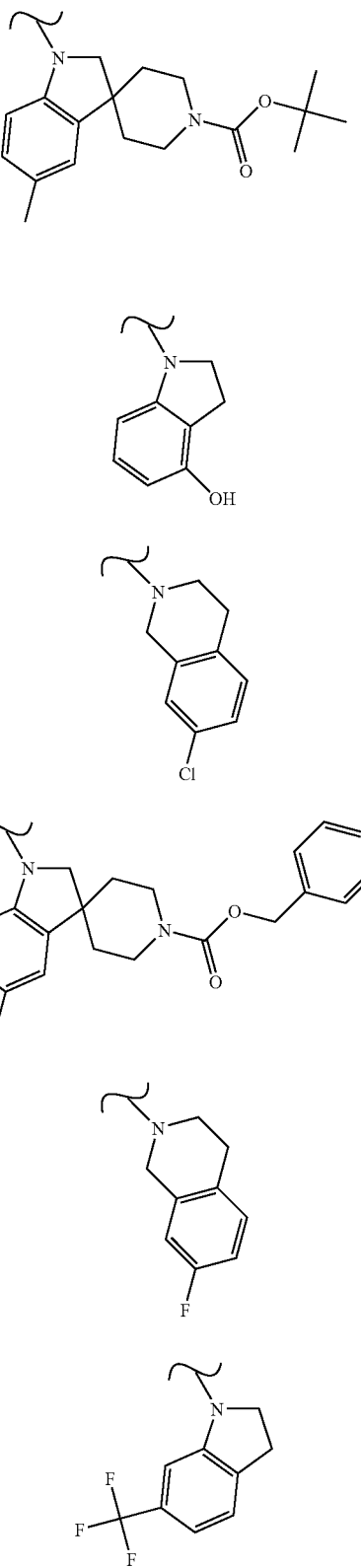

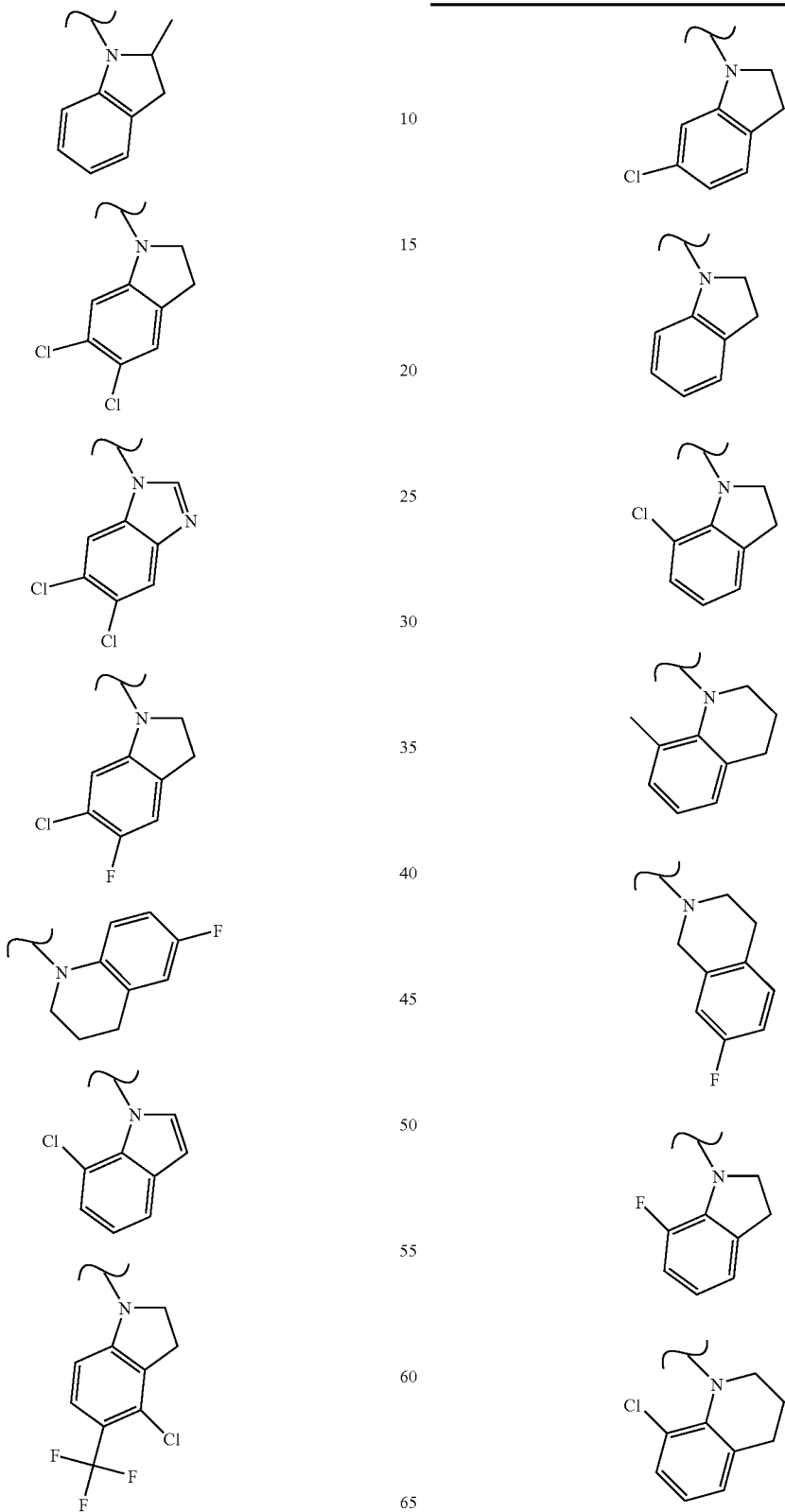

| 51 | 52 |
|---|---|
| -continued | -continued |
| R<sup>Q</sup> | R<sup>Q</sup> |
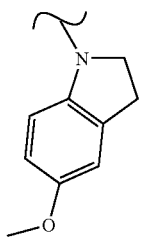
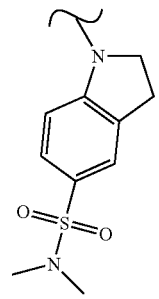
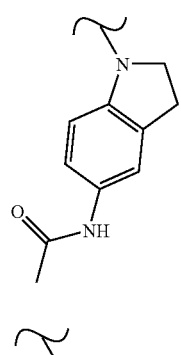
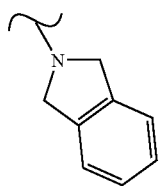
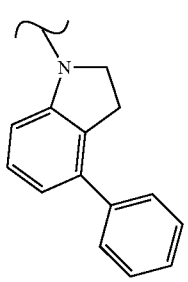
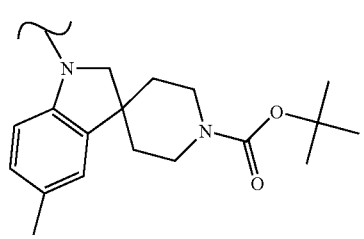
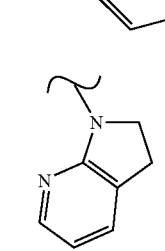
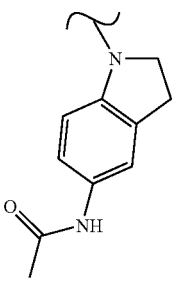
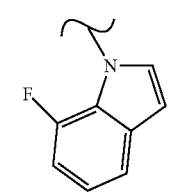
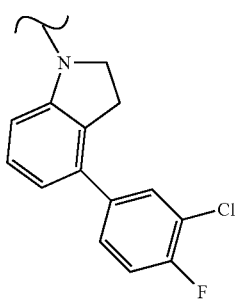
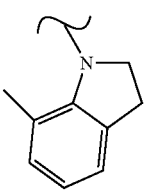
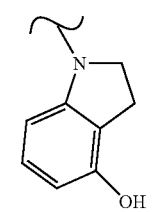

In one embodiment, x and y, each is 1-2.

In another embodiment, x is 0 and y is 3. Or, x is 1 and y is 2. Or, x and y, both are 2.

In one embodiment, ring A, together with W, $Y_1$, x and y is:

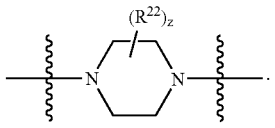

In another embodiment, ring A, together with W, $Y_1$, x and y is:

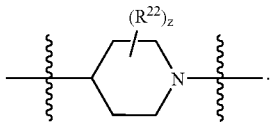

In another embodiment, ring A, together with W, $Y_1$, x and y is:

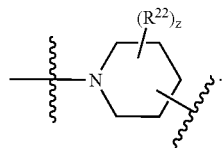

In another embodiment, ring A, together with W, $Y_1$, x and y is:

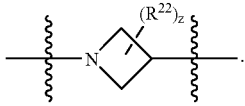

In another embodiment, ring A, together with W, $Y_1$, x and y is:

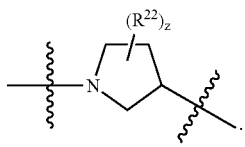

In another embodiment, ring A, together with W, $Y_1$, x and y is:

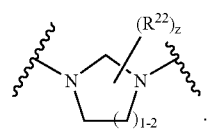

In another embodiment, ring A, together with W, $Y_1$, x and y is:

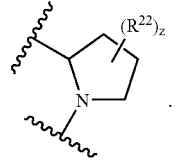

In one embodiment, the present invention provides compounds of formula IA or formula IB:

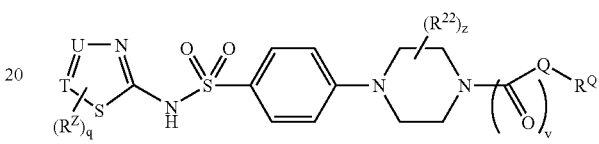

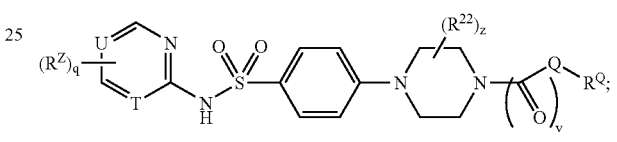

wherein:

U and T each is independently CH or N; provided that both U and T are not simultaneously N;

$R^{22}$ is $R^1$ or $R^2$;

$R^z$ is selected from $R^1$, $R^2$, or $R^5$;

q is 0-2;

v is 0 or 1;

Q is C1-C4 alkylidene, wherein up to two non-adjacent methylene units of Q are optionally and independently replaced by —CO—, —CS—, —COCO—, —$CONR^2$—, —$CONR^2NR^2$—, —$CO_2$—, —OCO—, —$NR^2CO_2$—, —O—, —$NR^2CONR^2$—, —$OCONR^2$—, —$NR^2NR^2$, —$NR^2NR^2CO$—, —$NR^2CO$—, —S—, —SO, —$SO_2$—, —$NR^2$—, —$SO_2NR^2$—, $NR^2SO_2$—, —$NR^2SO_2NR^2$—, or a spirocycloalkylene moiety; and $R^Q$ is a C1-C6 aliphatic group, a 3-8-membered saturated, partially unsaturated, or fully unsaturated monocyclic ring having 0-3 heteroatoms independently selected from O, S, N, or NH, or an 8-15 membered saturated, partially unsaturated, or fully unsaturated bicyclic ring or tricyclic fused or spirocyclic ring system having 0-5 heteroatoms independently selected from O, S, N, or NH;

In one embodiment, U is N and T is CH.

In another embodiment, T is N and U is CH.

In another embodiment, U and T, both are CH.

In one embodiment, $R^{22}$ is oxo.

In another embodiment, $R^{22}$ is C1-C4 alkyl. Exemplary embodiments include methyl, ethyl, or propyl.

In some embodiments, Q is C1-C4 alkylidene, wherein one methylene units of Q is optionally replaced by —CO—, —CS—, —O—, —S—, —SO, —$SO_2$—, —$NR^2$—, or a spirocycloalkylene moiety;

In another embodiment, $R^Q$ is as defined above.

In one embodiment, the present invention provides compounds of formula IA-i, formula IA-ii, formula IA-iii, formula IA-iv, formula IB-i, formula IB-ii, formula IB-iii, or formula IAB-iv:

IA-i
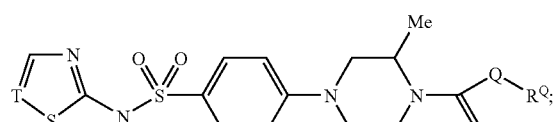

IA-ii
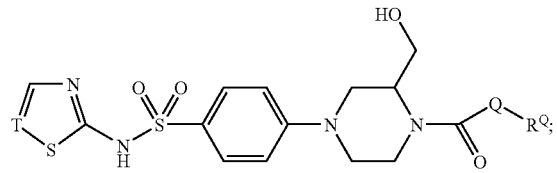

IA-iii
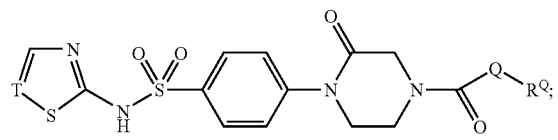

IB-i
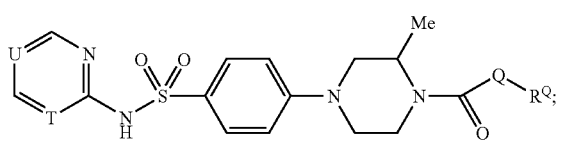

IB-ii

IB-iii
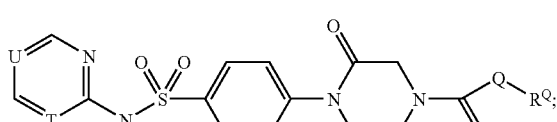

IA-iv
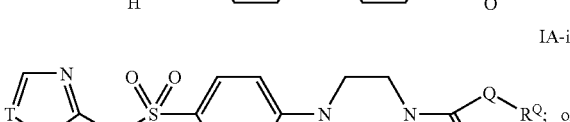

IB-iv
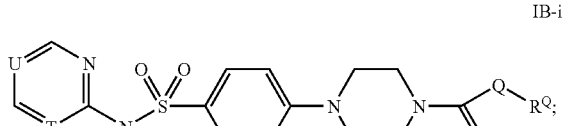

wherein:

Q is C1-C4 straight or branched alkylidene, wherein up to one methylene unit of Q is optionally and independently replaced by —O—;

T is CH or N;
U is CH or N;
$R^Q$ is phenyl,

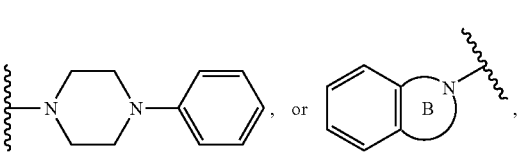

wherein ring B is a 5-7 membered heterocyclic or heteroaryl ring having a single nitrogen heteroatom;

wherein $R^Q$ is optionally substituted with up to 4 substituents independently selected from $R^1$, $R^2$, or $R^3$.

In one embodiment, $R^Q$ is selected from:

a
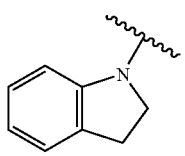

b
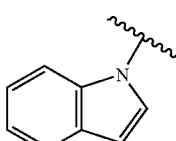

c
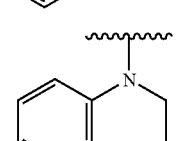

d
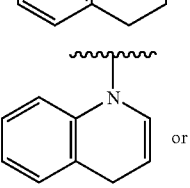
or e
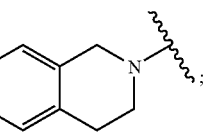
;

wherein $R^Q$ is optionally substituted with up to 4 substituents independently selected from $R^1$, $R^2$ or $R^3$.

In one embodiment, $R^Q$ is phenyl optionally substituted with up to 4 substituents independently selected from $R^1$, $R^2$, or $R^3$.

In one embodiment, $R^Q$ is

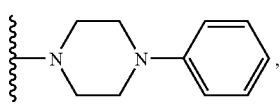

wherein $R^Q$ is optionally substituted with up to 4 substituents independently selected from $R^1$, $R^2$, or $R^3$.

In one embodiment, T is CH. In another embodiment, T is N.

In one embodiment, U is N and T is CH.

In another embodiment, T is N and U is CH.

In another embodiment, U and T, both are CH.

In one embodiment, Q is C1-C4 straight or branched alkylidene. Exemplary Q include —CH$_2$—, —CH$_2$—CH$_2$—, —CH(Me)-, —C(Me)$_2$-, —CH(i-Pr)—, etc.

In one embodiment of formula IA-i, formula IA-ii, formula IA-iii, or formula IA-iv:
U is CH and T is CH or N;
Q is —CH$_2$—, —CH$_2$—CH$_2$—, —CH(Me)-, or —C(Me)$_2$-; and
R$^Q$ is ring b or ring c above, wherein R$^Q$ is optionally substituted with up to three substituents selected from chloro, fluoro, or CF$_3$;

In one embodiment of formula IB-i, formula IB-ii, formula IB-iii, or formula IAB-iv:
U is CH and T is N;
Q is —CH$_2$—, —CH$_2$—CH$_2$—, —CH(Me)-, or —C(Me)$_2$-; and
R$^Q$ is ring b or ring c above, wherein R$^Q$ is optionally substituted with up to three substituents selected from chloro, fluoro, or CF$_3$;

In another embodiment, the present invention provides compounds of formula IIA or formula IIB:

IIA

IIB wherein U, T, R$^{22}$, R$^Z$, z, q, v, Q and R$^Q$ are as defined above.

In one embodiment of formula IIA or formula IIB, q is zero, and v is 1.

In one embodiment, T is CH. In another embodiment, T is N.

In one embodiment, U is N and T is CH.

In another embodiment, T is N and U is CH.

In another embodiment, U and T, both are CH.

In one embodiment, Q is C1-C4 straight or branched alkylidene. Exemplary Q include —CH$_2$—, —CH$_2$—CH$_2$—, —CH(Me)-, —C(Me)$_2$-, —CH(i-Pr)—, etc.

In one embodiment, z is 1, R$^{22}$ is OH on the carbon atom directly attached to the phenyl ring.

In one embodiment, R$^Q$ is selected from:

a b c d e or f wherein R$^Q$ is optionally substituted with up to 4 substituents independently selected from R$^1$, R$^2$, or R$^4$.

In one embodiment of formula IIA:
U is CH and T is CH or N;
q and z, both are zero;
v is 1;
Q is —CH$_2$—, —CH$_2$—CH$_2$—, or —CH(Me)-;
R$^Q$ is ring b or ring f, optionally substituted with up to 3 halo substituents.

In one embodiment of formula IIB:
U is CH and T is N;
q and z, both are zero;
v is 1;
Q is —CH$_2$—, —CH$_2$—CH$_2$—, or —CH(Me)-;
R$^Q$ is ring b or ring f, optionally substituted with up to 3 halo substituents.

In another embodiment, the present invention provides compounds of formula IIIA or formula IIIB:

IIIA

IIIB

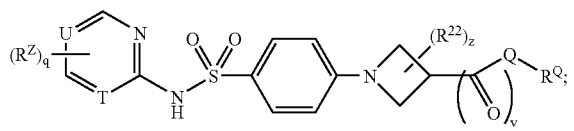

wherein U, T, $R^{22}$, $R^Z$, z, q, v, Q and $R^Q$ are as defined above.

In one embodiment of formula IIIA or formula IIIB, v, q, and z are both zero.

In another embodiment, v is zero and Q is —$CH_2$—NH—C(O)(C1-C4 alkylidene)-, —NH—C(O—(C1-C4 alkylidene)-. Exemplary Q include —NH—C(O)—$CH_2$—, —NH—C(O)—$CH_2$—$CH_2$—, —NH—C(O)—CH(Me)-, —$CH_2$—NH—C(O)CH(Me)-, —NH—C(O)—C(Me)$_2$-, —NH—C(O)—CH(i-Pr)—, etc.

In one embodiment, T is CH. In another embodiment, T is N.

In one embodiment, U is N and T is CH.

In another embodiment, T is N and U is CH.

In another embodiment, U and T, both are CH.

In another embodiment, the present invention provides compounds of formula IVA or formula IVB:

IVA

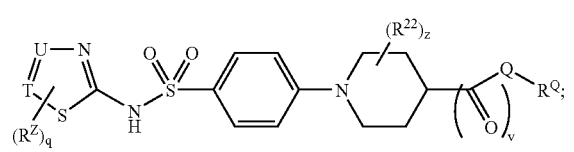

IVB

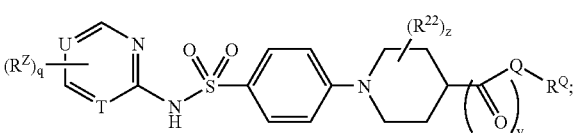

wherein U, T, $R^{22}$, $R^Z$, z, q, v, Q and $R^Q$ are as defined above.

In one embodiment of formula IVA or formula IVB, v, q, and z are both zero.

In one embodiment, T is CH. In another embodiment, T is N.

In one embodiment, U is N and T is CH.

In another embodiment, T is N and U is CH.

In another embodiment, U and T, both are CH.

In one embodiment, Q is NHC(O)C1-C4 straight or branched alkylidene, C1-C4 straight or branched alkylidene. Exemplary Q include —$CH_2$—, —$CH_2$—$CH_2$—, —CH(Me)-, —C(Me)$_2$-, —CH(i-Pr)—, —NHC(O)CH(Me)-, etc.

In one embodiment, $R^Q$ is selected from:

a

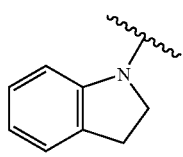

b

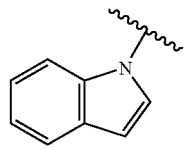

c

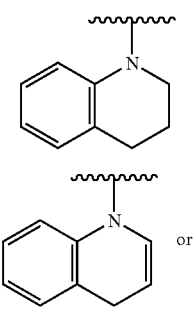

d or e

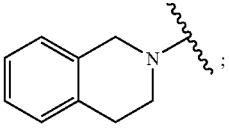

;

wherein $R^Q$ is optionally substituted with up to 4 substituents independently selected from $R^1$, $R^2$, or $R^4$.

In one embodiment of compound of formula IVA or formula IVB:

Q is —$CH_2$—, —$CH_2$—$CH_2$—, —CH(Me)-, or —C(Me)$_2$-; and $R^Q$ is ring b above, wherein $R^Q$ is optionally substituted with up to three substituents selected from chloro, fluoro, or $CF_3$;

In another embodiment, the present invention provides compounds of formula VA, formula VA-i, formula VB or formula VB-i:

VA

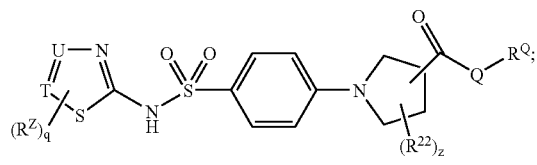

VA-i

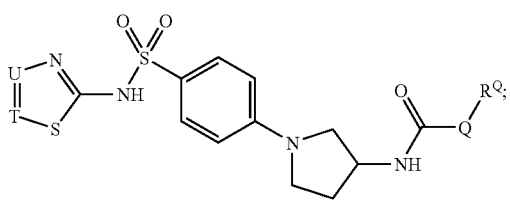

VB

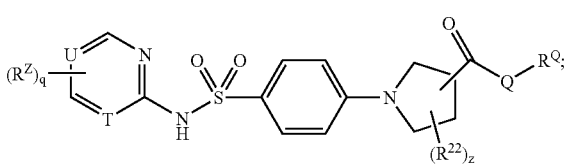

-continued

VB-i

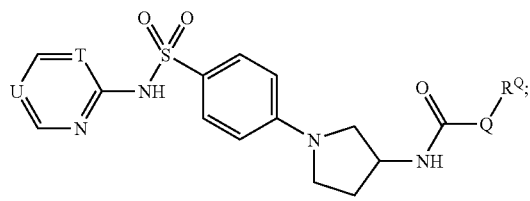

wherein U, T, R²², R^Z, z, q, v, Q and R^Q are as defined above.

In one embodiment, T is CH. In another embodiment, T is N.

In one embodiment, U is N and T is CH.

In another embodiment, T is N and U is CH.

In another embodiment, U and T, both are CH.

In one embodiment of formula VA-i or formula VB-i, R^Q is selected from:

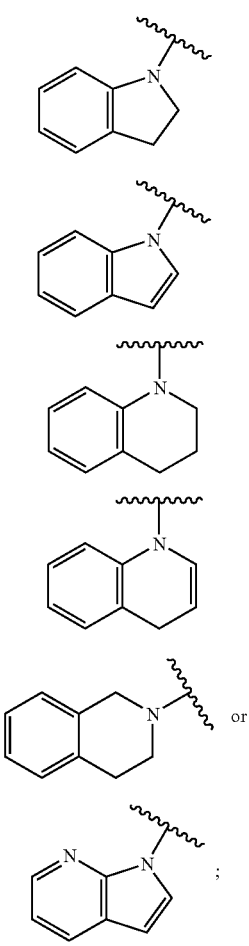

a b c d e f wherein R^Q is optionally substituted with up to 4 substituents independently selected from R¹, R², or R⁴.

In one embodiment of formula VA-i or formula VB-i:
Q is —CH₂— or —CH(Me)-; and
R^Q is ring b above, wherein R^Q is optionally substituted with up to three substituents selected from chloro, fluoro, or CF₃.

In another embodiment, the present invention provides compounds of formula VIA or formula VIB:

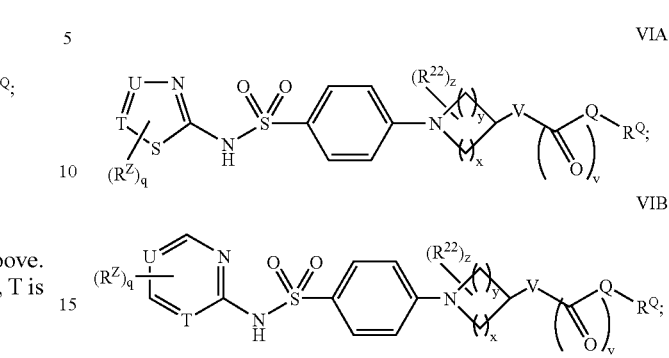

VIA

VIB wherein V is a bond, O, NR², or C(R²)₂ and U, T, R²², R^Z, z, q, v, Q and R^Q are as defined above.

In some embodiments, V is a bond, O, or NH.

In one embodiment of formula VIA or formula VIB, v, q, and z are both zero.

In one embodiment, T is CH. In another embodiment, T is N.

In one embodiment, U is N and T is CH.

In another embodiment, T is N and U is CH.

In another embodiment, U and T, both are CH.

In one embodiment, v is 0, Q and V each is a bond, and x, y, z, R²², together with the ring therein is:

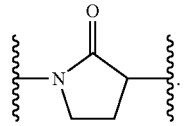

R^Q is phenyl,

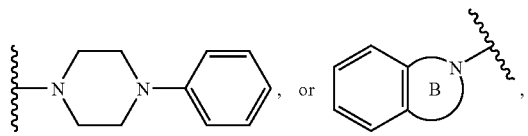

wherein ring B is a 5-7 membered heterocyclic or heteroaryl ring having a single nitrogen heteroatom;

wherein R^Q is optionally substituted with up to 4 substituents independently selected from R¹, R² or R³.

In one embodiment, the present invention provides compounds of formula VIA-i:

VIA-i

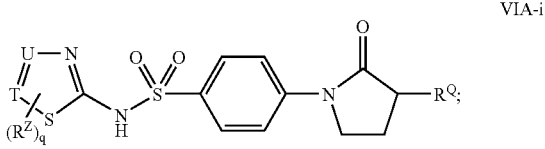

wherein:

U, T, $R^Z$, and q are as defined above; and $R^Q$ is

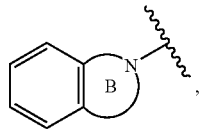

wherein ring B is a 5-7 membered heterocyclic or heteroaryl ring having a single nitrogen heteroatom; wherein $R^Q$ is optionally substituted with up to 4 substituents independently selected from $R^1$, $R^2$, or $R^3$.

In one embodiment, U and T, both are CH.

In another embodiment, U is CH and T is N.

In one embodiment, $R^Q$ is selected from:

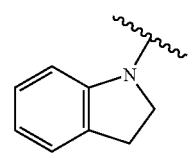

a

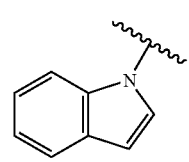

b

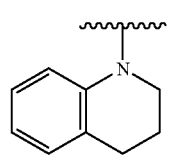

c

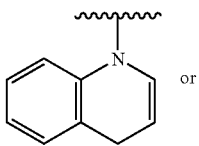

d or

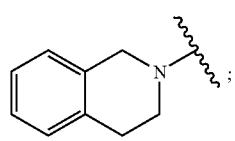

e

;

wherein $R^Q$ is optionally substituted with up to 4 substituents selected from $R^1$, $R^2$, or $R^3$.

Exemplary $R^Q$ in compounds of the present invention include:

| $R^Q$ |
|---|
| 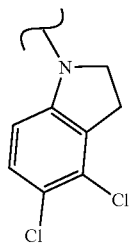 |
| 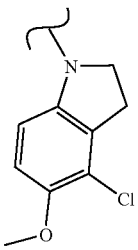 |
| 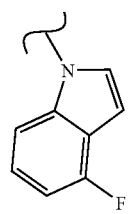 |
| 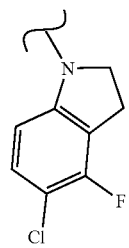 |
| 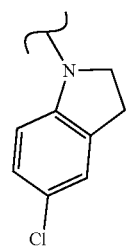 |
| 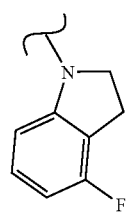 |

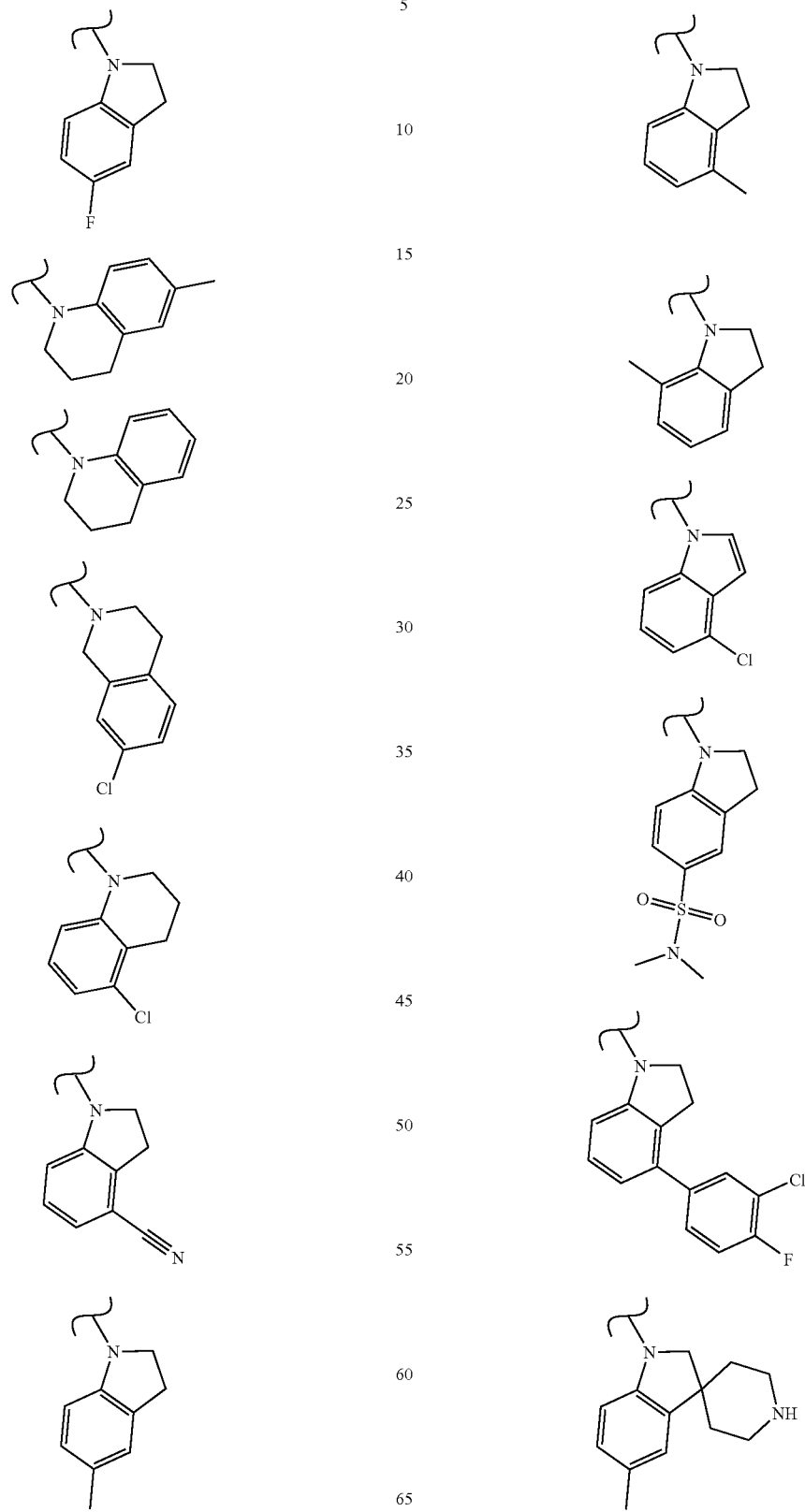

-continued
| $R^Q$ |
|---|
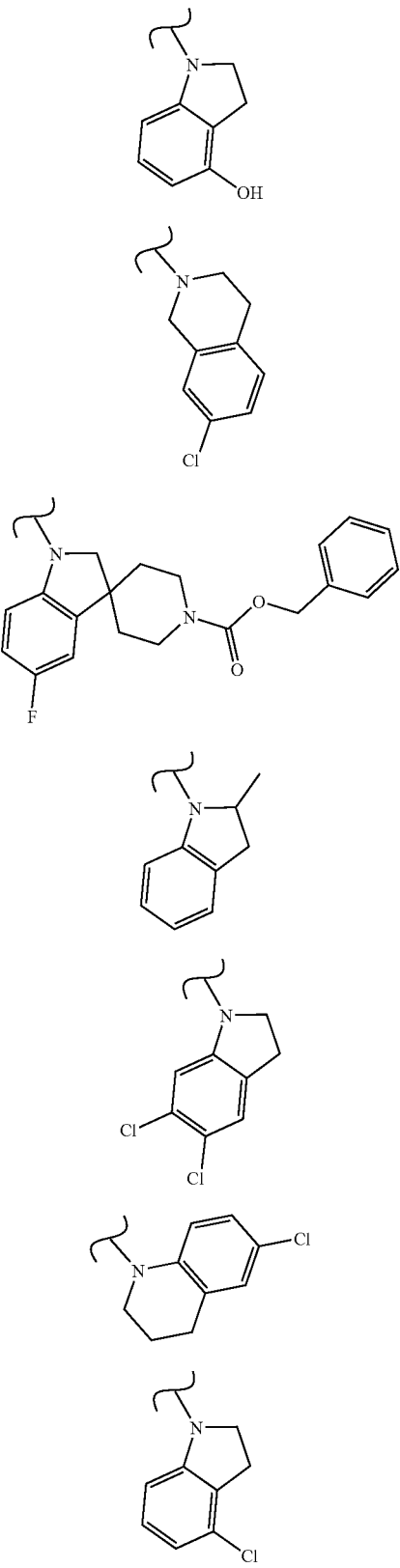
-continued
| $R^Q$ |
|---|
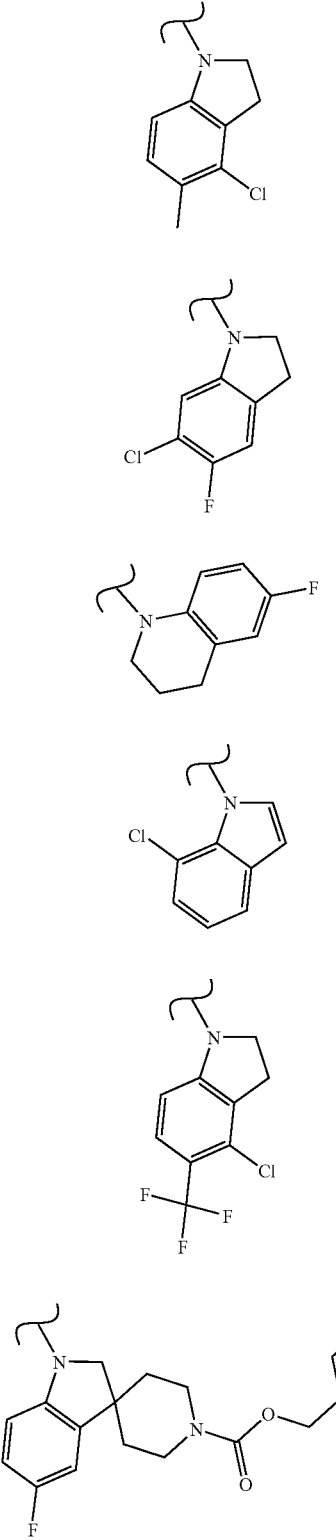

-continued
R<sup>Q</sup>
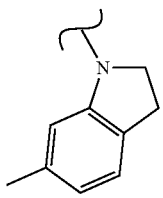
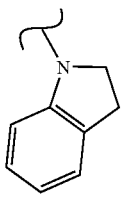
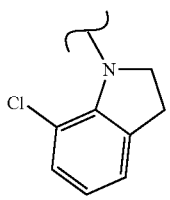
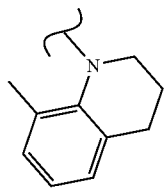
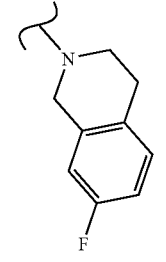
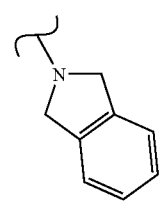
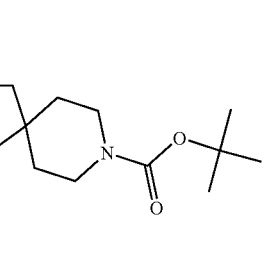
-continued
R<sup>Q</sup>
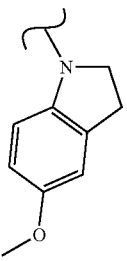
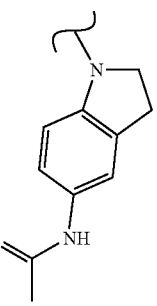
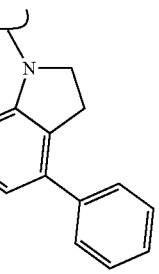
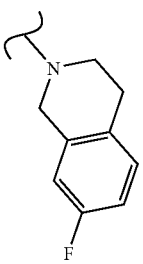
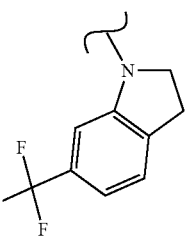
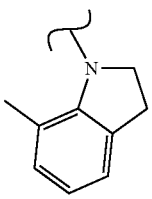

| -continued | -continued |
|---|---|
| R^Q | R^Q |
| 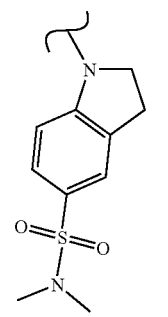 | 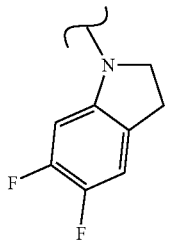 |
| 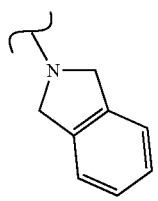 | 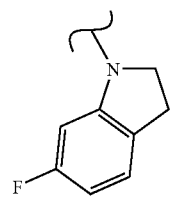 |
| 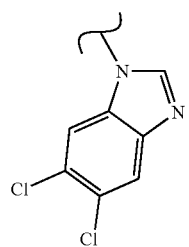 | 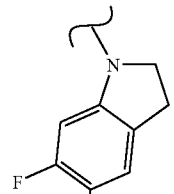 |
| 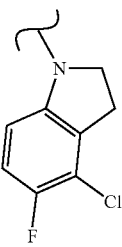 | 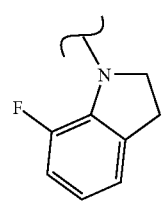 |
| 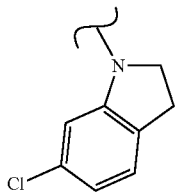 | 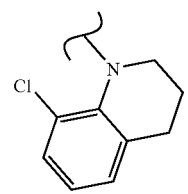 |
| 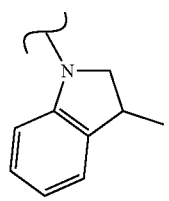 | 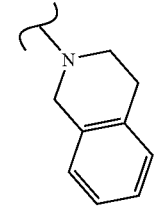 |
| | 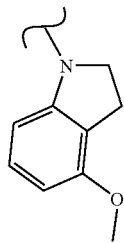 |

| 73 | 74 |
|---|---|
| -continued | -continued |
| R<sup>Q</sup> | R<sup>Q</sup> |
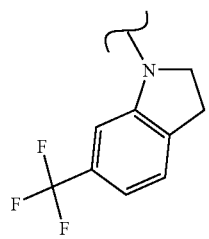
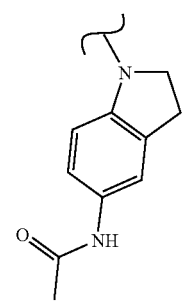
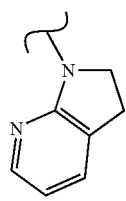
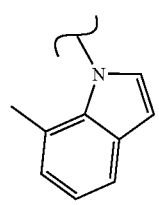
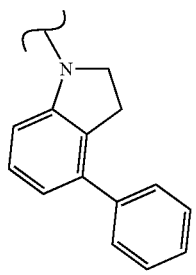
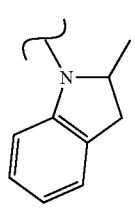
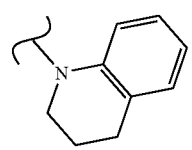
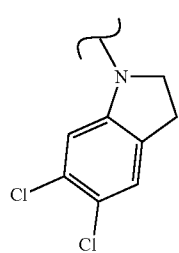
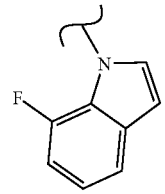
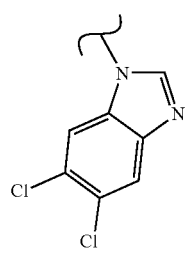
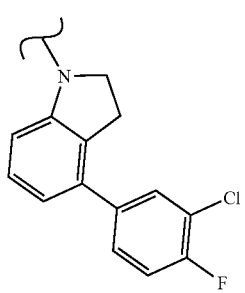

| $R^Q$ |
|---|
| 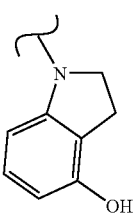 |

In one embodiment, the present invention provides compounds of formula VIA-ii:

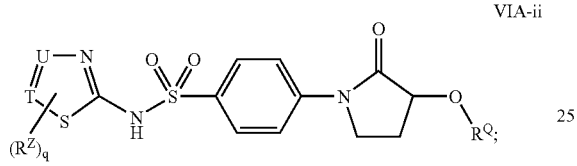

VIA-ii

U, T, $R^Z$, and q are as defined above; and wherein $R^Q$ is phenyl optionally substituted with up to 4 substituents independently selected from $R^1$, $R^2$, or $R^3$.

In one embodiment of formula VIA-ii, q is zero.

In one embodiment, T is CH. In another embodiment, T is N.

In one embodiment, U is N and T is CH.

In another embodiment, T is N and U is CH.

In another embodiment, U and T, both are CH.

Exemplary $R^Q$ in compounds of the present invention include:

| $R^Q$ |
|---|
| 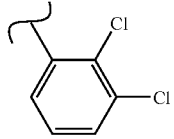 |
| 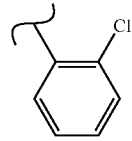 |
| 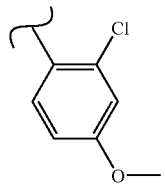 |

| $R^Q$ |
|---|
| 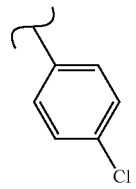 |
| 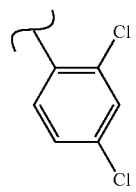 |
| 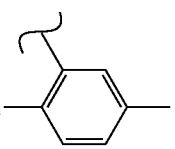 |
| 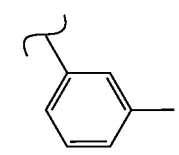 |
| 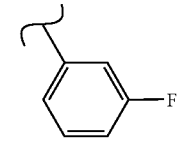 |
| 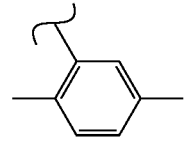 |
| 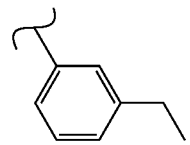 |
| 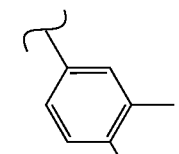 |
| 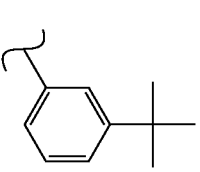 |

-continued
R^Q
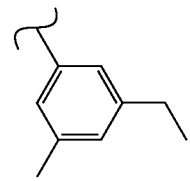
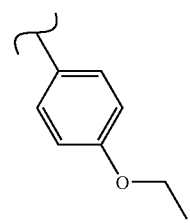
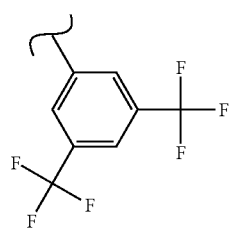
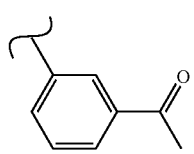
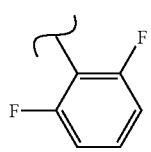
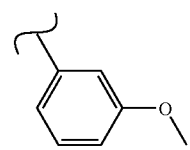
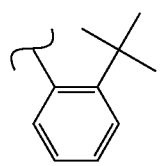
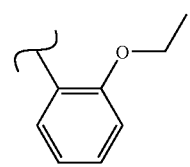
-continued
R^Q
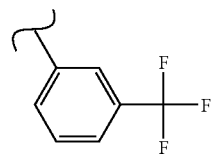
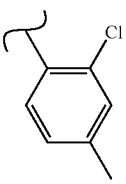
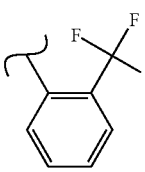
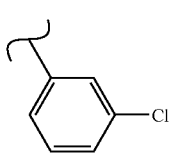
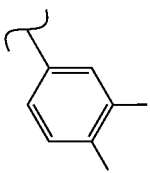
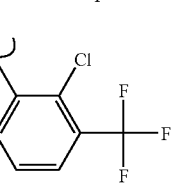

| $R^Q$ | $R^Q$ |
|---|---|
| 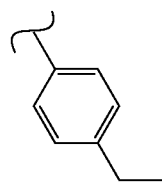 | 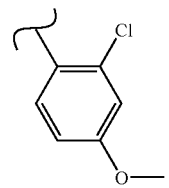 |
| 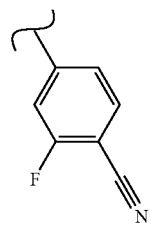 | 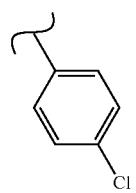 |
| 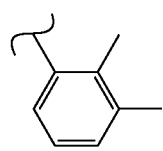 | 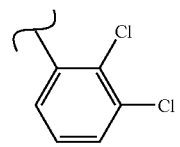 |
| 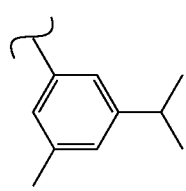 | 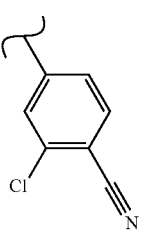 |
| 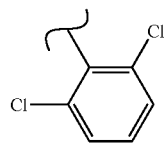 | 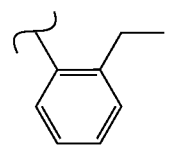 |
| 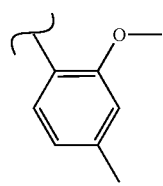 | 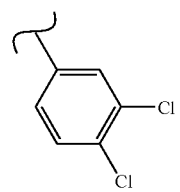 |
| 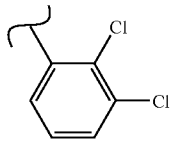 | 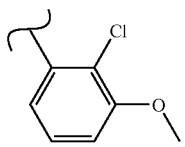 |
| 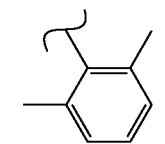 | 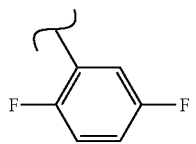 |

-continued
| $R^Q$ |
|---|
| 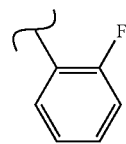 |
| 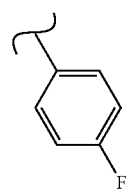 |
| 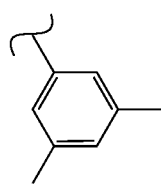 |
| 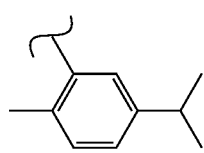 |
| 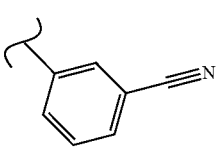 |
| 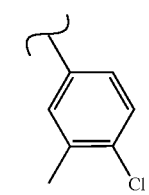 |
| 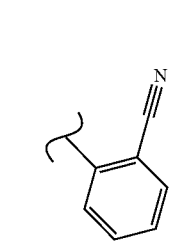 |
| 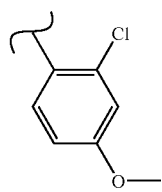 |
-continued
| $R^Q$ |
|---|
| 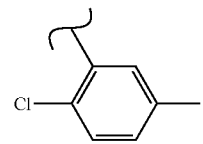 |
| 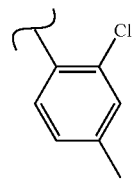 |
| 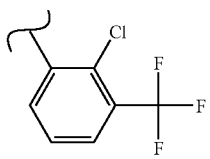 |
| 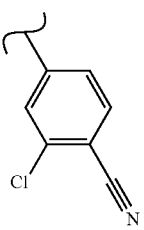 |
| 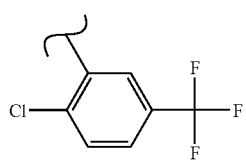 |
| 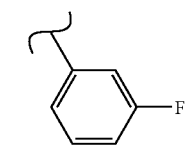 |
| 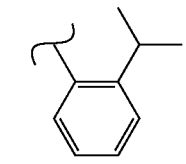 |
| 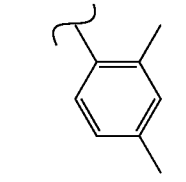 |

-continued
R^Q
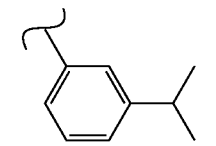
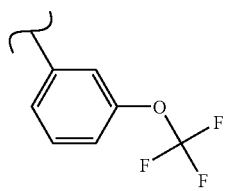
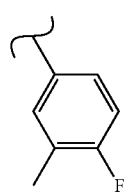
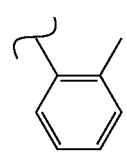
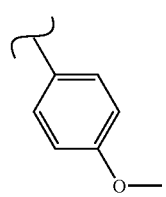
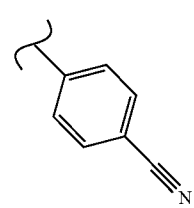
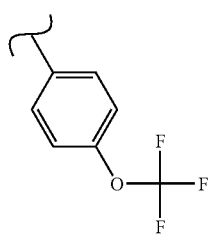
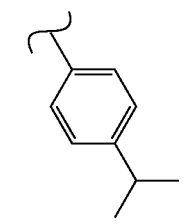
-continued
R^Q
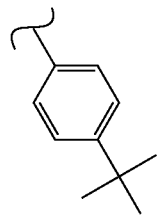
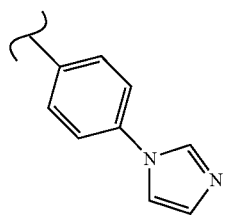
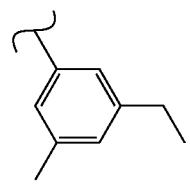
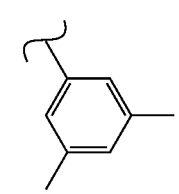
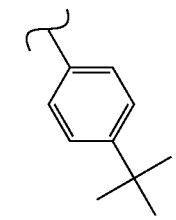
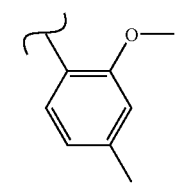
In one embodiment, the present invention provides compounds of formula VIA-iii:
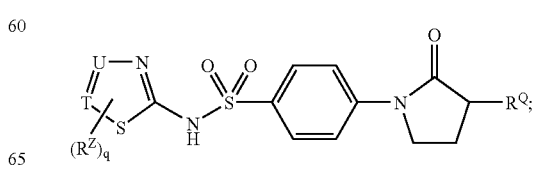
VIA-iii wherein U, T, $R^Z$, and q are as defined above; and $R^Q$ is

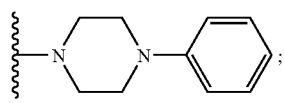

wherein $R^Q$ is optionally substituted with up to 4 substituents independently selected from $R^1$, $R^2$, or $R^3$.

In one embodiment of formula VIA-iii q is zero.

In one embodiment, T is CH. In another embodiment, T is N.

In one embodiment, U is N and T is CH.

In another embodiment, T is N and U is CH.

In another embodiment, U and T, both are CH.

Exemplary $R^Q$ in compounds of the present invention include embodiments wherein said optionally substituted phenyl ring attached to said piperazine is selected from:

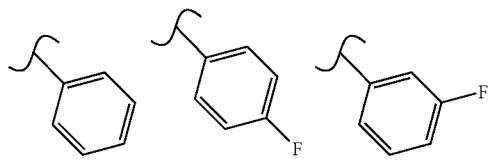

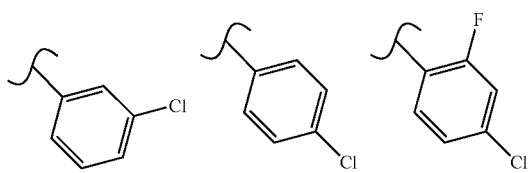

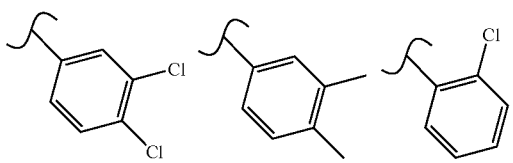

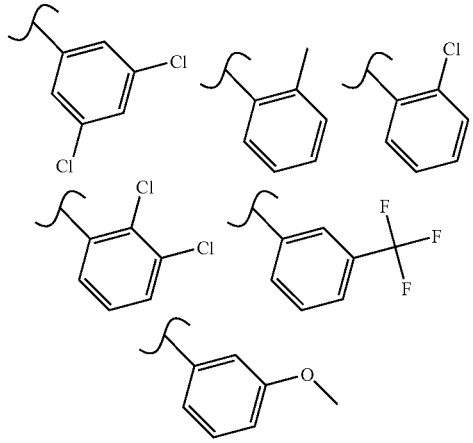

In one embodiment, the present invention provides compounds of formula VIIA or formula VIIB:

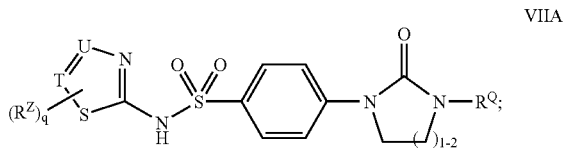

VIIA

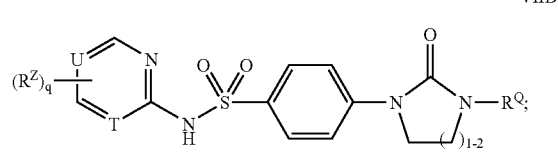

VIIB wherein U, T, $R^Z$, and $R^Q$, q are as defined above.

In one embodiment of formula VIIA or formula VIIB, q is zero.

In one embodiment, T is CH. In another embodiment, T is N.

In one embodiment, U is N and T is CH.

In another embodiment, T is N and U is CH.

In another embodiment, U and T, both are CH.

In one embodiment, the present invention provides compounds of formula VIIA-i or formula VIIB-i:

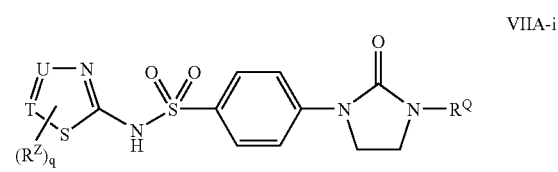

VIIA-i

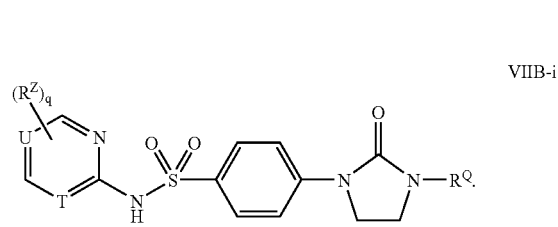

VIIB-i

In one embodiment, the present invention provides compounds of formula VIIA-ii or formula VIIB-ii:

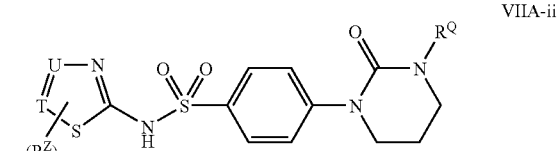

VIIA-ii

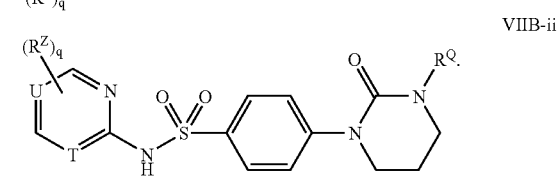

VIIB-ii

In one embodiment, the present invention provides compounds of formula VIIA-iii or formula VIIB-iii:

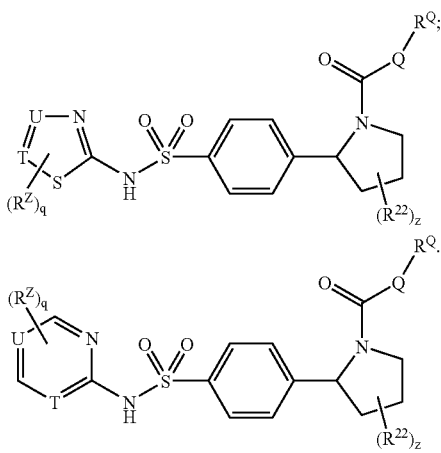

In one embodiment of formula VIIA-i or formula VIIA-ii, U is CH and T is N. Or, U and T both are CH.

In an alternative embodiment, the present invention provides compounds of formula I':

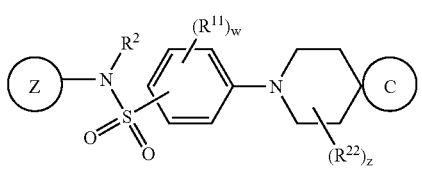

or a pharmaceutically acceptable salt thereof;
wherein:
ring Z is a 5-7 membered unsaturated or aromatic ring having 1-4 ring heteroatoms selected from O, S, or N, wherein Z is optionally substituted with up to q occurrences of $R^Z$ substitutents, wherein each $R^Z$ is independently selected from $R^1$, $R^2$, $R^3$, $R^4$, or $R^5$; and q is 0-4;
ring C is a 5-7 membered carbocyclic or heterocyclic ring having 0-2 ring atoms selected from O, S, or N, wherein ring C is fused to a phenyl ring; and
wherein said ring C together with said fused phenyl ring is optionally substituted with up to 5 substituents independently selected from $R^1$, $R^2$, $R^3$, $R^4$, or $R^5$;
$R^{11}$ is $R^2$ or Y;
$R^{22}$ is $R^1$, $R^2$, or $R^4$;
$R^1$ is oxo, $=NN(R^6)_2$, $=NN(R^7)_2$, $=NN(R^6R^7)$, $=N-OR^6$, $=N-OR^7$, $R^6$ or $(CH_2)_n-Y$;
n is 0, 1 or 2;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;
or
two $R^1$ on adjacent ring atoms, taken together, form 1,2-methylenedioxy or 1,2-ethylenedioxy;
$R^2$ is hydrogen or C1-C6 aliphatic, wherein each $R^2$ is optionally substituted with up to 2 substituents independently selected from $R^1$, $R^4$, or $R^5$;
$R^3$ is a C3-C8 cycloaliphatic, C6-C10 aryl, C3-C8 heterocyclic, or C5-C10 heteroaryl ring, wherein each $R^3$ is optionally substituted with up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6C(S)N(R^6)_2$, $NR^6C(S)NR^5R^6$, $NR^6C(S)N(R^5)_2$, $NR^5C(S)N(R^6)_2$, $NR^5C(S)NR^5R^6$, $NR^5C(S)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^6)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$;
$R^5$ is a C3-C8 cycloaliphatic, C6-C10 aryl, C3-C8 heterocyclic, or C5-C10 heteroaryl ring, wherein each $R^3$ is optionally substituted with up to 3 $R^1$ substituents;
$R^6$ is H or C1-C6 aliphatic, wherein $R^6$ is optionally substituted with a $R^7$ substituent;
$R^7$ is a C3-C8 cycloaliphatic, C6-C10 aryl, C3-C8 heterocyclic, or C5-C10 heteroaryl ring, and each $R^7$ is optionally substituted with up to 2 substituents independently selected from C1-C6 aliphatic or $(CH_2)_m-Z'$ wherein m is 0-2;
Z' is selected from halo, CN, $NO_2$, $C(halo)_3$, $CH(halo)_2$, $CH_2(halo)$, $-OC(halo)_3$, $-OCH(halo)_2$, $-OCH_2(halo)$, OH, S—(C1-C6) aliphatic, S(O)—(C1-C6) aliphatic, $SO_2$—(C1-C6)aliphatic, $NH_2$, NH—(C1-C6) aliphatic, $N((C1-C6)aliphatic)_2$, $N((C1-C6)aliphatic)R^8$, COOH, C(O)O—(C1-C6)aliphatic, or O—(C1-C6)aliphatic; and
$R^8$ is $CH_3(C(O)-$, C6-C10 aryl sulfonyl-, or C1-C6 alkyl sulfonyl-.

In one embodiment, ring C is an optionally substituted ring selected from:

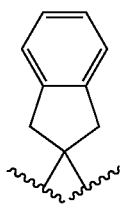

C-i

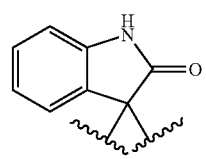

C-ii

-continued
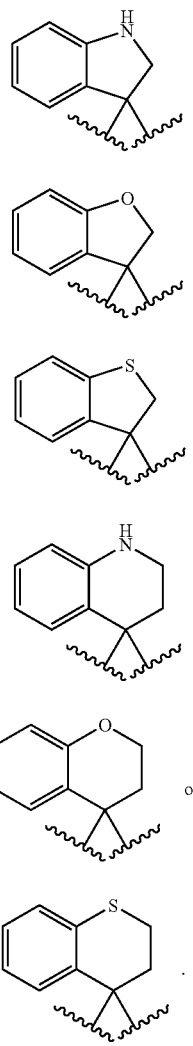
C-iii
C-iv
C-v
C-vi
C-vii
or
C-viii
Preferred embodiments of ring Z, $R^2$, $R^{11}$, $R^{22}$, w, and z in compounds of formula I' are as described above for compounds of formula I.
Exemplary compounds of the present invention are shown below in Table 2.
TABLE 2
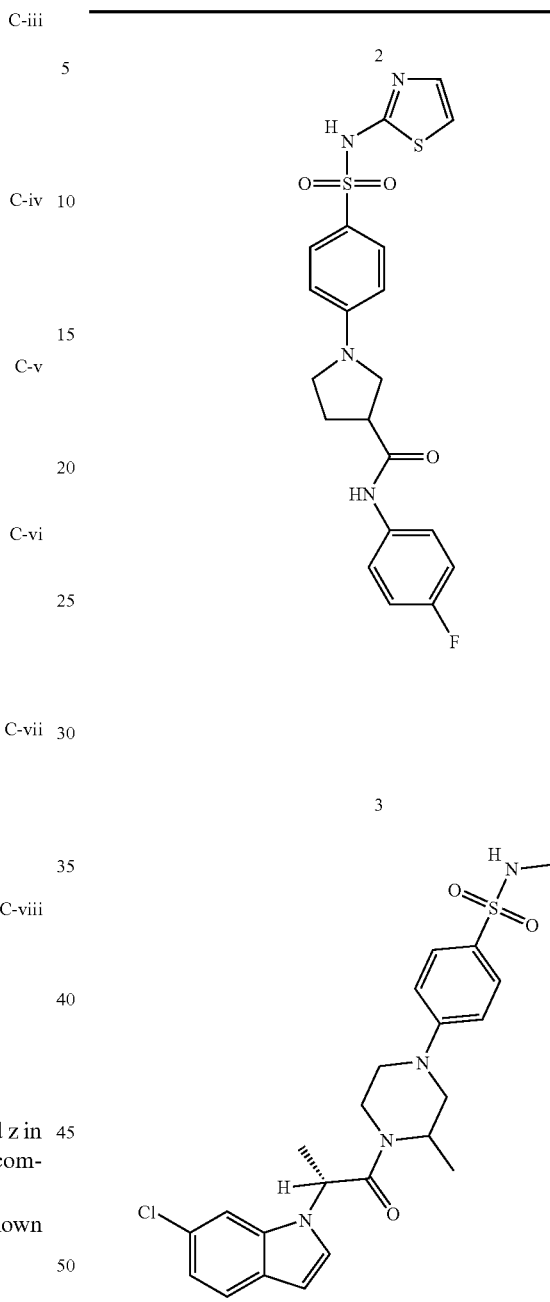
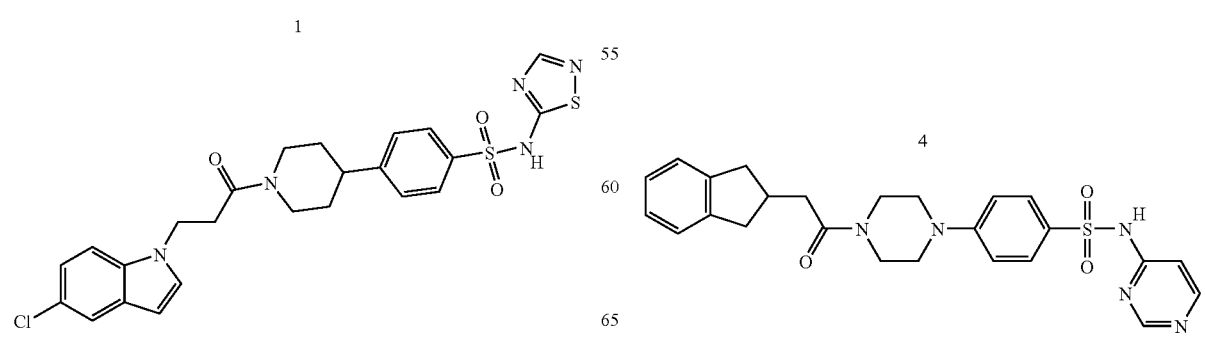

TABLE 2-continued
5
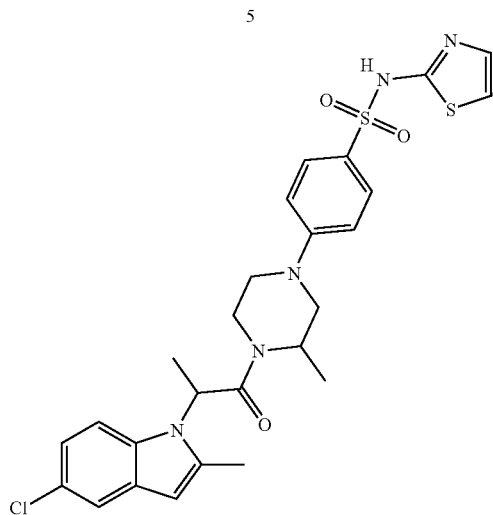
6
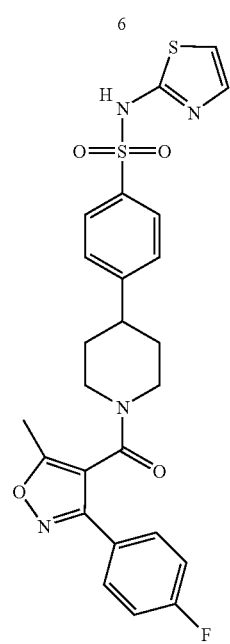
TABLE 2-continued
7
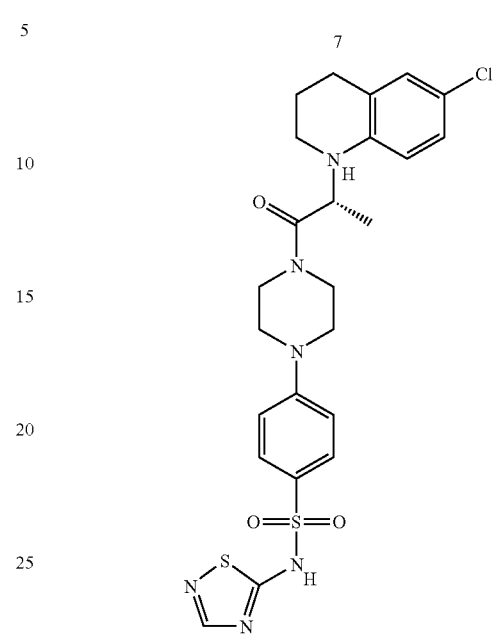
8
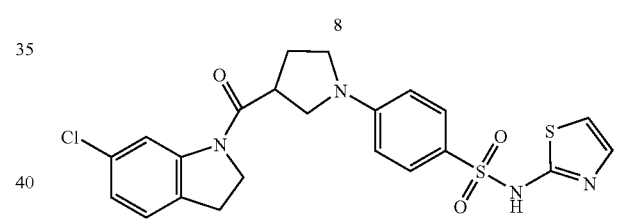
9
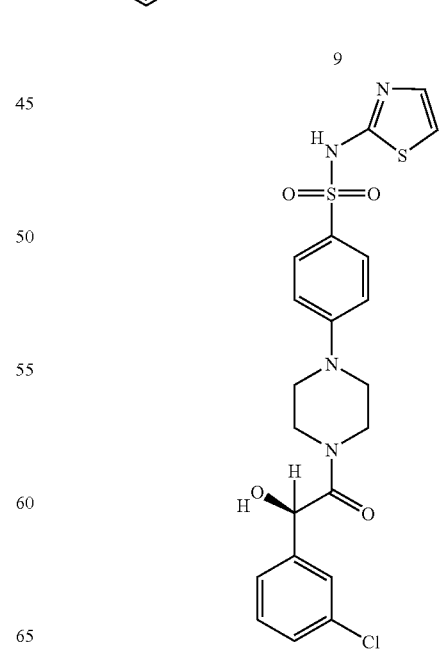

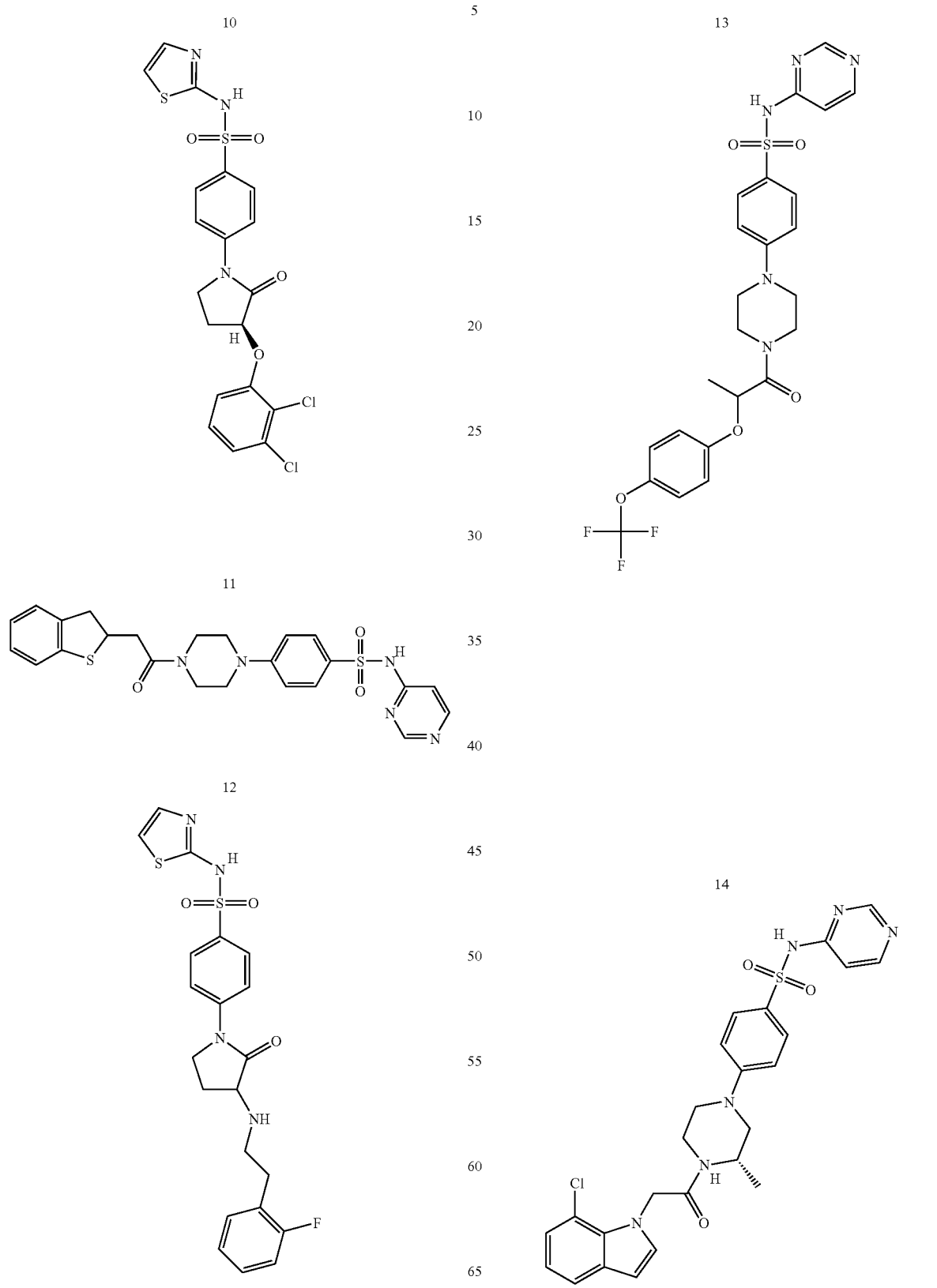

TABLE 2-continued
15
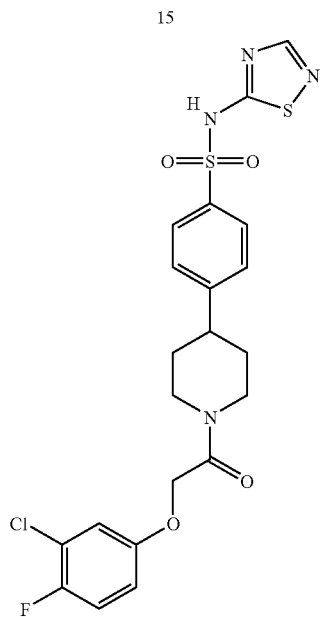
16
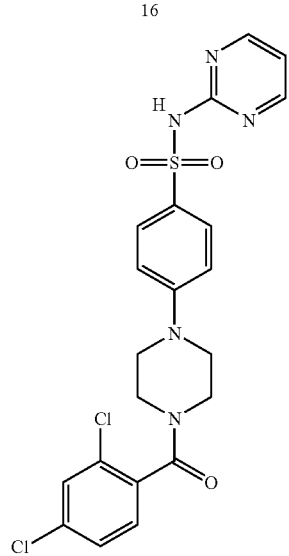
17
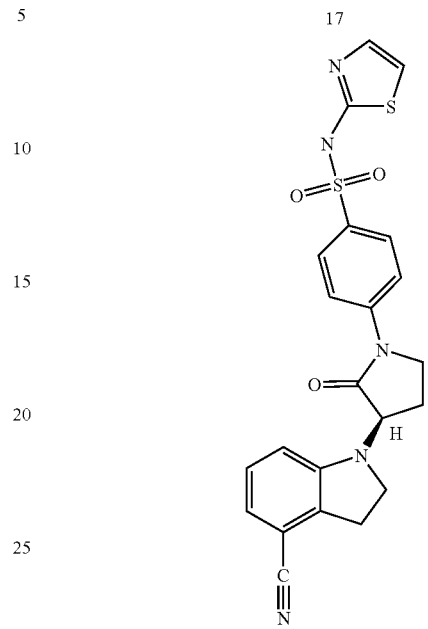
18
19
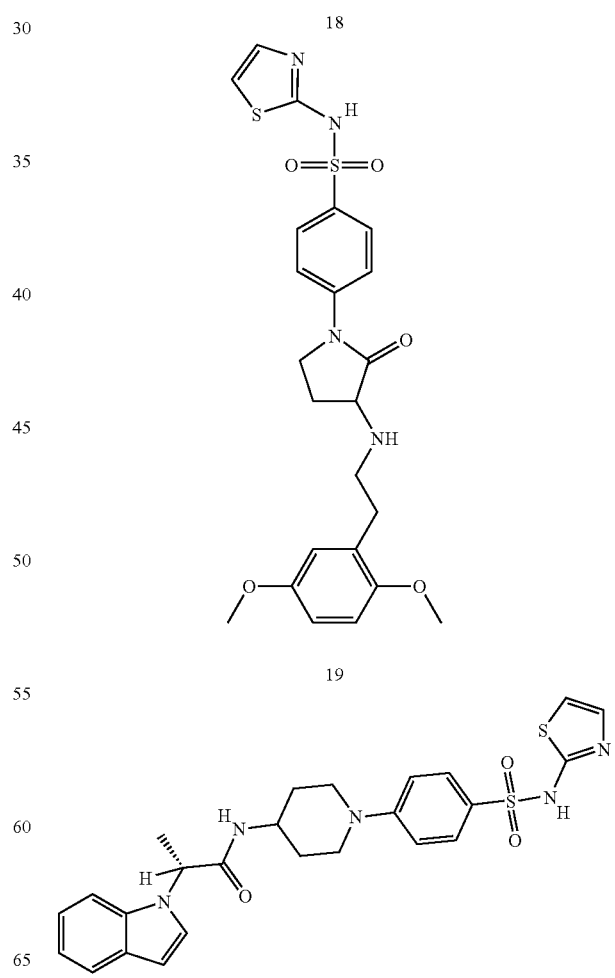

TABLE 2-continued
20
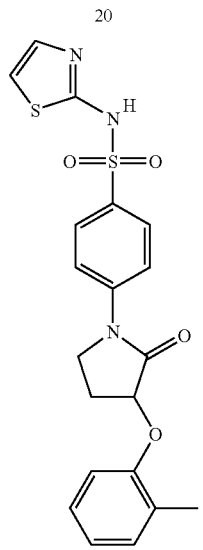
21
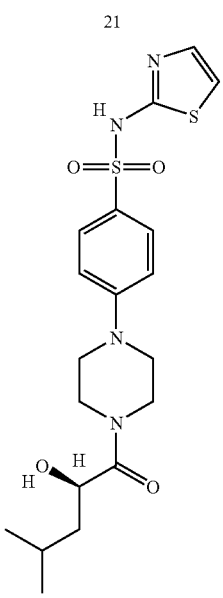
22
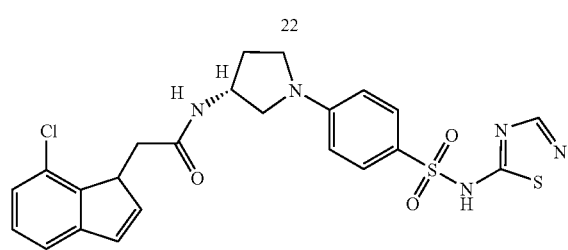
TABLE 2-continued
23
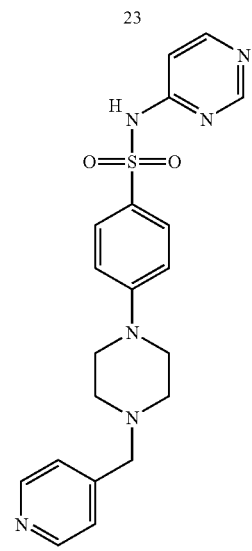
24
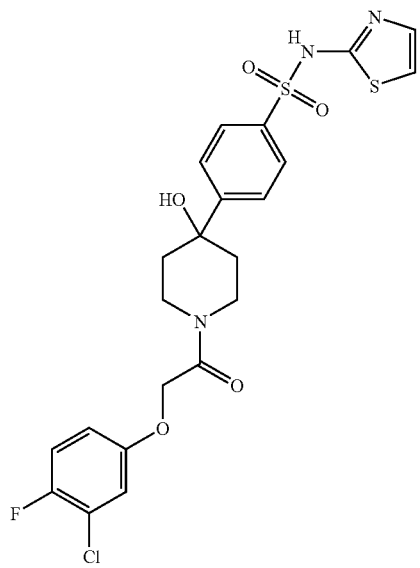

TABLE 2-continued
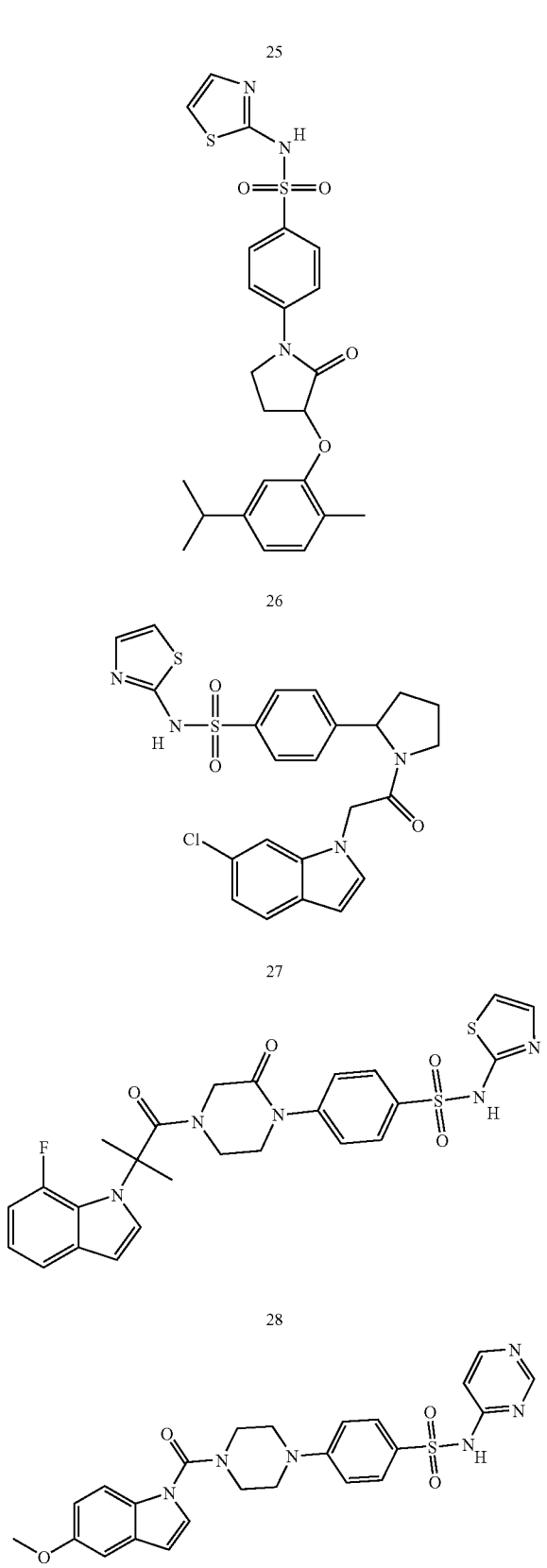
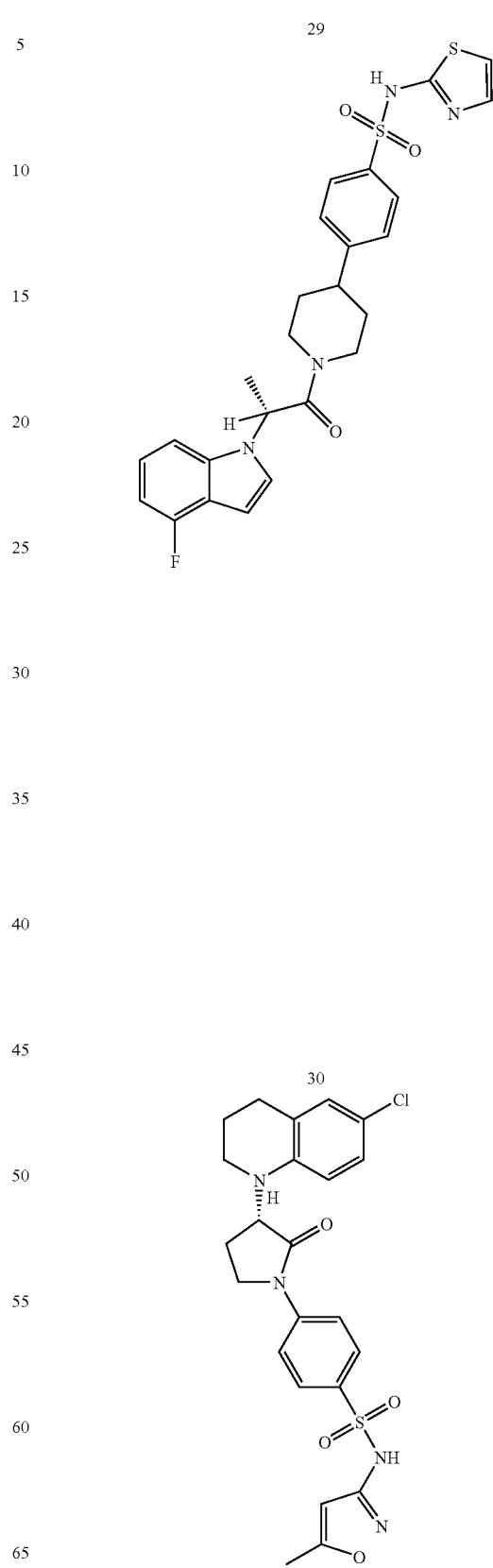

TABLE 2-continued
31
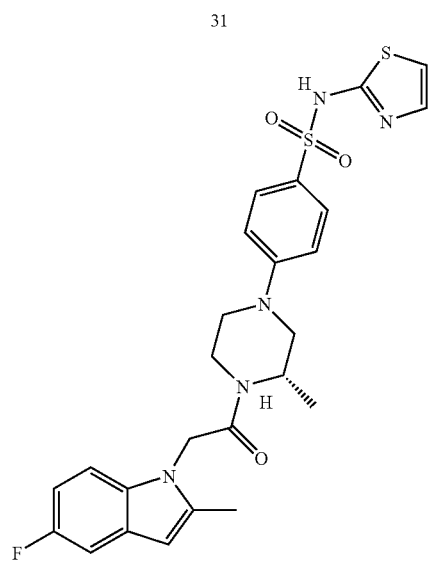
TABLE 2-continued
33
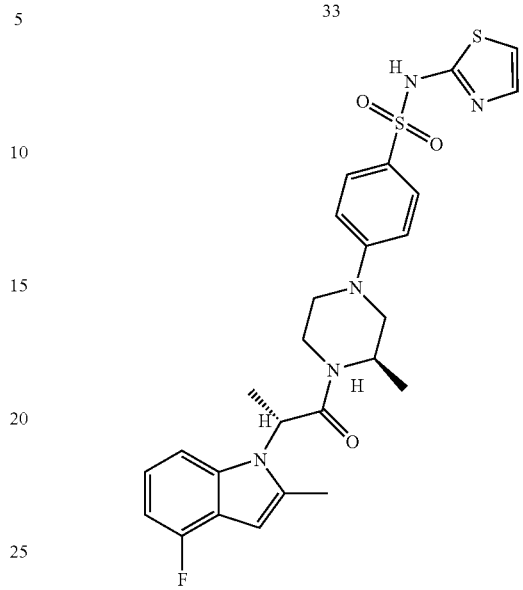
32
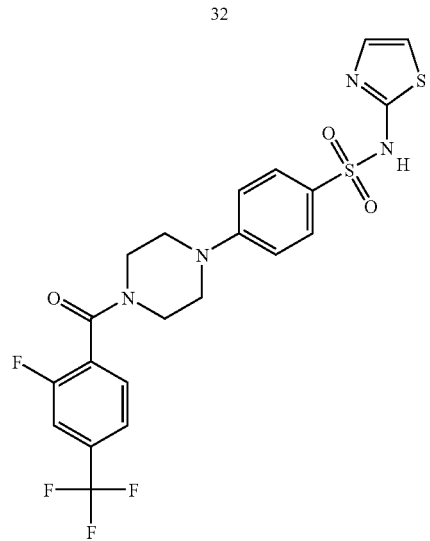
34
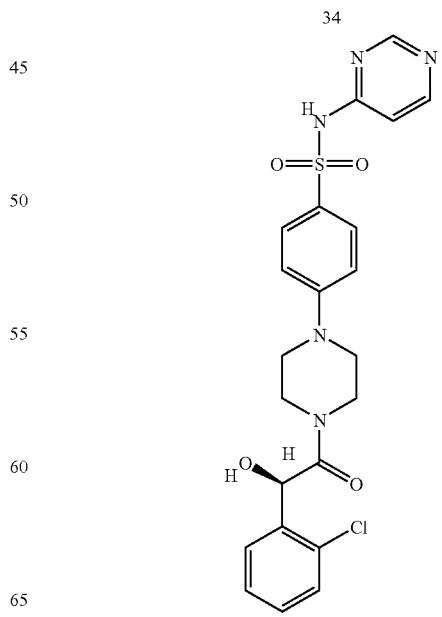

TABLE 2-continued
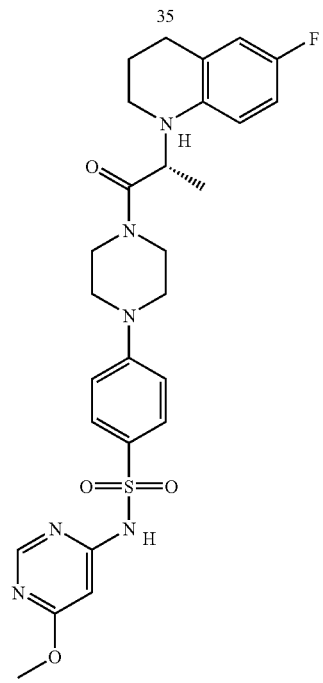
35
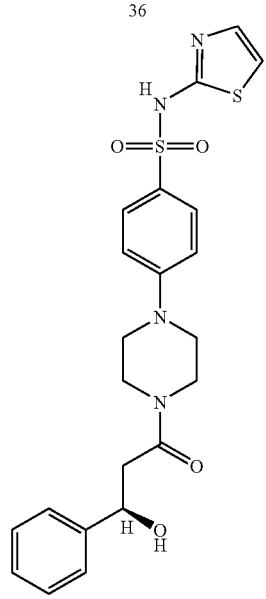
36
TABLE 2-continued
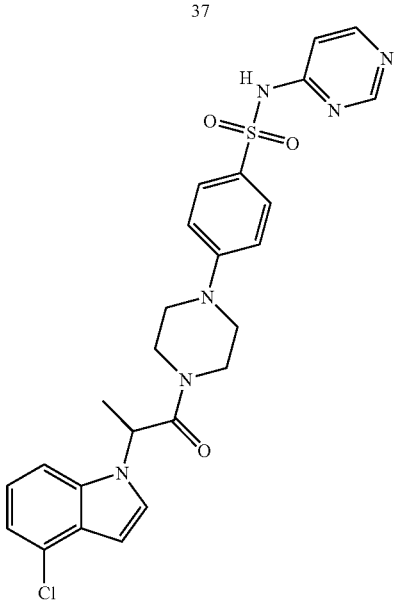
37
38

TABLE 2-continued
39
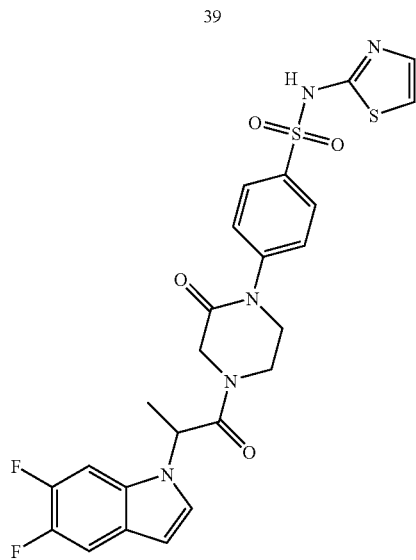
40
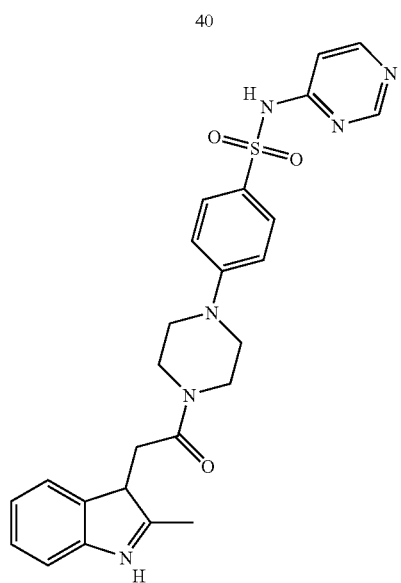
TABLE 2-continued
41
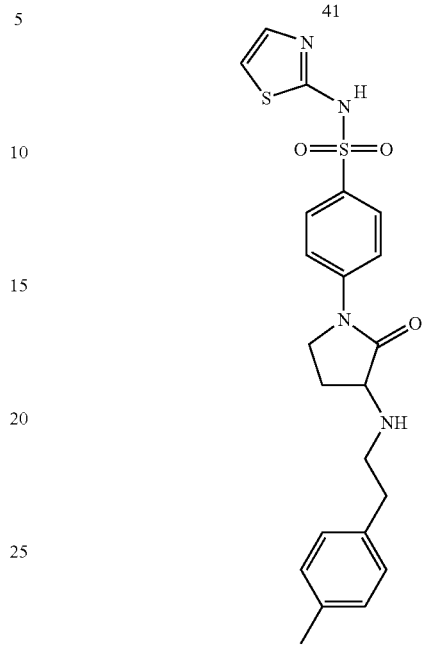
42
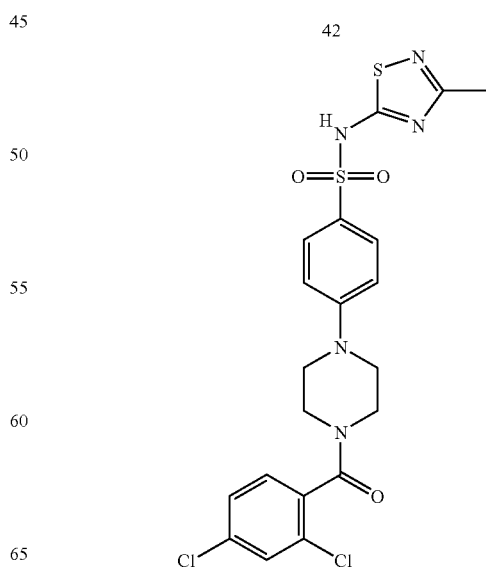

TABLE 2-continued
43
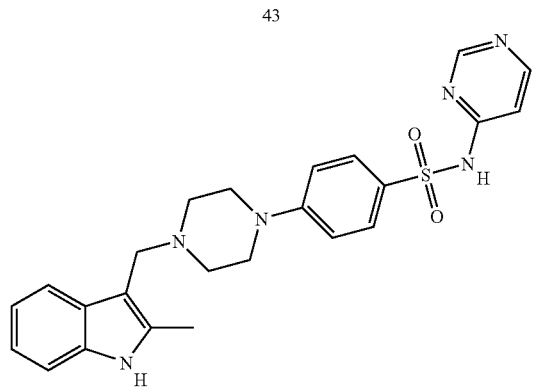
44
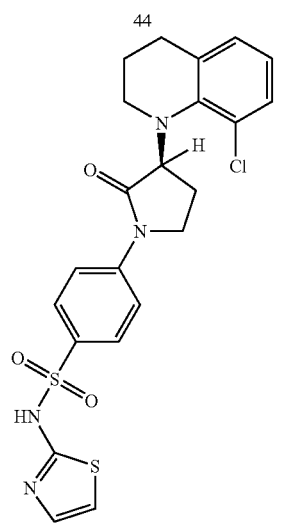
45
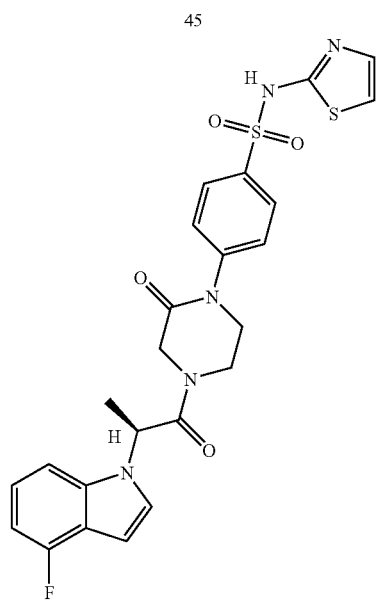
TABLE 2-continued
46
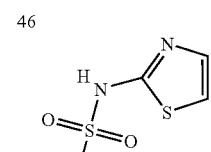
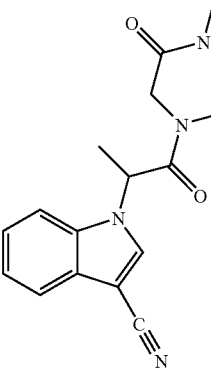
47
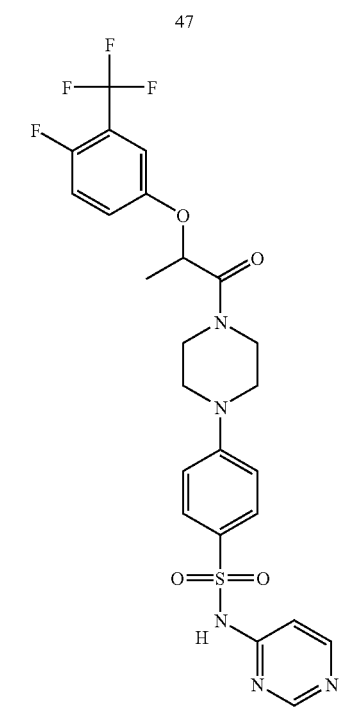

TABLE 2-continued
48
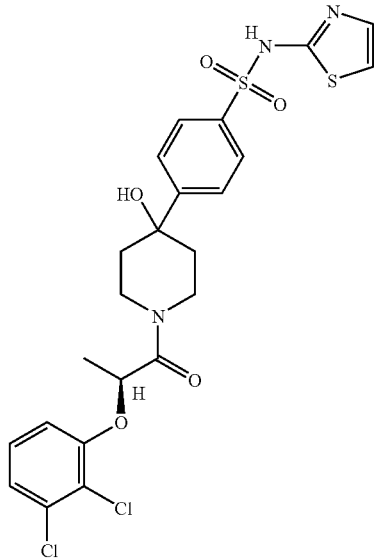
49
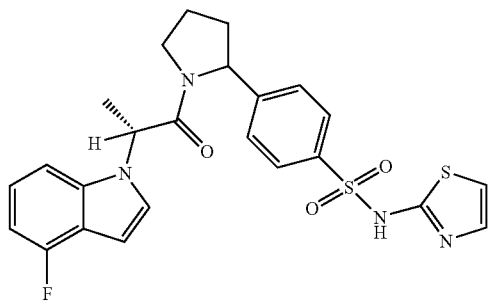
50
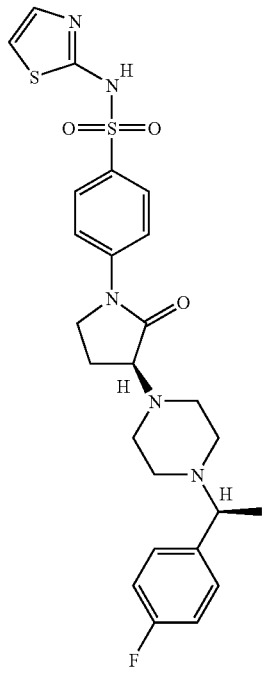
TABLE 2-continued
51
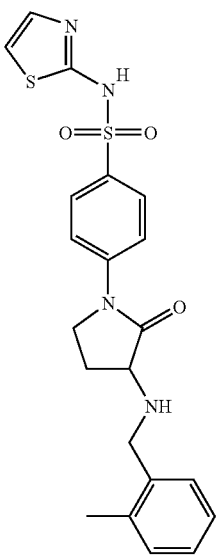
52
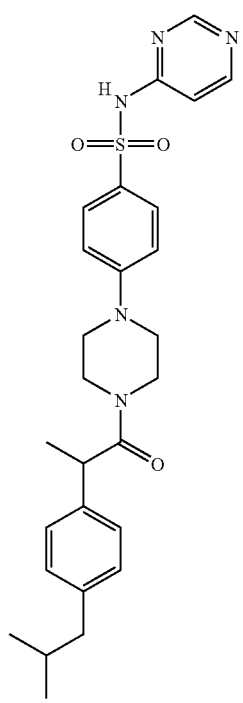

TABLE 2-continued
53
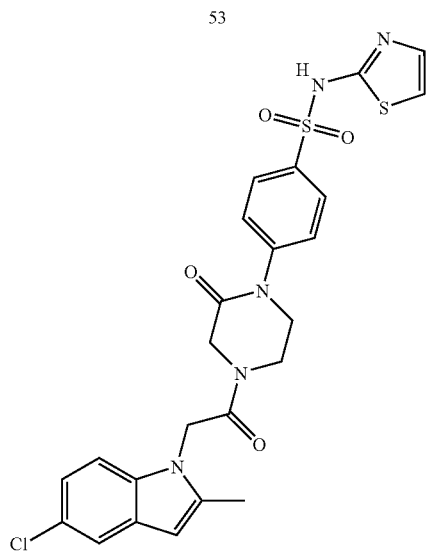
54
TABLE 2-continued
55
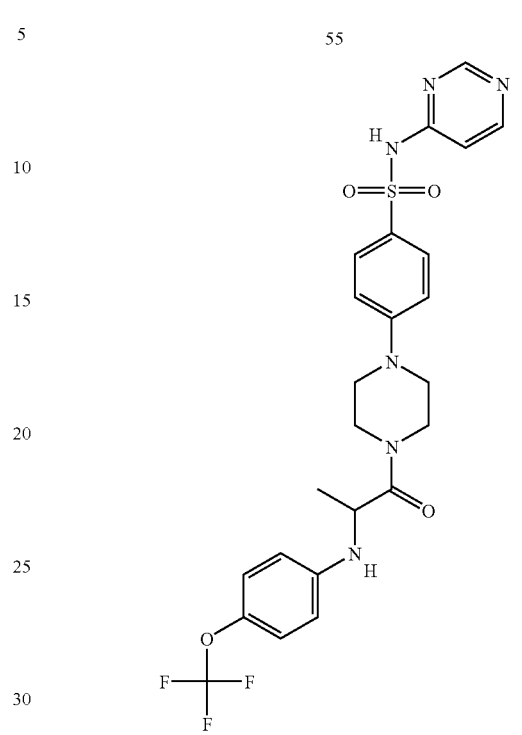
56
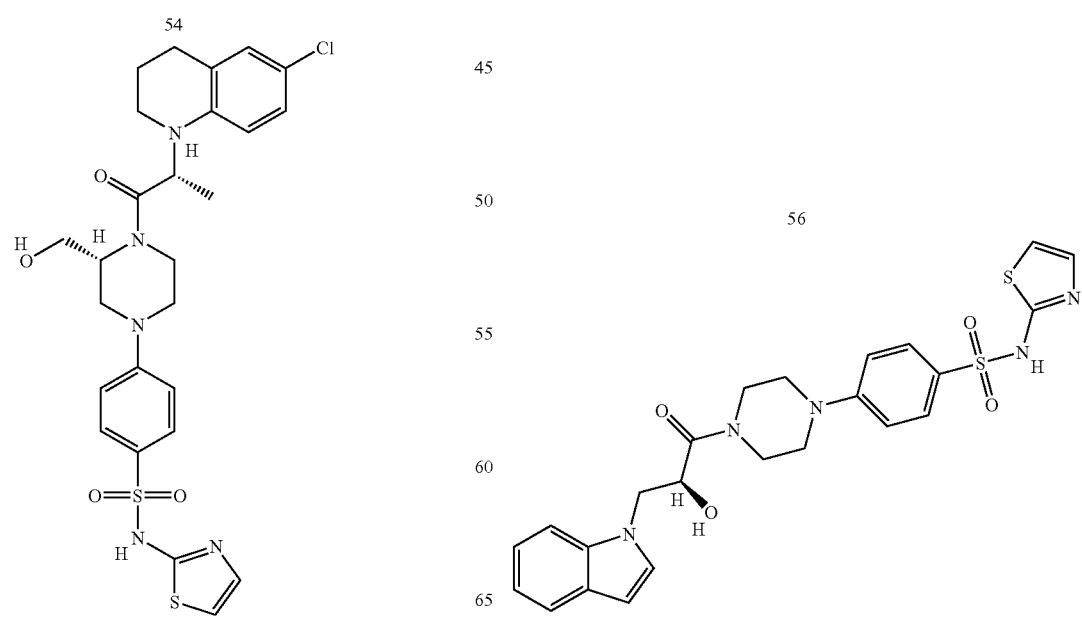

TABLE 2-continued
57
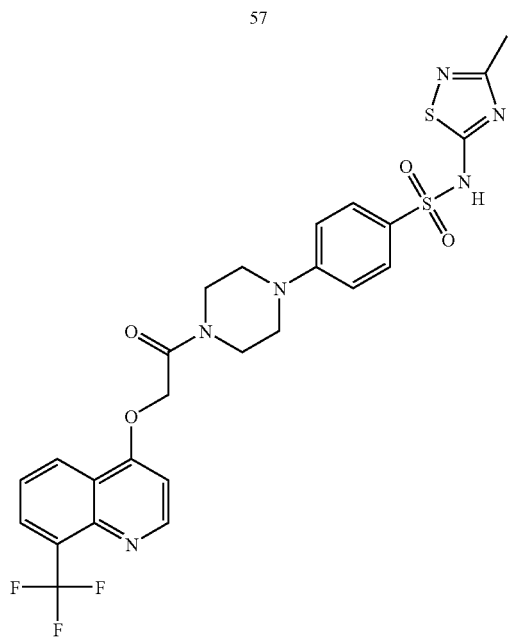
59
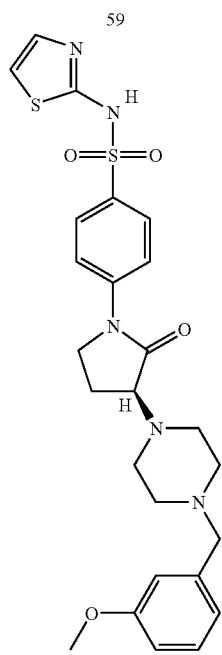
58
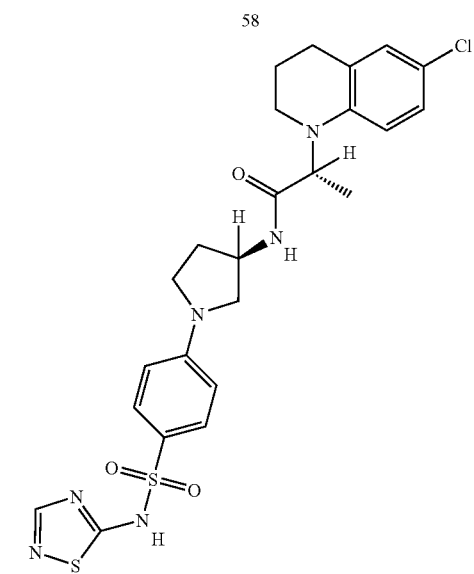
60
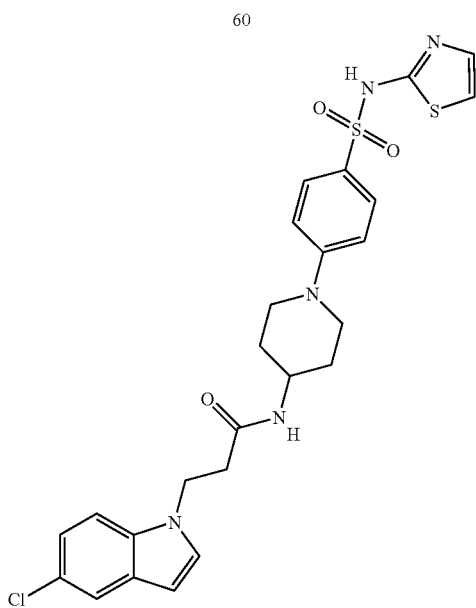

TABLE 2-continued
61
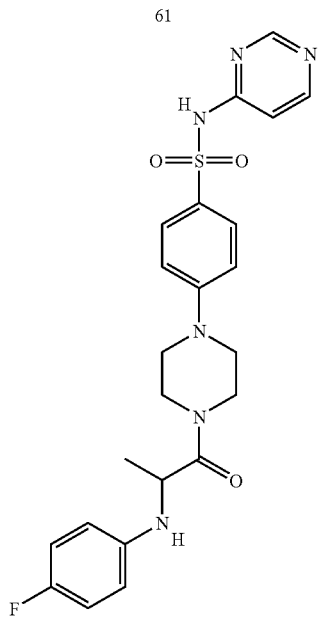
62
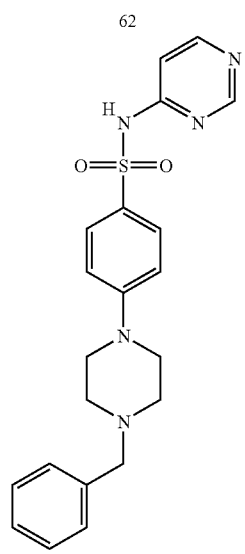
TABLE 2-continued
63
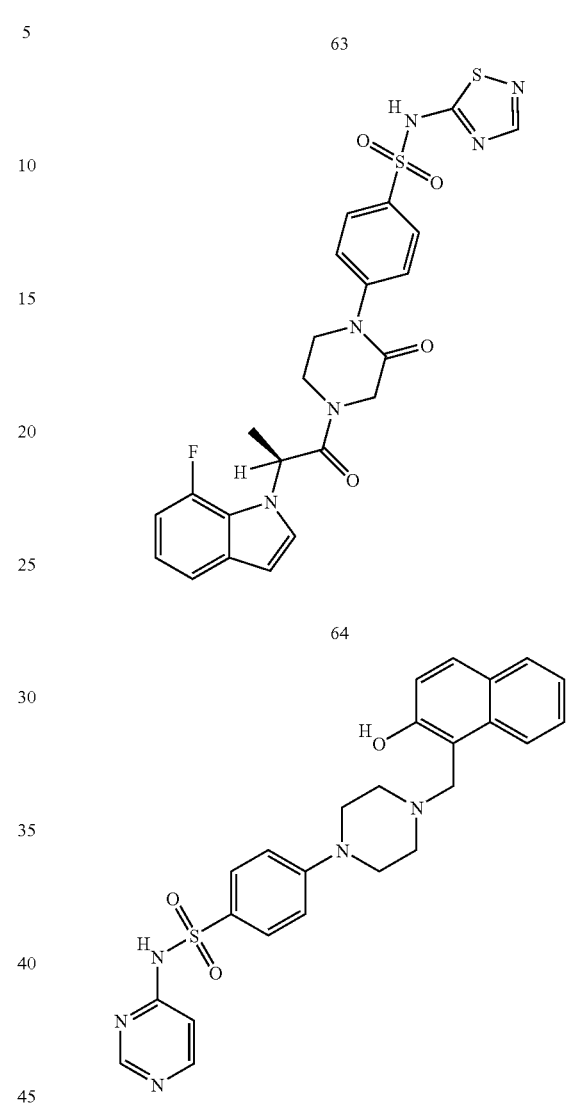
64
65
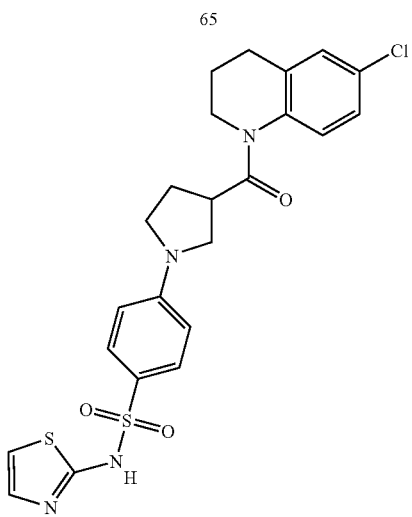

TABLE 2-continued
66
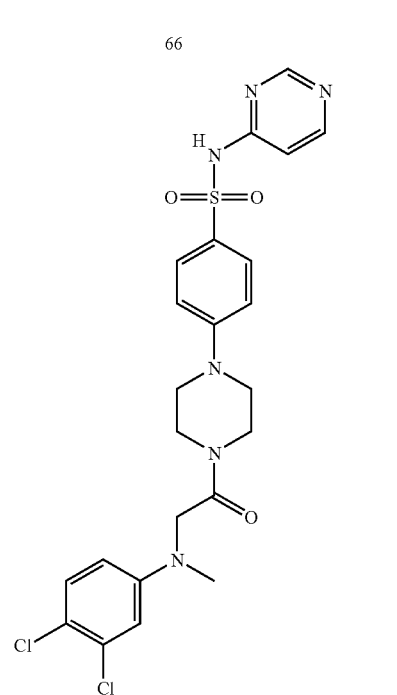
67
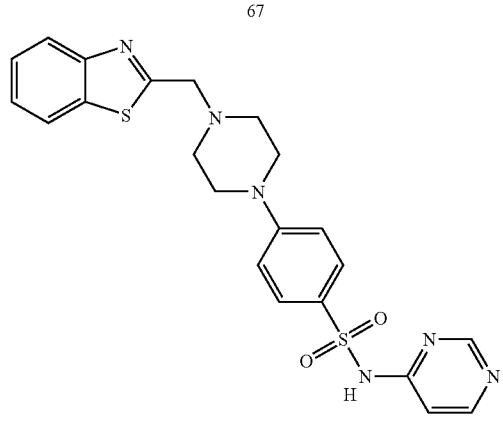
68
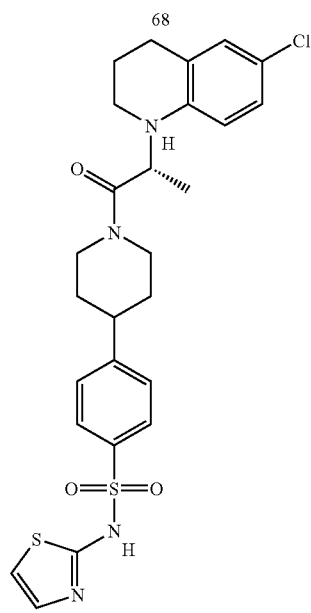
69
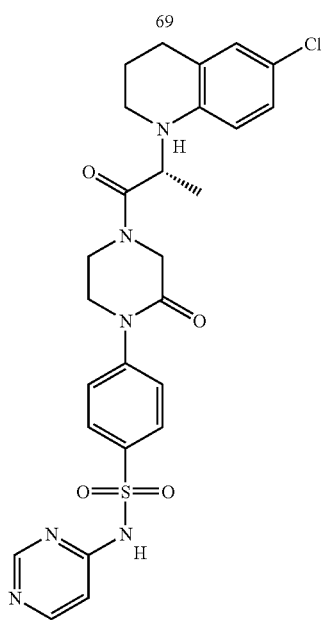

TABLE 2-continued
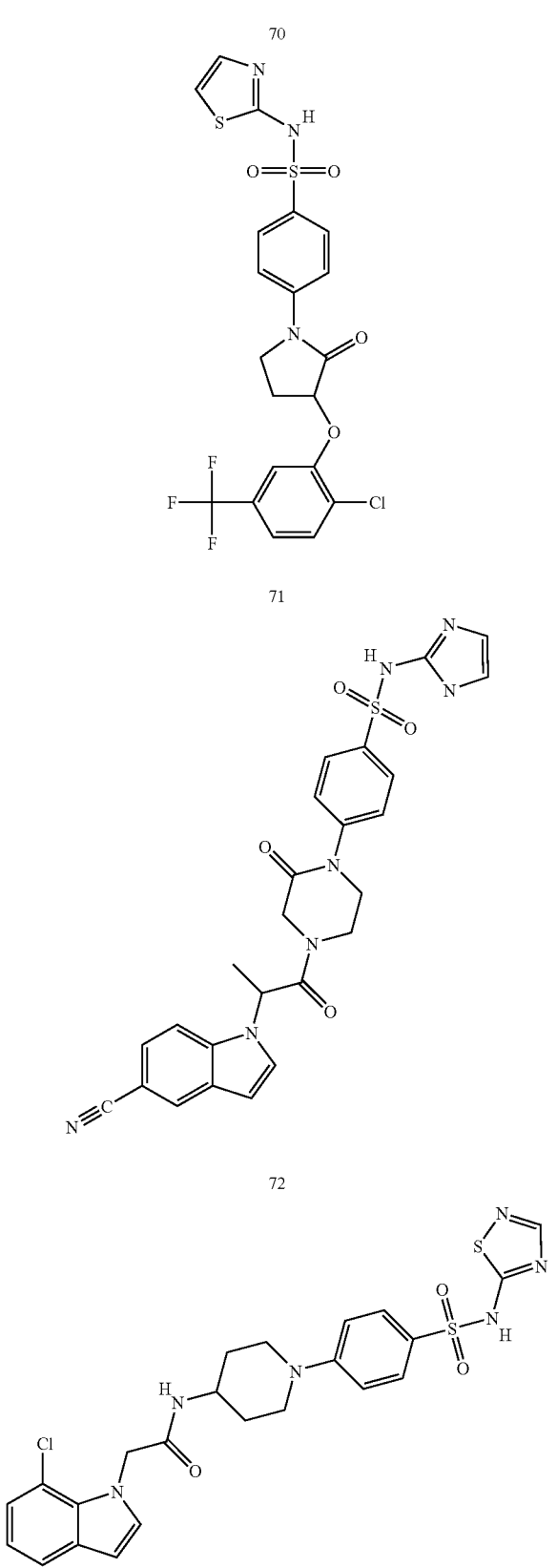
70
71
72
TABLE 2-continued
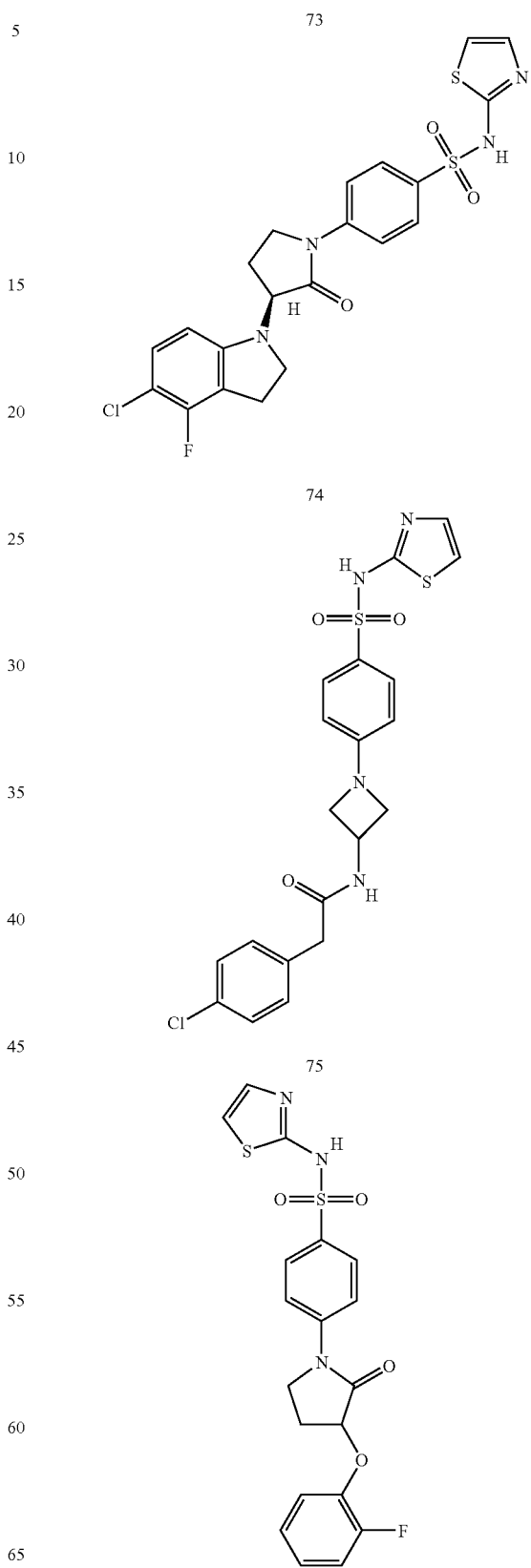
73
74
75

TABLE 2-continued
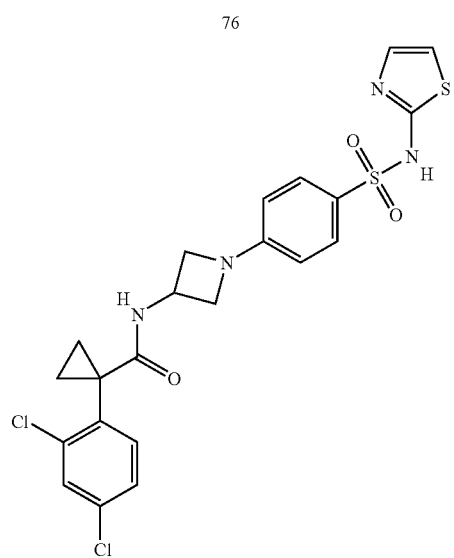
76
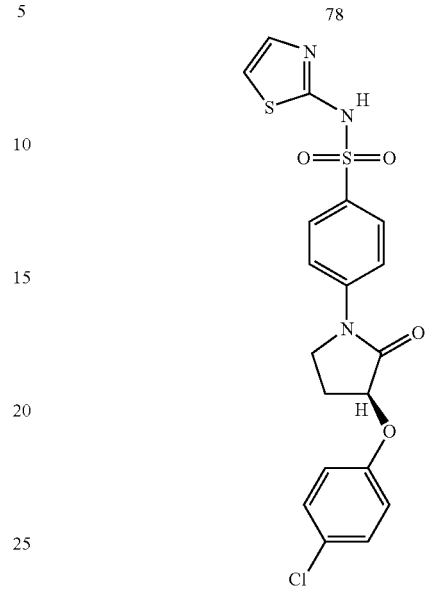
78
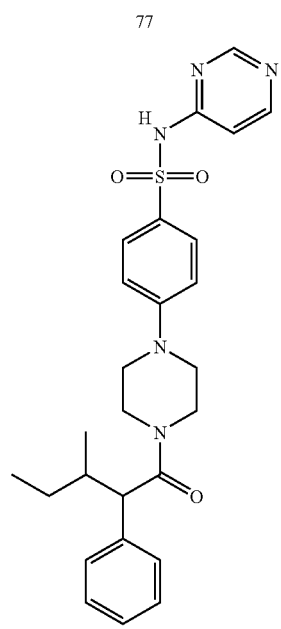
77
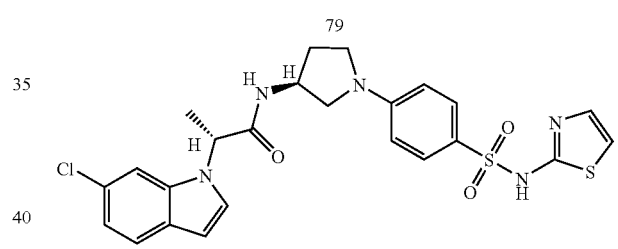
79
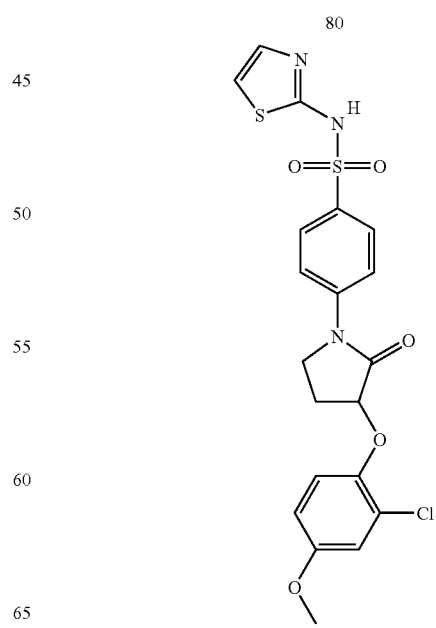
80

TABLE 2-continued
81
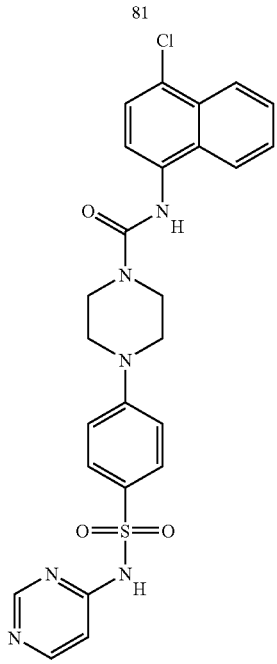
82
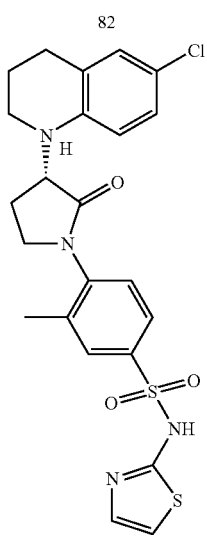
TABLE 2-continued
83
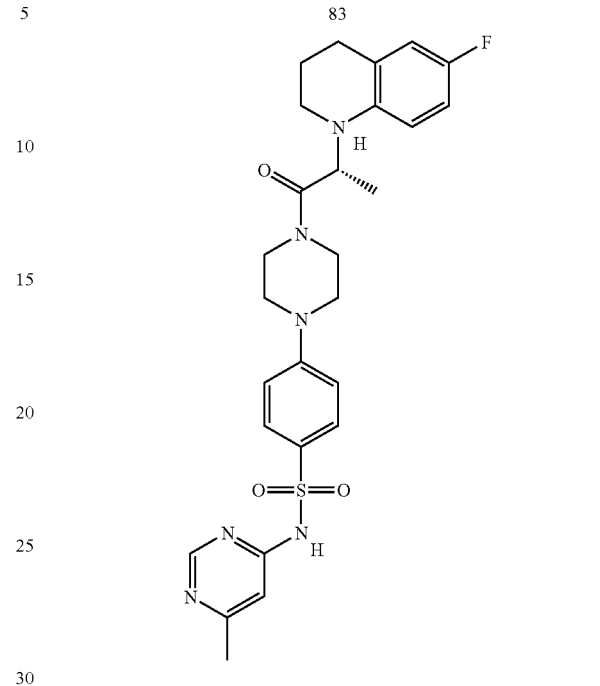
84
85
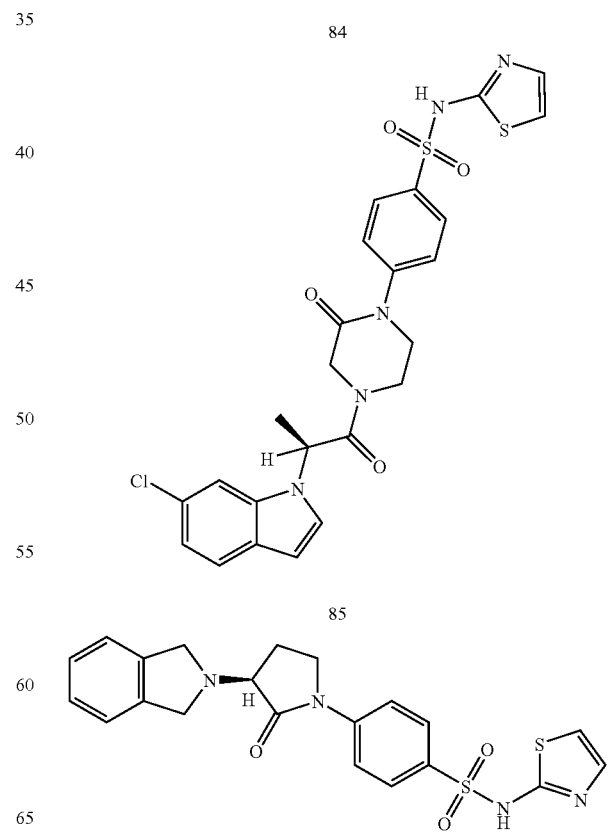

TABLE 2-continued
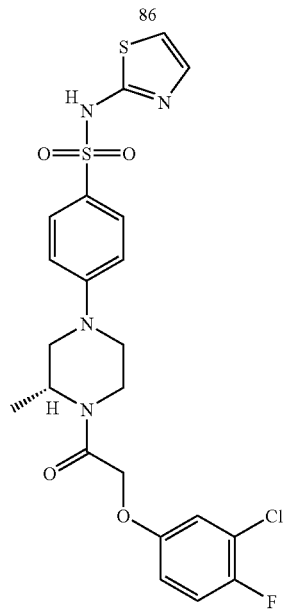
86
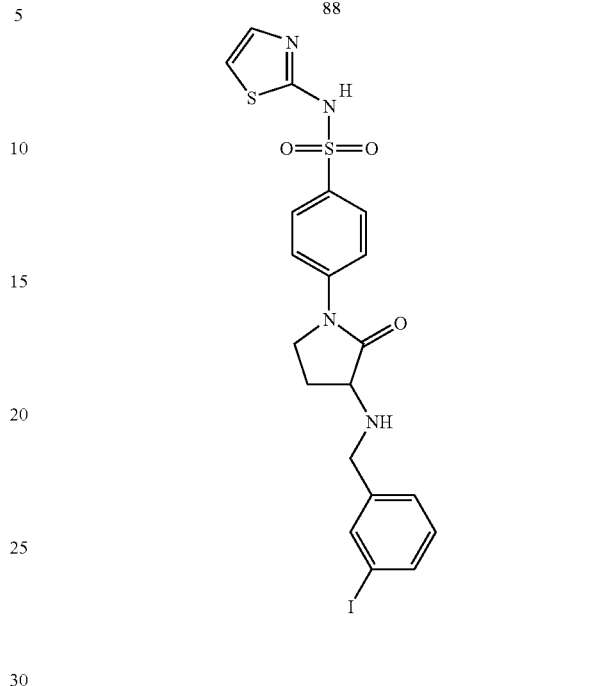
88
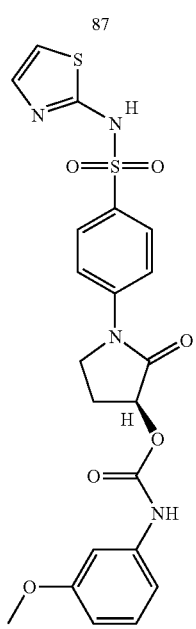
87
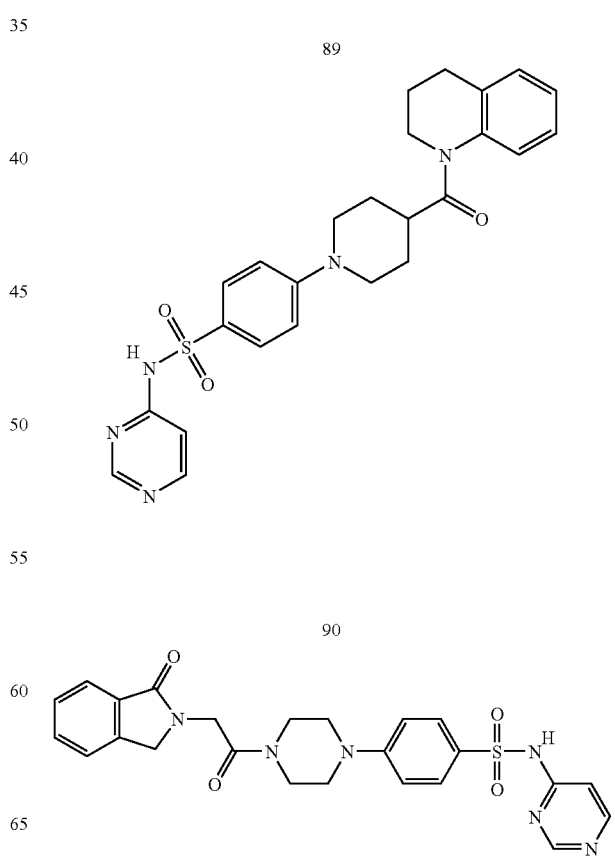
89
90

TABLE 2-continued
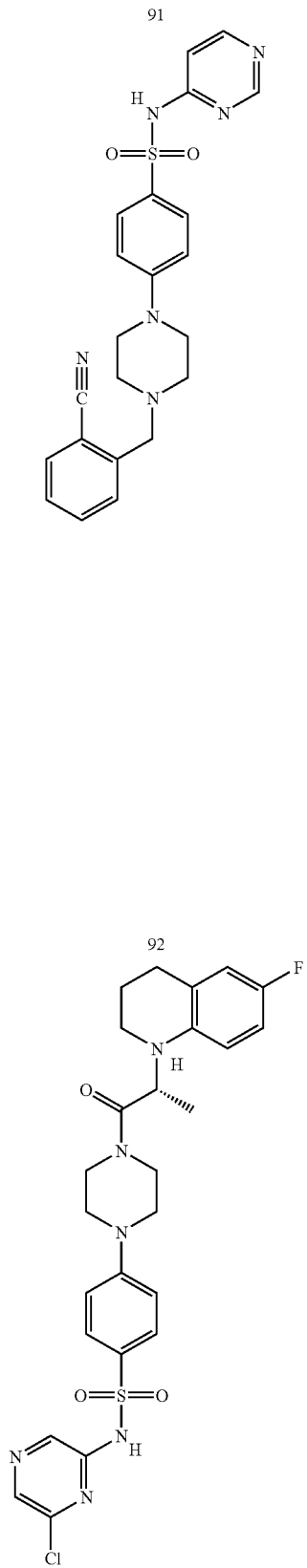
TABLE 2-continued
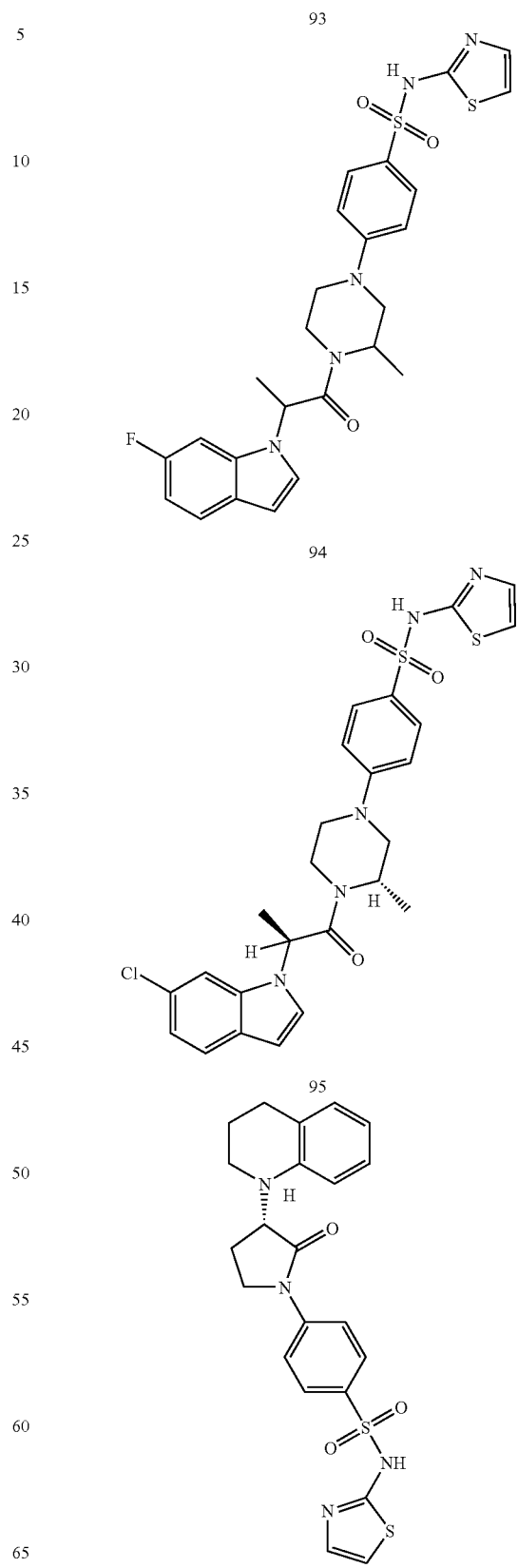

TABLE 2-continued
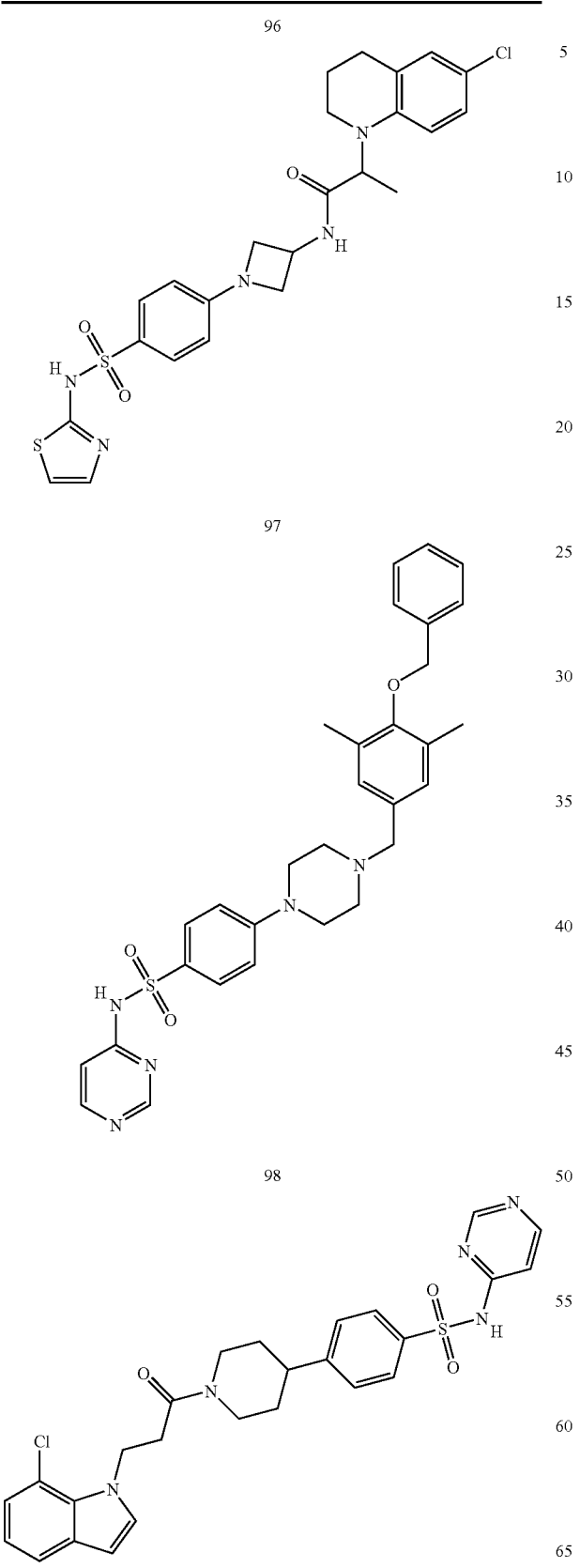

TABLE 2-continued
101
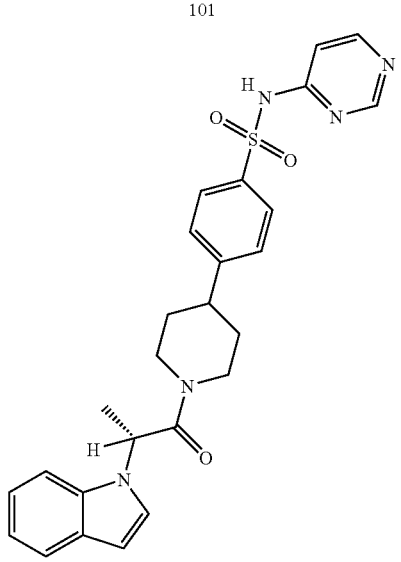
102
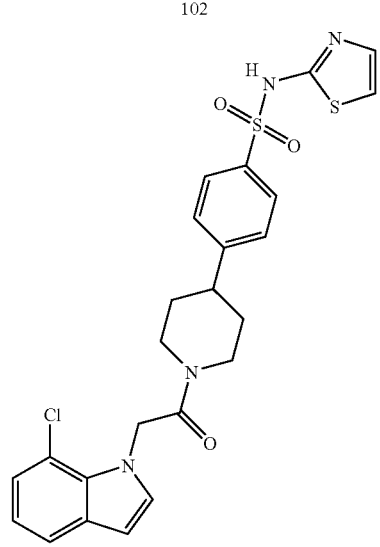
103
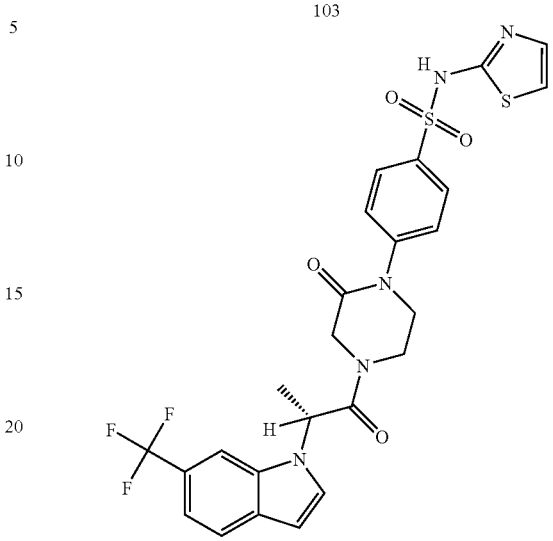
104
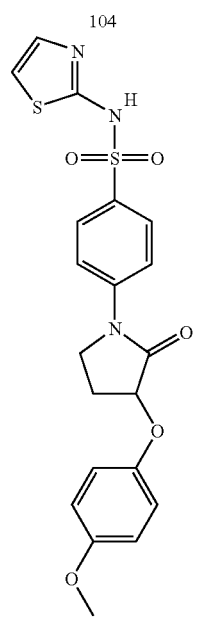

TABLE 2-continued
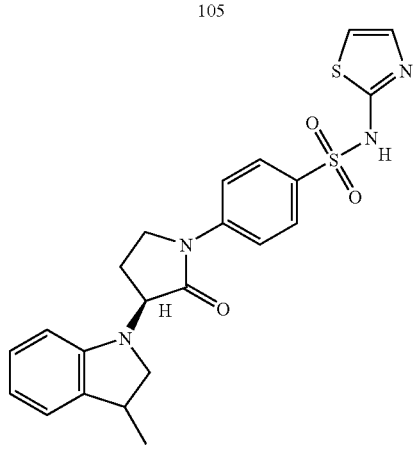
105
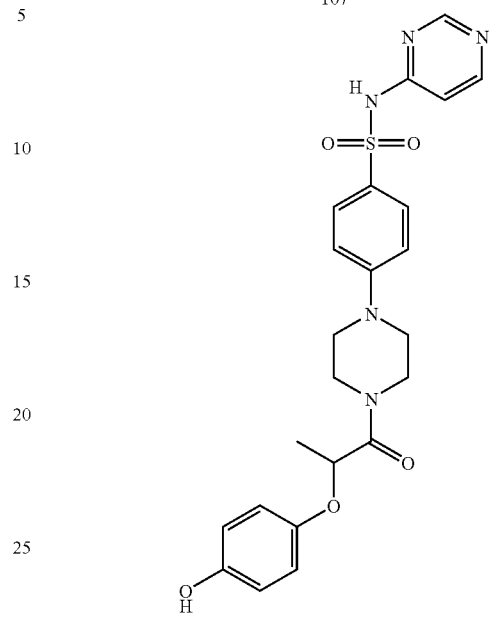
107
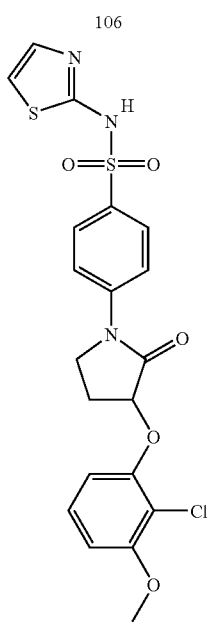
106
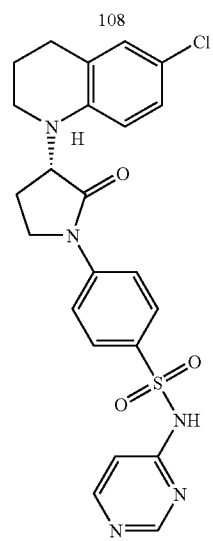
108

TABLE 2-continued
109
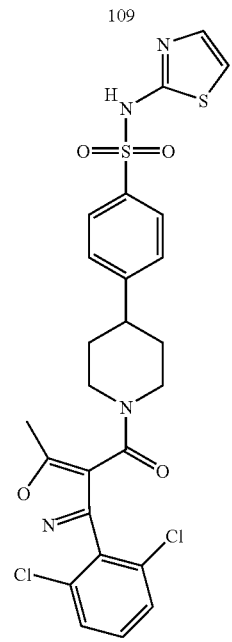
111
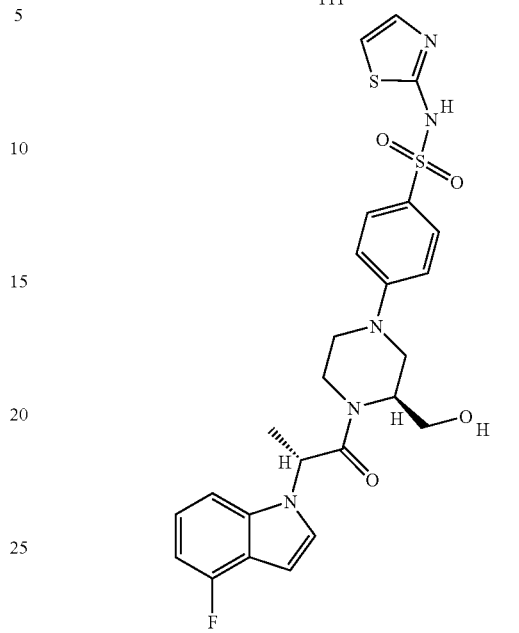
110
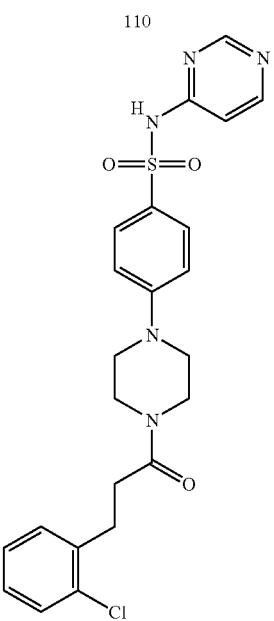
112
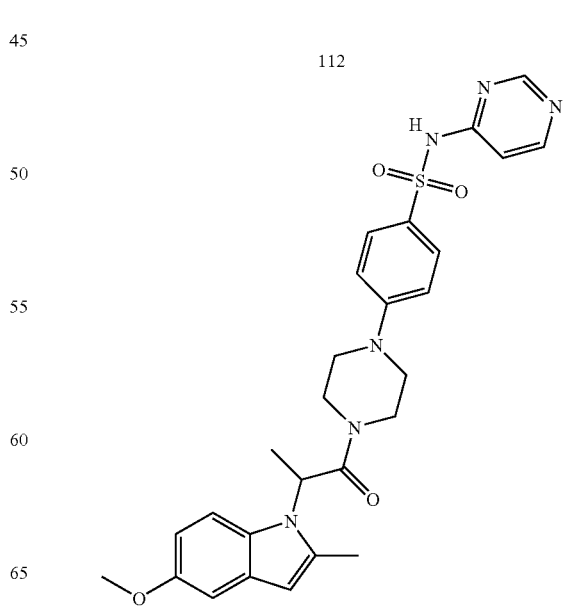

TABLE 2-continued
113
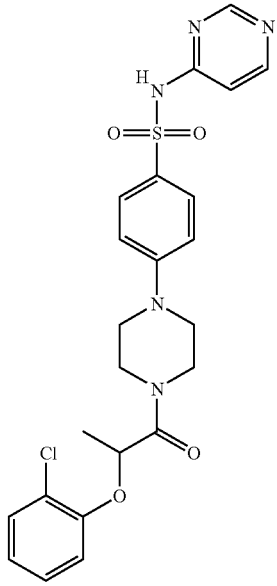
114
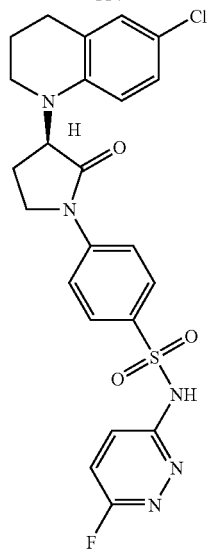
TABLE 2-continued
115
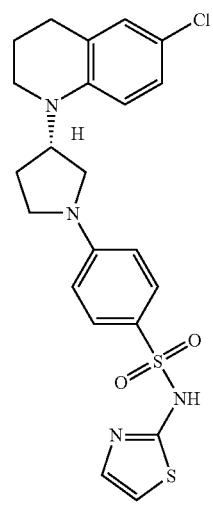
116
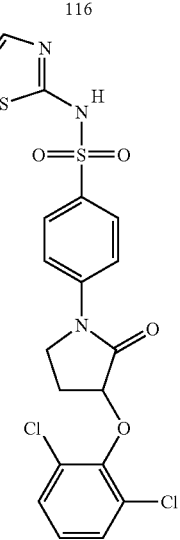

TABLE 2-continued
117
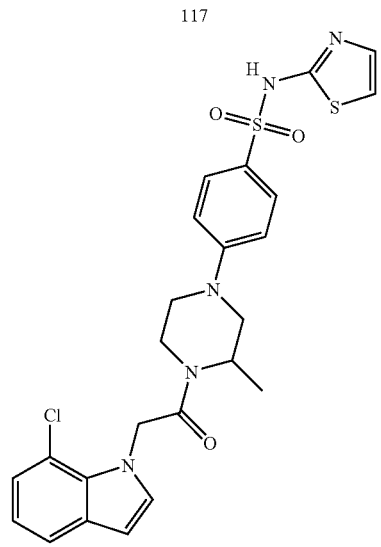
118
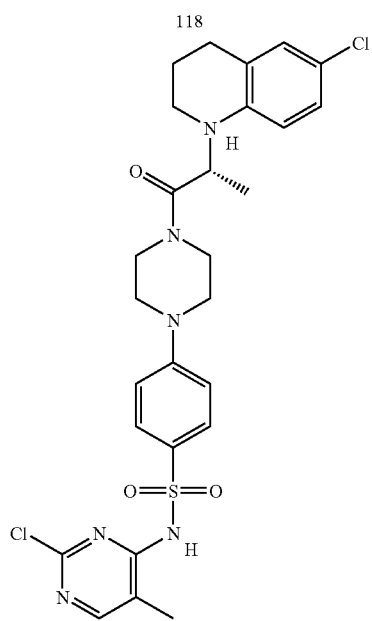
TABLE 2-continued
119
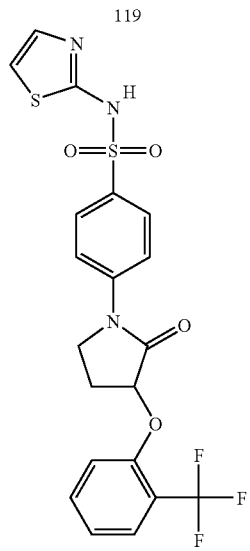
120
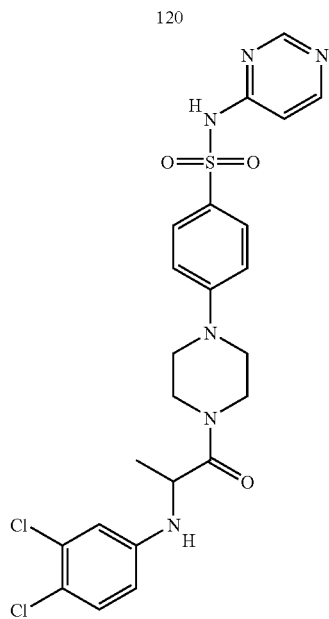

TABLE 2-continued
121
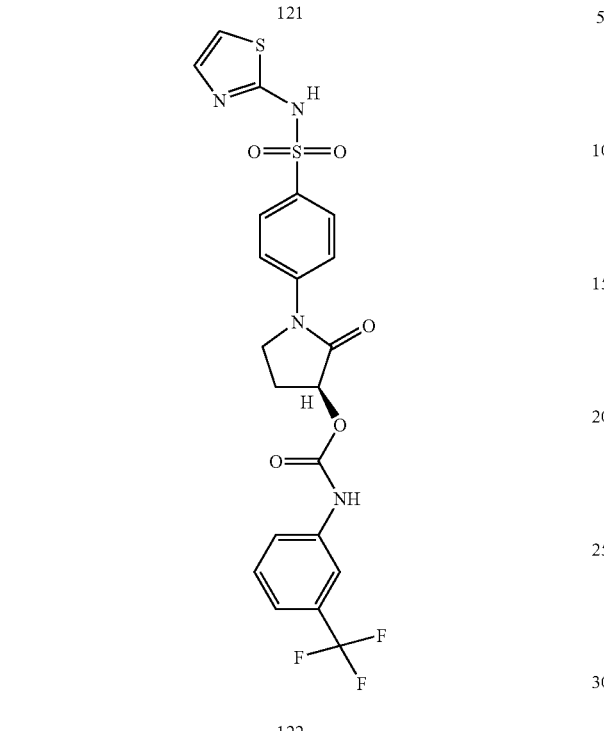
122
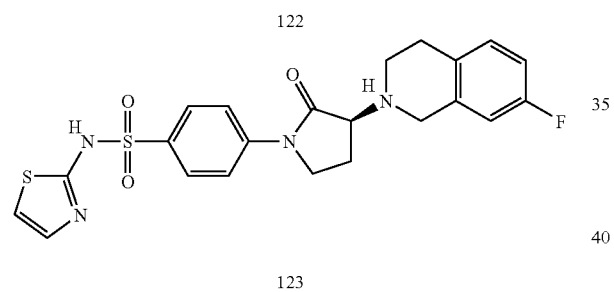
123
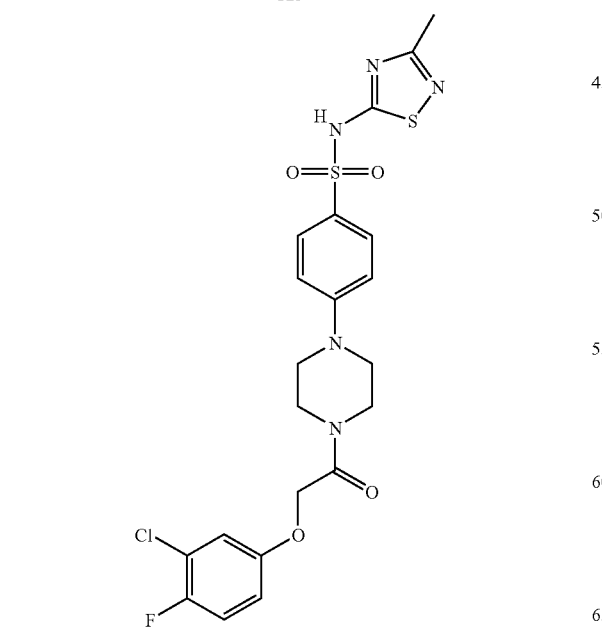
TABLE 2-continued
124
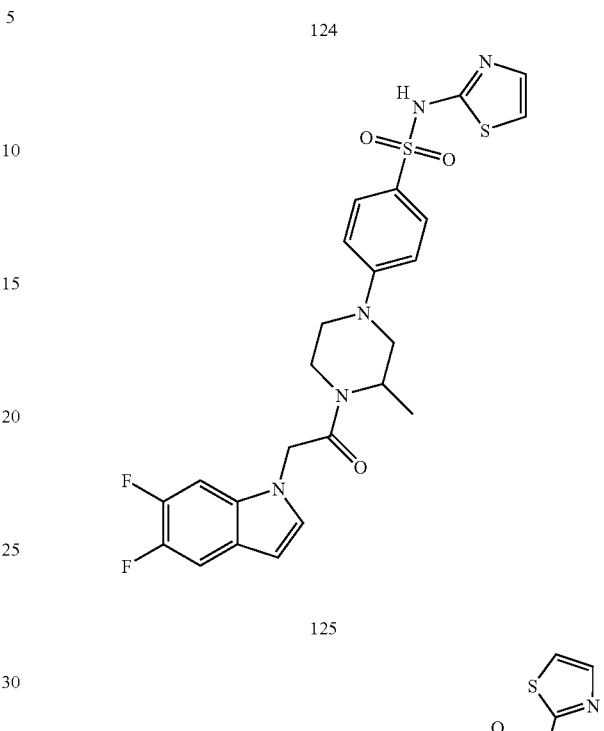
125
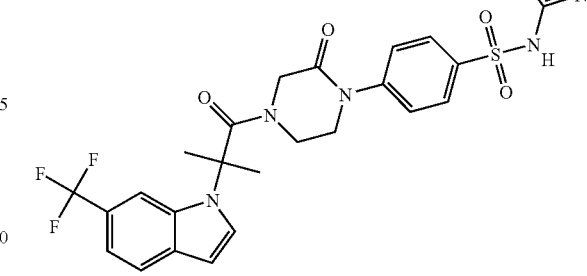
126
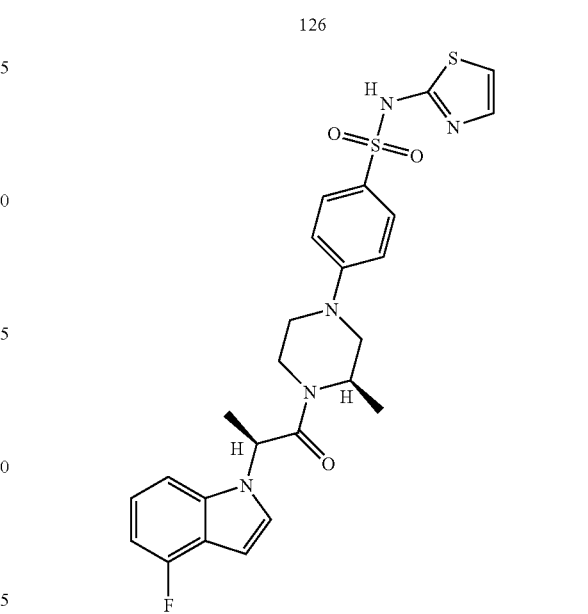

TABLE 2-continued
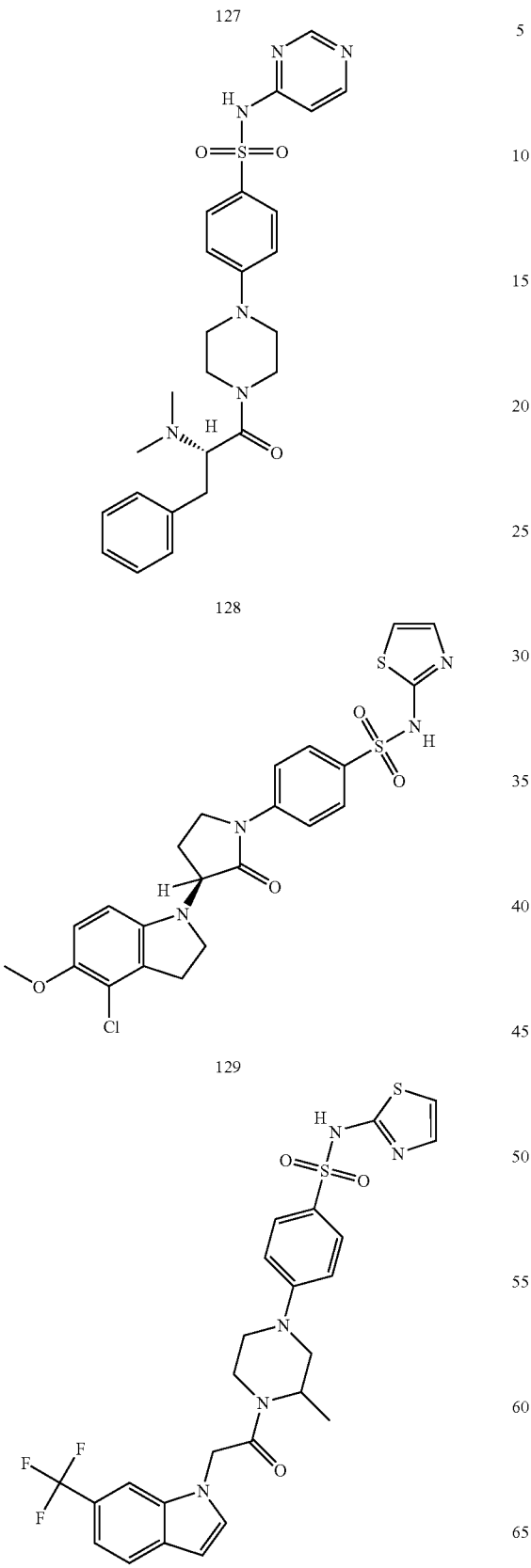
TABLE 2-continued

TABLE 2-continued
132
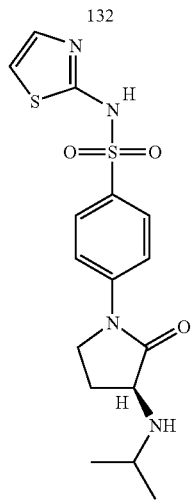
134
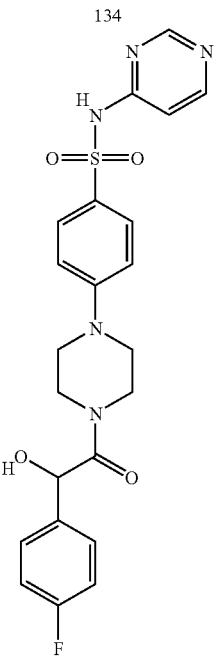
133
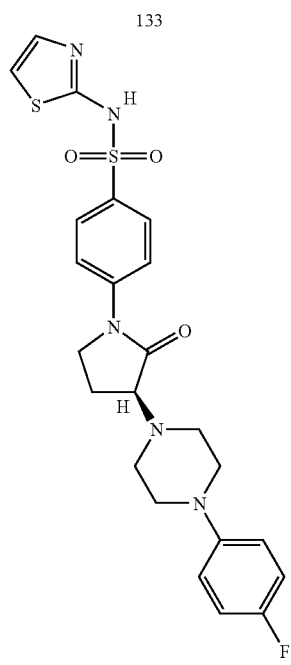
135
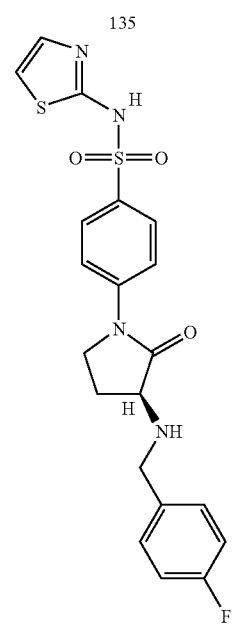

TABLE 2-continued
136
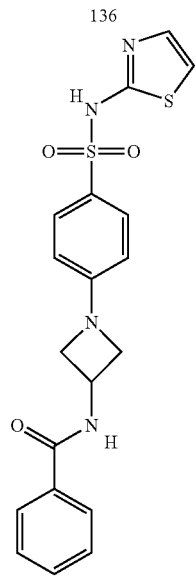
137
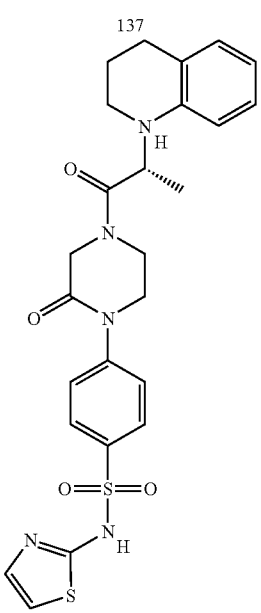
TABLE 2-continued
138
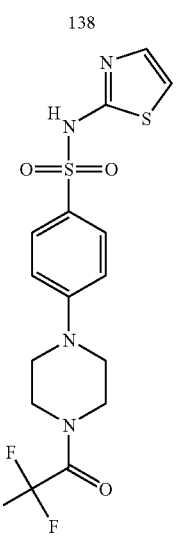
139
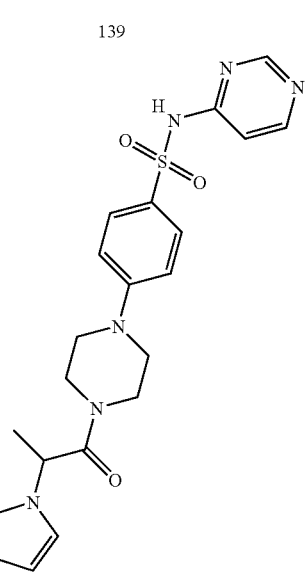

TABLE 2-continued
140
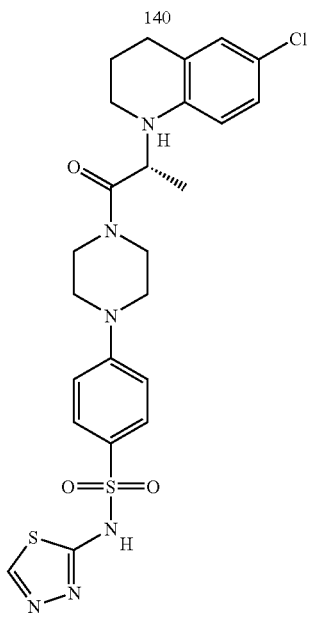
142
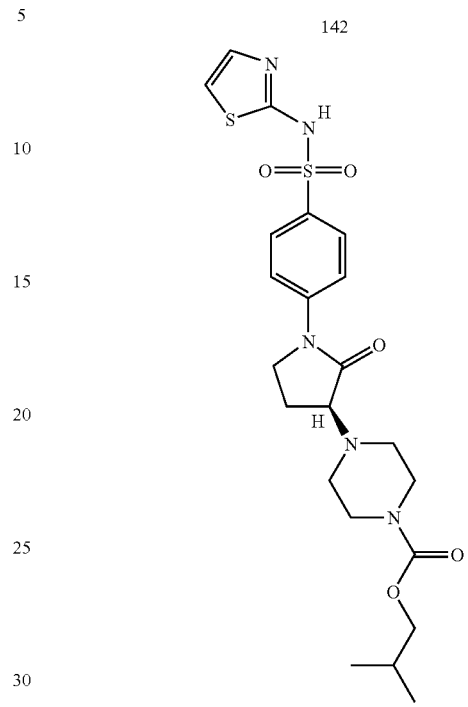
141
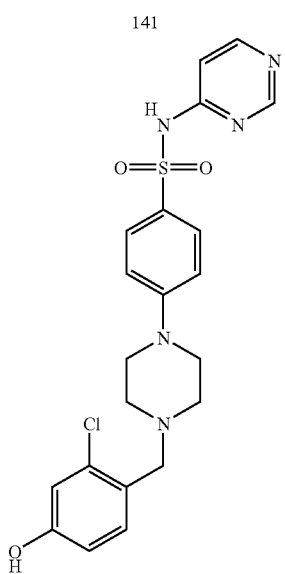
143
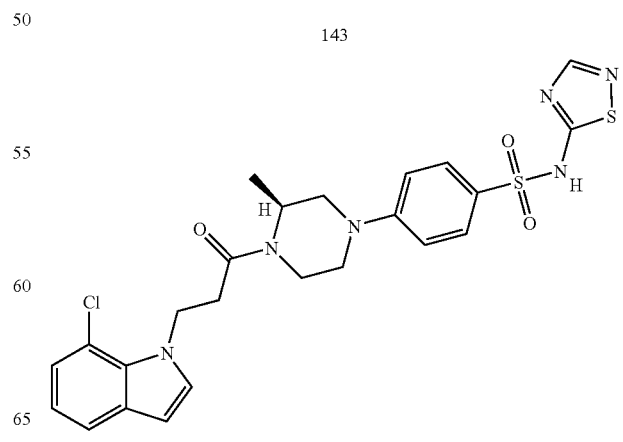

TABLE 2-continued
144
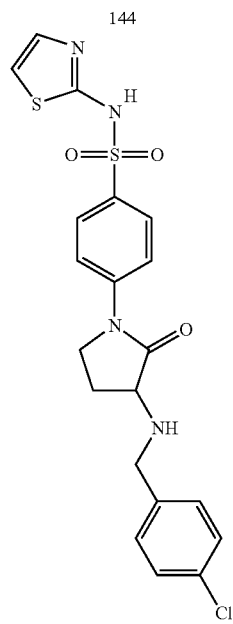
145
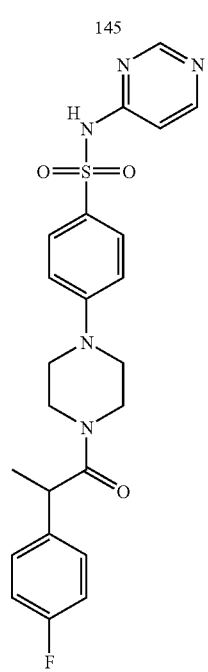
TABLE 2-continued
146
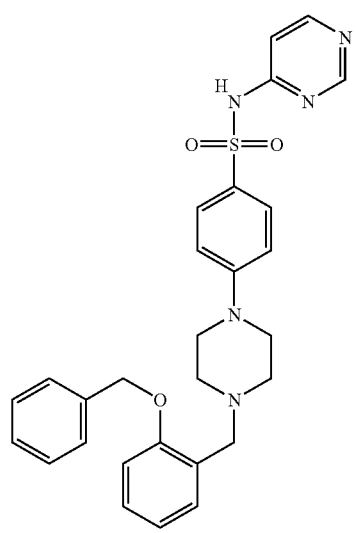
147
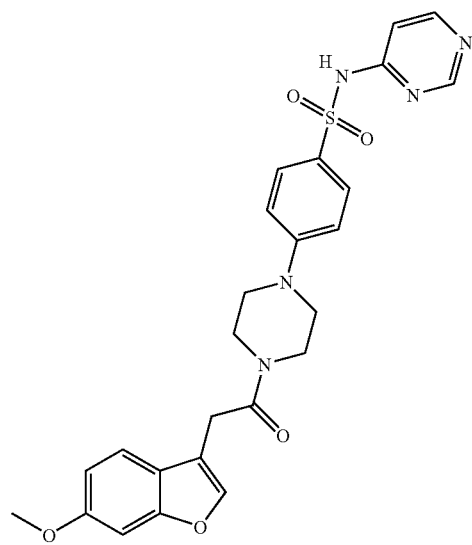

TABLE 2-continued
148
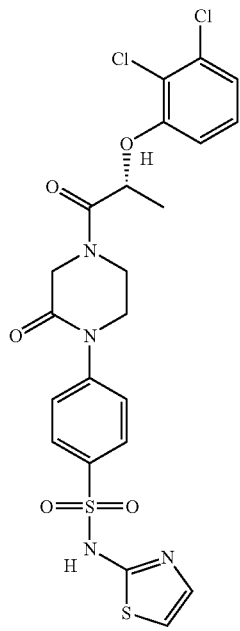
TABLE 2-continued
150
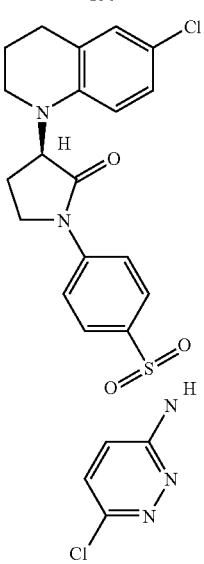
149
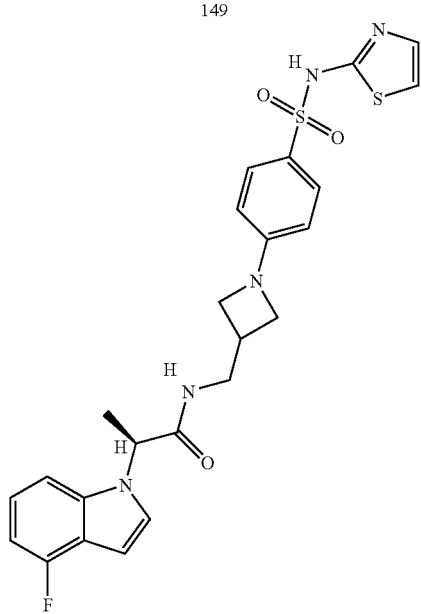
151
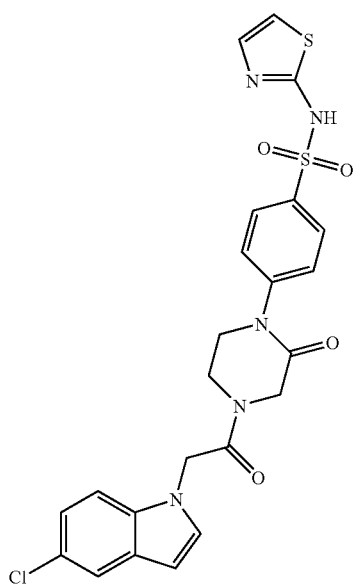

TABLE 2-continued
152
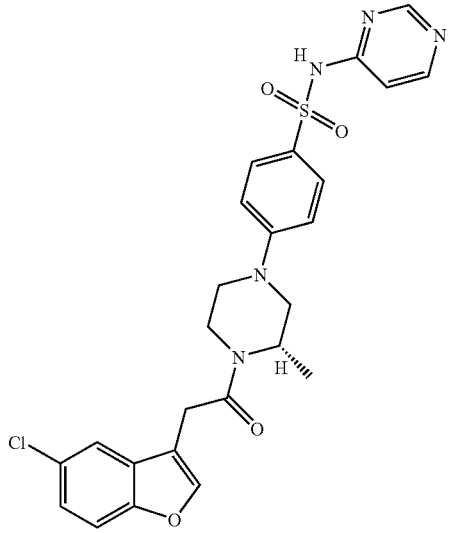
153
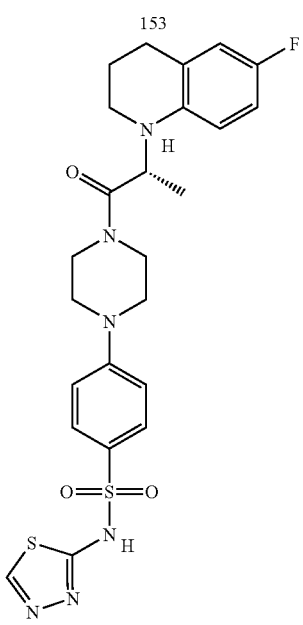
TABLE 2-continued
154
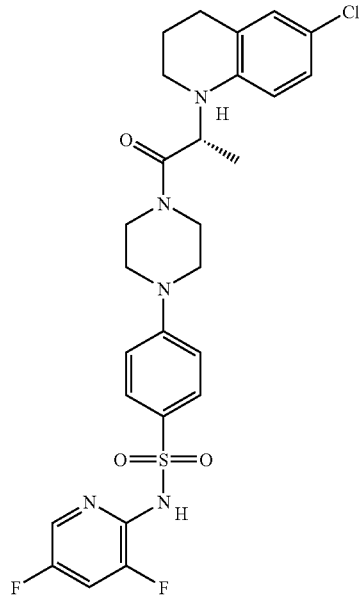
155
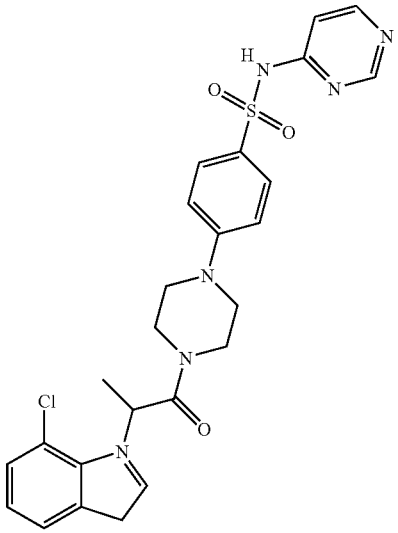

TABLE 2-continued
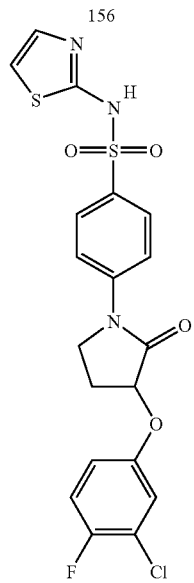
156
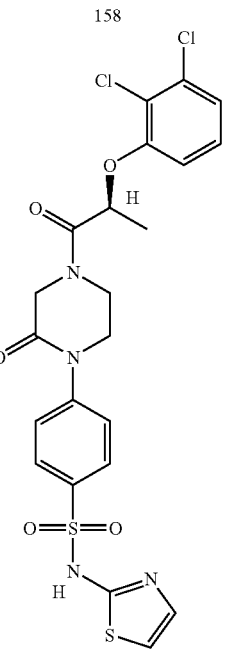
158
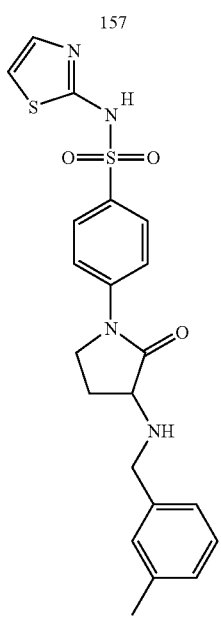
157
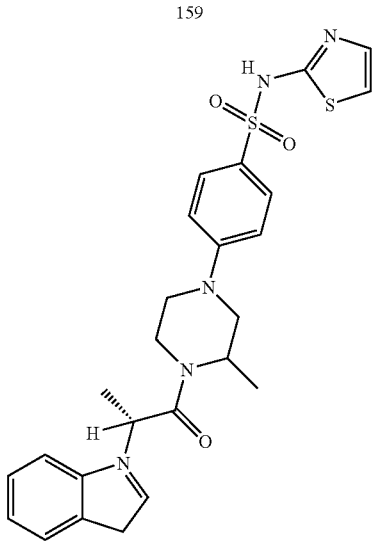
159

TABLE 2-continued
160
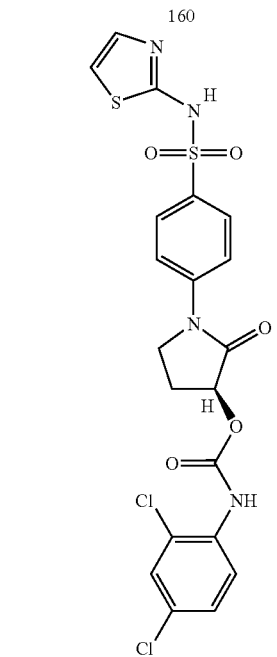
162
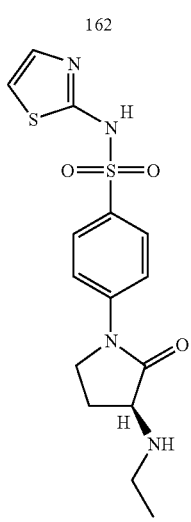
161
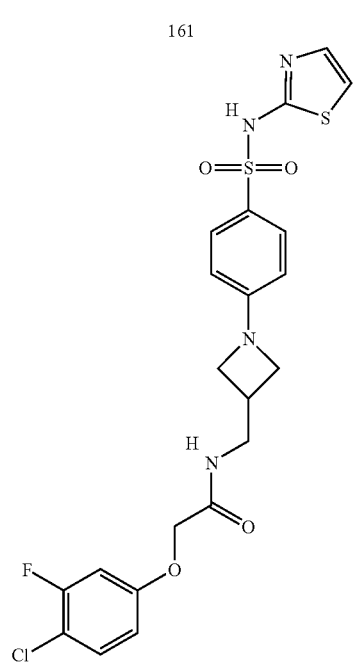
163
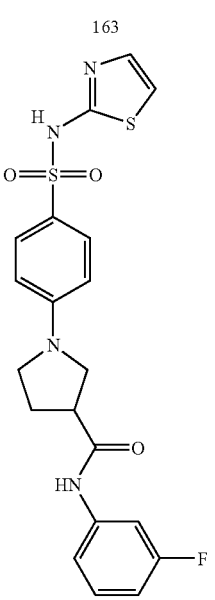

TABLE 2-continued
164
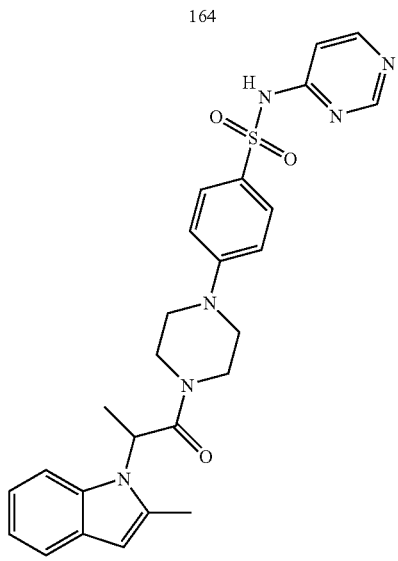
165
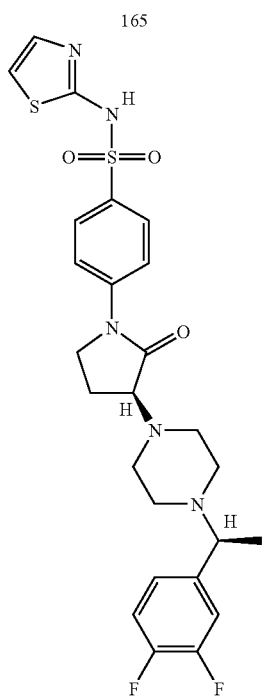
TABLE 2-continued
166
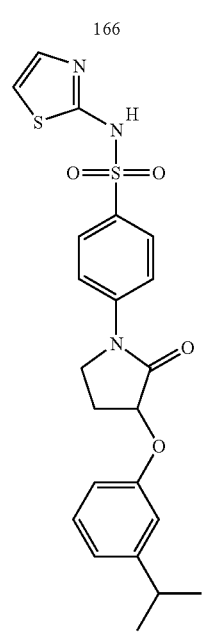
167
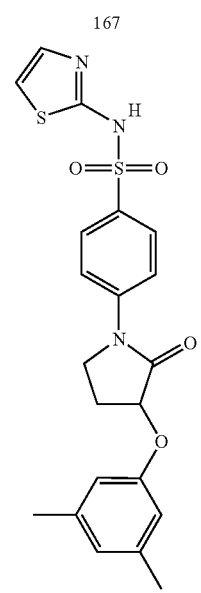

TABLE 2-continued
168
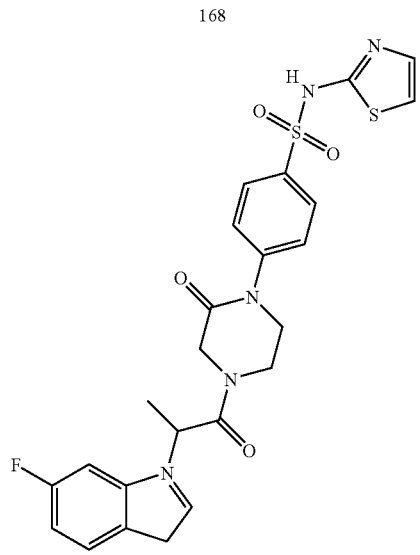
170
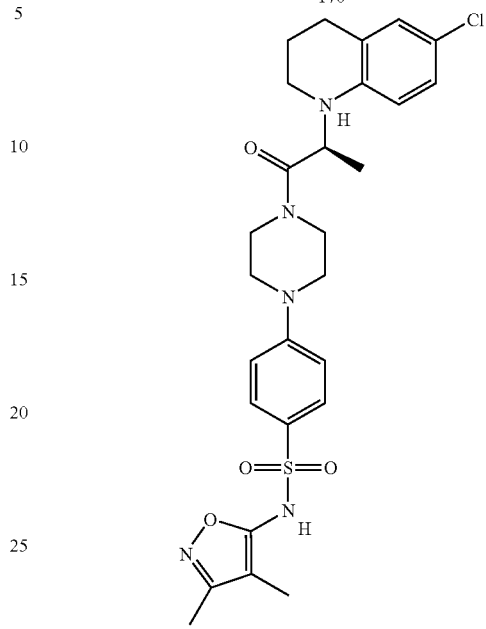
169
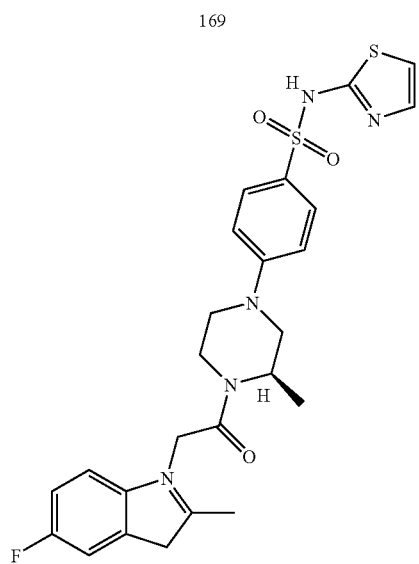
171
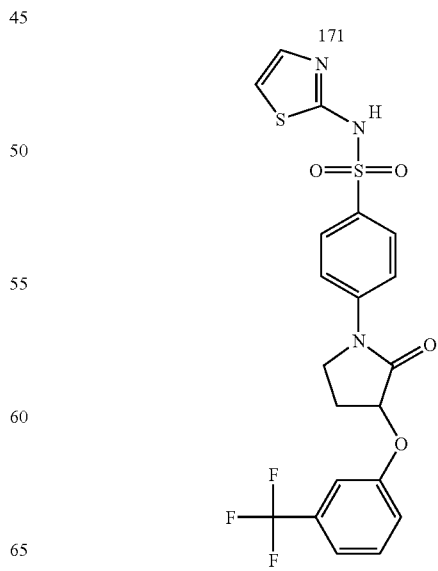

TABLE 2-continued
172
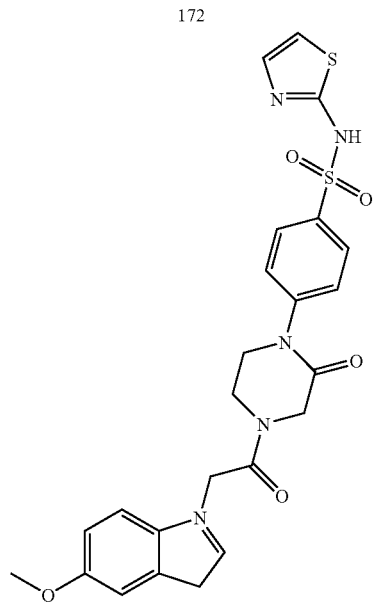
174
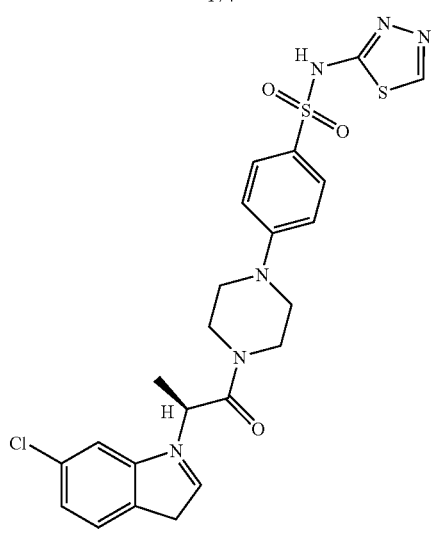
173
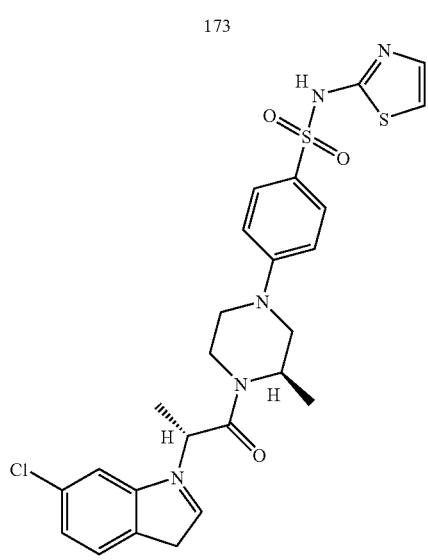
175
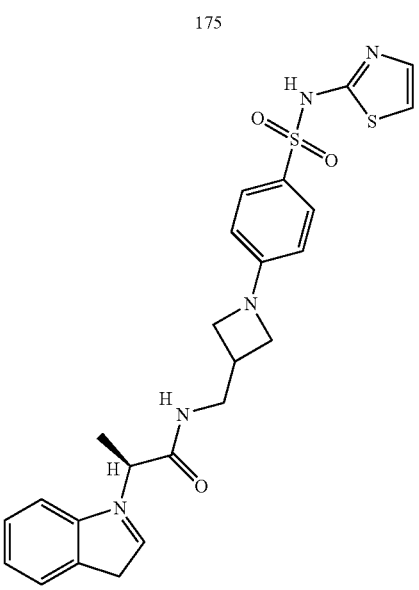

TABLE 2-continued
176
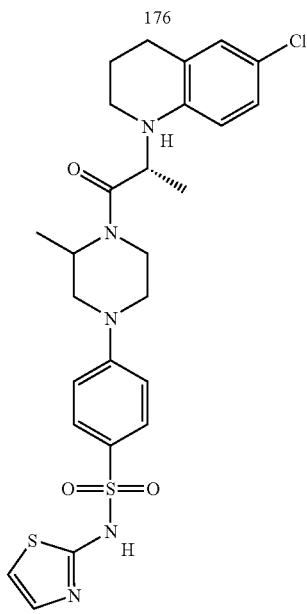
178
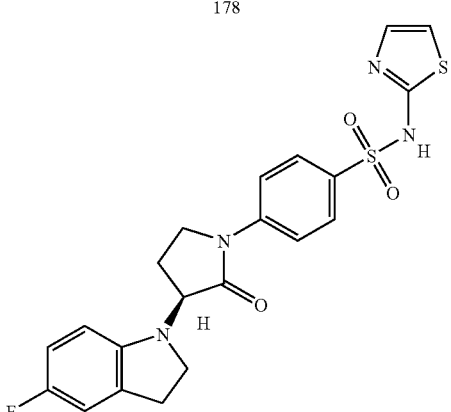
177
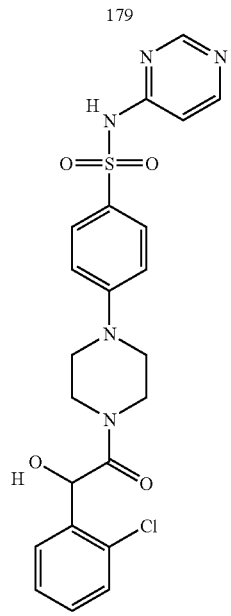
179

TABLE 2-continued
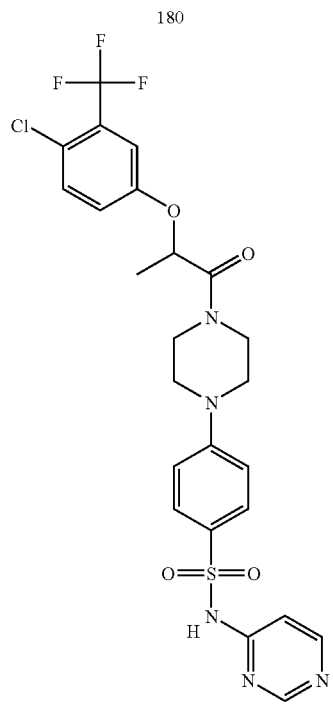
180
181
TABLE 2-continued
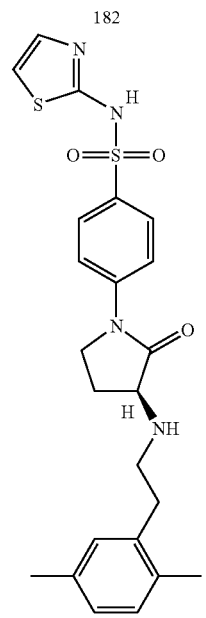
182
183

TABLE 2-continued
184
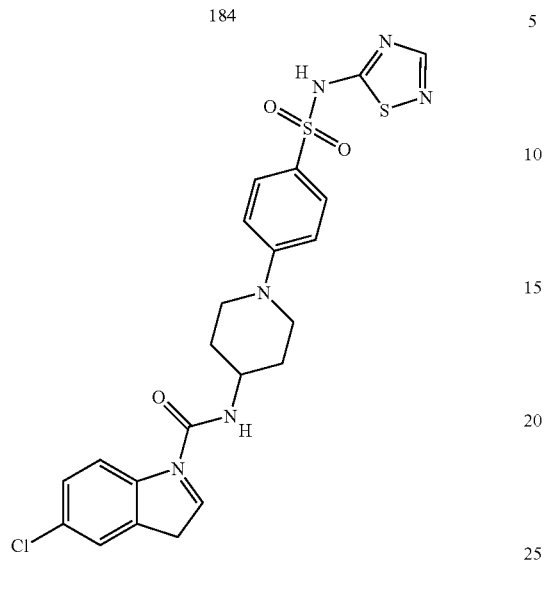
186
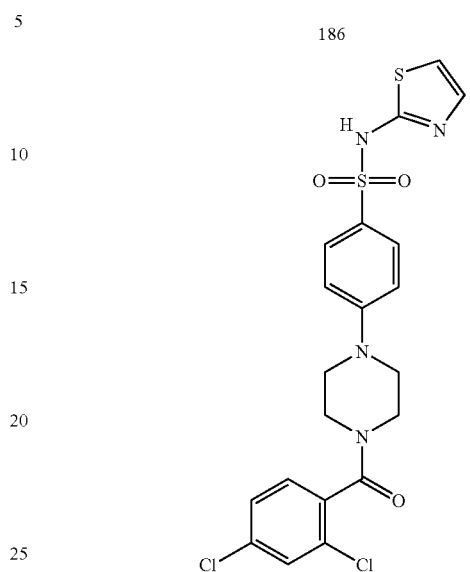
185
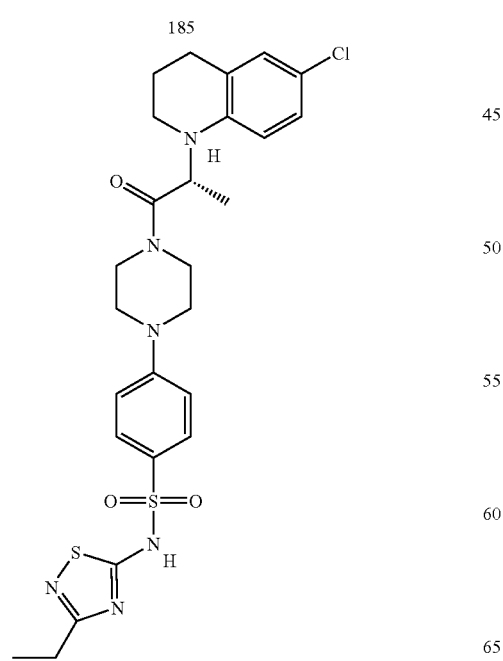
187
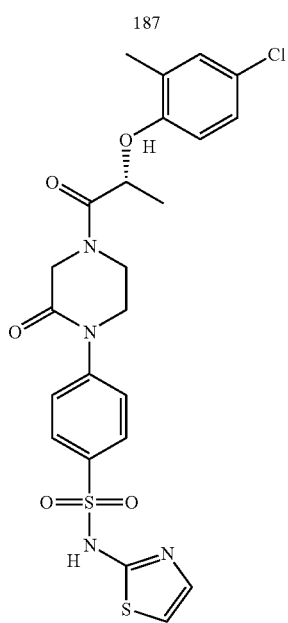

TABLE 2-continued
188
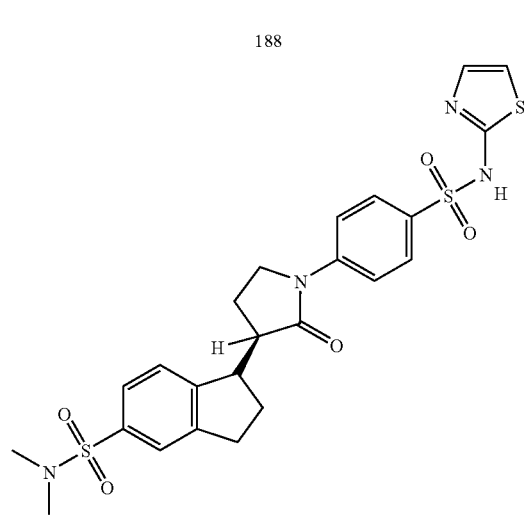
189
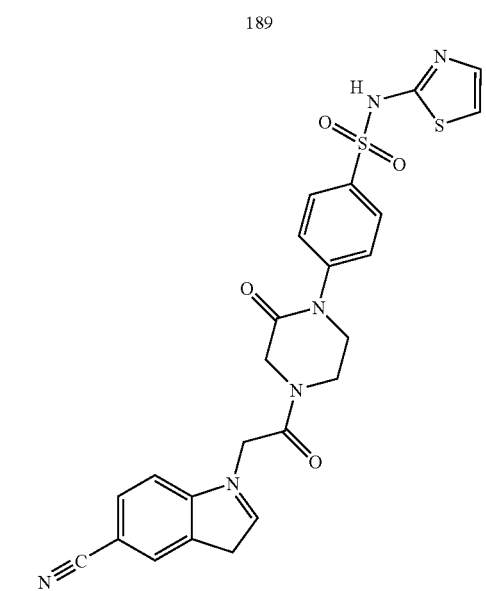
TABLE 2-continued
190
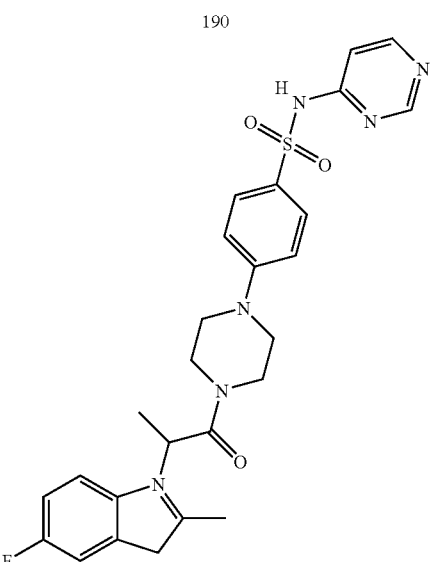
191
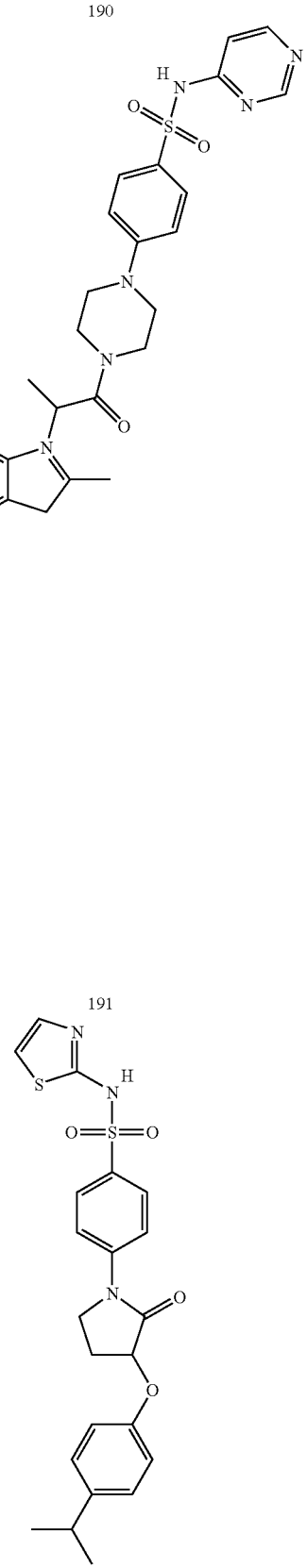

TABLE 2-continued
192
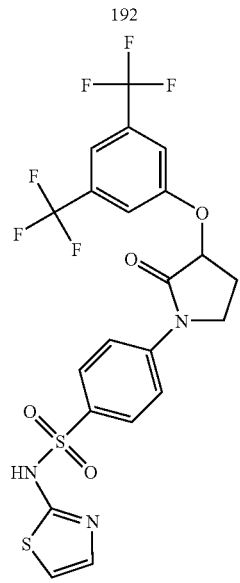
194
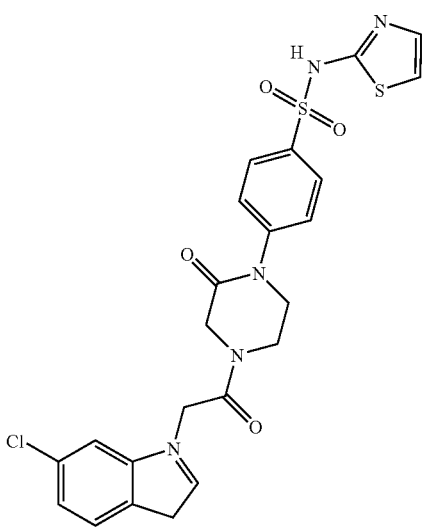
193
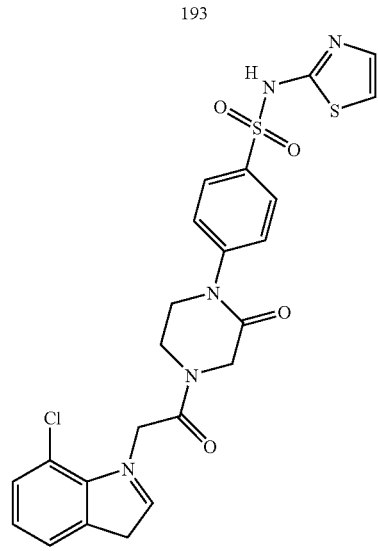
195

TABLE 2-continued
196 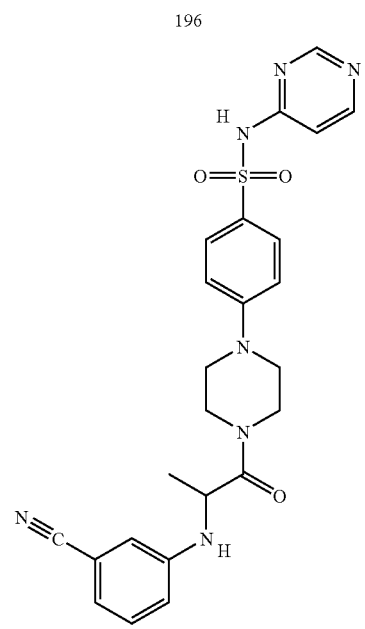
197 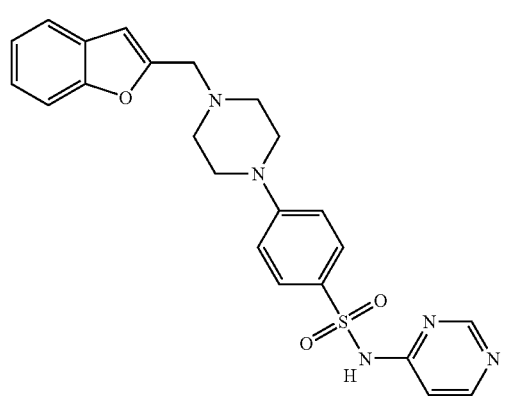
TABLE 2-continued
198 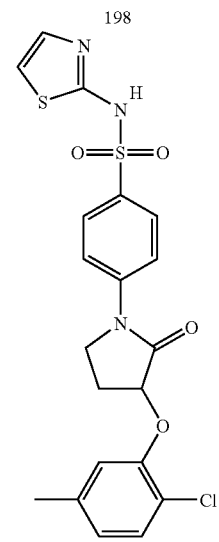
199 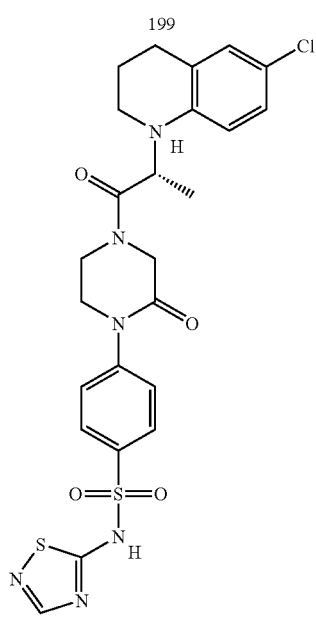

TABLE 2-continued
200
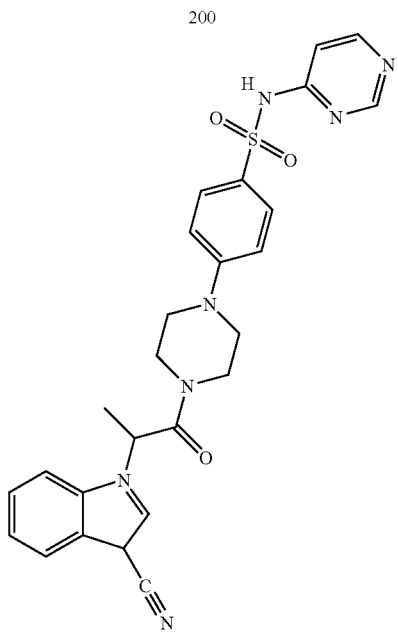
201
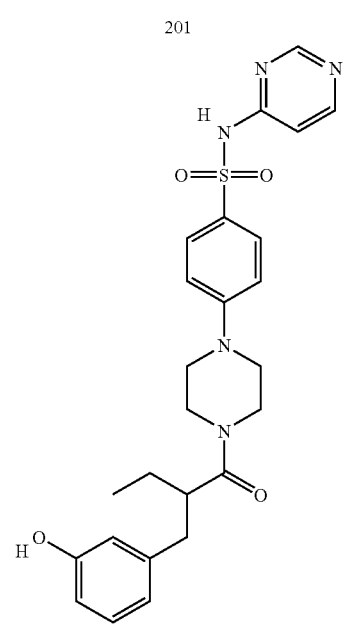
TABLE 2-continued
202
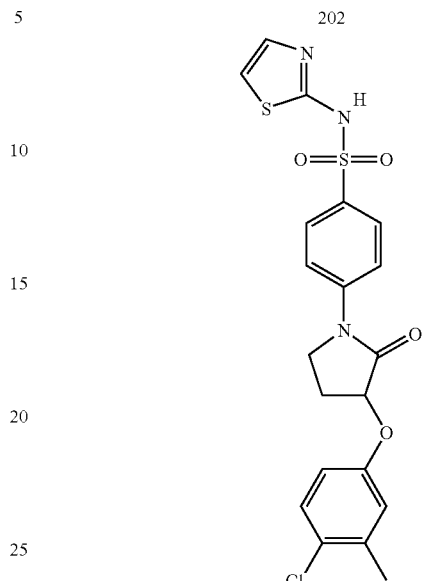
203
204
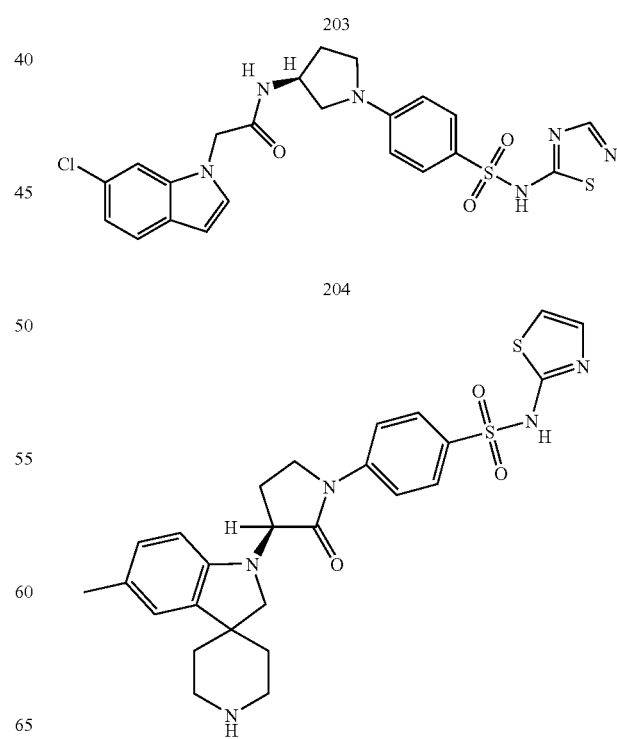

TABLE 2-continued
205
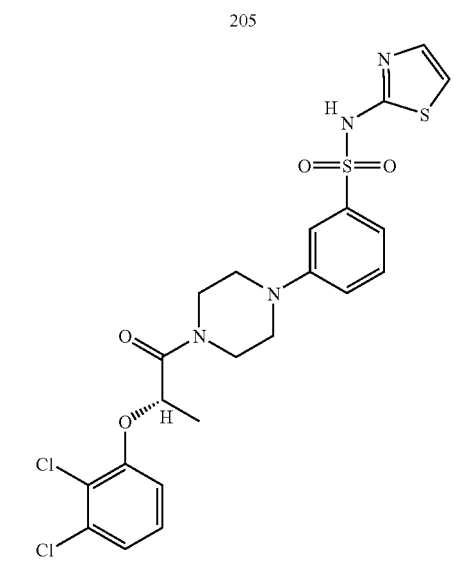
206
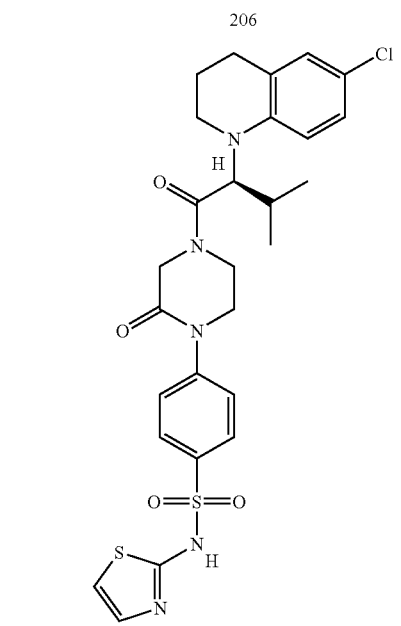
207
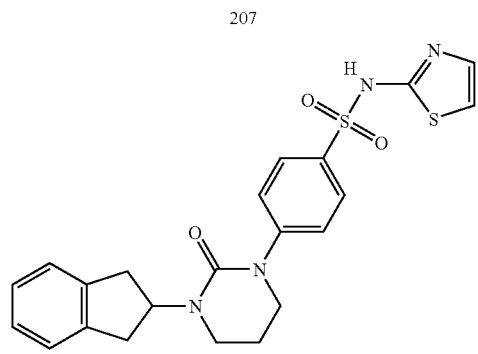
TABLE 2-continued
208
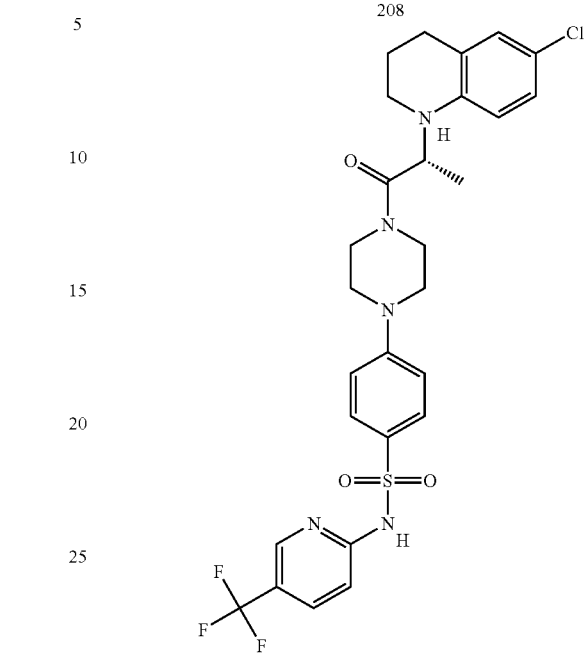
209
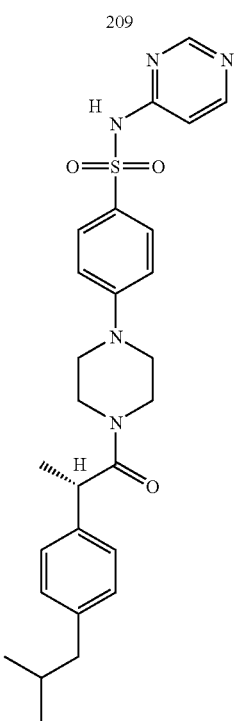

TABLE 2-continued
210
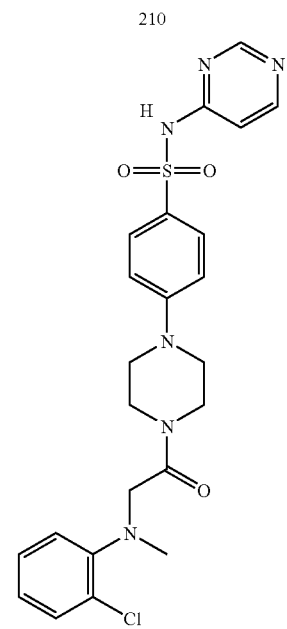
211
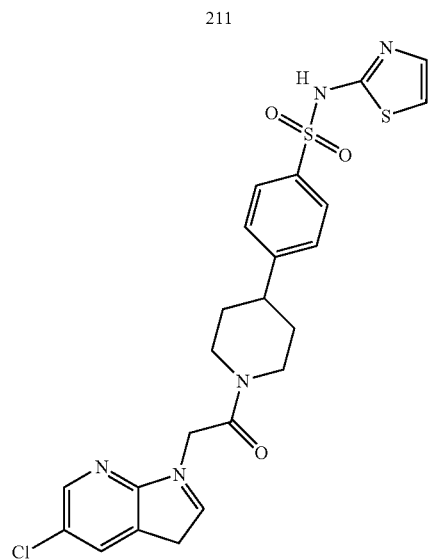
TABLE 2-continued
212
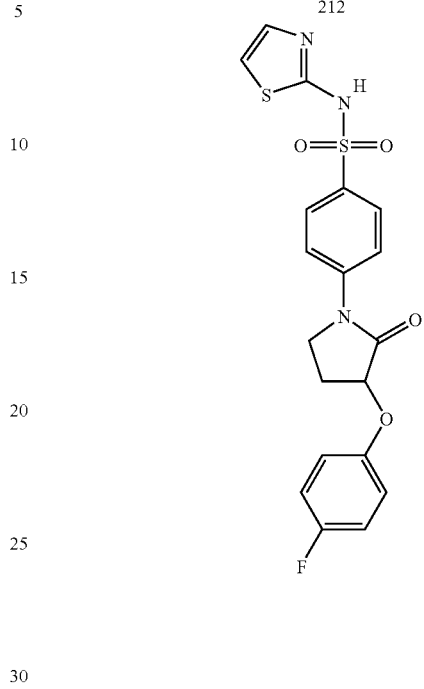
213
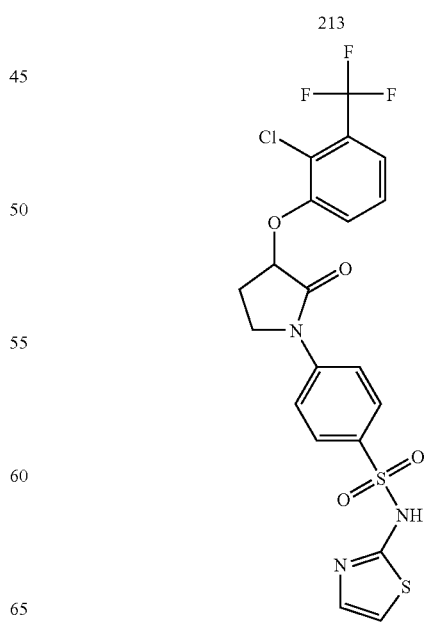

TABLE 2-continued
214
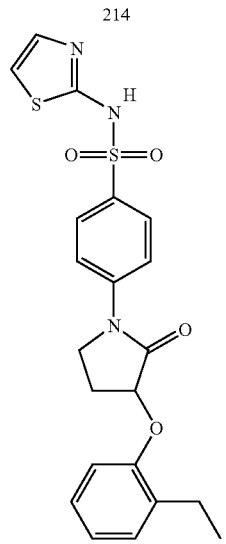
215
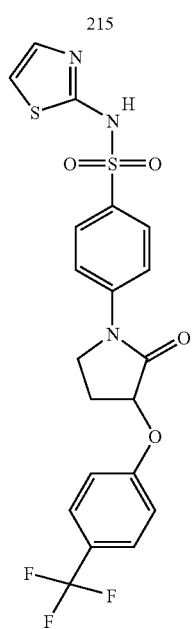
TABLE 2-continued
216
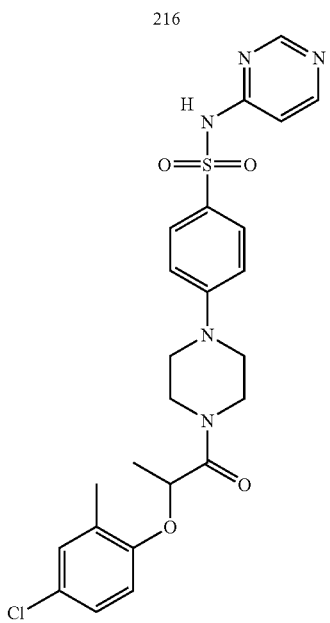
217
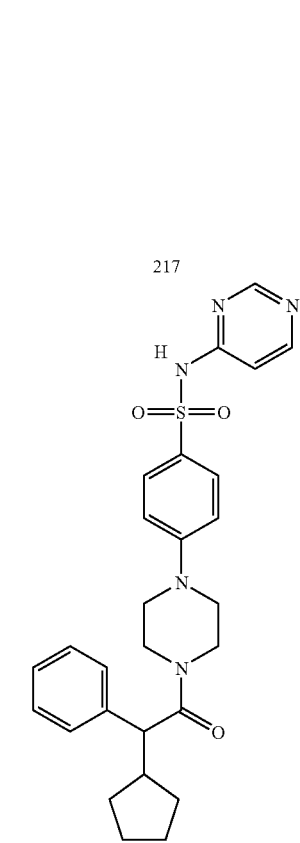

TABLE 2-continued
218
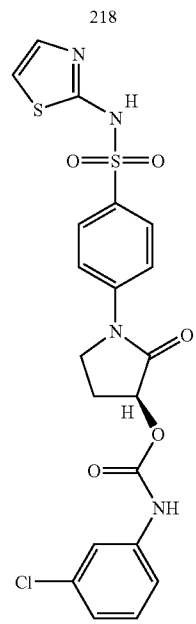
219
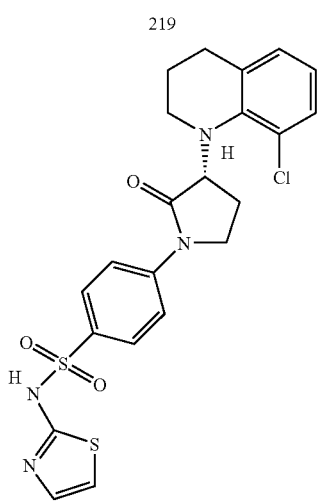
TABLE 2-continued
220
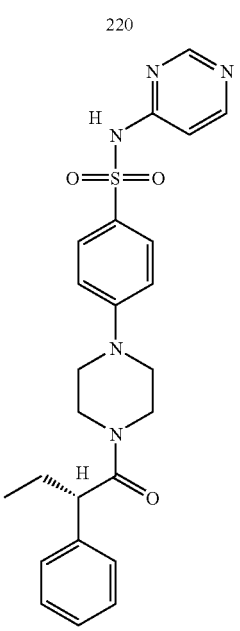
221
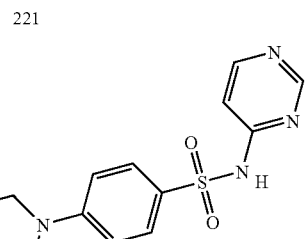

TABLE 2-continued
222
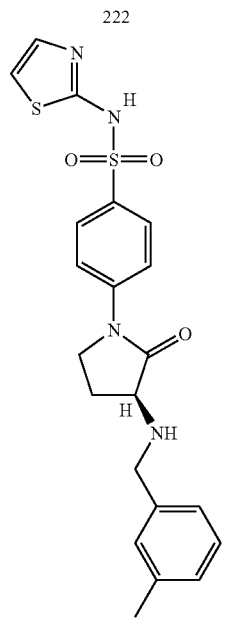
223
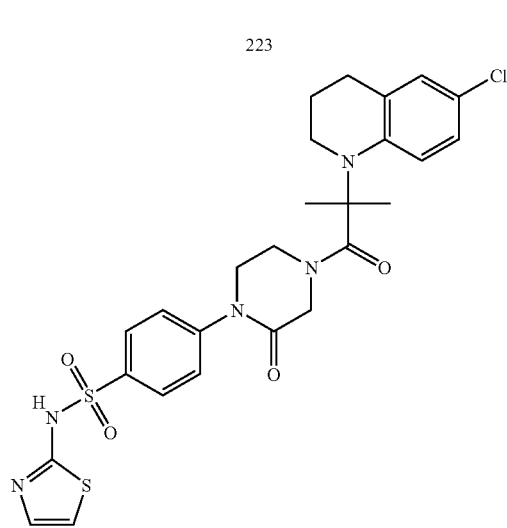
TABLE 2-continued
224
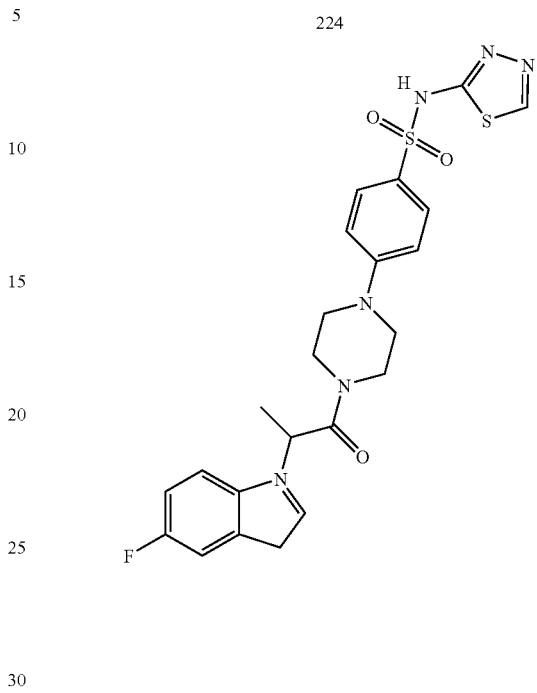
225
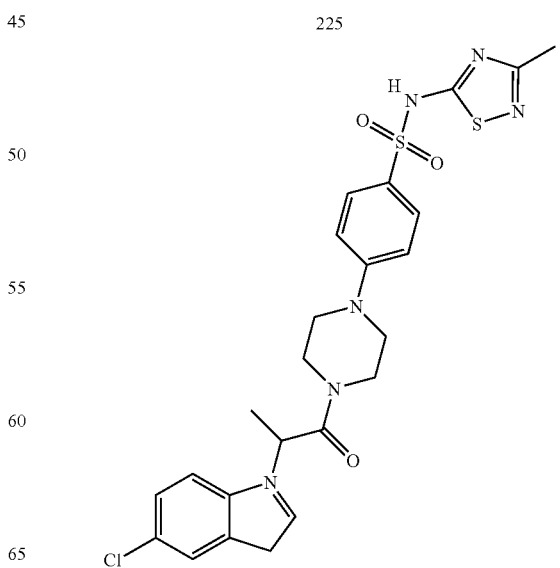

TABLE 2-continued
226
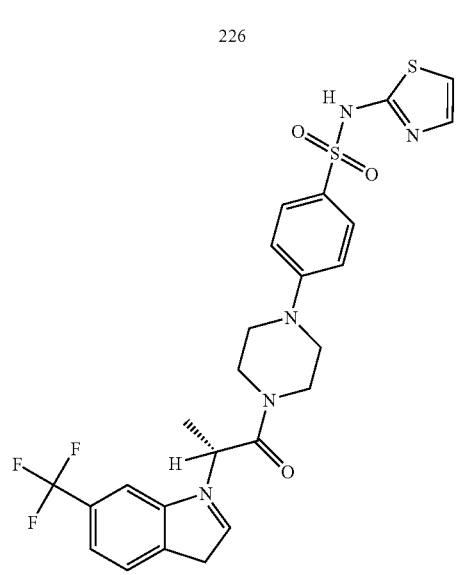
228
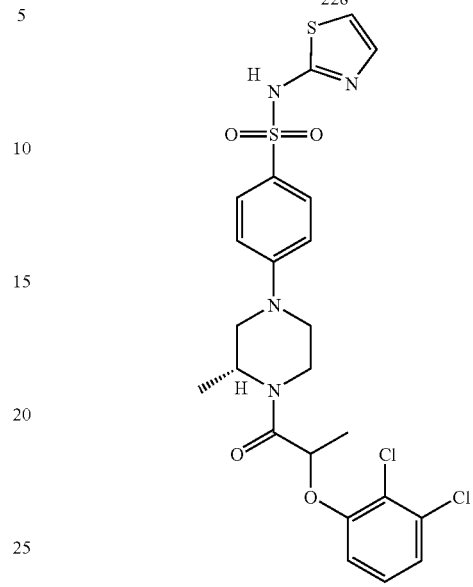
227
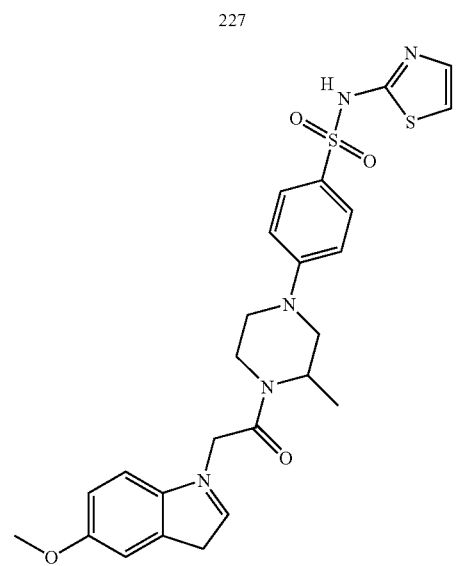
229
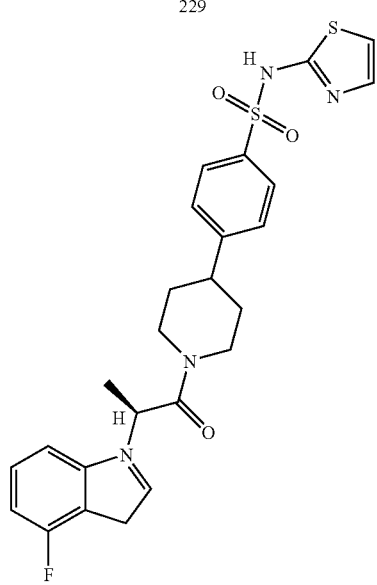

TABLE 2-continued
230
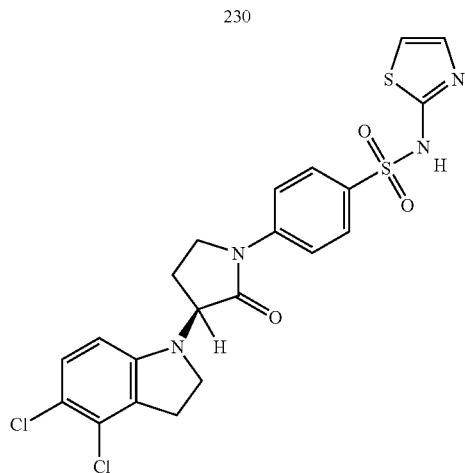
231
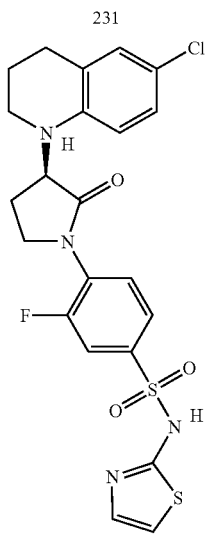
232
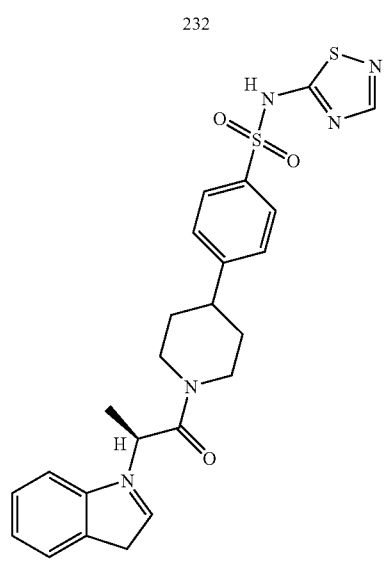
TABLE 2-continued
233
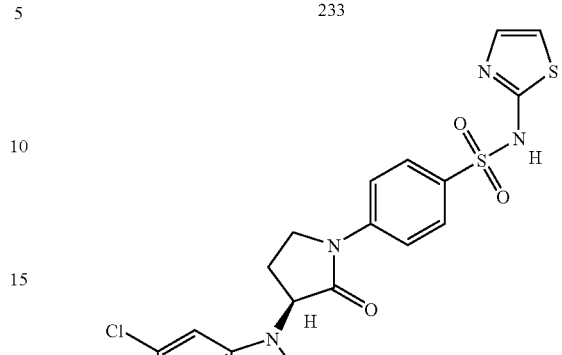
234
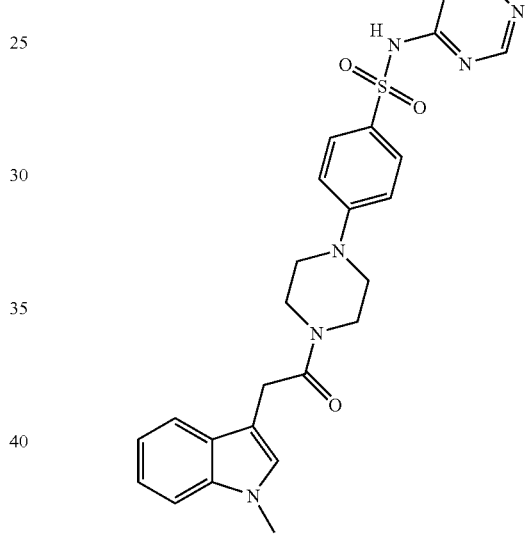
235
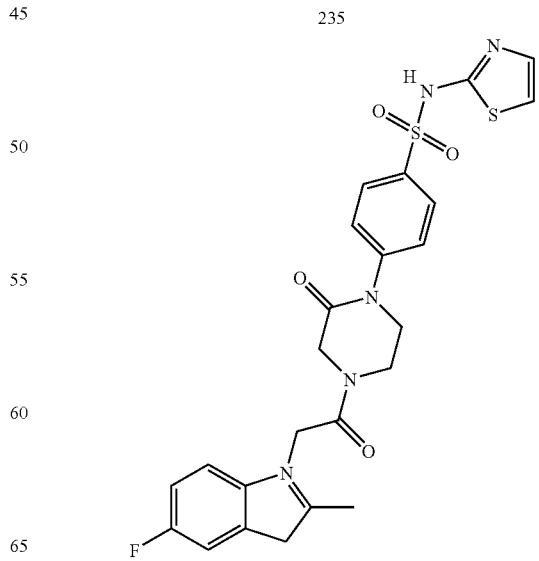

TABLE 2-continued
236
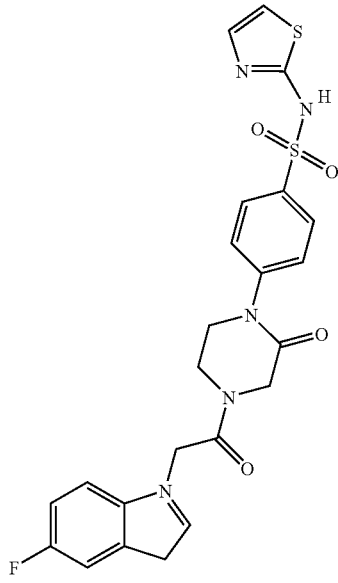
237
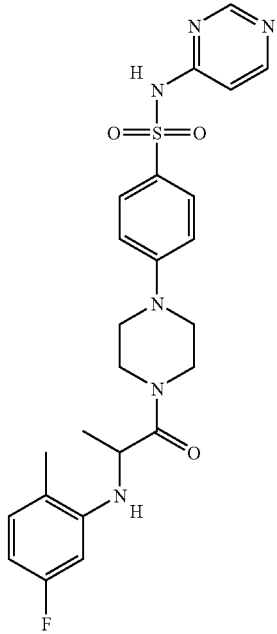
TABLE 2-continued
238
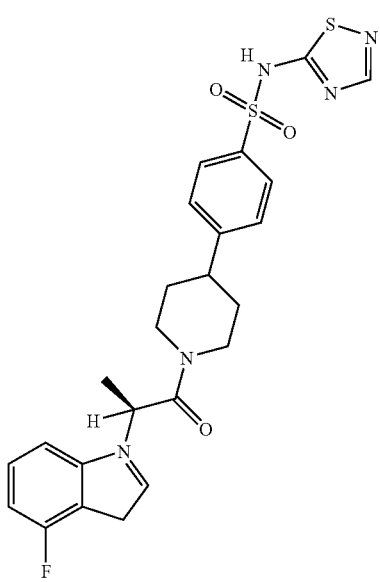
239
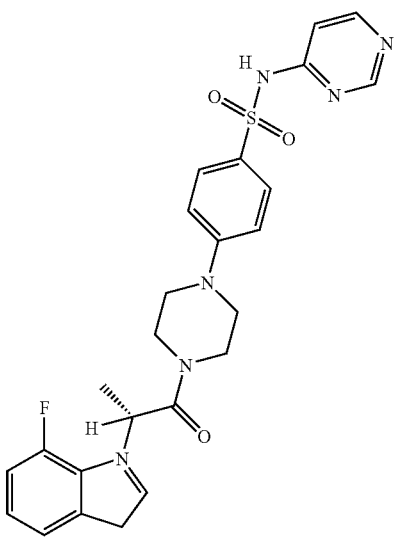

TABLE 2-continued
240
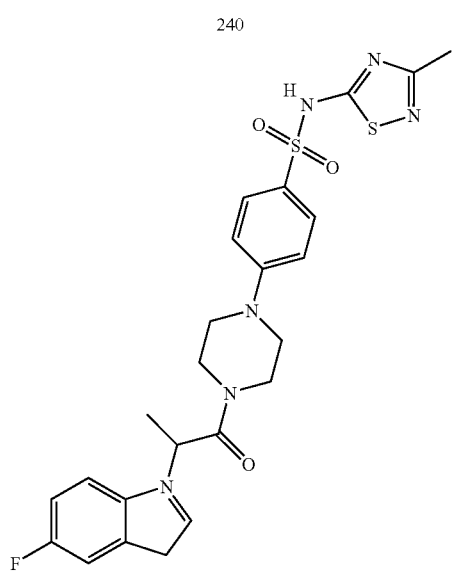
241
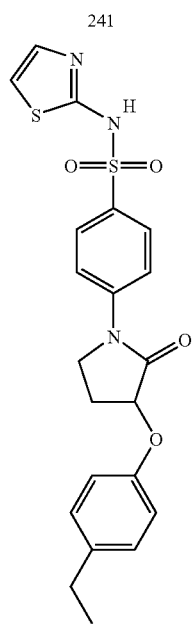
TABLE 2-continued
242
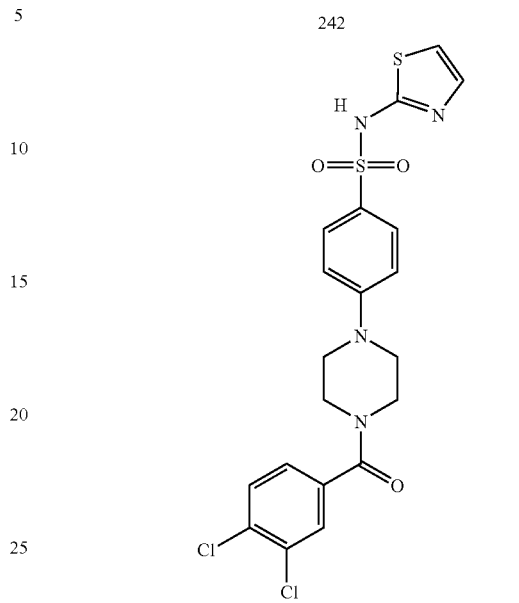
243
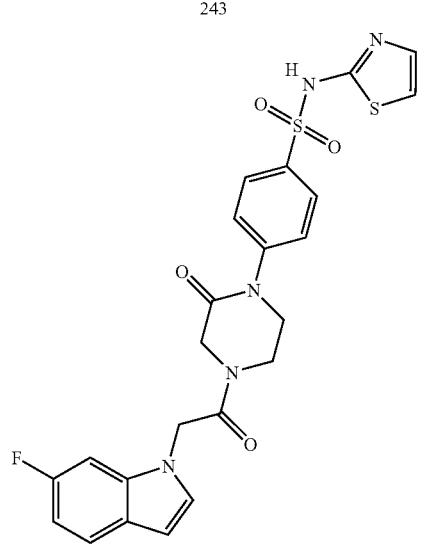

TABLE 2-continued
244
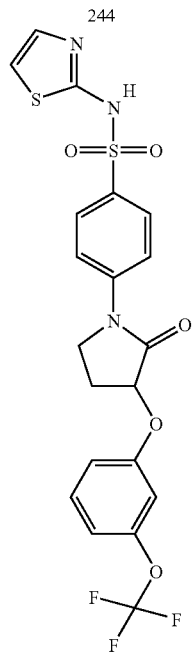
245
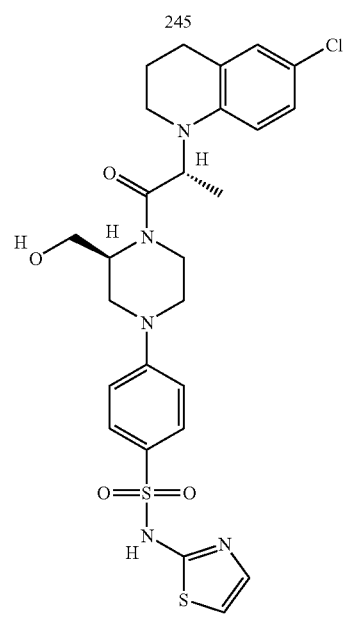
TABLE 2-continued
246
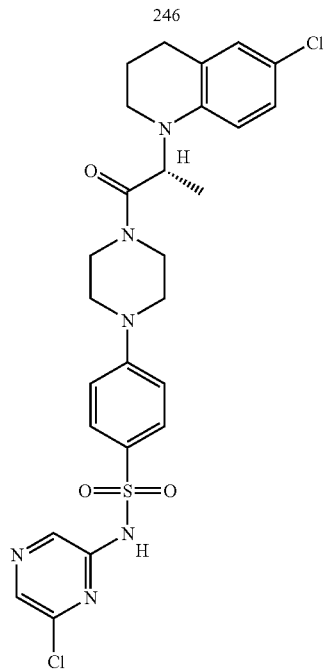
247
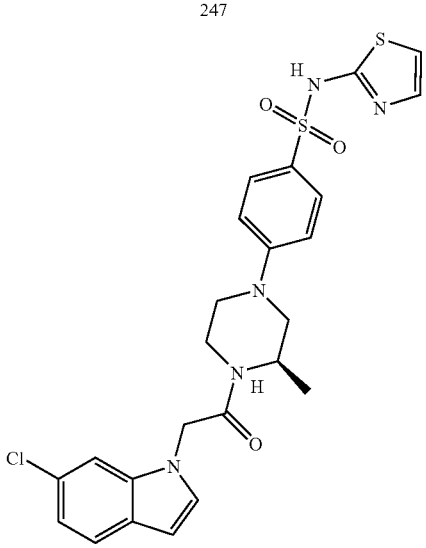

TABLE 2-continued
248
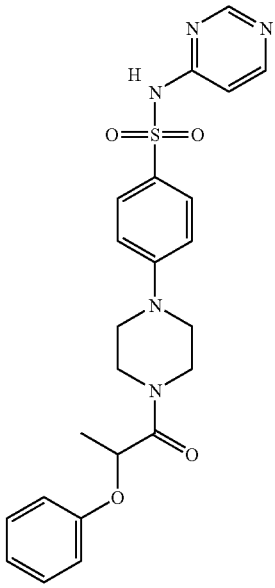
249
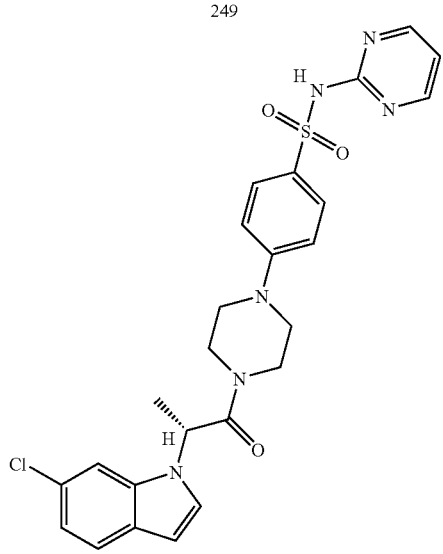
TABLE 2-continued
250
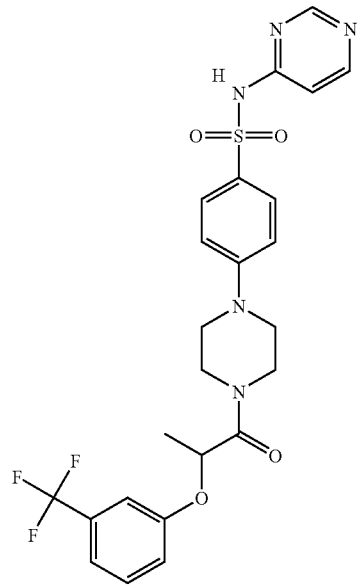
251
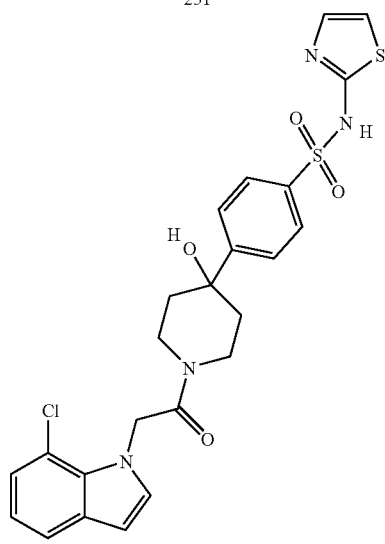

TABLE 2-continued
252
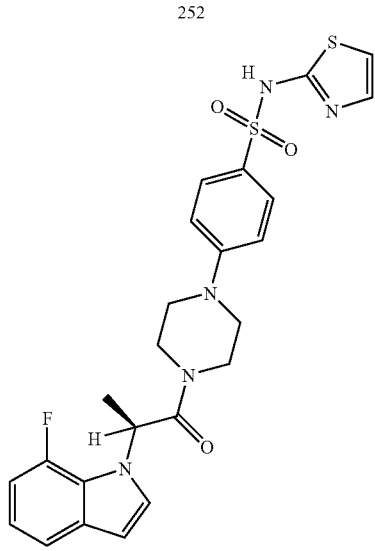
253
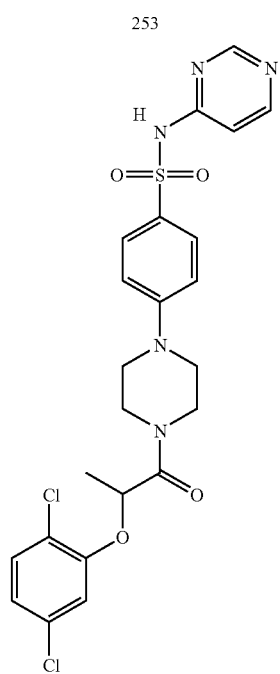
TABLE 2-continued
254
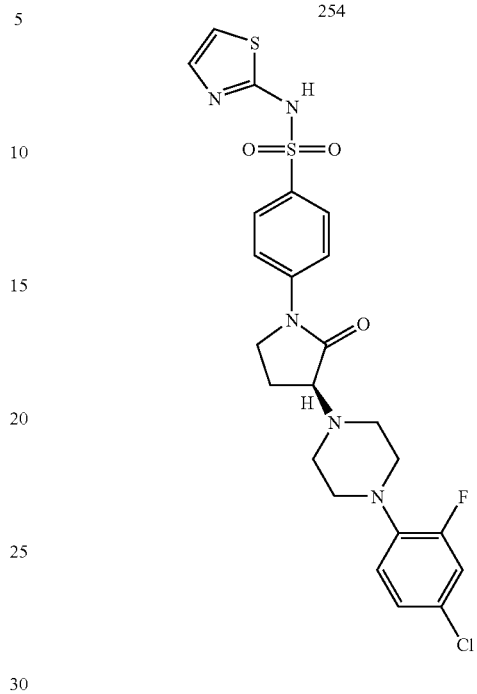
255

TABLE 2-continued
256
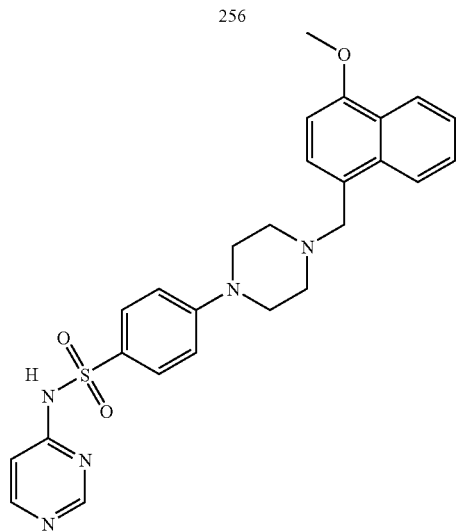
257
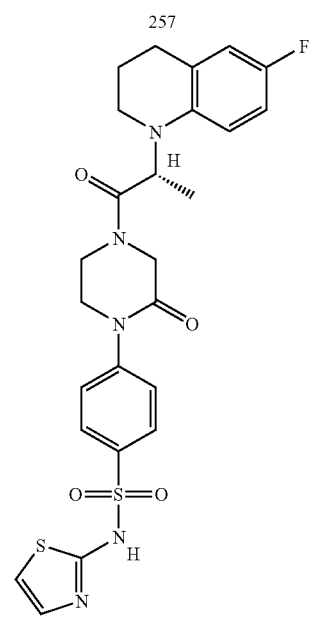
TABLE 2-continued
258
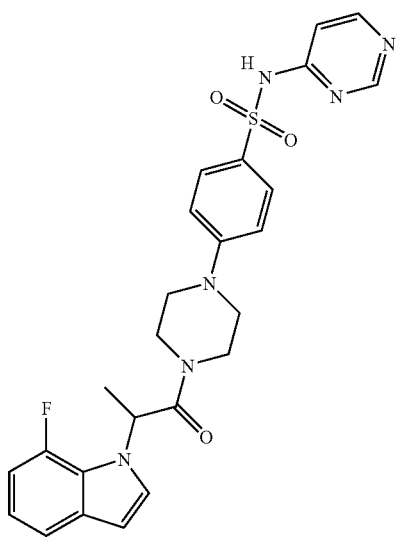
259
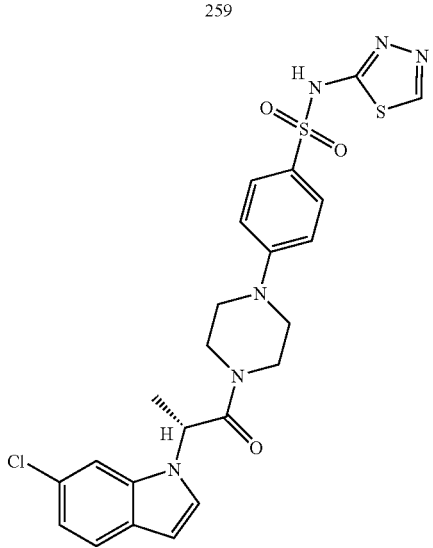

TABLE 2-continued
260
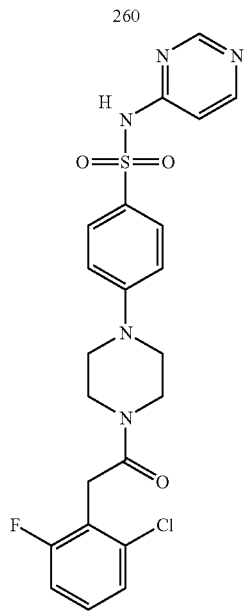
TABLE 2-continued
262
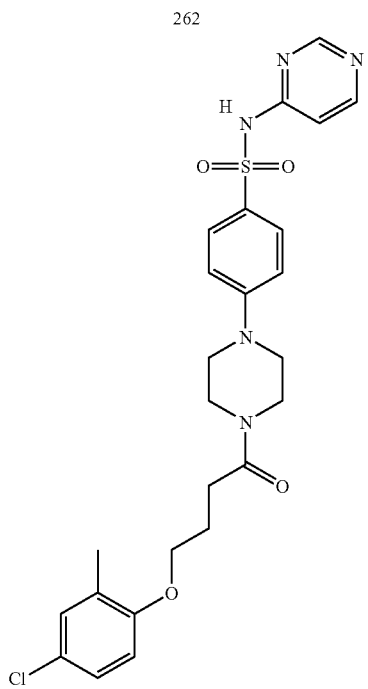
261
263

TABLE 2-continued
264
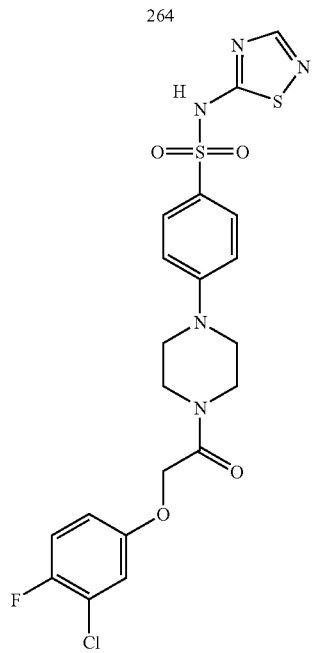
265
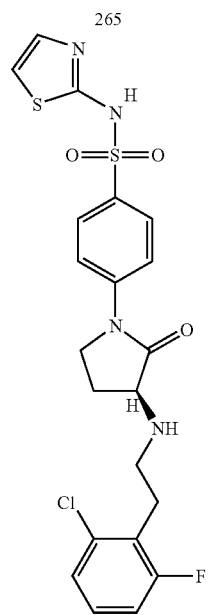
TABLE 2-continued
266
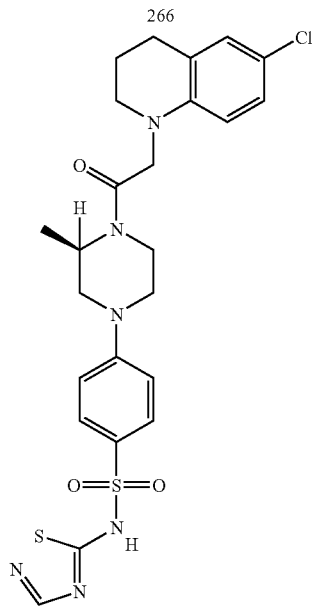
267
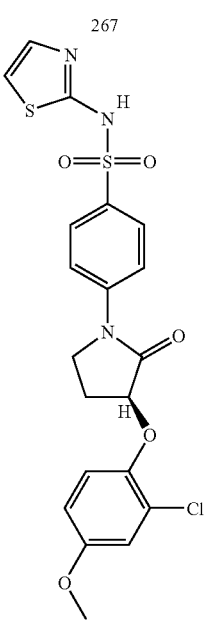

TABLE 2-continued
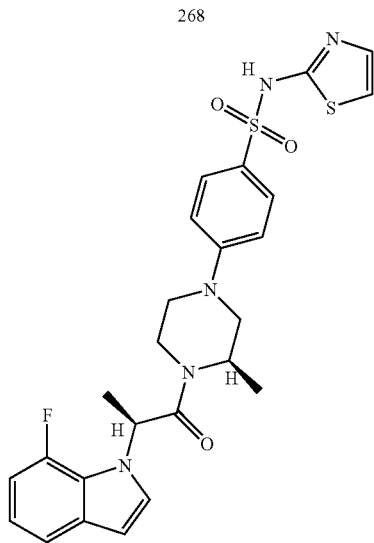
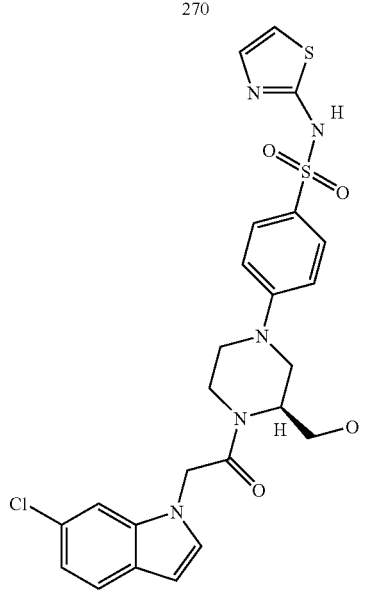
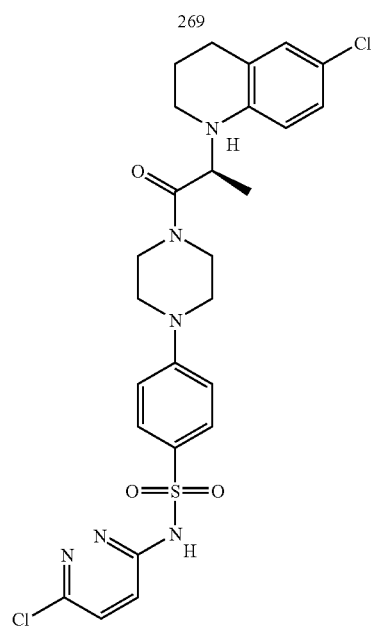
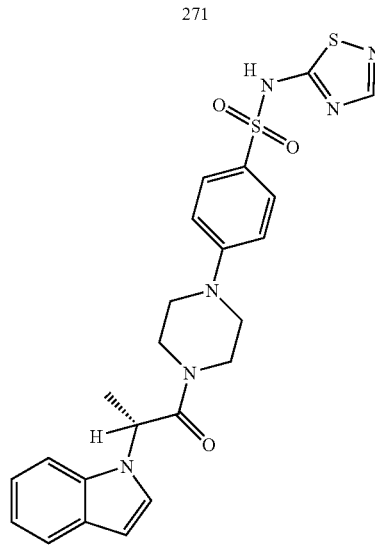

TABLE 2-continued
272
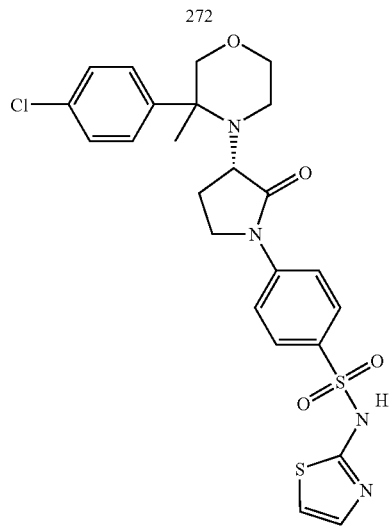
273
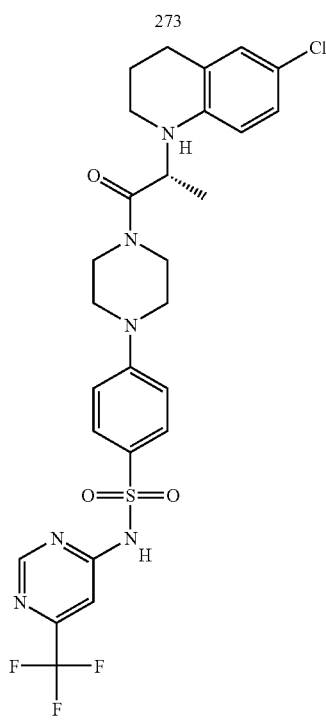
TABLE 2-continued
274
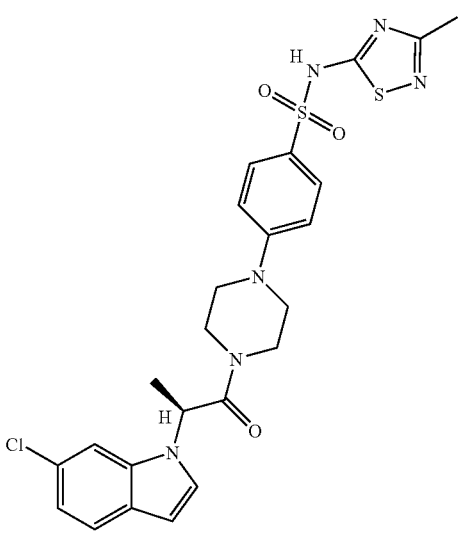
275
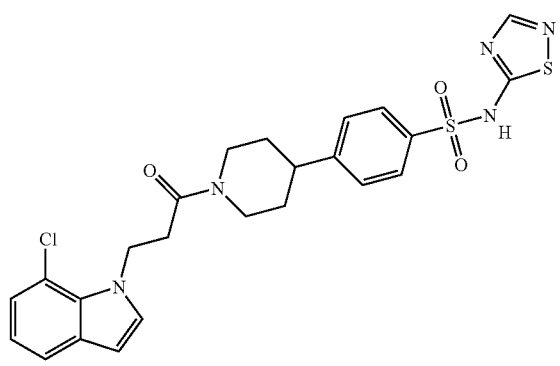

TABLE 2-continued
276
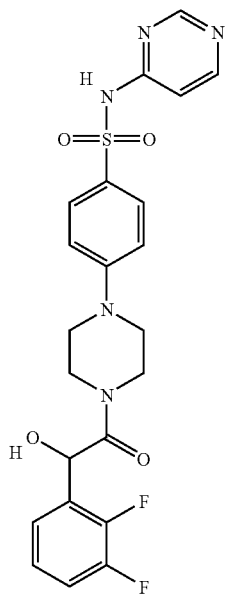
277
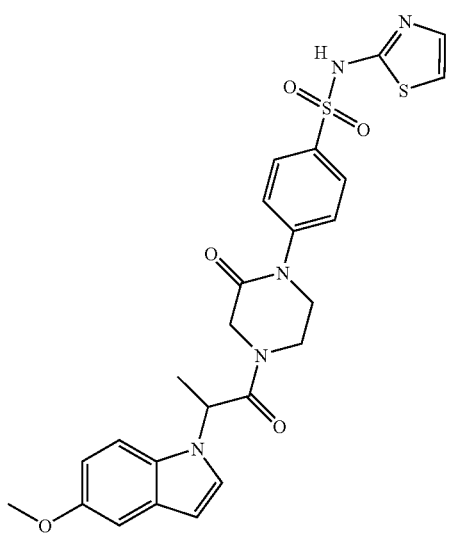
TABLE 2-continued
278
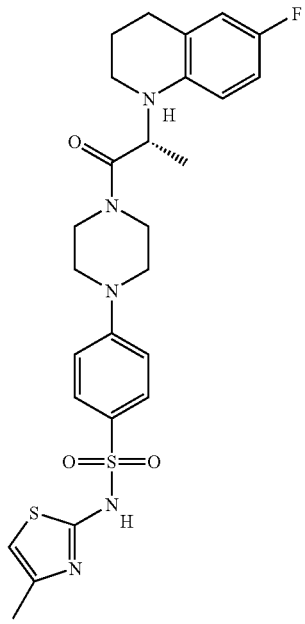
279
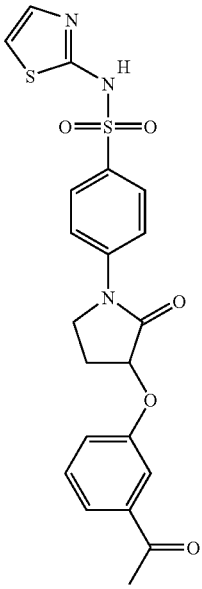

TABLE 2-continued
280
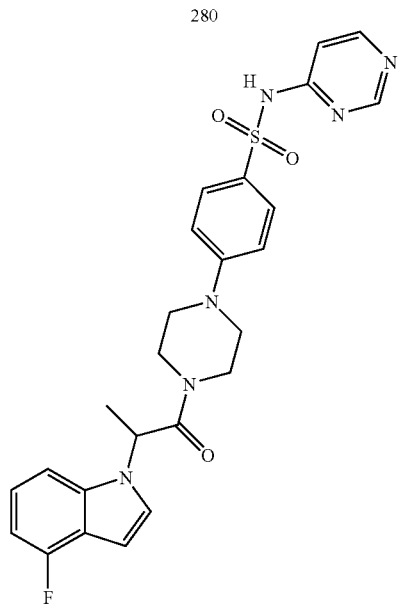
281
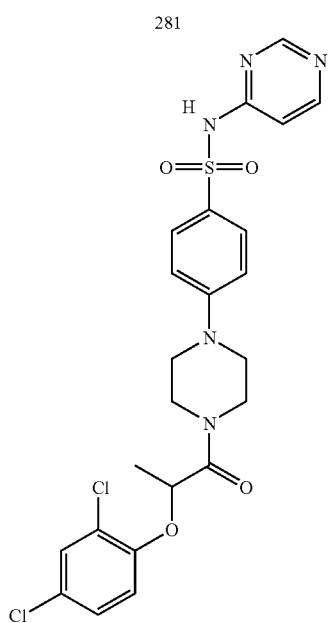
TABLE 2-continued
282
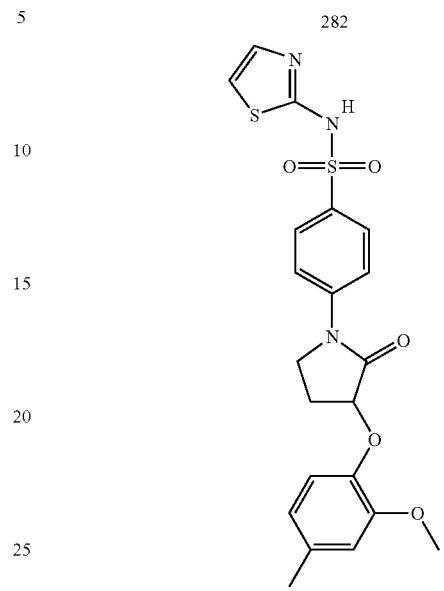
283
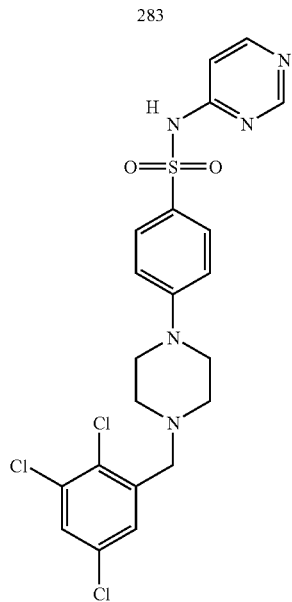

TABLE 2-continued
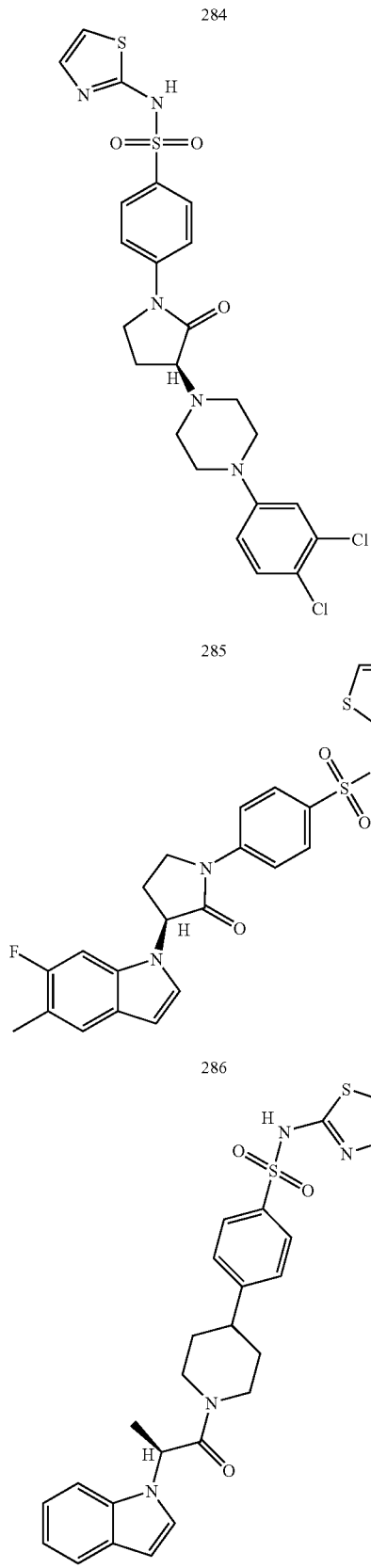
TABLE 2-continued
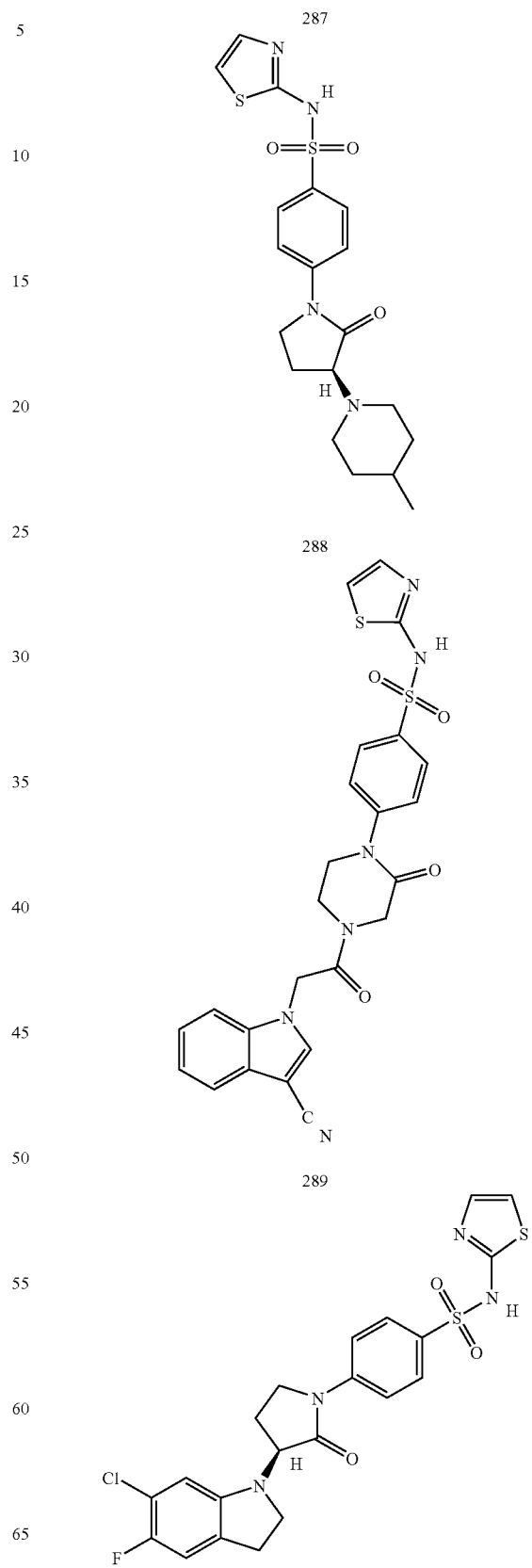

TABLE 2-continued
290
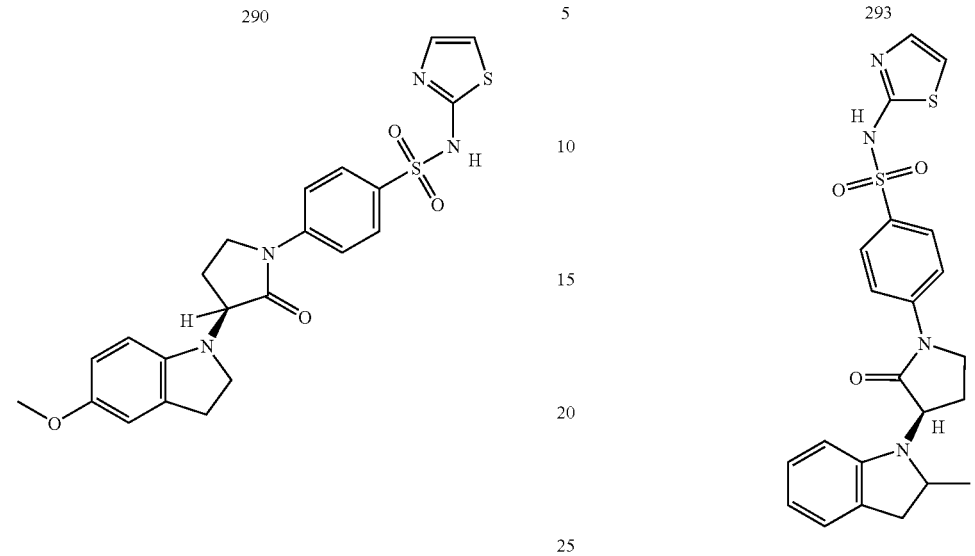
291
293
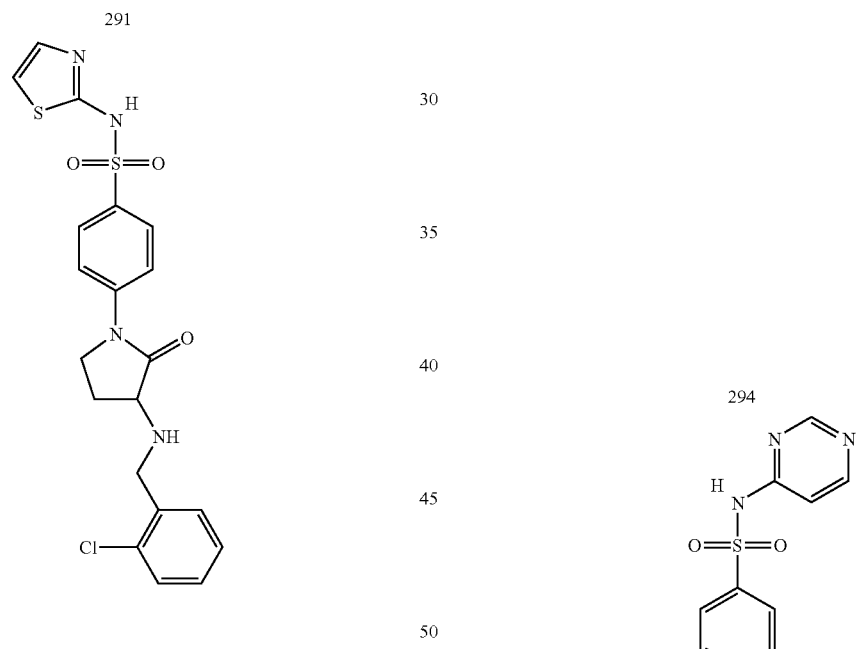
292
294
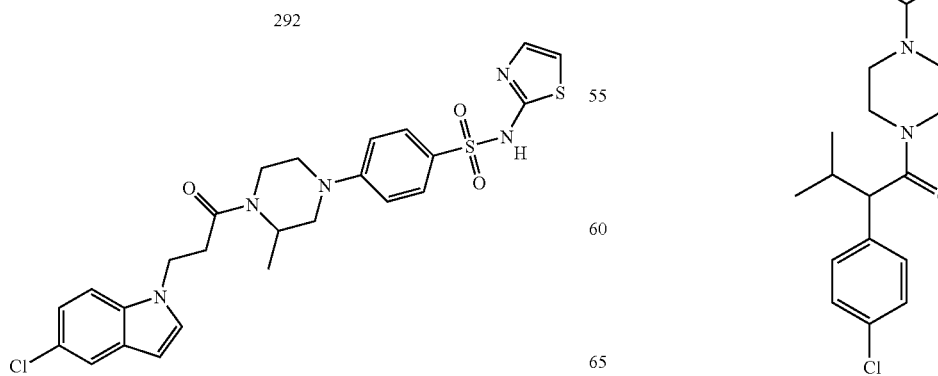

TABLE 2-continued
295
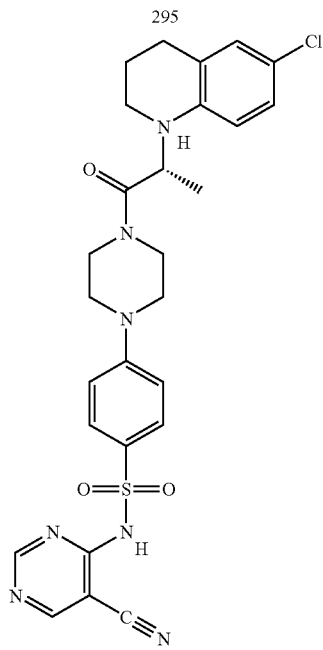
296
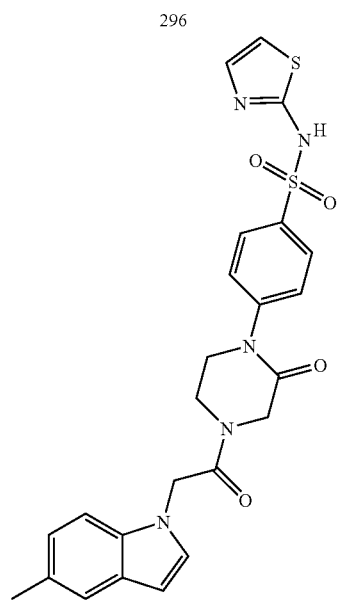
TABLE 2-continued
297
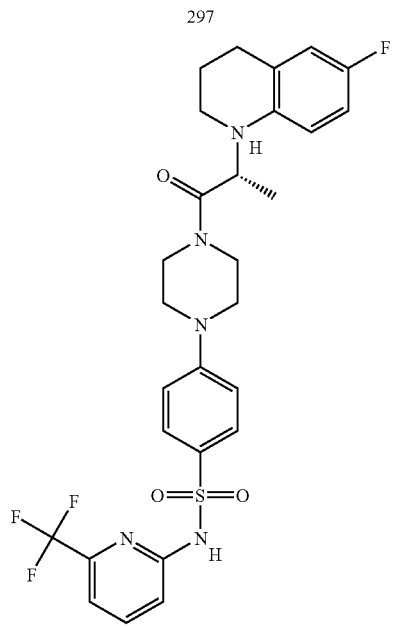
298
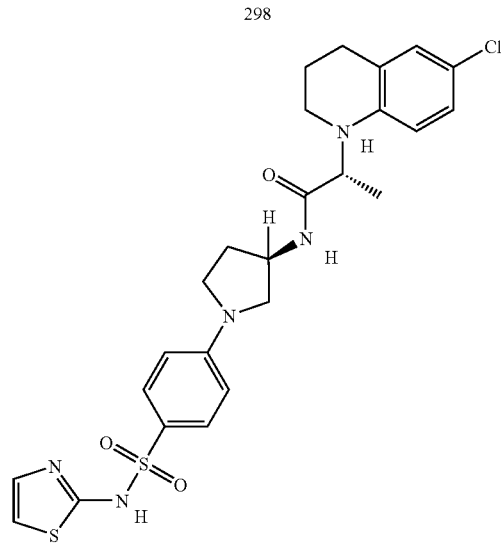

TABLE 2-continued
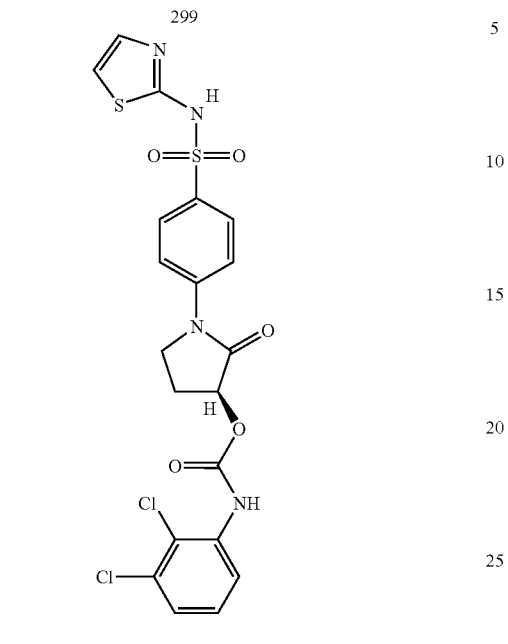
299
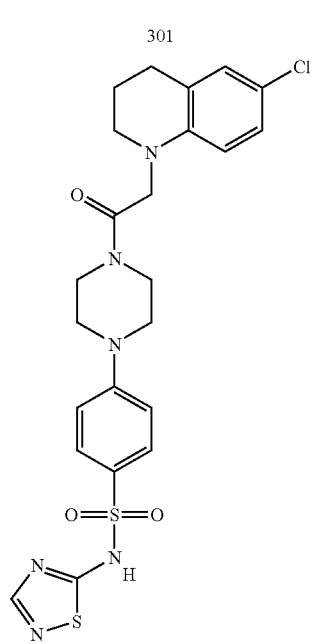
301
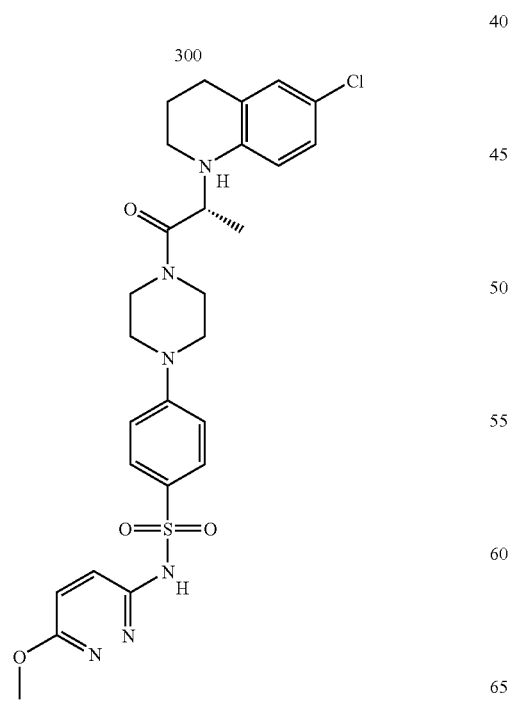
300
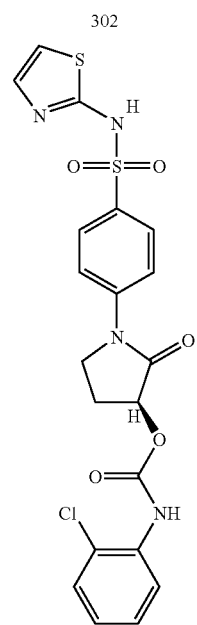
302

TABLE 2-continued
303
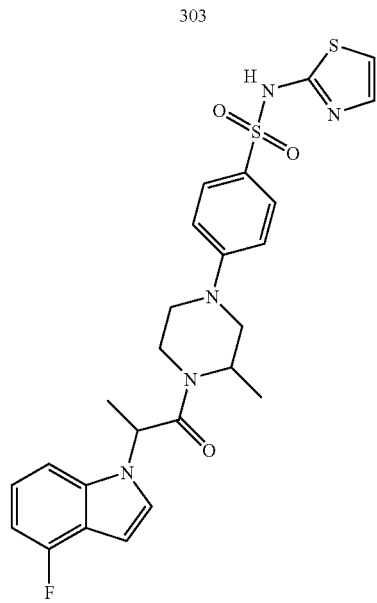
304
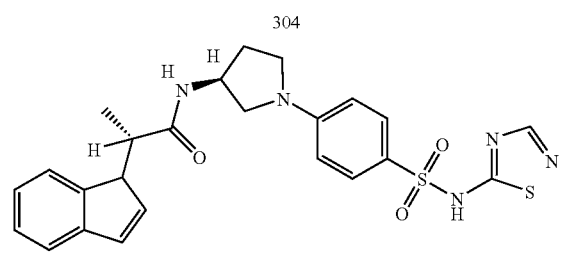
305
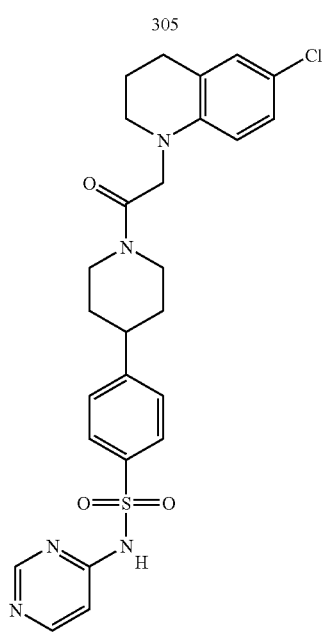
TABLE 2-continued
306
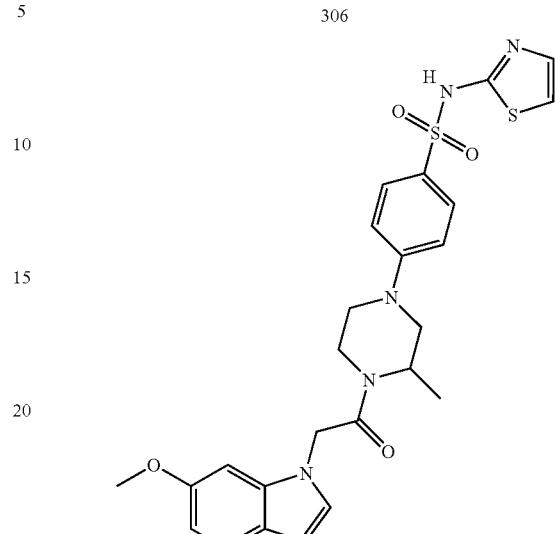
307
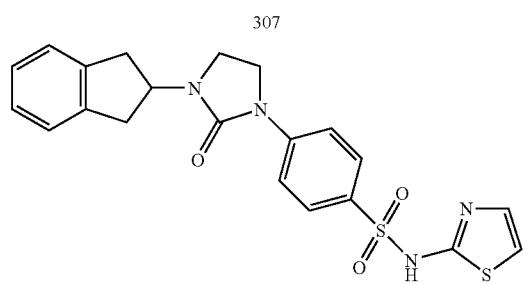
308
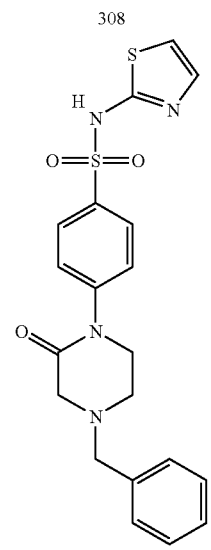

TABLE 2-continued
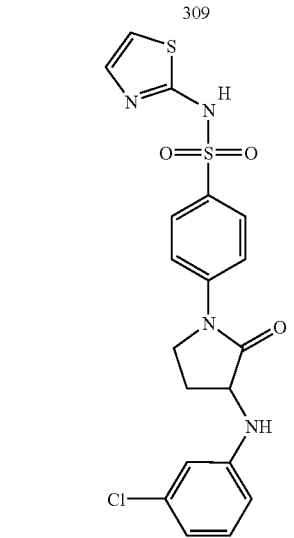
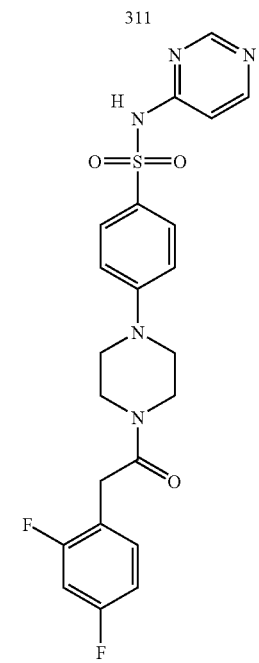
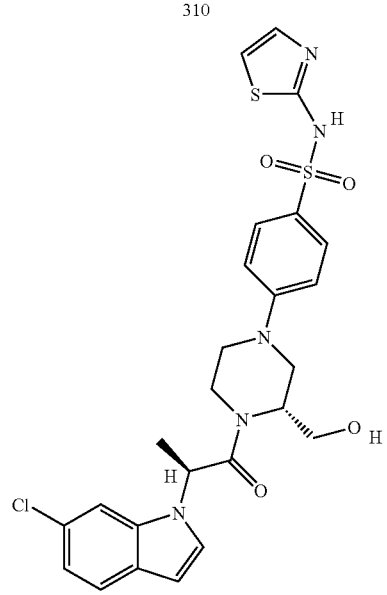
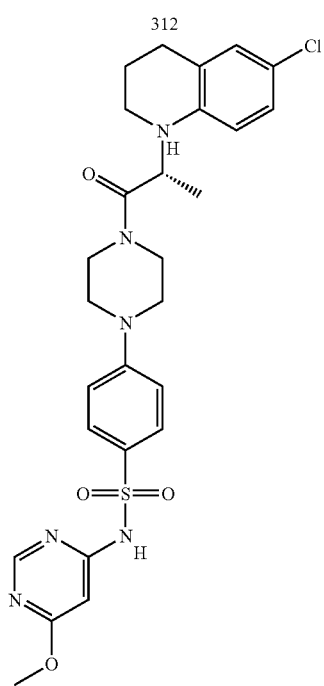

TABLE 2-continued
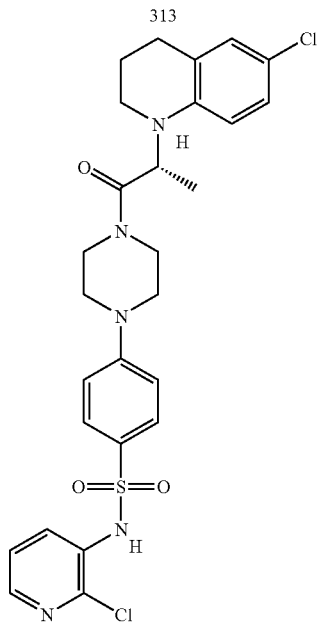
313
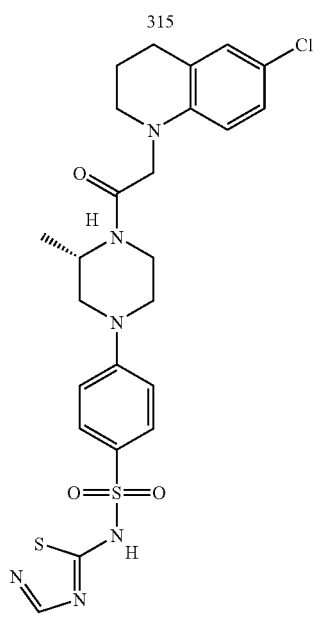
315
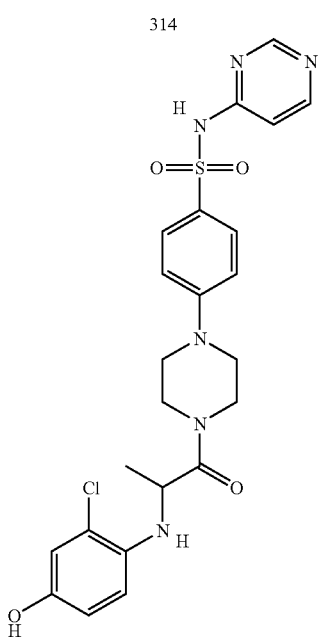
314
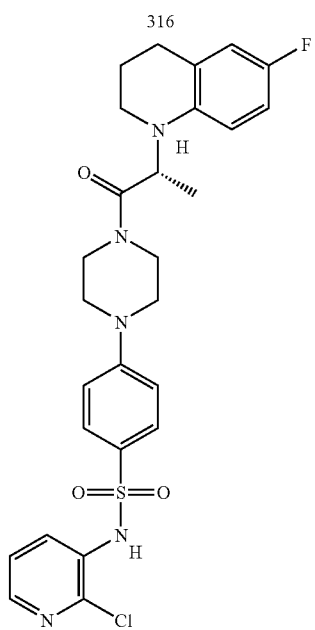
316

TABLE 2-continued
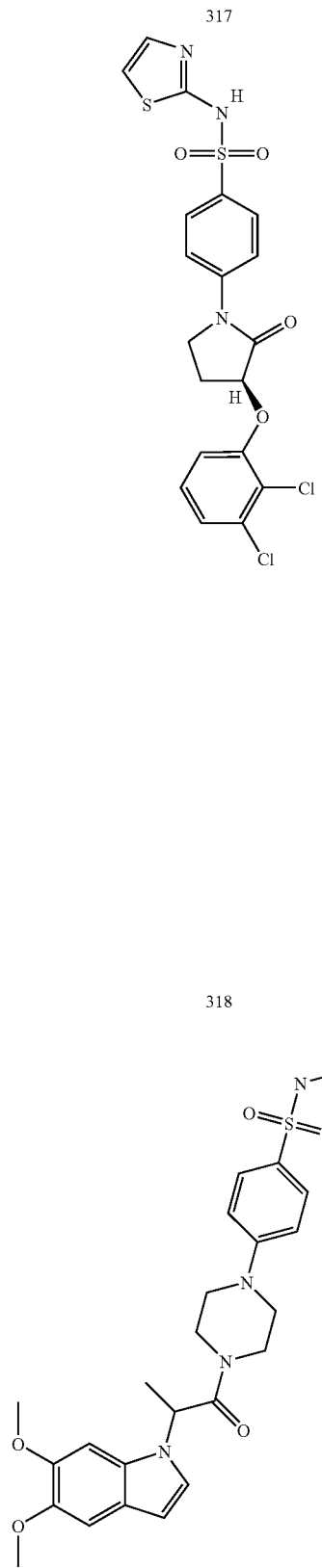
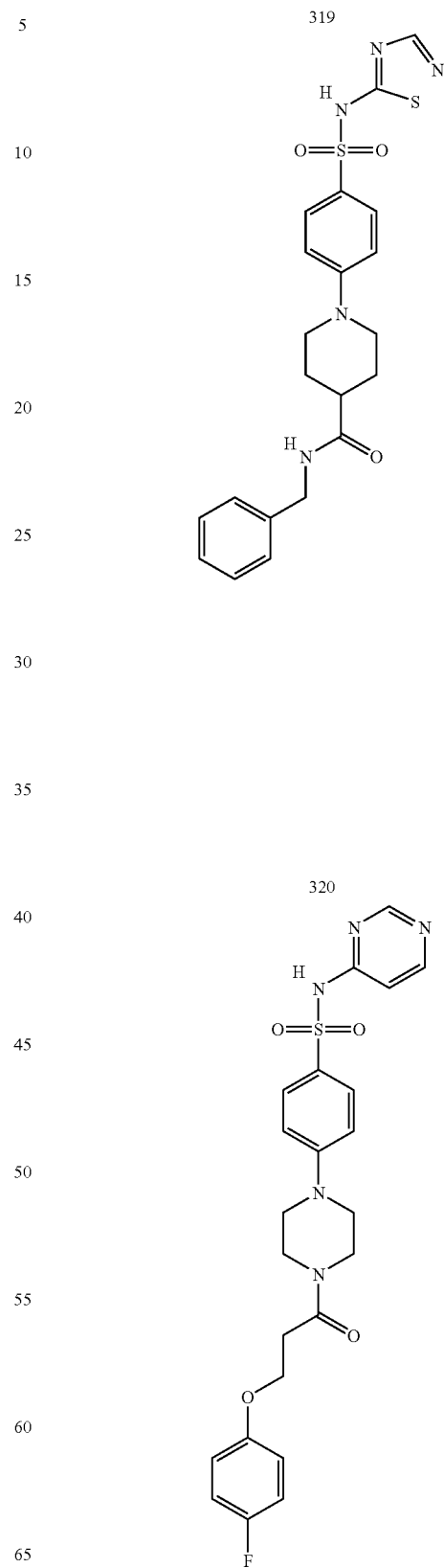

TABLE 2-continued
321
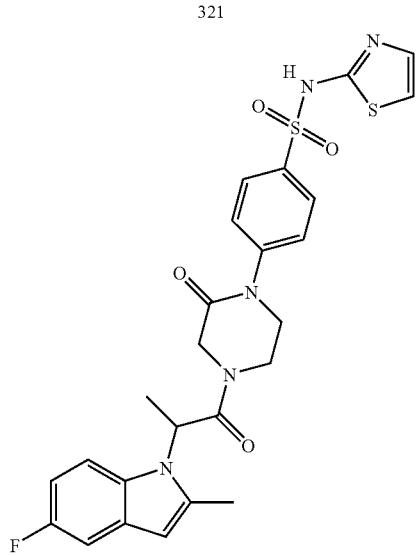
322
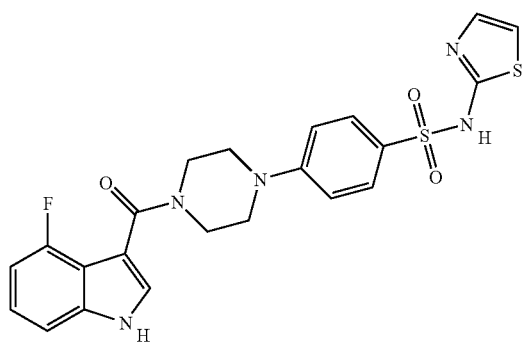
323
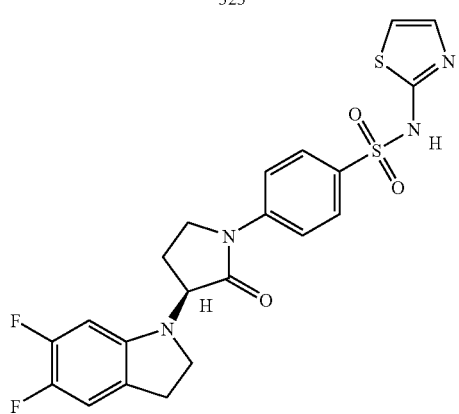
TABLE 2-continued
324
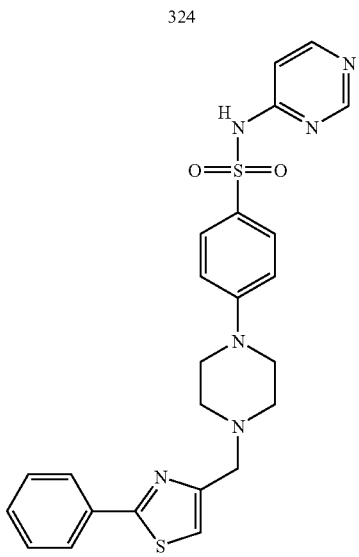
325
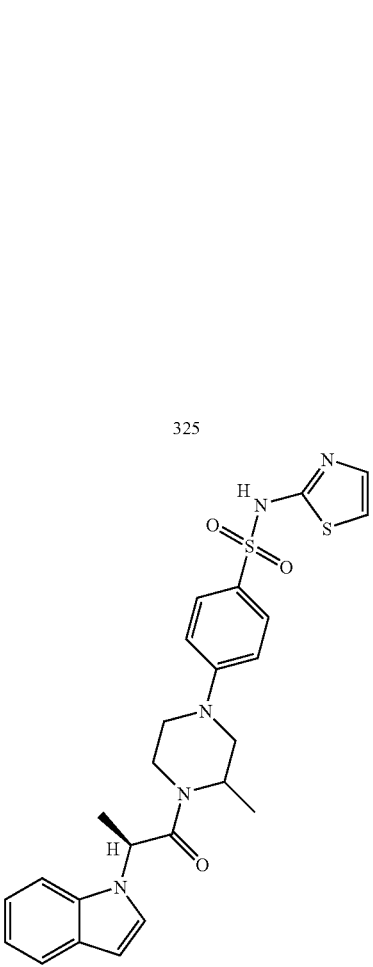

TABLE 2-continued
327
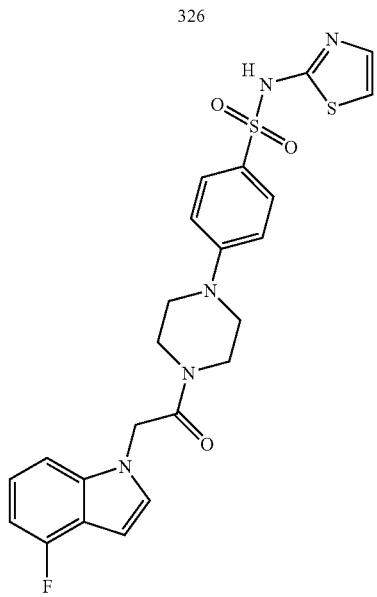
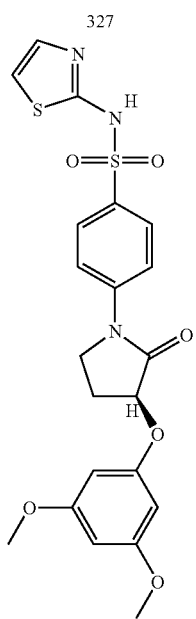
TABLE 2-continued
328
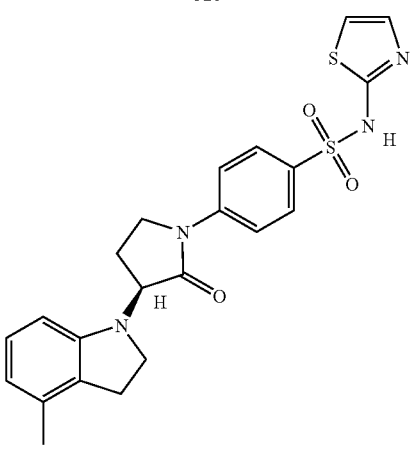
329
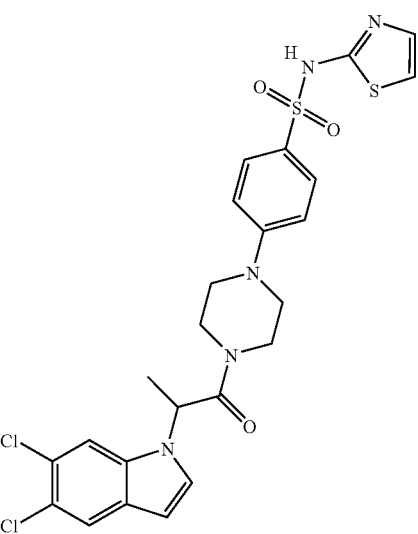

TABLE 2-continued
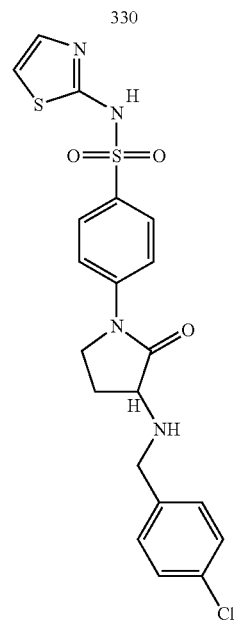
330
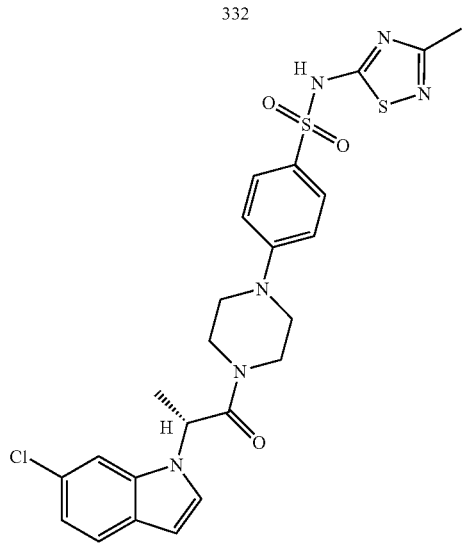
332
TABLE 2-continued
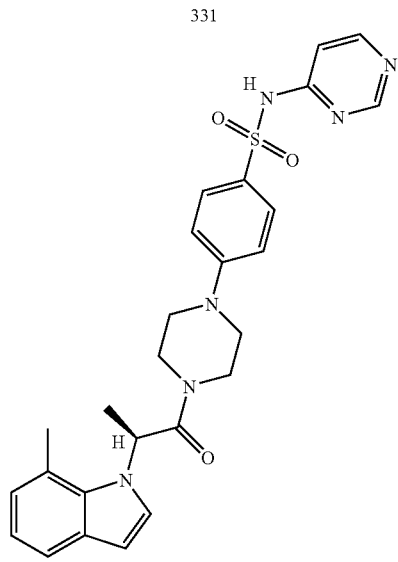
331
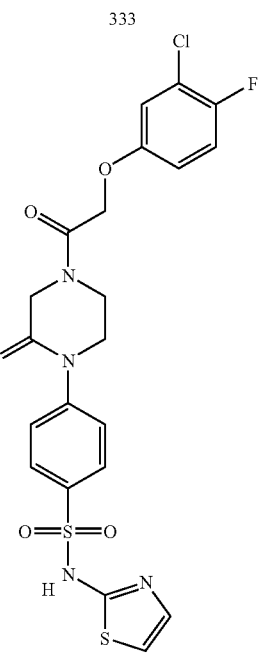
333

TABLE 2-continued
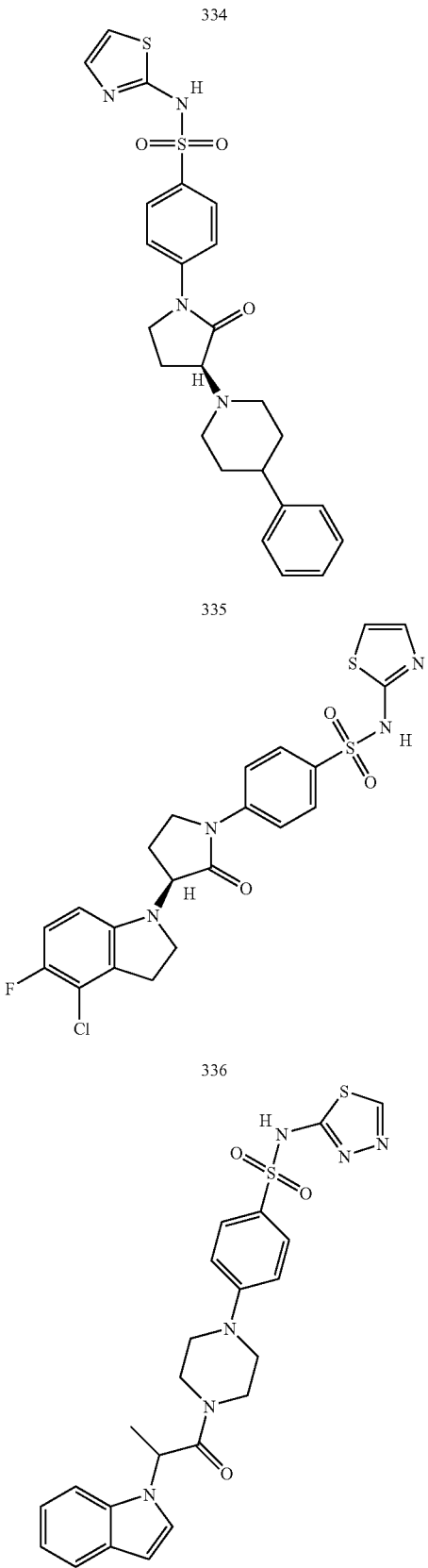
334
335
336
TABLE 2-continued
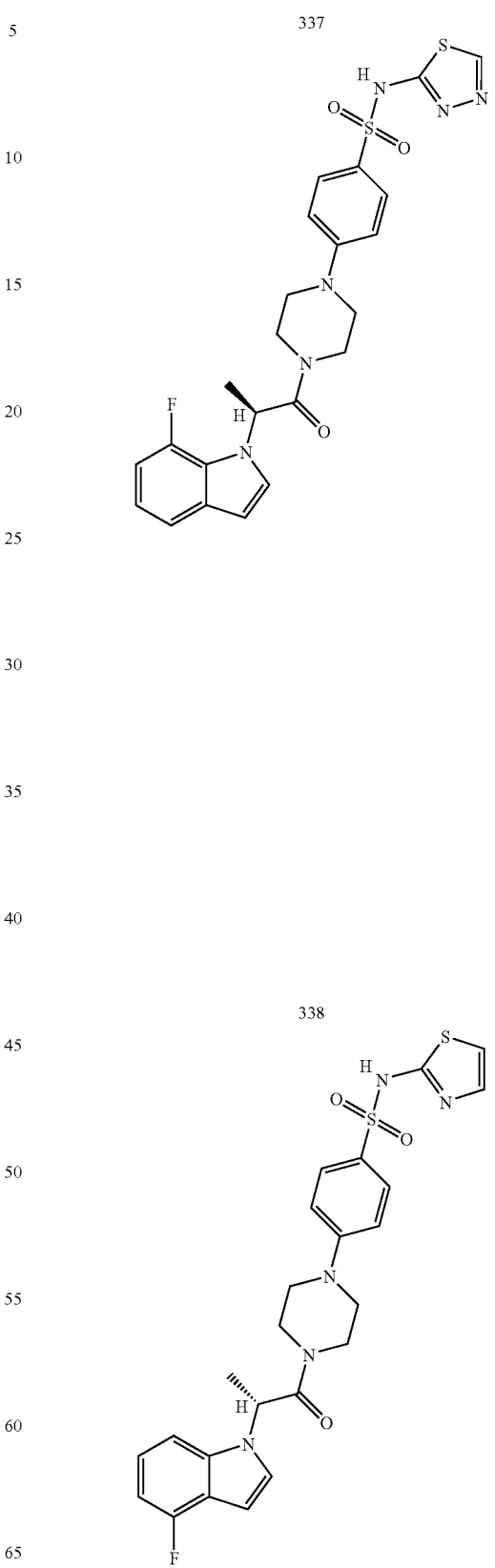
337
338

TABLE 2-continued
TABLE 2-continued
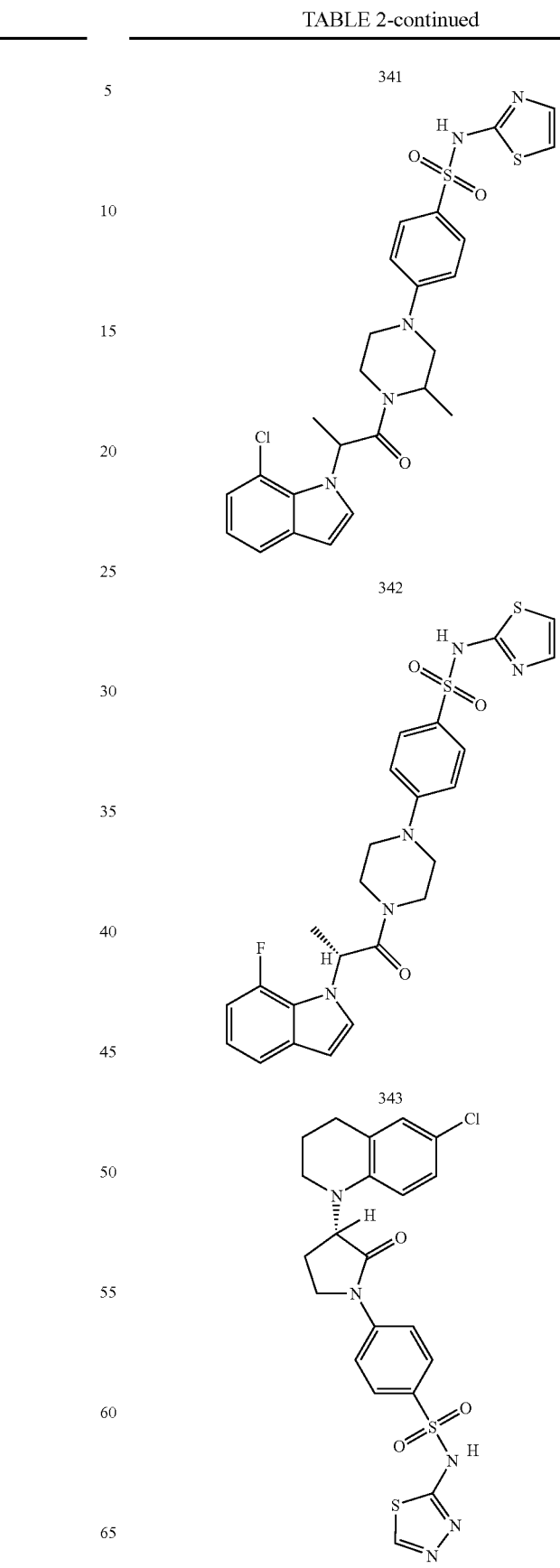

TABLE 2-continued
344
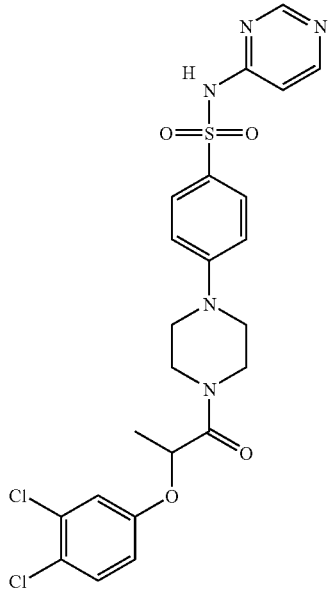
345
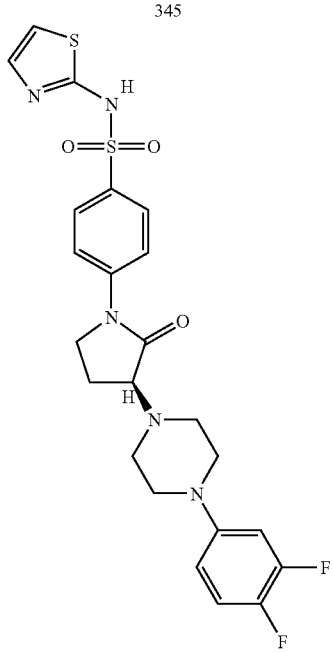
TABLE 2-continued
346
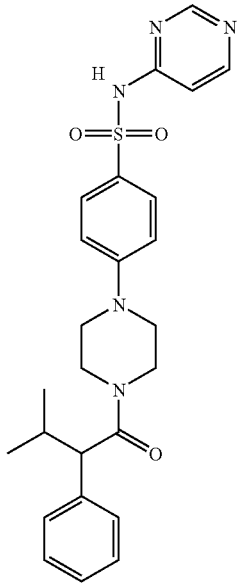
347
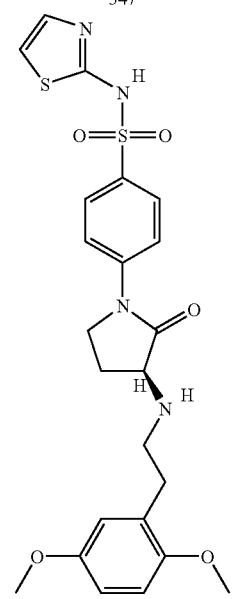

TABLE 2-continued
348
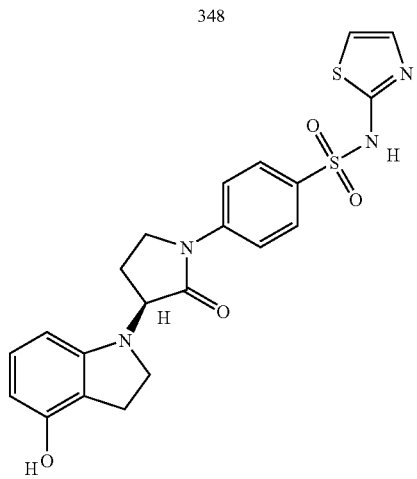
349
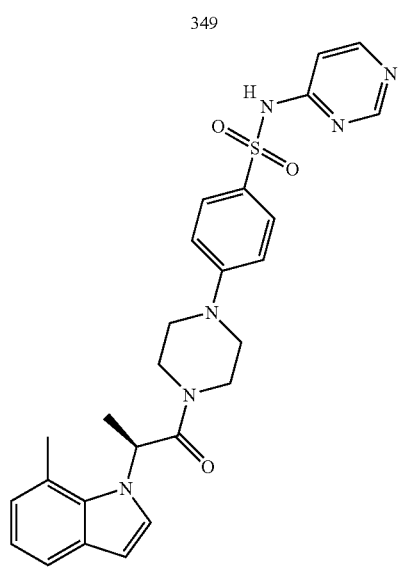
350
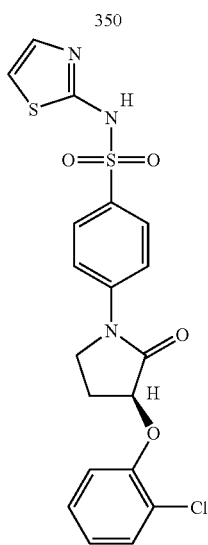
TABLE 2-continued
351
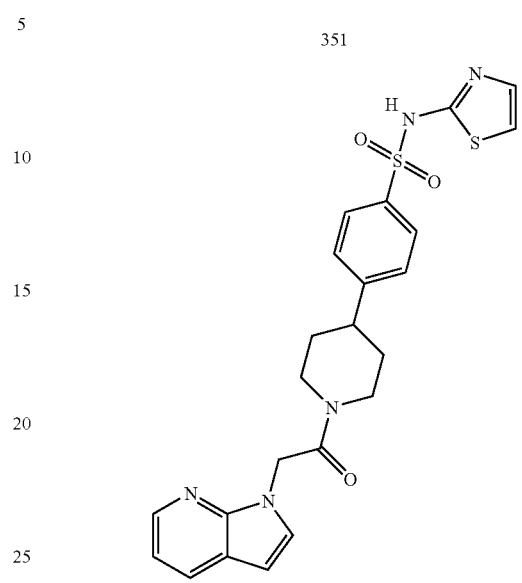
352
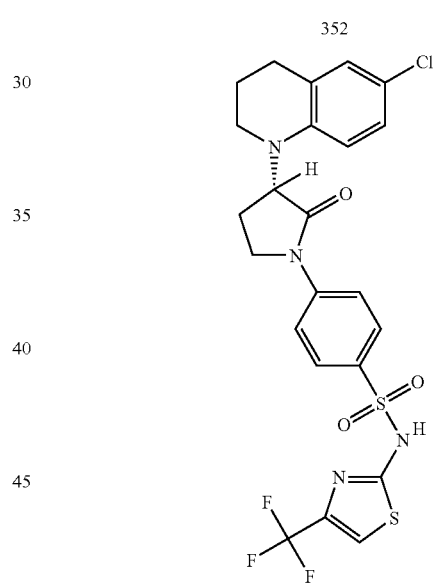
353
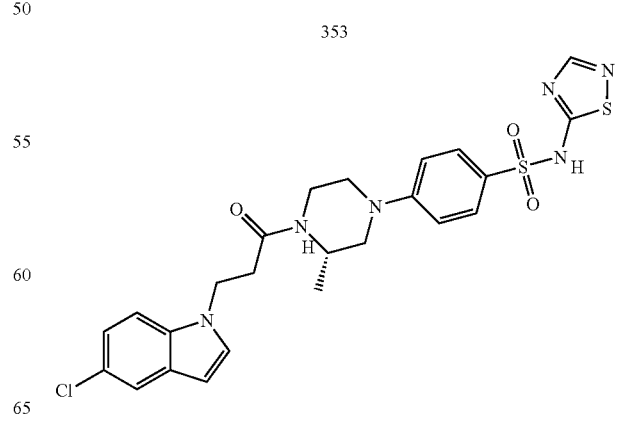

TABLE 2-continued
354
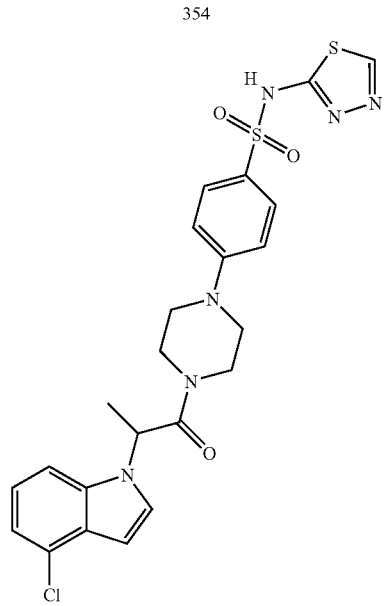
355
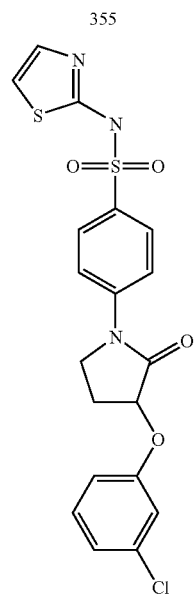
TABLE 2-continued
356
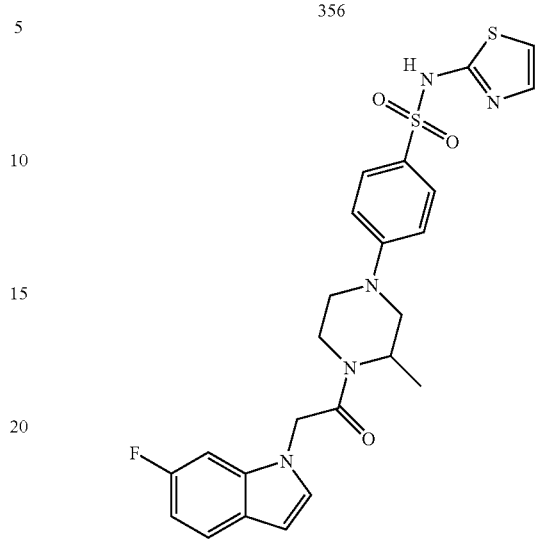
357
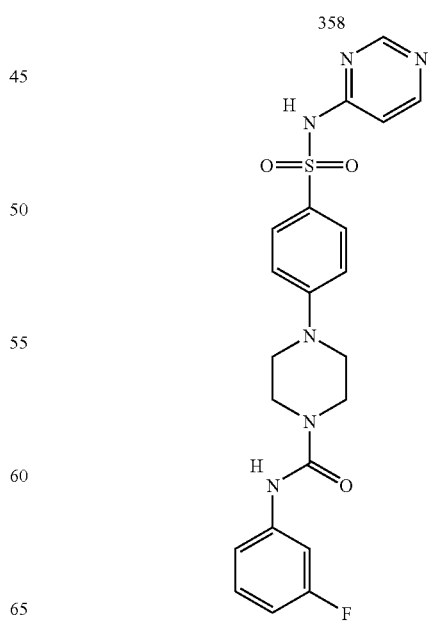
358

TABLE 2-continued
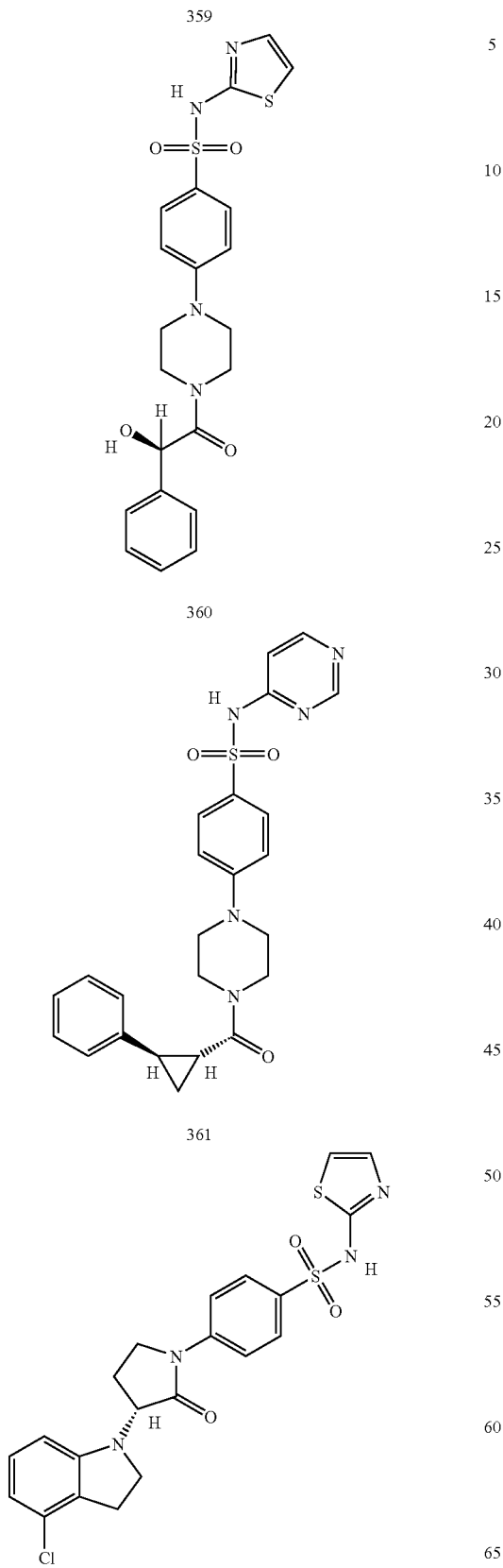
359
360
361
TABLE 2-continued
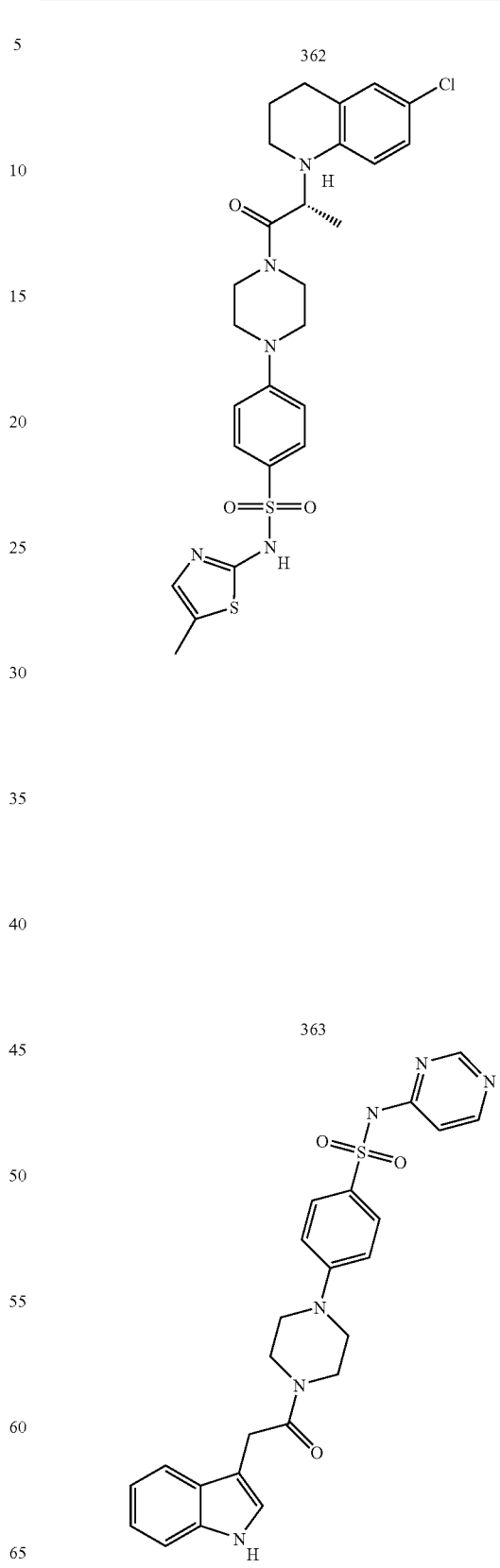
362
363

TABLE 2-continued
364
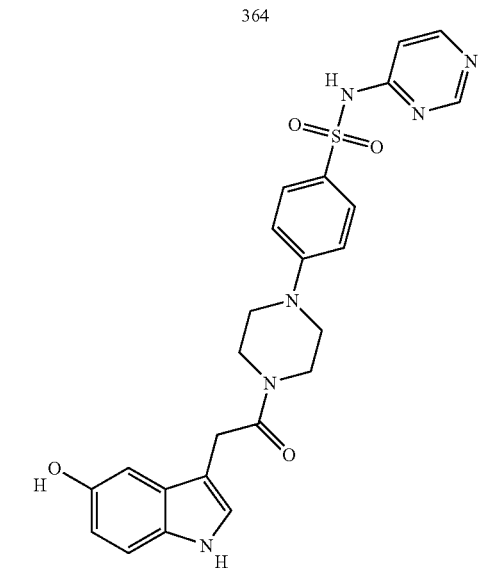
365
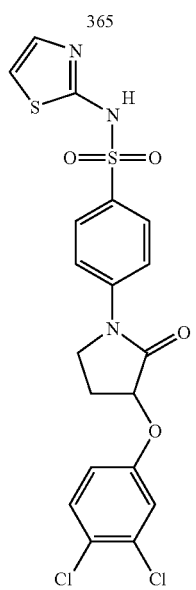
366
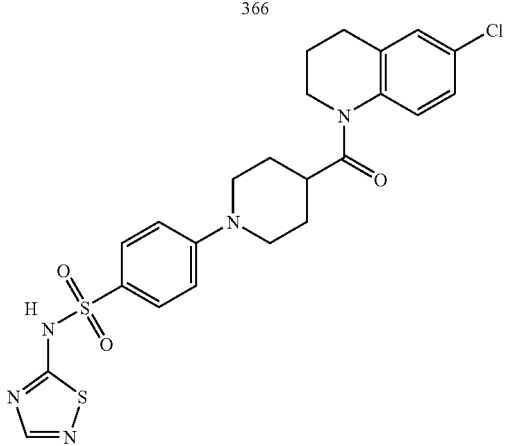
TABLE 2-continued
367
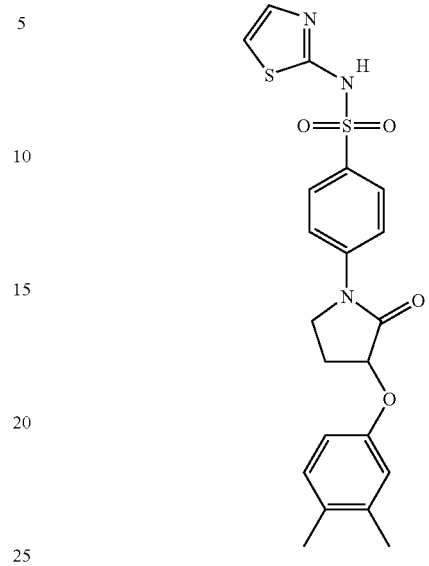
368
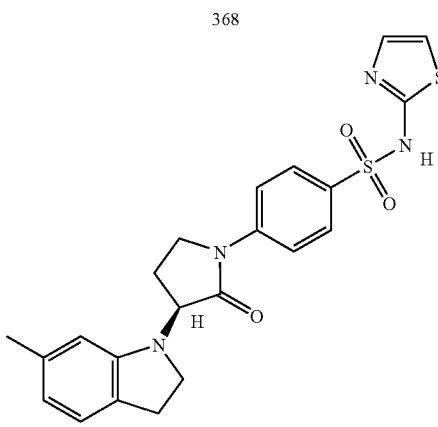
369
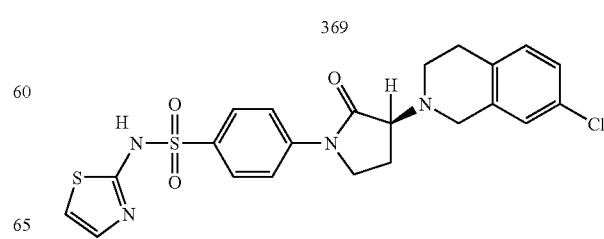

TABLE 2-continued
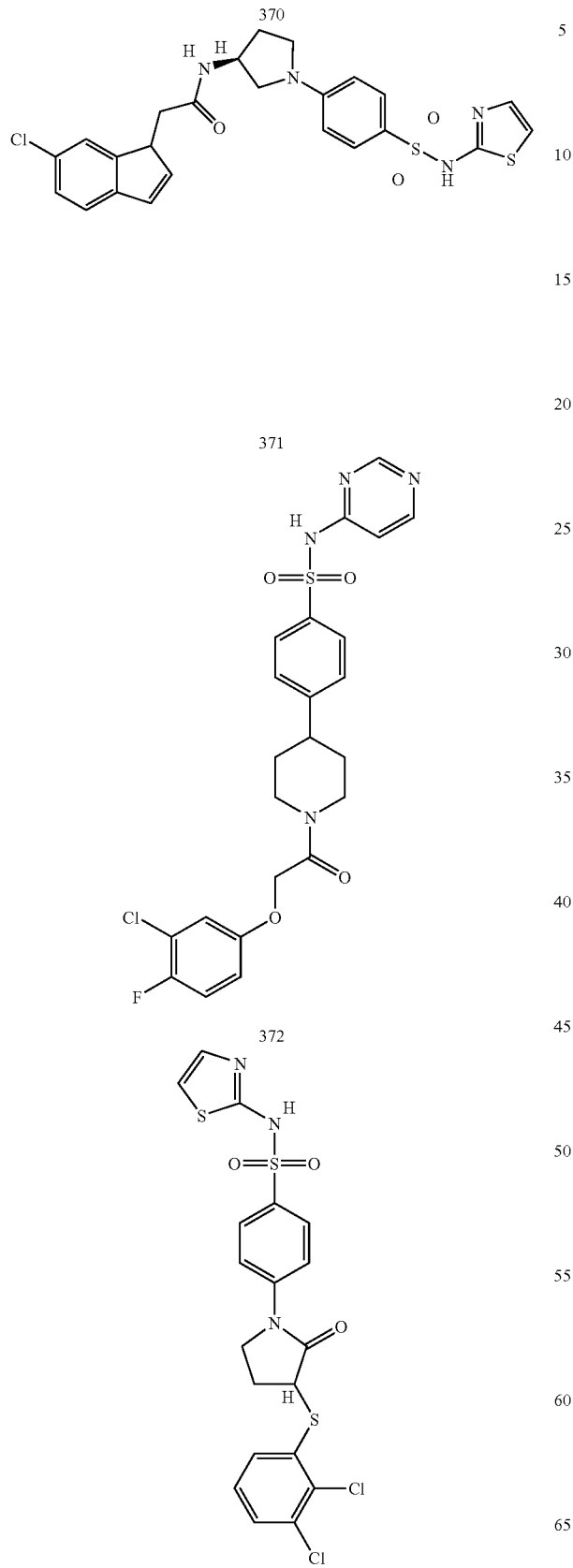
TABLE 2-continued
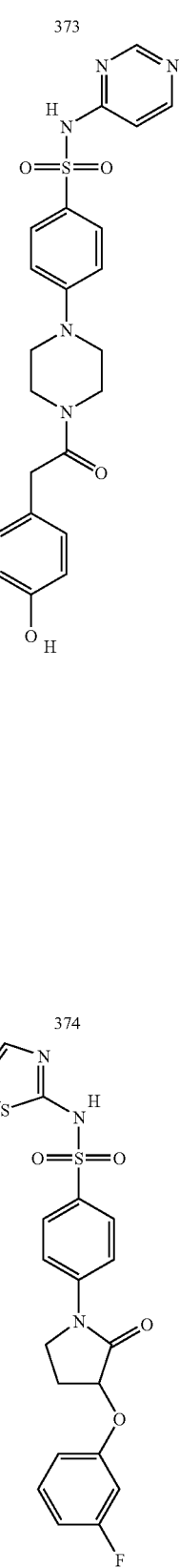

TABLE 2-continued
375
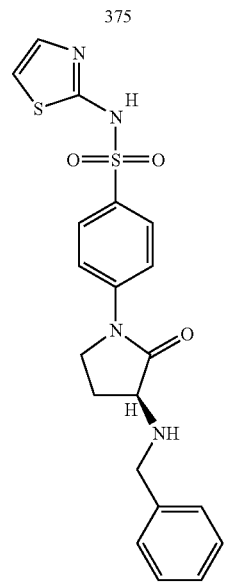
376
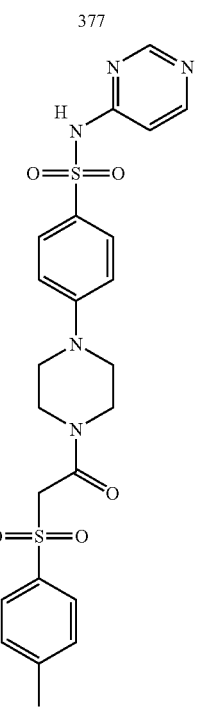
TABLE 2-continued
377
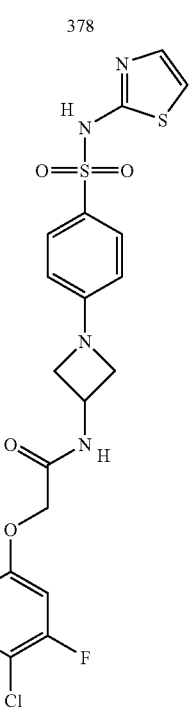
378

TABLE 2-continued
379
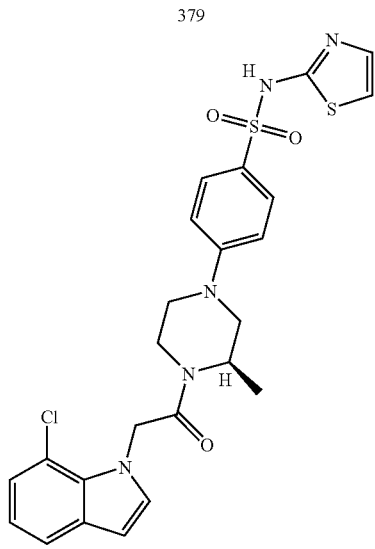
382
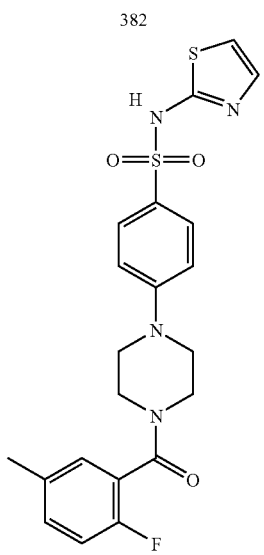
380
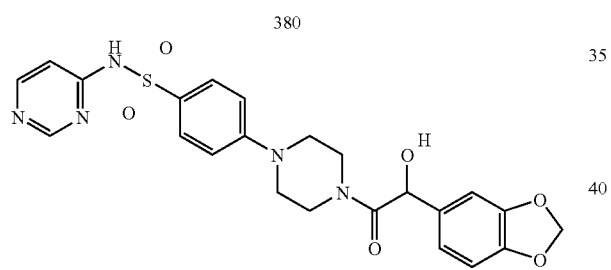
381
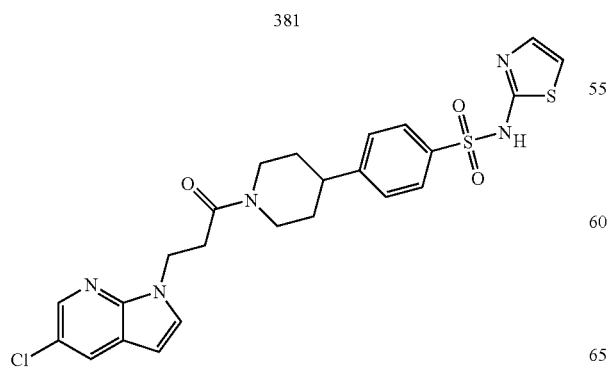
383
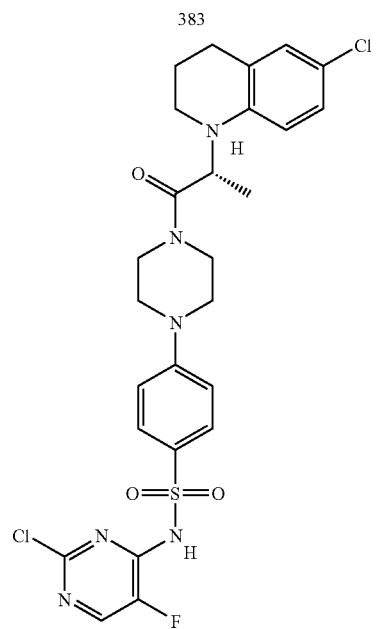

TABLE 2-continued
384
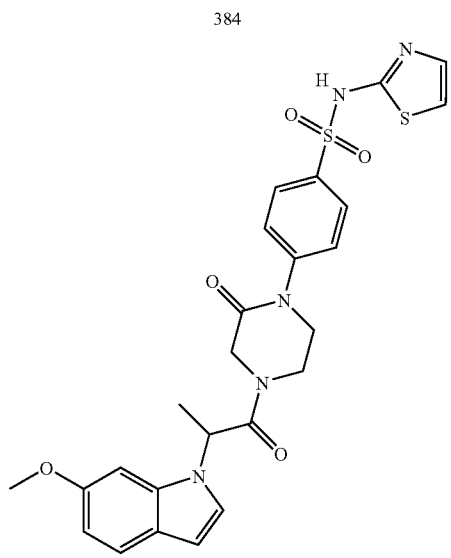
385
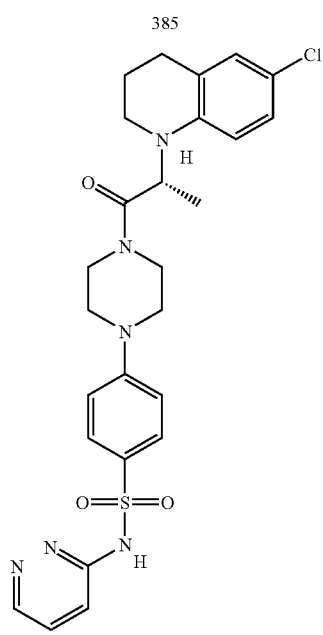
TABLE 2-continued
386
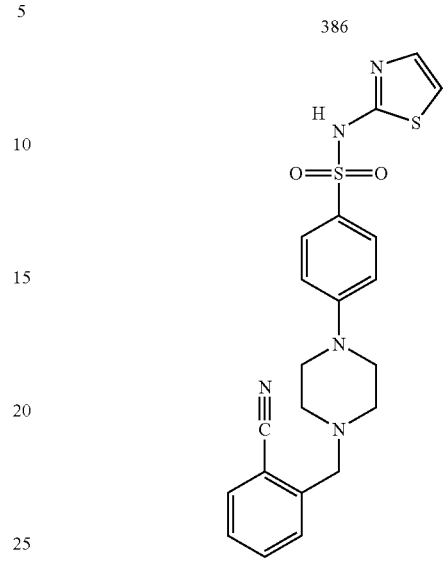
387
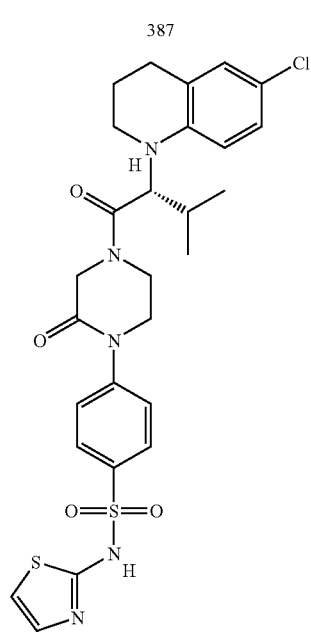

TABLE 2-continued
388
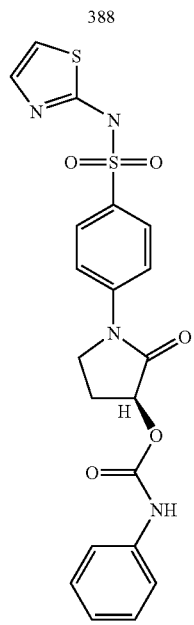
390
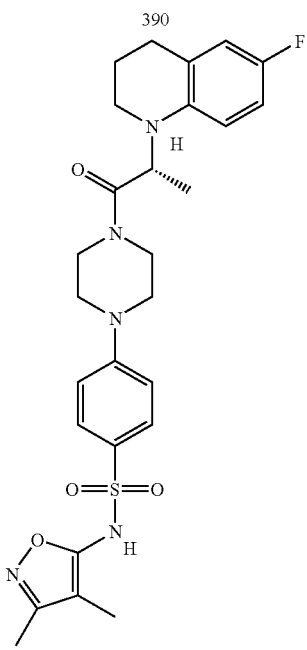
389
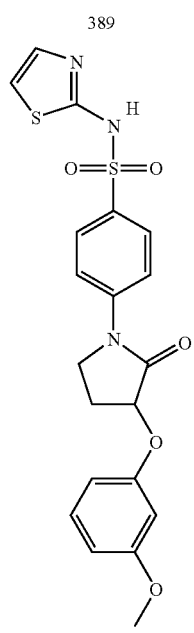
391
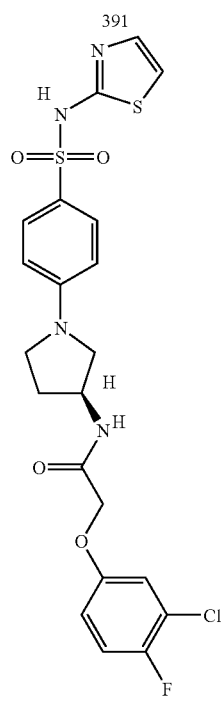

TABLE 2-continued
392
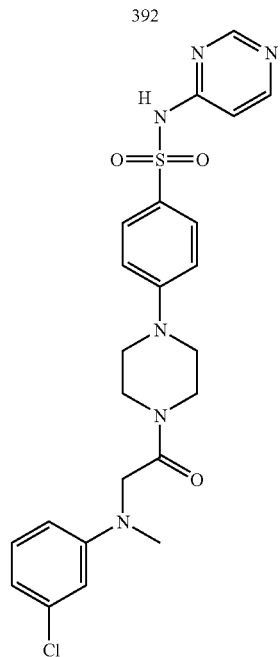
393
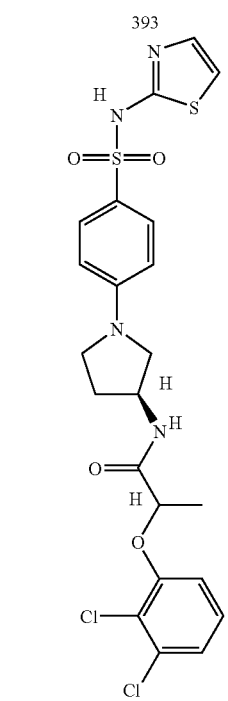
TABLE 2-continued
394
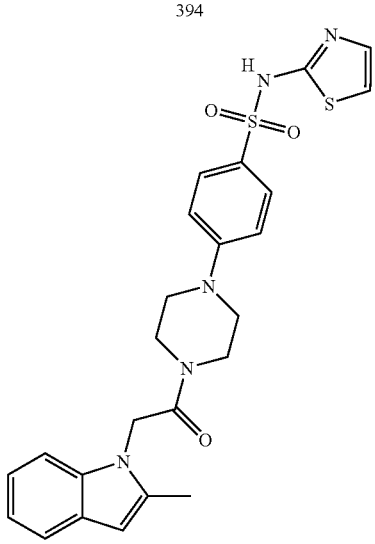
395

TABLE 2-continued
396
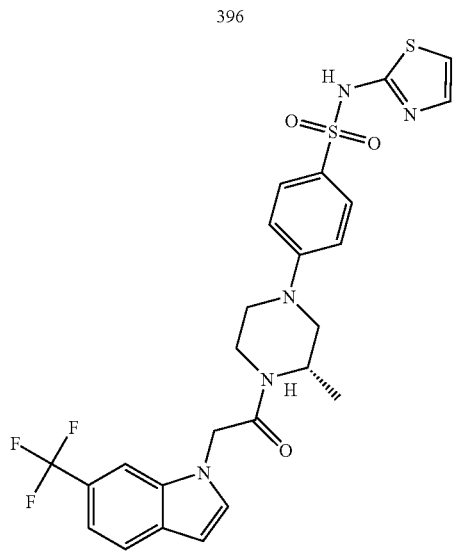
397
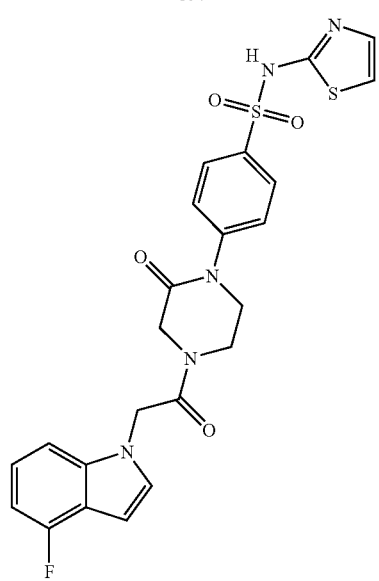
TABLE 2-continued
398
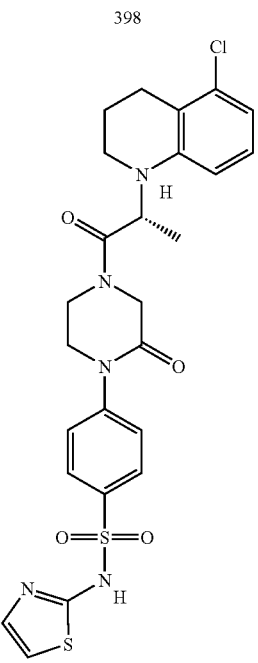
399
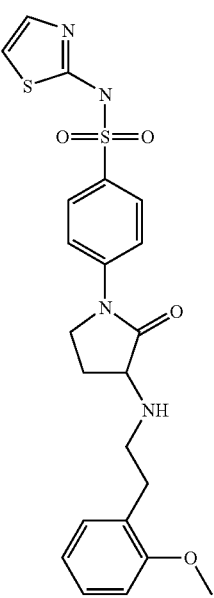

TABLE 2-continued
400
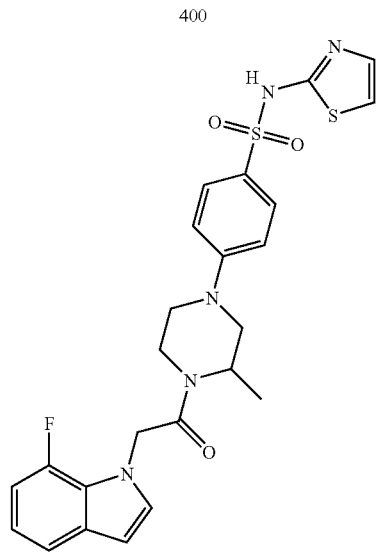
401
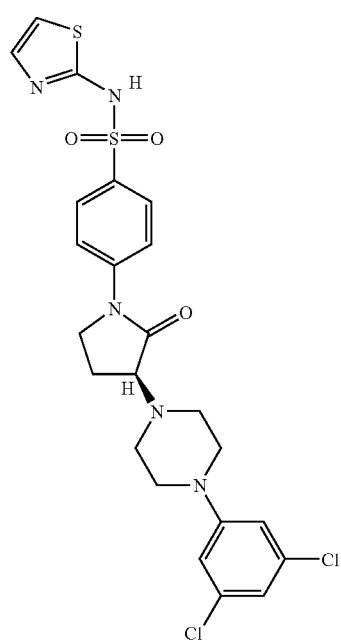
TABLE 2-continued
402
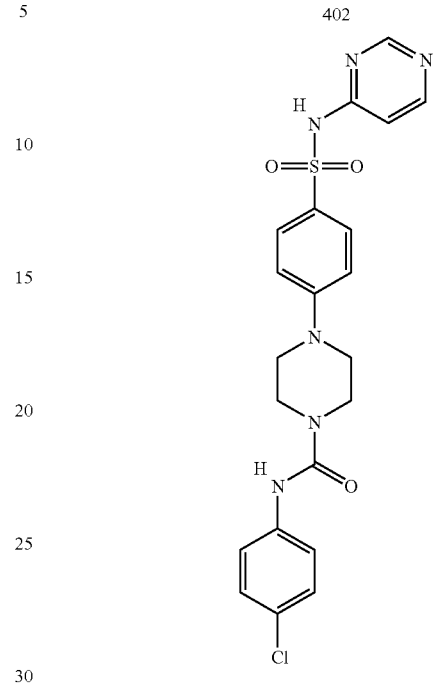
403
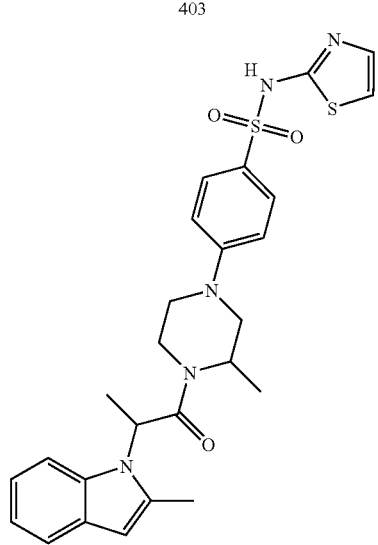

TABLE 2-continued
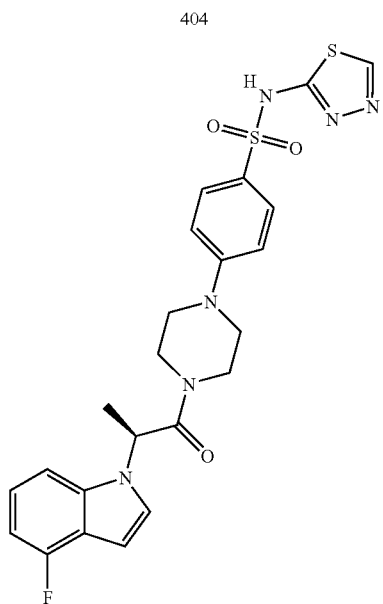
404
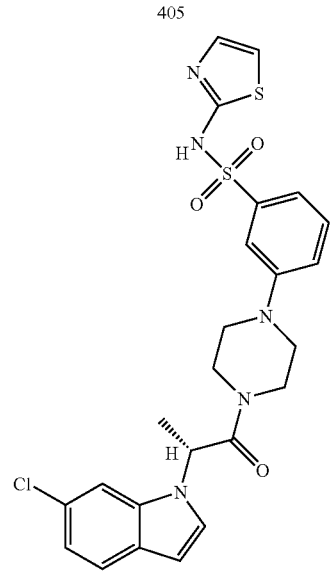
405
TABLE 2-continued
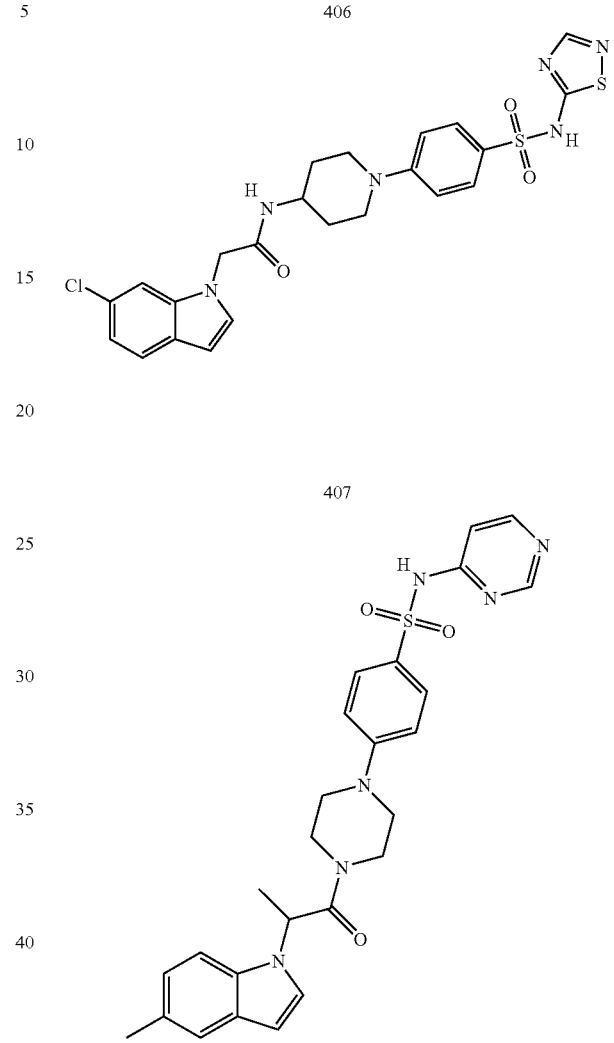
406
407
408

TABLE 2-continued
409
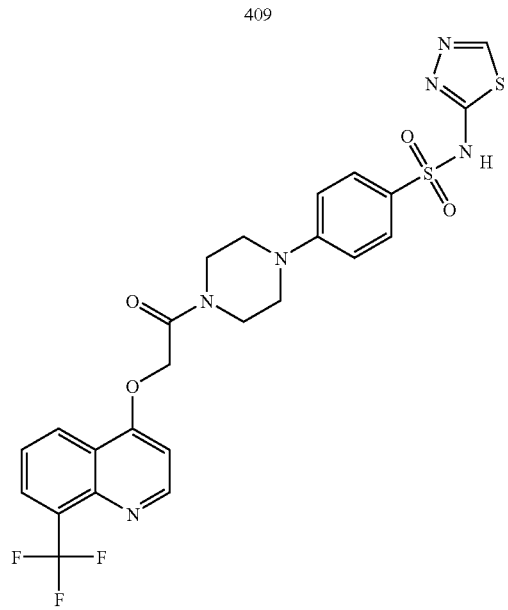
410
411
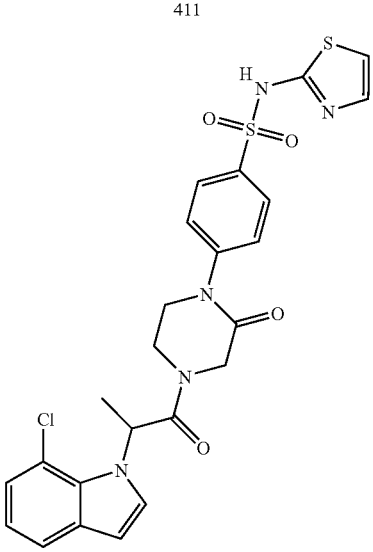
412
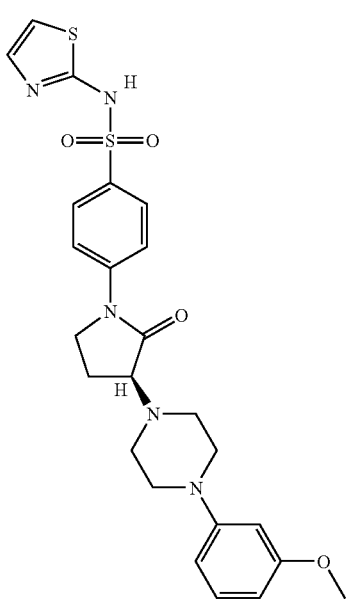

TABLE 2-continued
413
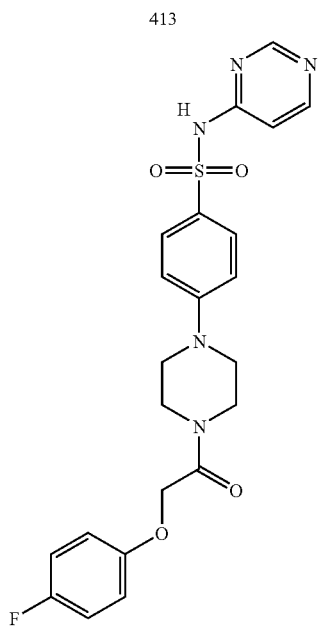
414
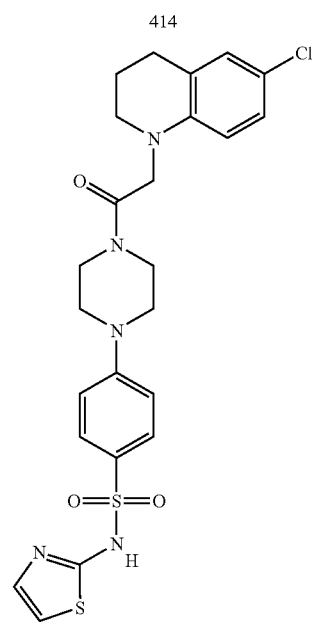
TABLE 2-continued
415
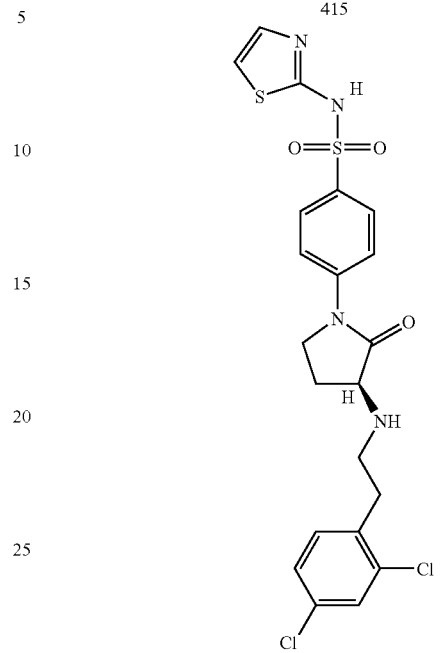
416
417
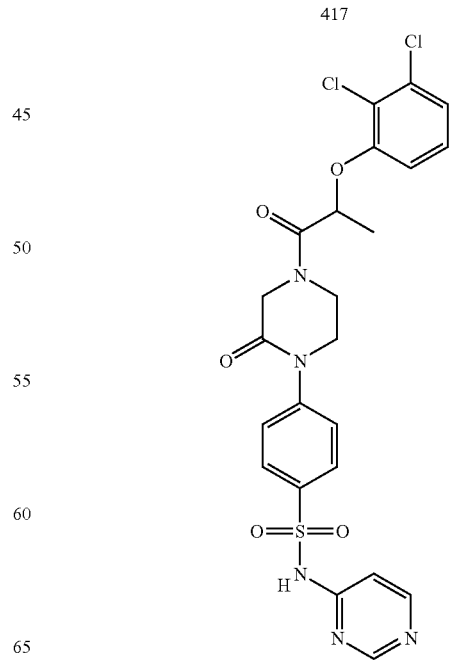

TABLE 2-continued
418
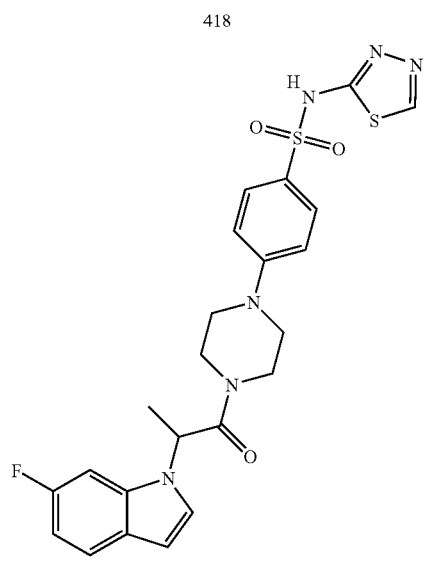
419
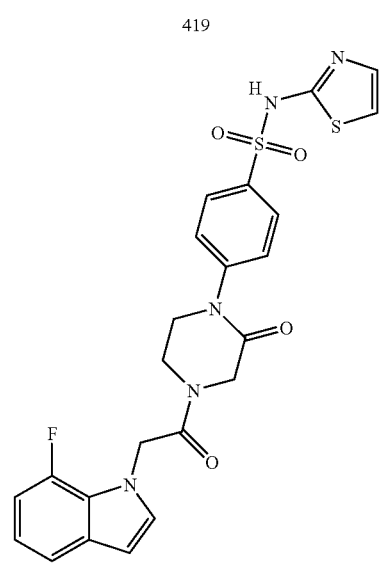
TABLE 2-continued
420
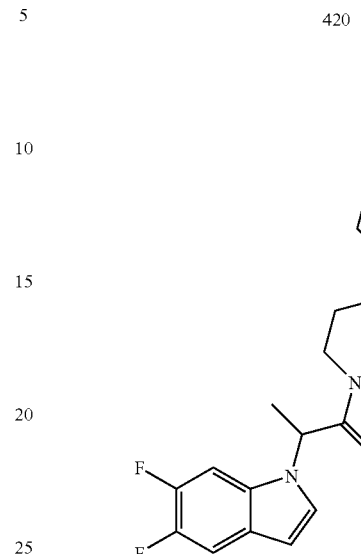
421
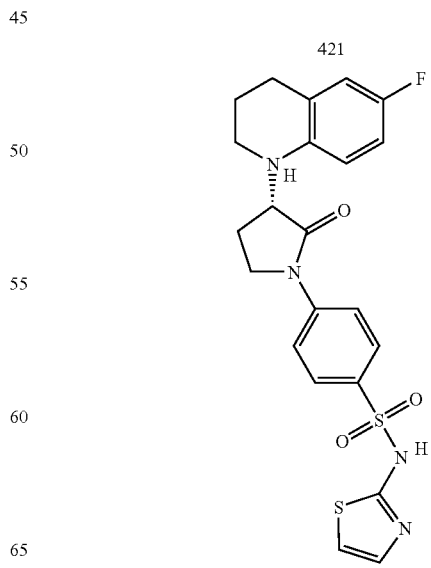

TABLE 2-continued
422
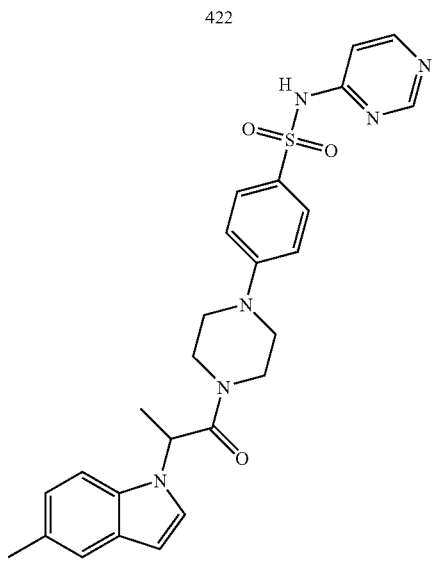
423
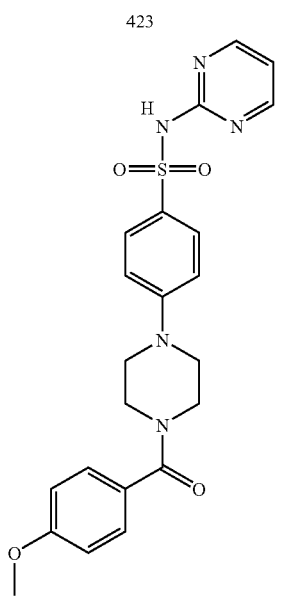
TABLE 2-continued
424
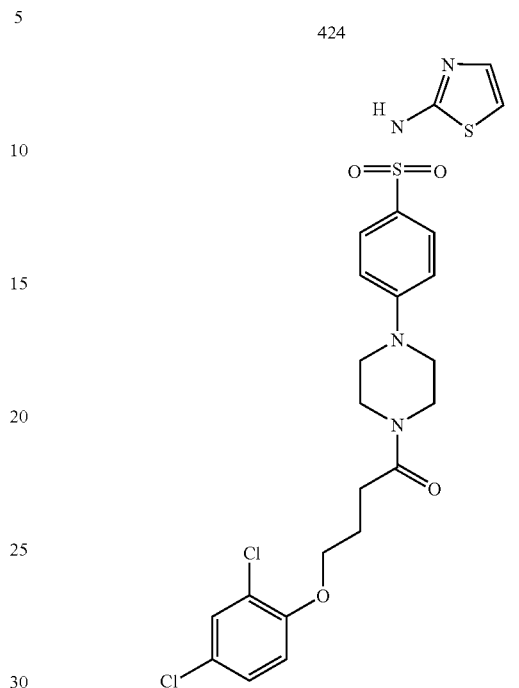
425
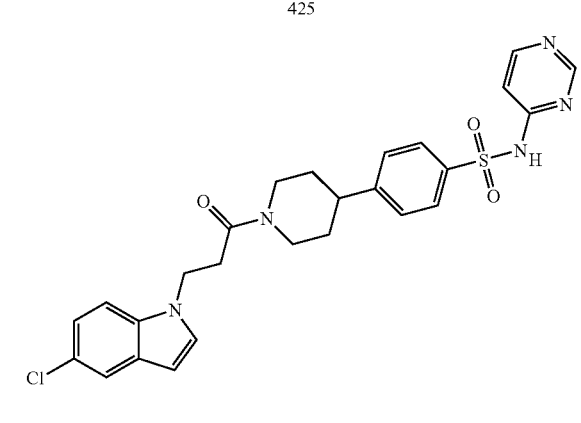

TABLE 2-continued
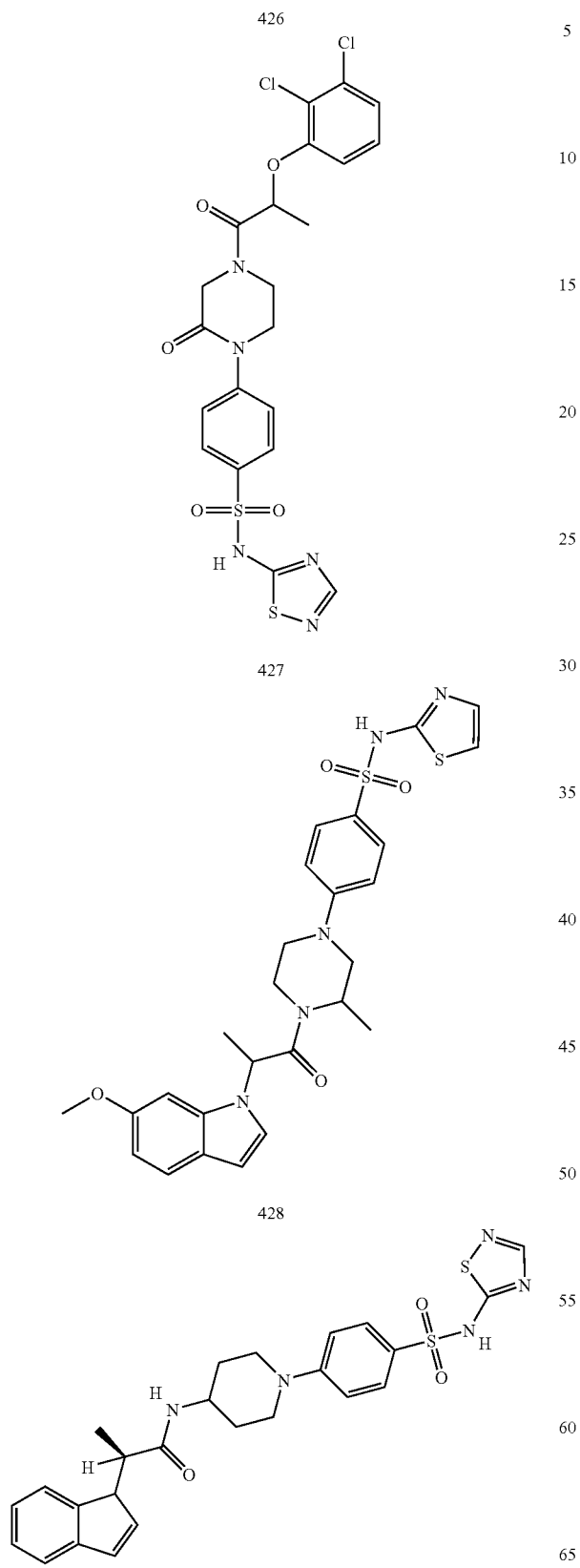
TABLE 2-continued
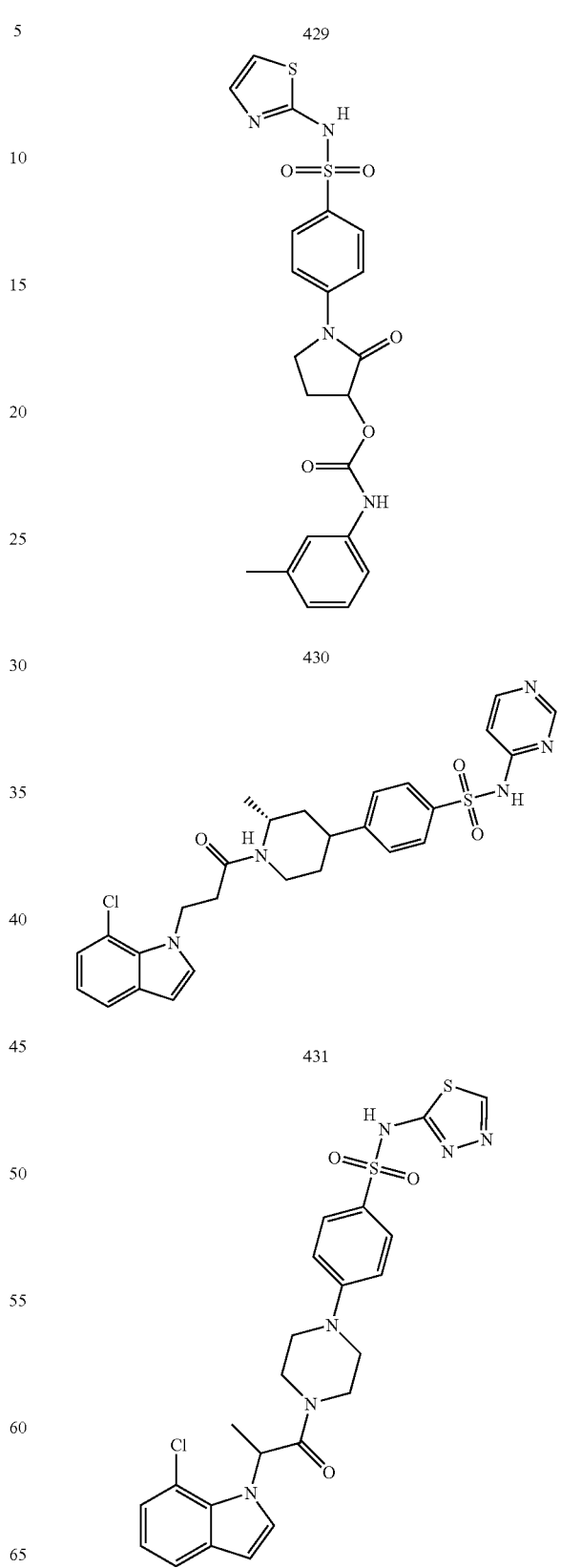

TABLE 2-continued
432
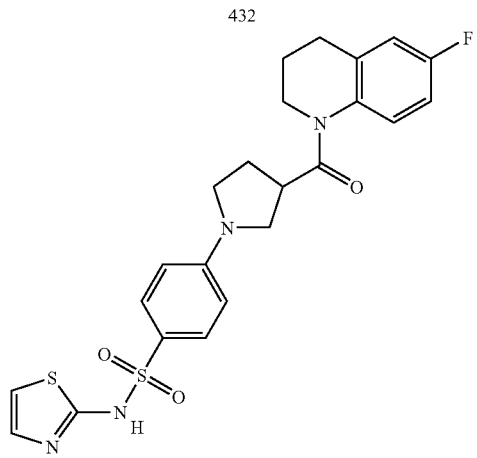
433
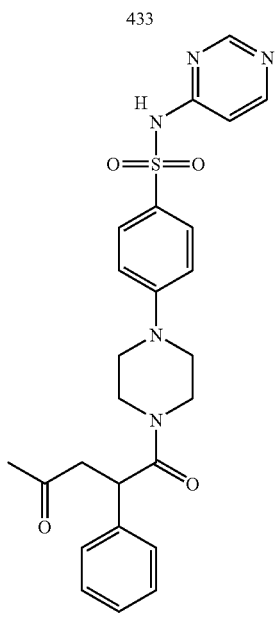
434
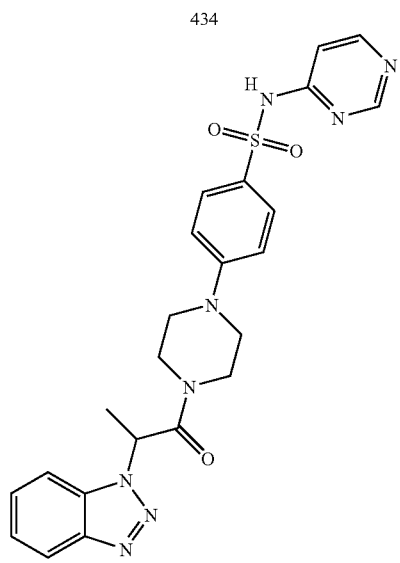
TABLE 2-continued
435
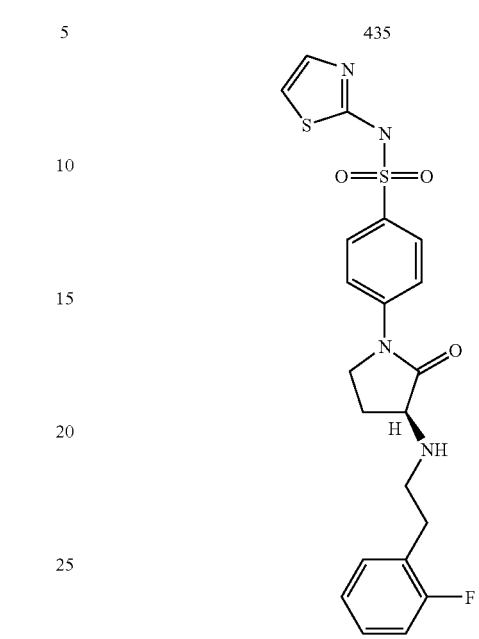
436
437
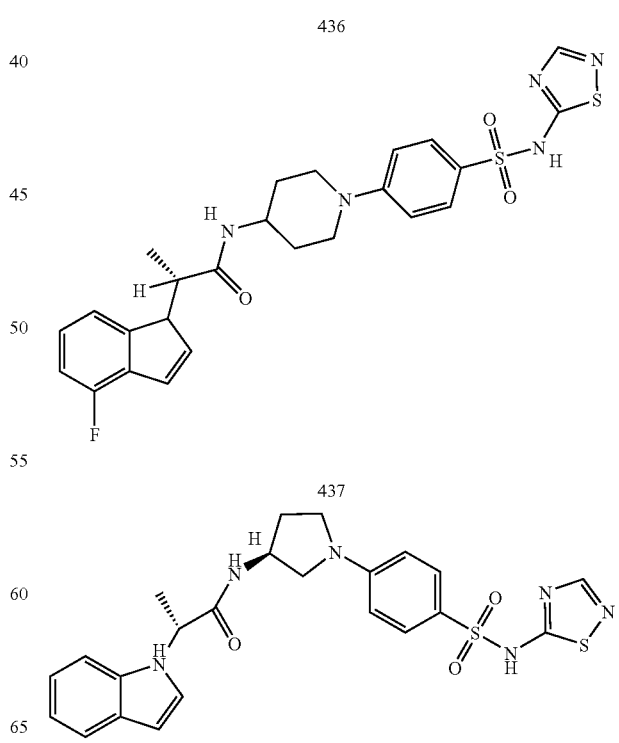

TABLE 2-continued
438
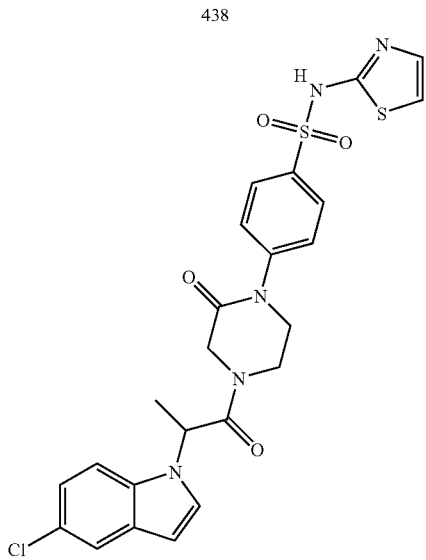
439
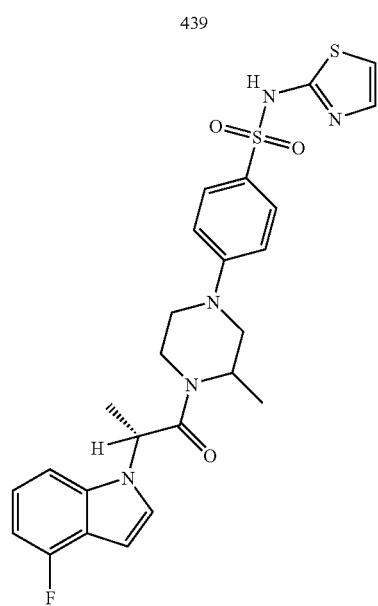
TABLE 2-continued
440
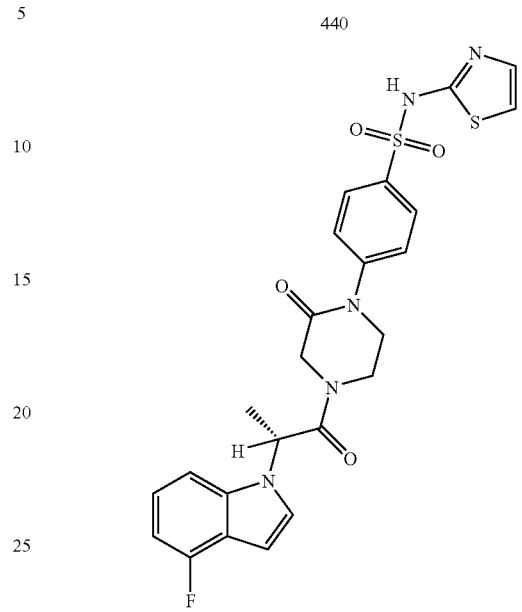
441
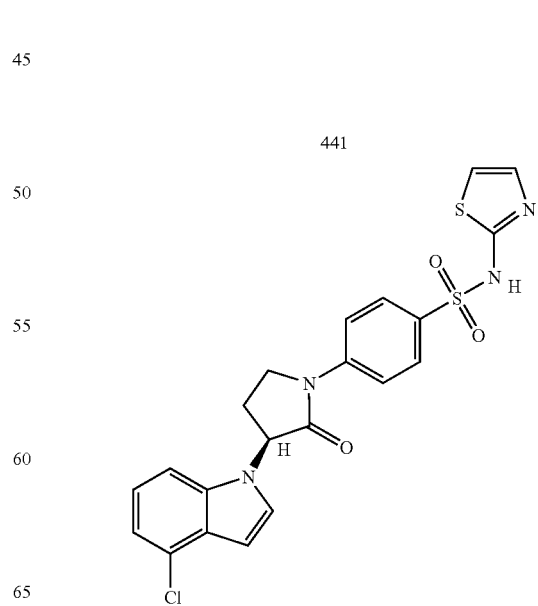

TABLE 2-continued
442
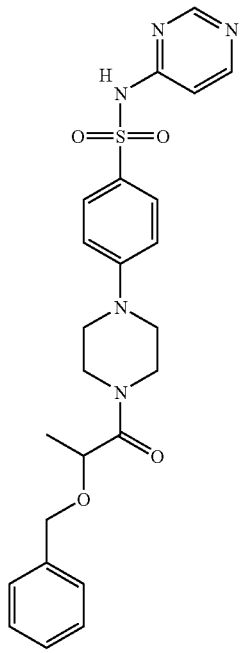
TABLE 2-continued
444
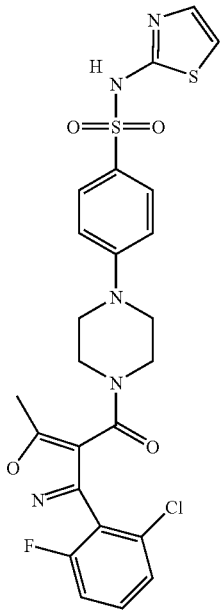
443
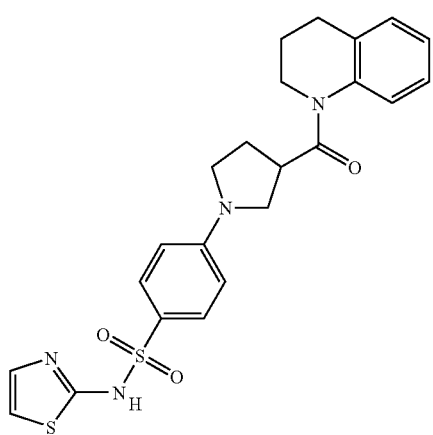
445
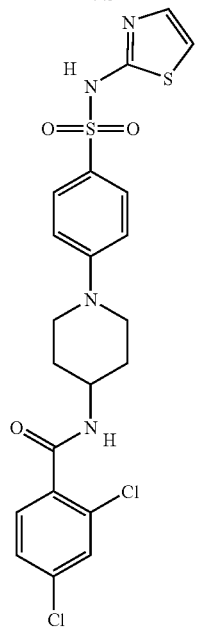

TABLE 2-continued
446
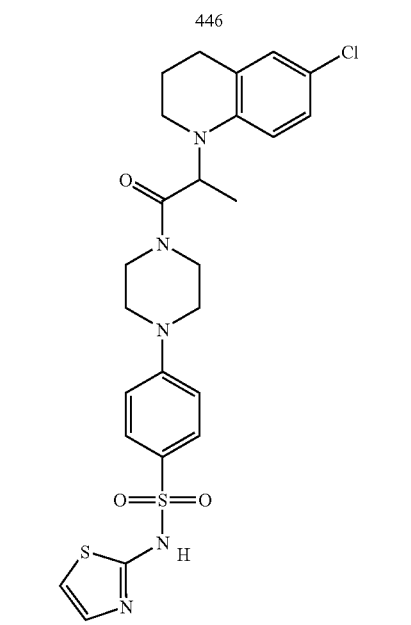
447
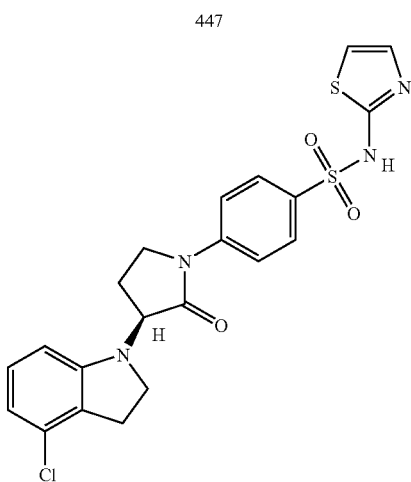
448
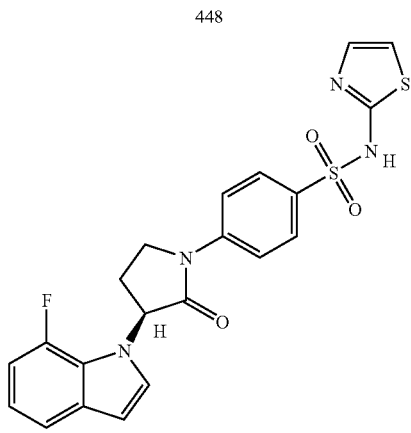
TABLE 2-continued
449
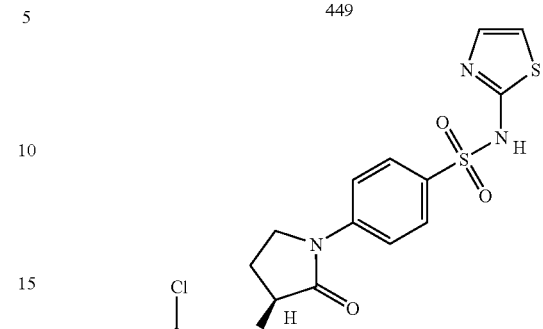
450
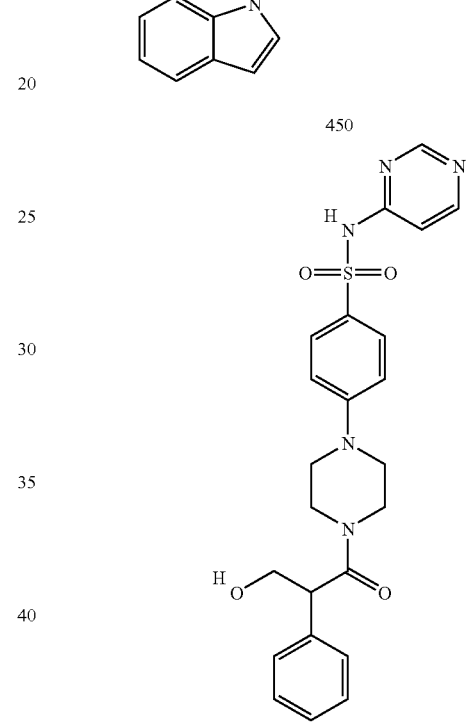
451
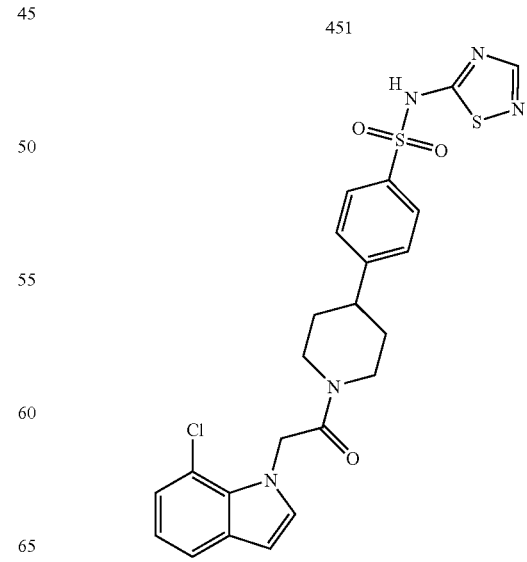

TABLE 2-continued
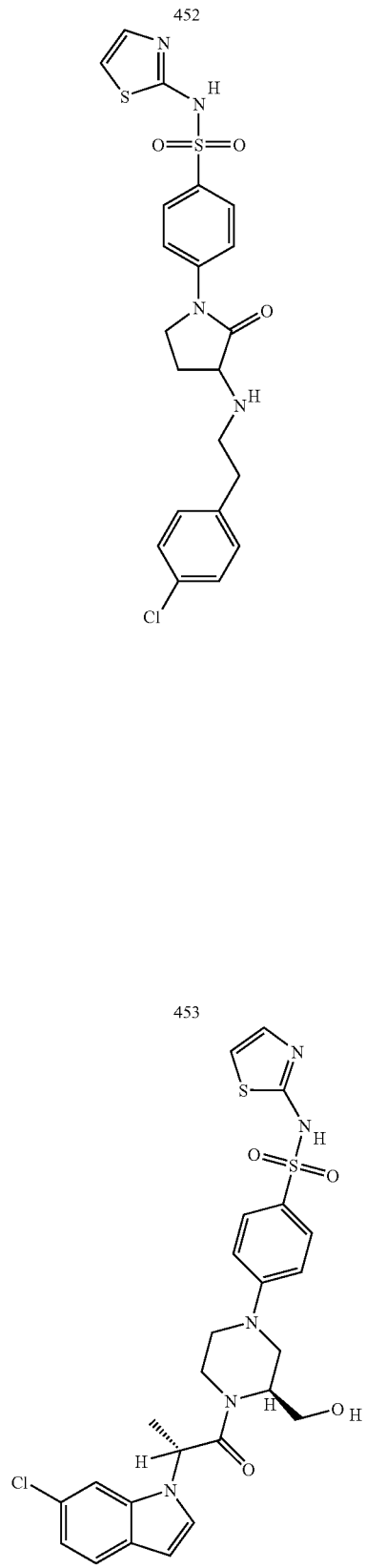
TABLE 2-continued
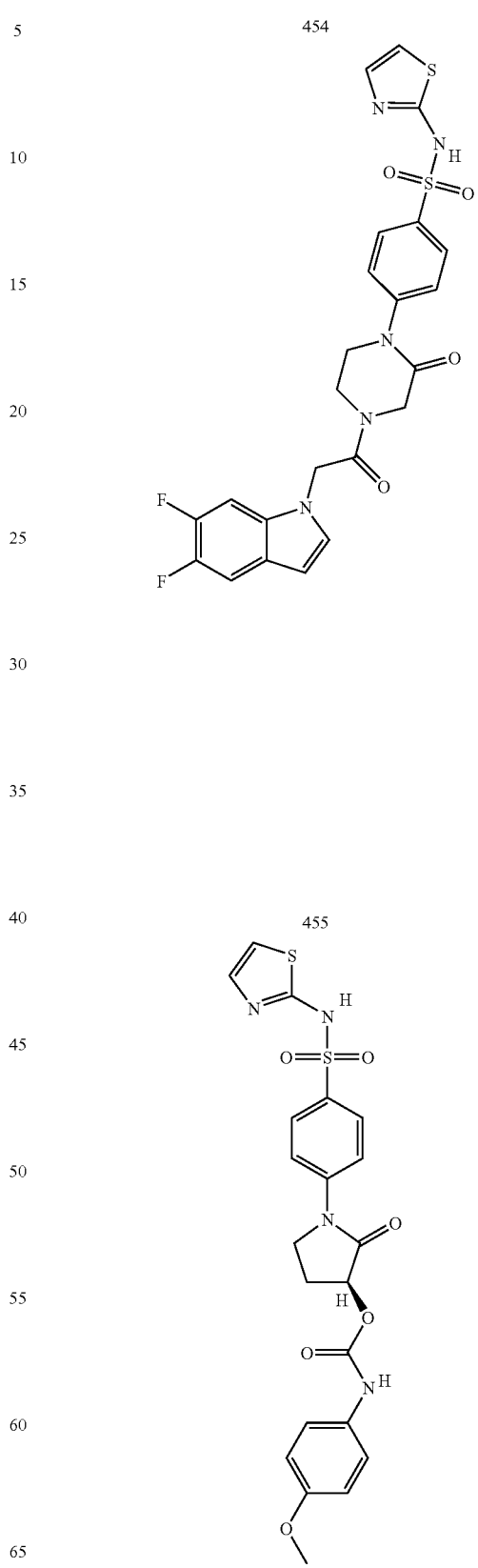

TABLE 2-continued
456
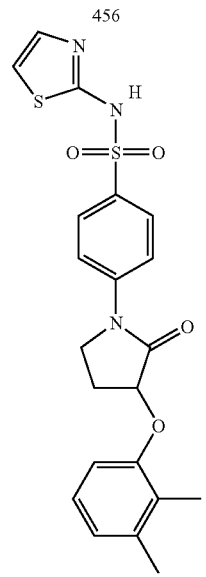
TABLE 2-continued
458
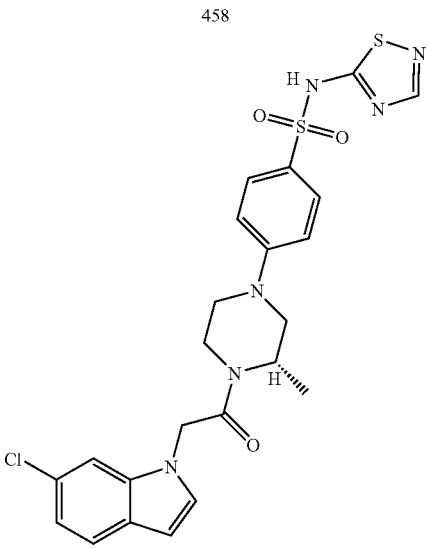
457
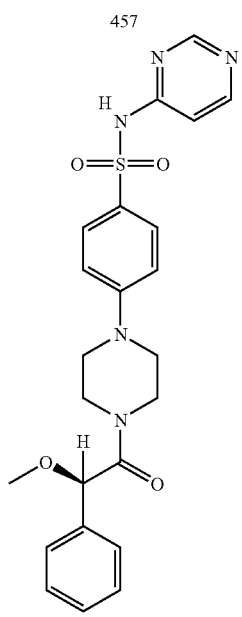
459
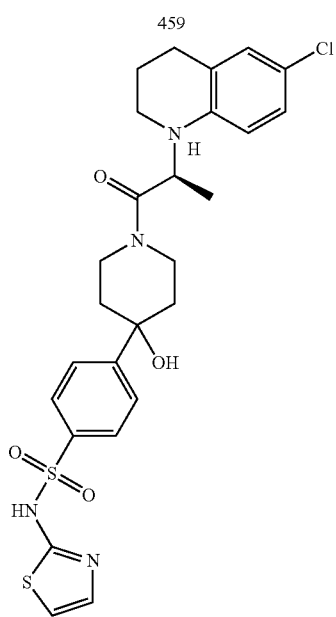

TABLE 2-continued
460
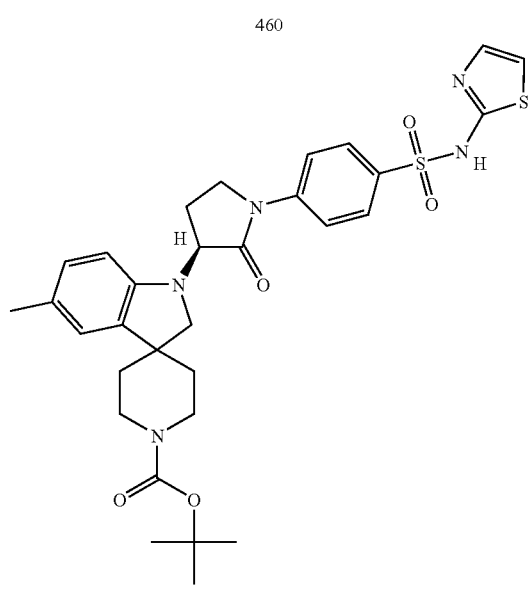
461
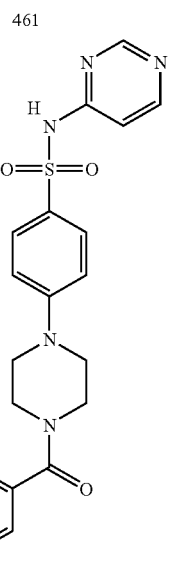
TABLE 2-continued
462
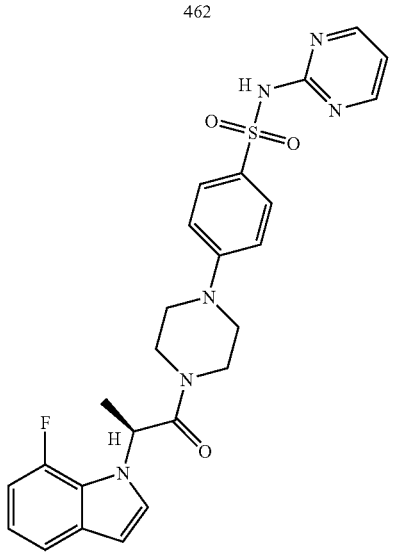
463
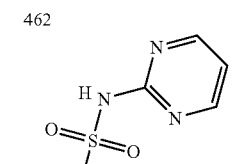

TABLE 2-continued
464
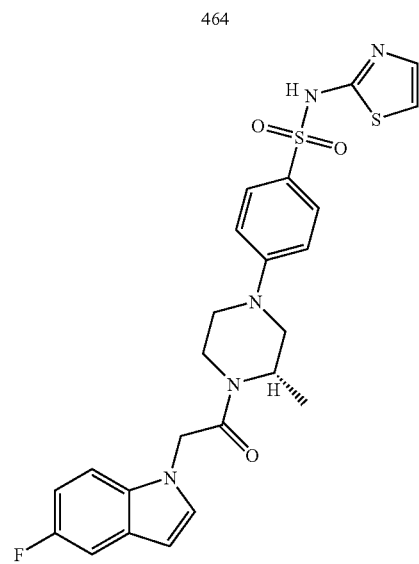
465
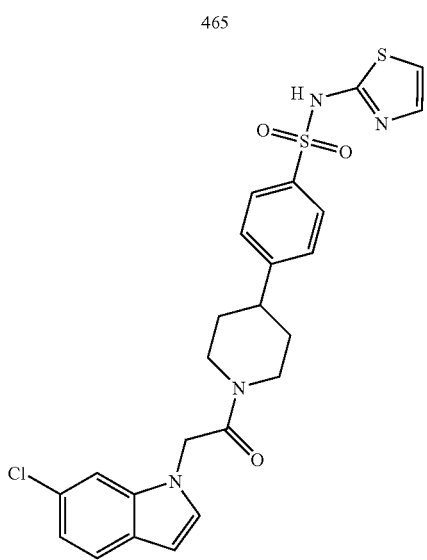
TABLE 2-continued
466
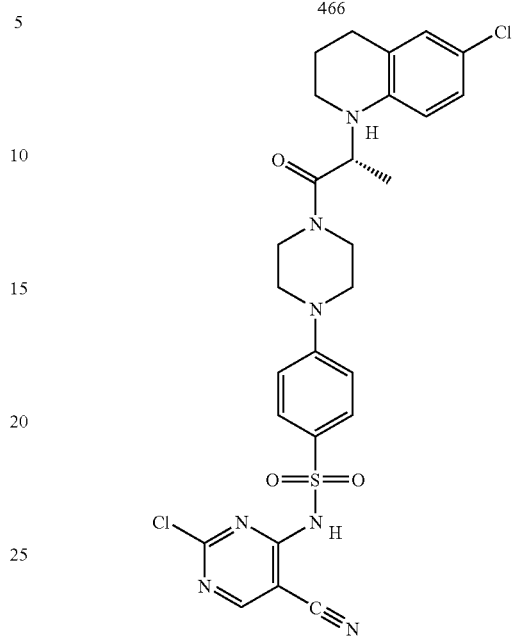
467
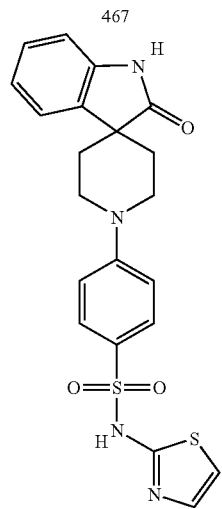

TABLE 2-continued
468
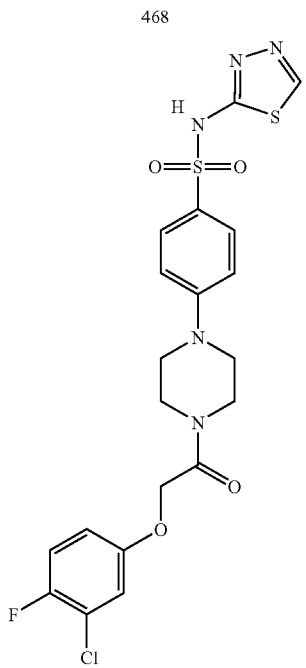
469
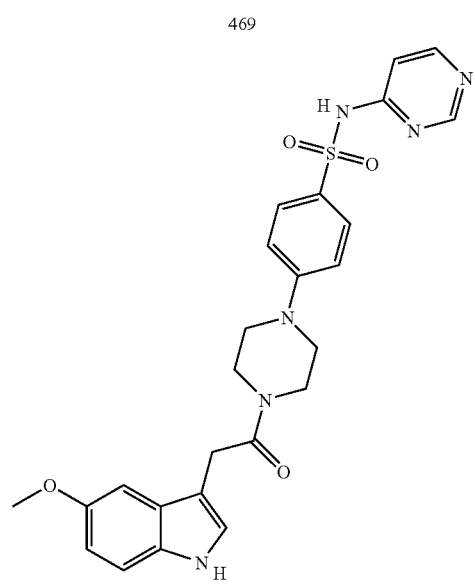
TABLE 2-continued
470
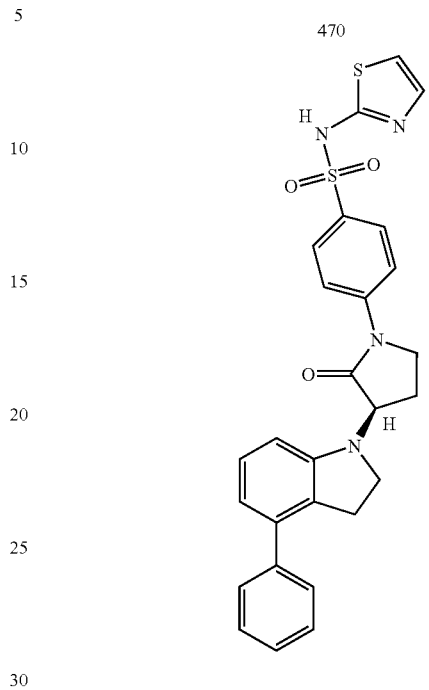
471
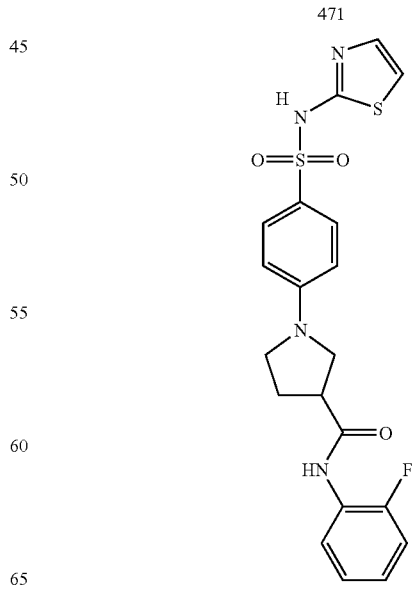

TABLE 2-continued
472
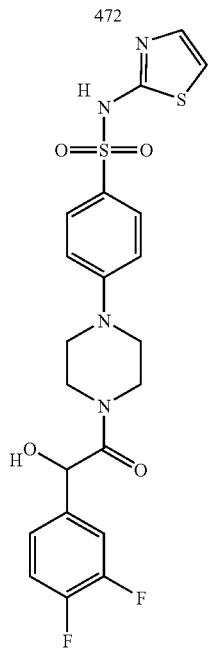
473
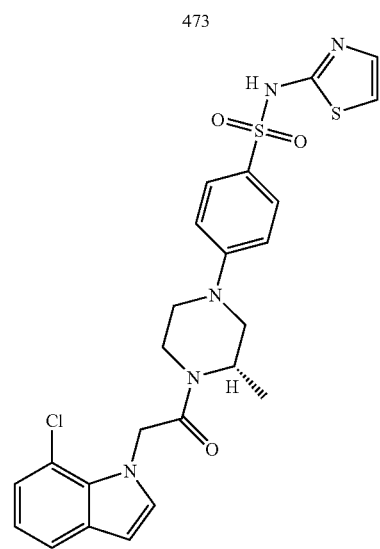
TABLE 2-continued
474
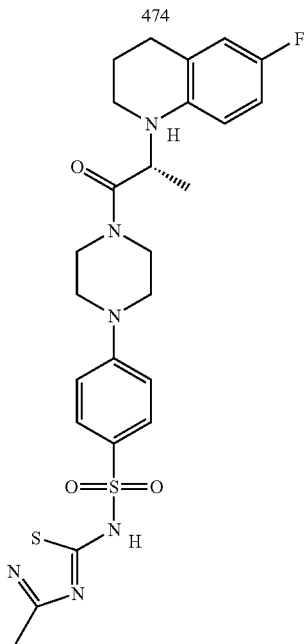
475
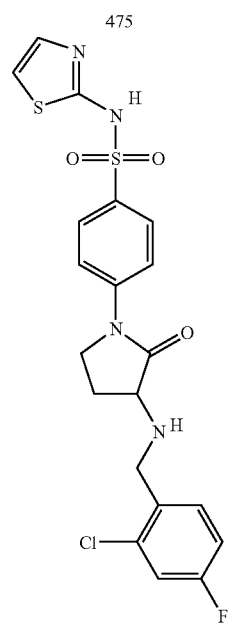

TABLE 2-continued
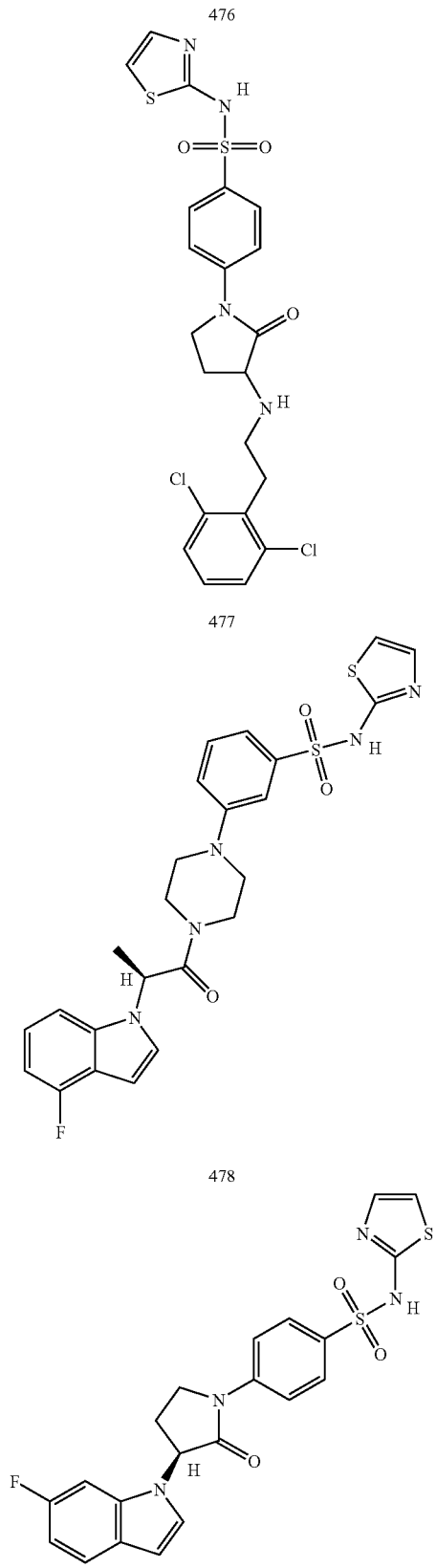
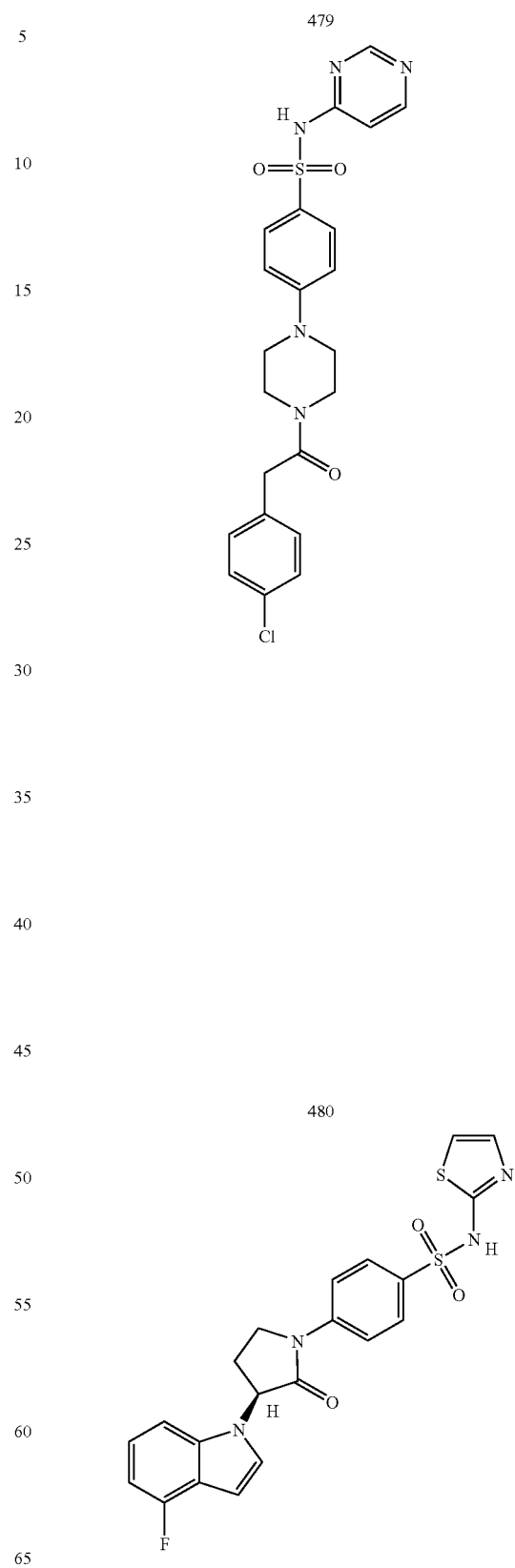

TABLE 2-continued
481
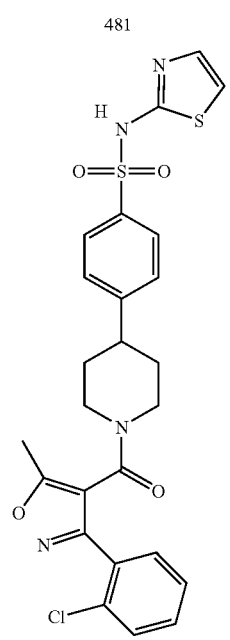
482
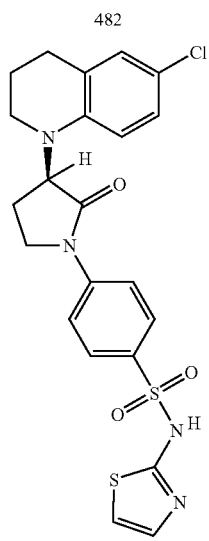
TABLE 2-continued
483
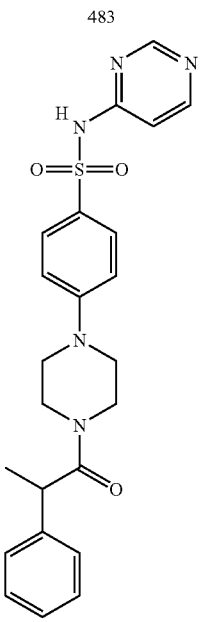
484
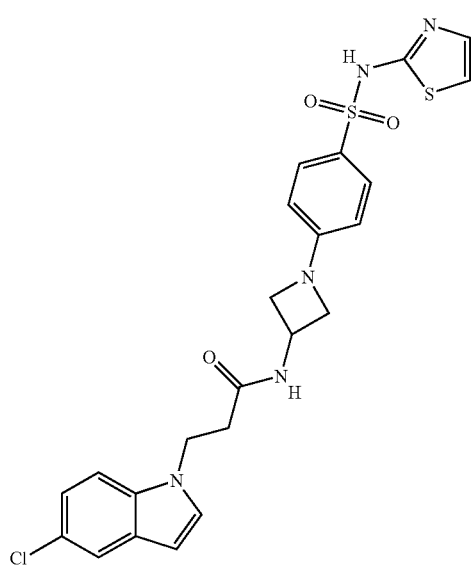

TABLE 2-continued
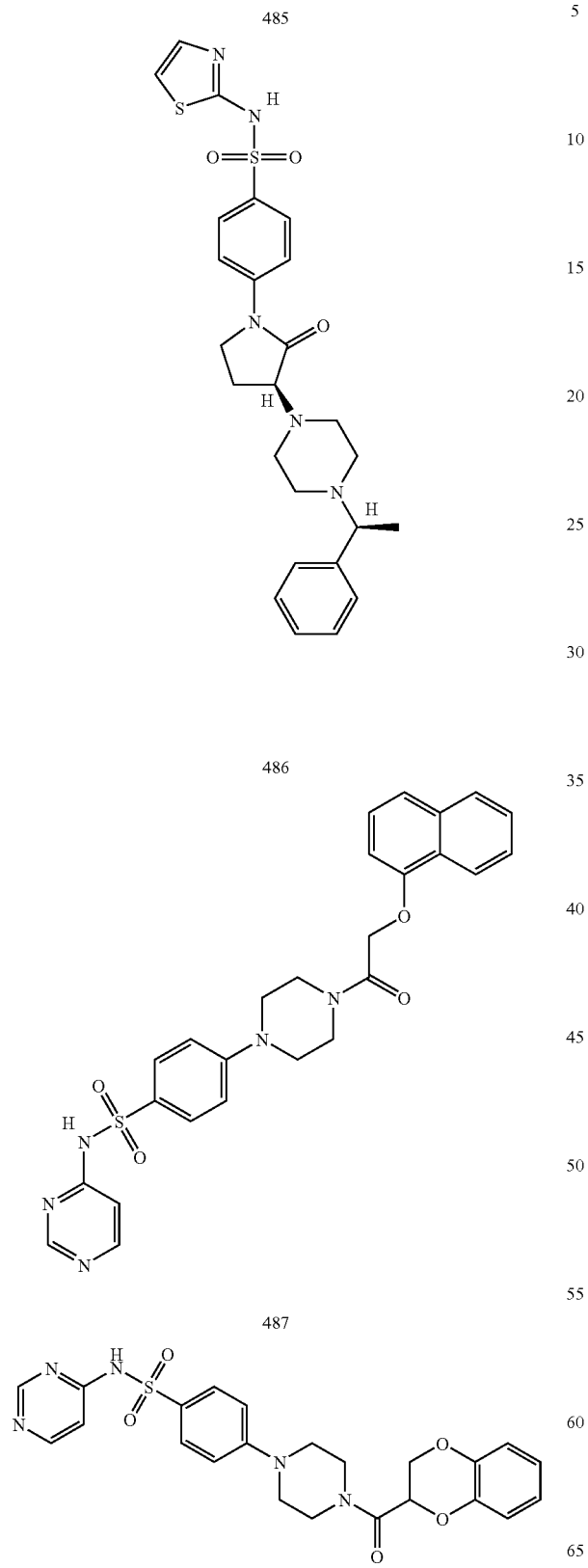
TABLE 2-continued
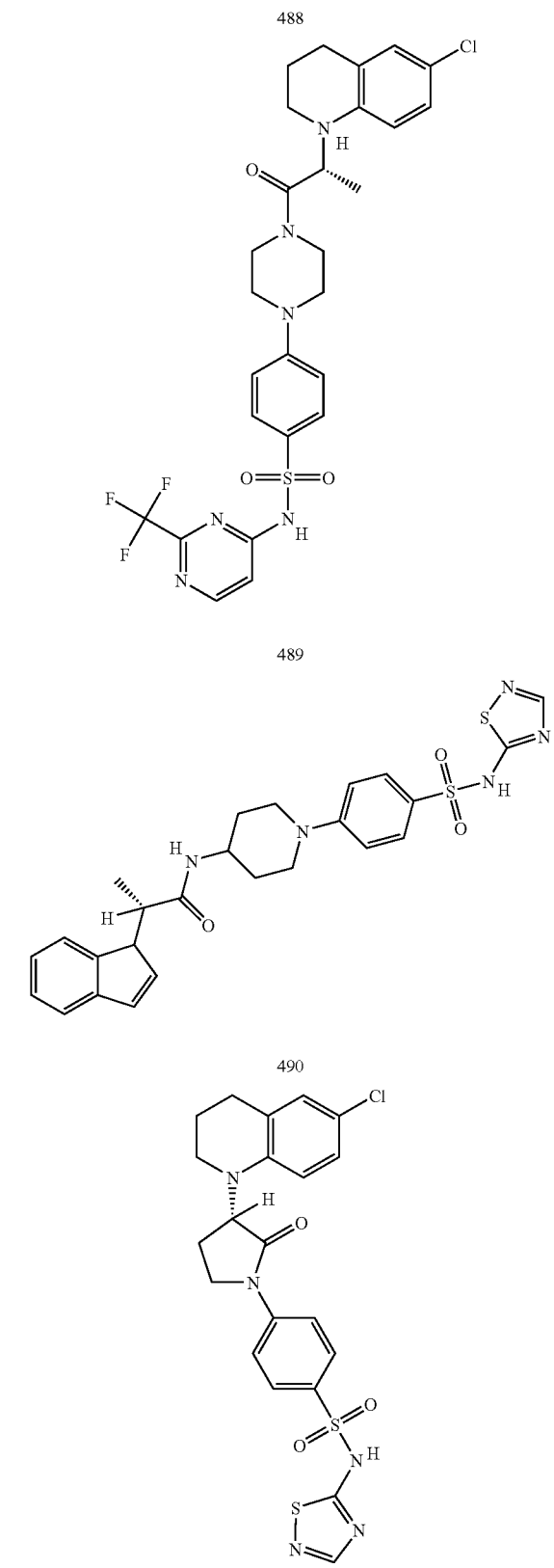

TABLE 2-continued
491
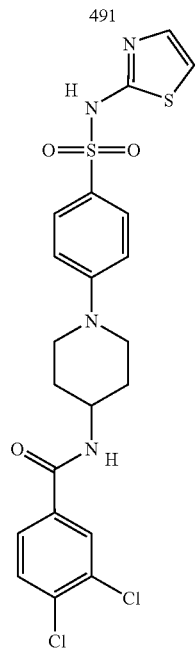
493
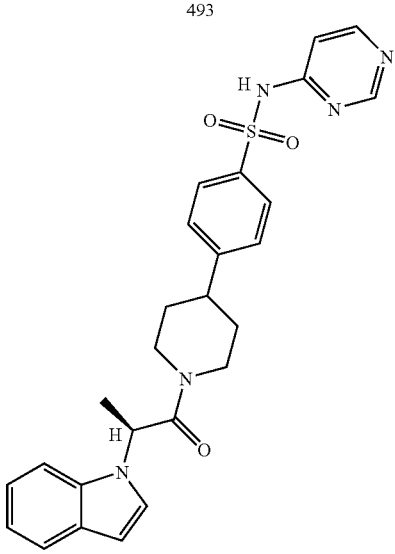
492
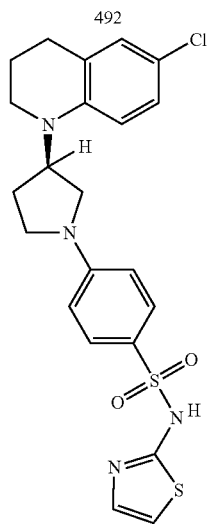
494
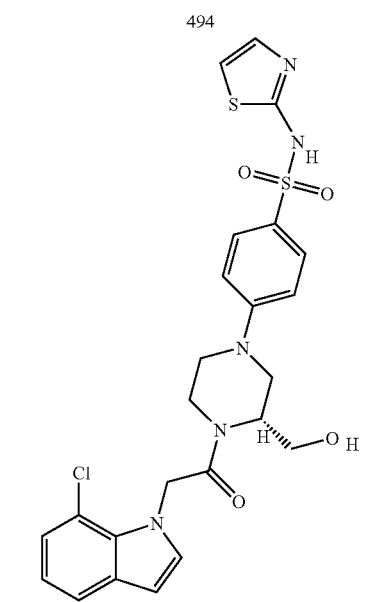

TABLE 2-continued
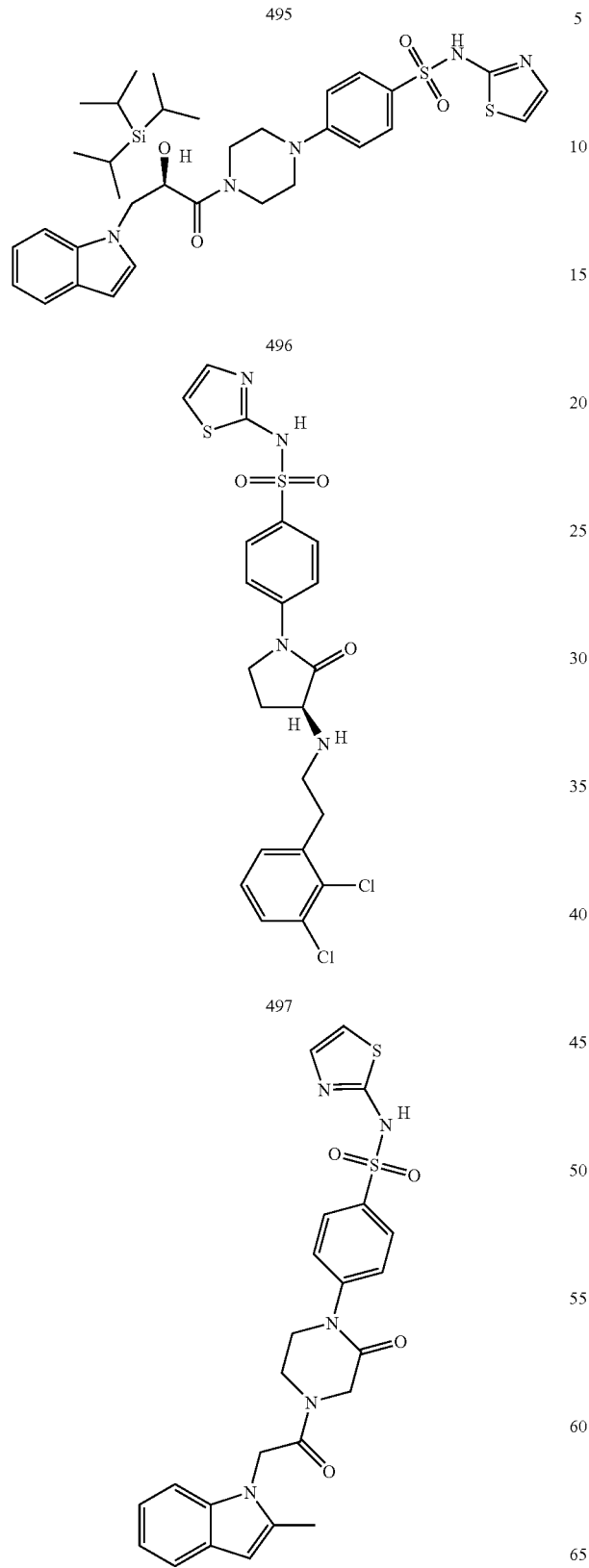
TABLE 2-continued

TABLE 2-continued
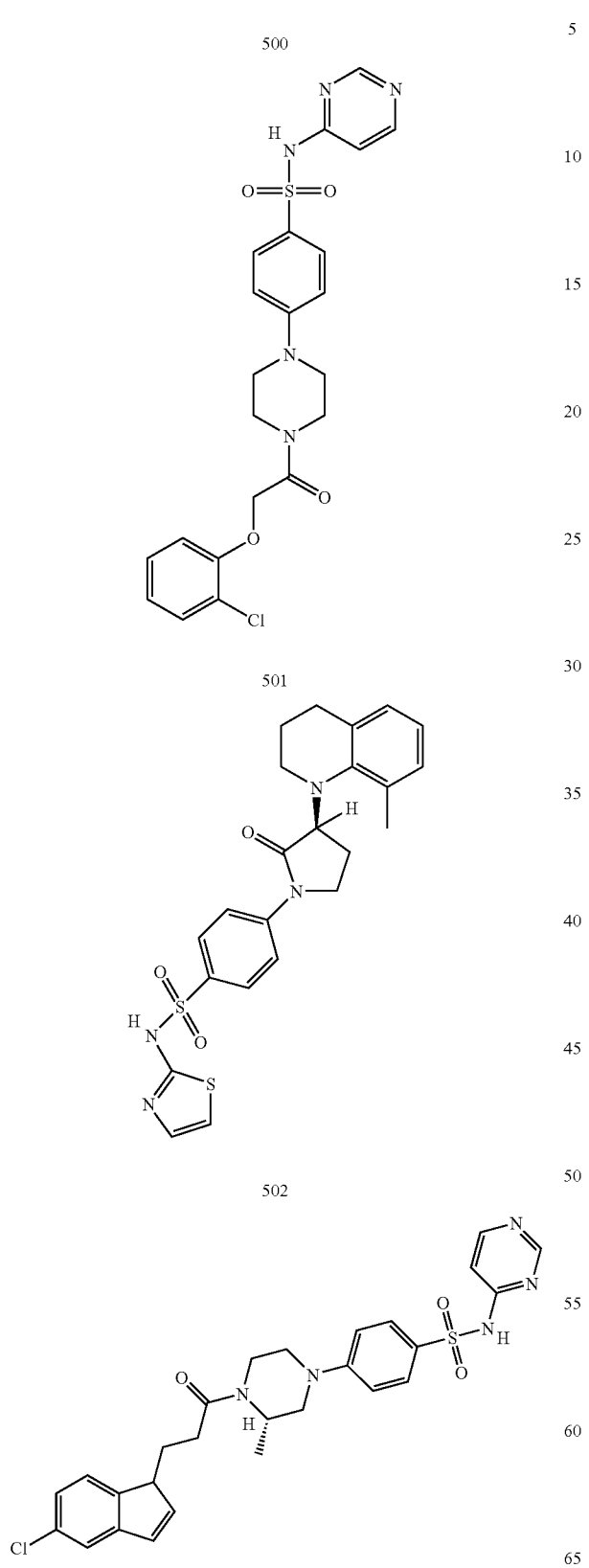
TABLE 2-continued
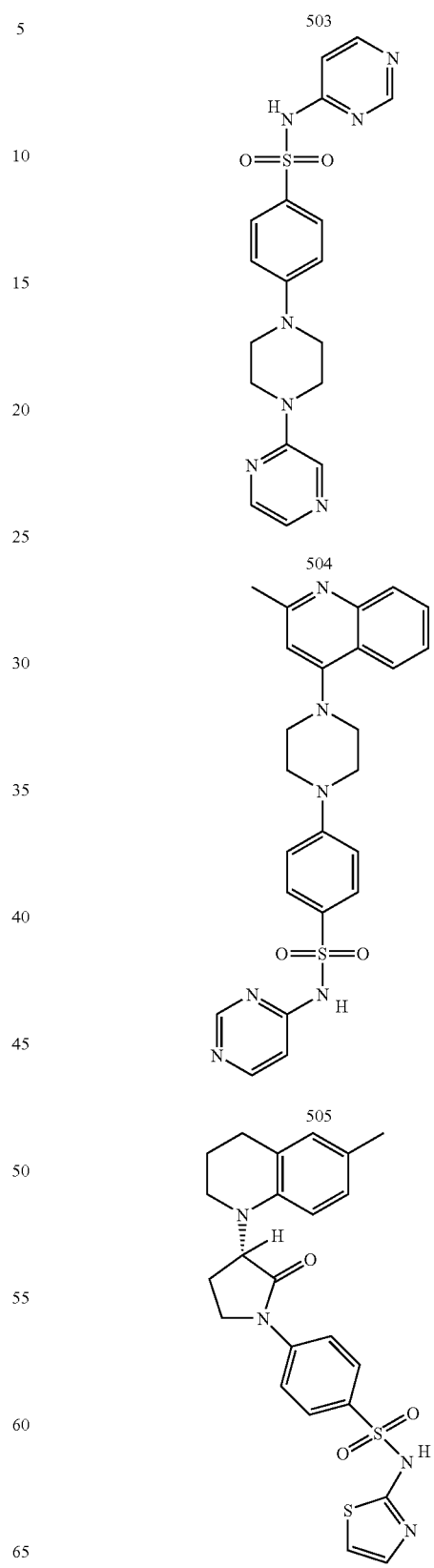

TABLE 2-continued
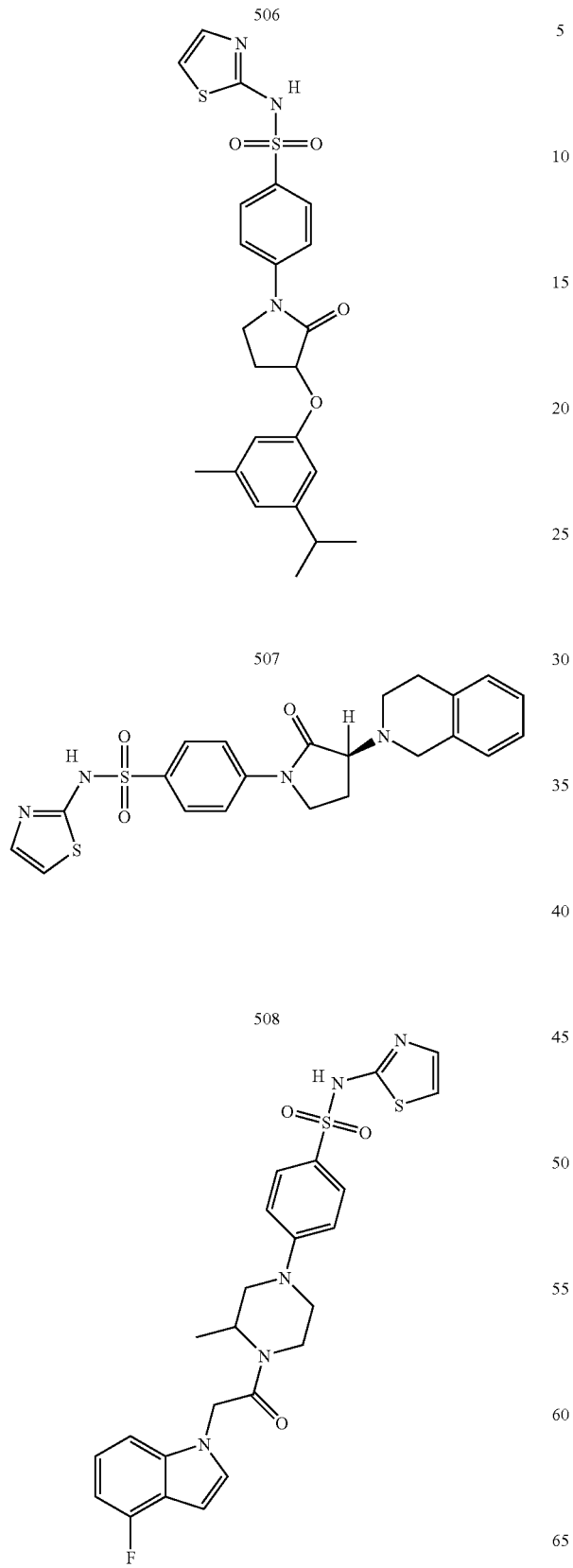
TABLE 2-continued
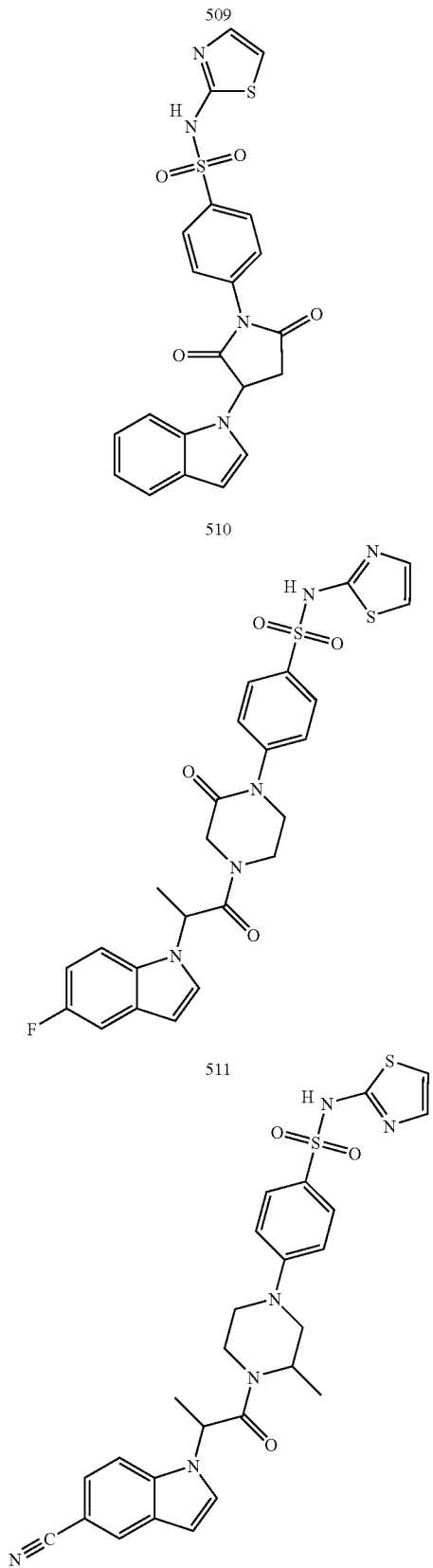

TABLE 2-continued
512
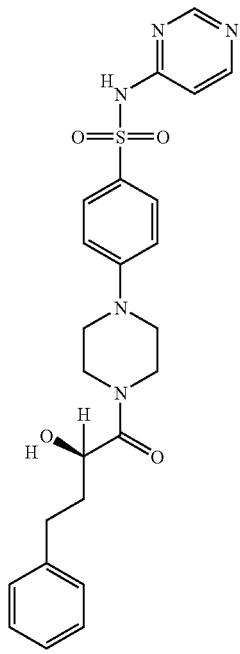
513
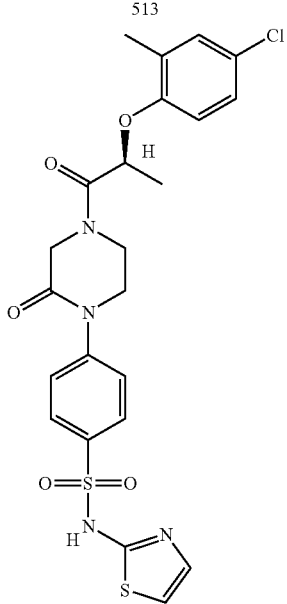
TABLE 2-continued
514
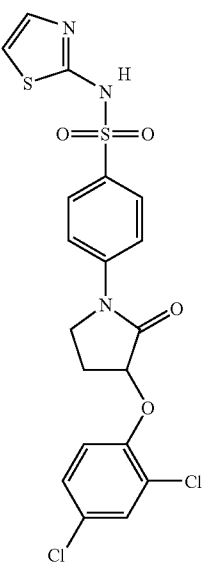
515
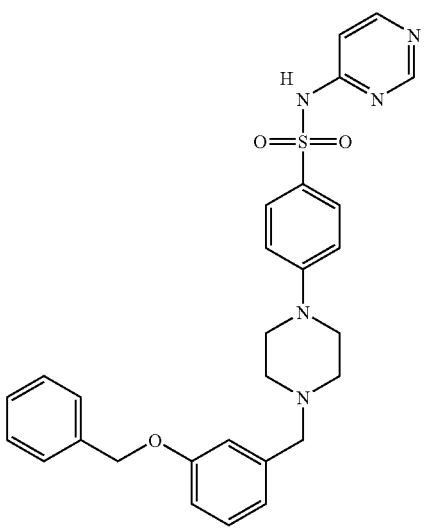

TABLE 2-continued
516
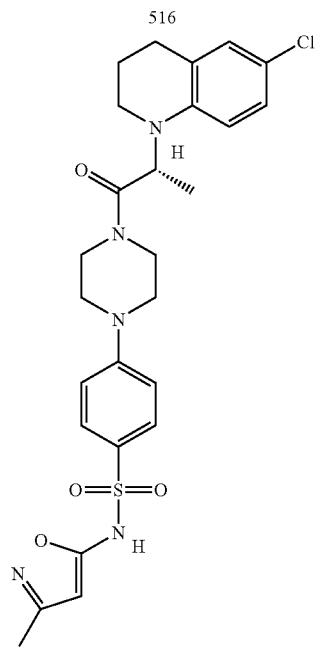
517
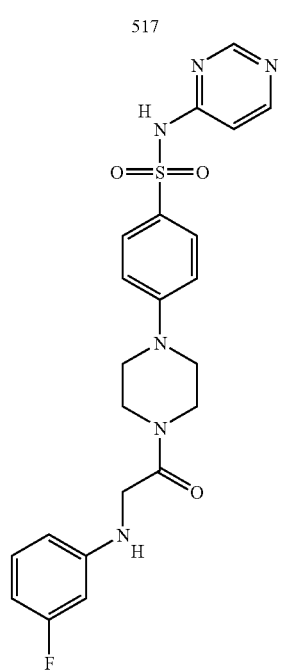
TABLE 2-continued
518
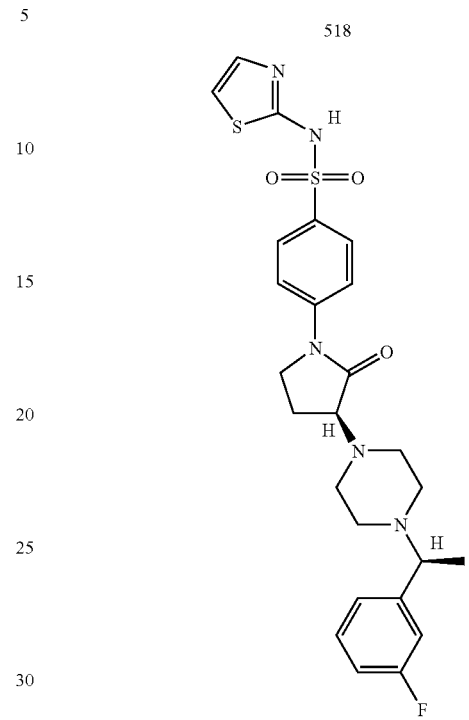
519
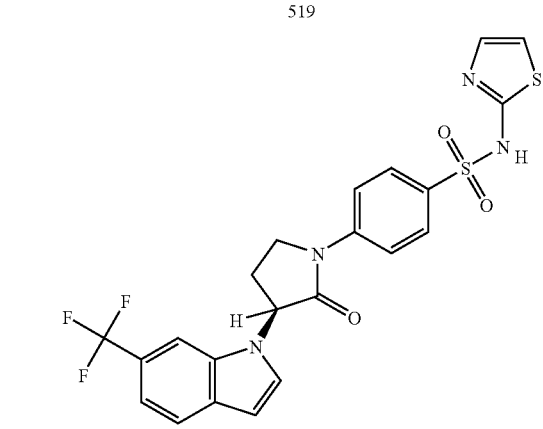

TABLE 2-continued
520
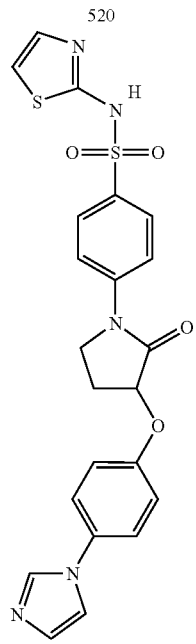
521
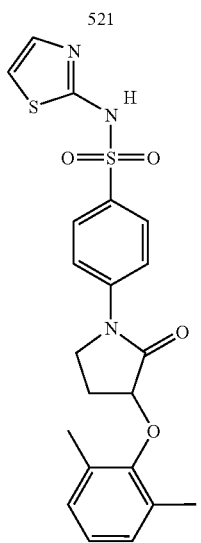
TABLE 2-continued
522
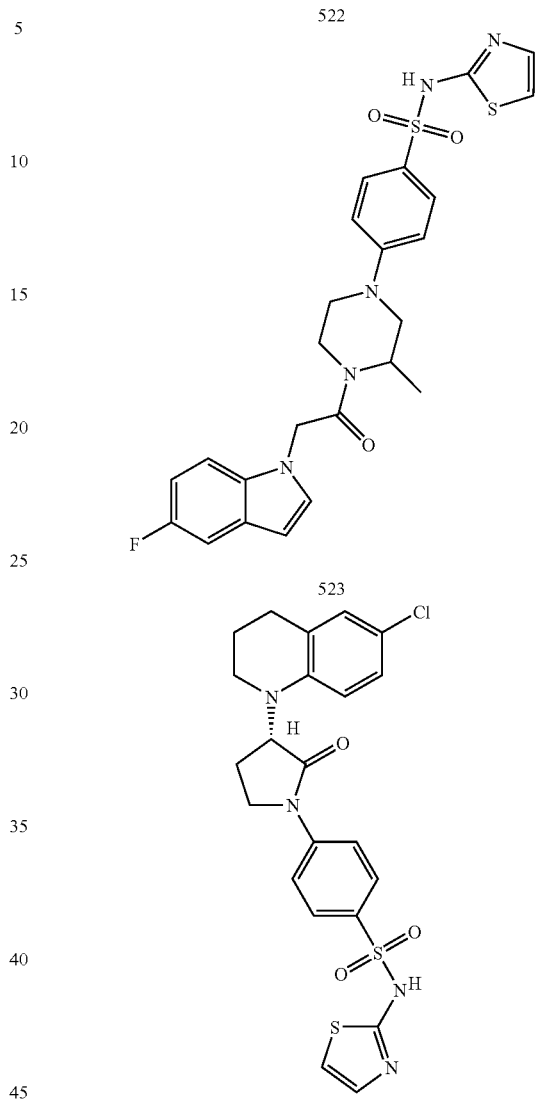
523
524
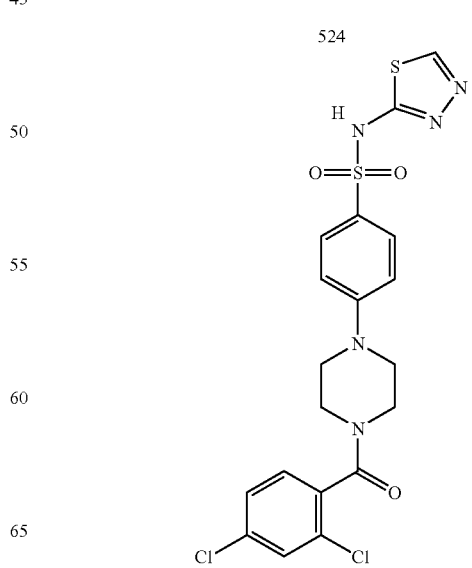

TABLE 2-continued
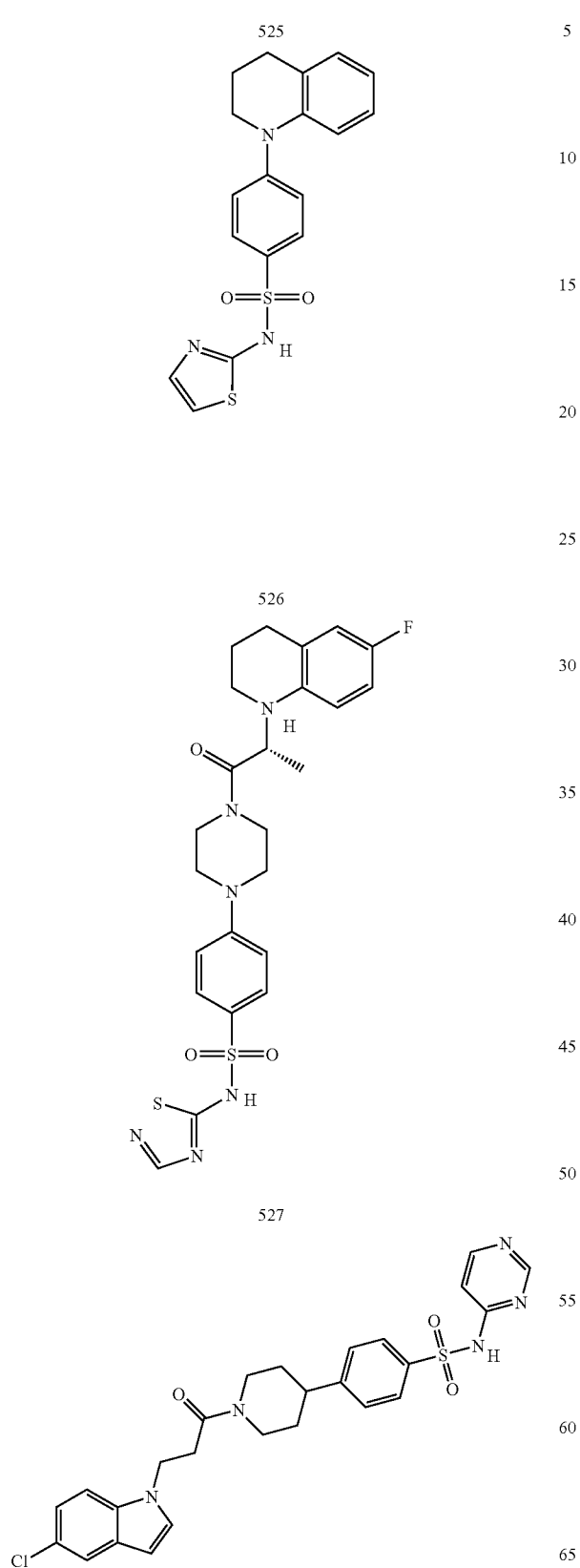
TABLE 2-continued
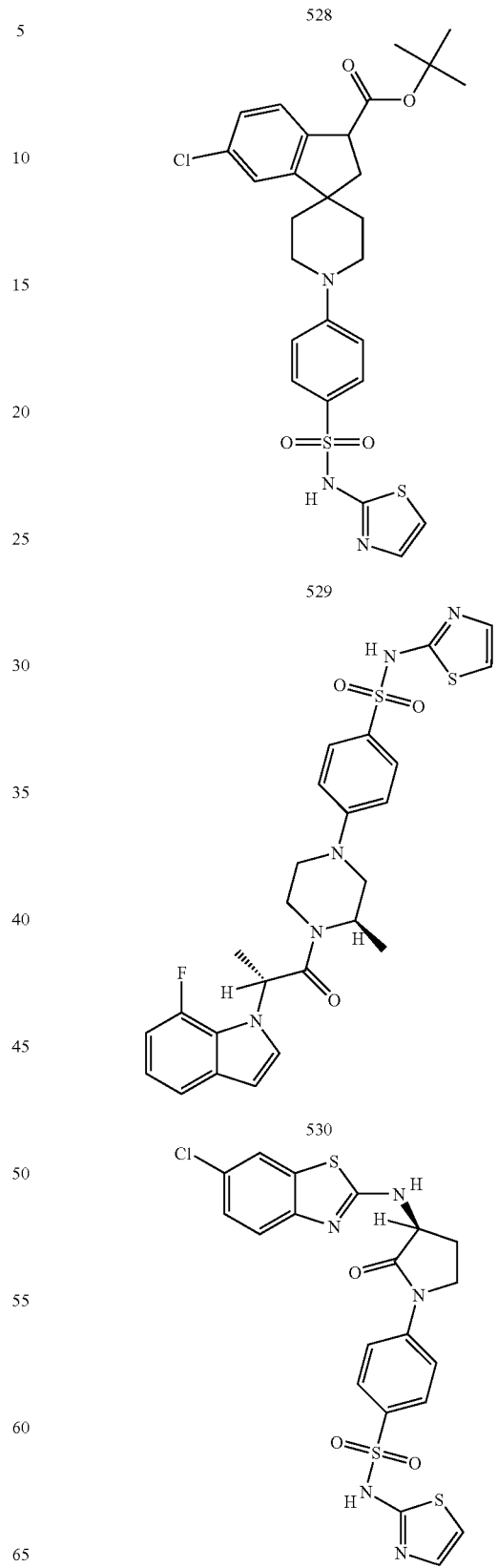

TABLE 2-continued
531
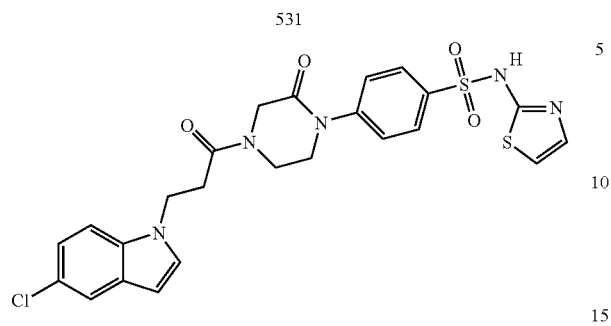
532
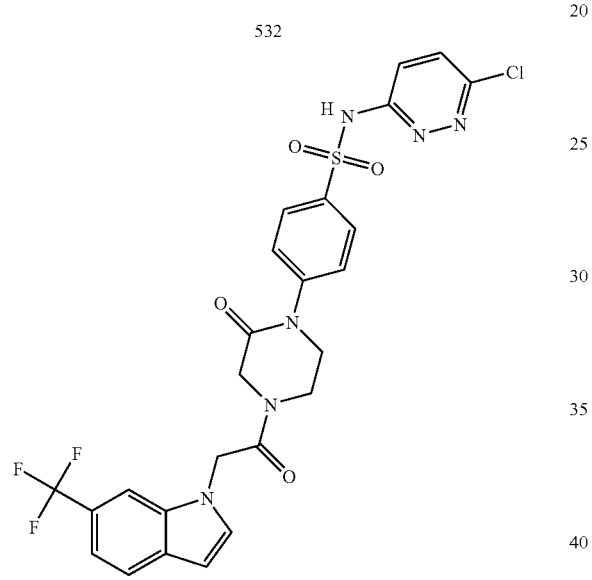
533
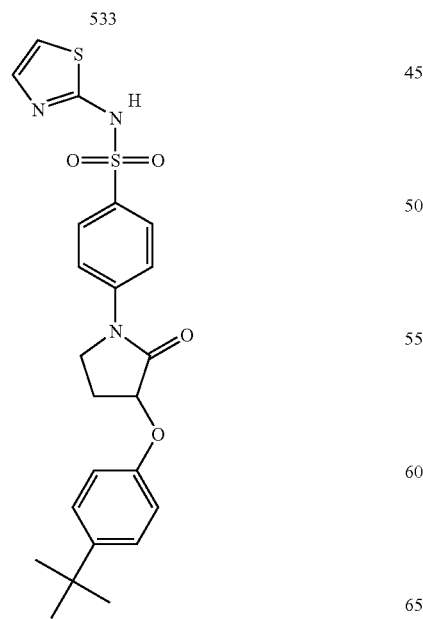
TABLE 2-continued
534
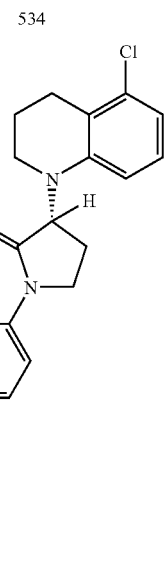
535
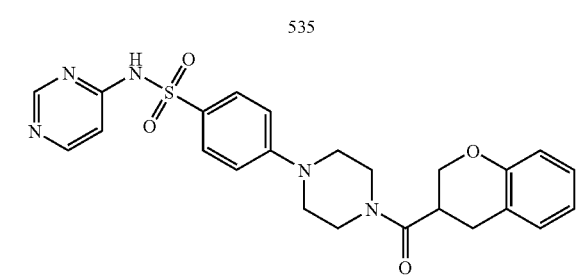
536
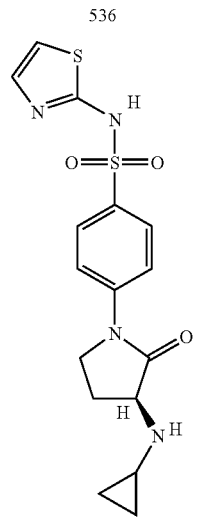

TABLE 2-continued
537
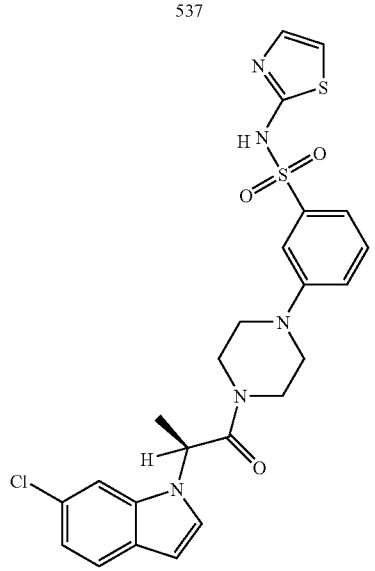
538
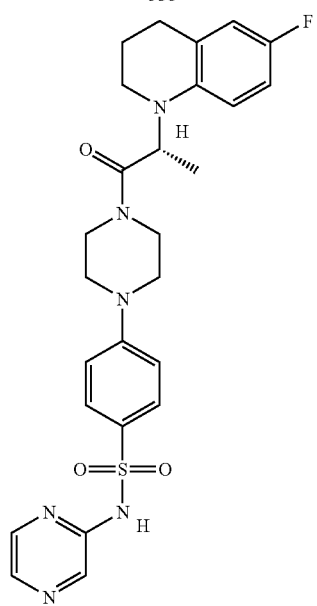
TABLE 2-continued
539
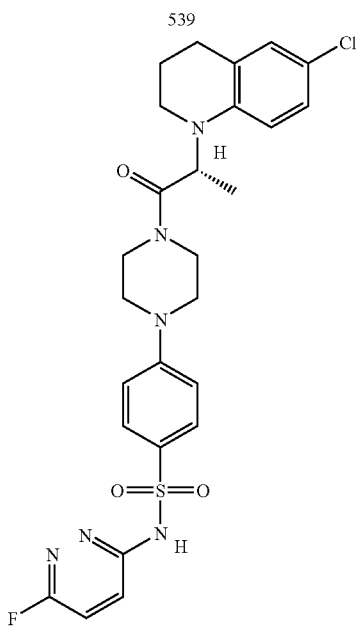
540

TABLE 2-continued
541
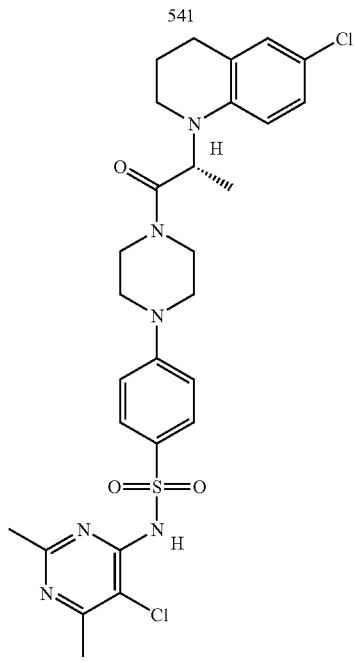
542
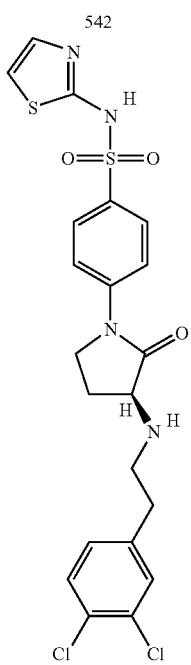
TABLE 2-continued
543
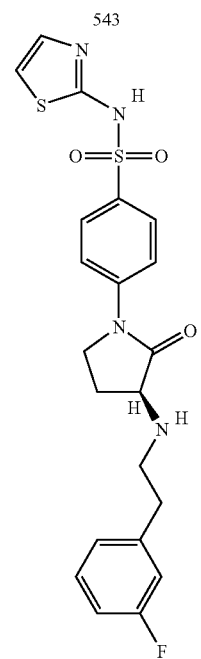
544
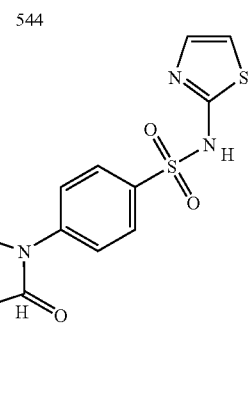
545
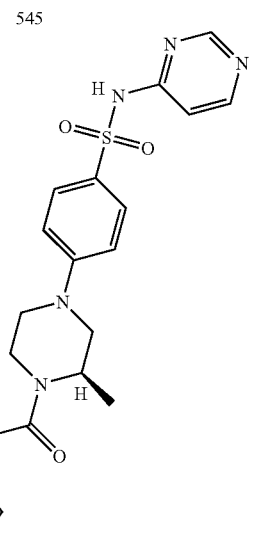

TABLE 2-continued
546
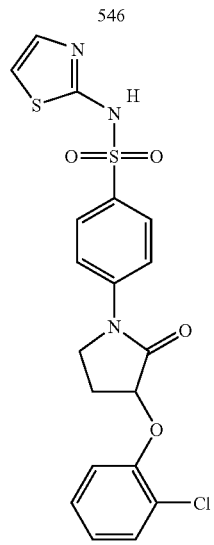
TABLE 2-continued
548
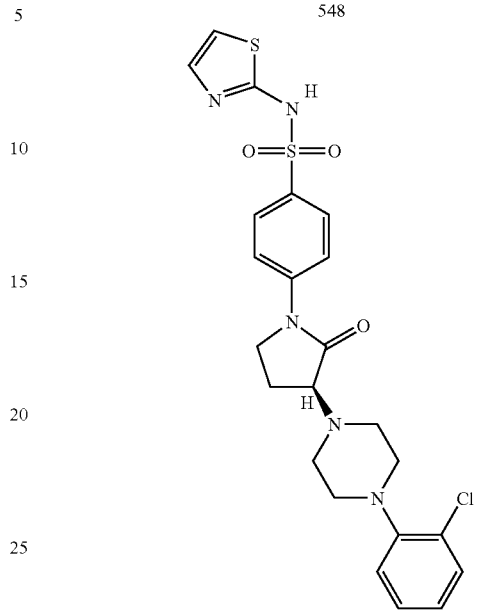
547
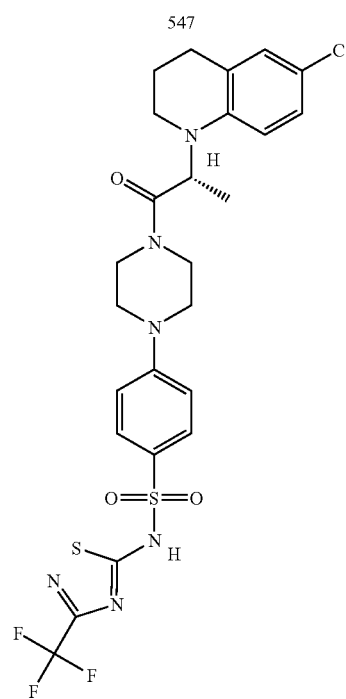
549
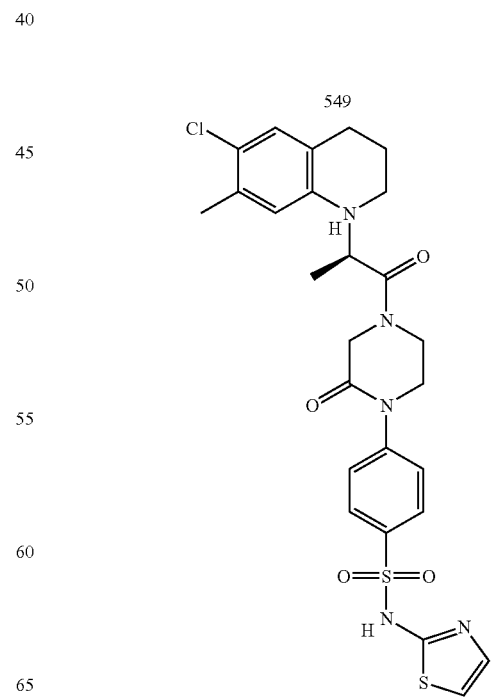

TABLE 2-continued
550
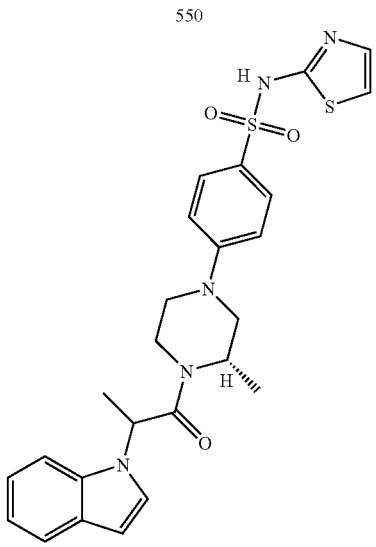
551
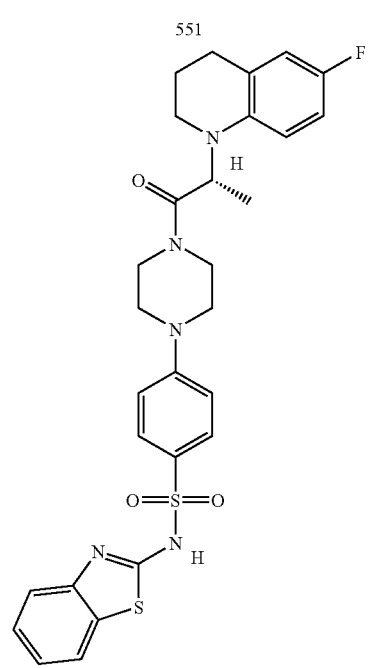
552
553
554

TABLE 2-continued
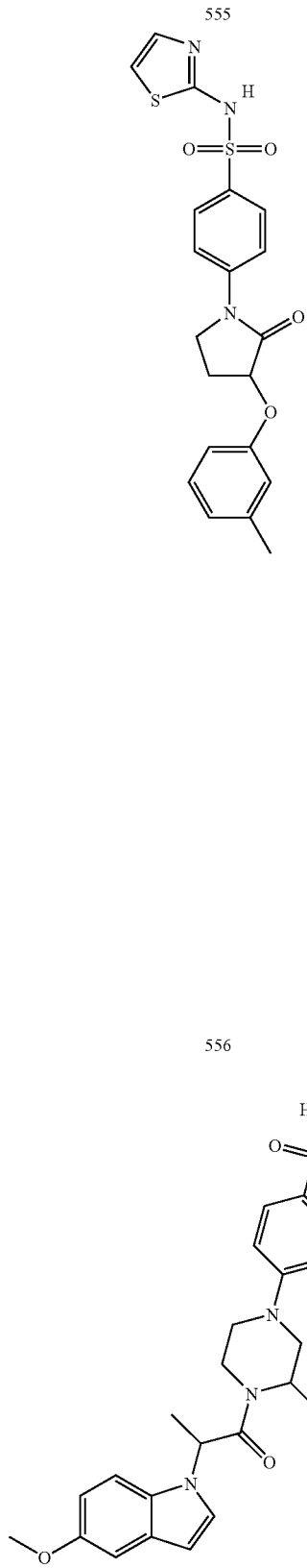
TABLE 2-continued
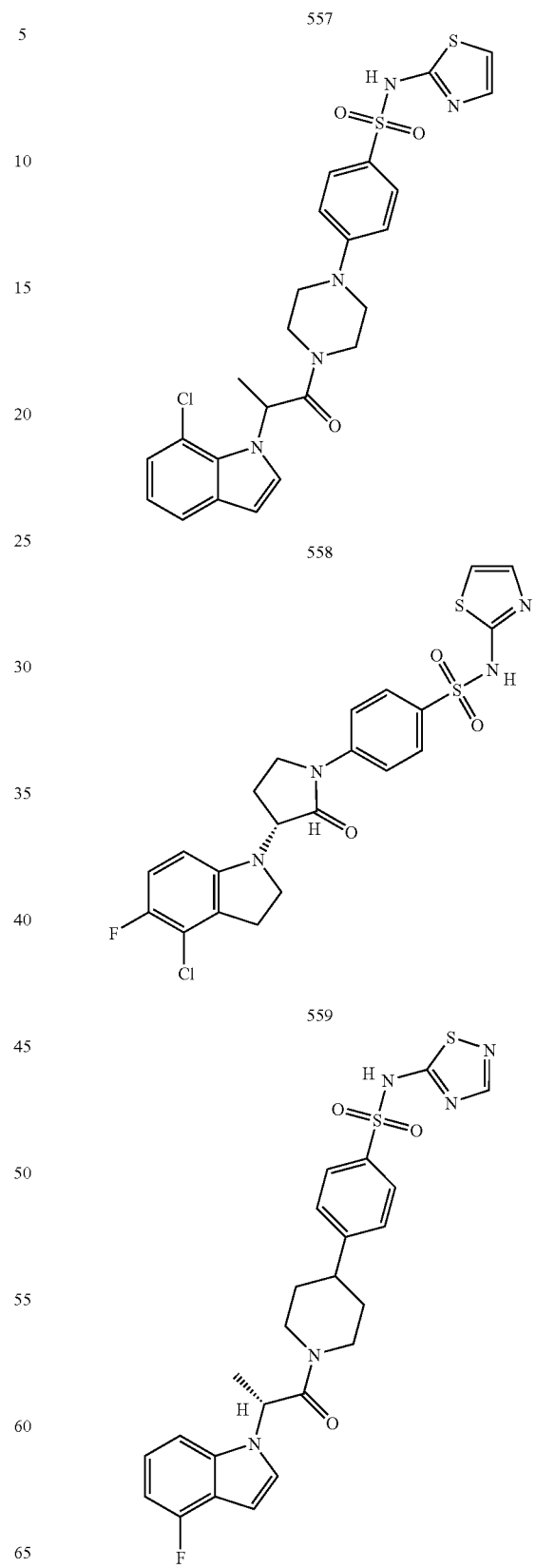

TABLE 2-continued
560
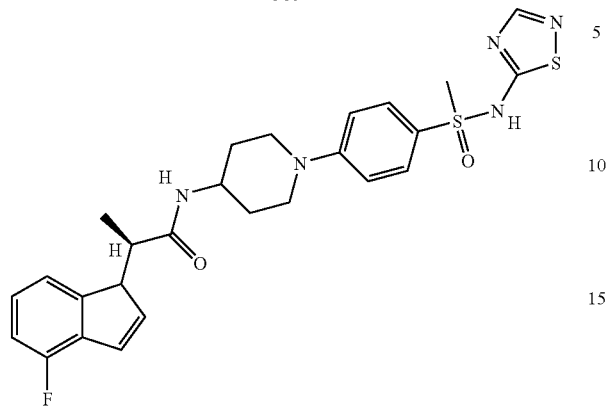
561
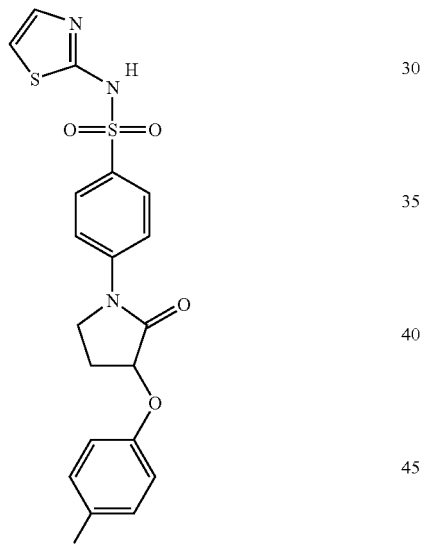
562
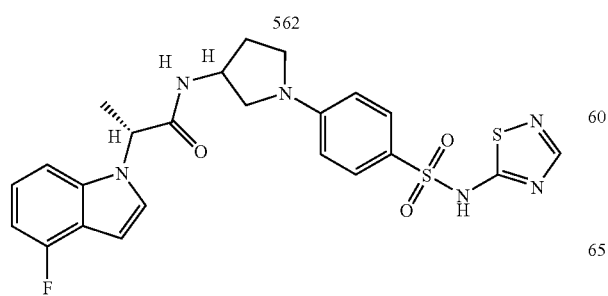
TABLE 2-continued
563
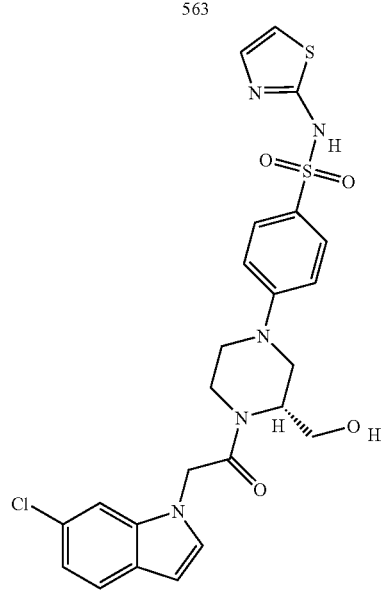
564
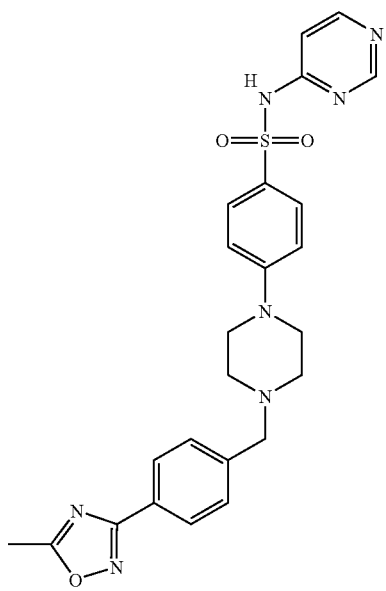

TABLE 2-continued
565
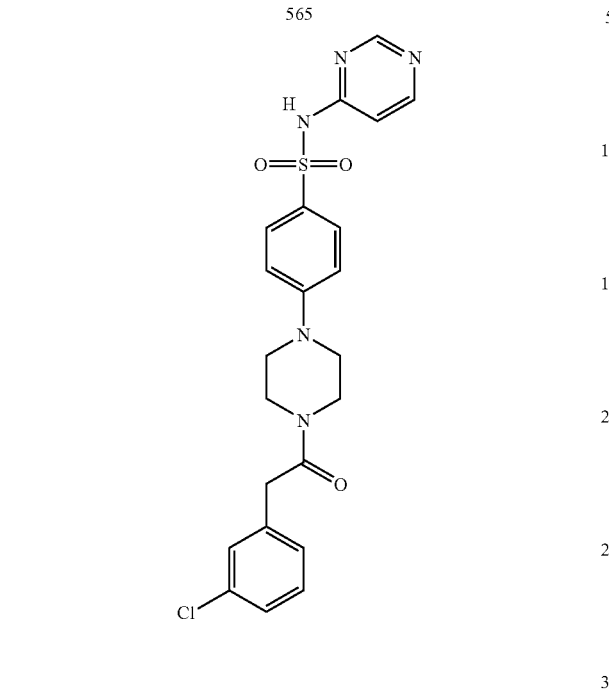
566
567
TABLE 2-continued
568
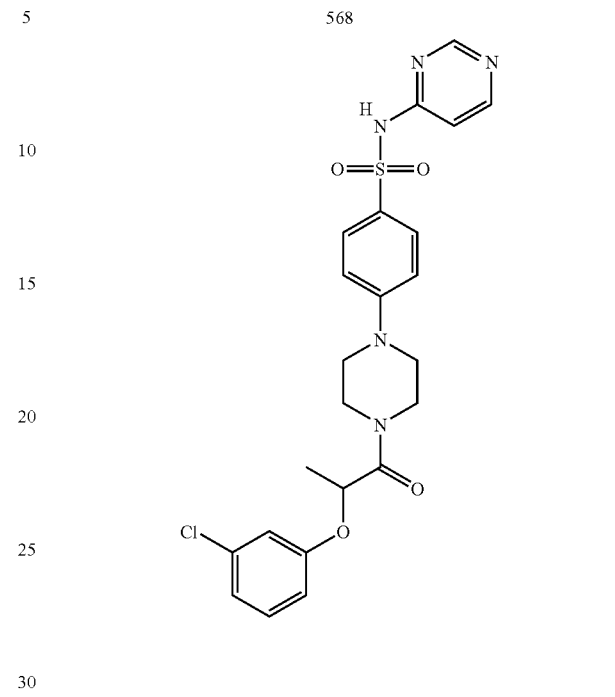
569
570

341
TABLE 2-continued
342
TABLE 2-continued
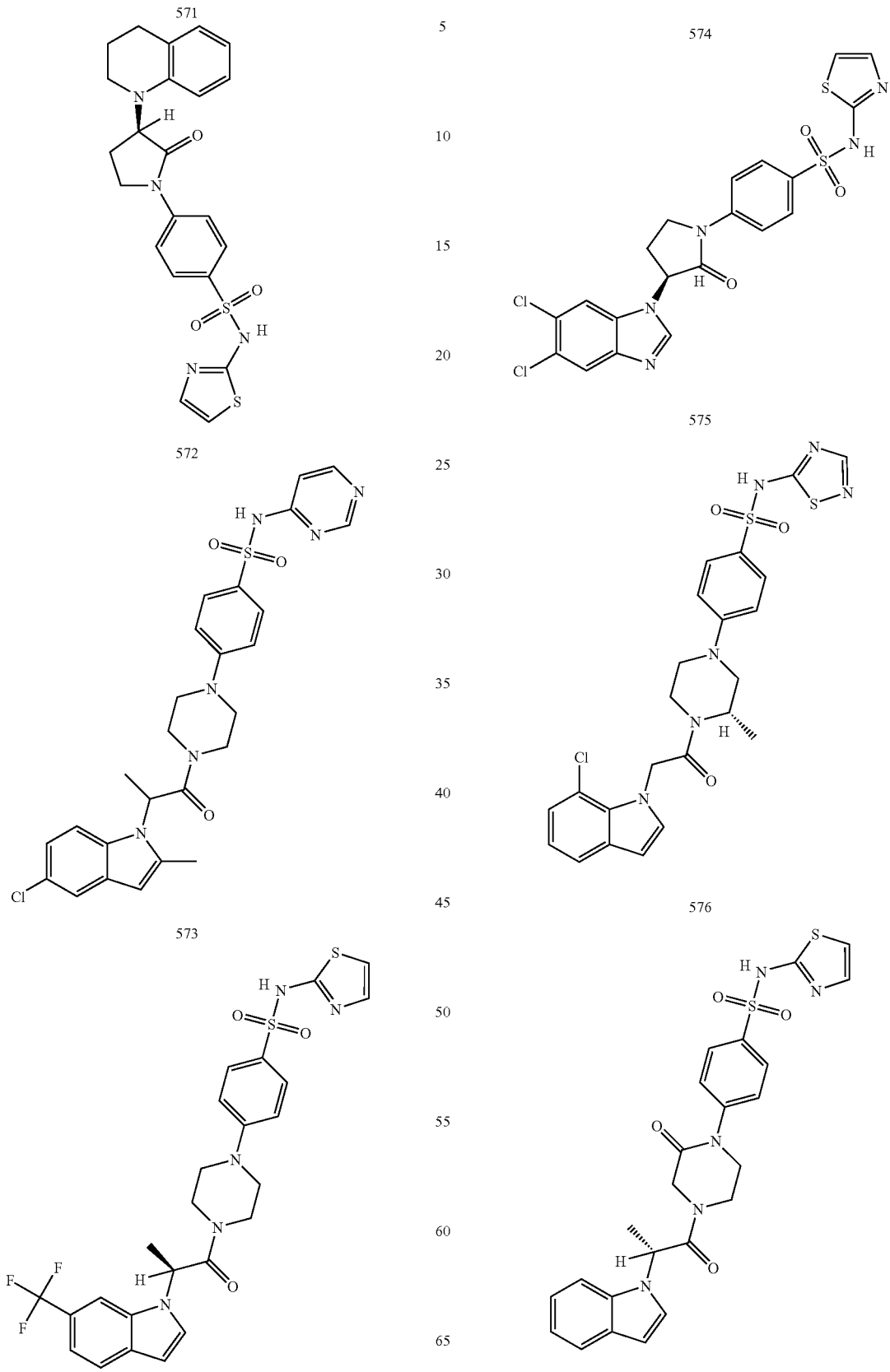

TABLE 2-continued

577

578

579

580

TABLE 2-continued
581
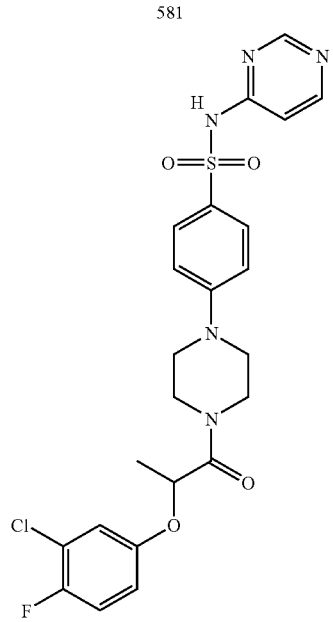
583
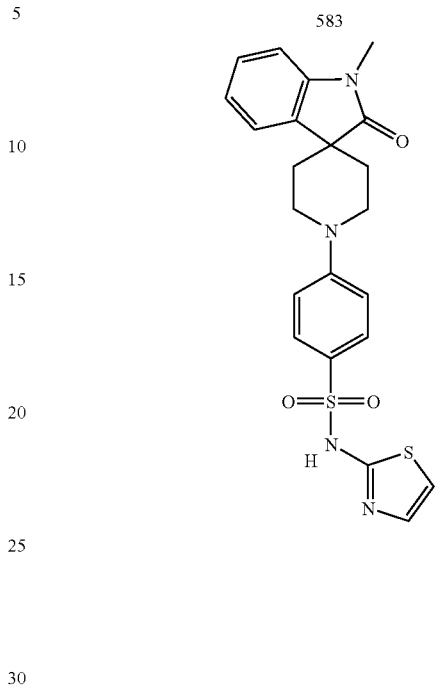
582
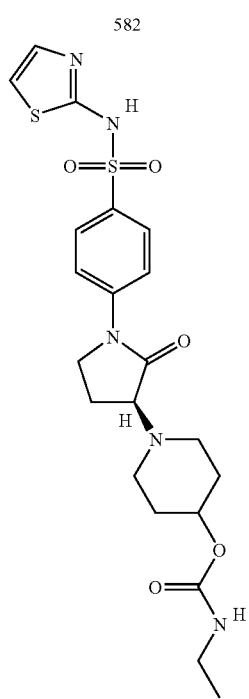
584
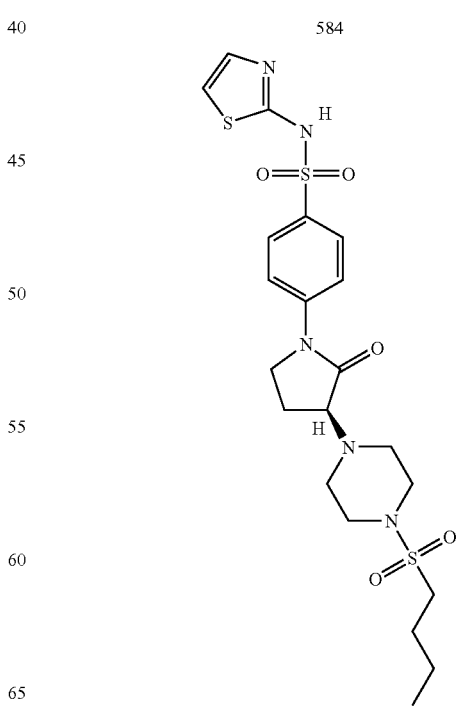

TABLE 2-continued
585
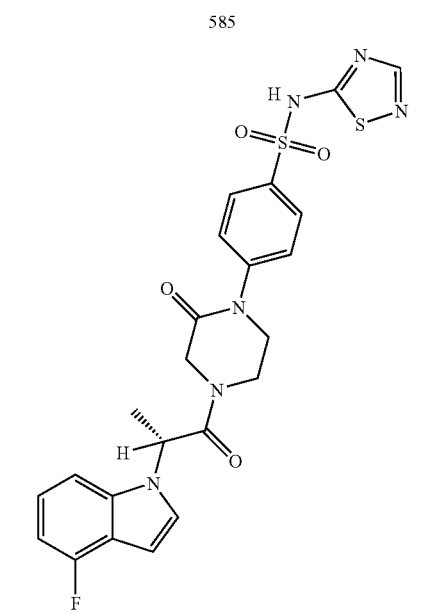
586
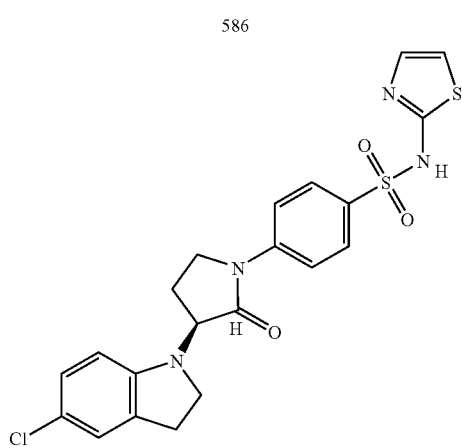
TABLE 2-continued
587
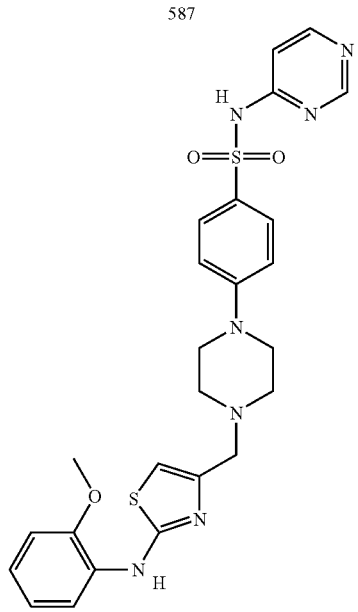
588
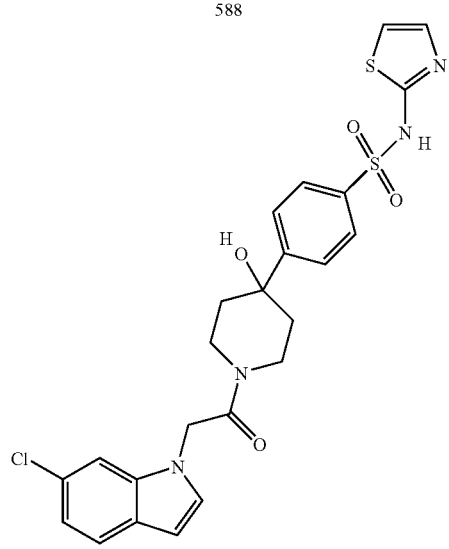

TABLE 2-continued
589
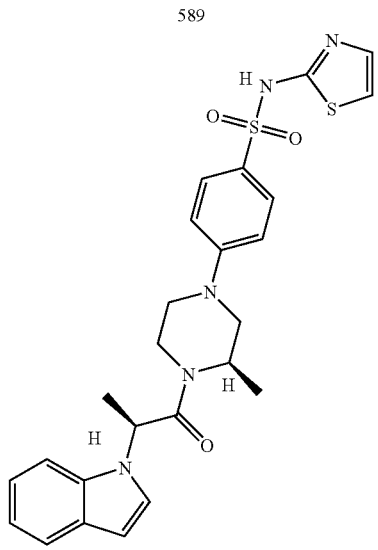
590
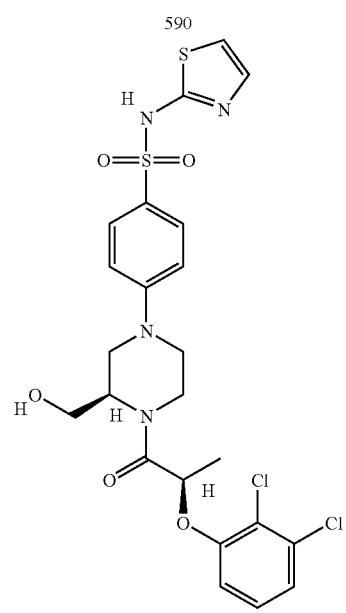
TABLE 2-continued
591
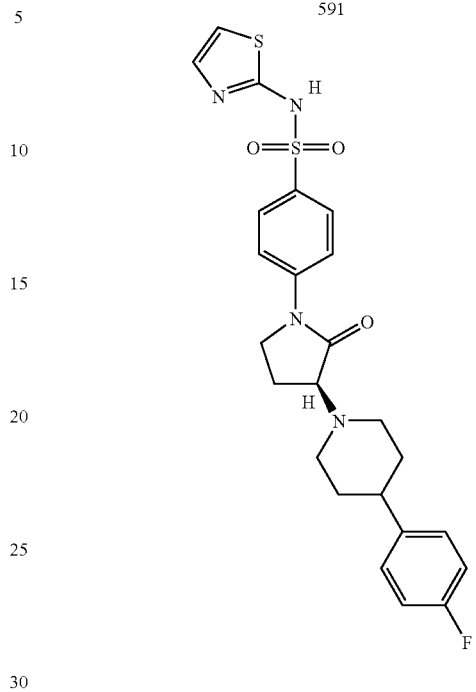
592
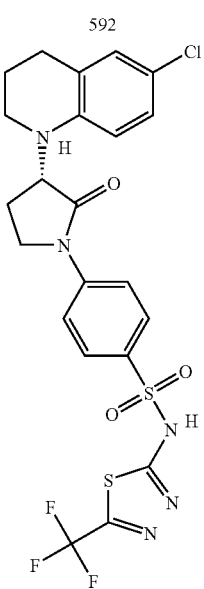

TABLE 2-continued
593
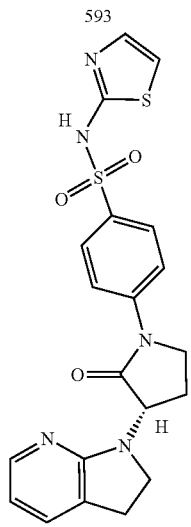
594
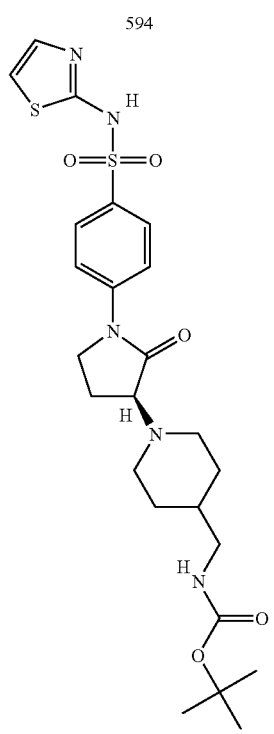
TABLE 2-continued
595
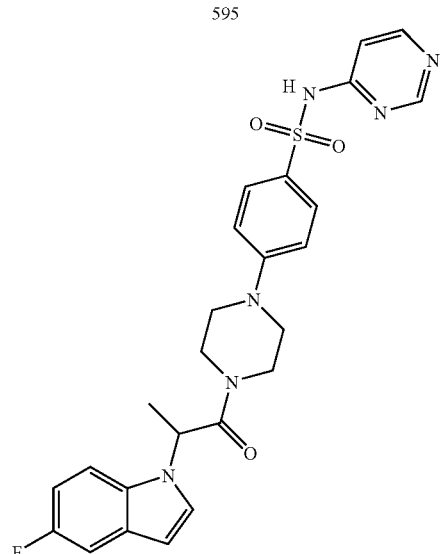
596
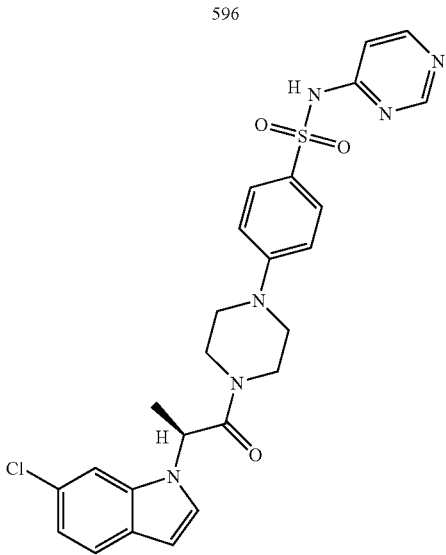

TABLE 2-continued
597
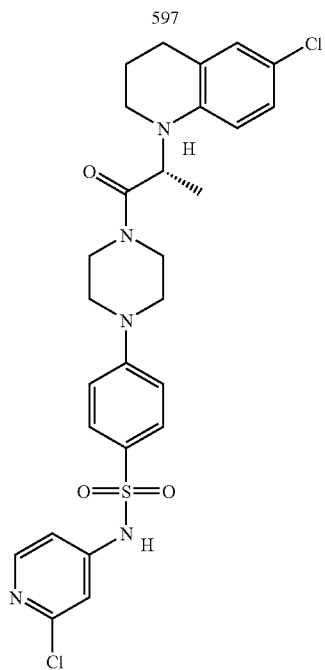
598
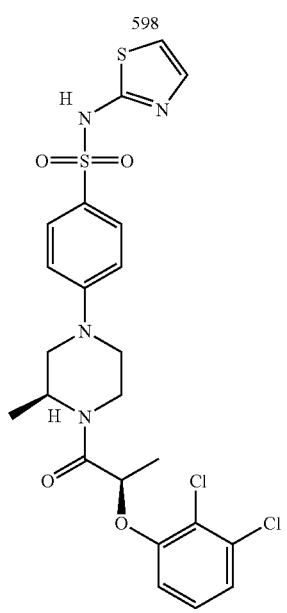
TABLE 2-continued
599
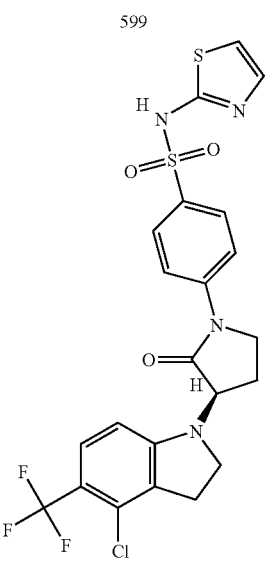
600
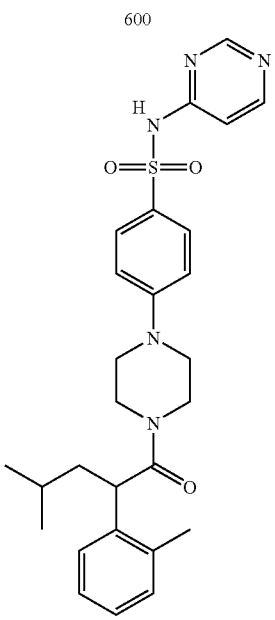

TABLE 2-continued
601
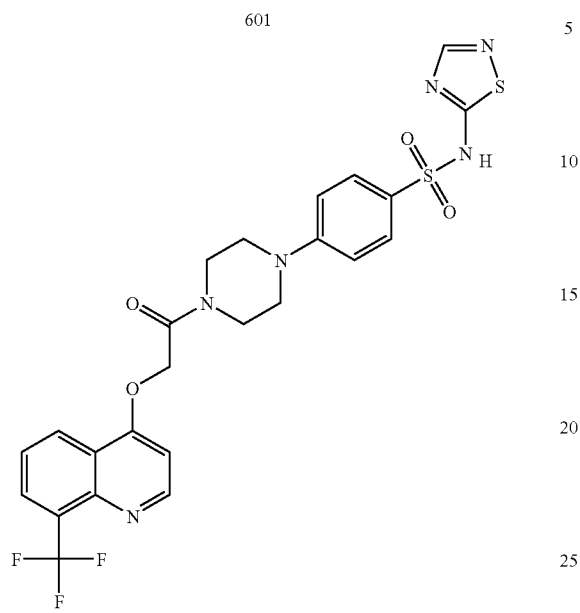
602
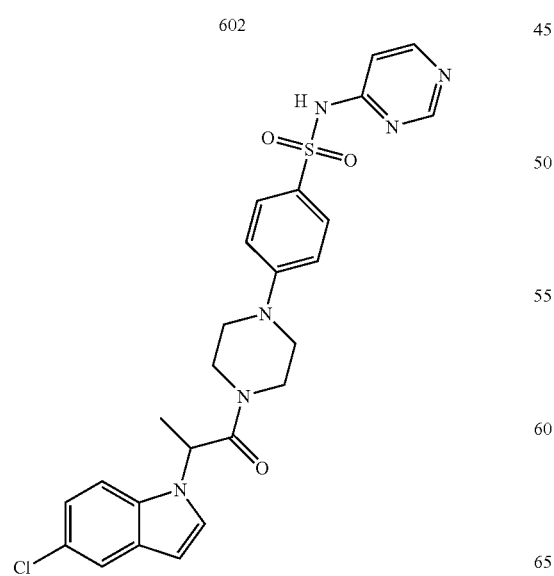
TABLE 2-continued
603
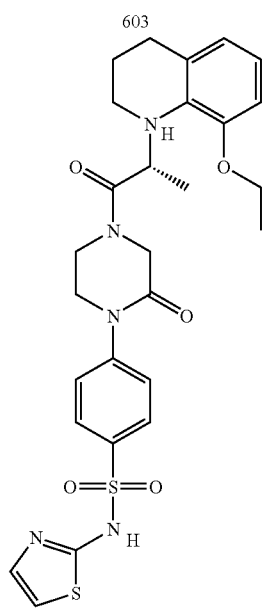
604
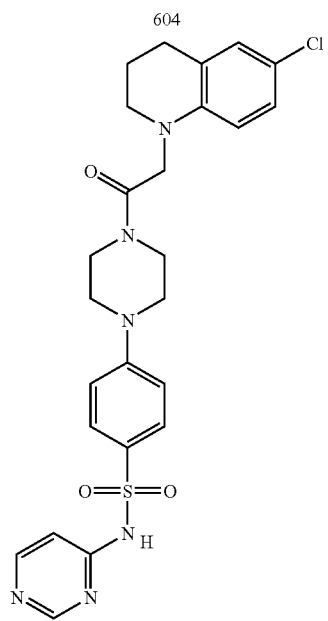

TABLE 2-continued
605
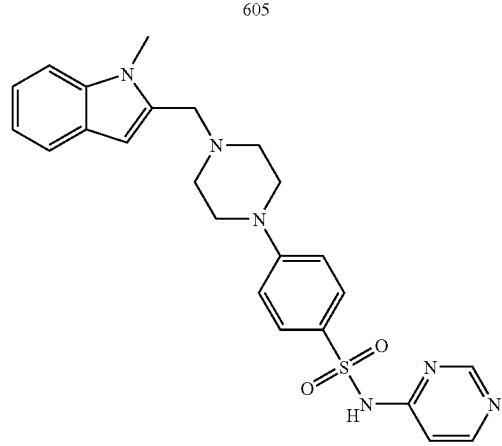
606
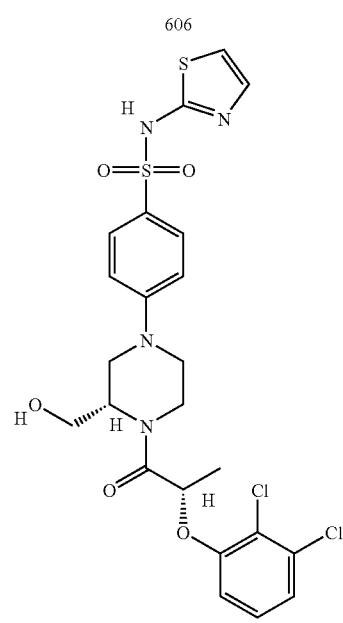
TABLE 2-continued
607
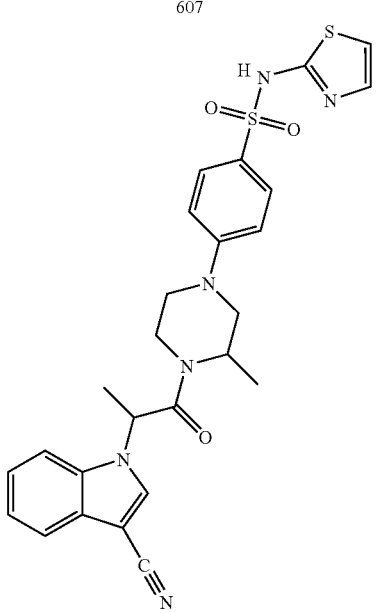
608
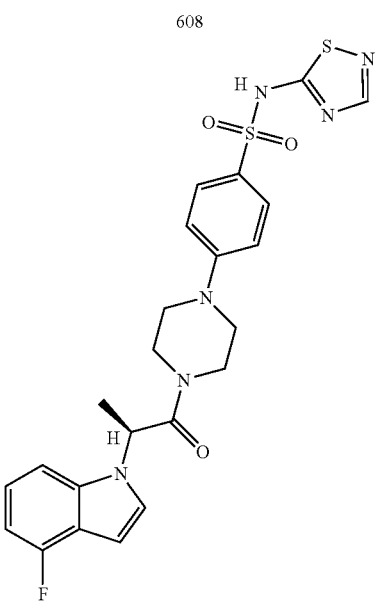

TABLE 2-continued
609
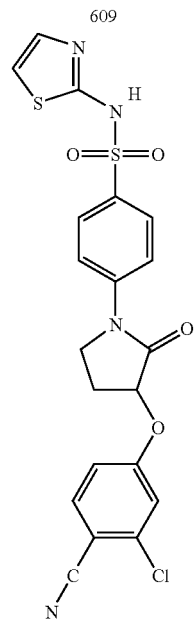
610
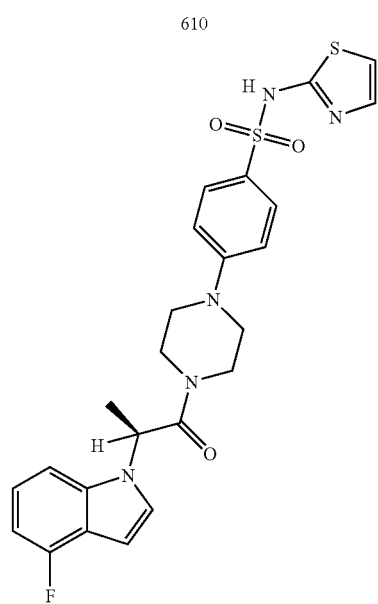
TABLE 2-continued
611
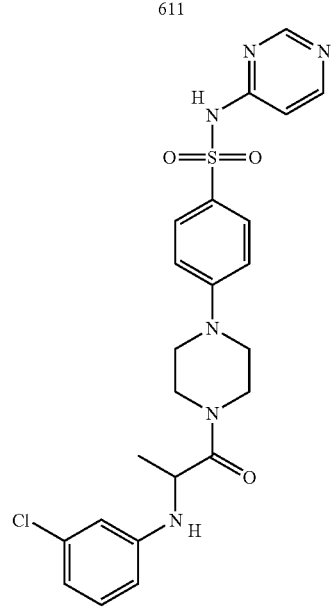
612
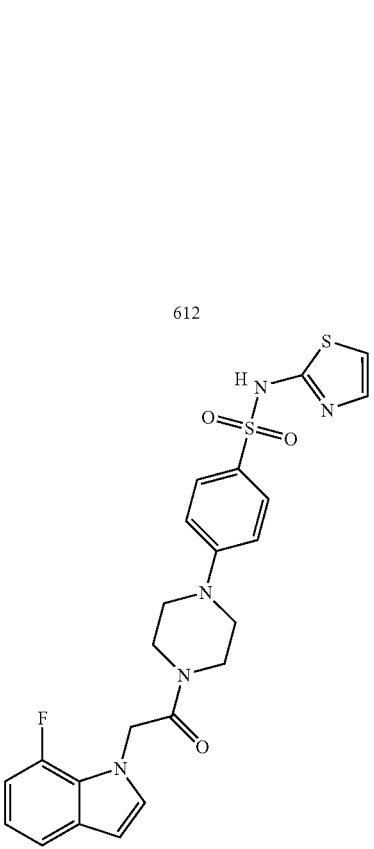

TABLE 2-continued
613
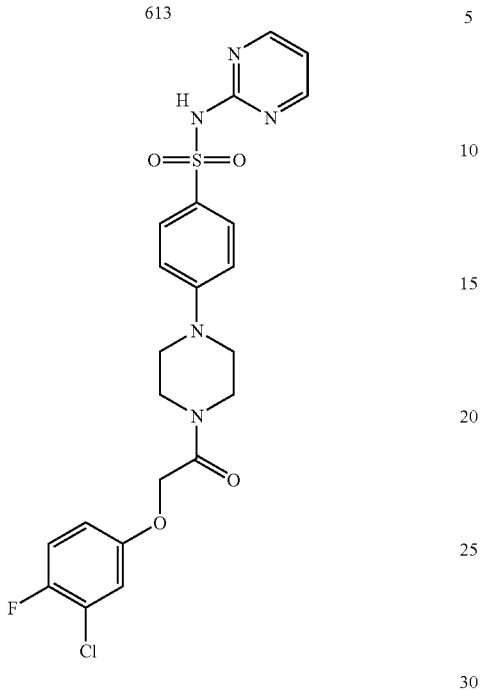
614
615
TABLE 2-continued
616
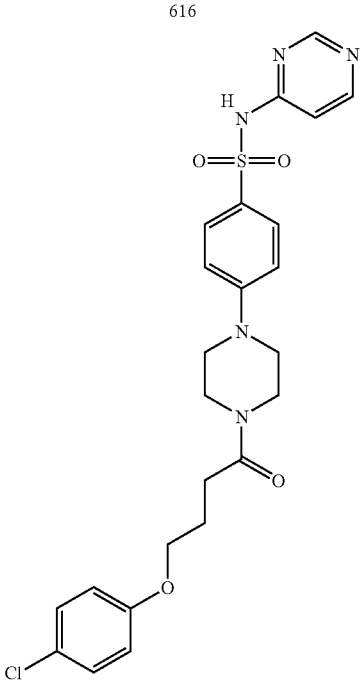
617
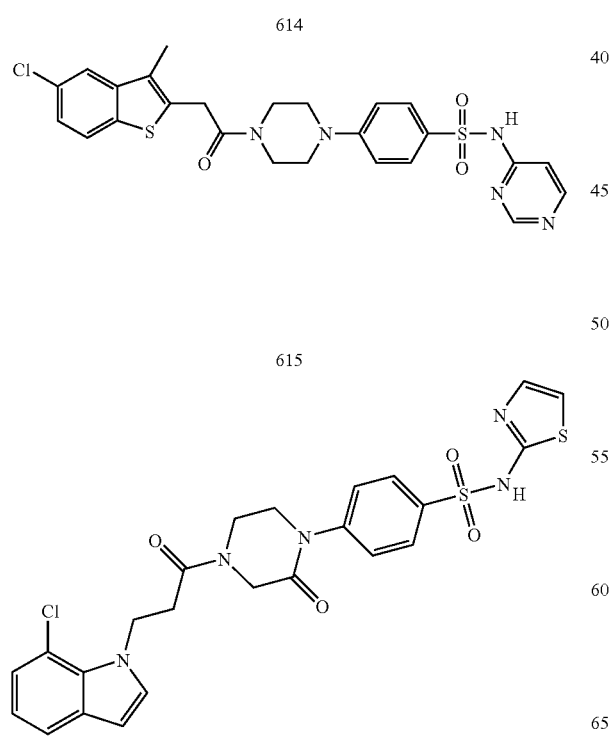

TABLE 2-continued
618
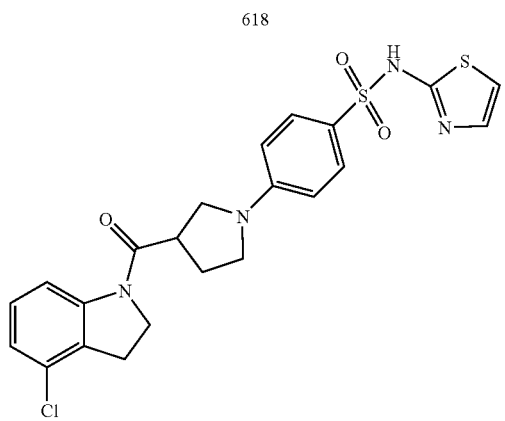
619
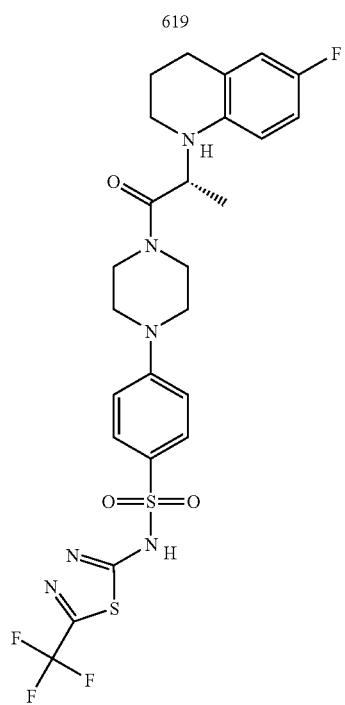
TABLE 2-continued
620
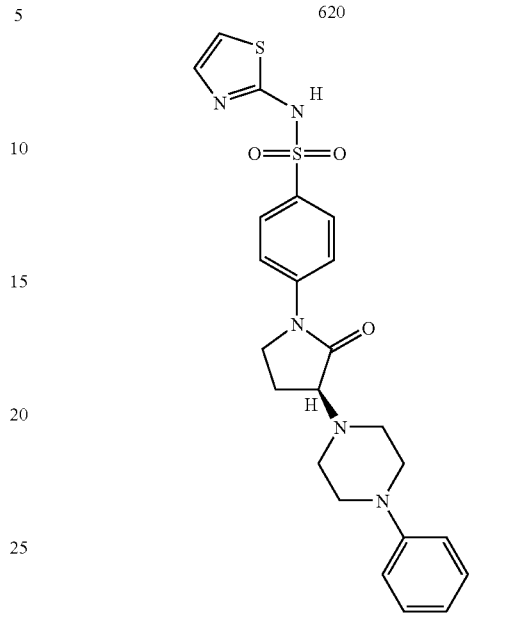
621
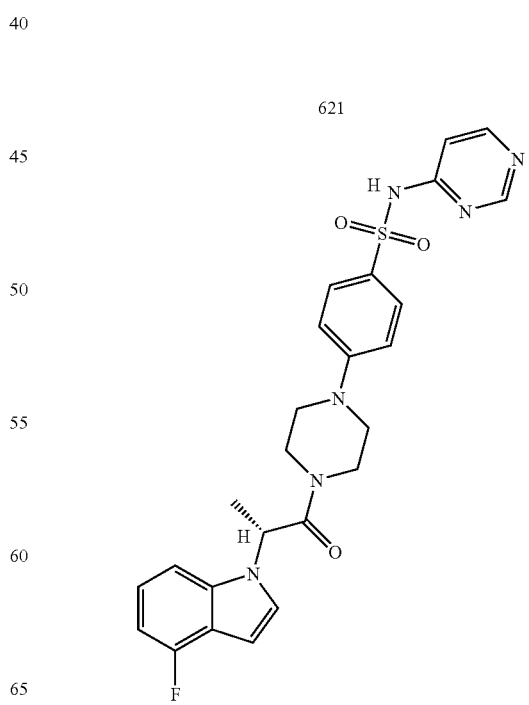

TABLE 2-continued
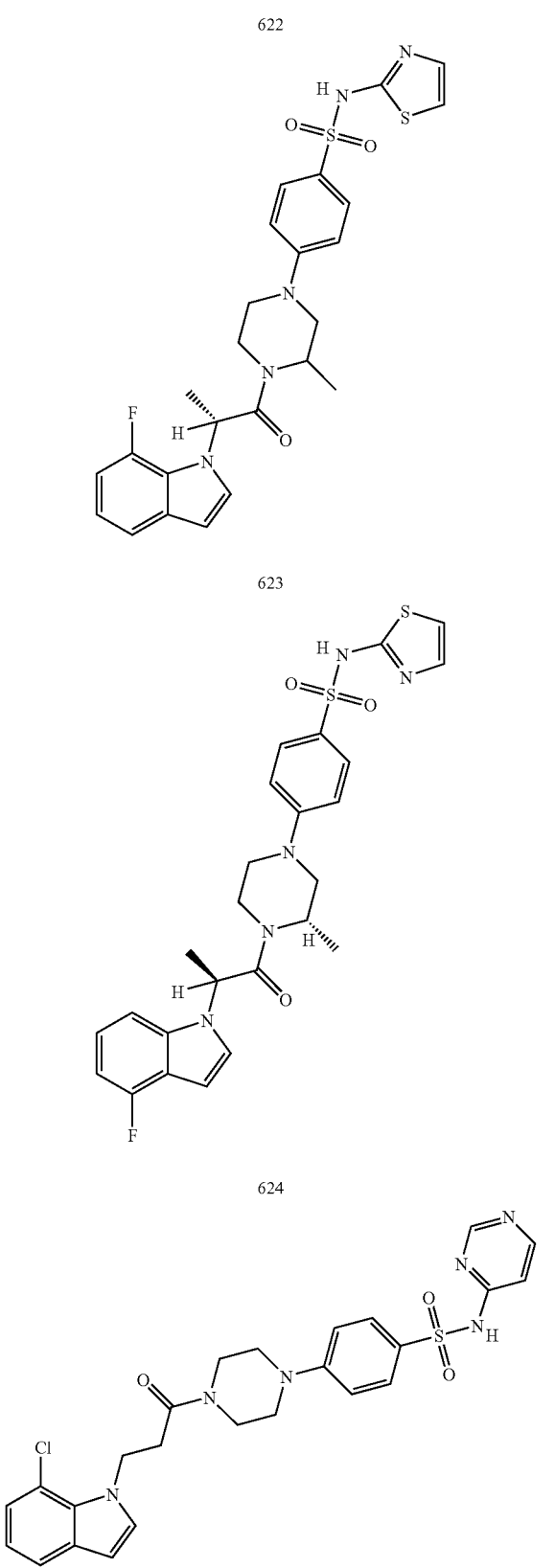
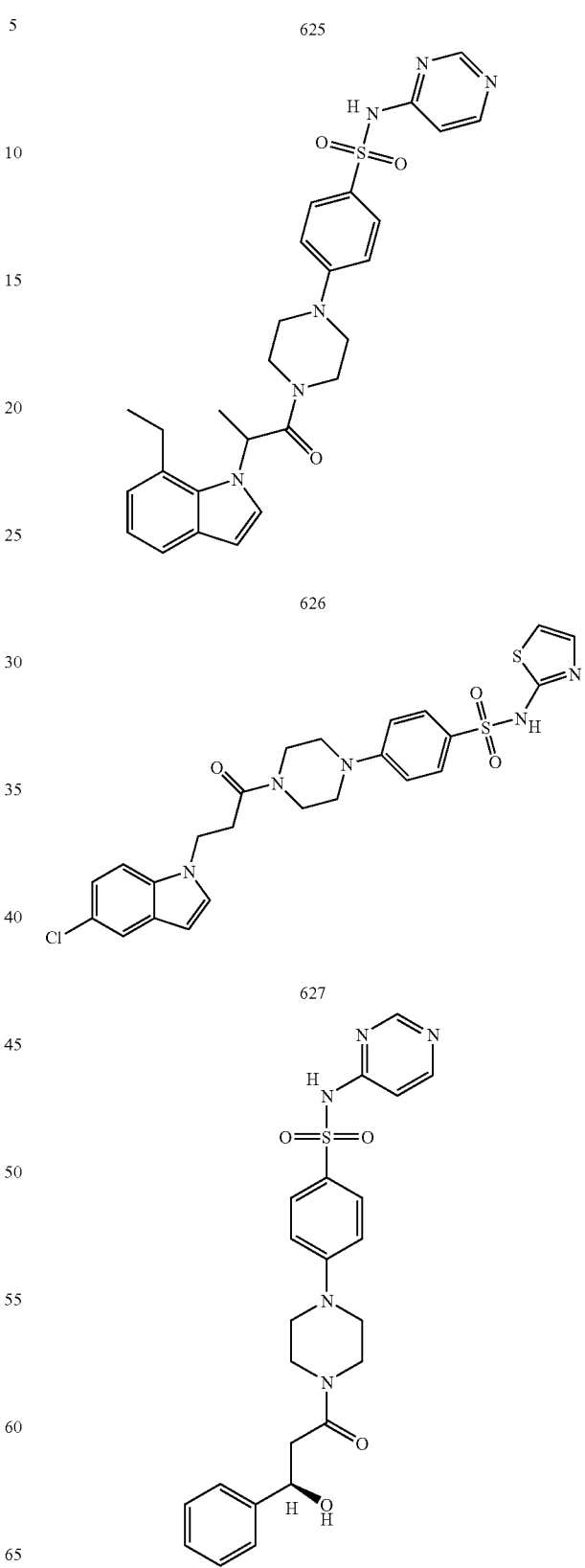

TABLE 2-continued
628
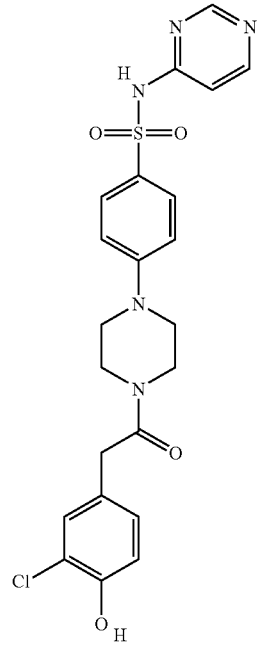
629
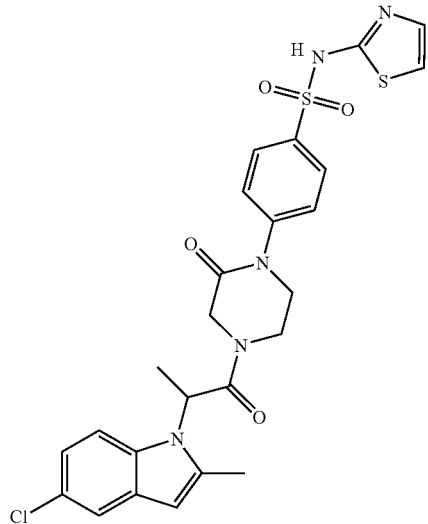
TABLE 2-continued
630
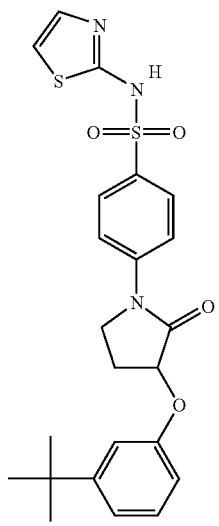
631
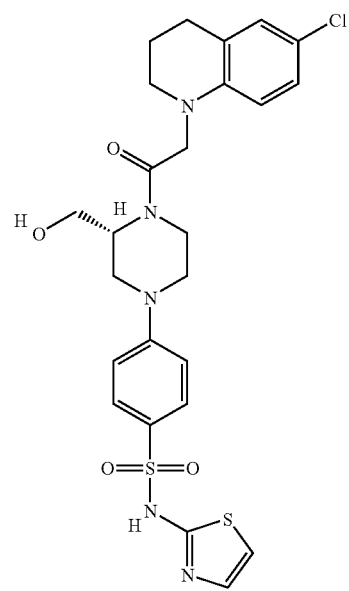

TABLE 2-continued
632
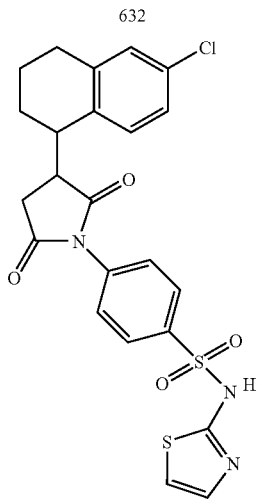
633
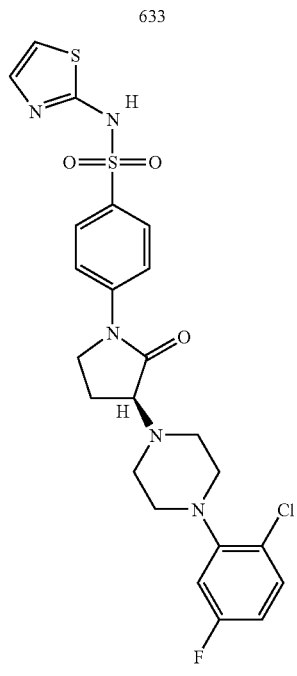
TABLE 2-continued
634
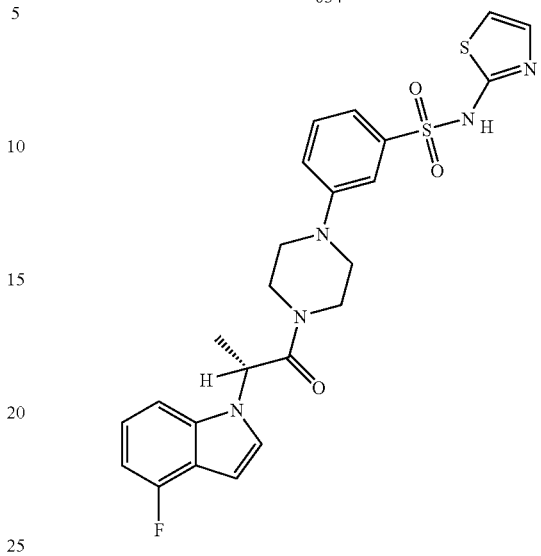
635
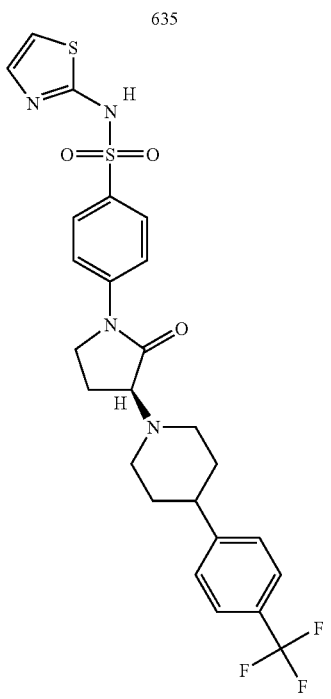

TABLE 2-continued
636
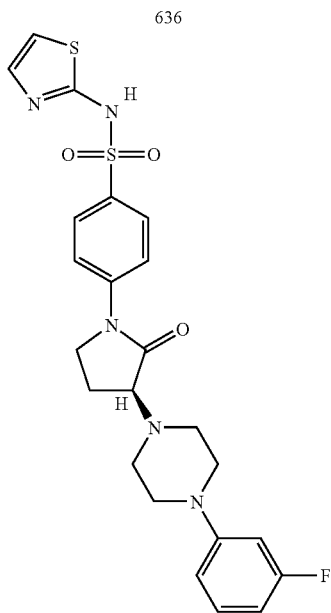
637
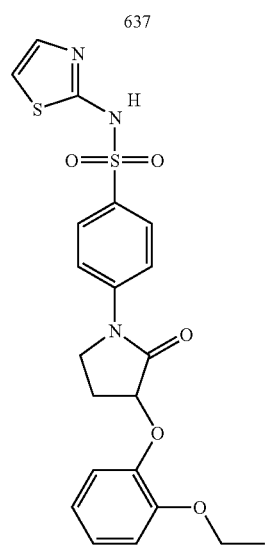
TABLE 2-continued
638
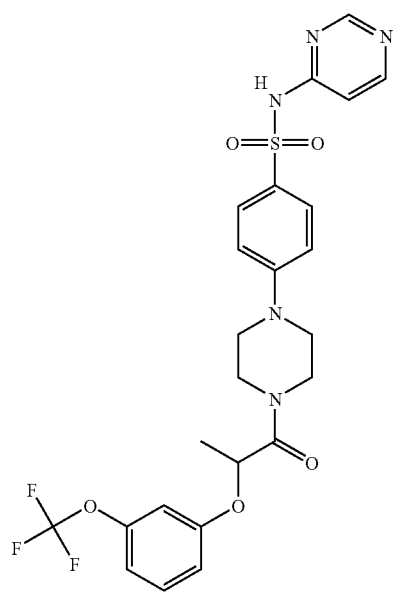
639
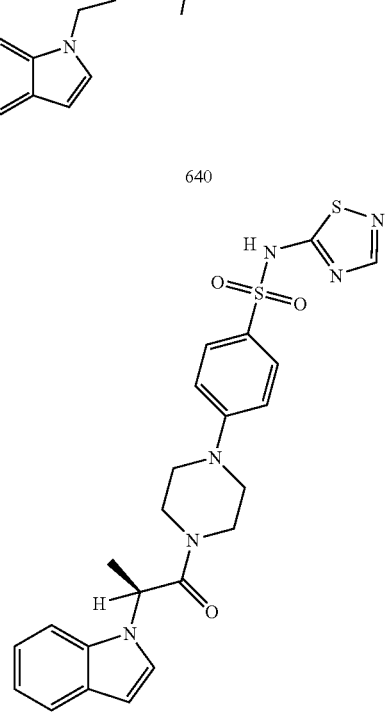
640

TABLE 2-continued
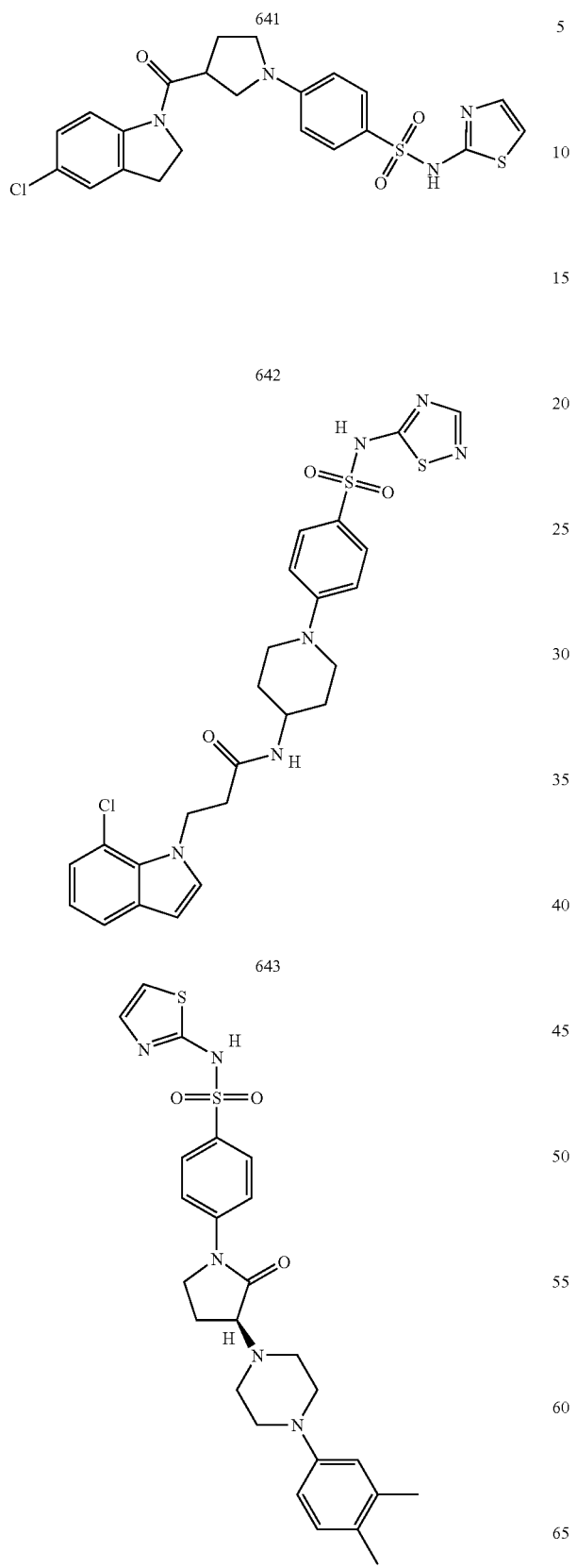
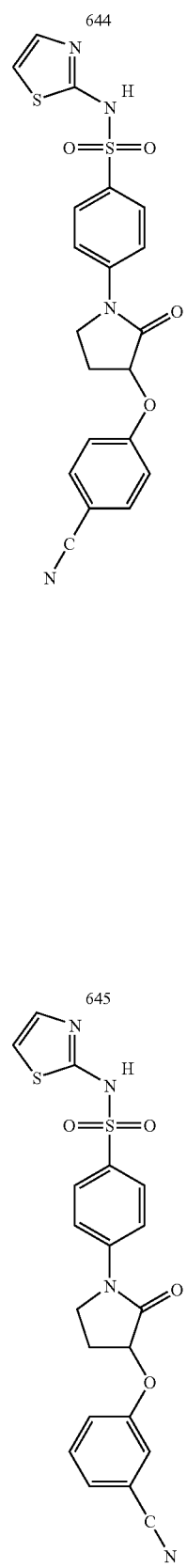

TABLE 2-continued
646
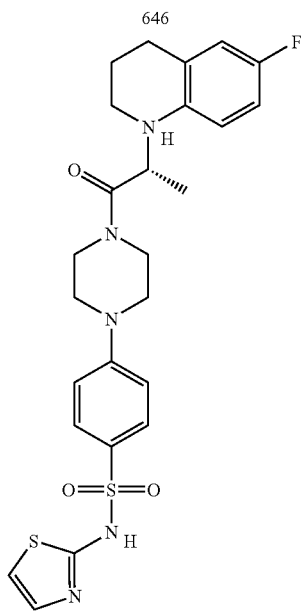
TABLE 2-continued
648
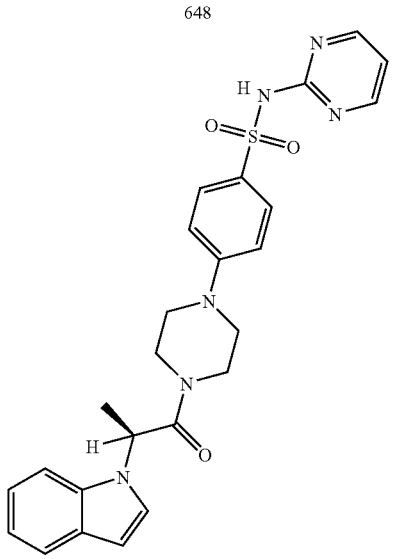
647
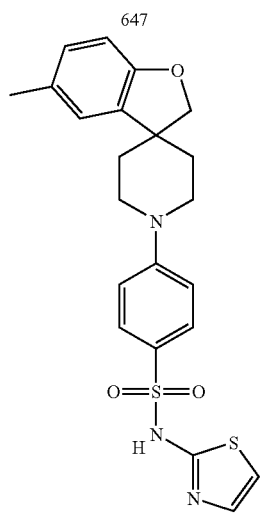
649

TABLE 2-continued
650
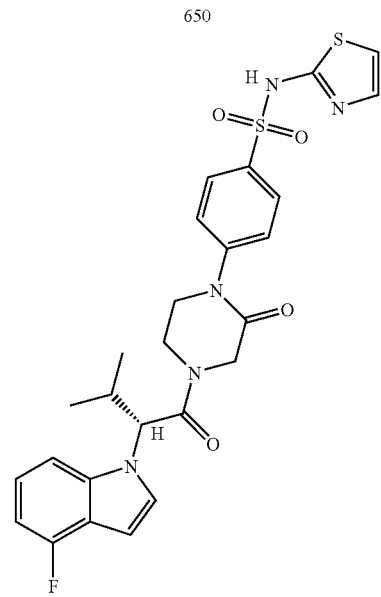
651
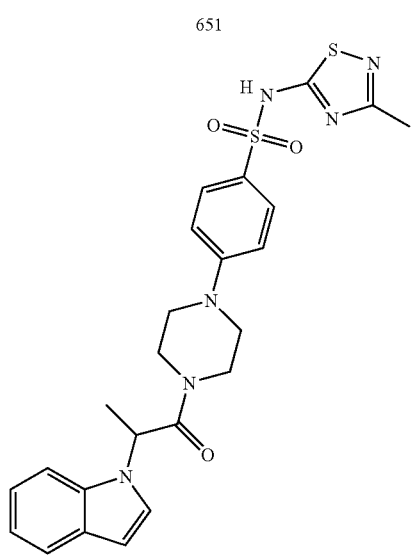
TABLE 2-continued
652
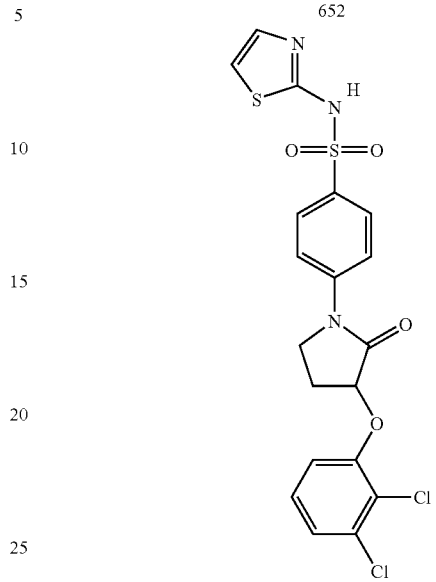
653
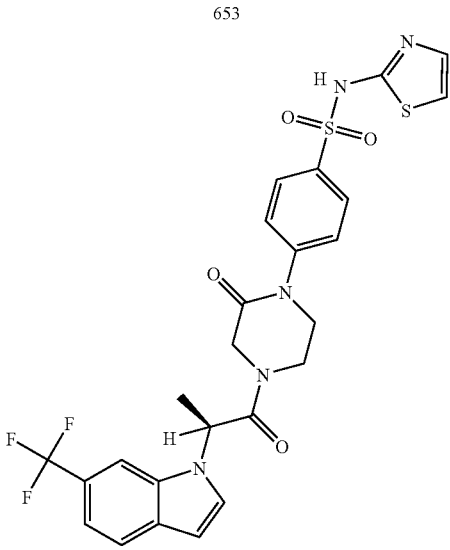

TABLE 2-continued
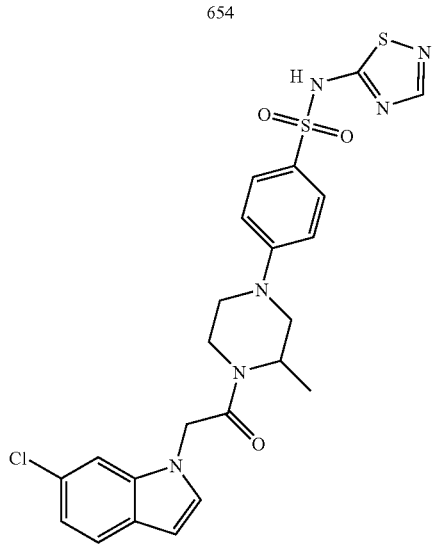
654
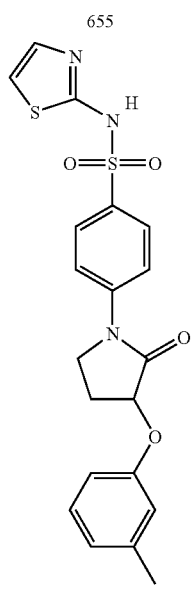
655
TABLE 2-continued
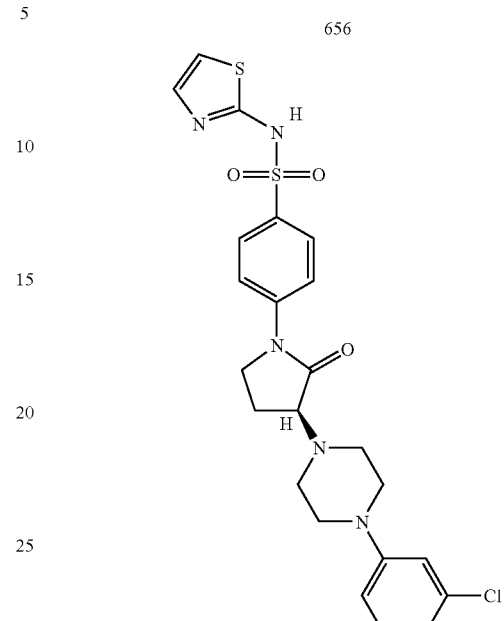
656
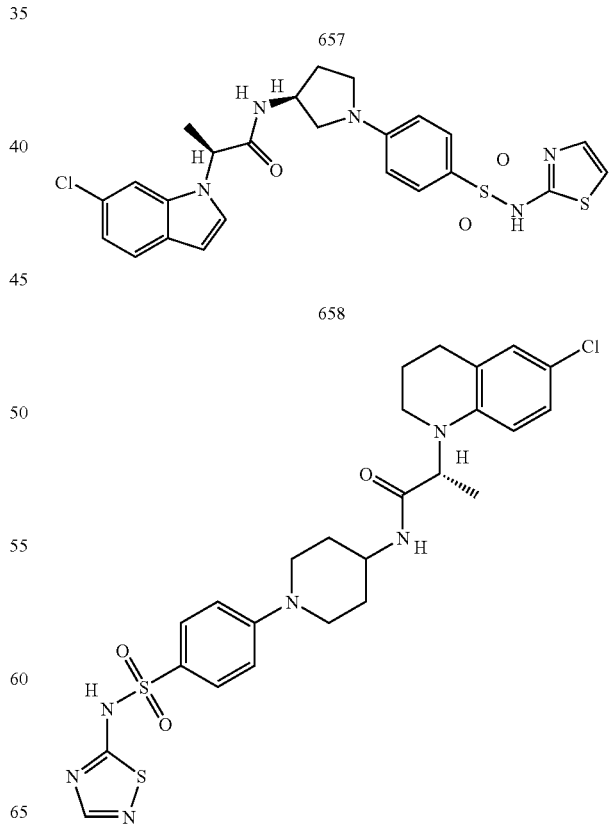
657
658

TABLE 2-continued
659
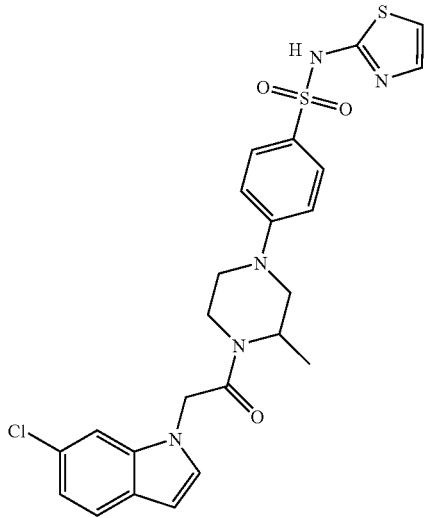
TABLE 2-continued
661
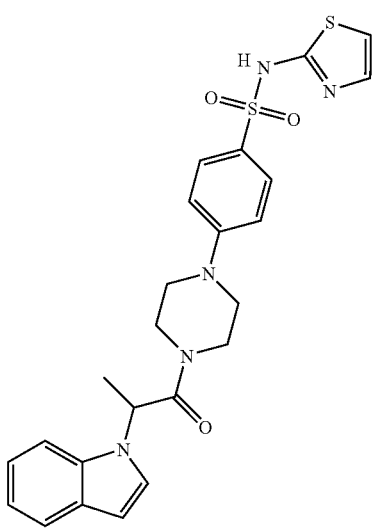
660
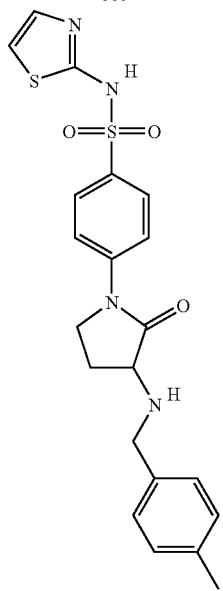
662
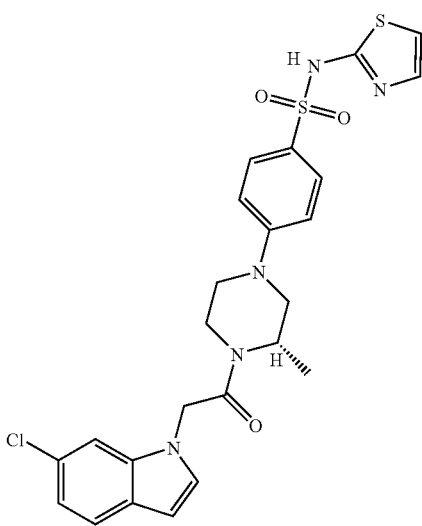

TABLE 2-continued
663
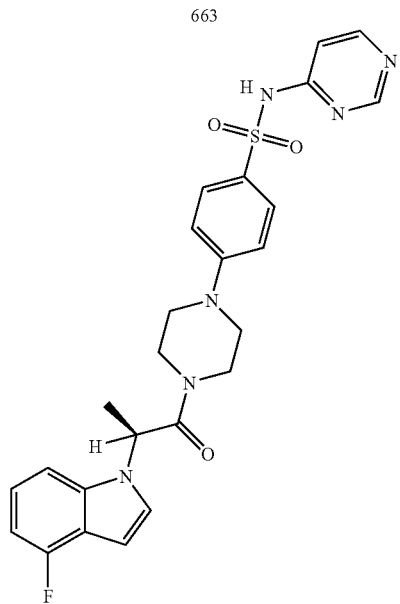
664
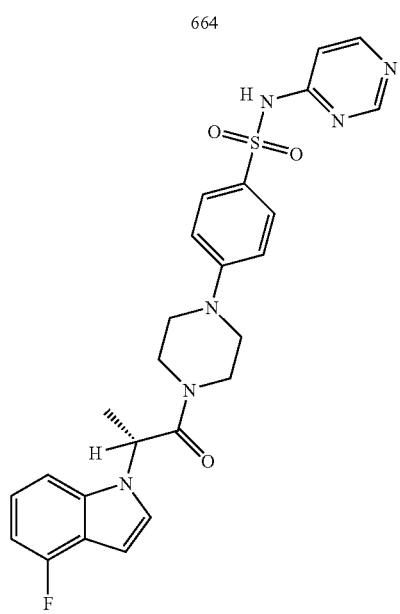
TABLE 2-continued
665
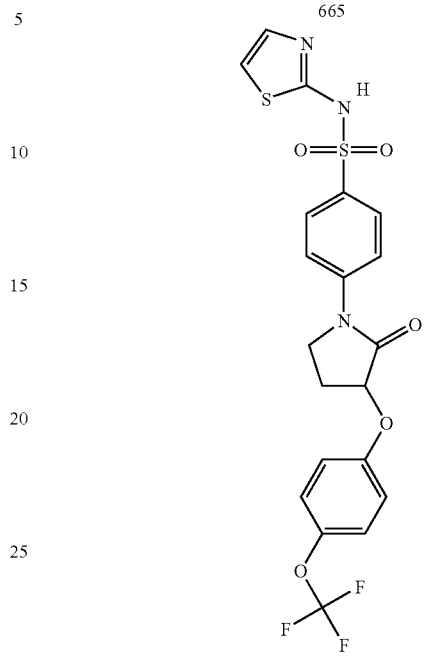
666
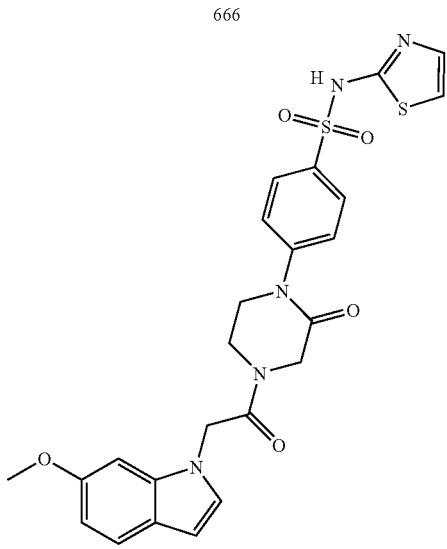

TABLE 2-continued
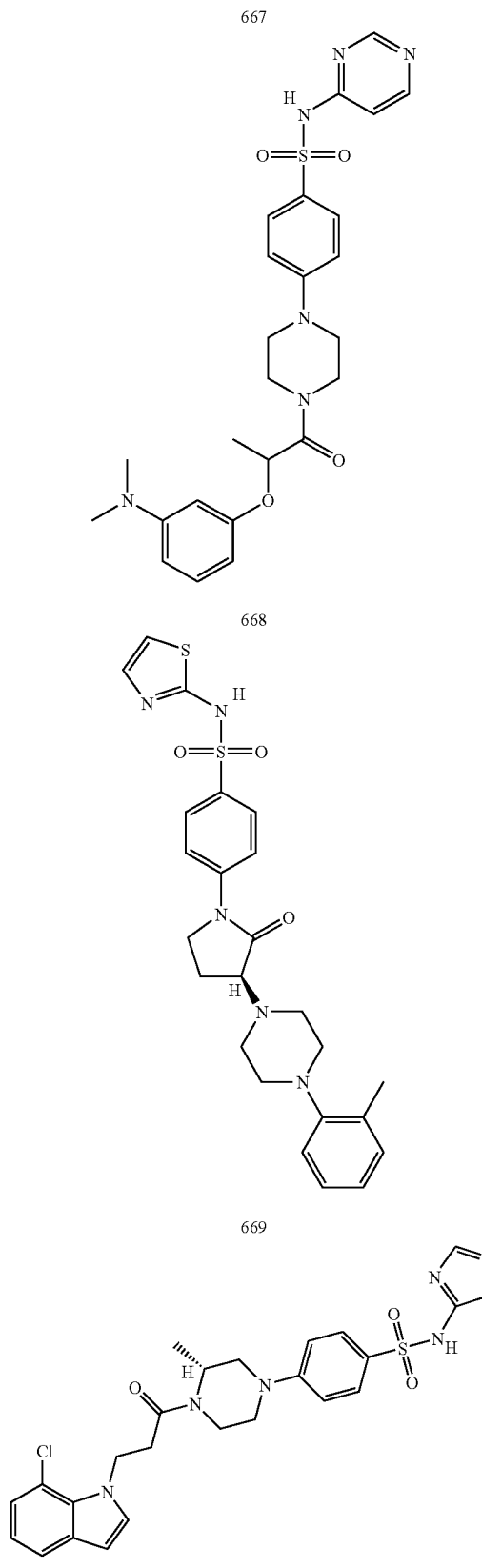
TABLE 2-continued
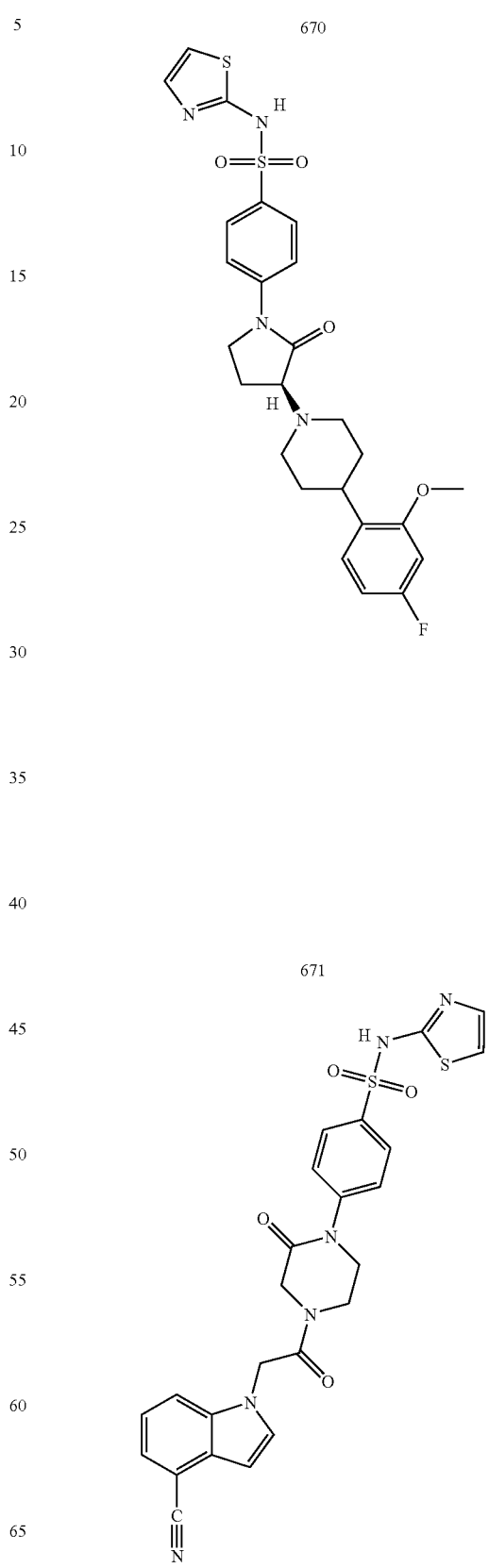

TABLE 2-continued
672
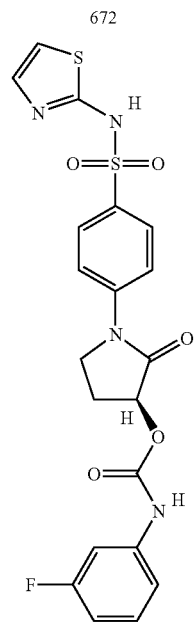
673
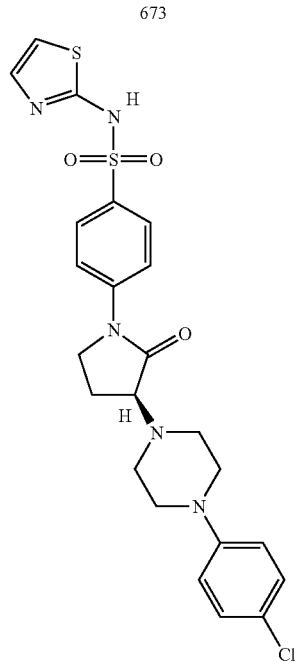
TABLE 2-continued
674
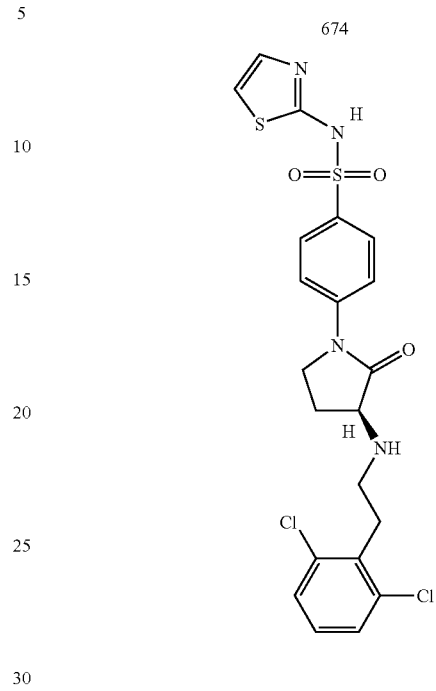
675
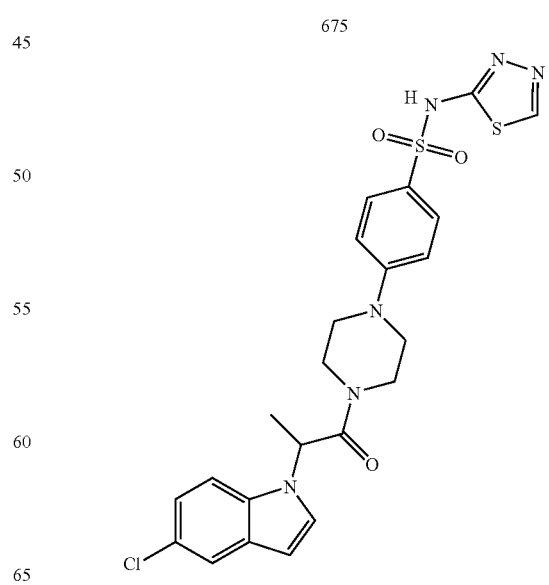

TABLE 2-continued
676
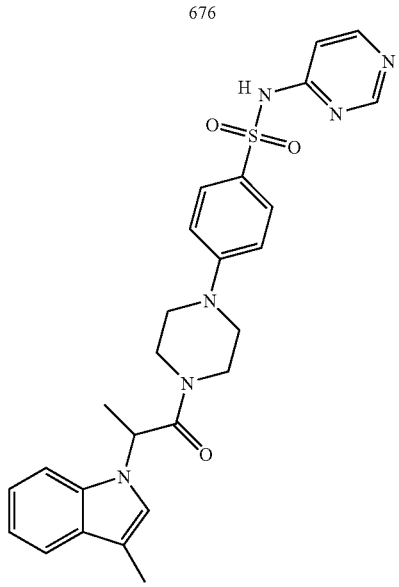
677
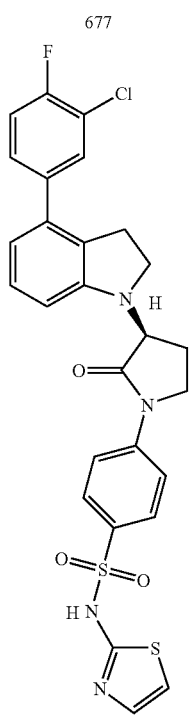
TABLE 2-continued
678
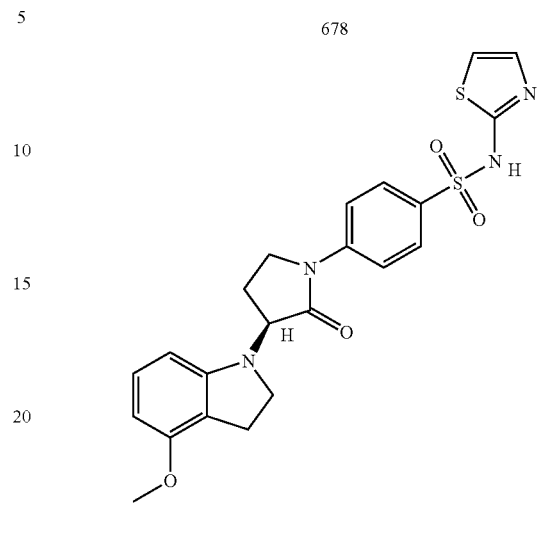
679
680
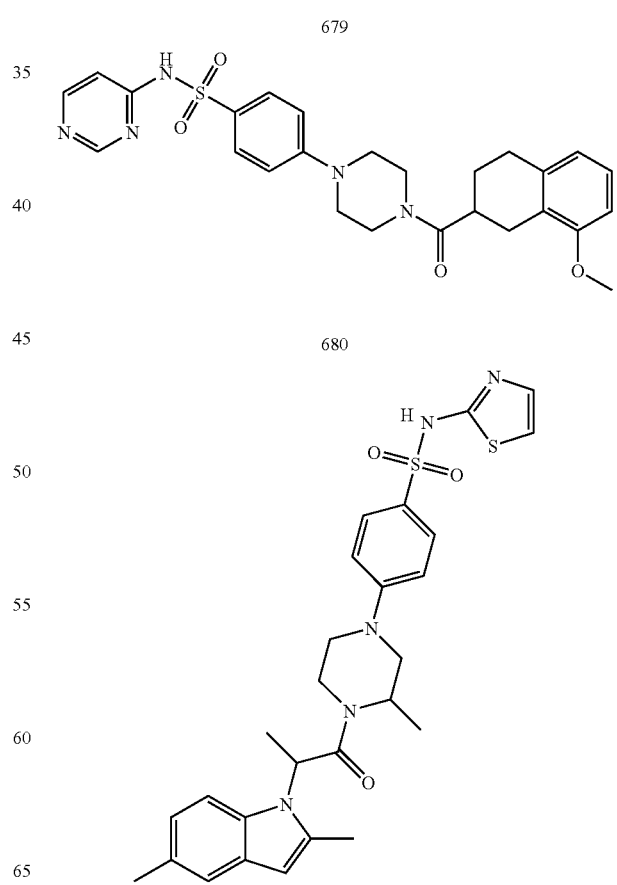

TABLE 2-continued
681
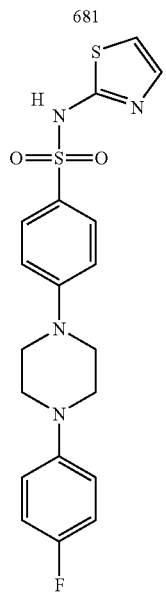
682
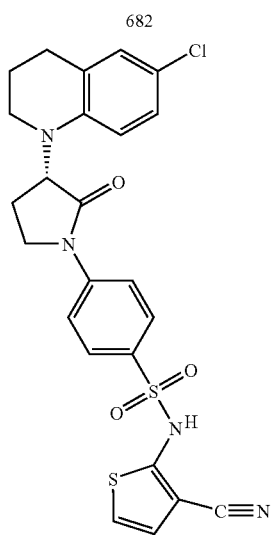
TABLE 2-continued
683
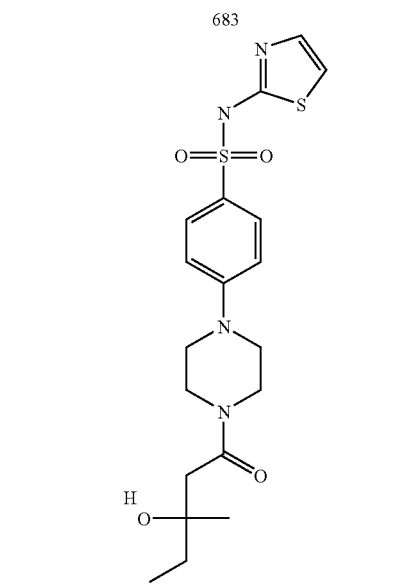
684
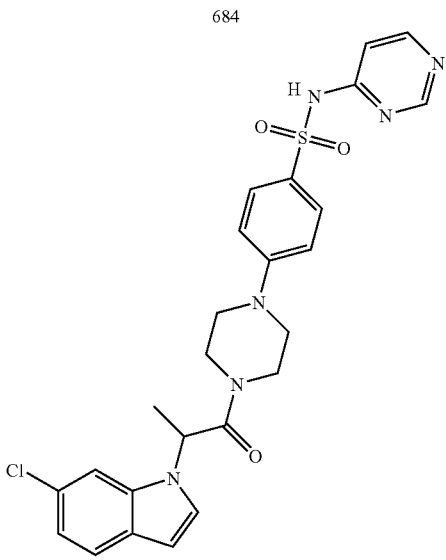

TABLE 2-continued
697
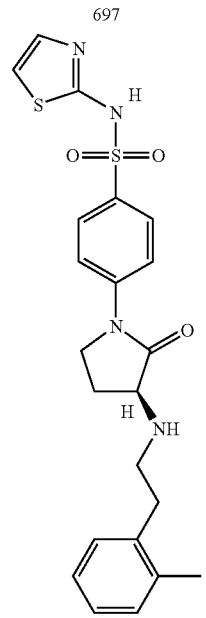
698
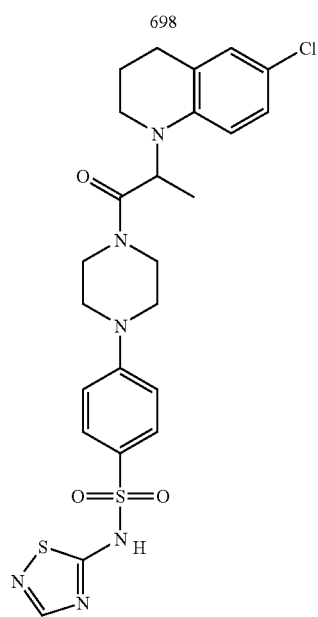
TABLE 2-continued
699
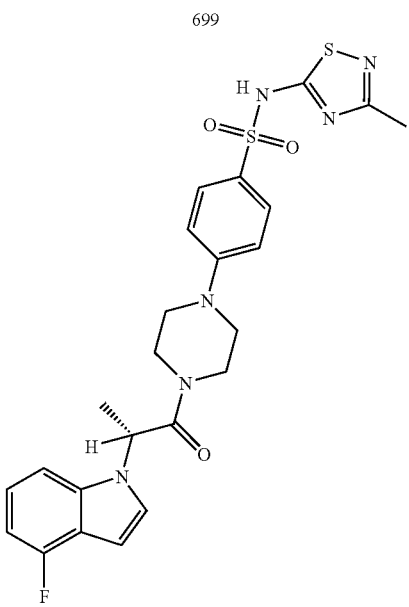
700
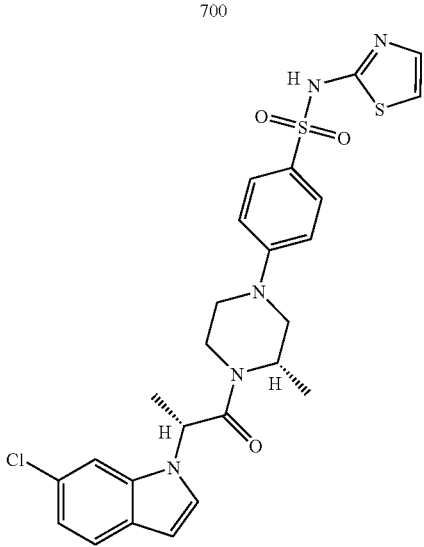

TABLE 2-continued
701
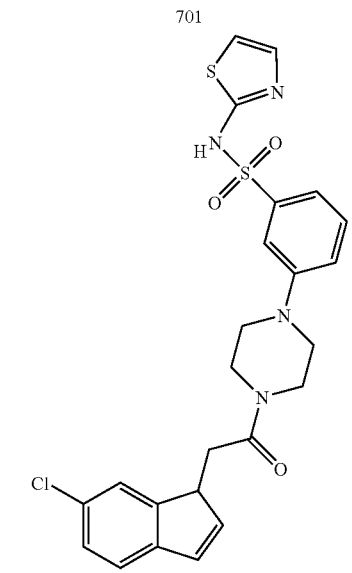
702
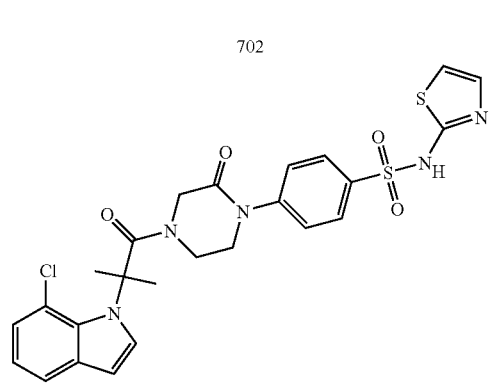
703
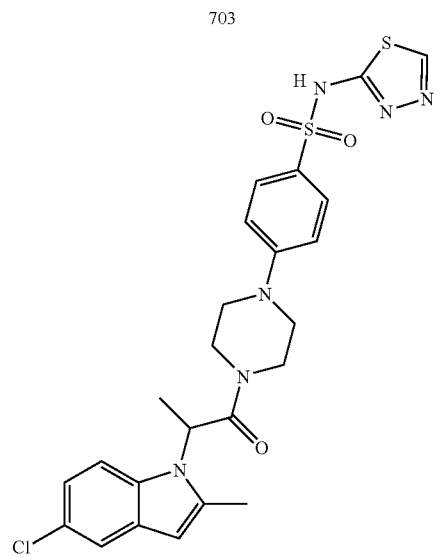
TABLE 2-continued
704
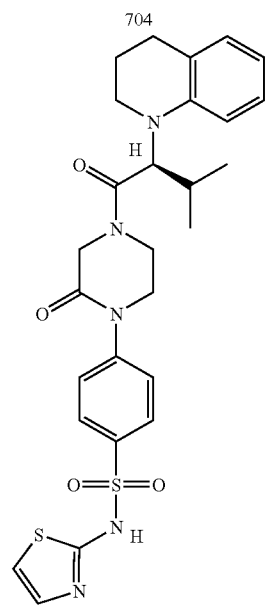
705
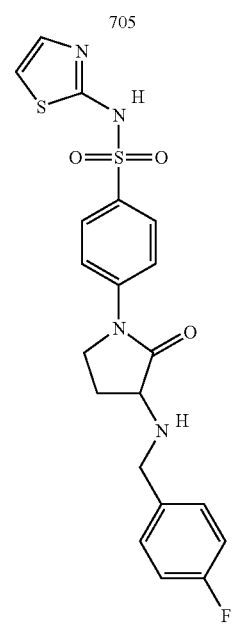

TABLE 2-continued
706
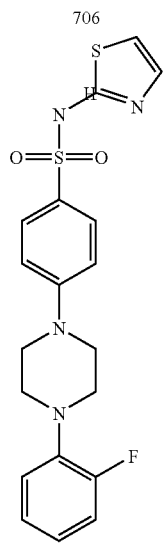
707
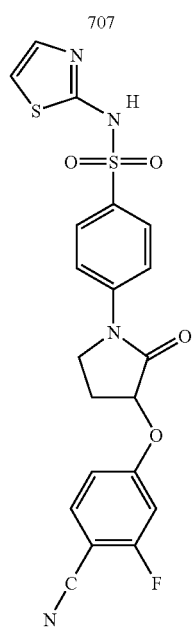
TABLE 2-continued
708
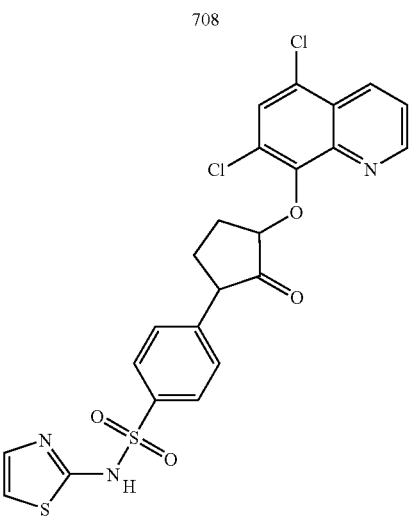
709
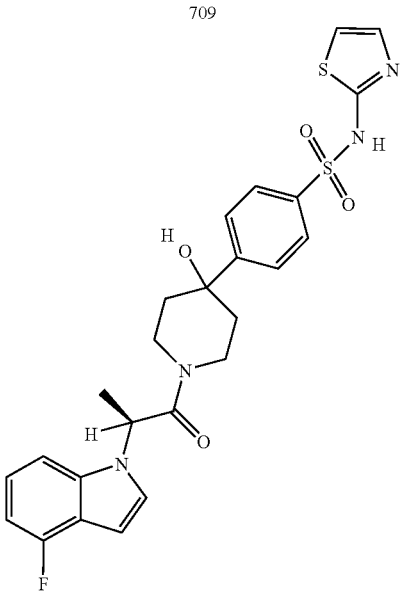

TABLE 2-continued
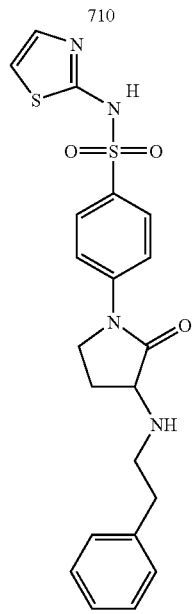
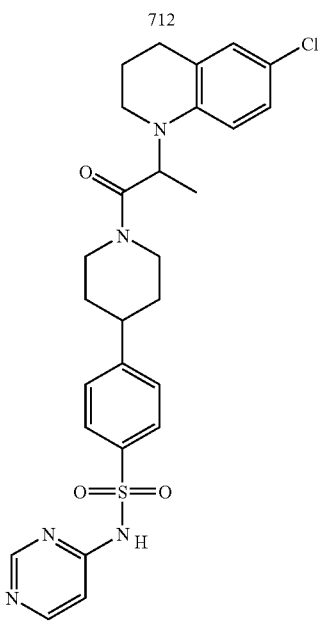
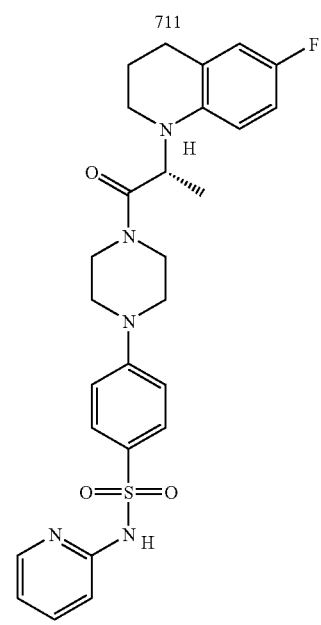
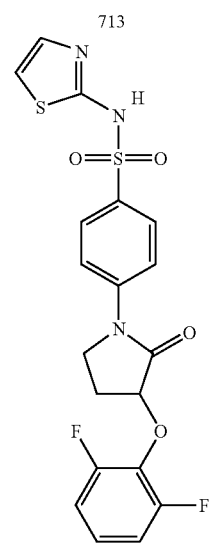

TABLE 2-continued
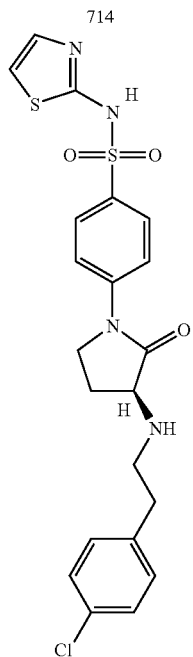
714
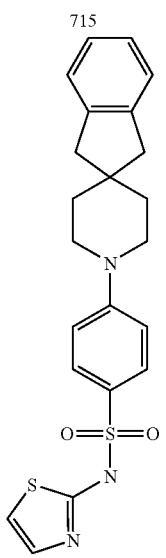
715
TABLE 2-continued
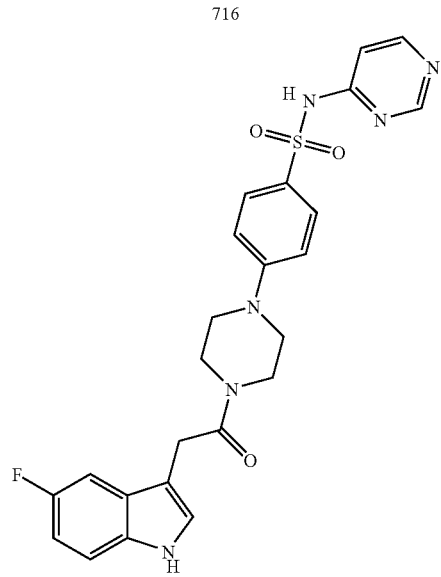
716
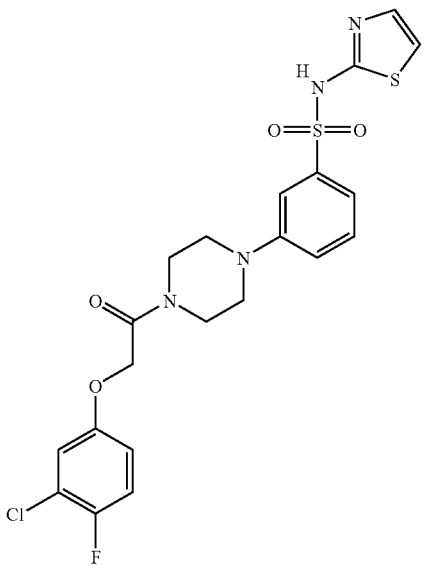
717

TABLE 2-continued
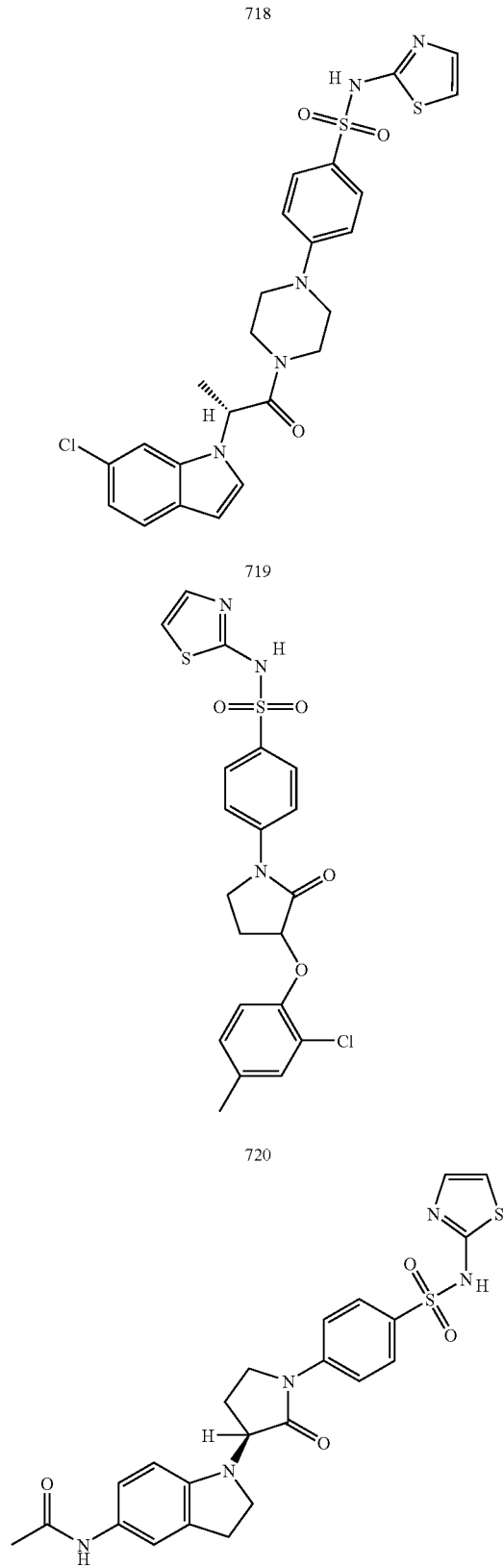

TABLE 2-continued
723
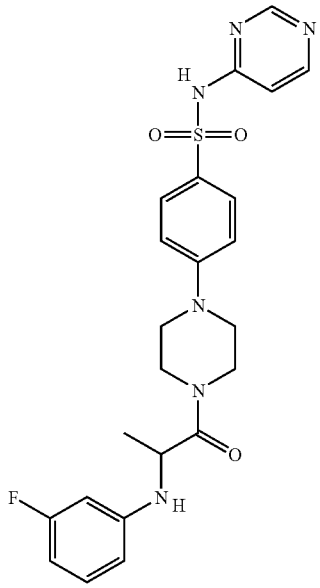
724
726
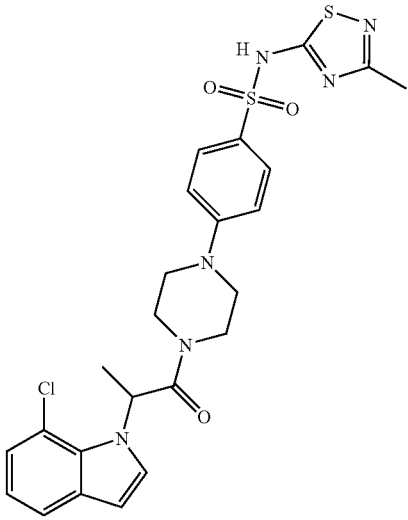
727
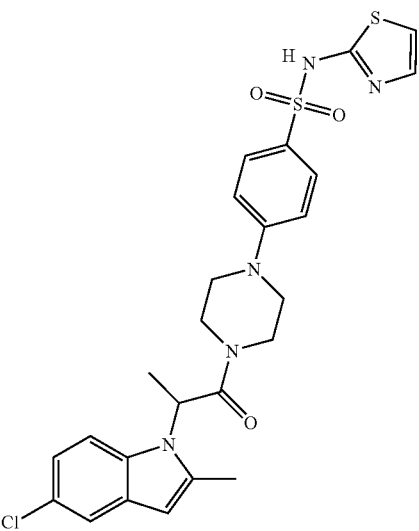
728
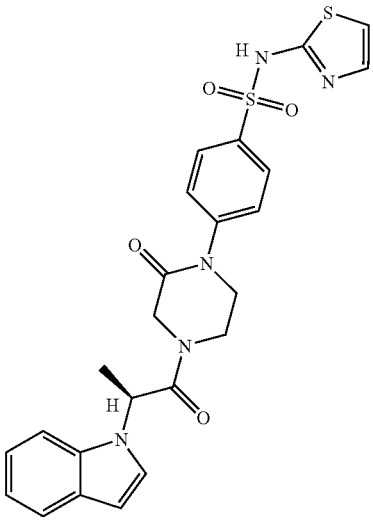
725
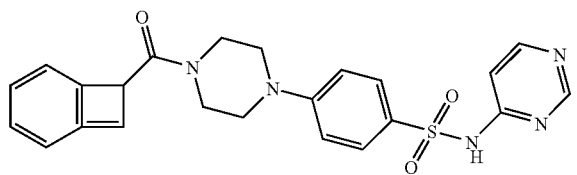

TABLE 2-continued
729
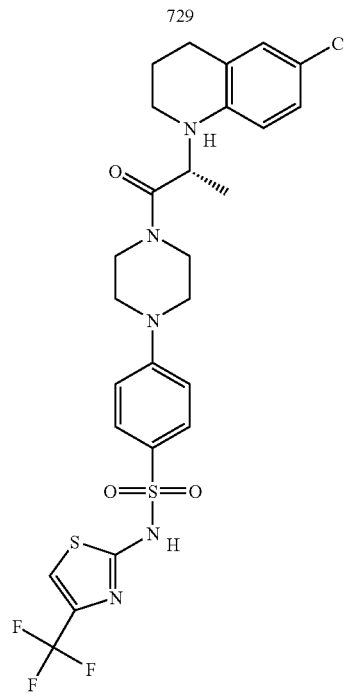
731
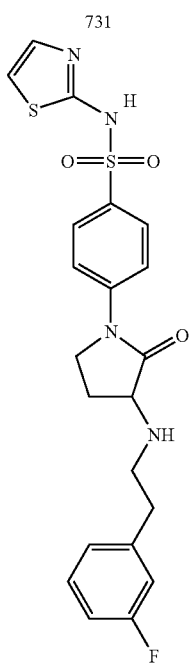
730
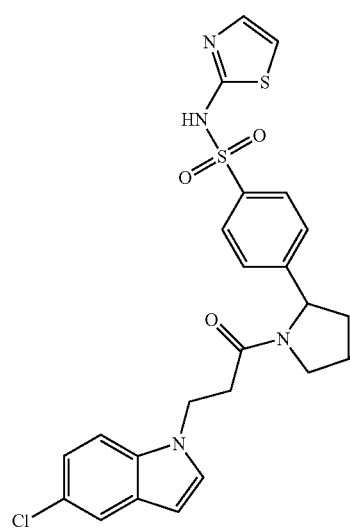
732
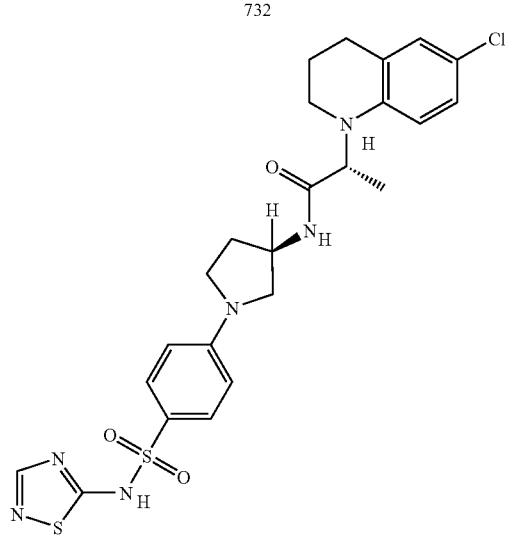

TABLE 2-continued
733
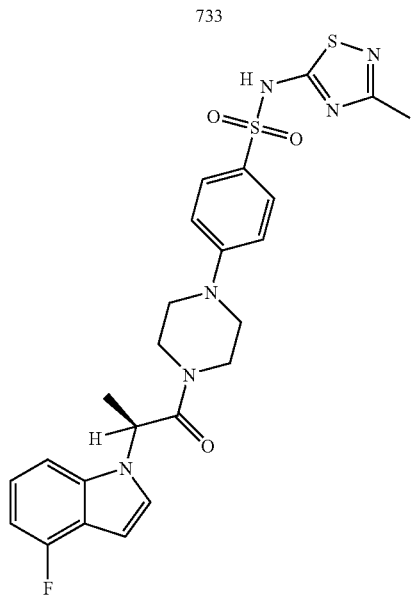
734
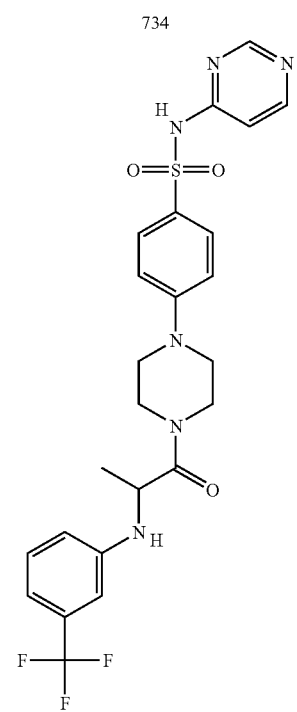
TABLE 2-continued
735
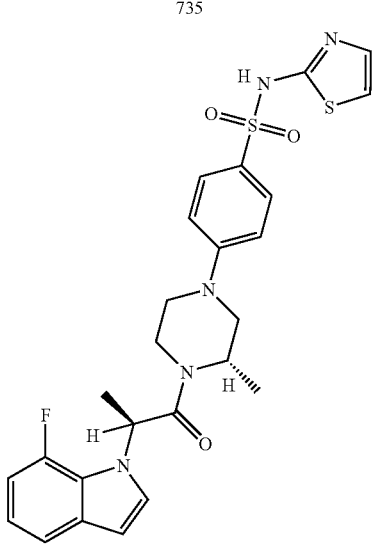
736
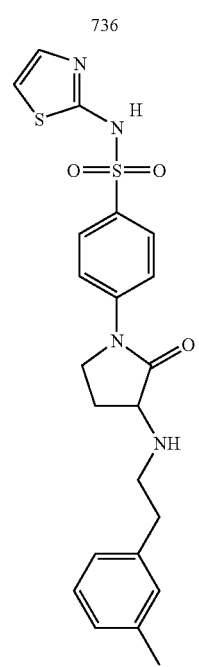

TABLE 2-continued
737
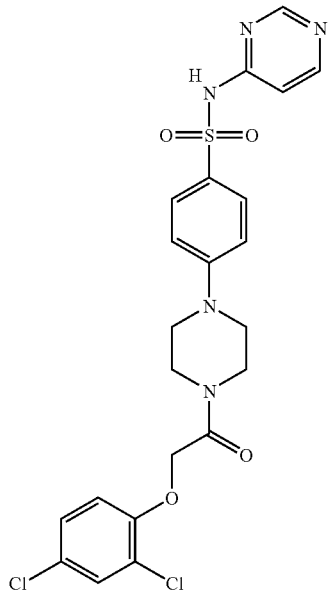
738
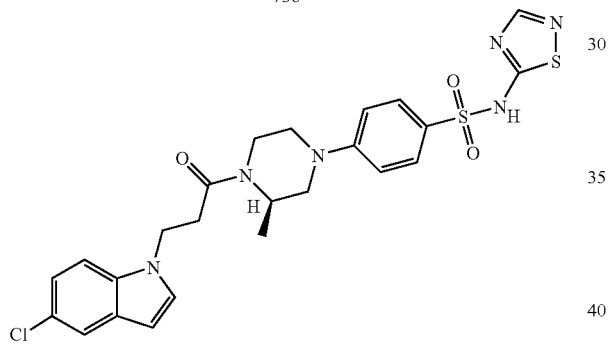
739
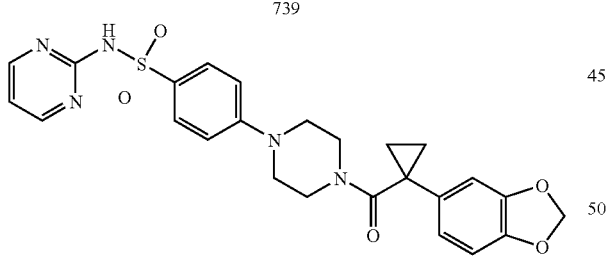
740
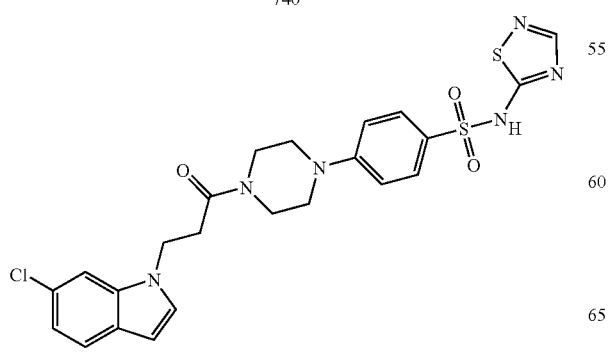
TABLE 2-continued
741
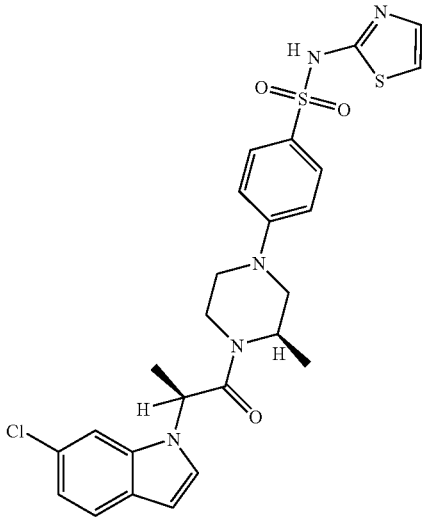
742
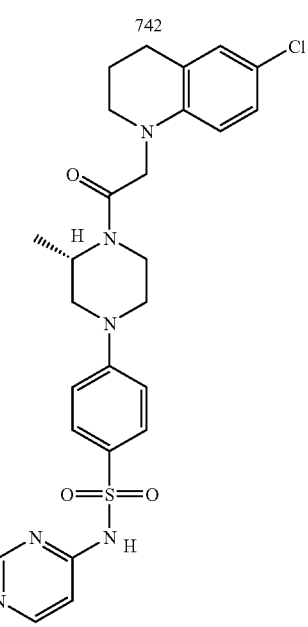

TABLE 2-continued
743
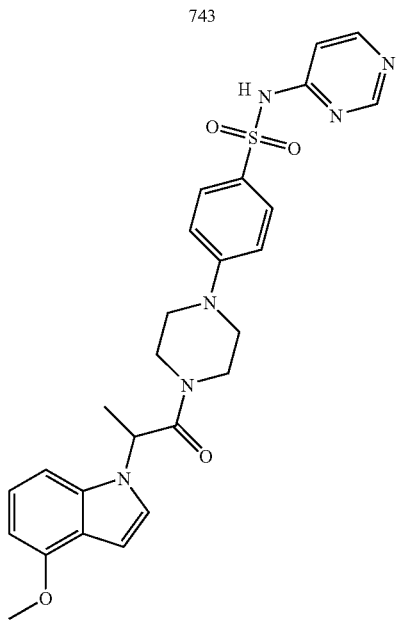
744
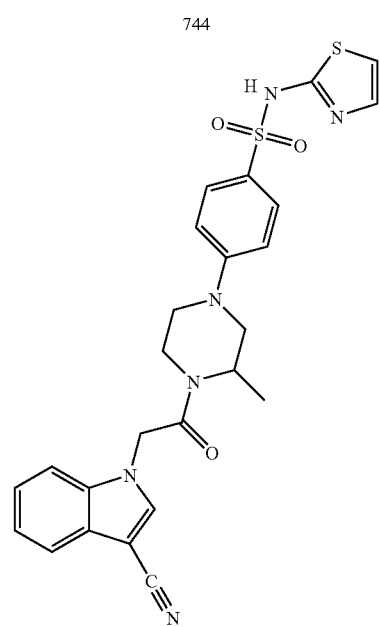
TABLE 2-continued
745
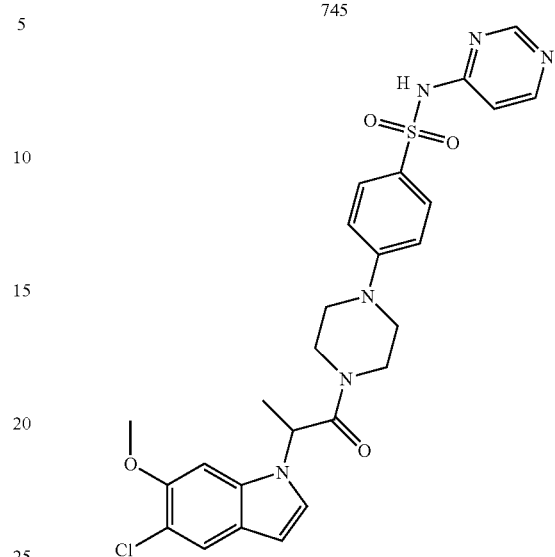
746
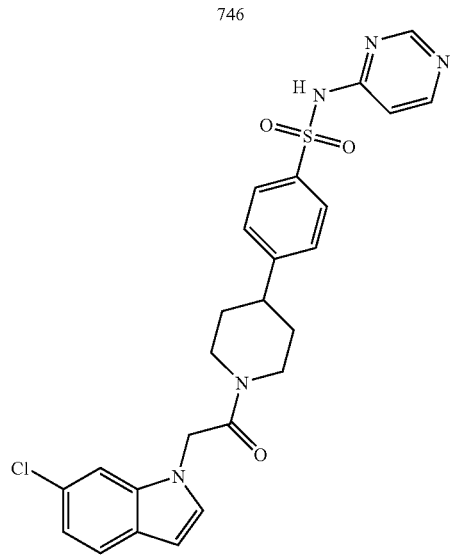

TABLE 2-continued
747
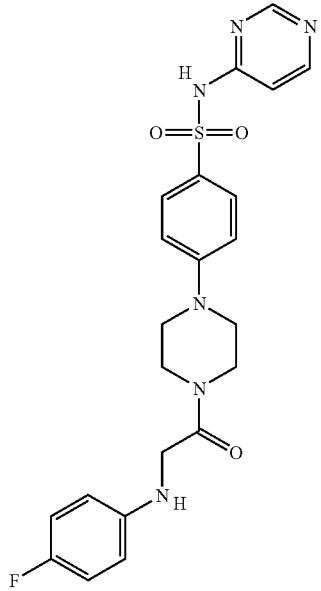
748
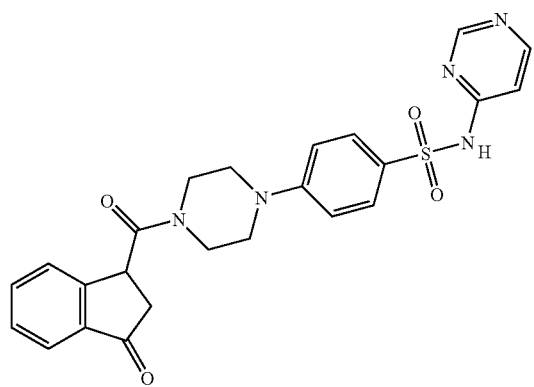
749
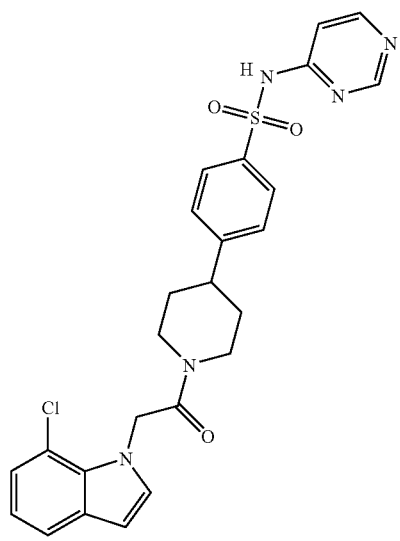
TABLE 2-continued
0750
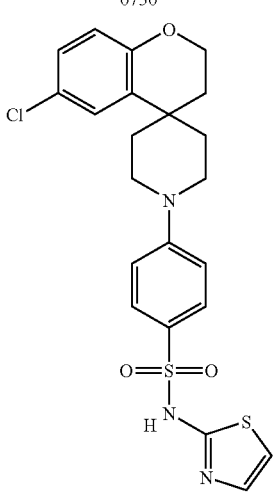
751
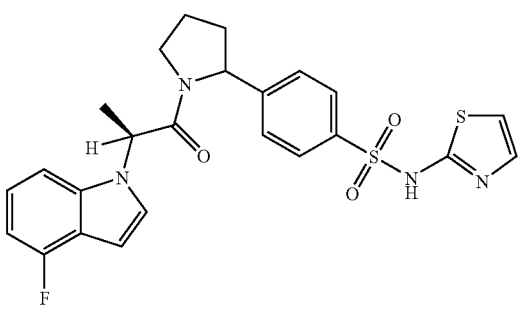
752
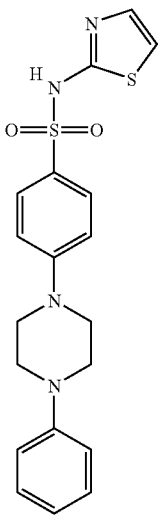

TABLE 2-continued
753
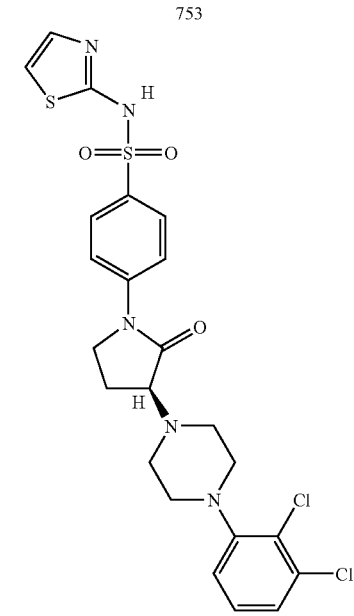
TABLE 2-continued
755
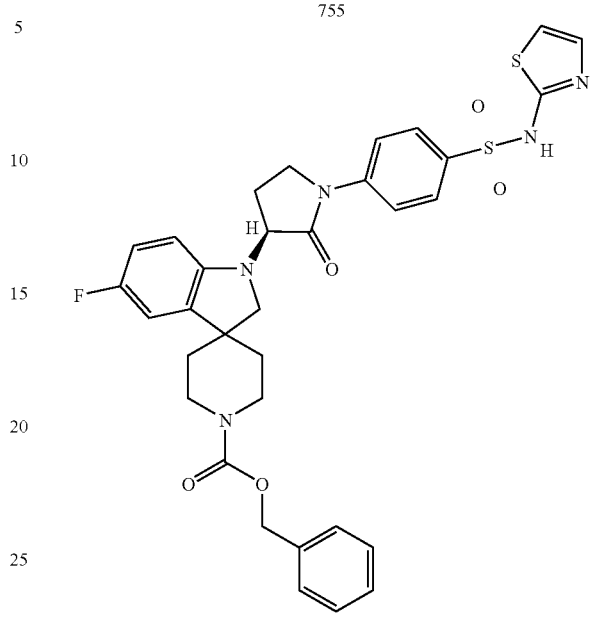
754
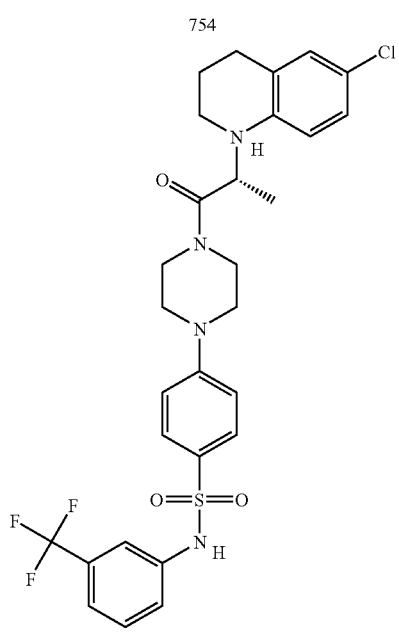
756
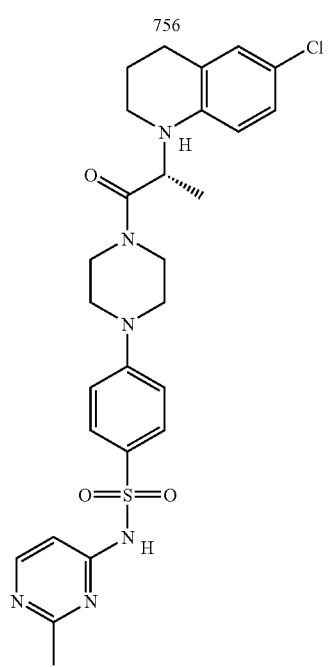

TABLE 2-continued
757
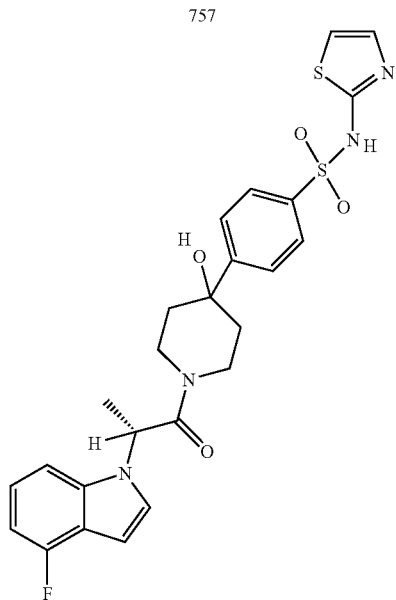
758
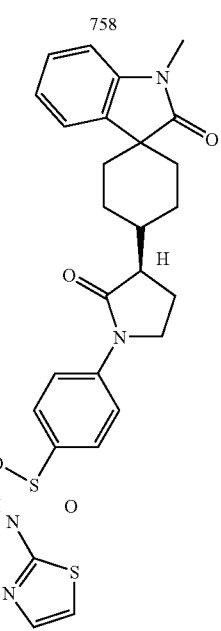
TABLE 2-continued
759
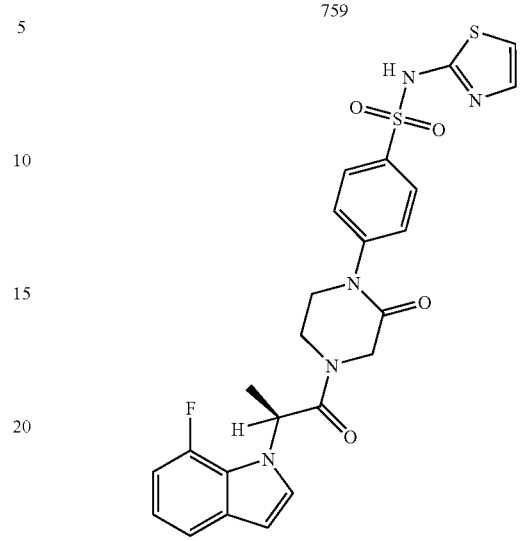
760
761
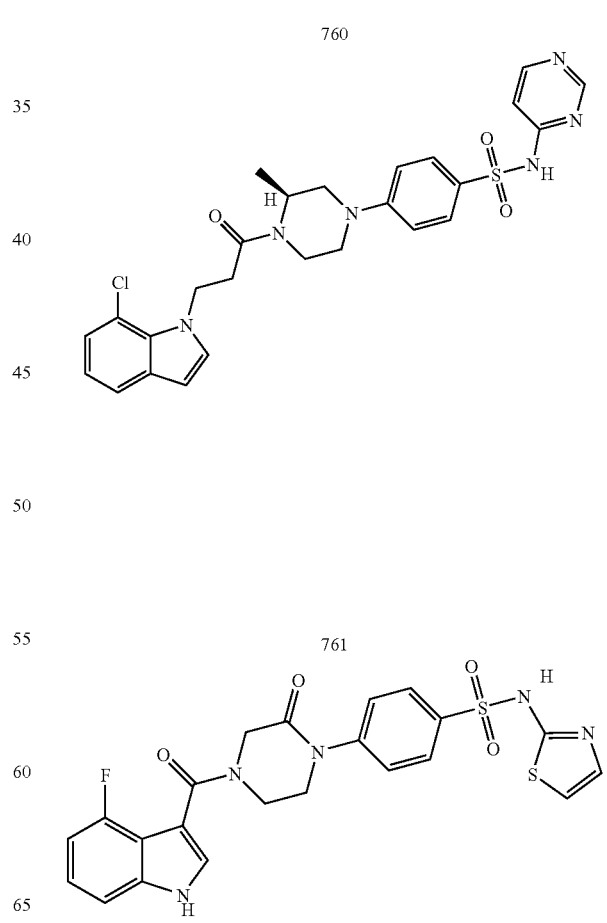

421
TABLE 2-continued
762
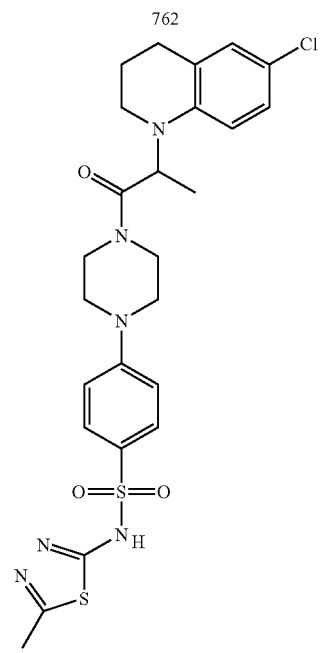
763
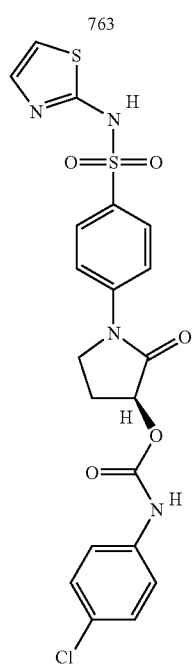
422
TABLE 2-continued
764
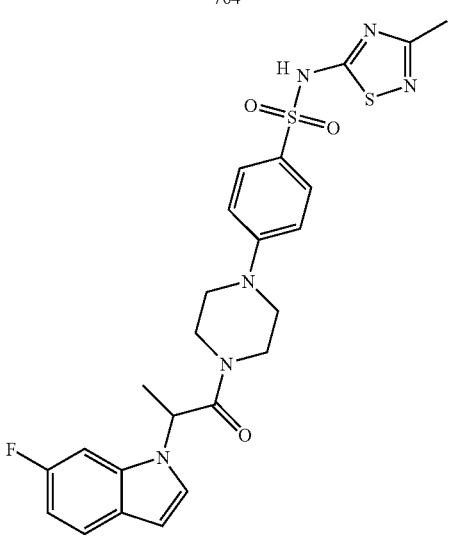
765
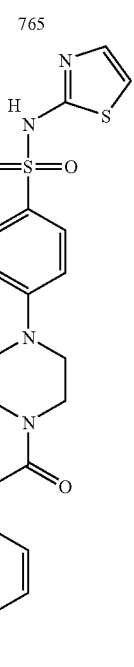

TABLE 2-continued
766
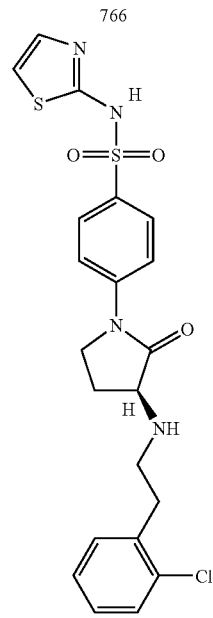
767
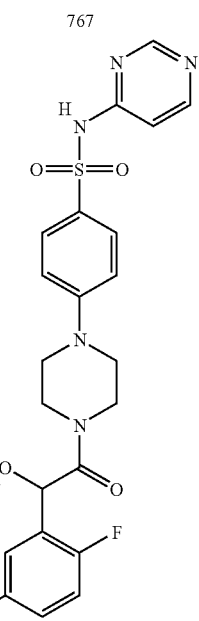
768
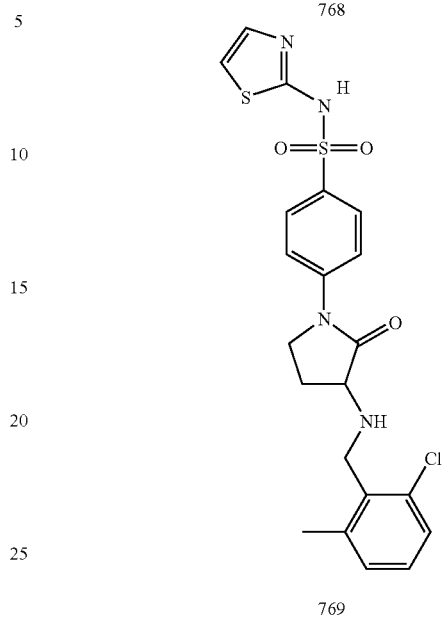
769
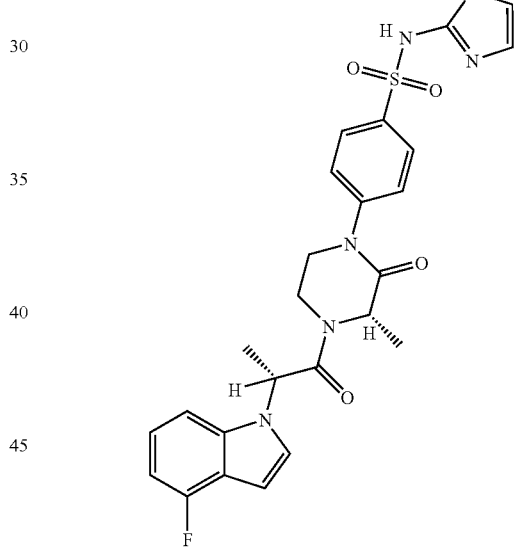
770
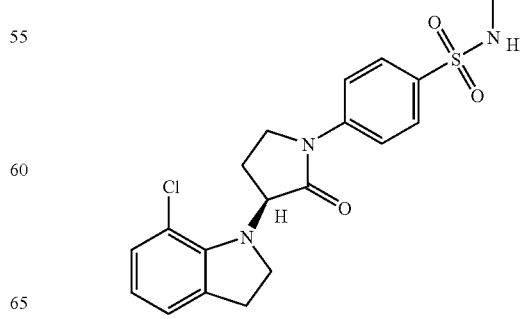

TABLE 2-continued
771
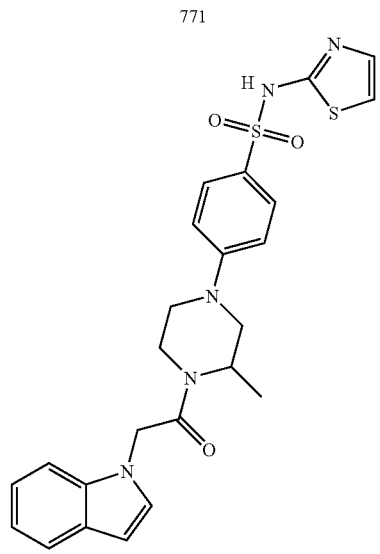
773
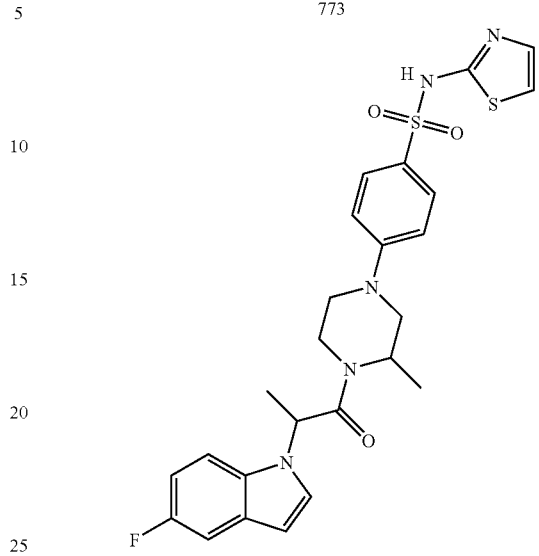
772
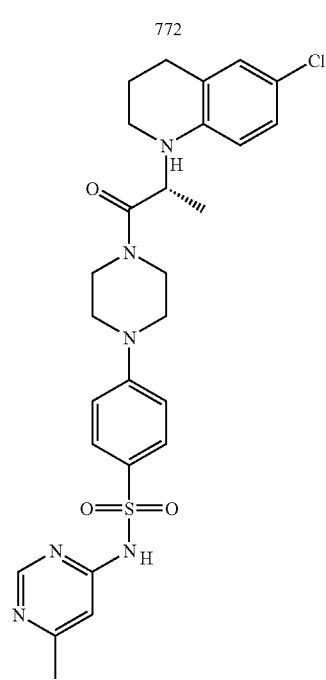
774
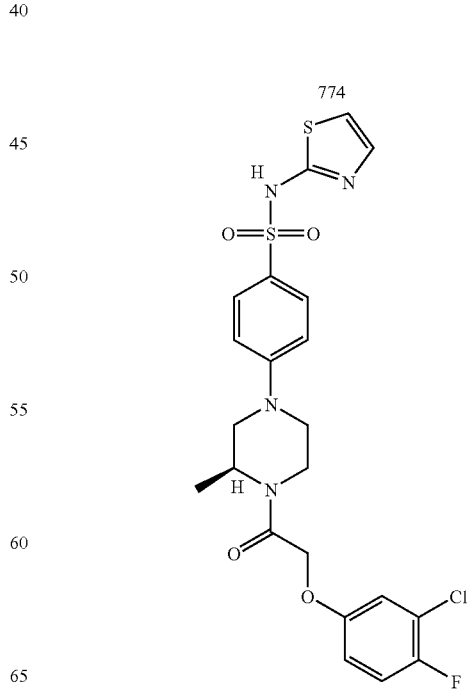

TABLE 2-continued
775
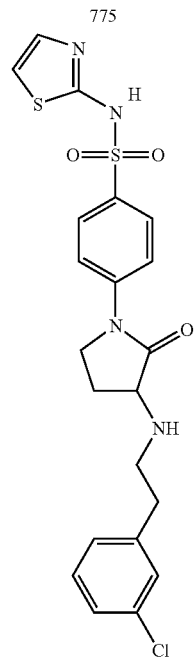
776
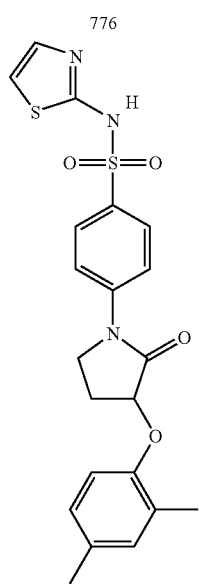
TABLE 2-continued
777
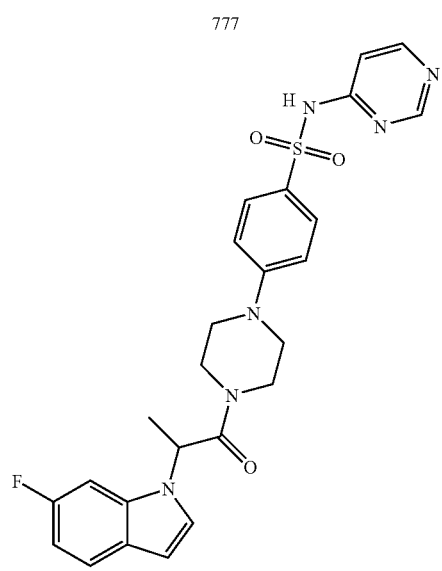
778
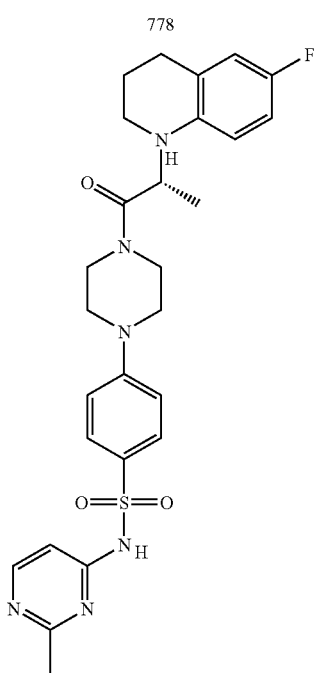

TABLE 2-continued
779
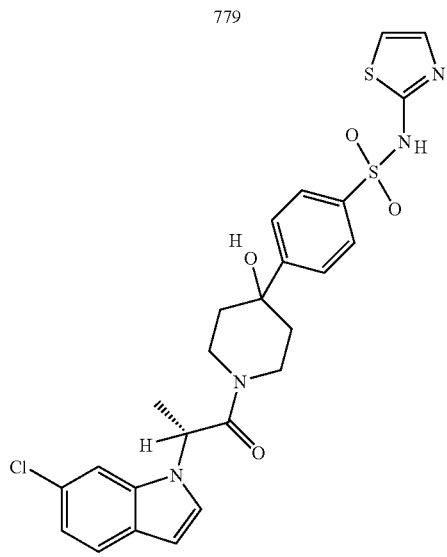
780
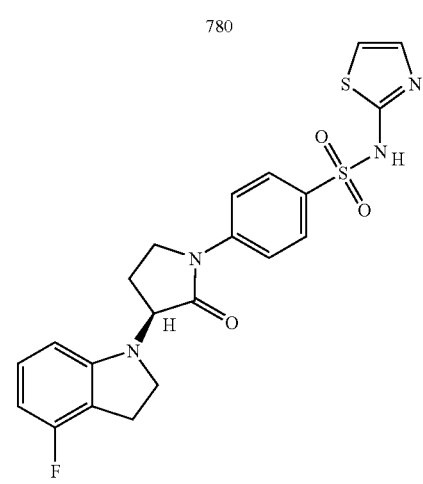
781
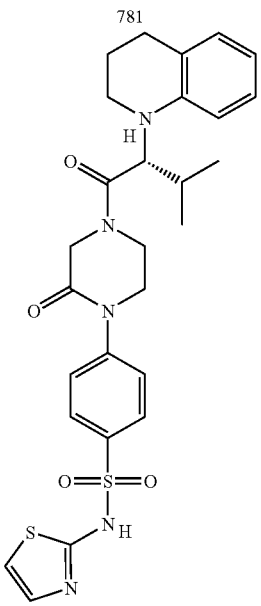
TABLE 2-continued
782
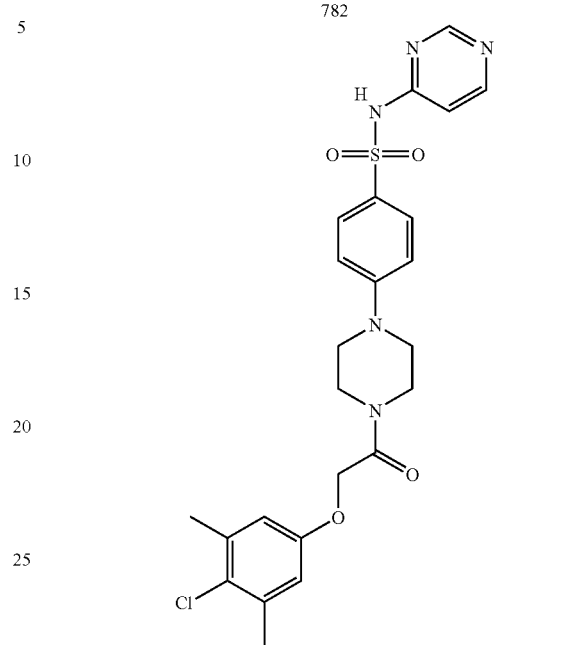
783
784
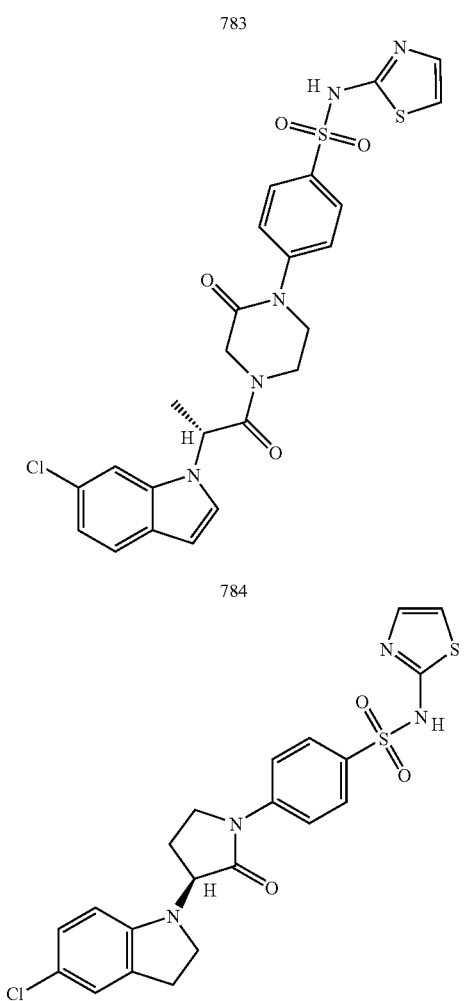

TABLE 2-continued
785
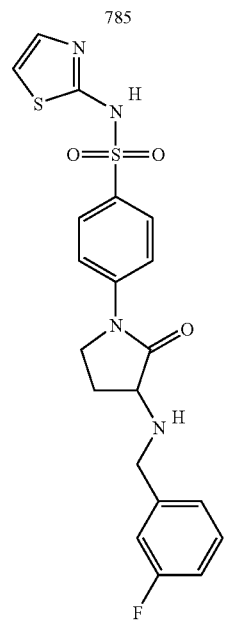
TABLE 2-continued
787
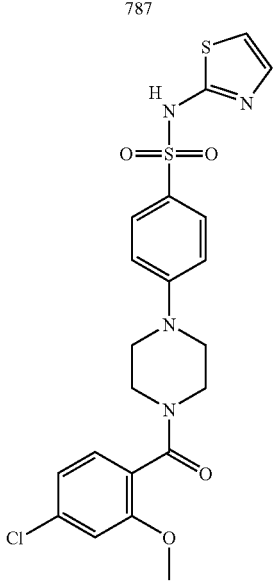
786
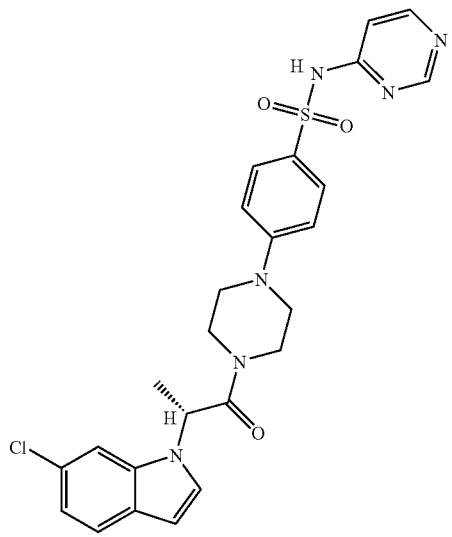
788

TABLE 2-continued
789
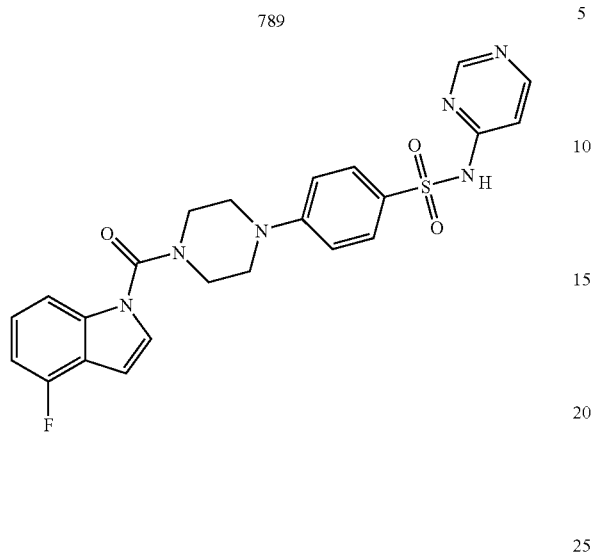
790
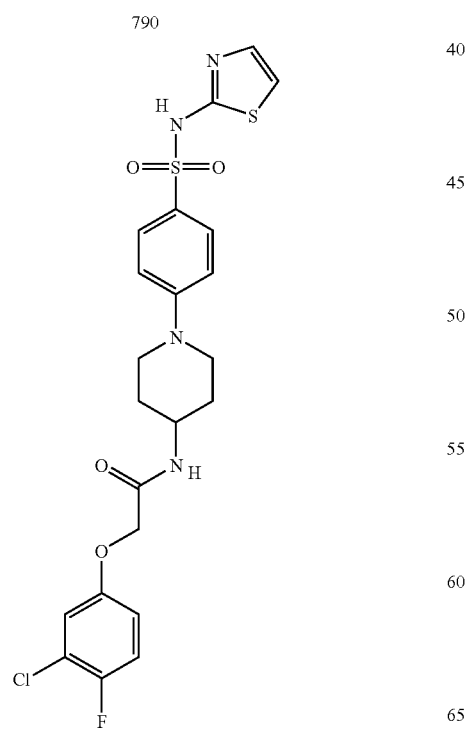
TABLE 2-continued
791
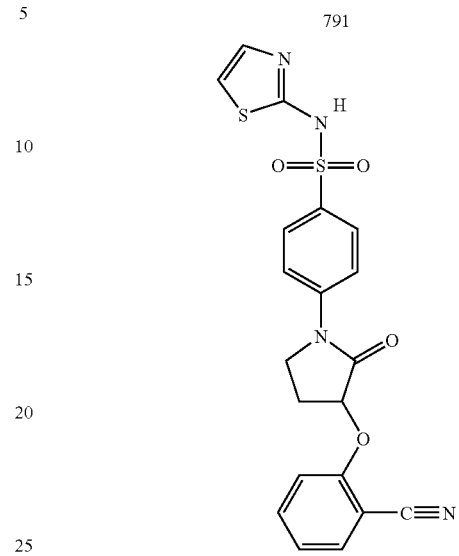
792
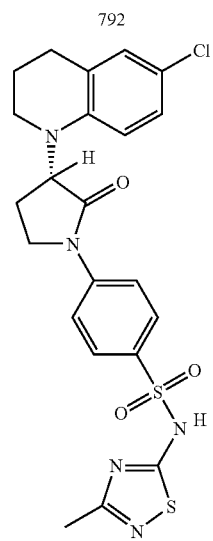

TABLE 2-continued

TABLE 2-continued
798
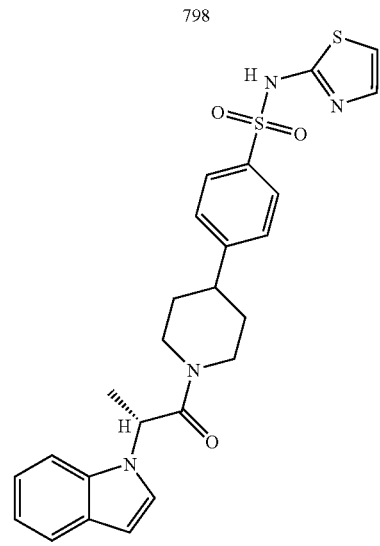
799
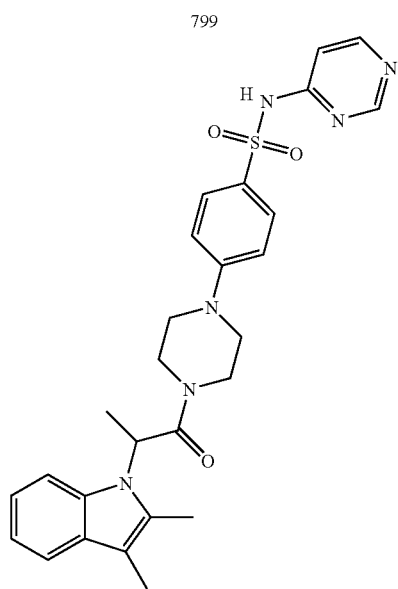
TABLE 2-continued
800
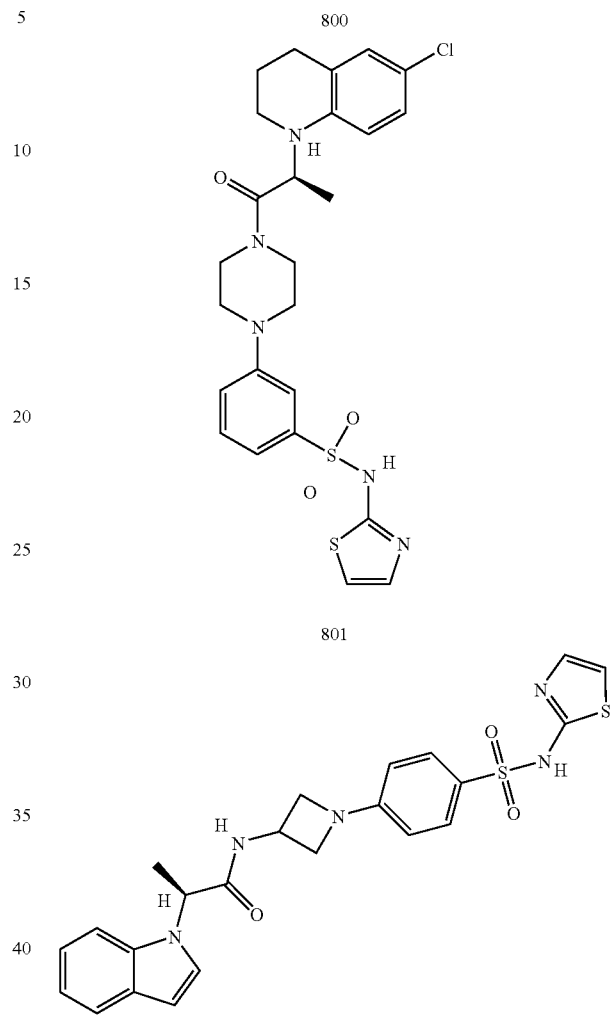
801
802
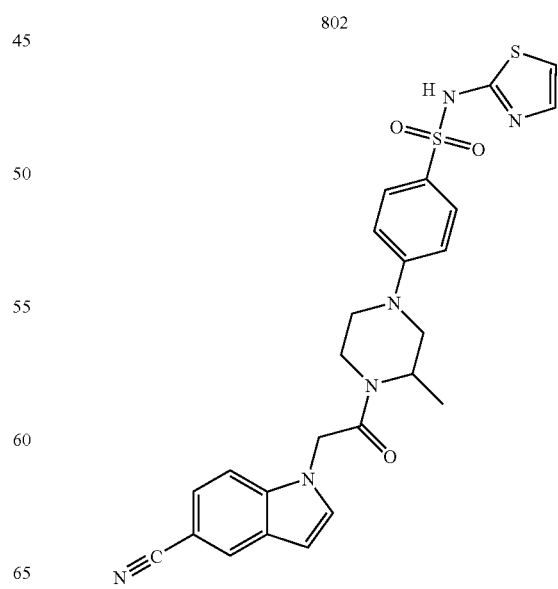

TABLE 2-continued
803
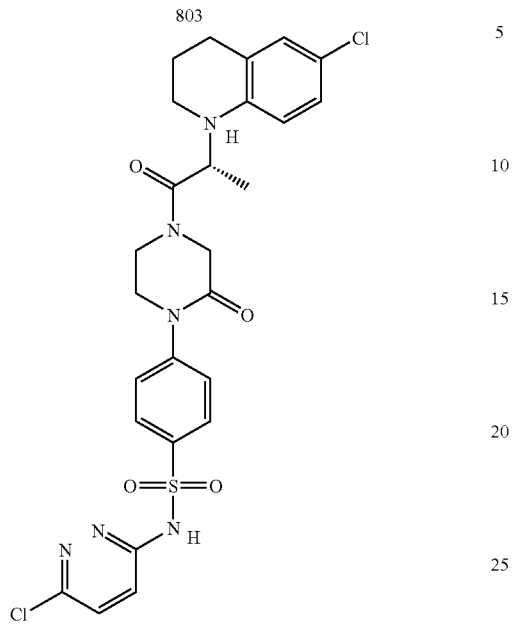
804
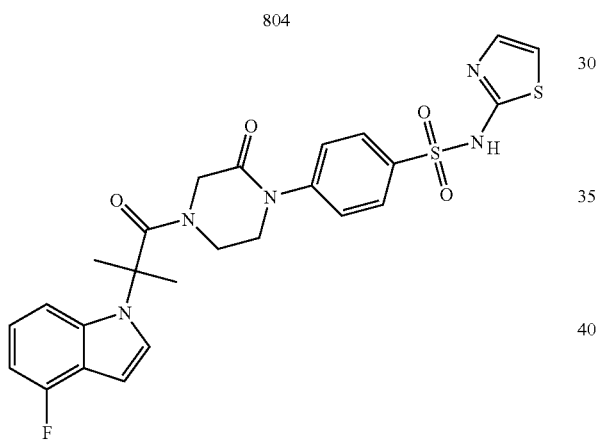
805
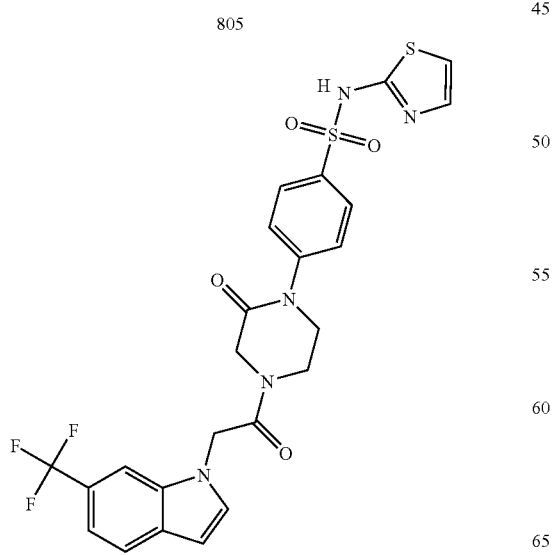
TABLE 2-continued
806
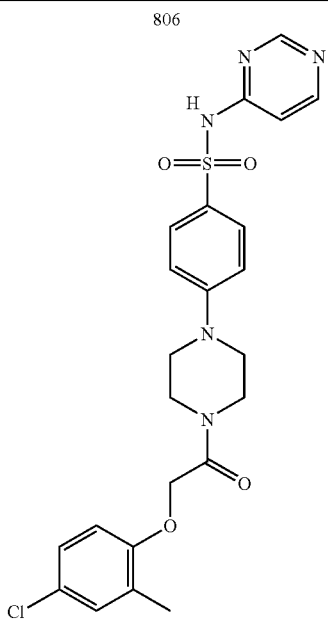
807
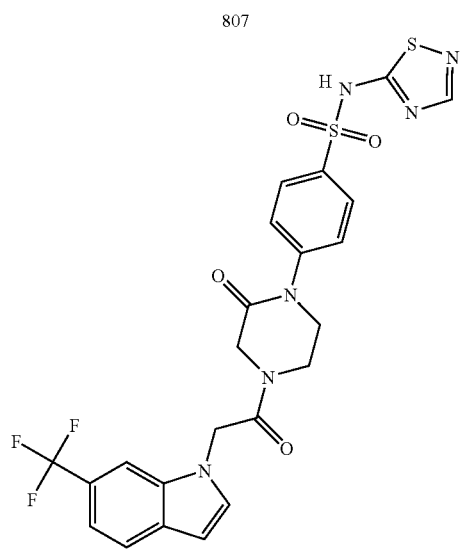

TABLE 2-continued
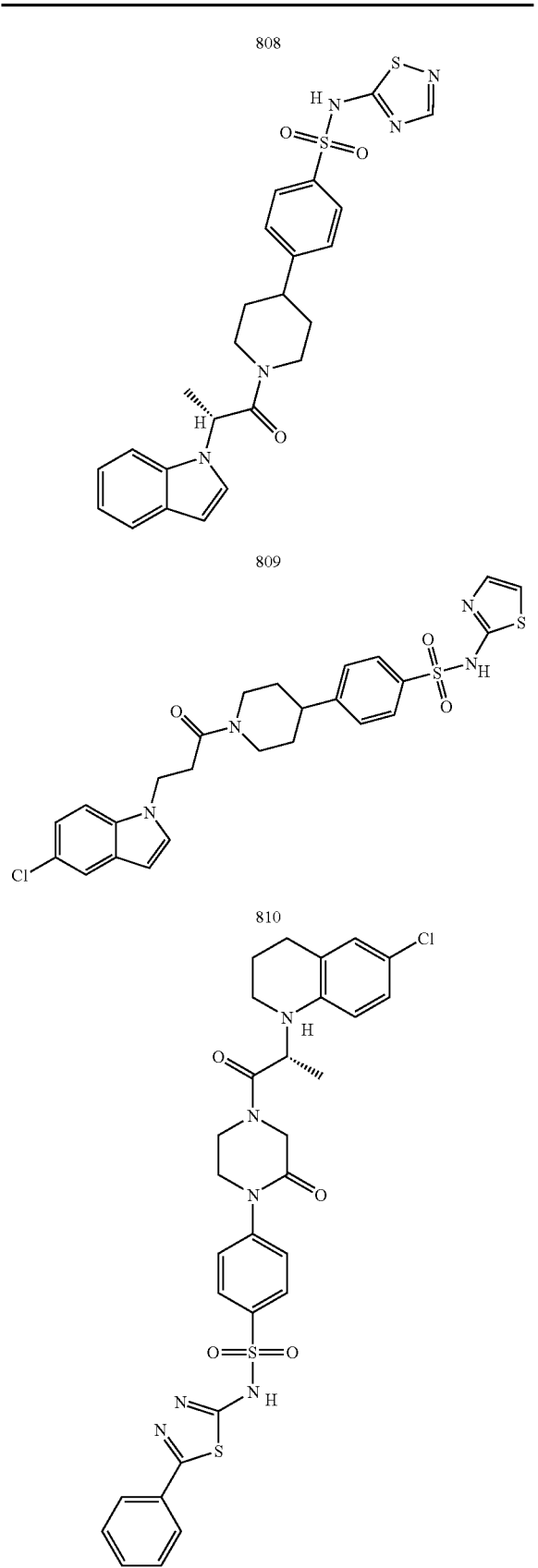
TABLE 2-continued
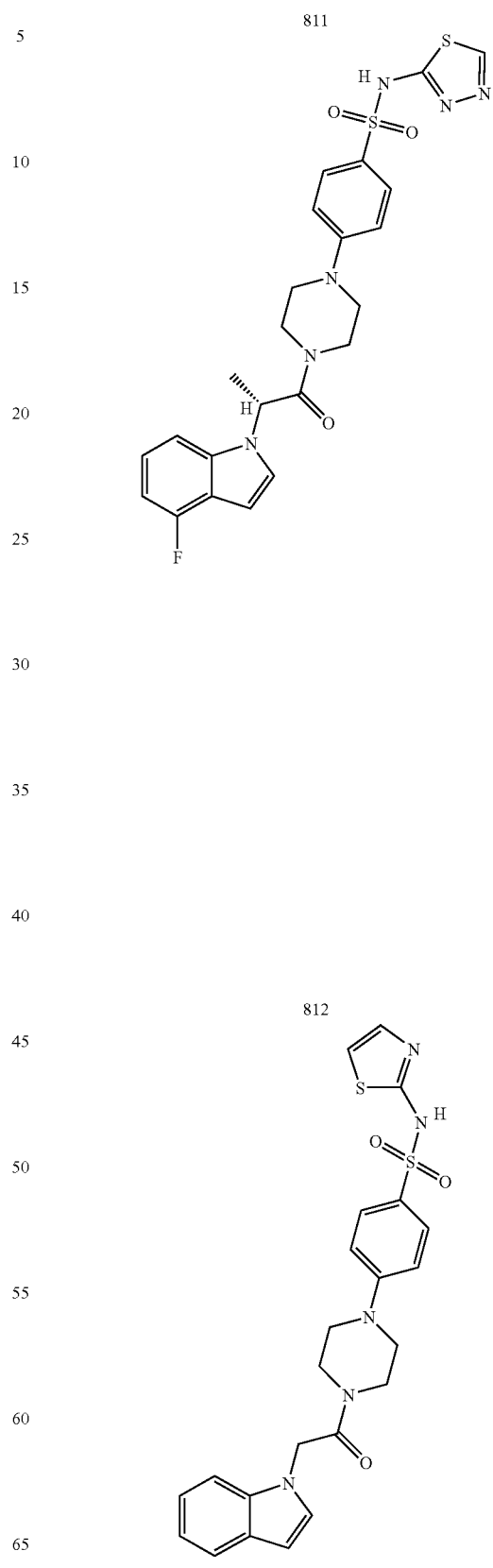

TABLE 2-continued
813
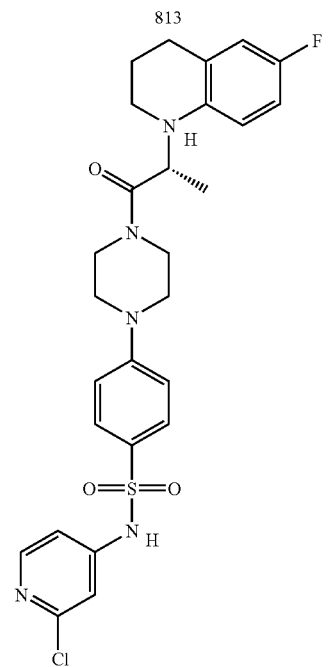
815
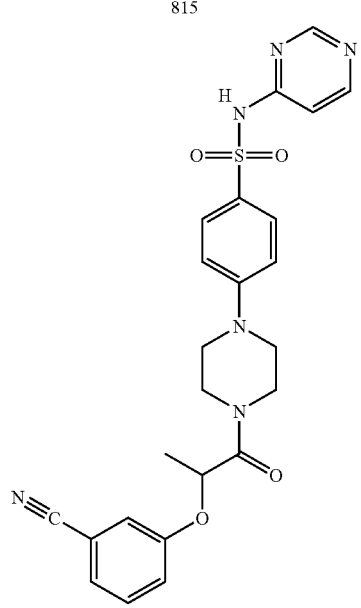
814
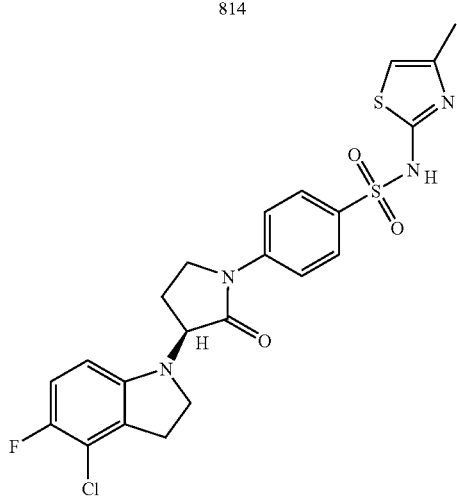
816

TABLE 2-continued
817
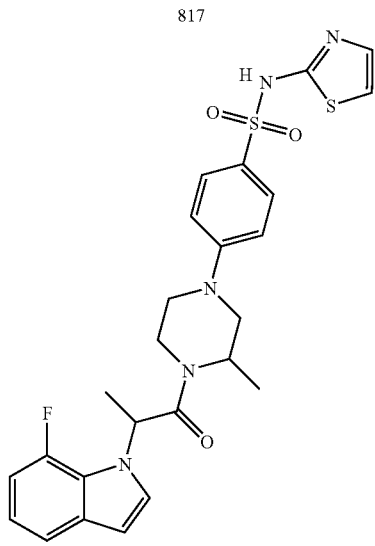
818
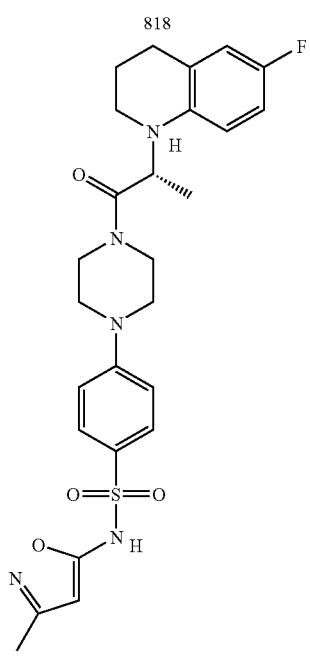
TABLE 2-continued
819
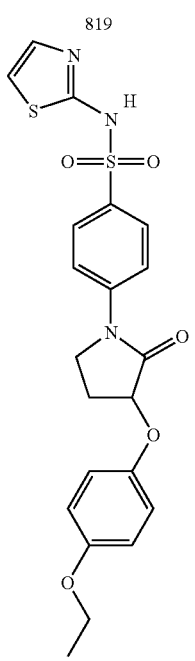
820
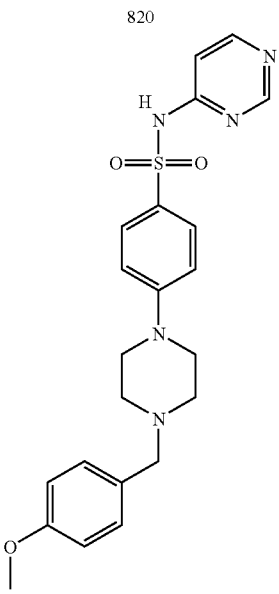

TABLE 2-continued
821
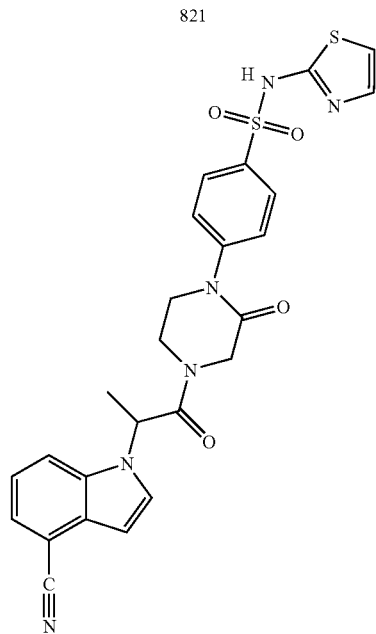
822
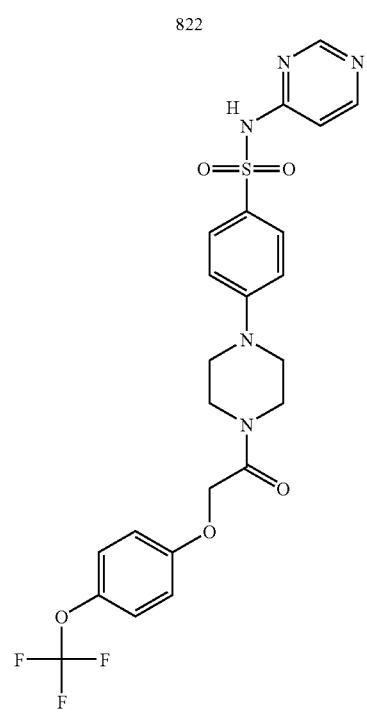
TABLE 2-continued
823
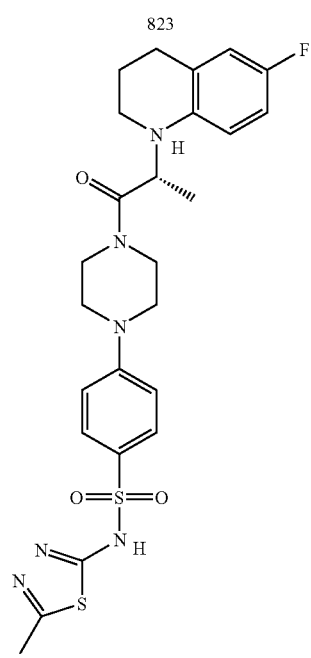
824
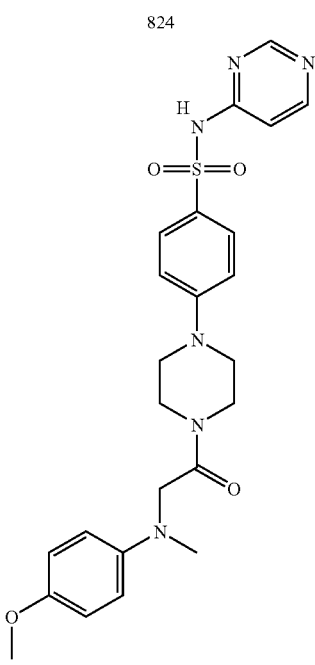

TABLE 2-continued
825
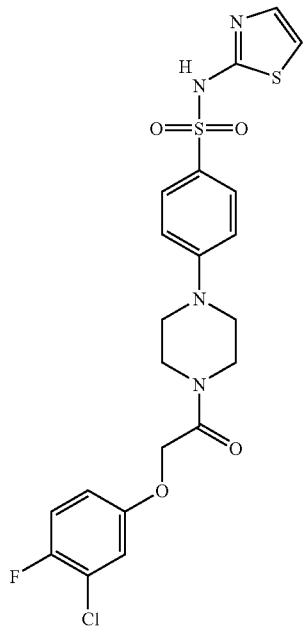
826
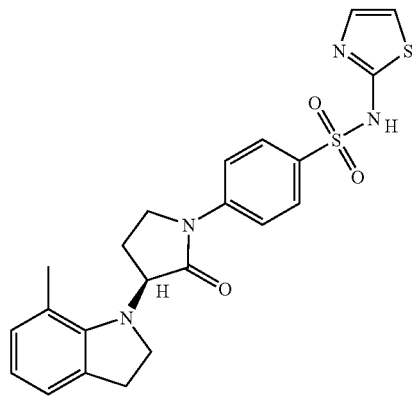
827
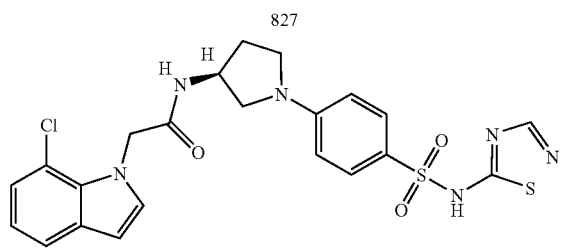
TABLE 2-continued
828
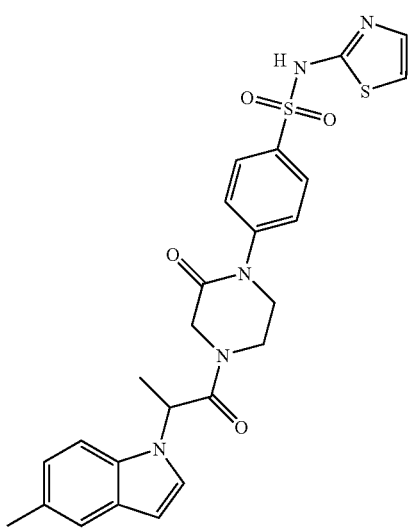
829
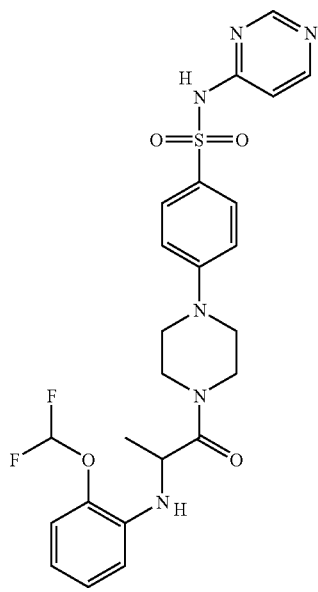

TABLE 2-continued
830
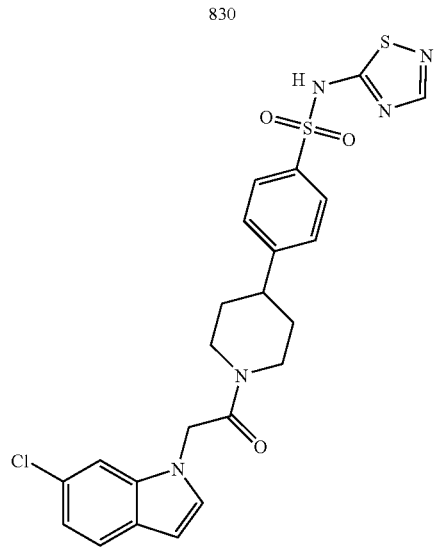
831
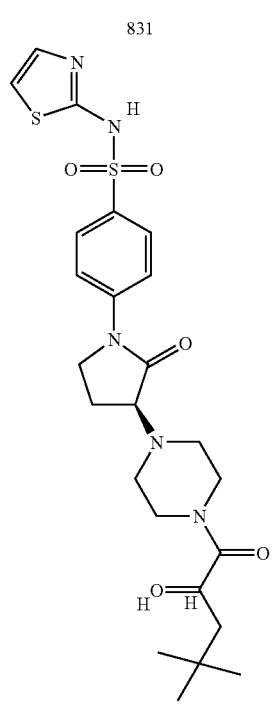
832
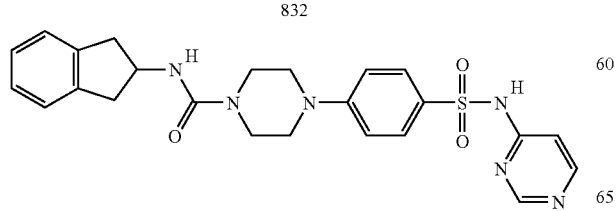
TABLE 2-continued
833
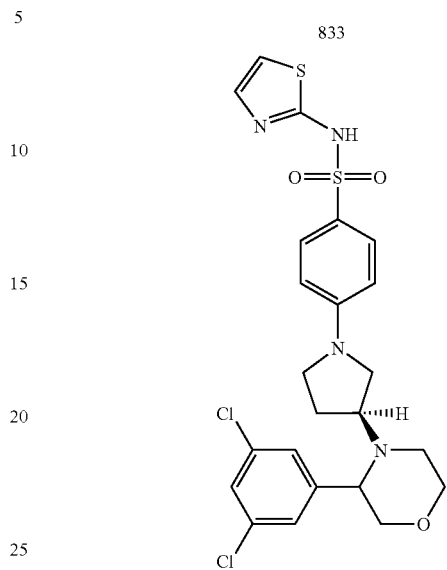
834
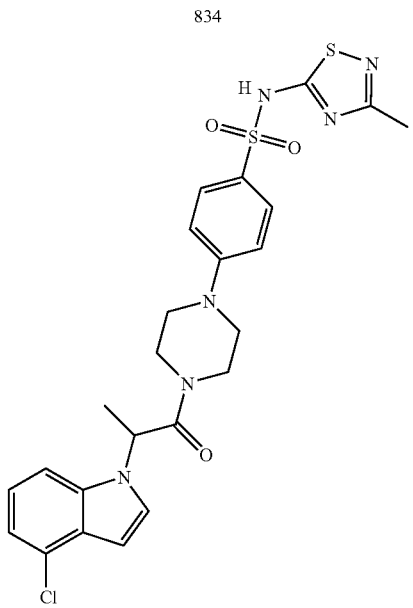

TABLE 2-continued
835
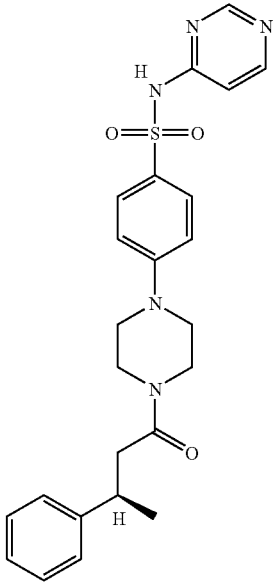
836
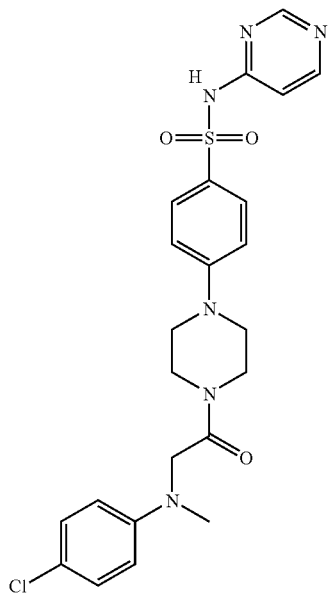
837
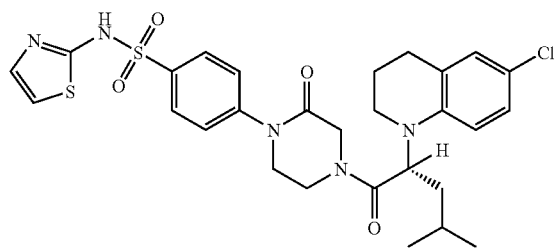
TABLE 2-continued
838
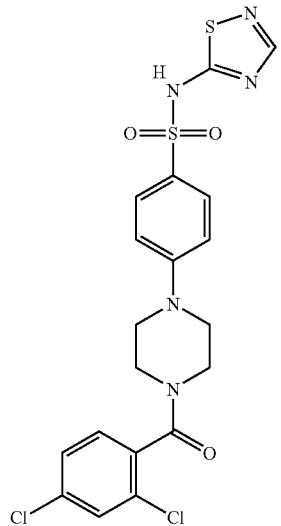
839
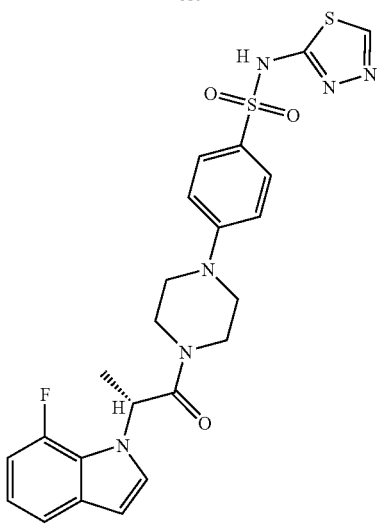
840
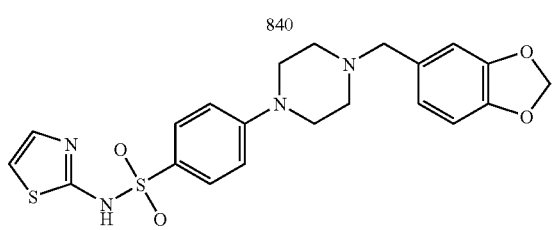

TABLE 2-continued
841
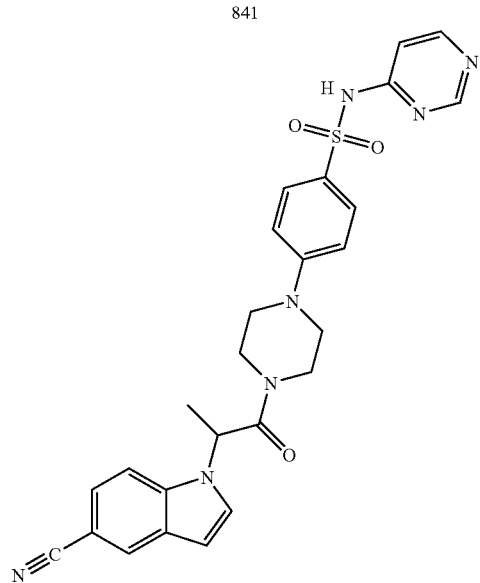
842
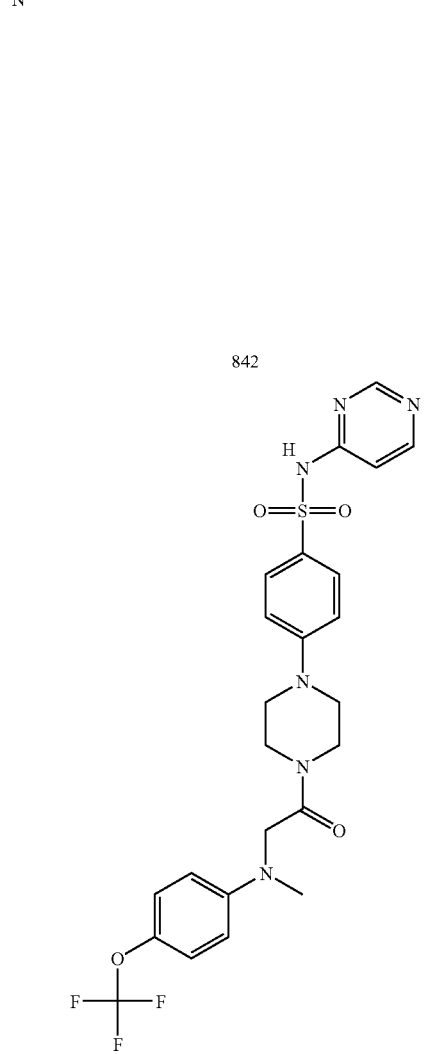
TABLE 2-continued
843
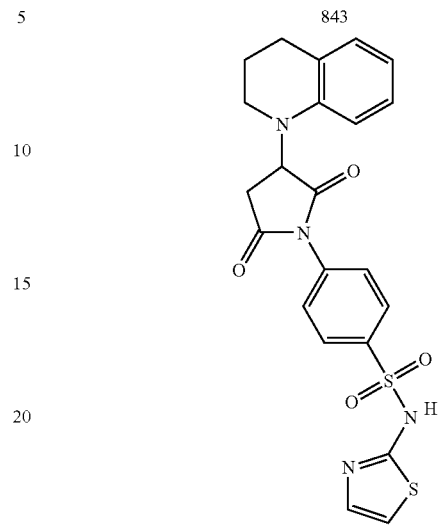
844
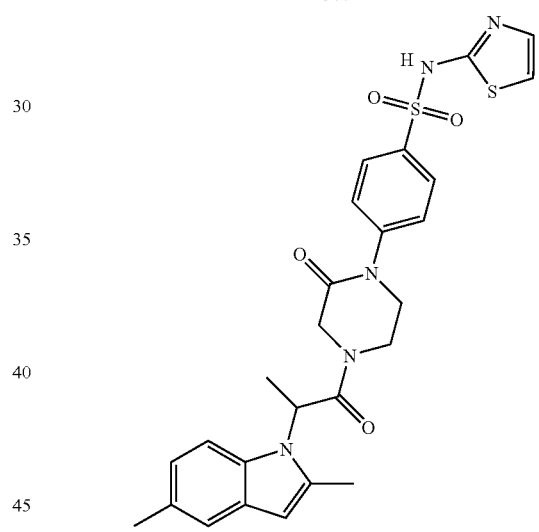
845
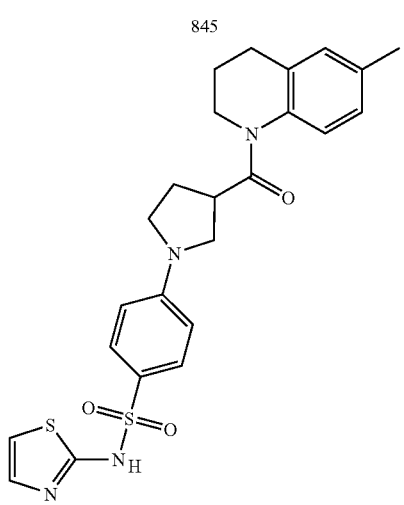

TABLE 2-continued
846
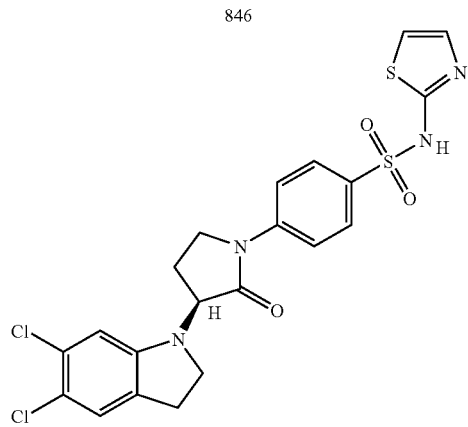
847
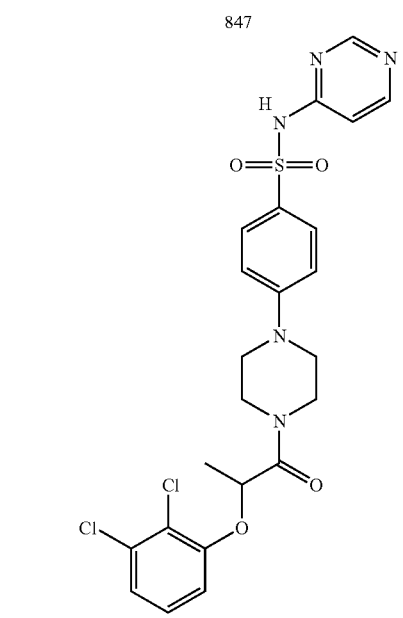
848
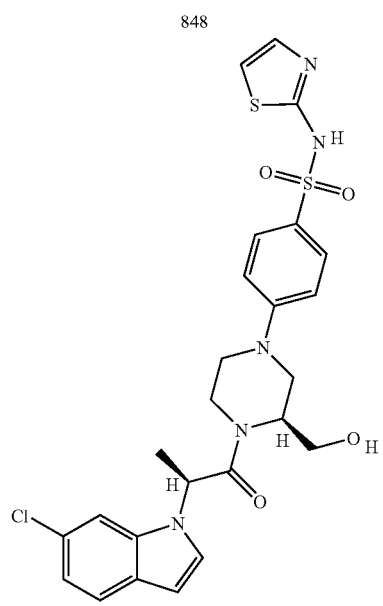
TABLE 2-continued
849
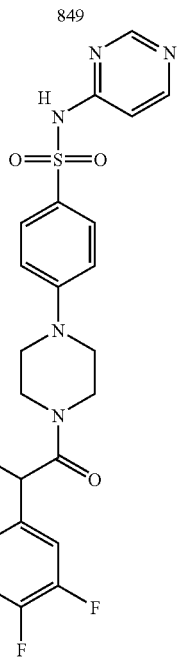
850

TABLE 2-continued
851
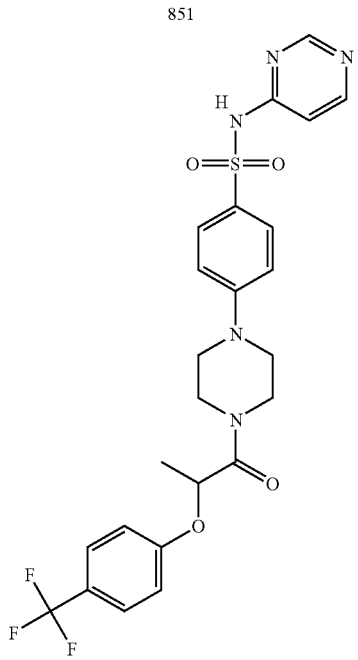
852
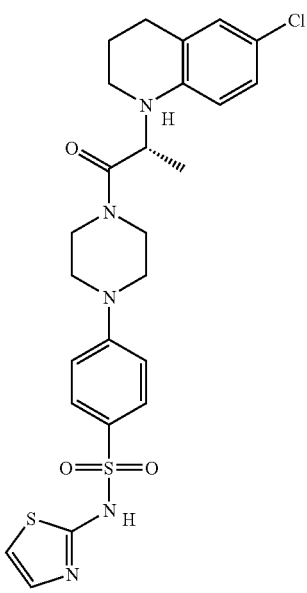
853
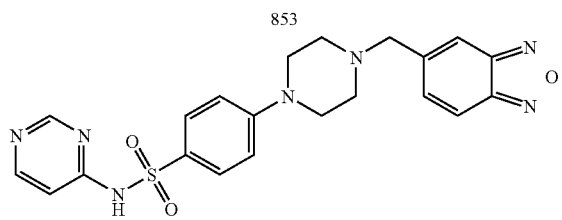
TABLE 2-continued
854
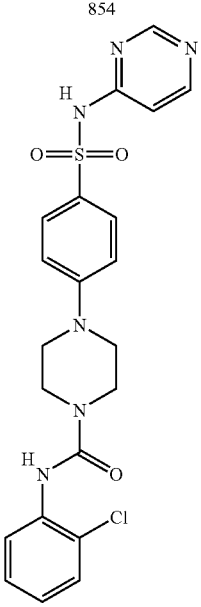
855
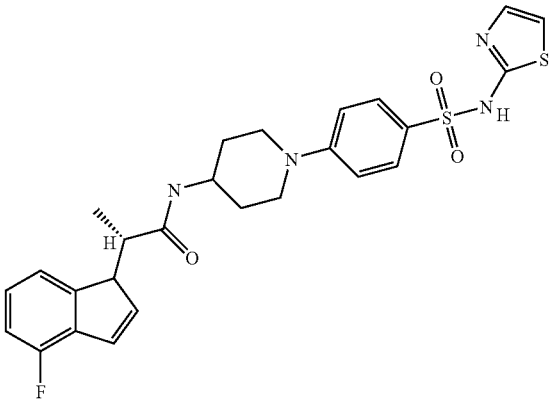
856
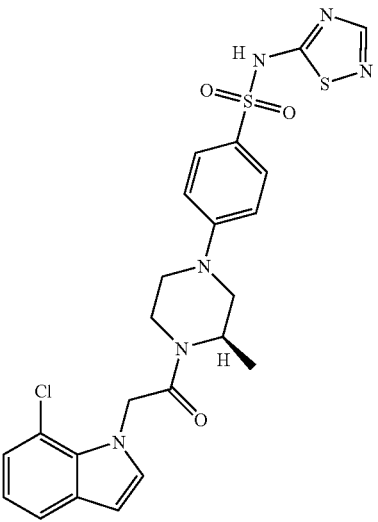

TABLE 2-continued
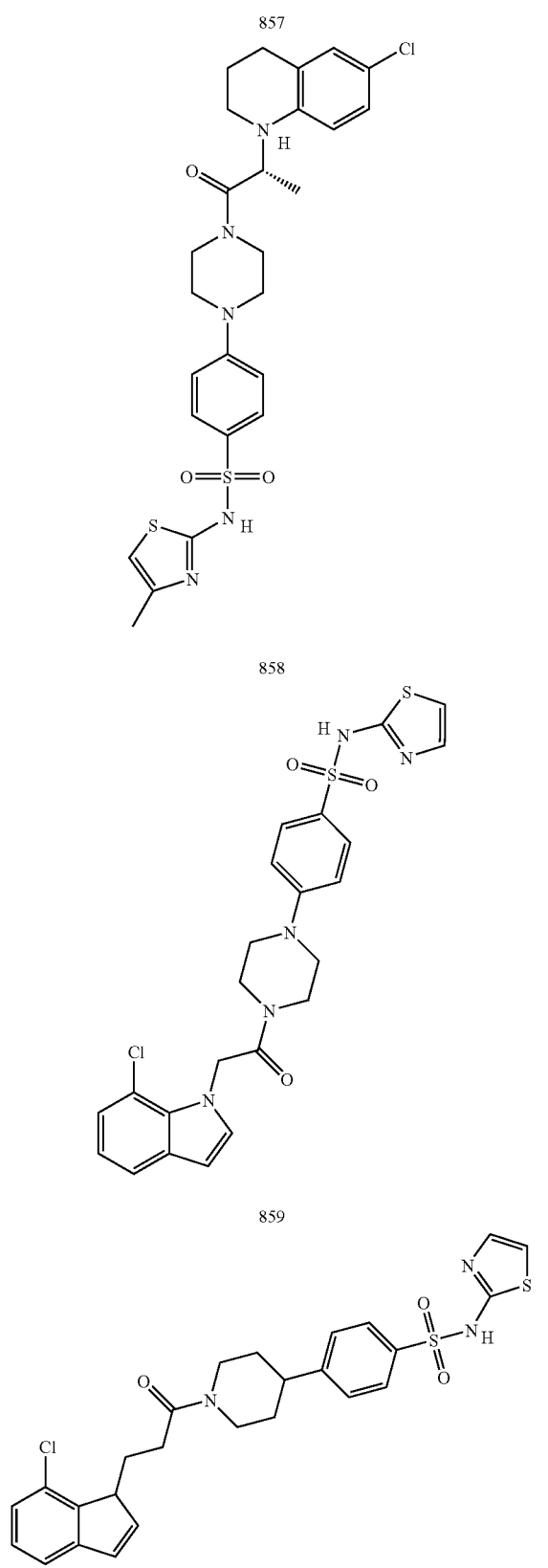
TABLE 2-continued
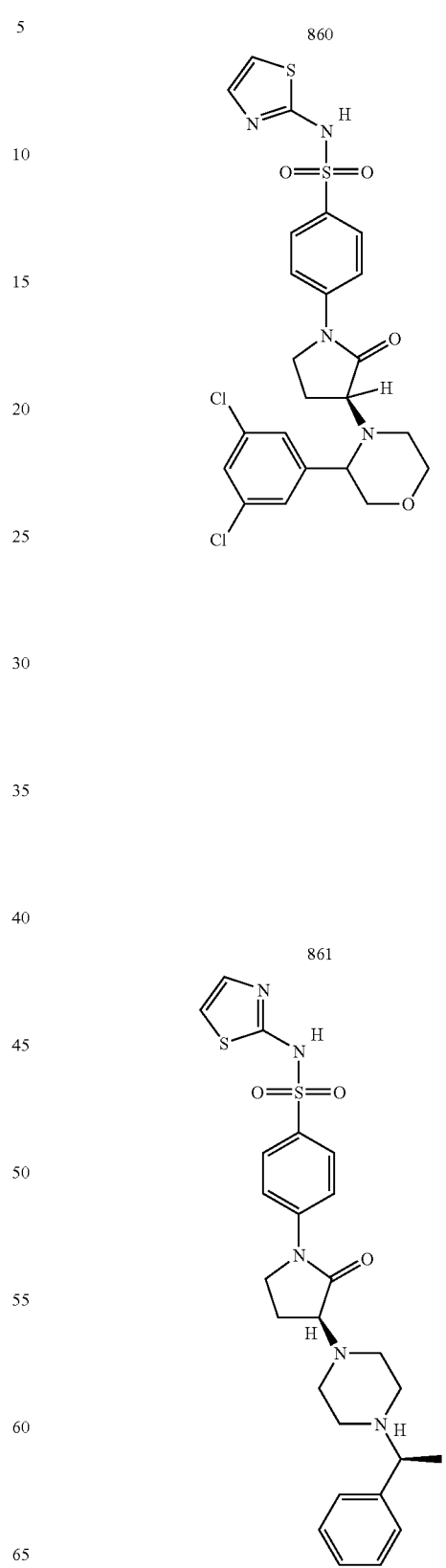

TABLE 2-continued
862
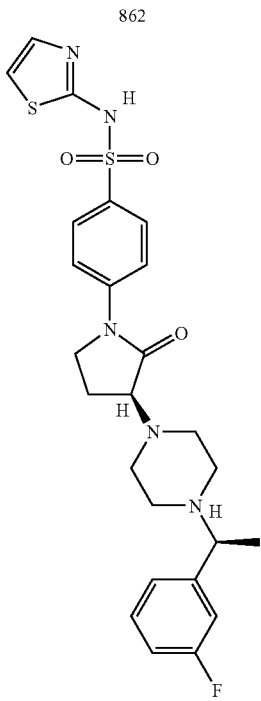
863
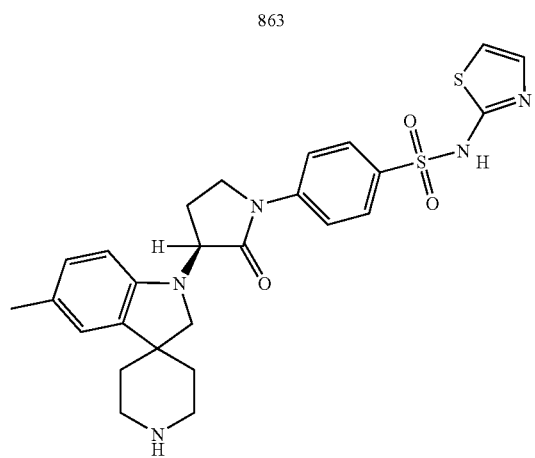
TABLE 2-continued
864
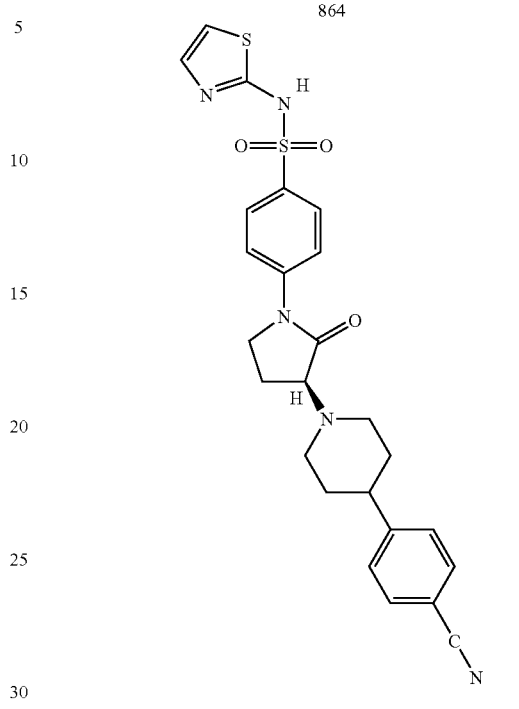
865
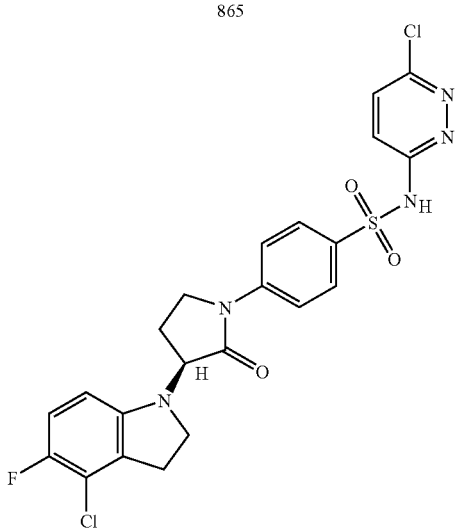

TABLE 2-continued
866
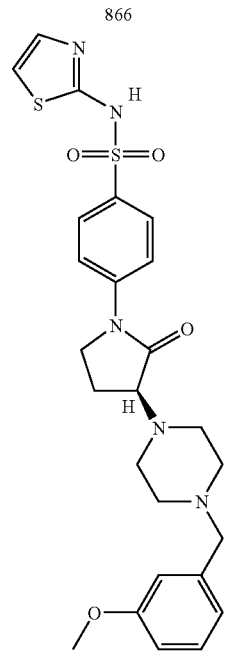
867
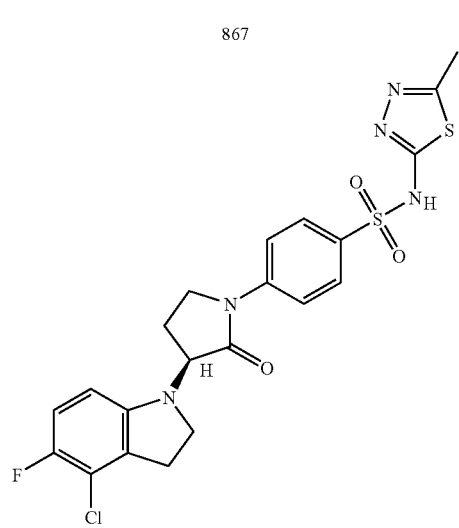
TABLE 2-continued
868
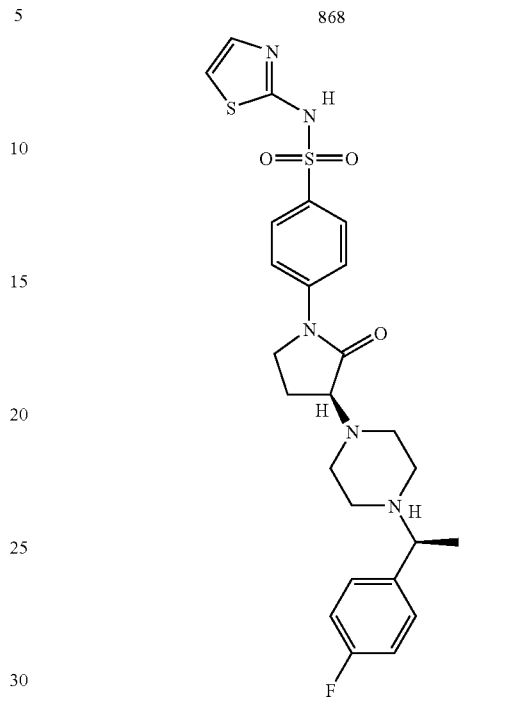
869
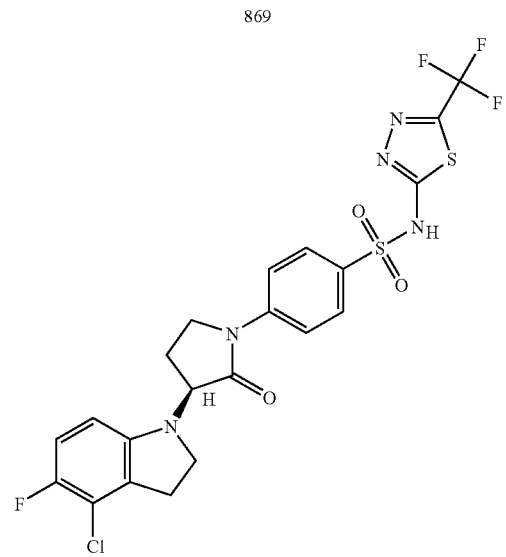

TABLE 2-continued
870
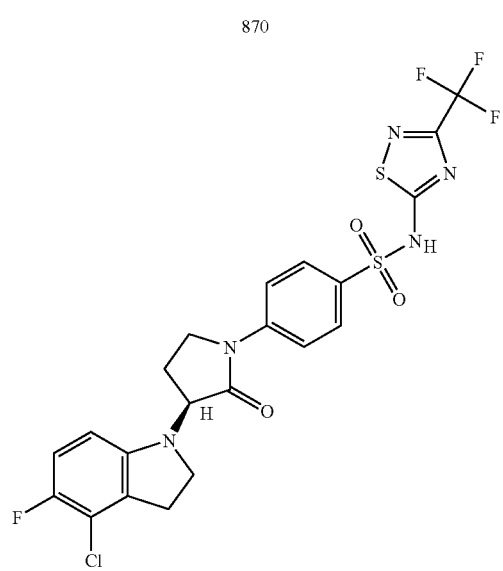
871
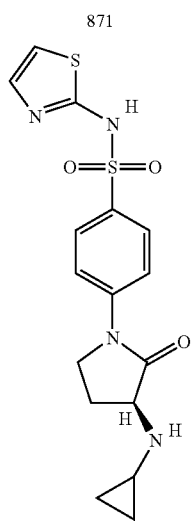
872
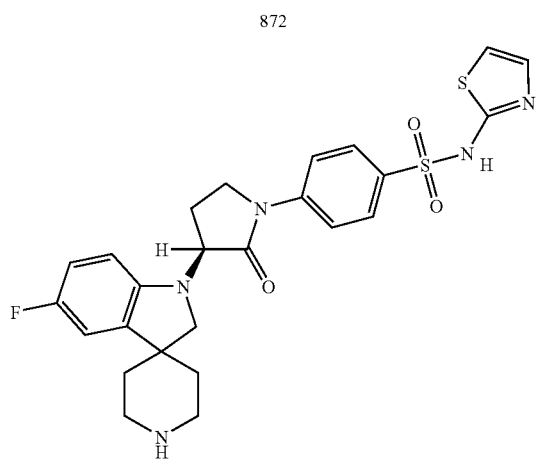
873
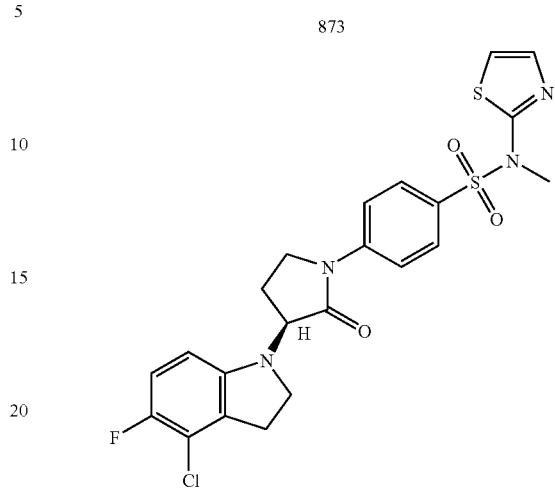
874
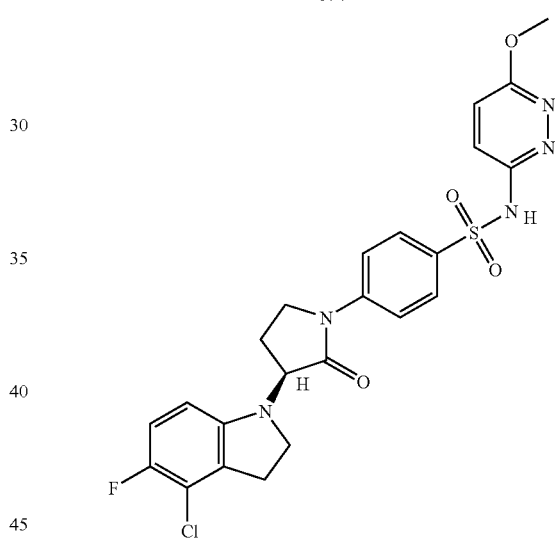
875
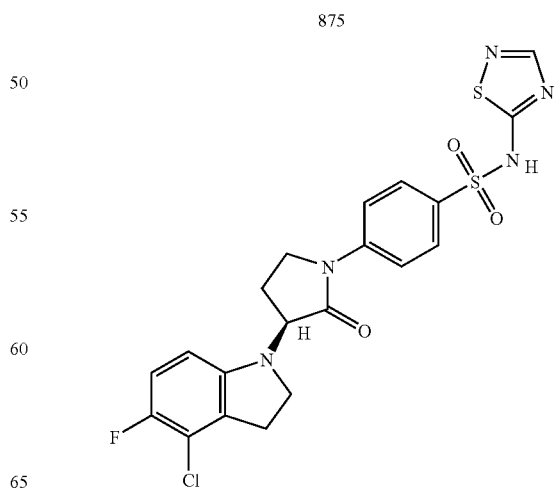

TABLE 2-continued
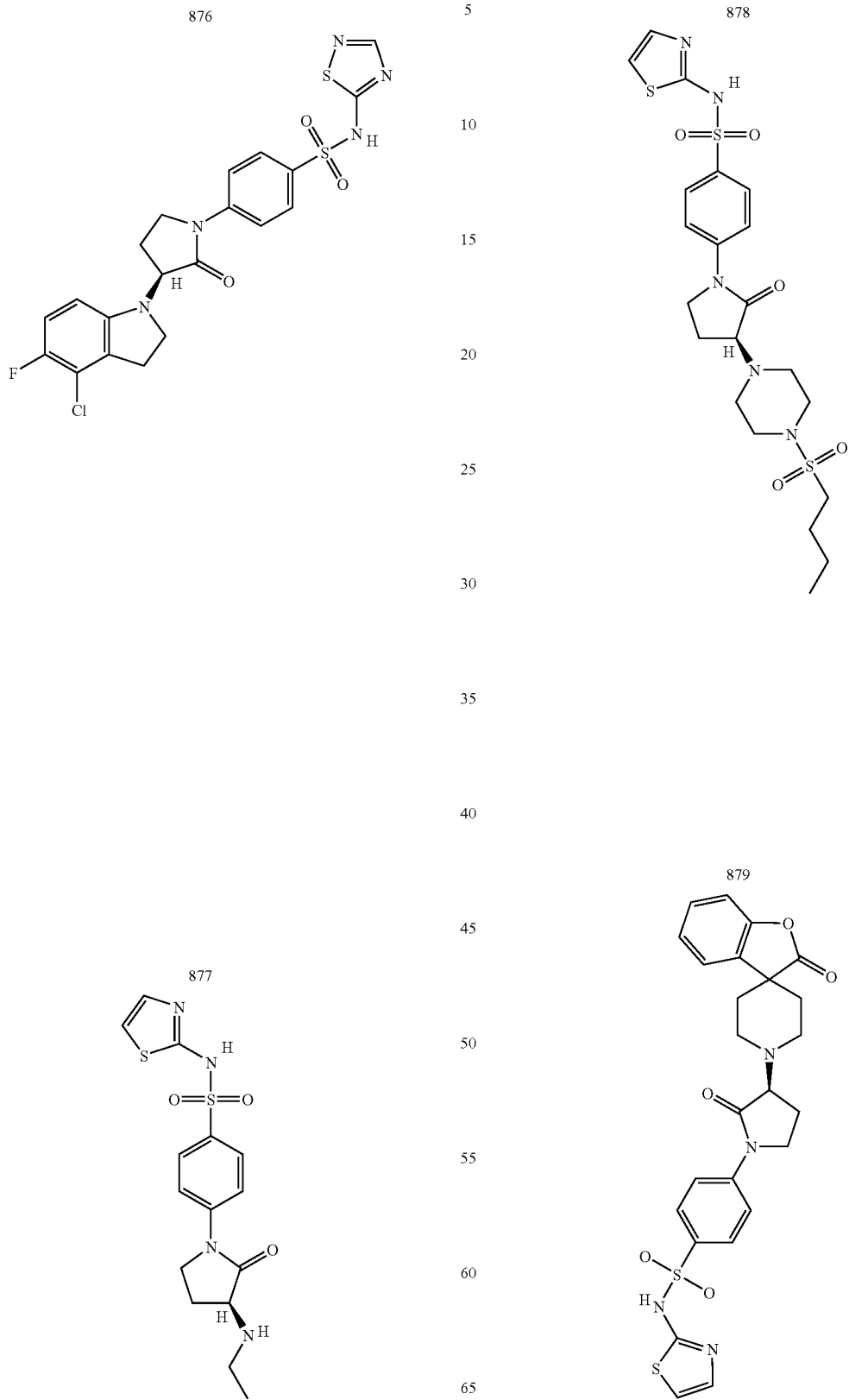

TABLE 2-continued
880
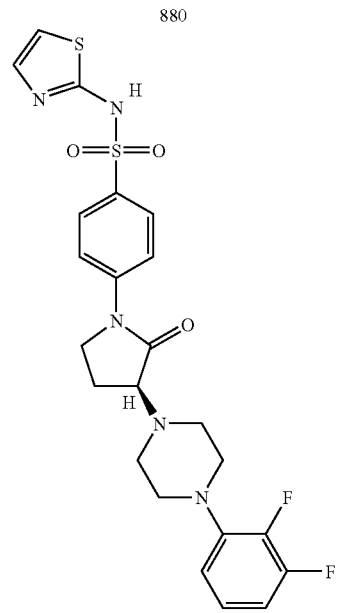
TABLE 2-continued
882
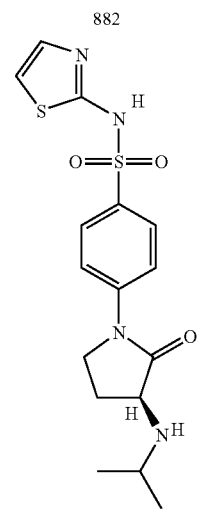
881
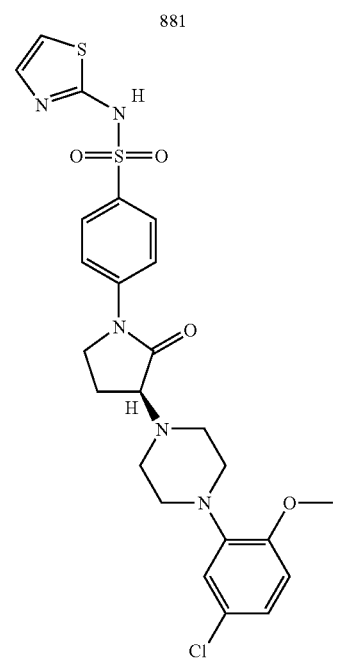
883
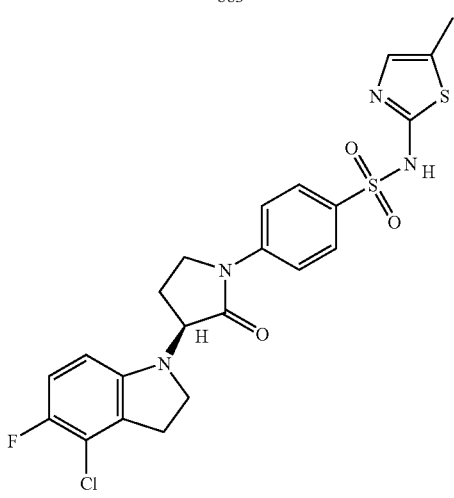

TABLE 2-continued
884
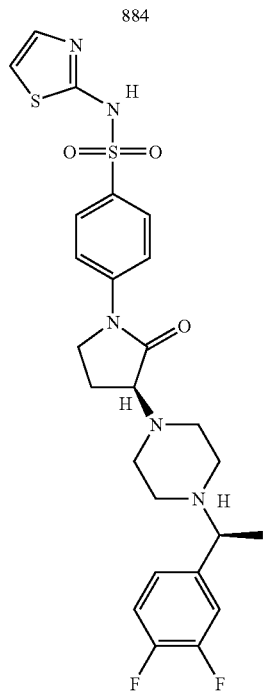
885
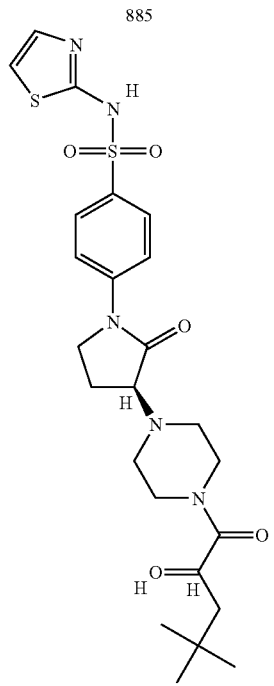
TABLE 2-continued
886
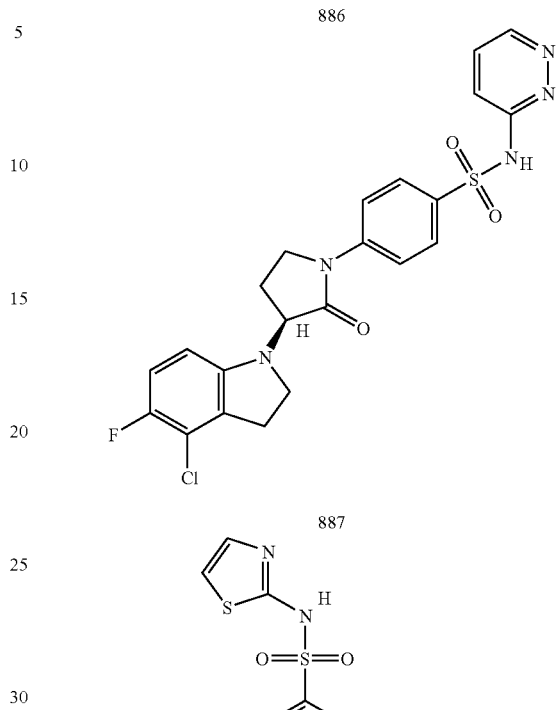
887
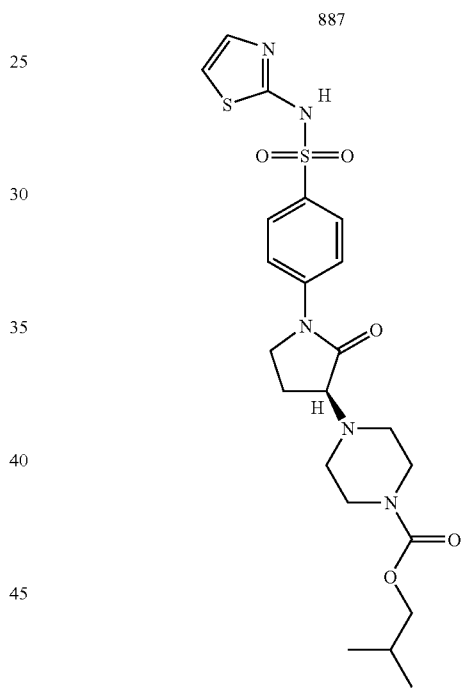
888
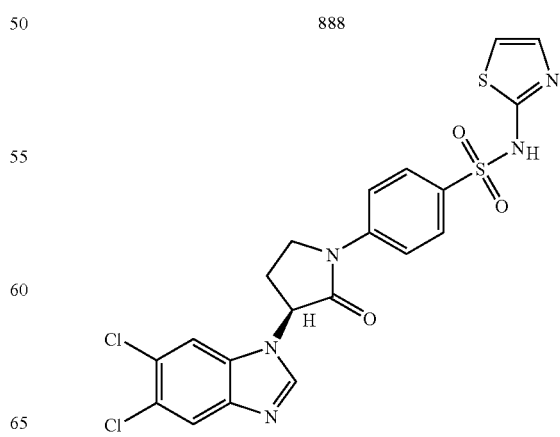

TABLE 2-continued
889
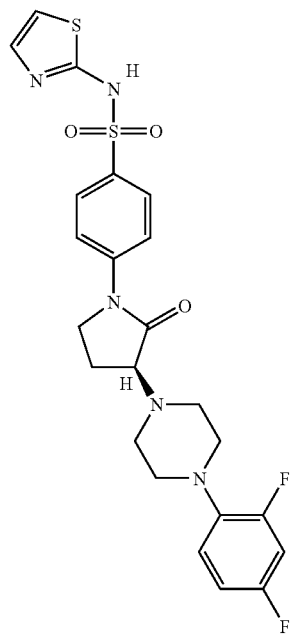
890
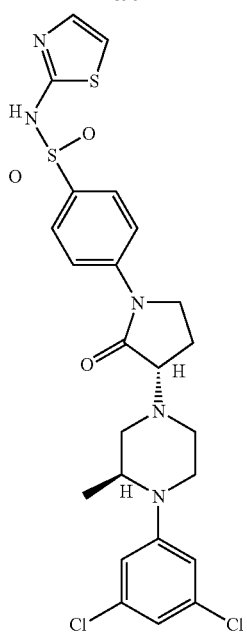
TABLE 2-continued
891
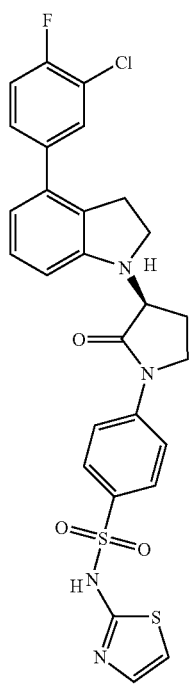
892
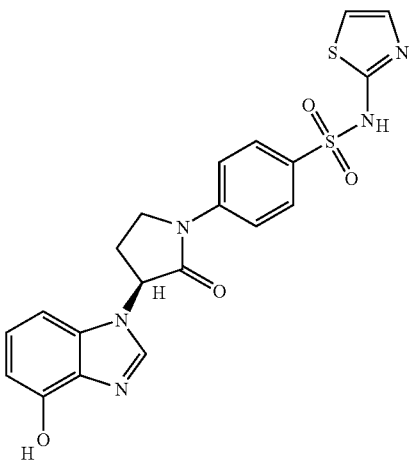

TABLE 2-continued
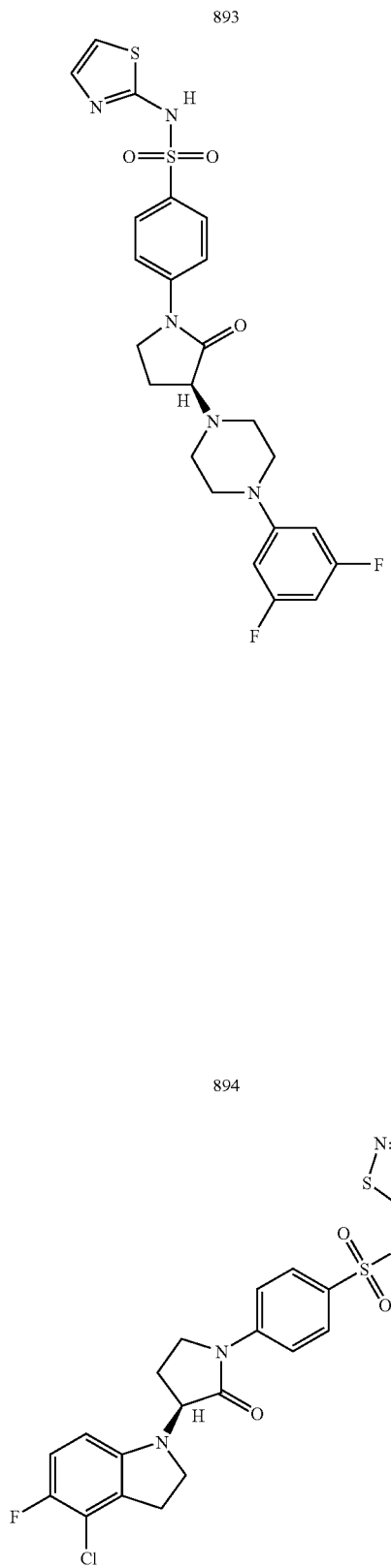
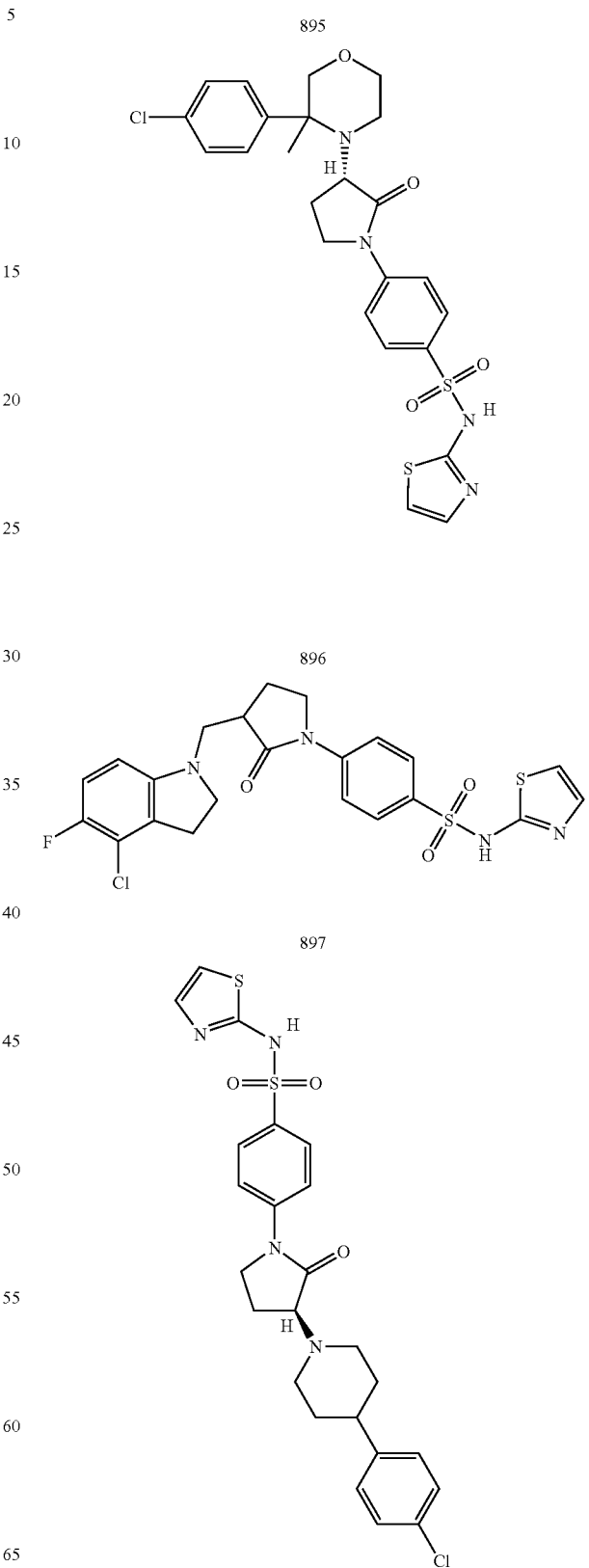

TABLE 2-continued
898
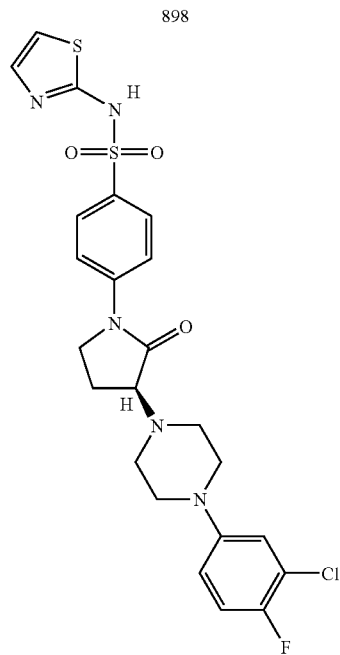
899
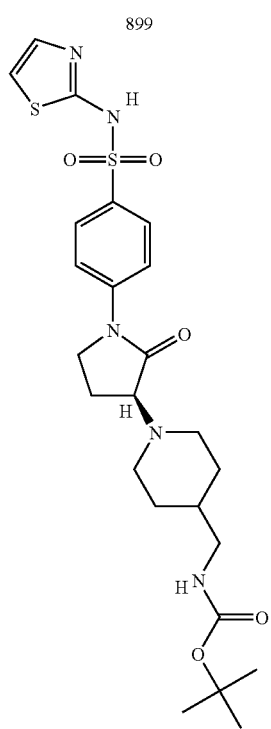
TABLE 2-continued
900
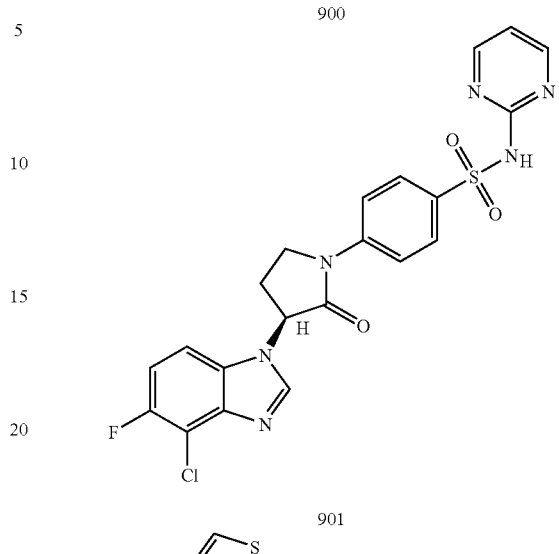
901
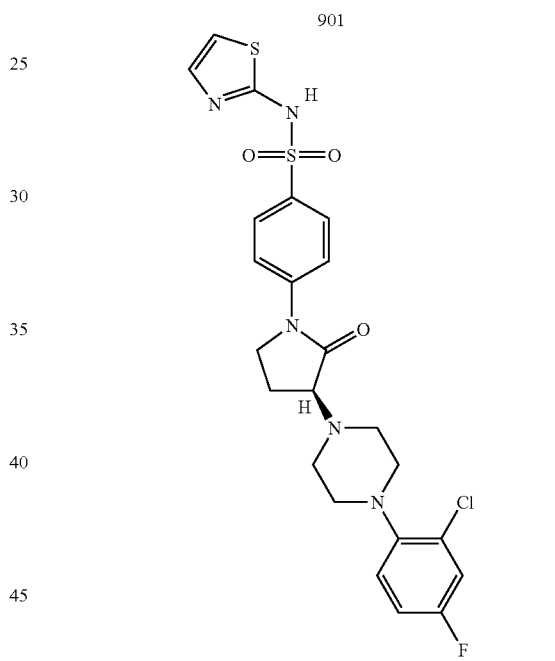
902
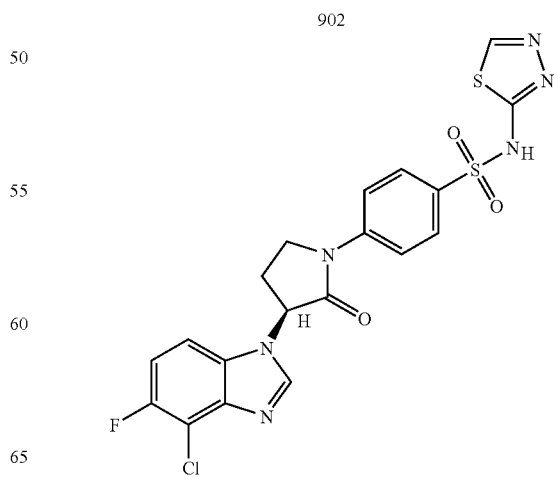

The compounds of the present invention may be prepared readily using methods known in the art. Illustrated below in Scheme 1 through Scheme 6 are methods for preparing the compounds of the present invention.

General Scheme 1

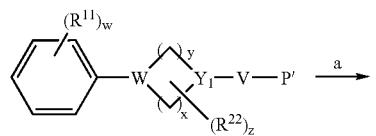

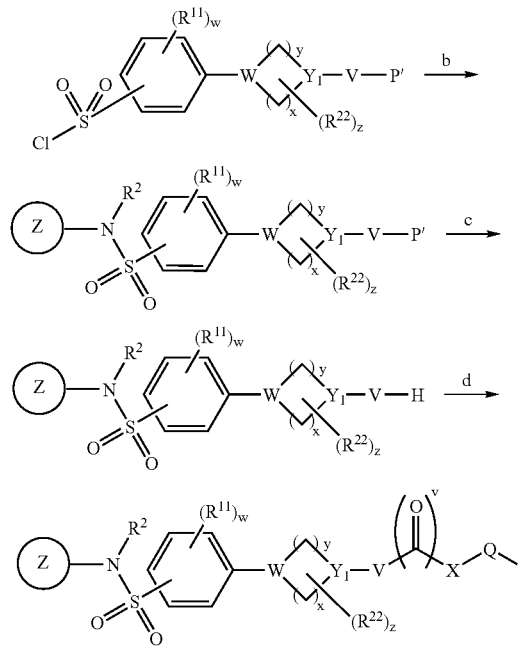

P'=H or PG, PG=protecting group; (a) ClSO₃H; (b) Z(NR²)H, base; (c) deprotection (if P' is PG); (d) R^Q-Q-X—CO₂H, HATU or BOP, base.

General Scheme 2

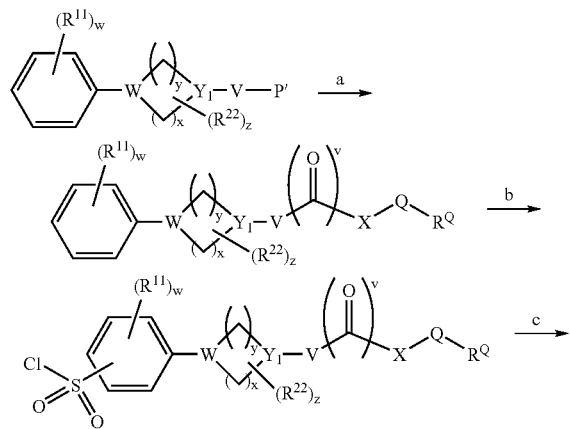

-continued

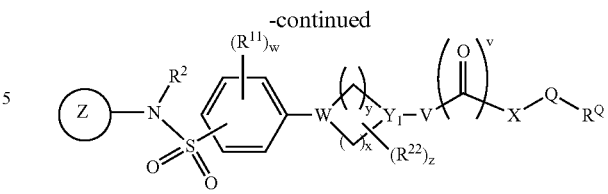

P'=H or PG, PG=protecting group; (a) deprotection if P' is PG; R^Q-Q-X—CO₂H, HATU or BOP, base. (b) ClSO₃H; (b) Z(NR²)H, base.

General Scheme 3

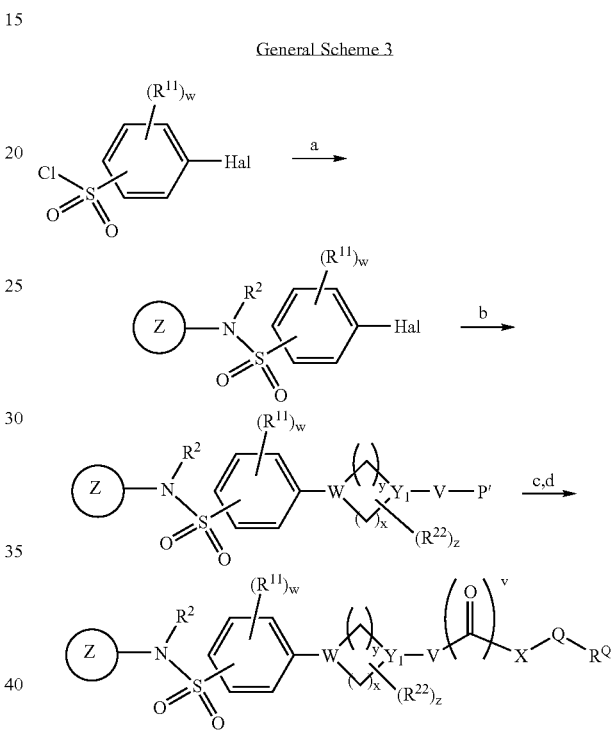

P'=H or PG, PG=protecting group; Hal=halogen (a) Z(NR²)H, base (b) biphenyl-2-yl-di-tert-butylphosphine, Pd₂(dba)₃, NaOtBu, toluene, 70° C.; (c,d) if P=PG then deprotection; R^Q-Q-X—CO₂H, HATU or BOP, base.

General Scheme 4

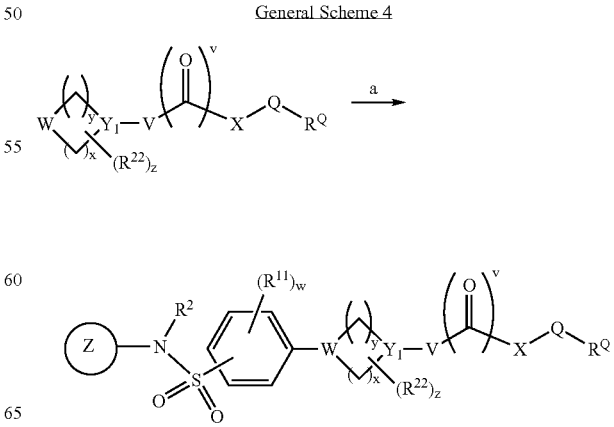

(a) biphenyl-2-yl-di-tert-butylphosphine, Pd$_2$(dba)$_3$, NaOtBu, toluene.

General Scheme 5

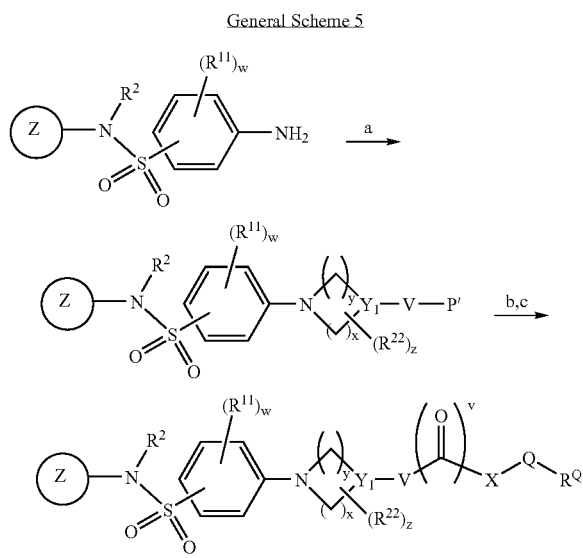

P=H or PG, PG=protecting group; (a) cyclization or condensation; (b, c) If P=PG, then deprotection; R$^Q$-Q-X—CO$_2$H, HATU or BOP, base.

General Scheme 6

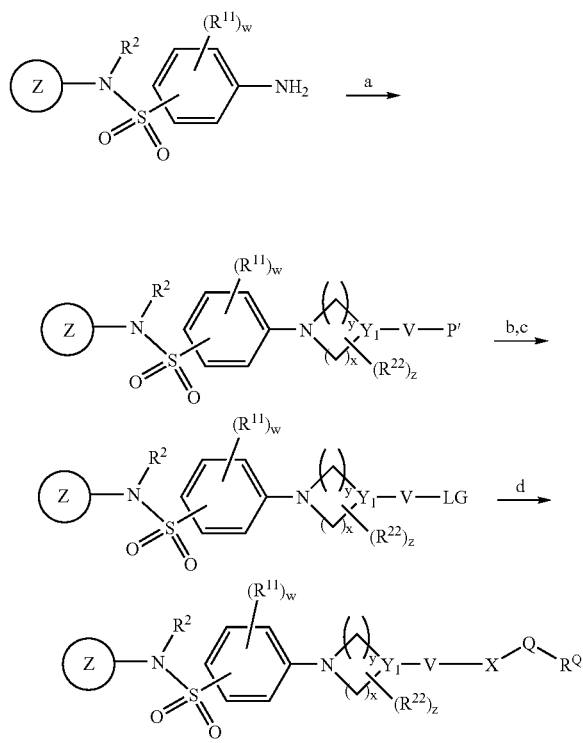

P=H or PG, PG=protecting group; LG=leaving group (a) cyclization or condensation; (b, c) if P=PG, then deprotection, addition of LG, leaving group. (d) R$^Q$-Q-X Intermediates
1. A compound having formula N-1:

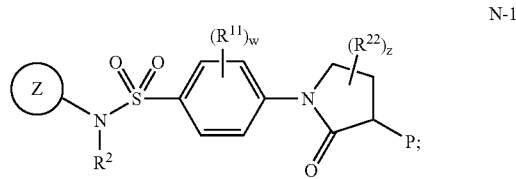

wherein:
ring Z is a 5-7 membered unsaturated or aromatic ring having 1-4 ring heteroatoms selected from O, S, or N, wherein Z is optionally substituted with up to q occurrences of R$^Z$ substitutents, wherein each R$^Z$ is independently selected from R$^1$, R$^2$, R$^3$, R$^4$, or R$^5$; and q is 0-4;
w is 0-4;
z is 0-4;
P is —O-PG or a suitable leaving group;
PG is a suitable leaving group;
R$^{11}$ is R$^2$ or Y;
R$^{22}$ is R$^1$, R$^2$, or R$^4$;
R$^1$ is (CH$_2$)$_n$—Y;
n is 0, 1 or 2;
Y is halo, CN, NO$_2$, CF$_3$, OCF$_3$, OH, SR$^6$, S(O)R$^6$, SO$_2$R$^6$, NH$_2$, NHR$^6$, N(R$^6$)$_2$, NR$^6$R$^8$, COOH, COOR$^6$ or OR$^6$;
R$^2$ is hydrogen or C1-C6 aliphatic, wherein each R$^2$ is optionally substituted with up to 2 substituents independently selected from R$^1$, R$^4$, or R$^5$;
R$^3$ is a C3-C8 cycloaliphatic, C6-C10 aryl, C3-C8 heterocyclic, or C5-C10 heteroaryl ring, wherein each R$^3$ is optionally substituted with up to 3 substituents independently selected from R$^1$, R$^2$, R$^4$ or R$^5$;
R$^4$ is OR$^5$, OR$^6$, OC(O)R$^6$, OC(O)R$^5$, OC(O)OR$^6$, OC(O)OR$^6$, OC(O)N(R$^6$)$_2$, OC(O)N(R$^5$)$_2$, OC(O)N(R$^6$R$^5$), OP(O)(OR$^6$)$_2$, OP(O)(OR$^5$)$_2$, OP(O)(OR$^6$)(OR$^5$), SR$^6$, SR$^5$, S(O)R$^6$, S(O)R$^5$, SO$_2$R$^6$, SO$_2$R$^5$, SO$_2$N(R$^5$)$_2$, SO$_2$N(R$^5$)$_2$, SO$_2$NR$^5$R$^6$, SO$_3$R$^6$, SO$_3$R$^5$, C(O)R$^5$, C(O)OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^6$, C(O)N(OR$^5$)R$^6$, C(O)N(OR$^6$)R$^5$, C(O)N(OR$^5$)R$^5$, C(NOR$^6$)R$^6$, C(NOR$^6$)R$^5$, C(NOR$^5$)R$^6$, C(NOR$^5$)R$^5$, N(R$^6$)$_2$, N(R$^5$)$_2$, N(R$^5$R$^6$), NR$^5$C(O)R$^5$, NR$^6$C(O)R$^6$, NR$^6$C(O)R$^5$, NR$^5$C(O)OR$^6$, NR$^5$C(O)OR$^6$, NR$^6$C(O)OR$^5$, NR$^5$C(O)OR$^5$, NR$^6$C(O)N(R$^6$)$_2$, NR$^6$C(O)NR$^5$R$^6$, NR$^6$C(O)N(R$^5$)$_2$, NR$^5$C(O)N(R$^6$)$_2$, NR$^5$C(O)NR$^5$R$^6$, NR$^5$C(O)N(R$^5$)$_2$, NR$^6$C(S)N(R$^6$)$_2$, NR$^6$C(S)NR$^5$R$^6$, NR$^6$C(S)N(R$^5$)$_2$, NR$^5$C(S)N(R$^6$)$_2$, NR$^5$C(S)NR$^5$R$^6$, NR$^5$C(S)N(R$^5$)$_2$, NR$^6$SO$_2$R$^6$, NR$^6$SO$_2$R$^5$, NR$^5$SO$_2$R$^5$, NR$^6$SO$_2$N(R$^6$)$_2$, NR$^6$SO$_2$NR$^5$R$^6$, NR$^6$SO$_2$N(R$^5$)$_2$, NR$^5$SO$_2$NR$^5$R$^6$, NR$^5$SO$_2$N(R$^5$)$_2$, N(OR$^6$)R$^6$, N(OR$^6$)R$^5$, N(OR$^5$)R$^5$, N(OR$^5$)R$^6$, P(O)(OR$^6$)N(R$^6$)$_2$, P(O)(OR$^6$)N(R$^5$R$^6$), P(O)(OR$^6$)N(R$^5$)$_2$, P(O)(OR$^5$)N(R$^5$R$^6$), P(O)(OR$^5$)N(R$^6$)$_2$, P(O)(OR$^5$)N(R$^5$)$_2$, P(O)(OR$^6$)$_2$, P(O)(OR$^5$)$_2$, or P(O)(OR$^6$)(OR$^5$);
R$^5$ is a C3-C8 cycloaliphatic, C6-C10 aryl, C3-C8 heterocyclic, or C5-C10 heteroaryl ring, wherein each R$^5$ is optionally substituted with up to 3 R$^1$ substituents;
R$^6$ is H or C1-C6 aliphatic, wherein R$^6$ is optionally substituted with a R$^7$ substituent;
R$^7$ is a C3-C8 cycloaliphatic, C6-C10 aryl, C3-C8 heterocyclic, or C5-C10 heteroaryl ring, and each R$^7$ is optionally substituted with up to 2 substituents independently selected from C1-C6 aliphatic or (CH$_2$)$_m$-Z' wherein m is 0-2;
Z' is selected from halo, CN, NO$_2$, C(halo)$_3$, CH(halo)$_2$, CH$_2$(halo), —OC(halo)$_3$, —OCH(halo)$_2$, —OCH$_2$(halo), OH, S—(C1-C6) aliphatic, S(O)—(C1-C6) aliphatic, SO$_2$—(C1-C6)aliphatic, NH$_2$, NH—(C1-C6)aliphatic, N((C1-C6)aliphatic)$_2$, N((C1-C6)aliphatic)R$^8$, COOH, C(O)O(—(C1-C6)aliphatic), or O—(C1-C6)aliphatic; and R$^8$ is CH$_3$C(O)—, C6-C10 aryl sulfonyl-, or C1-C6 alkyl sulfonyl-.

In one embodiment, PG is a suitable protecting group. Exemplary such leaving groups include methoxymethyl, methoxyethyl, tetrahydropyranyl, allycarbonate, trimethylsilyl, t-butyl-diphenylsilyl, t-butyl-dimethyl-silyl, acetate, benzoyl, benzyl, p-methoxybenzyl, etc. Other suitable protecting groups are well known to one of skill in the art, e.g., Greene, T. W.; Wuts, P. G. M. "Protecting Groups in Organic Synthesis", 3rd Ed; John Wiley & Sons, Inc.: New York, 1999; Chapter 2, p 17-245.

In another embodiment, P is a suitable leaving group. A suitable leaving group, as used herein is a group capable of displacement. See, "Advanced Organic Chemistry: Reactions, Mechanisms, and Structure," pp. 339-357, Jerry March, 4$^{th}$ Ed., John Wiley & Sons (1992).

Exemplary such leaving groups include trifluoromethanesulfonate, methanesulfonate, tosylate, halo, etc. Other suitable leaving groups are well known to one of skill in the art.

In another embodiment, the present invention provides compounds of formula N-2:

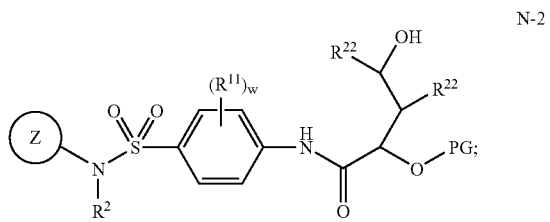

N-2 wherein:
ring Z is a 5-7 membered unsaturated or aromatic ring having 1-4 ring heteroatoms selected from O, S, or N, wherein Z is optionally substituted with up to q occurrences of R$^Z$ substitutents, wherein each R$^Z$ is independently selected from R$^1$, R$^2$, R$^3$, R$^4$, or R$^5$; and q is 0-4;

w is 0-4;

PG is a suitable protecting group;

R$^{11}$ is R$^2$ or Y;

R$^{22}$ is R$^1$, R$^2$, or R$^4$;

R$^1$ is (CH$_2$)$_n$—Y;

n is 0, 1 or 2;

Y is halo, CN, NO$_2$, CF$_3$, OCF$_3$, OH, SR$^6$, S(O)R$^6$, SO$_2$R$^6$, NH$_2$, NHR$^6$, N(R$^6$)$_2$, NR$^6$R$^8$, COOH, COOR$^6$ or OR$^6$;

R$^2$ is hydrogen or C1-C6 aliphatic, wherein each R$^2$ is optionally substituted with up to 2 substituents independently selected from R$^1$, R$^4$, or R$^5$;

R$^3$ is a C3-C8 cycloaliphatic, C6-C10 aryl, C3-C8 heterocyclic, or C5-C10 heteroaryl ring, wherein each R$^3$ is optionally substituted with up to 3 substituents, independently selected from R$^1$, R$^2$, R$^4$ or R$^5$;

R$^4$ is OR$^5$, OR$^6$, OC(O)R$^6$, OC(O)R$^5$, OC(O)OR$^6$, OC(O)OR$^5$, OC(O)N(R$^6$)$_2$, OC(O)N(R$^5$)$_2$, OC(O)N(R$^6$R$^5$), OP(O)(OR$^6$)$_2$, OP(O)(OR$^5$)$_2$, OP(O)(OR$^6$)(OR$^5$), SR$^6$, SR$^5$, S(O)R$^6$, S(O)R$^5$, SO$_2$R$^6$, SO$_2$R$^5$, SO$_2$N(R$^5$)$_2$, SO$_2$N(R$^6$)$_2$, SO$_2$NR$^5$R$^6$, SO$_3$R$^6$, SO$_3$R$^5$, C(O)R$^5$C(O)OR$^5$, C(O)R$^6$, C(O)OR$^6$, C(O)OR$^5$, C(O)N(R$^6$)$_2$, C(O)N(R$^5$)$_2$, C(O)N(OR$^5$)R$^6$, C(O)N(OR$^5$)$_2$, C(O)N(OR$^6$)R$^5$, C(O)N(OR$^5$)R$^5$, C(NOR)R$^6$, C(NOR$^6$)R$^5$, C(NOR$^5$)R$^6$, C(NOR$^5$)R$^5$, N(R$^6$)$_2$, N(R$^5$)$_2$, N(R$^5$R$^6$), NR$^6$C(O)R$^5$, NR$^6$C(O)R$^6$, NR$^6$C(O)R$^5$, NR$^6$C(O)OR$^6$, NR$^5$C(O)OR$^6$, NR$^6$C(O)OR$^5$, NR$^5$C(O)OR$^5$, NR$^6$C(O)N(R$^6$)$_2$, NR$^6$C(O)NR$^5$R$^6$, NR$^6$C(O)N(R$^5$)$_2$, NR$^5$C(O)N(R$^6$)$_2$, NR$^5$C(O)NR$^5$R$^6$, NR$^5$C(O)N(R$^5$)$_2$, NR$^6$C(S)N(R$^6$)$_2$, NR$^6$C(S)NR$^5$R$^6$, NR$^6$C(S)N(R$^5$)$_2$, NR$^5$C(S)N(R$^6$)$_2$, NR$^5$C(S)NR$^5$R$^6$, NR$^5$C(S)N(R$^5$)$_2$, NR$^6$SO$_2$R$^6$, NR$^6$SO$_2$R$^5$, NR$^5$SO$_2$R$^5$, NR$^6$SO$_2$N(R$^6$)$_2$, NR$^6$SO$_2$NR$^5$R$^6$, NR$^6$SO$_2$N(R$^5$)$_2$, NR$^5$SO$_2$NR$^5$R$^6$, NR$^5$SO$_2$N(R$^5$)$_2$, N(OR$^6$)R$^6$, N(OR$^6$)R$^5$, N(OR$^5$)R$^5$, N(OR$^5$)R$^6$, P(O)(OR$^6$)N(R$^6$)$_2$, P(O)(OR$^6$)N(R$^5$R$^6$), P(O)(OR$^6$)N(R$^5$)$_2$, P(O)(OR$^5$)N(R$^5$R$^6$), P(O)(OR$^5$)N(R$^6$)$_2$, P(O)(OR$^5$)N(R$^5$)$_2$, P(O)(OR$^6$)$_2$, P(O)(OR$^5$)$_2$, or P(O)(OR$^6$)(OR$^5$);

R$^5$ is a C3-C8 cycloaliphatic, C6-C10 aryl, C3-C8 heterocyclic, or C5-C10 heteroaryl ring, wherein each R$^5$ is optionally substituted with up to 3 R$^1$ substituents;

R$^6$ is H or C1-C6 aliphatic, wherein R$^6$ is optionally substituted with a R$^7$ substituent;

R$^7$ is a C3-C8 cycloaliphatic, C6-C10 aryl, C3-C8 heterocyclic, or C5-C10 heteroaryl ring, and each R$^7$ is optionally substituted with up to 2 substituents independently selected from C1-C6 aliphatic, or (CH$_2$)$_m$-Z' wherein m is 0-2;

Z' is selected from halo, CN, NO$_2$, C(halo)$_3$, CH(halo)$_2$, CH$_2$(halo), —OC(halo)$_3$, —OCH(halo)$_2$, —OCH$_2$(halo), OH, S—(C1-C6) aliphatic, S(O)—(C1-C6) aliphatic, SO$_2$—(C1-C6)aliphatic, NH$_2$, NH—(C1-C6) aliphatic, N((C1-C6)aliphatic)$_2$, N((C1-C6)aliphatic)R$^8$, COOH, C(O)O(—(C1-C6)aliphatic), or O—(C1-C6)aliphatic; and R$^8$ is CH$_3$C(O)—, C6-C10 aryl sulfonyl-, or C1-C6 alkyl sulfonyl-.

In one embodiment, P is a suitable protecting group. Exemplary such leaving groups include methoxymethyl, methoxyethyl, tetrahydropyranyl, allycarbonate, trimethylsilyl, t-butyl-diphenylsilyl, t-butyl-dimethylsilyl, acetate, benzoyl, benzyl, p-methoxybenzyl, etc. Other suitable protecting groups are well known to one of skill in the art, e.g., Green, T. W.; Wuts, P. G. M. "Protecting Groups in Organic Synthesis", 3rd Ed; John Wiley & Sons, Inc.: New York, 1999; Chapter 2, p 17-245.

In another embodiment, the present invention provides compounds having formula N-3:

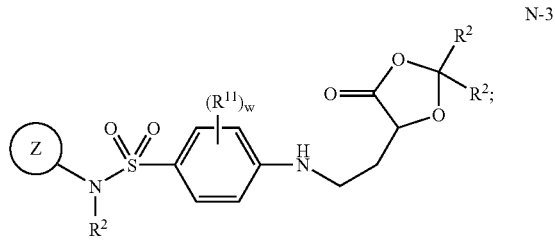

N-3 wherein:
ring Z is a 5-7 membered unsaturated or aromatic ring having 1-4 ring heteroatoms selected from O, S, or N, wherein Z is optionally substituted with up to q occurrences of R$^Z$ substitutents, wherein each R$^Z$ is independently selected from R$^1$, R$^2$, R$^3$, R$^4$, or R$^5$; and q is 0-4;

w is 0-4;

$R^1$ is $R^2$ or Y;

$R^{22}$ is $R^1$, $R^2$, or $R^4$;

$R^1$ is $(CH_2)_n$—Y;

n is 0, 1 or 2;

Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or OR;

$R^2$ is hydrogen or C1-C6 aliphatic, wherein each $R^2$ is optionally substituted with up to 2 substituents independently selected from $R^1$, $R^4$, or $R^5$;

$R^3$ is a C3-C8 cycloaliphatic, C6-C10 aryl, C3-C8 heterocyclic, or C5-C10 heteroaryl ring, wherein each $R^3$ is optionally substituted with up to 3 substituents independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6C(S)N(R^6)_2$, $NR^6C(S)NR^5R^6$, $NR^6C(S)N(R^5)_2$, $NR^5C(S)N(R^6)_2$, $NR^5C(S)NR^5R^6$, $NR^5C(S)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^6)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$;

$R^5$ is a C3-C8 cycloaliphatic, C6-C10 aryl, C3-C8 heterocyclic, or C5-C10 heteroaryl ring, wherein each $R^5$ is optionally substituted with up to 3 $R^1$ substituents;

$R^6$ is H or C1-C6 aliphatic, wherein $R^6$ is optionally substituted with a $R^7$ substituent;

$R^7$ is a C3-C8 cycloaliphatic, C6-C10 aryl, C3-C8 heterocyclic, or C5-C10 heteroaryl ring, and each $R^7$ is optionally substituted with up to 2 substituents independently selected from C1-C6 aliphatic, or $(CH_2)_m$-Z' wherein m is 0-2;

Z' is selected from halo, CN, $NO_2$, $C(halo)_3$, $CH(halo)_2$, $CH_2(halo)$, —$OC(halo)_3$, —$OCH(halo)_2$, —$OCH_2(halo)$, OH, S—(C1-C6) aliphatic, S(O)—(C1-C6) aliphatic, $SO_2$—(C1-C6)aliphatic, $NH_2$, NH—(C1-C6)aliphatic, N((C1-C6)aliphatic)$_2$, N((C1-C6)aliphatic)$R^8$, COOH, C(O)O(—(C1-C6)aliphatic), or O—(C1-C6)aliphatic; and $R^8$ is $CH_3C(O)$—, C6-C10 aryl sulfonyl-, or C1-C6 alkyl sulfonyl-.

In yet another embodiment, the present invention provides compounds having formula N-4:

wherein:

J is wherein L is —CH=CH—, —$CH_2$—$CH_2$—, or —$CH_2$—$CH_2$—$CH_2$—;

wherein J is optionally substituted with up to 4 substituents independently selected from $R^1$, $R^2$, or $R^3$;

$R^{11}$ is $R^2$ or Y;

$R^{22}$ is $R^1$, $R^2$, or $R^4$;

$R^1$ is $(CH_2)_n$—Y;

n is 0, 1 or 2;

Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;

$R^2$ is hydrogen or C1-C6 aliphatic, wherein each $R^2$ is optionally substituted with up to 2 substituents independently selected from $R^1$, $R^4$, or $R^5$;

$R^3$ is a C3-C8 cycloaliphatic, C6-C10 aryl, C3-C8 heterocyclic, or C5-C10 heteroaryl ring, wherein each $R^3$ is optionally substituted with up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6C(S)N(R^6)_2$, $NR^6C(S)NR^5R^6$, $NR^6C(S)N(R^5)_2$, $NR^5C(S)N(R^6)_2$, $NR^5C(S)NR^5R^6$, $NR^5C(S)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^6)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$;

$R^5$ is a C3-C8 cycloaliphatic, C6-C10 aryl, C3-C8 heterocyclic, or C5-C10 heteroaryl ring, wherein each $R^5$ is optionally substituted with up to 3 $R^1$ substituents;

$R^6$ is H or C1-C6 aliphatic, wherein $R^6$ is optionally substituted with a $R^7$ substituent;

$R^7$ is a C3-C8 cycloaliphatic, C6-C10 aryl, C3-C8 heterocyclic, or C5-C10 heteroaryl ring, and each $R^7$ is optionally substituted with up to 2 substituents independently selected from C1-C6 aliphatic, or $(CH_2)_m$-Z' wherein m is 0-2;

Z' is selected from halo, CN, $NO_2$, $C(halo)_3$, $CH(halo)_2$, $CH_2(halo)$, —$OC(halo)_3$, —$OCH(halo)_2$, —$OCH_2(halo)$, OH, S—(C1-C6) aliphatic, S(O)—(C1-C6) aliphatic, $SO_2$—(C1-C6)aliphatic, $NH_2$, NH—(C1-C6)aliphatic, N((C1-C6)aliphatic)$_2$, N((C1-C6)aliphatic)$R^8$, COOH, C(O)O(—(C1-C6)aliphatic), or O—(C1-C6)aliphatic; and $R^8$ is $CH_3C(O)$—, C6-C10 aryl sulfonyl-, or C1-C6 alkyl sulfonyl-.

In compounds of formula N-1, formula N2, formula N-3, and formula N-4, the preferred embodiments of ring Z, $R^1$, $R^2$, $R^3$, $R^4$, $R^5$, $R^6$, $R^7$, $R^8$, $R^{11}$, $R^{22}$, w, and Z are as described above for compounds of formula I.

Uses, Formulation and Administration

Pharmaceutically Acceptable Compositions

As discussed above, the present invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof.

In certain embodiments, a method of treatment or lessening the severity of stroke, cerebral ischemia, traumatic brain injury, amyotrophic lateral sclerosis, stress- or exercise induced angina, palpitations, hypertension, migraine, or abnormal gastro-intestinal motility is provided comprising administering an effective amount of a compound, or a pharmaceutically acceptable composition comprising a compound to a subject in need thereof.

In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitus or cancer pain is provided comprising administering an effective amount of a compound or a pharmaceutically acceptable composition to a subject in need thereof.

In certain embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; angina-induced pain is provided, comprising administering an effective amount of a compound or a pharmaceutically acceptable composition to a subject in need thereof.

In certain embodiments of the present invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the present invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the present invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.3 and/or NaV1.1.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9, activity in a biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9, activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

General methods. $^1$H NMR (400 MHz) and $^{13}$C NMR (100 MHz) spectra were obtained as solutions in deuteriochloroform (CDCl$_3$) or dimethyl sulfoxide-D$_6$ (DMSO). Mass spectra (MS) were obtained using an Applied Biosystems API EX LC/MS system equipped with a Phenomenex 50×4.60 mm luna-5μ C18 column. The LC/MS eluting system was 10-99% acetonitrile in H$_2$O with 0.035% v/v trifluoroacetic acid using a 4.5 minute linear gradient and a flow rate of 4.0 mL/minute. Silica gel chromatography was performed using silica gel-60 with a particle size of 230-400 mesh. Pyridine, dichloromethane (CH$_2$Cl$_2$), tetrahydrofuran (THF), were from Aldrich Sure-Seal bottles kept under dry nitrogen. All reactions were stirred magnetically unless otherwise noted. Unless specified otherwise, all temperatures refer to internal reaction temperatures.

Example 1

2,2,2-Trifluoro-1-(4-phenylpiperazin-1-yl)ethanone

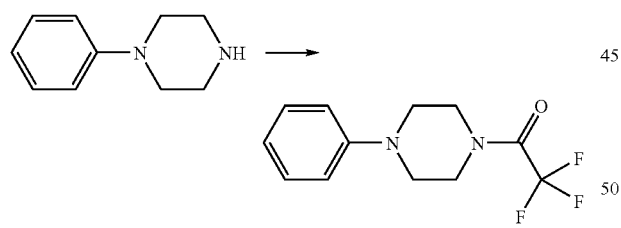

Under an N$_2$ atmosphere at −78° C., 2,2,2-trifluoroacetic anhydride (5.6 g, 4.3 mL, 30.8 mmol) was added dropwise to a solution of 1-phenylpiperazine (5.0 g, 4.7 mL, 30.8 mmol), triethylamine (3.1 g, 4.3 mL, 30.8 mmol), and CH$_2$Cl$_2$ (50 mL). The reaction was allowed to warm to RT over a period of 30 minutes. After evaporating the solvents under reduced pressure, purification via silica gel chromatography using 7/3 hexanes/EtOAc gave 2,2,2-trifluoro-1-(4-phenylpiperazin-1-yl)ethanone as a white solid (6.1 g, 62%). $^1$H NMR (400 MHz, DMSO-d6) δ 7.27-7.23 (m, 2H), 6.98-6.96 (m, 2H), 6.86-6.82 (m, 1H), 3.74-3.69 (m, 4H), 3.24-3.21 (m, 4H). LC/MS (10%-99% CH$_3$CN (0.035% TFA)/H$_2$O (0.05% TFA)), m/z: M+1 obs=258.90; t$_R$=3.06 min.

4-(4-(2,2,2-Trifluoroacetyl)piperazin-1-yl)benzene-1-sulfonyl chloride

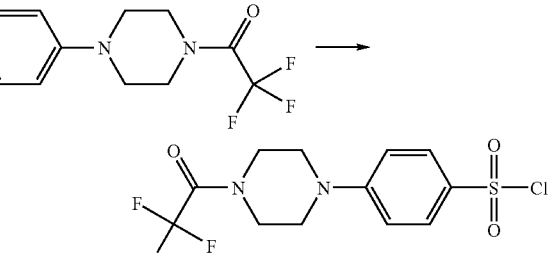

A mixture of 2,2,2-trifluoro-1-(4-phenylpiperazin-1-yl) ethanone (1.0 g, 3.9 mmol) and chlorosulfonic acid (6 mL) was heated at 155° C. for 15 min. After cooling to RT, the mixture was poured into ice water and extracted with EtOAc. The organic layer was concentrated and purified via silica gel chromatography using 7/3 hexanes/EtOAc to obtain 4-(4-(2,2,2-trifluoroacetyl)piperazin-1-yl)benzene-1-sulfonyl chloride as a yellow solid (1.0 g, 72%). $^1$H NMR (400 MHz, CDCl$_3$) δ 7.93-7.89 (m, 2H), 6.96-6.92 (m, 2H), 3.88 (t, J=5.3 Hz, 2H), 3.83 (t, J=5.1 Hz, 2H), 3.55-3.52 (m, 4H).

General Procedure 1

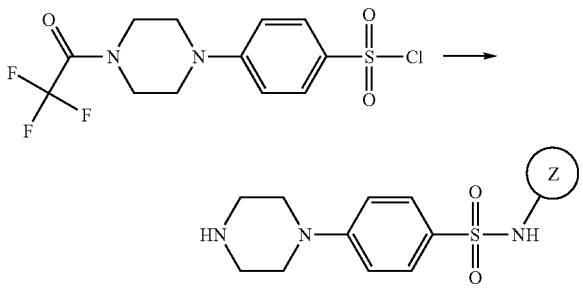

Under an N$_2$ atmosphere, a mixture of the sulfonyl chloride (1 mmol) and aminoheterocycle (1 mmol), and pyridine (1.0 mL) was stirred at RT for 19 h. The crude product was purified via silica gel chromatography using MeOH in CH$_2$Cl$_2$.

N-(Thiazol-2-yl)-4-(4-(2,2,2-trifluoroacetyl)piperazin-1-yl)benzenesulfonamide

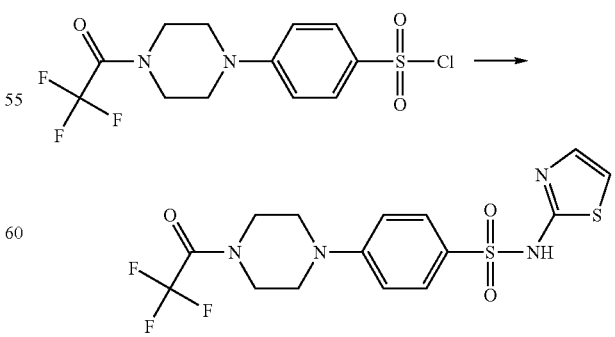

Synthesized according to general procedure 1. The crude product was purified via silica gel chromatography using 3%

MeOH in CH₂Cl₂. The resulting oil was taken up in a 2:1 mixture of CH₂Cl₂:Et₂O (12 mL) and cooled at 0° C. for 20 minutes. The formed precipitate was filtered off and dried under vacuum to obtain N-(thiazol-2-yl)-4-(4-(2,2,2-trifluoroacetyl)piperazin-1-yl)benzenesulfonamide as a white solid (280 mg, 28%). LC/MS (10%-99% CH₃CN (0.035% TFA)/H₂O (0.05% TFA)), m/z: M+1 obs=421.10; $t_R$=2.68 min.

Synthesis of 1,2,4-Thiadiazol-5-ylamine

Method A (E)-N'-Carbamothioyl-N,N-dimethylformimidamide

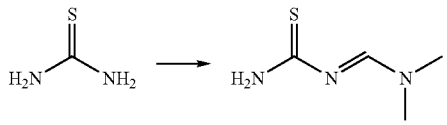

Under an N₂ atmosphere at RT, 1,1-dimethoxy-N,N-dimethylmethanamine (174 mL, 150 g, 1.31 mol) was added to a mixture of thiourea (90.0 g, 1.2 mol) and MeOH (950 mL), and the reaction was heated to reflux for 4 h. The mixture was allowed to cool to RT and stirred for 19 h. The reaction was then cooled to 0° C. and stirred for 1 h. The formed precipitate was filtered off and washed with a 1:1 mixture of MeOH and hexanes to obtain (E)-N'-carbamothioyl-N,N-dimethylformimidamide as a white solid (133 g, 85%). ¹H NMR (400 MHz, DMSO-d6) δ 8.62 (s, 1H), 8.20 (s, 1H), 7.9.3 (s, 1H), 3.13 (s, 3H), 2.99 (s, 3H). LC/MS (10%-99% CH₃CN (0.035% TFA)/H₂O (0.05% TFA)), m/z: M+1 obs=132.0; $t_R$=0.37 min.

1,2,4-Thiadiazol-5-ylamine

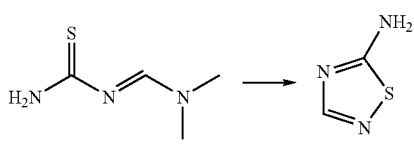

A mixture of (E)-N'-carbamothioyl-N,N-dimethylformimidamide (3.9 g, 30 mmol), hydroxylamine-O-sulfonic acid (3.7 g, 33 mmol) and EtOH (100 mL) was heated at 80° C. for 8 h. After cooling to RT, triethylamine was added, and the mixture was stirred at RT for 19 h. The solvents were evaporated under reduced pressure, and the residue was taken up in a 9:1 mixture of CH₂Cl₂:MeOH (10 mL) and purified via silica gel chromatography using 5% MeOH in CH₂Cl₂ to obtain 1,2,4-thiadiazol-5-amine as a white solid (1.4 g, 47%). ¹H NMR (400 MHz, DMSO-d6) δ 7.95 (s, 2H), 7.85 (s, 1H).

LC/MS (10%-99% CH₃CN (0.035% TFA)/H₂O (0.05% TFA)), m/z: M+1 obs=102.1; $t_R$=0.39 min.

Method B 1,2,4-Thiadiazol-5-ylamine

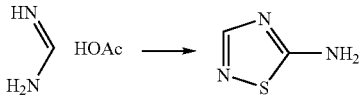

To a solution of formamidine (HOAc salt, 500 g, 4.8 mol) in MeOH (1500 mL) was added potassium thiocyanate (465 g, 4.8 mol). After stirring at room temperature for 10 min, a solution of sodium methoxide (520 g, 9.6 mol) in MeOH (1500 mL) was added to the resulting solution at 0° C., and then bromine (250 mL, 4.8 mol) was added dropwise to the solution at −15° C. After stirring at −10° C. for 0.5 h, 0° C. for 0.5 h, and at room temperature for 3 h, MeOH was removed under reduced pressure. The residue was dissolved in EtOAc, and the insoluble material was filtered. The filtrate was poured into a saturated aqueous NaCl solution, and the aqueous layer was extracted with EtOAc. The organic layer was dried over Na₂SO₄ and evaporated under reduced pressure. The residual gum was extracted with Et₂O to give the crude compound [1,2,4]thiadiazol-5-ylamine (221 g), which was used in the next step without further purification.

1,2,4-Thiadiazol-5-ylamine hydrochloride

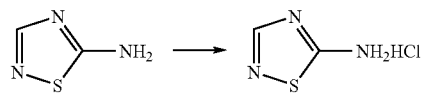

To a solution of 1,2,4-thiadiazol-5-ylamine (220 g, 2.19 mol) in MeOH (1000 mL) was added solution of HCl in MeOH (4 M, 1000 mL). After addition, the resulting suspension was stirred at room temperature for 1 h. The solid product was collected by filtration, washed with MeOH, and dried to give 1,2,4-thiadiazol-5-amine hydrochloride (137.7 g, 21% over two steps). ¹H NMR (300 MHz, D₂O) δ 8.02 (s, 1H). MS (ESI) m/e (M+H⁺) 101.2.

N-(1,2,4-Thiadiazol-5-yl)-4-(4-(2,2,2-trifluoroacetyl)piperazin-1-yl)benzenesulfonamide

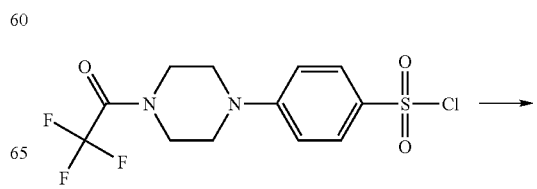

-continued

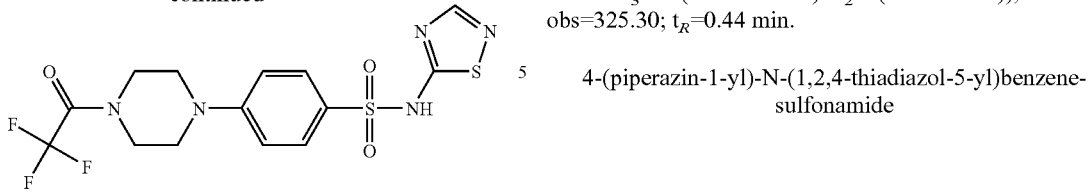

Synthesized according to general procedure 1. The crude product was purified via silica gel chromatography using 5% MeOH in CH₂Cl₂ and triturated with a 2:1 mixture of CH₂Cl₂:Et₂O to obtain N-(1,2,4-thiadiazol-5-yl)-4-(4-(2,2,2-trifluoroacetyl)piperazin-1-yl)benzenesulfonamide as a white solid (900 mg, 20%). LC/MS (10%-99% CH₃CN (0.035% TFA)/H₂O (0.05% TFA)), m/z: M+1 obs=422.30; $t_R$=2.80 min.

General Procedure 2

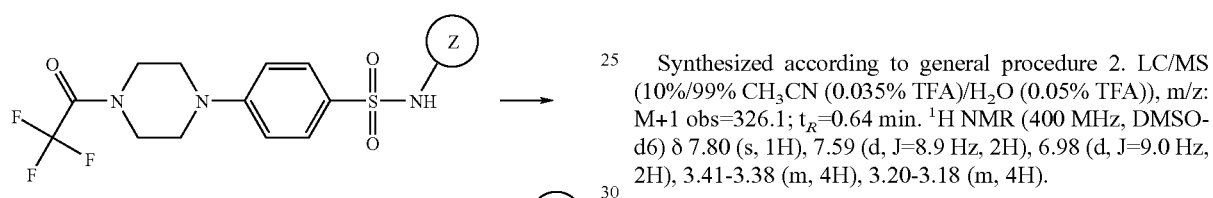

A solution of sulfonamide (1 equivalent), NaOH (10 equivalents), and H₂O (0.25 M) was stirred at RT for 1 h, then cooled to 0° C. Acetic acid (10 equivalents) was added, and the reaction was stirred at 0° C. for 20 min. The formed precipitate was filtered off and dried under vacuum to give the desired product.

4-(piperazin-1-yl)-N-(thiazol-2-yl)benzenesulfonamide

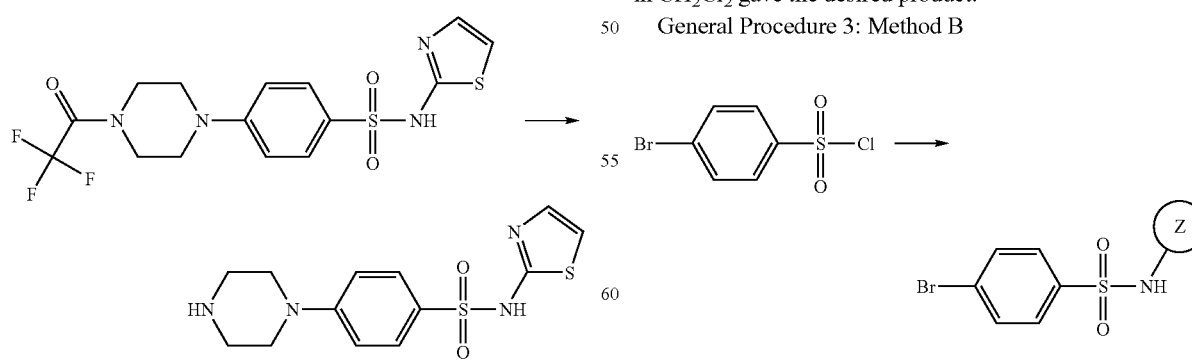

Synthesized according to general procedure 2. ¹H NMR (400 MHz, DMSO-d6) δ 7.59 (d, J=8.9 Hz, 2H), 7.09 (d, J=4.3 Hz, 1H), 6.95 (d, J=9.0 Hz, 2H), 6.62 (d, J=4.3 Hz, 1H), 3.25 (t, J=5.1 Hz, 4H), 2.96 (t, J=5.1 Hz, 4H). LC/MS (10%/99% CH₃CN (0.035% TFA)/H₂O (0.05% TFA)), m/z: M+1 obs=325.30; $t_R$=0.44 min.

4-(piperazin-1-yl)-N-(1,2,4-thiadiazol-5-yl)benzene-sulfonamide

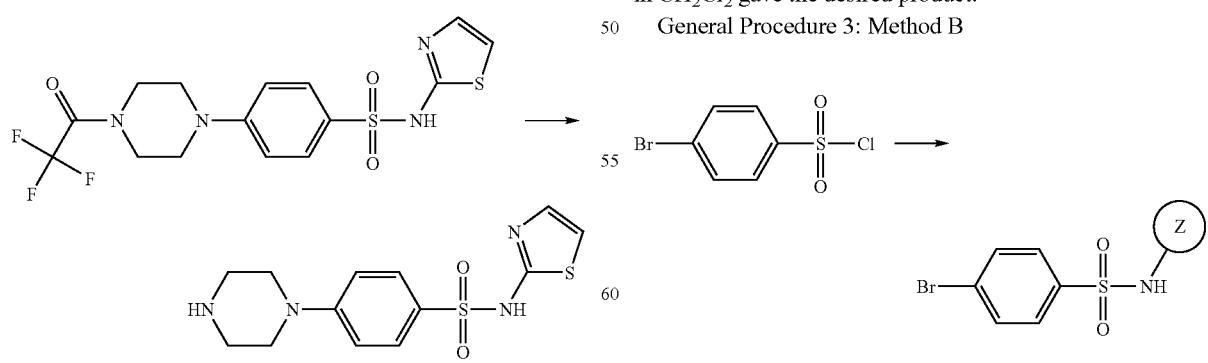

Synthesized according to general procedure 2. LC/MS (10%/99% CH₃CN (0.035% TFA)/H₂O (0.05% TFA)), m/z: M+1 obs=326.1; $t_R$=0.64 min. ¹H NMR (400 MHz, DMSO-d6) δ 7.80 (s, 1H), 7.59 (d, J=8.9 Hz, 2H), 6.98 (d, J=9.0 Hz, 2H), 3.41-3.38 (m, 4H), 3.20-3.18 (m, 4H).

General Procedure 3: Method A

A mixture of 4-bromobenzene-1-sulfonyl chloride (1 equivalent), amino heterocycle (1 equivalent) and pyridine (2.2-4.4 M) was stirred under an N₂ atmosphere at RT for 19 h. Purification via silica gel chromatography using 5% MeOH in CH₂Cl₂ gave the desired product.

General Procedure 3: Method B

A mixture of 4-bromobenzene-1-sulfonyl chloride (1 equivalent, 1 mmol), amino heterocycle (1 equivalent, 1 mmol), 1,4-diazabicyclo[2.2.2]octane (DABCO) (1 equivalent, 1 mmol) and acetonitrile (4.8 mL) was stirred at RT

4-Bromo-N-(thiazol-2-yl)benzenesulfonamide

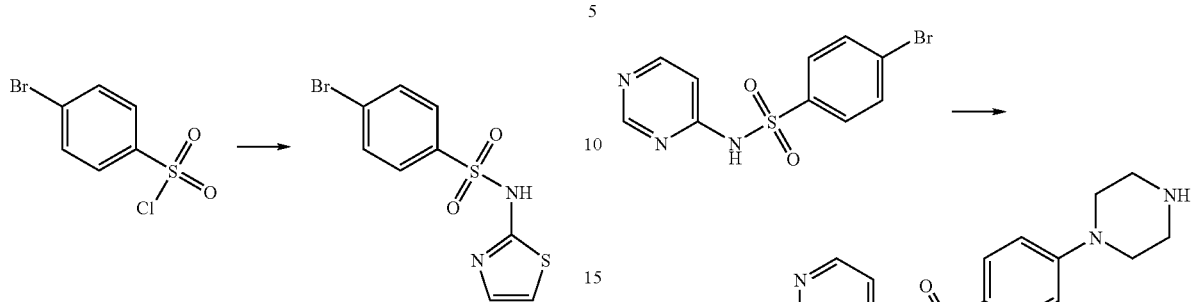

Synthesized according to general procedure 3, method A. Yield: 99%. $^1$H NMR (400 MHz, DMSO-d6) δ 7.77-7.71 (m, 4H), 7.29 (d, J=4.6 Hz, 1H), 6.87 (d, J=4.6 Hz, 1H). LC/MS (10%-99% CH$_3$CN (0.035% TFA)/H$_2$O (0.05% TFA)), m/z: M+1 obs=319.0; $t_R$=3.22 min.

4-Bromo-N-(pyrimidin-4-yl)benzenesulfonamide

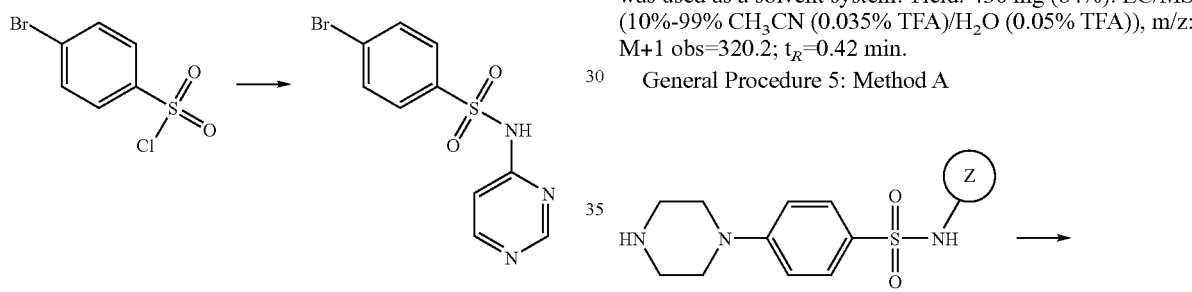

Synthesized according to general procedure 3, method B. LC/MS (10%-99% CH$_3$CN (0.035% TFA)/H$_2$O (0.05% TFA)), m/z: M+1 obs=313.9; $t_R$=1.91 min.

General Procedure 4

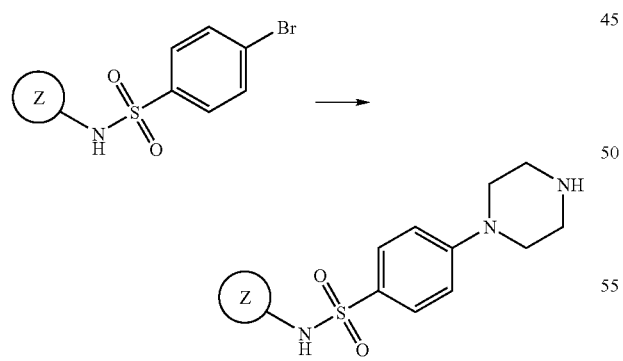

A mixture of 4-bromobenzenesulfonamide (1 equivalent), piperazine (1-10 equivalents), Pd$_2$(dba)$_3$ (0.02-0.075 equivalents), 2-(di-t-butylphosphino)biphenyl (0.08-0.2 equivalents), NaO-tBu (2-6 equivalents) and toluene (0.1-0.4 M of 4-bromobenzenesulfonamide) was heated at 80° C. for 2-6 h. Purification via silica gel chromatography using 10% MeOH in CH$_2$Cl$_2$ (with addition of 1-2% triethylamine) gave the desired product.

4-(piperazin-1-yl)-N-(pyrimidin-4-yl)benzenesulfonamide

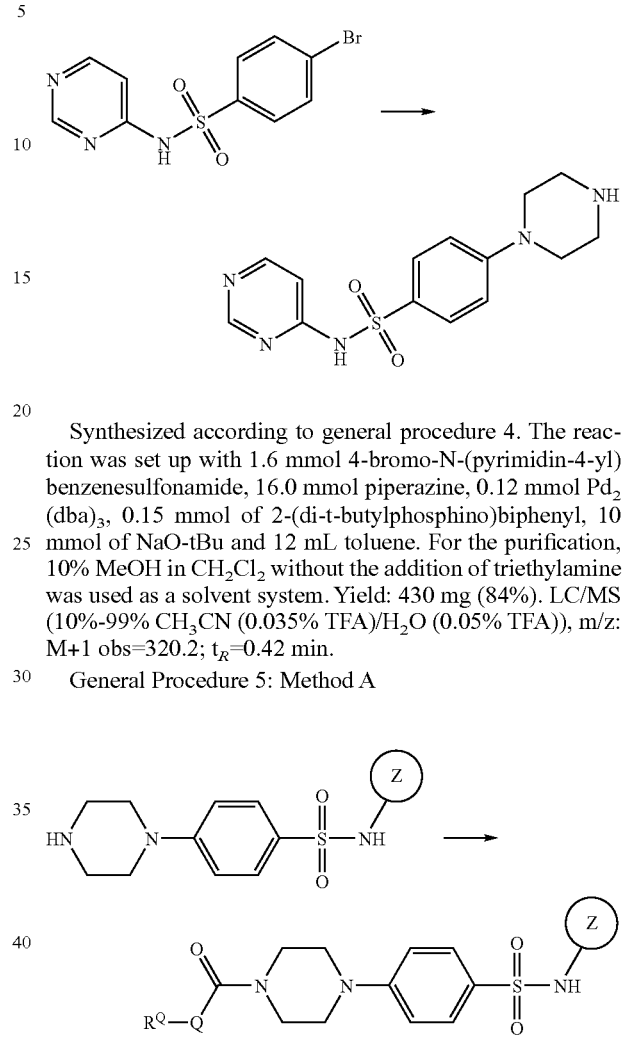

Synthesized according to general procedure 4. The reaction was set up with 1.6 mmol 4-bromo-N-(pyrimidin-4-yl) benzenesulfonamide, 16.0 mmol piperazine, 0.12 mmol Pd$_2$(dba)$_3$, 0.15 mmol of 2-(di-t-butylphosphino)biphenyl, 10 mmol of NaO-tBu and 12 mL toluene. For the purification, 10% MeOH in CH$_2$Cl$_2$ without the addition of triethylamine was used as a solvent system. Yield: 430 mg (84%). LC/MS (10%-99% CH$_3$CN (0.035% TFA)/H$_2$O (0.05% TFA)), m/z: M+1 obs=320.2; $t_R$=0.42 min.

General Procedure 5: Method A

A solution of the sulfonamide (1 equivalent), BOP-reagent (1-1.5 equivalent), triethylamine (1-1.5 equivalent), and carboxylic acid (1-1.5 equivalent) in DMF (0.3-0.5 M) was stirred under an N$_2$ atmosphere at RT for 19 h. Purification via reverse phase HPLC using 10%-99% CH$_3$CN (0.035% TFA)/H$_2$O (0.05% TFA) gave the desired product.

General Procedure 5: Method B

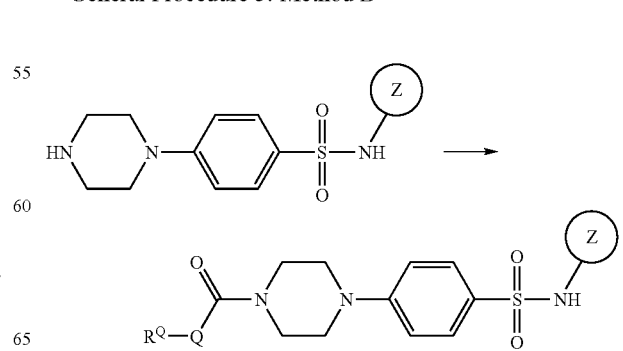

To the carboxylic acid (1.5 equivalent, 0.17 mmol) and NaHCO₃ (1.5 equivalent, 0.17 mmol) was added HATU (1.5 equivalent, 0.17 mmol) in DMF (0.15-0.25M, 0.25 mL). A solution of sulfonamide (1 equivalent, 0.11 mmol) in DMF (0.15-0.25M, 0.25 mL) was then added and the reaction mixture was stirred at RT for 19 h. Purification via reverse phase HPLC using 10%-99% CH₃CN (0.035% TFA)/H₂O (0.05% TFA) gave the desired product.

(2R)-2-(4-Fluoro-indol-1-yl)-propionic acid

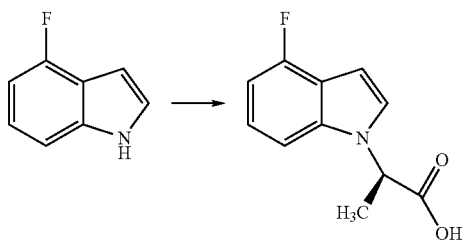

To a cooled (0-5° C.) solution of 4-fluoro-indole (44.2 g, 327 mmol) in dry DMF (400 mL) was added sodium hydride (55-65% dispersion in mineral oil, 36 g, 817 mmol) in portions. The resulting suspension was stirred at 0-5° C. for 20 minutes. (2S)-(−)-2-Bromopropionic acid (31.8 mL, 343 mmol) was added dropwise. During the addition, the temperature was kept below 10° C. by cooling in an ice-bath. Upon completion of addition, the mixture was stirred at RT for 2 hours. The mixture was poured into water (1300 mL), and the aqueous solution was washed with heptanes (400 mL) and EtOAc (2×400 mL). The aqueous layer was acidified with concentrated aqueous HCl solution (85 mL, pH<1), and extracted with EtOAc (2×400 mL). The combined organic layers were washed with 1 N aq. HCl solution (2×300 mL) and with a saturated aqueous NaCl solution (300 mL). The solution was dried over sodium sulfate, filtered, and evaporated to dryness to afford a yellow oil (67.6 g, 99%, 82% ee). This oil (67.6 g, 323 mmol) was dissolved in 200 mL n-butyl acetate and (S)-L-(−)-α-methylbenzylamine (41.1 mL, 323 mmol) was added to the warm (50° C.) solution. The mixture was left crystallizing over the weekend. The formed solid was collected by filtration and washed with butyl acetate and heptanes (2×) (68.7 g, 91% ee). This material was recrystallized twice from 500 mL water/15% ethanol (1$^{st}$ recr.: 95% ee, 2$^{nd}$ recr.: 97.5% ee). This material was dissolved in EtOAc (300 mL) and washed with 1 N aqueous HCl (2×200 mL) and saturated aqueous NaCl solution (200 mL), dried over sodium sulfate, filtered, and evaporated to dryness giving (2R)-2-(4-fluoro-indol-1-yl)-propionic acid (18.7 g, 28%) as a greenish oil (purity: 97.5%).

(R)-4-(4-(2-(4-Fluoro-1H-indol-1-yl)propanoyl)piperazin-1-yl)-N-(thiazol-2-yl)benzenesulfonamide

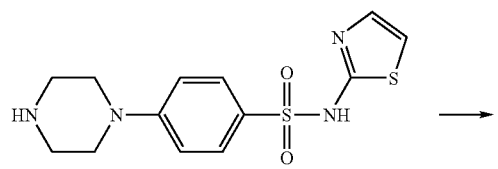

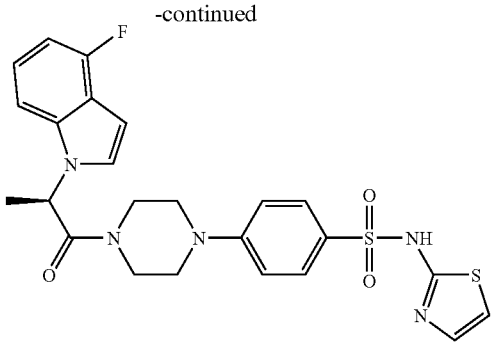

Synthesized according to general procedure 5, method A. The reaction was set up with 0.08 mmol 4-(piperazin-1-yl)-N-(thiazol-2-yl)benzenesulfonamide, 0.08 mmol (2R)-2-(4-fluoro-indol-1-yl)-propionic acid, 0.08 mmol BOP reagent, 0.08 mmol triethylamine and 200 μL DMF. LC/MS (10%-99% CH₃CN (0.035% TFA)/H₂O (0.05% TFA)), m/z: M+1 obs=514.50; t$_R$=3.03 min.

(R)-4-{4-[2-(4-Fluoro-1H-indol-1-yl)propionyl]piperazin-1-yl}-N-[1,2,4]thiadiazol-5-yl benzenesulfonamide

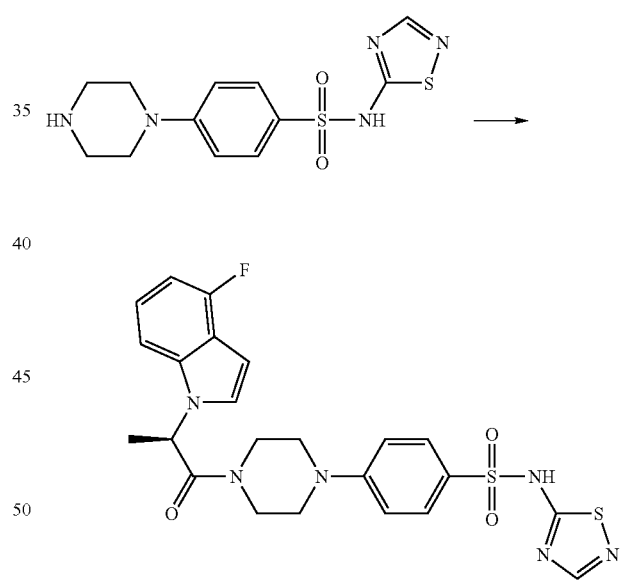

Synthesized according to general procedure 5, method B. The reaction was set up with 0.61 mmol 4-(piperazin-1-yl)-N-(1,2,4-thiadiazol-5-yl)benzenesulfonamide, 0.61 mmol (2R)-2-(4-fluoro-indol-1-yl)-propionic acid, 0.61 mmol HATU, 0.61 mmol N,N-diisopropyl ethyl amine and 2 mL (1:1) DMF:methylene dichloride to get (R)-4-{4-[2-(4-Fluoro-1H-indol-1-yl)propionyl]piperazin-1-yl}-N-[1,2,4]thiadiazol-5-yl benzenesulfonamide as a white solid (200 mg, 63% yield). LC/MS (10%-99% CH₃CN (0.035% TFA)/H₂O (0.05% TFA)), m/z: M+1 obs=515.3; t$_R$=3.16 min. ¹H NMR (400 MHz, DMSO-d6) δ 8.16 (s, 1H), 7.56 (d, J=9.0 Hz, 2H), 7.47 (s, 1H), 7.37 (s, 1H), 7.15-7.09 (m, 1H), 6.94 (d, J=9.1

Hz, 2H), 6.84-6.79 (m, 1H), 6.54 (d, J=3.2 Hz, 1H), 5.87-5.82 (m, 1H), 3.66 (d, J=4.6 Hz, 2H), 3.58-3.53 (m, 2H), 3.17-3.09 (m, 4H), 1.59 (s, 3H).

2-(3-Chloro-4-fluorophenoxy)acetic acid

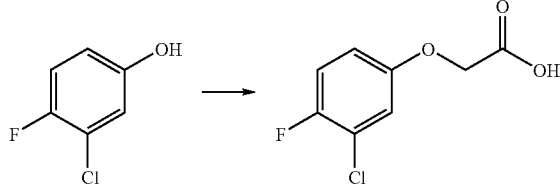

To a stirring solution of finely ground KOH (1.2 g, 20.4 mmol) in DMSO (6 mL) was added 3-chloro-4-fluorophenol (1.0 g, 6.8 mmol). The mixture was stirred for 10 minutes at RT, then cooled to 0° C. Methyl bromoacetate (1.25 g, 8.2 mmol) was added, and the reaction was slowly warmed to RT and stirred overnight. H$_2$O (10 mL) and MeOH (10 mL) were added to the mixture, and the reaction was stirred for 1 h. After removing MeOH under reduced pressure, H$_2$O (100 mL) and Et$_2$O (50 mL) were added, and the layers were separated. The aqueous phase was acidified to pH 2 with an aqueous concentrated HCl solution and extracted with CH$_2$Cl$_2$ (200 mL). The organic layer was dried over MgSO$_4$, filtered, concentrated, and dried to give 2-(3-chloro-4-fluorophenoxy)acetic acid as a white solid (1.1 g, 79%). $^1$H NMR (400 MHz, CDCl$_3$) δ 7.10 (t, J=8.8 Hz, 1H), 7.01-6.98 (m, 1H), 6.84-6.80 (m, 1H), 4.68 (s, 2H).

4-(4-(2-(3-Chloro-4-fluorophenoxy)acetyl)piperazin-1-yl)-N-(thiazol-2-yl)benzenesulfonamide

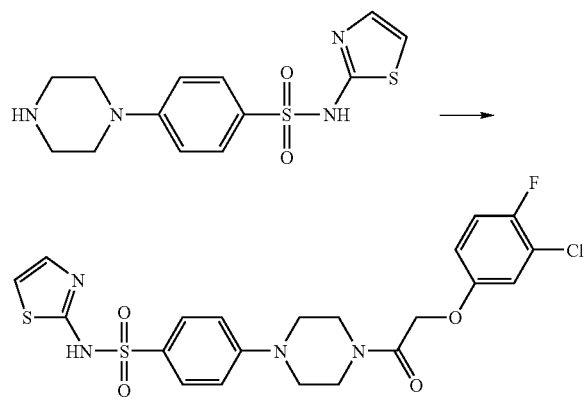

Synthesized according to general procedure 5, method A. The reaction was set up with 0.08 mmol 4-(piperazin-1-yl)-N-(thiazol-2-yl)benzenesulfonamide, 0.08 mmol 2-(3-chloro-4-fluorophenoxy)acetic acid, 0.08 mmol BOP reagent, 0.08 mmol triethylamine and 200 μL DMF. $^1$H NMR (400 MHz, DMSO-d6) δ 7.62 (d, J=9.0 Hz, 2H), 7.33 (t, J=9.1 Hz, 1H), 7.23-7.19 (m, 2H), 7.01 (d, J=9.1 Hz, 2H), 6.97-6.93 (m, 1H), 6.78 (d, J=4.5 Hz, 1H), 4.92 (s, 2H), 3.58 (t, J=5.0 Hz, 4H), 3.30 (d, J=5.0 Hz, 4H). LC/MS (10%-99% CH$_3$CN (0.035% TFA)/H$_2$O (0.05% TFA)), m/z: M+1 obs=511.30; t$_R$=2.95 mm.

6-Chloro-1,2,3,4-tetrahydroquinoline

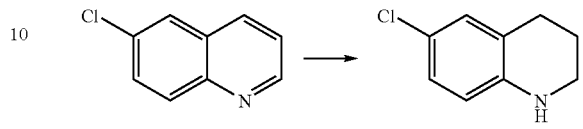

A flask filled with a mixture of 6-chloroquinoline (12.0 g, 73.3 mmol), PtO$_2$ (2.16 g, 13 mol %), and MeOH (500 mL, 6.15 M) was flushed with N$_2$ and then equipped with a balloon filled with H$_2$. The reaction was kept under H$_2$ atmosphere and stirred for 4 h. The mixture was filtered through Celite and washed with CH$_2$Cl$_2$. Purification via silica gel chromatography using 50% CH$_2$Cl$_2$ in hexanes gave 6-chloro-1,2,3,4-tetrahydroquinoline (7.7 g, 62%). $^1$H NMR (400 MHz, DMSO-d6) δ 6.85-6.83 (m, 2H), 6.42-6.39 (m, 1H), 5.82 (s, 1H), 3.17-3.13 (m, 2H), 2.64 (t, J=6.3 Hz, 2H), 1.78-1.72 (m, 2H). LC/MS (10%-99% CH$_3$CN (0.035% TFA)/H$_2$O (0.05% TFA)), m/z: M+1 obs=168.2; t$_R$=1.57 min.

(R)-Ethyl 2-(6-chloro-3,4-dihydroquinolin-1(2H)-yl)propanoate

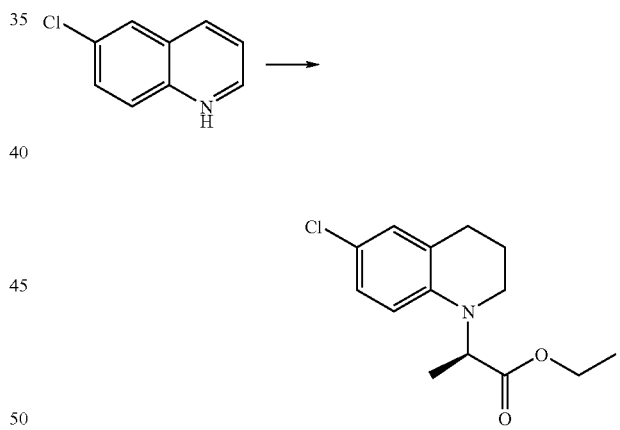

Under an N$_2$ atmosphere at RT, ethyl-O-trifluoromethyl-sulfonyl-L-lactate (1.2 mL, 6.56 mmol) was slowly added to a stirring solution of 6-chloro-1,2,3,4-tetrahydroquinoline (1.0 g, 5.97 mmol) and 2,6-lutidine (0.8 mL, 6.87 mmol) in 1,2-dichloroethane (15 mL), and the reaction was heated at 70° C. overnight. The mixture was washed with H$_2$O and extracted twice with CH$_2$Cl$_2$. The organic layer was dried over MgSO$_4$, filtered, and concentrated. Purification via silica gel chromatography using 0-20% EtOAc in hexanes gave (R)-ethyl 2-(6-chloro-3,4-dihydroquinolin-1(2H)-yl)propanoate as a yellow oil (1.54 g, 96%). $^1$H NMR (300 MHz, CDCl$_3$): δ 6.9 (m, 2H), 6.46 (d, 1H), 4.4 (q, 1H), 4.16 (m, 2H), 3.29 (m, 2H), 2.71 (m, 2H), 1.93 (m, 2H), 1.49 (d, 3H), 1.22 (t, 3H).

(R)-2-(6-Chloro-3,4-dihydroquinolin-1(2H)-yl)propanoic acid

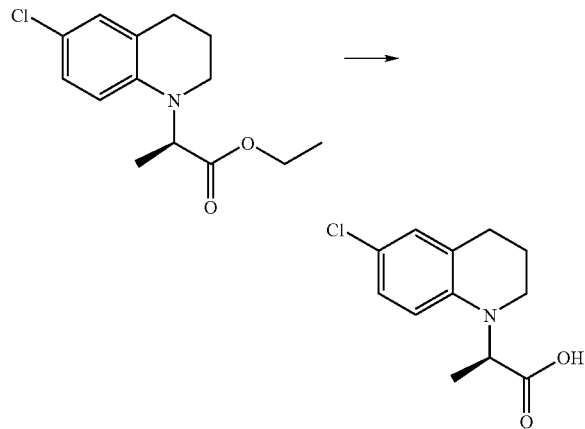

At 0° C., an aqueous 2.0 M KOH solution (7.5 mL, 14.9 mmol) was added to a stirring solution of (R)-ethyl 2-(6-chloro-3,4-dihydroquinolin-1(2H)-yl)propanoate (1.0 g, 3.73 mmol) in MeOH (7.5 mL). The reaction was allowed to warm to RT and left stirring overnight. Due to the instability of the final product as a solid, the solution containing (R)-2-(6-chloro-3,4-dihydroquinolin-1(2H)-yl)propanoic acid was used for the next step without further work up.

(R)-4-(4-(2-(6-Chloro-3,4-dihydroquinolin-1(2H)-yl) propanoyl)piperazin-1-yl)-N-(1,2,4-thiadiazol-5-yl) benzenesulfonamide

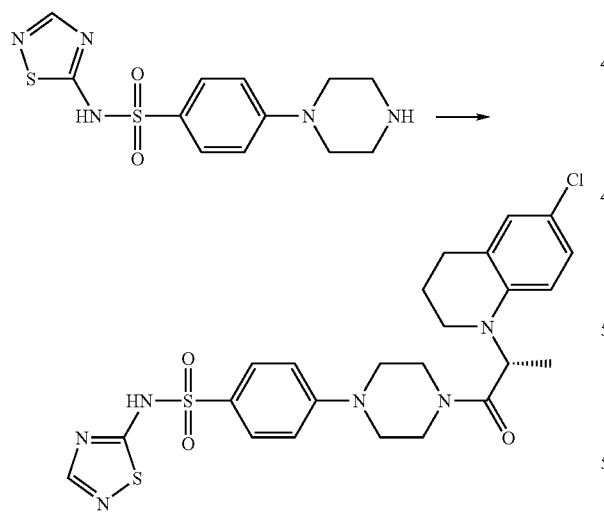

Synthesized according to general procedure 5, method B. The reaction was set up with 4.5 mmol 4-(piperazin-1-yl)-N-(1,2,4-thiadiazol-5-yl)benzenesulfonamide, 4.5 mmol (R)-2-(6-chloro-3,4-dihydroquinolin-1(2H)-yl)propanoic acid, 5.5 mmol HATU, 5.4 mmol sodium bicarbonate and 12 mL (1:1) DMF:methylene dichloride to get (R)-4-(4-(2-(6-Chloro-3,4-dihydroquinolin-1(2H)-yl)propanoyl)piperazin-1-yl)-N-(1, 2,4-thiadiazol-5-yl)benzenesulfonamide as a white solid (1.5 g, 61% yield). LC/MS (10%-99% CH$_3$CN (0.035% TFA)/ H$_2$O (0.05% TFA)), m/z: M+1 obs=547.5; t$_R$=3.44 min. $^1$H NMR (400 MHz, DMSO-d6) δ 8.48 (s, 1H), 7.58 (d, J=9.1 Hz, 2H), 7.04-6.96 (m, 4H), 6.78 (d, J=9.1 Hz, 1H), 4.88-4.84 (m, 1H), 3.73-3.69 (m, 1H), 3.58-3.53 (m, 1H), 3.43-3.37 (m, 4H), 3.26-3.18 (m, 2H), 3.11-2.95 (m, 2H), 2.73-2.64 (m, 2H), 1.84-1.73 (m, 2H), 1.84-1.08 (m, 3H).

3-(5-Chloro-1H-indol-1-yl)propanoic acid

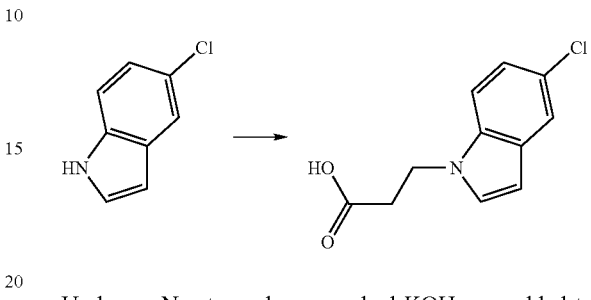

Under an N$_2$ atmosphere, crushed KOH was added to a solution of 5-chloro-1H-indole (2.0 g, 13.2 mmol) in DMSO (19 mL, 0.7 M), and the mixture was stirred for 2 h at RT. Methyl 3-bromopropanoate (1.9 mL, 17.2 mmol) was added dropwise, and the reaction was continued to stir at RT overnight. After diluting with H$_2$O, the reaction was cleared with a 4.5 N aqueous KOH solution and washed 3 times with CH$_2$Cl$_2$. The aqueous layer was acidified with a 2N HCl solution to pH 3 and extracted 3 times with CH$_2$Cl$_2$. The organic fractions were combined, dried over MgSO$_4$, filtered, and concentrated. Purification via silica gel chromatography using 0-8% MeOH in CH$_2$Cl$_2$ gave 3-(5-chloro-1H-indol-1-yl)propanoic acid (2 g, 68%). $^1$H NMR (400 MHz, DMSO-d6) δ 7.58 (d, J=2.0 Hz, 1H), 7.54 (d, J=8.7 Hz, 1H), 7.44 (d, J=3.1 Hz, 1H), 7.13 (dd, J=8.7, 2.1 Hz, 1H), 6.42 (dd, J=3.2, 0.7 Hz, 1H), 4.40 (t, J=6.8 Hz, 2H), 2.75 (t, J=6.8 Hz, 2H). LC/MS (10%-99% CH$_3$CN (0.035% TFA)/H$_2$O (0.05% TFA)), m/z: M+1 obs=224.5; t$_R$=2.74 min.

4-(4-(3-(5-Chloro-1H-indol-1-yl)propanoyl)piper-azin-1-yl)-N-(1,2,4-thiadiazol-5-yl)benzenesulfona-mide

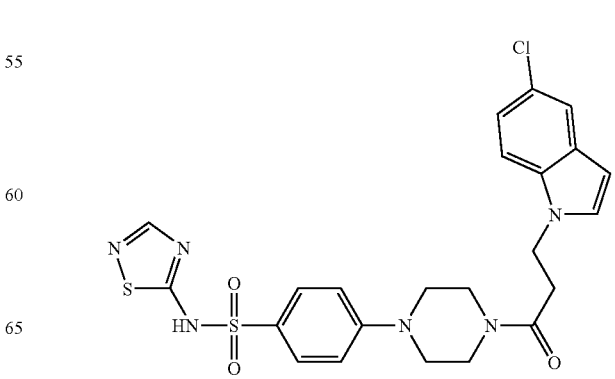

Synthesized according to general procedure 5, method A. The reaction was set up with 0.11 mmol 4-(piperazin-1-yl)-N-(1,2,4-thiadiazol-5-yl)benzenesulfonamide, 0.11 mmol 3-(5-chloro-1H-indol-1-yl)propanoic acid, 0.11 mmol BOP reagent, 0.11 mmol triethylamine and 250 μL DMF. Yield 53%. $^1$H NMR (400 MHz, DMSO-d6) δ 8.42 (s, 1H), 7.61-7.46 (m, 5H), 7.12 (dd, J=8.7, 2.1 Hz, 1H), 6.97 (d, J=9.1 Hz, 2H), 6.40 (d, J=2.5 Hz, 1H), 4.43 (t, J=6.8 Hz, 2H), 3.55 (t, J=5.2 Hz, 2H), 3.44 (t, J=4.9 Hz, 2H), 3.22 (t, J=5.1 Hz, 2H), 3.17 (t, J=5.0 Hz, 2H), 2.83-2.79 (m, 2H). LC/MS (10%-99% CH$_3$CN (0.035% TFA)/H$_2$O (0.05% TFA)), m/z: M+1 obs=531.1; $t_R$=3.15 min.

4-(4-(2-(6-Chloro-3,4-dihydroquinolin-1(2H)-yl)propanoyl)piperazin-1-yl)-N-(pyrimidin-4-yl)benzenesulfonamide

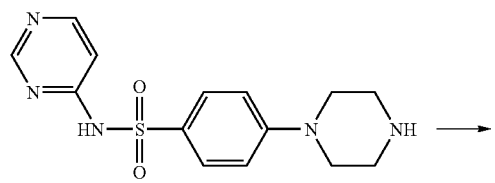

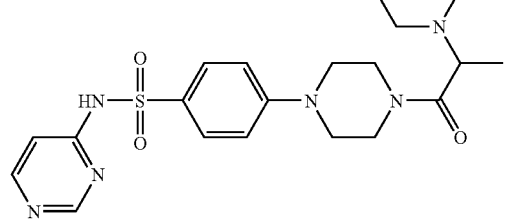

Synthesized according to general procedure 5, method A. The reaction was set up with 0.11 mmol 4-(piperazin-1-yl)-N-(pyrimidin-4-yl)benzenesulfonamide, 0.17 mmol 2-(6-chloro-3,4-dihydroquinolin-1(2H)-yl)propanoic acid, 0.17 mmol BOP reagent, 0.17 mmol triethylamine and 300 μL DMF. LC/MS (10%-99% CH$_3$CN (0.035% TFA)/H$_2$O (0.05% TFA)), m/z: M+1 obs=541.1; $t_R$=3.11 min.

4-(4-(3-(5-Chloro-1H-indol-1-yl)propanoyl)piperazin-1-yl)-N-(pyrimidin-4-yl)benzenesulfonamide

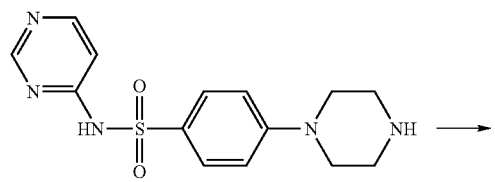

-continued

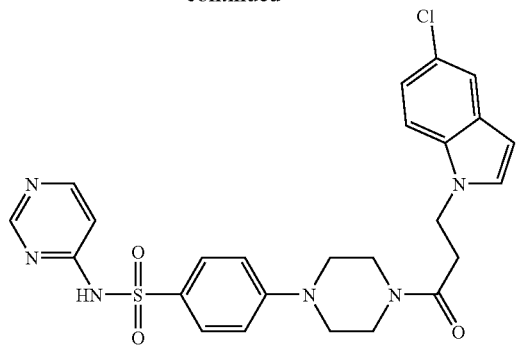

Synthesized according to general procedure 5, method A. The reaction was set up with 0.11 mmol 4-(piperazin-1-yl)-N-(pyrimidin-4-yl)benzenesulfonamide, 0.17 mmol 3-(5-chloro-1H-indol-1-yl)propanoic acid, 0.17 mmol BOP reagent, 0.17 mmol triethylamine and 300 μL DMF. LC/MS (10%-99% CH$_3$CN (0.035% TFA)/H$_2$O (0.05% TFA)), m/z: M+1 obs=525.2; $t_R$=2.87 min.

4-{4-[2-(2,3-Dichloro-phenoxy)-propionyl]-piperazin-1-yl}-N-pyrimidin-4-yl-benzenesulfonamide

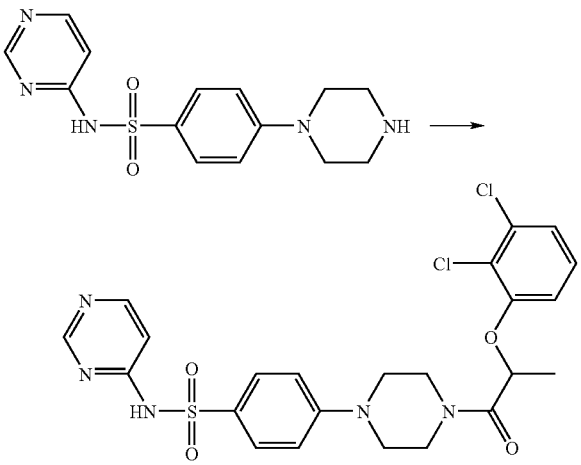

Synthesized according to general procedure 5, method B. LC/MS (10%-99% CH$_3$CN (0.035% TFA)/H$_2$O (0.05% TFA)), m/z: M+1 obs=536.3; $t_R$=2.71 min.

4-{4-[2-(4-Chloro-2-methyl-phenoxy)-acetyl]-piperazin-1-yl}-N-pyrimidin-4-yl-benzenesulfonamide

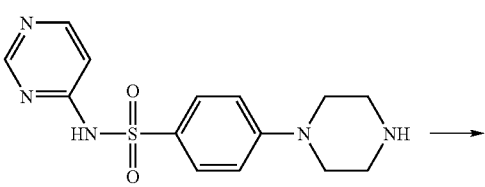

-continued

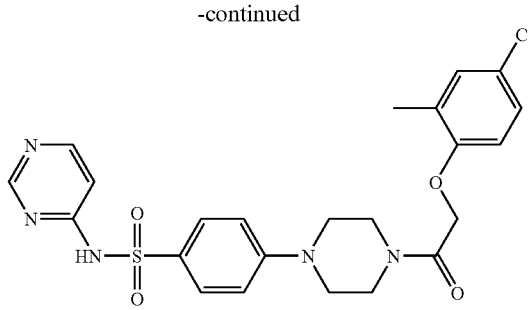

Synthesized according to general procedure 5, method B. LC/MS (10%-99% CH$_3$CN (0.035% TFA)/H$_2$O (0.05% TFA)), m/z: M+1 obs=502.0; t$_R$=2.65 min.

General Procedure 6

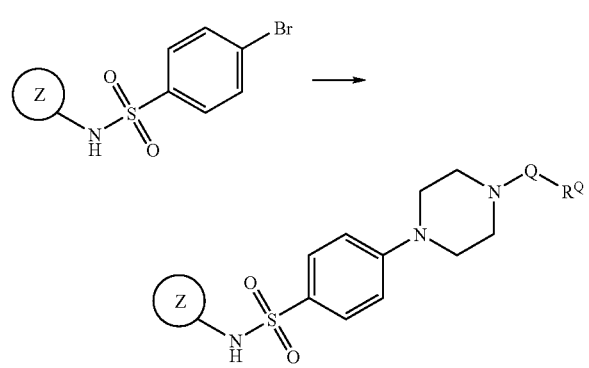

A mixture of 4-bromosulfonamide (1 equivalent), piperazine (1-10 equivalents), Pd$_2$(dba)$_3$ (0.02-0.075 equivalents), 2-(di-t-butylphosphino)biphenyl (0.08-0.2 equivalents), NaO-tBu (2-6 equivalents) and toluene (0.1-0.4 M of 4-bromobenzenesulfonamide) was heated at 80° C. for 2-6 h. Purification via silica gel chromatography using 10% MeOH in CH$_2$Cl$_2$ (with addition of 1-2% triethylamine) gave the desired product.

4-{1-[3,4-methylenedioxybenzyl]-piperazin-1-yl}-N-(thiazol-2-yl)benzenesulfonamide

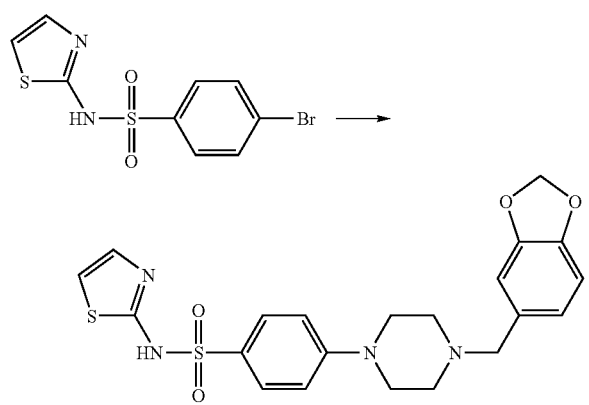

Synthesized according to general procedure 6. LC/MS (10%-99% CH$_3$CN (0.035% TFA)/H$_2$O (0.05% TFA)), m/z: M+1 obs=459.3; t$_R$=2.2 min.

4-{1-[2-fluorophenyl]-piperazin-1-yl}-N-(thiazol-2-yl)benzenesulfonamide

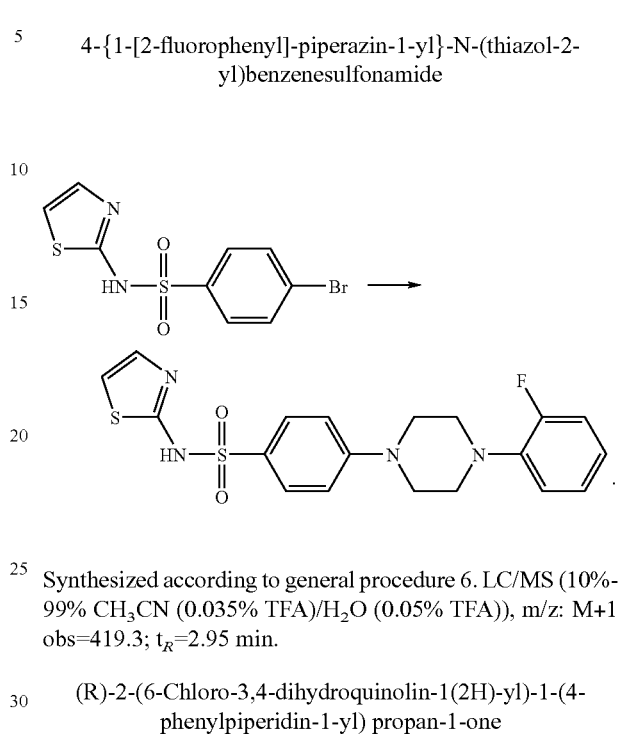

Synthesized according to general procedure 6. LC/MS (10%-99% CH$_3$CN (0.035% TFA)/H$_2$O (0.05% TFA)), m/z: M+1 obs=419.3; t$_R$=2.95 min.

(R)-2-(6-Chloro-3,4-dihydroquinolin-1(2H)-yl)-1-(4-phenylpiperidin-1-yl) propan-1-one

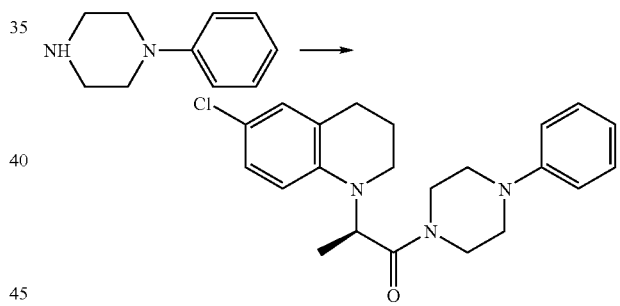

To a 0° C. solution of (R)-2-(6-chloro-3,4-dihydroquinolin-1 (2H)-yl)-propanoic acid (16.91 g, 57 mmol) in a (1:1) mixture of methylene dichloride and DMF (150 mL), was added HATU (21.7 g, 57 mmol). The reaction mixture was stirred at this temperature for 10 minutes. To this was added, 1-phenylpiperazine (8.7 mL, 57 mmol), followed by addition of sodium bicarbonate (4.79 g, 57 mmol). Upon completion of addition, the mixture was stirred at 0° C. for 4 hours. The reaction mixture was diluted with 250 mL of methylene chloride and washed with water (1500 mL) and 1M HCl solution (2×250 mL). The organic layer was dried over magnesium sulfate, filtered, and concentrated. Purification via silica gel chromatography using 20-50% ethyl acetate in hexane gave (R)-2-(6-chloro-3,4-dihydroquinolin-1(2H)-yl)-1-(4-phenylpiperizin-1-yl)propan-1-one as a white solid (11.84 g, 54%). LC/MS (10%-99% CH$_3$CN (0.035% TFA)/H$_2$O (0.05% TFA)), m/z: M+1 obs=384.3; t$_R$=3.59 min.

515

4-(4-((R)-2-(6-chloro-3,4-dihydroquinolin-1(2H)-yl)propanoyl)piperazin-1-yl)benzene-1-sulfonyl chloride

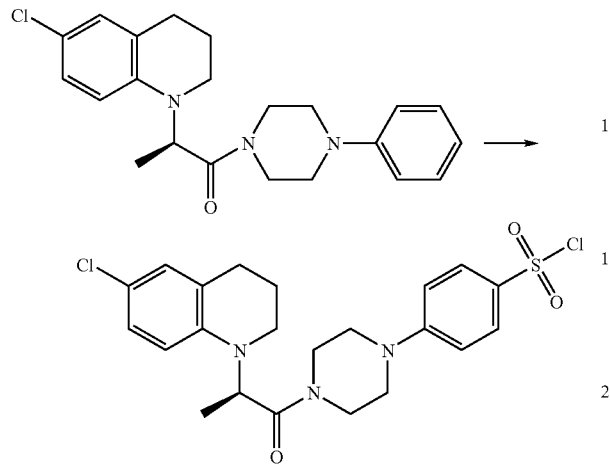

To a 0° C. solution of chlorosulfonic acid, was added (R)-2-(6-chloro-3,4-dihydroquinolin-1(2H)-yl)-1-(4-phenylpiperazin-1-yl)propan-1-one over 5 minutes. The resultant solution was heated to 120° C. for 2 hrs. The reaction mixture was cooled and carefully poured into ice-water (750 mL). The solution was extracted with methylene chloride (4×250 mL). The organic layer was dried over magnesium sulfate, filtered, and concentrated. Purification via silica gel chromatography using 40-70% ethyl acetate in hexane gave 4-(4-((R)-2-(6-chloro-3,4-dihydroquinolin-1(2H)-yl)propanoyl)piperazin-1-yl)benzene-1-sulfonyl chloride as a yellow oil (760 mg, 10%). LC/MS (10%-99% CH$_3$CN (0.035% TFA)/H$_2$O (0.05% TFA)), m/z: M+1 obs=482.3; t$_R$=3.65 min.

General Procedure 7: Method A

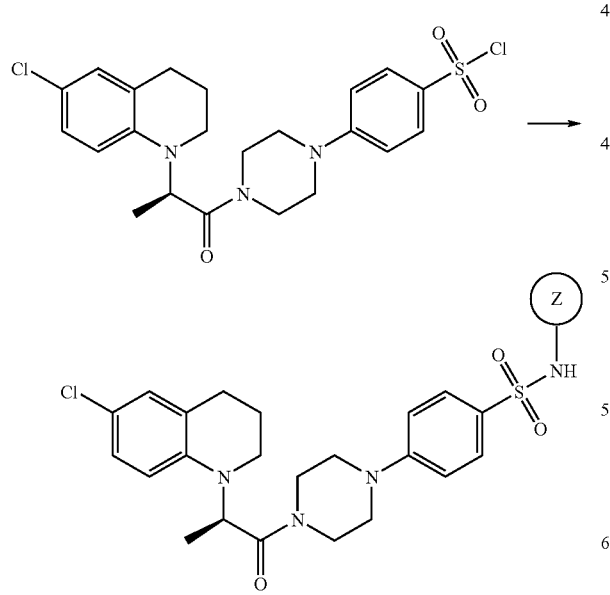

A solution of 4-(4-((R)-2-(6-chloro-3,4-dihydroquinolin-1(2H)-yl) propanoyl)piperazin-1-yl)benzene-1-sulfonyl chloride (1 equivalent), phosphazene base P1-tBu-tris(tetramethylene) (5 equivalents), and amine (1 equivalent) in acetonitrile (0.3-0.5 M) was stirred under an N$_2$ atmosphere at

516

RT for 19 h. Purification via reverse phase HPLC using 10%-99% CH$_3$CN (0.035% TFA)/H$_2$O (0.05% TFA) gave the desired product.

General Procedure 7: Method B

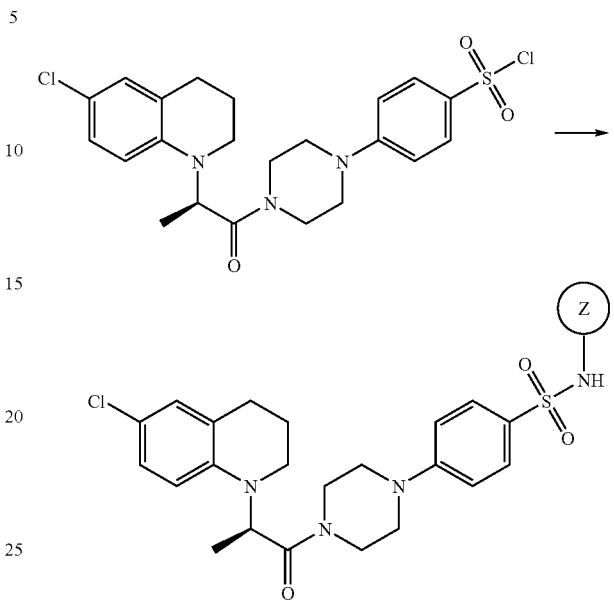

A solution of 4-(4-((R)-2-(6-chloro-3,4-dihydroquinolin-1(2H)-yl)propanoyl)piperazin-1-yl)benzene-1-sulfonyl chloride (1 equivalent), DABCO (5 equivalents), and amine (1 equivalent) in acetonitrile (0.3-0.5 M) was stirred under an N$_2$ atmosphere at RT for 19 h. Purification via reverse phase HPLC using 10%-99% CH$_3$CN (0.035% TFA)/H$_2$O (0.05% TFA) gave the desired product.

(R)-4-(4-(2-(6-Chloro-3,4-dihydroquinolin-1(2H)-yl)propanoyl)piperazin-1-yl)-N-(1,3,4-thiadiazol-2-yl)benzenesulfonamide

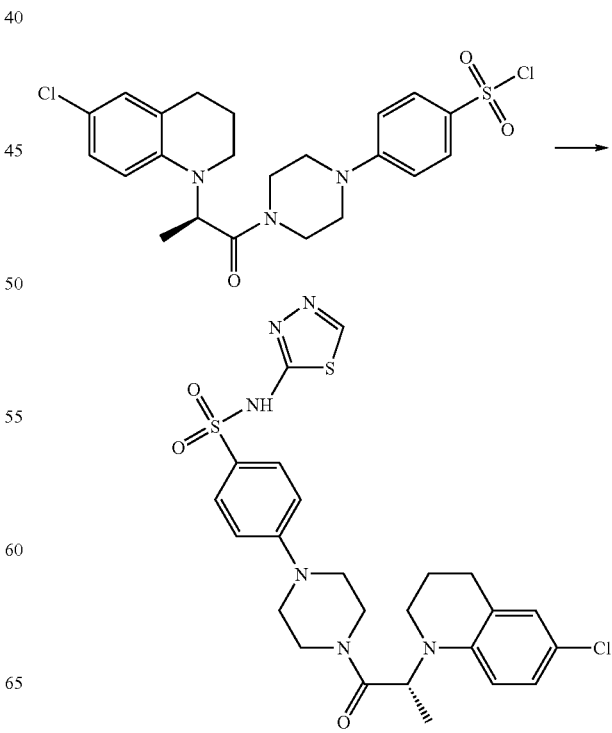

517

Synthesized according to general procedure 7: method A. LC/MS (10%-99% CH₃CN (0.035% TFA)/H₂O (0.05% TFA)), m/z: M+1 obs=547; $t_R$=3.09 min.

(R)-4-(4-(2-(6-Chloro-3,4-dihydroquinolin-1(2H)-yl)propanoyl)piperazin-1-yl)-N-(3-methylisothiazol-5-yl)benzenesulfonamide

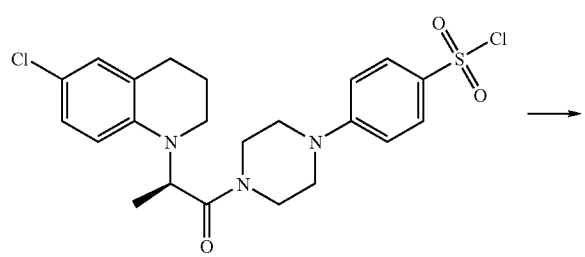

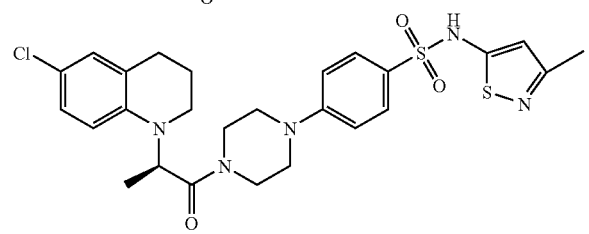

Synthesized according to general procedure 7: method A. LC/MS (10%-99% CH₃CN (0.035% TFA)/H₂O (0.05% TFA)), m/z: M+1 obs=560; $t_R$=3.31 min.

(R)-4-(4-(2-(6-Chloro-3,4-dihydroquinolin-1(2H)-yl)propanoyl)piperazin-1-yl)-N-(6-chloropyridazin-3-yl)benzenesulfonamide

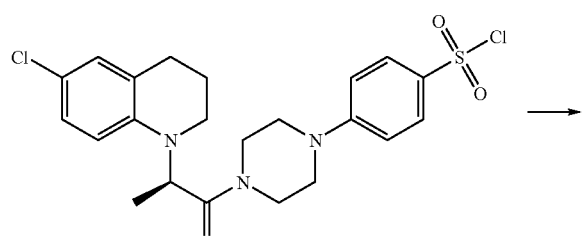

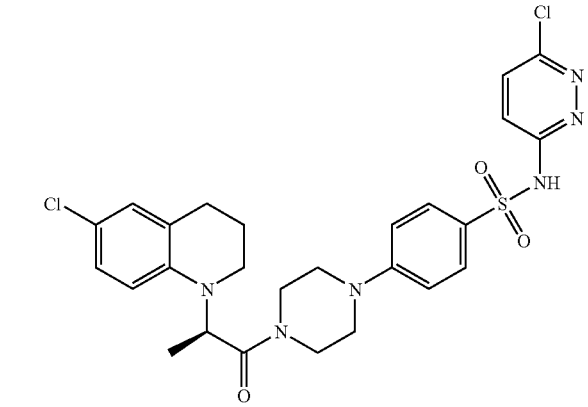

Synthesized according to general procedure: 7 method A. LC/MS (10%-99% CH₃CN (0.035% TFA)/H₂O (0.05% TFA)), m/z: M+1 obs=560; $t_R$=3.31 min.

518

(R)-4-(4-(2-(6-Chloro-3,4-dihydroquinolin-1(2H)-yl)propanoyl)piperazin-1-yl)-N-(6-chloropyrazin-2-yl)benzenesulfonamide

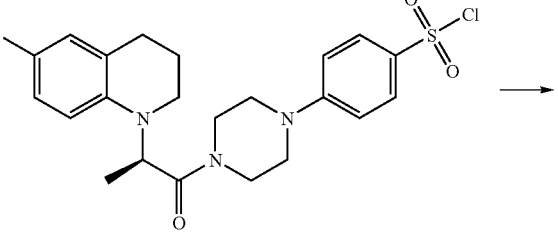

Synthesized according to general procedure: 7 method A. LC/MS (10%-99% CH₃CN (0.035% TFA)/H₂O (0.05% TFA)), m/z: M+1 obs=575.2; $t_R$=3.45 min.

(R)-4-(4-(2-(6-Chloro-3,4-dihydroquinolin-1(2H)-yl)propanoyl)piperazin-1-yl)-N-(2-methylpyrimidin-4-yl)

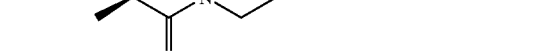

Synthesized according to general procedure 7: method B. LC/MS (10%-99% CH₃CN (0.035% TFA)/H₂O (0.05% TFA)), m/z: M+1 obs=555.3; $t_R$=2.49 min.

519

(R)-4-(4-(2-(6-Chloro-3,4-dihydroquinolin-1(2H)-yl)propanoyl)piperazin-1-yl)-N-(6-methylpyrimidin-4-yl)benzenesulfonamide

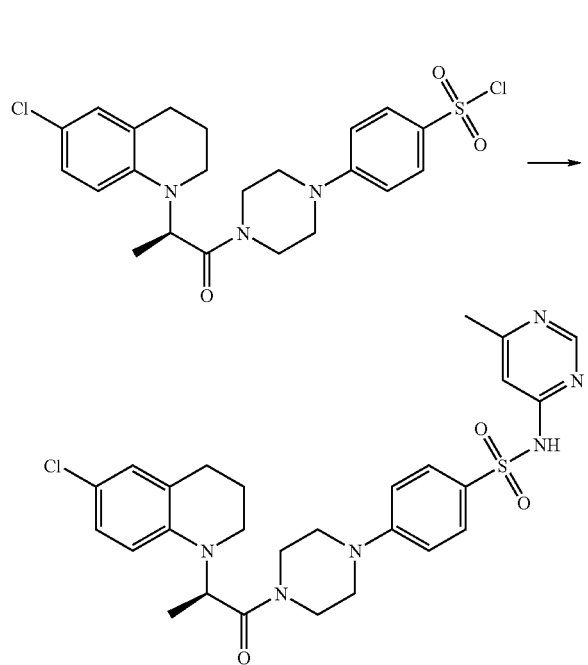

Synthesized according to general procedure 7: method B. LC/MS (10%-99% CH$_3$CN (0.035% TFA)/H$_2$O (0.05% TFA)), m/z: M+1 obs=555.3; t$_R$=2.57 min.

Example 2

General Procedure 8

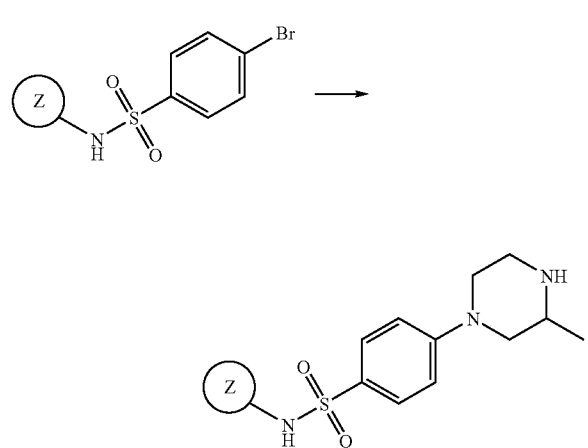

A mixture of 4-bromobenzenesulfonamide (1 equivalent), 2-methylpiperazine (1-10 equivalents), Pd$_2$(dba)$_3$ (0.02-0.075 equivalents), 2-(di-t-butylphosphino)biphenyl (0.08-0.2 equivalents), NaO-tBu (2-6 equivalents) and toluene (0.1-0.4 M of 4-bromobenzenesulfonamide) was heated at 80° C. for 2-6 h. Purification via silica gel chromatography using 10% MeOH in CH$_2$Cl$_2$ (with addition of 1-2% triethylamine) gave the desired product.

520

4-(3-Methylpiperazin-1-yl)-N-(thiazol-2-yl)benzenesulfonamide

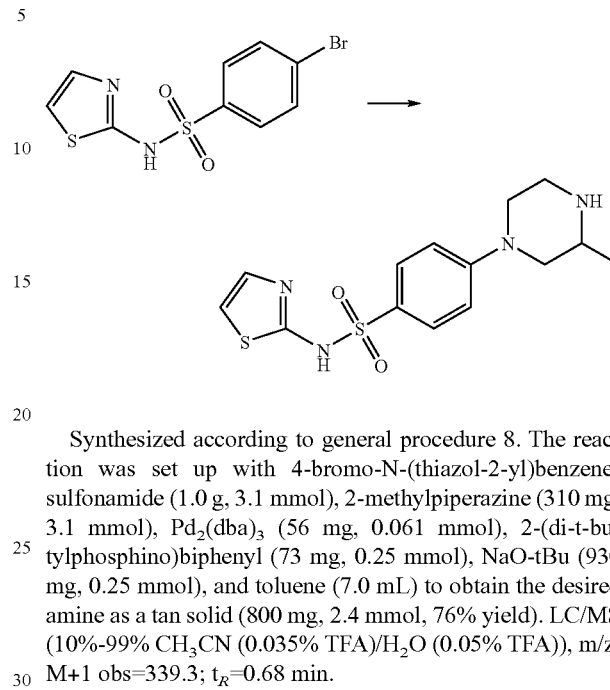

Synthesized according to general procedure 8. The reaction was set up with 4-bromo-N-(thiazol-2-yl)benzenesulfonamide (1.0 g, 3.1 mmol), 2-methylpiperazine (310 mg, 3.1 mmol), Pd$_2$(dba)$_3$ (56 mg, 0.061 mmol), 2-(di-t-butylphosphino)biphenyl (73 mg, 0.25 mmol), NaO-tBu (930 mg, 0.25 mmol), and toluene (7.0 mL) to obtain the desired amine as a tan solid (800 mg, 2.4 mmol, 76% yield). LC/MS (10%-99% CH$_3$CN (0.035% TFA)/H$_2$O (0.05% TFA)), m/z: M+1 obs=339.3; t$_R$=0.68 min.

4-(3-Methylpiperazin-1-yl)-N-(1,2,4-thiadiazol-5-yl)benzenesulfonamide

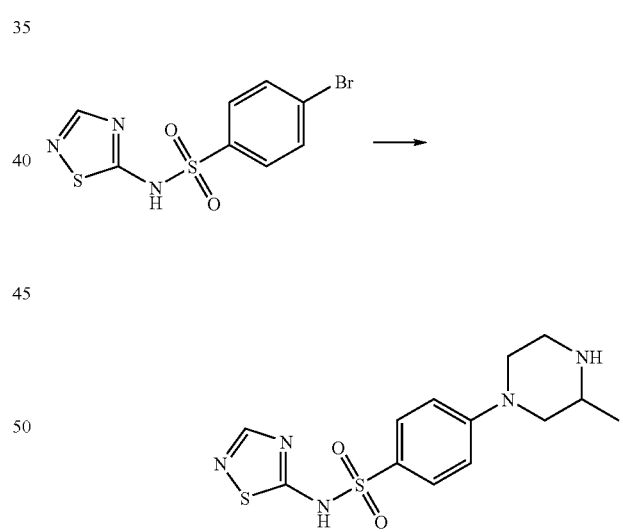

Synthesized according to general procedure 8. The reaction was set up with 4-bromo-N-(1,2,4-thiadiazol-5-yl)benzenesulfonamide (1.0 g, 3.1 mmol), 2-methylpiperazine (310 mg, 3.1 mmol, Pd$_2$(dba)$_3$ (56 mg, 0.061 mmol), 2-(di-t-butylphosphino)biphenyl (73 mg, 0.25 mmol), NaO-tBu (930 mg, 10 mmol), and toluene (7.0 mL). For the purification, 10% MeOH in CH$_2$Cl$_2$ with the addition of 2% triethylamine was used as a solvent system to obtain the desired amide as a tan solid (130 mg, 0.38 mmol, 12% yeild). LC/MS (10%-99% CH$_3$CN (0.035% TFA)/H$_2$O (0.05% TFA)), m/z: M+1 obs=340.3;

521
(R)-4-(3-Methylpiperazin-1-yl)-N-(1,2,4-thiadiazol-5-yl)benzenesulfonamide

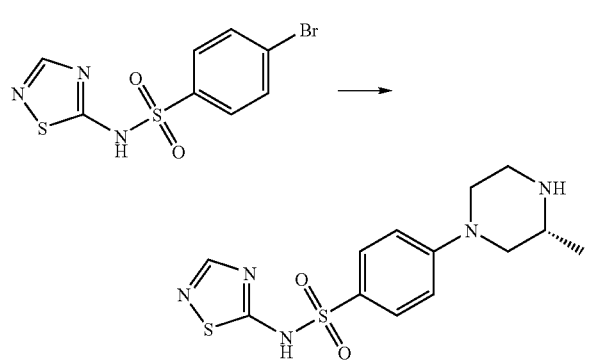

Synthesized according to general procedure 8. The reaction was set up with 4-bromo-N-(1,2,4-thiadiazol-5-yl)benzenesulfonamide (4.7 mmol), (R)-2-methylpiperazine (4.7 mmol), Pd$_2$(dba)$_3$ (0.12 mmol), 2-(di-t-butylphosphino)biphenyl (0.50 mmol), NaO-tBu (10 mmol), and toluene (12 mL). For the purification, 10% MeOH in CH$_2$Cl$_2$ with the addition of 1% triethylamine was used as a solvent system to obtain the desired amine as a white solid (300 mg, 19% yield). LC/MS (10%-99% CH$_3$CN (0.035% TFA)/H$_2$O (0.05% TFA)), m/z: M+1 obs=340.2; t$_R$=1.56 min.

(S)-4-(3-Methylpiperazin-1-yl)-N-(1,2,4-thiadiazol-5-yl)benzenesulfonamide

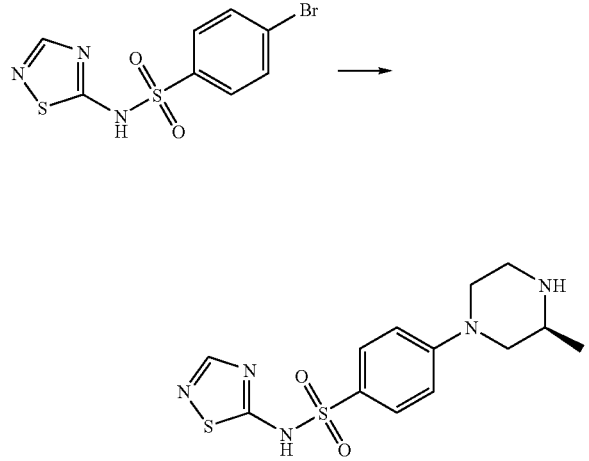

Synthesized according to general procedure 8. The reaction was set up with 4-bromo-N-(1,2,4-thiadiazol-5-yl)benzenesulfonamide (4.7 mmol), (S)-2-methylpiperazine (4.7 mmol), Pd$_2$(dba)$_3$ (0.12 mmol) 2-(di-t-butylphosphino)biphenyl (0.50 mmol), NaO-tBu (10 mmol), and toluene (12 mL). For the purification, 10% MeOH in CH$_2$Cl$_2$ with the addition of 1% tri ethylamine was used as a solvent system to obtain the desired amine as a white solid (300 mg, 19% yield). LC/MS (10%-99% CH$_3$CN (0.035% TFA)/H$_2$O (0.05% TFA)), m/z: M+1 obs=340.2; t$_R$=1.40 min.

522
(R)-4-(3-Methylpiperazin-1-yl)-N-(pyrimidin-4-yl)benzenesulfonamide

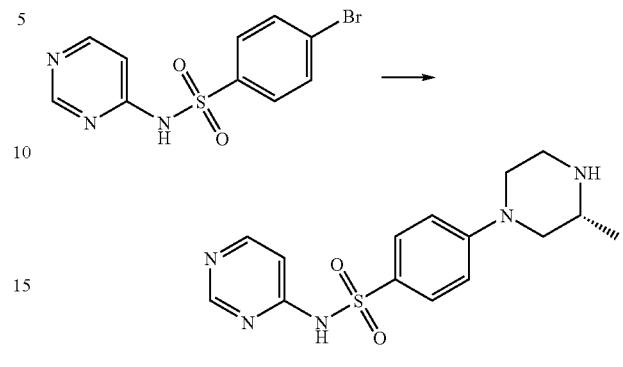

Synthesized according to general procedure 8. The reaction was set up with 4-bromo-N-(pyrimidin-4-yl)benzenesulfonamide (2.4 mmol), (R)-2-methylpiperazine (4.7 mmol), Pd(dba)$_3$ (0.12 mmol) 2-(di-t-butylphosphino)biphenyl (0.50 mmol), NaO-tBu (10 mmol), and toluene (12 mL). For the purification, 10% MeOH in CH$_2$Cl$_2$ with the addition of 1% triethylamine was used as a solvent system to obtain the desired amine as a white solid. (900 mg, 100% yield). LC/MS (10%/99% CH$_3$CN (0.035% TFA)/H$_2$O (0.05% TFA)), m/z: M+1 obs=334.3; t$_R$=0.4 min.

(S)-4-(3-Methylpiperazin-1-yl)-N-(pyrimidin-4-yl)benzenesulfonamide

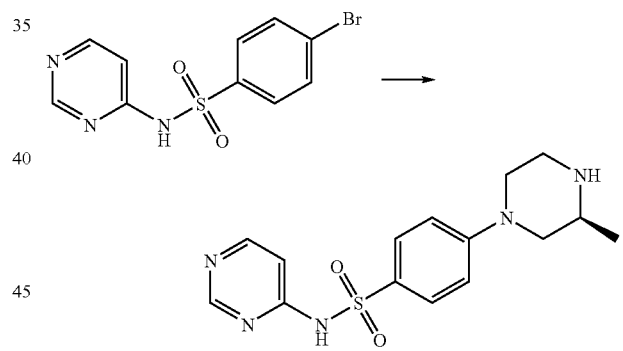

Synthesized according to general procedure 8. The reaction was set up with 4-bromo-N-(pyrimidin-4-yl)benzenesulfonamide (2.4 mmol), (S)-2-methylpiperazine (4.7 mmol), Pd$_2$(dba)$_3$ (0.12 mmol), 2-(di-t-butylphosphino)biphenyl (0.50 mmol), NaO-tBu (10 mmol), and toluene (12 mL). For the purification, 10% MeOH in CH$_2$Cl$_2$ with the addition of 1% triethylamine was used as a solvent system to obtain the desired amine as a white solid (300 mg, 38% yield). LC/MS (10%-99% CH$_3$CN (0.035% TFA)/H$_2$O (0.05% TFA)), m/z: M+1 obs=334.3; t$_R$=0.39 min.

General Procedure 9, Method A

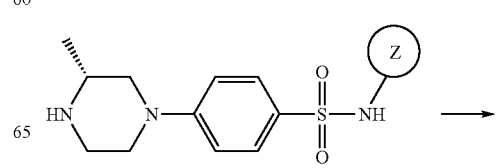

-continued

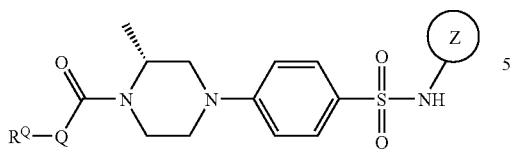

A mixture of methylpiperazine (1.0 equivalent), carboxylic acid (1.0 equivalent), BOP reagent (1.0 equivalent), triethylamine (1.0 equivalent), and DMF (0.5-1.0 M of 4-methylpiperazine) was stirred at 25° C. for 2-6 h. Purification via silica gel chromatography using 5% MeOH in $CH_2Cl_2$ gave the desired product.

General Procedure 9, Method B

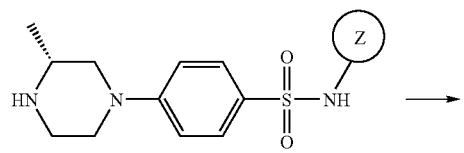

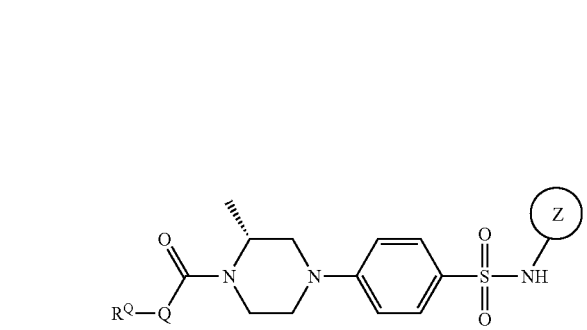

A mixture of methylpiperazine (1.0 equivalent), carboxylic acid (1.0 equivalent), HATU reagent (1.0 equivalent), sodium bicarbonate (1.5 equivalents), and DMF/$CH_2Cl_2$-1/1 (0.5-1.0 M of 4-methylpiperazine) was stirred at 25° C. for 19 h. Purification via silica gel chromatography using 10% MeOH in $CH_2Cl_2$ gave the desired product.

(S)-4-(4-(2-(5-fluoro-1H-indol-1-yl)acetyl)-3-methylpiperazin-1-yl)-N-(thiazol-2-yl)benzenesulfonamide

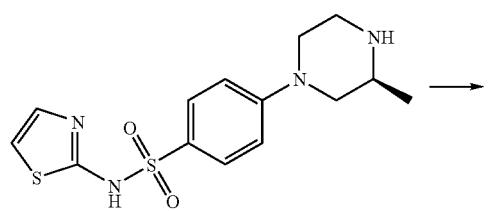

-continued

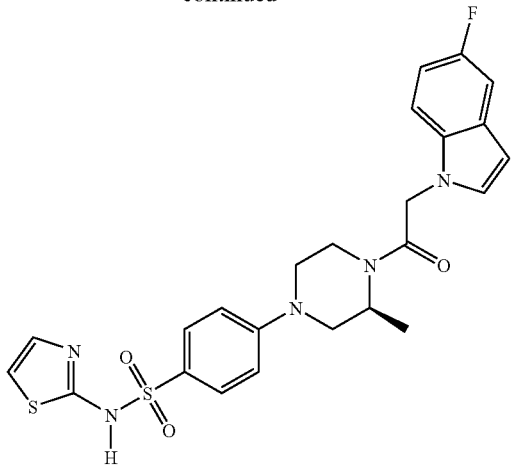

Synthesized according to general procedure 9, method B. The reaction was set up with (S)-4-(3-methylpiperazin-1-yl)-N-(thiazol-2-yl)benzenesulfonamide (250 mg, 0.74 mmol), 2-(5-fluoro-1H-indol-1-yl)acetic acid (143 mg, 0.74 mmol), HATU reagent (281 mg, 0.74 mmol), sodium bicarbonate (93 mg, 1.11 mmol), and DMF/$CH_2Cl_2$-1/1 (4.0 mL) to obtain the desired amide as a white solid (200 mg, 0.39 mmol, 53% yield). $^1$H NMR (400 MHz, DMSO-d6) δ (mixture of rotamers) 7.63-7.59 (m, 2H), 7.35 (s, 1H), 7.30 (dd, J=2.5, 9.9 Hz, 2H), 7.21 (d, J=4.6 Hz, 1H), 7.00 (s, 1H), 6.95 (td, J=9.2, 3.9 Hz, 2H), 6.76 (d, J=4.5 Hz, 1H), 6.43 (d, J=3.0 Hz, 1H), 5.41-5.04 (m, 2H), 4.52 (s, 1/2H), 4.38 (s, 1/2H), 4.21-4.05 (m, 1/2H), 3.93-3.82 (m, 1/2H), 3.81-3.48 (m, 3H), 1.33 (s, 1.5H), 1.14 (s, 1.5H). LC/MS (10%-99% $CH_3CN$ (0.035% TFA)/$H_2O$ (0.05% TFA), m/z: M+1 obs=514.5; $t_R$=3.07 min.

4-(4-((R)-2-(1H-Indol-1-yl)propanoyl)-3-methylpiperazin-1-yl)-N-(thiazol-2-yl)benzenesulfonamide

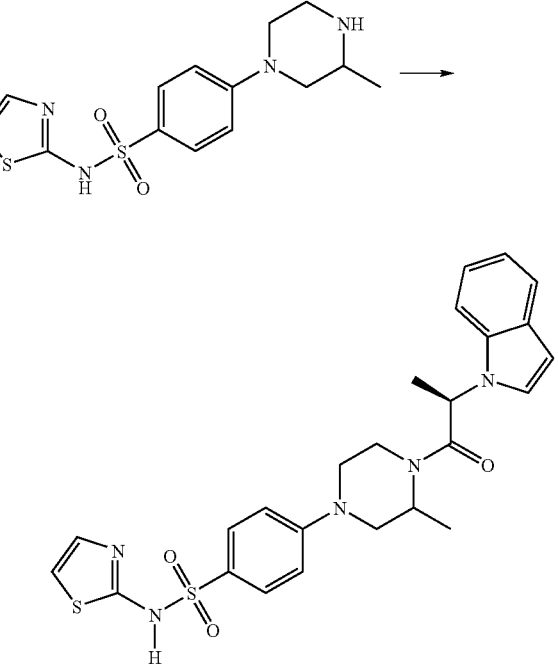

525

Synthesized according to general procedure 9, method A. The reaction was set up with 0.1 mmol 4-(3-methylpiperazin-1-yl)-N-(thiazol-2-yl)benzenesulfonamide, 0.1 µmol 2-(5-fluoro-1H-indol-1-yl)acetic acid, 0.1 µmol BOP reagent, 0.1 mmol triethylamine and DMF (300 µL). LC/MS (100%-99% CH$_3$CN (0.035% TFA)/H$_2$O (0.05% TFA)), m/z: M+1 obs=510.4; t$_R$=3.08 min.

4-(4-(3-(5-Chloro-1H-indol-1-yl)propanoyl)-3-methylpiperazin-1-yl)-N-(1,2,4-thiadiazol-5-yl)benzenesulfonamide

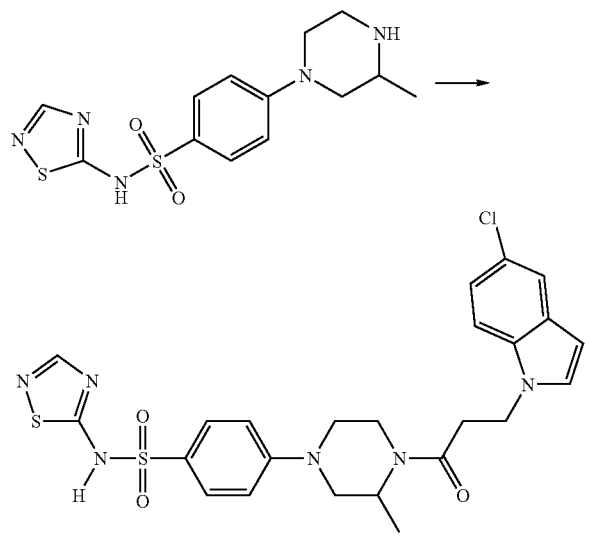

Synthesized according to general procedure 9, method A. The reaction was set up with 0.1 mmol 4-(3-methylpiperazin-1-yl)-N-(1,2,4-thiadiazol-5-yl)benzenesulfonamide, 0.1 mmol 3-(5-chloro-1H-indol-1-yl)propanoic acid, 0.1 mmol BOP reagent, 0.1 mmol triethylamine and DMF (300 µL). LC/MS (10%-99% CH$_3$CN (0.035% TFA)/H$_2$O (0.05% TFA)), m/z: M+1 obs=545.5; t$_R$=3.26 min.

(R)-4-(4-(2-(7-Chloro-1H-indol-1-yl)acetyl)-3-methylpiperazin-1-yl)-N-(1,2,4-thiadiazol-5-yl)benzenesulfonamide

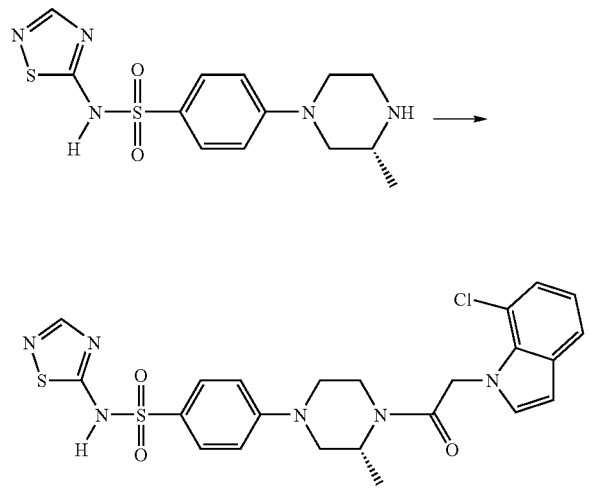

526

Synthesized according to general procedure 9, method B. The reaction was set up with (R)-4-(3-methylpiperazin-1-yl)-N-(1,2,4-thiadiazol-5-yl)benzenesulfonamide (400 mg, 1.2 mmol), 2-(7-chloro-1H-indol-1-yl)acetic acid (250 mg, 0.15 mmol), HATU reagent (390 mg, 0.15 mmol), sodium bicarbonate (151 mg, 1.8 mmol), and DMF/CH$_2$Cl$_2$-1/1 (1.0 mL) to obtain the desired amide as a white solid (230 mg, 36% yield). LC/MS (10%-99% CH$_3$CN (0.035% TFA)/H$_2$O (0.05% TFA)), m/z: M+1 obs=531.0; t$_R$=3.21 min.

(S)-4-(4-(3-(5-Chloro-1H-indol-1-yl)propanoyl)-3-methylpiperazin-1-yl)-N-(1,2,4-thiadiazol-5-yl)benzenesulfonamide

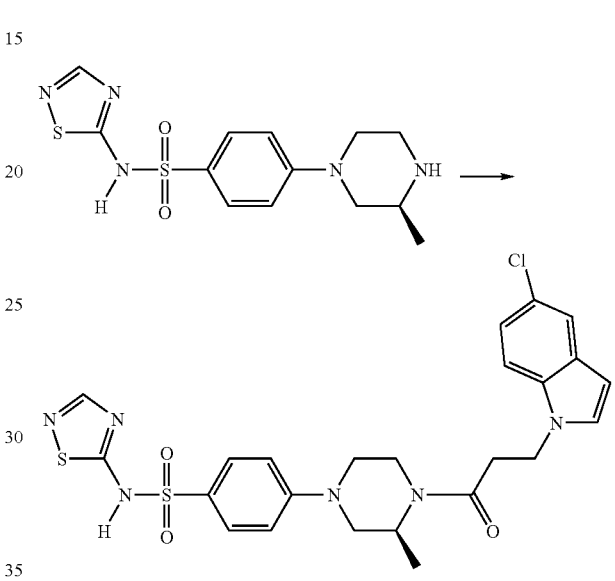

Synthesized according to general procedure 9, method A. The reaction was set up with 0.1 mmol (S)-4-(3-methylpiperazin-1-yl)-N-(1,2,4-thiadiazol-5-yl)benzenesulfonamide, 0.15 mmol 3-(5-chloro-1H-indol-1-yl)propanoic acid, 0.15 mmol BOP reagent, 0.15 mmol triethylamine and DMF (300 µL). LC/MS (10%-99% CH$_3$CN (0.035% TFA)/H$_2$O (0.05% TFA)), m/z: M+1 obs=545.0; t$_R$=3.25 min.

4-(4-(2-(6-chloro-1H-indol-1-yl)acetyl)-3-methylpiperazin-1-yl)-N-(1,2,4-thiadiazol-5-yl)benzenesulfonamide

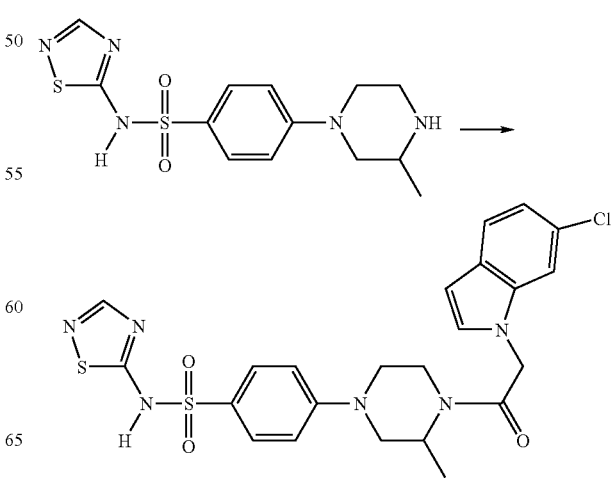

527

Synthesized according to general procedure 9, method A. The reaction was set up with 4-(3-methylpiperazin-1-yl)-N-(1,2,4-thiadiazol-5-yl)benzenesulfonamide (35 mg, 0.10 mmol) 2-(6-chloro-1H-indol-1-yl)acetic acid (23 mg, 0.10 mmol), BOP reagent (46 mg, 0.10 mmol), triethylamine (14 μL, 0.10 mmol), and DMF (300 μL). LC/MS (10%-99% $CH_3CN$ (0.035% TFA)/$H_2O$ (0.05% TFA)), m/z: M+1 obs=545.0; $t_R$=3.25 min.

4-(4-(3-(5-chloro-1H-indol-1-yl)propanoyl)-3-methylpiperazin-1-yl)-N-(1,2,4-thiadiazol-5-yl)benzenesulfonamide

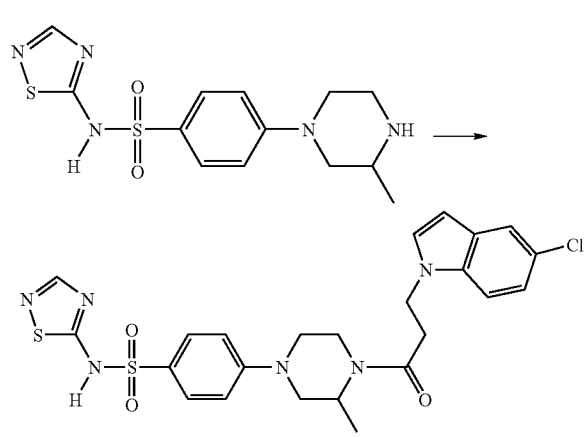

Synthesized according to general procedure 9, method A. The reaction was set up with 4-(3-methylpiperazin-1-yl)-N-(1,2,4-thiadiazol-5-yl)benzenesulfonamide, (35 mg, 0.10 mmol) 3-(5-chloro-1H-indol-1-yl)propanoic acid (25 mg, 0.10 mmol), BOP reagent (46 mg, 0.10 mmol), triethylamine (14 μL, 0.10 mmol), and DMF (300 μL). LC/MS (10%-99% $CH_3CN$ (0.035% TFA)/$H_2O$ (0.05% TFA)), m/z: M+1 obs=545.0; $t_R$=3.25 min.

(R)-4-(4-(3-(7-chloro-1H-indol-1-yl)propanoyl)-3-methylpiperazin-1-yl)-N-(pyrimidin-4-yl)benzenesulfonamide

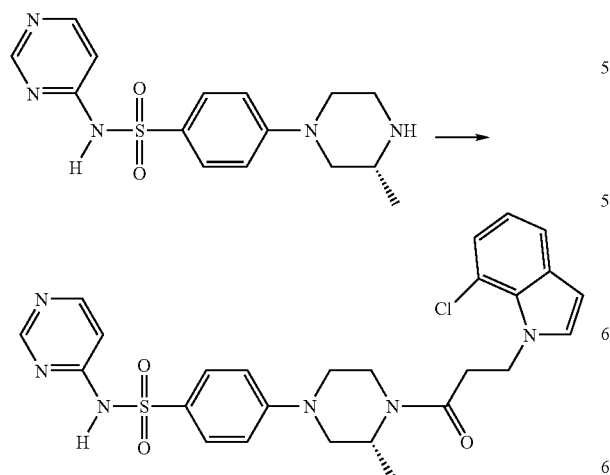

528

Synthesized according to general procedure 9, method A. The reaction was set up with 0.1 mmol (R)-4-(3-methylpiperazin-1-yl)-N-(pyrimidin-4-yl)benzenesulfonamide, 0.15 mmol 3-(7-chloro-1H-indol-1-yl)propanoic acid, 0.15 mmol BOP reagent, 0.15 mmol triethylamine and DMF (300 μL). LC/MS (10%/99% $CH_3CN$ (0.035% TFA)/$H_2O$ (0.05% TFA)), m/z: M+1 obs=539.5; $t_R$=2.89 min.

(S)-4-(4-(2-(6-Chloro-3,4-dihydroquinolin-1(2H)-yl) acetyl)-3-methylpiperazin-1-yl)-N-(pyrimidin-4-yl) benzenesulfonamide

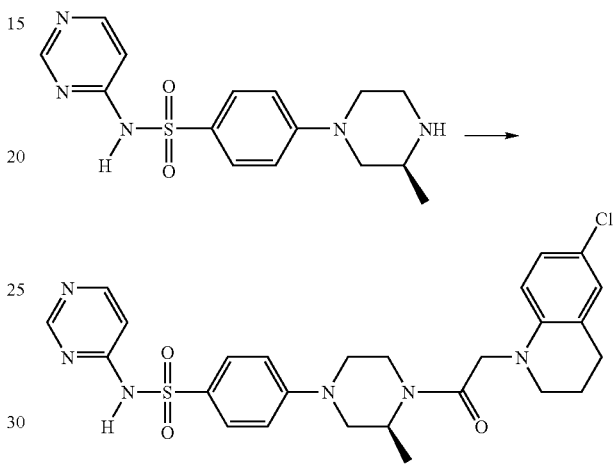

Synthesized according to general procedure 9, method A. The reaction was set up with 0.1 mmol (S)-4-(3-methylpiperazin-1-yl)-N-(pyrimidin-4-yl)benzenesulfonamide, 0.15 mmol 2-(6-chloro-3,4-dihydroquinolin-1(2H)-yl)acetic acid, 0.15 mmol BOP reagent, 0.15 mmol triethylamine and DMF (300 μL). LC/MS (10%-99% $CH_3CN$ (0.035% TFA)/$H_2O$ (0.05% TFA)), m/z: M+1 obs=541.5; $t_R$=2.96 min.

Example 3

(R)-tert-Butyl-3-(O-tert-butyldiphenylsilane)methyl-piperazine-1-carboxylate

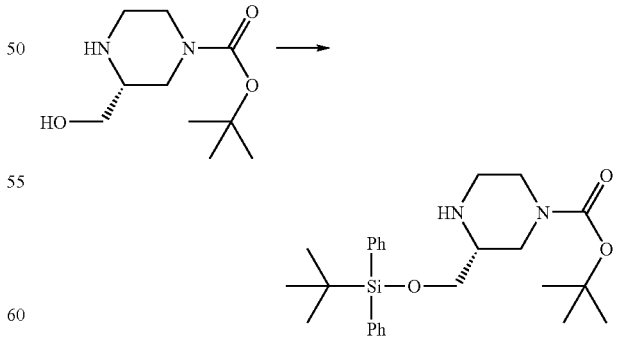

A mixture of (R)-tert-butyl-3-(hydroxymethyl)piperazine-1-carboxylate (1 g, 4.62 mmol) and imidazole (0.629 g, 9.24 mmol) was dissolved in $CH_2Cl_2$ (10 mL). Tert-butylchlorodiphenylsilane (1.18 mL, 5.08 mmol) was added dropwise over 10 minutes. Upon completion of addition, the mixture was stirred at RT for 3 hours. The reaction mixture was diluted with 50 mL of $CH_2Cl_2$ and washed with saturated aqueous sodium bicarbonate (3×20 mL), brine (2×20 mL), dried over magnesium sulfate, and concentrated. Purification via silica gel chromatography using 2-10% methanol in $CH_2Cl_2$ gave (R)-tert-butyl-3-(O-tert-butyldiphenylsilane)methyl-piperazine-1-carboxylate as a white solid (1.7 g, 81%). $^1$H NMR (400 MHz, DMSO-d6) δ 7.63-7.61 (m, 5H), 7.48-7.45 (m, 5H), 4.13-3.44 (m, 5H), 2.80 (d, J=11.8 Hz, 2H), 2.66 (d, J=5.7 Hz, 2H), 1.40 (s, 9H), 1.01 (s, 9H). LC/MS (10%-99% $CH_3CN$ (0.035% TFA)/$H_2O$ (0.05% TFA)), m/z: M+1 obs=455.5; $t_R$=3.05 min.

(R)-2-(O-tert-butyldiphenylsilane)methyl-piperazine dihydrochloride

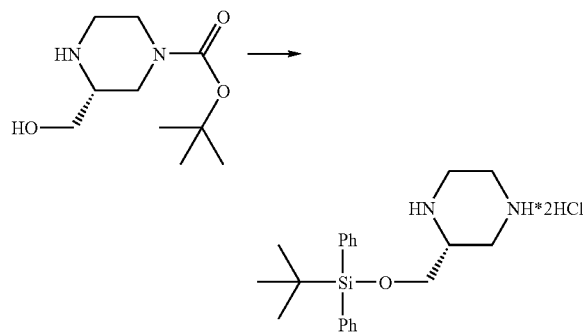

Under $N_2$ atmosphere, a solution of (R)-tert-butyl-3-(O-tert-butyldiphenylsilane)methyl-piperazine-1-carboxylate (1.7 g, 3.74 mmol) in a solution of HCl in 1,4-dioxane (4 M, 60 mL) was stirred at RT for 16 h. The formed precipitate was filtered off and washed with 1,4-dioxane (20 mL) to give 2-(O-tert-butyldiphenylsilane)methyl-piparizine dihydrochloride (1.4 g, 88%). LC/MS (10%-99% $CH_3CN$ (0.035% TFA)/$H_2O$ (0.05% TFA)), m/z: M+1 obs=355.5; $t_R$=2.42 min.

General Procedure 10

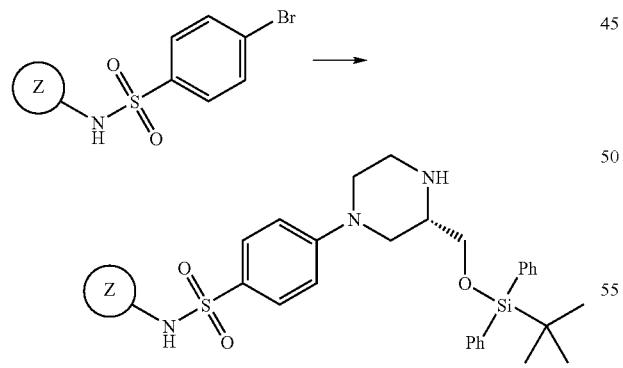

A mixture of 4-bromobenzenesulfonamide (1 equivalent), piperazine (1-10 equivalents), $Pd_2(dba)_3$ (0.02-0.075 equivalents), 2-(di-t-butylphosphino) biphenyl (0.08-0.2 equivalents), NaO-tBu (2-6 equivalents) and toluene (0.1-0.4 M of 4-bromobenzenesulfonamide) was heated at 80° C. for 1-6 h. Purification via silica gel chromatography using 10% MeOH in $CH_2Cl_2$ (with addition of 1-2% triethylamine) gave the desired product.

4-((R)-2-O-tert-butyldiphenylsilane)methyl-piperazine-N-(thiazol-2-yl)benzenesulfonamide

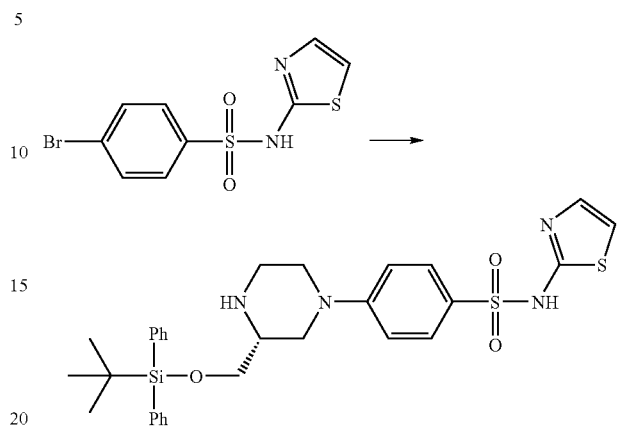

Prepared using general procedure 10. A mixture of (R)-2-(O-tert-butyldiphenylsilane)methyl-piperazine-dihydrochloride (1 g, 2.33 mmol), 4-bromo-N-(thiazol-2-yl)benzenesulfonamide (0.74 g, 2.33 mmol), $Pd_2(dba)_3$ (426 mg, 0.466 mmol), 4,5-bis(diphenyl)phosphino-9,9-dimethyl xanthene (270 mg, 0.466 mmol), NaO-tBu (1.34 g, 13.98 mmol) was purged with $N_2$ (3 times). 1,4-Dioxane (20 mL) was added to the above mixture under $N_2$. The reaction was stirred at 80° C. for 1 h, cooled and filtered over Celite. The filtrate was concentrated. Purification via silica gel chromatography using 2-10% methanol in $CH_2Cl_2$ gave 4-((R)-3-(O-tert-butyldiphenylsilane)methyl-piperazine-N-(thiazol-2-yl)benzenesulfonamide as a white solid (0.85 g, 64%). LC/MS (10%-99% $CH_3CN$ (0.035% TFA)/$H_2O$ (0.05% TFA)), m/z: M+1 obs=593.4; $t_R$=2.97 min.

General Procedure 11

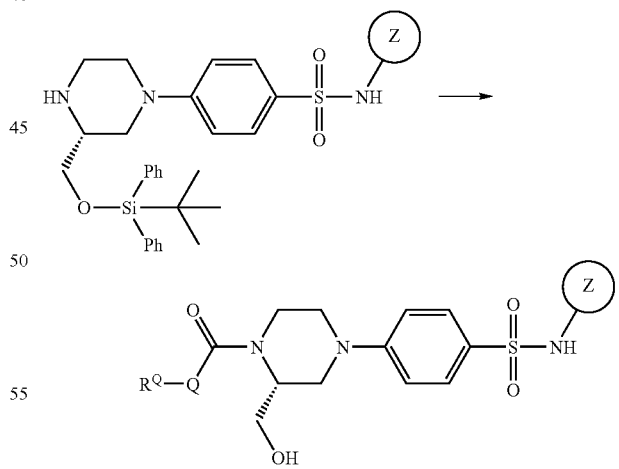

To the carboxylic acid (1.2 equivalent, 0.17 mmol) and $NaHCO_3$ (2 equivalent, 0.22 mmol) was added HATU (1.2 equivalent, 0.17 mmol) in DMF (0.15-0.25M, 0.25 mL). A solution of the amine (1 equivalent, 0.11 mmol) in DMF (0.15-0.25M, 0.25 mL) was then added and the reaction mixture was stirred at RT for 19 h. The reaction mixture was diluted with 5 mL of ethyl acetate and washed with water (3×5 mL), saturated aqueous sodium bicarbonate (3×5 mL) and

(S)-2-(2,3-Dichlorophenoxy)-1-((R)-2-(hydroxymethyl)-4-(4-N-(thiazol-2-yl)benzenesulfonamide) piperazin-1-yl)propan-1-one

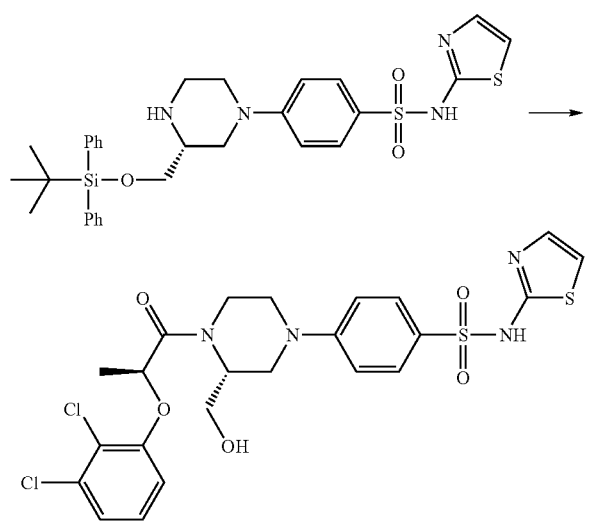

Prepared using general procedure 11. A solution of (S)-2-(2,3-dichlorophenoxy) propanoic acid (285.3 mg, 1.21 mmol) and HATU (456 mg, 1.21 mmol) in DMF (10 mL) was stirred under an $N_2$ atmosphere at 0° C. for 1 h. To this mixture, 4-((R)-2-O-tert-butyldiphenylsilane)methyl-piperazine-N-(thiazol-2-yl)benzenesulfonamide (600 mg, 1.0 mmol) and $NaHCO_3$ (201 mg, 2.4 mmol) were added under an $N_2$ atmosphere at RT, and the reaction was stirred for 16 h. The reaction mixture was diluted with ethyl acetate (30 mL), washed with water (3×50 mL), saturated aqueous sodium bicarbonate (3×50 mL) and with brine (2×50 mL). The organic layer was dried over magnesium sulfate, filtered, and concentrated. Purification via silica gel chromatography using 20-100% ethyl acetate in hexane gave crude (S)-2-(2,3-dichlorophenoxy)-1-((R)-2-(O-tert-butyldiphenylsilane)-4-(4-N-(thiazol-2-yl)benzenesulfonamide)piperazin-1-yl)propan-1-one (2.0 g). The crude material was dissolved in THF (5 mL) and cooled to 0° C. To this was added a solution of 1 M TBAF in THF (5 mL, 5 mmol). The reaction mixture was stirred at RT for 4 h, concentrated and purified via silica gel chromatography using 5% methanol in $CH_2Cl_2$ to give (S)-2-(2,3-Dichlorophenoxy)-1-((R)-2-(hydroxymethyl)-4-(4-N-(thiazol-2-yl)benzenesulfonamide)piperazin-1-yl)propan-1-one (200 mg, 34%). LC/MS (10%-99% $CH_3CN$ (0.035% TFA)/$H_2O$ (0.05% TFA)), m/z: M+1 obs=571.2; $t_R$=2.95 min. $^1$H NMR (400 MHz, DMSO-d6) δ 7.61 (d, J=9.0 Hz, 2H), 7.28-7.18 (m, 3H), 7.01-6.95 (m, 2H), 6.88-6.87 (m, 1H), 6.78 (d, J=4.5 Hz, 1H), 5.54-4.93 (m, 2H), 4.39-3.49 (m, 6H), 3.02-2.86 (m, 2H), 1.52 (d, J=6.4 Hz, 3H).

4-((R)-4-(R)-2-(6-Chloro-3,4-dihydroquinolin-1(2H)-yl)propanoyl)-3-(hydroxymethyl)piperazin-1-yl)-N-(thiazol-2-yl)benzenesulfonamide

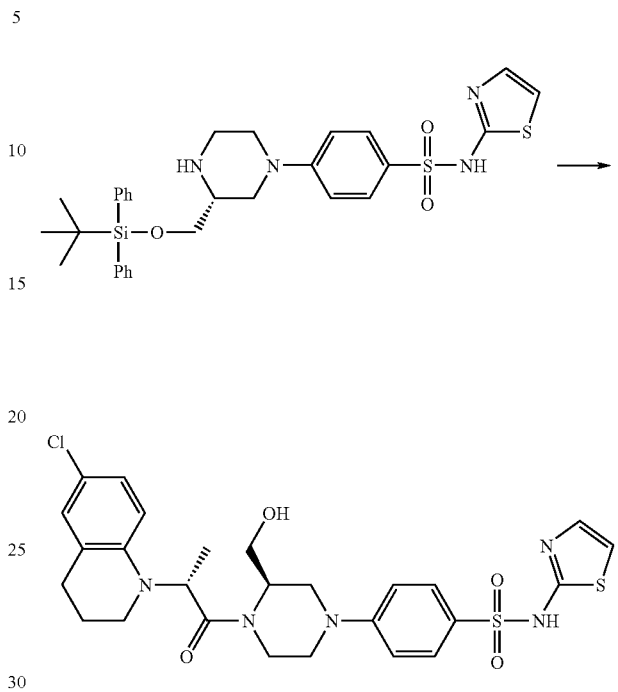

Prepared using general procedure 11. A solution of (R)-2-(6-chloro-3,4-dihydroquinolin-1-(2H)-yl)propanoic acid (483 mg, 2.01 mmol) and HATU (763 mg, 2.01 mmol) in DMF (5 mL) was stirred under an $N_2$ atmosphere at 0° C. for 1 h. To this mixture, 4-((R)-2-O-tert-butyldiphenylsilane)methyl-piperazine-N-(thiazol-2-yl)benzenesulfonamide (1000 mg, 1.68 mmol) and $NaHCO_3$ (282 mg, 3.36 mmol) were added under an $N_2$ atmosphere at RT, and the reaction was stirred for 16 hr. The reaction mixture was diluted with ethyl acetate (30 mL), washed with water (3×50 mL), saturated aqueous sodium bicarbonate (3×50 mL) and with brine (2×50 mL). The organic layer was dried over magnesium sulfate, filtered, and concentrated. Purification via silica gel chromatography using 20-100% ethyl acetate in hexane gave crude 4-((R)-4-(R)-2-(6-chloro-3,4-dihydroquinolin-1(2H)-yl)propanoyl)-3-(O-tert-butyldiphenylsilane)methyl-piperazine)-N-(thiazol-2-yl)benzenesulfonamide (1.0 g, 74%). The crude material was dissolved in THF (5 mL) and cooled to 0° C. To this was added a solution of 1 M TBAF in THF (2 mL, 2 mmol). The reaction mixture was stirred at RT for 4 h, concentrated and purified via silica gel chromatography using 5% methanol in $CH_2Cl_2$ to give 4-((R)-4-(R)-2-(6-chloro-3,4-dihydroquinolin-1(2H)-yl)propanoyl)-3-(hydroxymethyl)piperazin-1-yl)-N-(thiazol-2-yl)benzenesulfonamide (400 mg, 41% over 2 steps). LC/MS (10%-99% $CH_3CN$ (0.035% TFA)/$H_2O$ (0.05% TFA)), m/z: M+1 obs=576.13; $t_R$=3.14 min. $^1$H NMR (400 MHz, DMSO-d6) δ 7.58 (d, J=11.5 Hz, 2H), 7.21 (d, J=7.8 Hz, 1H), 7.03-6.92 (m, 4H), 6.78-6.76 (m, 2H), 5.00-4.79 (m, 2H), 4.43 (d, J=2.9 Hz, 1H), 4.06-3.38 (m, 5H), 3.20-2.59 (m, 6H), 1.87-1.72 (m, 2H), 1.24 (s, 3H).

4-((R)-4-((S)-2-(6-Chloro-1H-indol-1-yl)propanoyl)-3-(hydroxymethyl)piperazin-1-yl)-N-(thiazol-2-yl)benzenesulfonamide

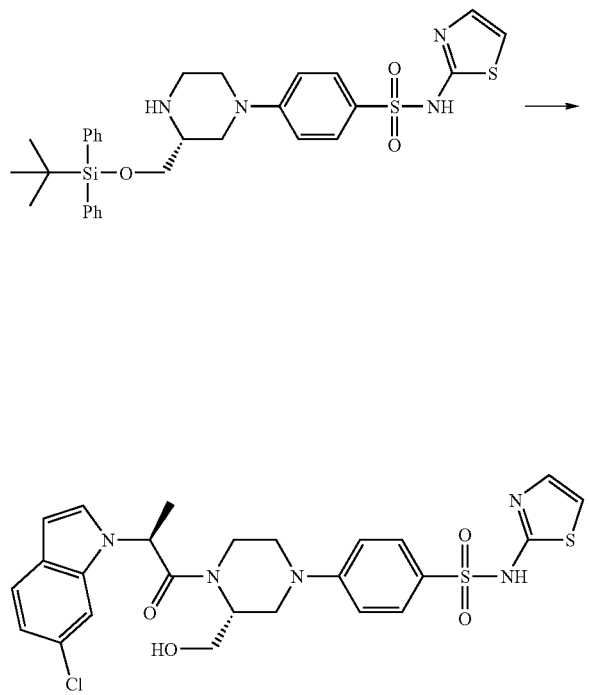

Prepared using general procedure 11. A solution of (S)-2-(6-chloro-1H-indol-1-yl) propanoic acid (207.3 mg, 0.93 mmol) and HATU (353.9 mg, 0.93 mmol) in DMF (5 mL) was stirred under an N$_2$ atmosphere at 0° C. for 1 h. To this mixture, 4-((R)-2-O-tert-butyldiphenylsilane)methyl-piperazine-N-(thiazol-2-yl)benzenesulfonamide (460 mg, 0.77 mmol) and NaHCO$_3$ (141 mg, 1.68 mmol) were added under an N$_2$ atmosphere at RT, and the reaction was stirred for 16 h. The reaction mixture was diluted with ethyl acetate (30 mL), washed with water (3×50 mL), saturated aqueous sodium bicarbonate (3×50 mL) and with brine (2×50 mL). The organic layer was dried over magnesium sulfate, filtered, and concentrated. Purification via silica gel chromatography using 20-100% ethyl acetate in hexane gave crude 4-((R)-4-(S)-2-(6-chloro-1H-indol-1-yl) propanoyl)-3-(O-tert-butyldiphenylsilane)methyl-piperazine)-N-(thiazol-2-yl)benzenesulfonamide (0.32 g, 51%). The crude material was dissolved in THF (5 mL) and cooled to 0° C. To this was added a solution of 1 M TBAF in THF (1 mL, 1 mmol). The reaction mixture was stirred at RT for 4 h, concentrated and purified via silica gel chromatography using 5% methanol in CH$_2$Cl$_2$ to give 4-((R)-4-((S)-2-(6-chloro-1H-indol-1-yl)propanoyl)-3-(hydroxymethyl)piperazin-1-yl)-N-(thiazol-2-yl)benzene-sulfonamide (120 mg, 50% over 2 steps). LC/MS (10%-99% CH$_3$CN (0.035% TFA)/H$_2$O (0.05% TFA)), m/z: M+1 obs=560.2; $t_R$=3.02 min. $^1$H NMR (400 MHz, DMSO-d6) δ 7.66 (s, 1H), 7.57 (t, J=9.7 Hz, 3H), 7.44-7.39 (m, 1H), 7.21 (d, J=4.6 Hz, 1H), 7.07-7.03 (m, 1H), 6.93 (dd, J=16.4, 9.0 Hz, 2H), 6.76 (d, J=4.6 Hz, 1H), 6.51 (t, J=3.4 Hz, 1H), 5.85-5.80 (m, 1H), 5.16 (t, J=5.5 Hz, 1H), 4.95 (t, J=5.2 Hz, 1H), 4.50 (s, 1H), 4.31 (d, J=14.4 Hz, 1H), 4.05-3.37 (m, 3H), 3.03-2.90 (m, 2H), 1.57-1.51 (m, 3H).

Example 4

4-Benzyl-1-phenylpiperazin-2-one

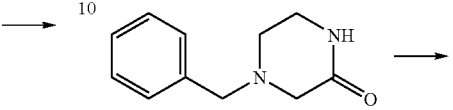

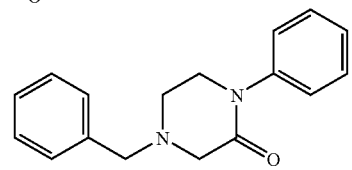

To a 25 mL microwave vessel was added 4-bromobenzene (6.1 g, 39.0 mmol), 4-benzylpiperazin-2-one (5.0 g, 36.3 mmol), potassium carbonate (3.6 g, 26.3 mmol), and copper (I) iodide (500 mg, 2.6 mmol). The reaction vessel was sealed and purged with nitrogen. Anhydrous NMP (8.0 mL) was added via syringe. The vessel was heated via microwave at 220° C. for 40 minutes. The mixture was filtered through a bed of celite followed by CH$_2$Cl$_2$ (20 mL). The filtrate was purified via silica gel chromatography using 2% MeOH in CH$_2$Cl$_2$ to obtain the desired piperazinone as a white solid (3.4 g, 12.7 mmol, 50% yield). $^1$H NMR (400 MHz, CDCl$_3$) δ 7.42-7.24 (m, 10H), 3.69 (t, J=5.4 Hz, 1H), 3.63 (s, 1H), 3.40-3.31 (m, 2H), 2.84 (s, 1H), 2.81 (t, J=5.2 Hz, 1H). LC/MS (10%-99% CH$_3$CN (0.035% TFA)/H$_2$O (0.05% TFA)), m/z: M+1 obs=267.3; $t_R$=1.63 min.

1-Phenylpiperazin-2-one

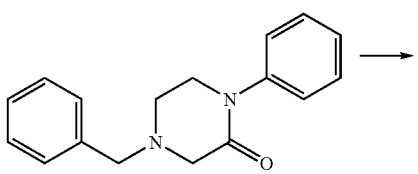

A mixture of 4-benzyl-1-phenylpiperazin-2-one (13.0 g, 48.8 mmol), 10% palladium on carbon (700 mg), and acetic acid (150 mL) was stirred under hydrogen at atmospheric pressure for 3 hours. The reaction was purged with nitrogen and filtered through a bed of celite. The filtrate was concentrated and the residue was purified via silica gel chromatography using 10% MeOH in CH$_2$Cl$_2$ to obtain the desired piperazinone as a white solid (8.3 g, 146.8 mmol, 96% yield). $^1$H NMR (400 MHz, CDCl$_3$) δ 7.43-7.38 (m, 2H), 7.30-7.26 (m, 3H), 3.70-3.67 (m, 4H), 3.35 (s, 1H), 3.22 (t, J=5.5 Hz, 2H). LC/MS (10%-99% CH$_3$CN (0.035% TFA)/H$_2$O (0.05% TFA)), m/z: M+1 obs=177.2; t$_R$=0.44 min.

1-Phenyl-4-(2,2,2-trifluoroacetyl)piperazin-2-one

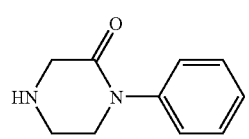

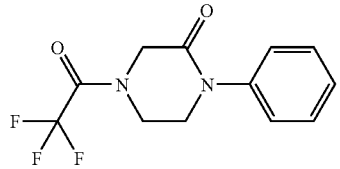

To a stirring solution of 1-phenylpiperazin-2-one (1.3 g, 7.1 mmol), triethylamine (0.72 g, 7.1 mmol), and CH$_2$Cl$_2$ (20 mL), at −78° C., was added trifluoroacetic anhydride (1.48 g, 7.1 mmol) dropwise over 10 minutes. The mixture was then allowed to warm to 25° C. over 30 minutes. The reaction mixture was partitioned between CH$_2$Cl$_2$ and water. The organic portion was evaporated and purified via silica gel chromatography using 30% EtOAc in hexanes to obtain the desired amide as a white solid (1.2 g, 4.4 mmol, 62% yield). LC/MS (10%-99% CH$_3$CN (0.035% TFA)/H$_2$O (0.05% TFA)), m/z: M+1 obs=272.8; t$_R$=2.48 min. $^1$H NMR (400 MHz, CDCl$_3$) δ 7.51-7.40 (m, 2H), 7.39-7.21 (m, 3H), 4.45 (s, 2H), 4.11-3.98 (m, 2H), 3.86-3.81 (m, 2H).

4-(2-Oxo-4-(2,2,2-trifluoroacetyl)piperazin-1-yl) benzene-1-sulfonyl chloride

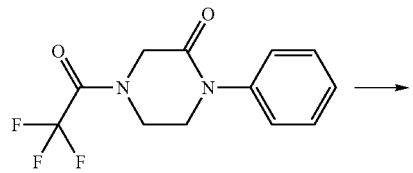

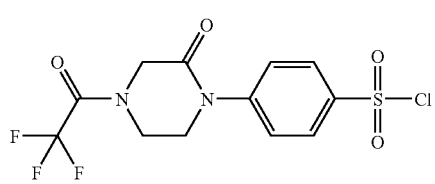

A stirring solution of 1-phenyl-4-(2,2,2-trifluoroacetyl) piperazin-2-one (1.2 g, 4.4 mmol) and chlorosulfonic acid (3.0 mL), under N$_2$, was heated at 80° C. for 40 minutes. The mixture was cooled to 0° C. and poured into ice-water (150 mL) followed by the addition of EtOAc (300 mL). The organic portion was evaporated and purified via silica gel chromatography using 50% EtOAc in hexanes to obtain the desired sulfonyl chloride as a clear oil (900 mg, 2.4 mmol, 55% yield). LC/MS (10%-99% CH$_3$CN (0.035% TFA)/H$_2$O (0.05% TFA)), m/z: M+1 obs=370.8; t$_R$=3.02 min. $^1$H NMR (400 MHz, CDCl$_3$) δ 8.12 (d, 2H), 7.65 (d, 2H), 4.51 (s, 2H), 4.11 (t, 2H), 3.93 (t, 2H).

General Procedure 12, Method A

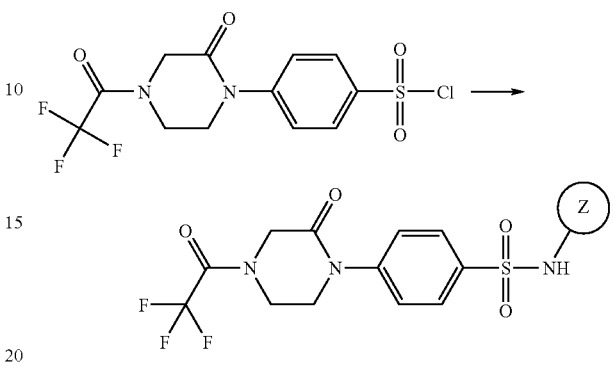

Under an N$_2$ atmosphere, a mixture of the sulfonyl chloride (1 mmol) and aminoheterocycle (1 mmol), and pyridine (1.0 mL) was stirred at RT for 19 h. The crude product was purified via silica gel chromatography using MeOH in CH$_2$Cl$_2$.

General Procedure 12, Method B

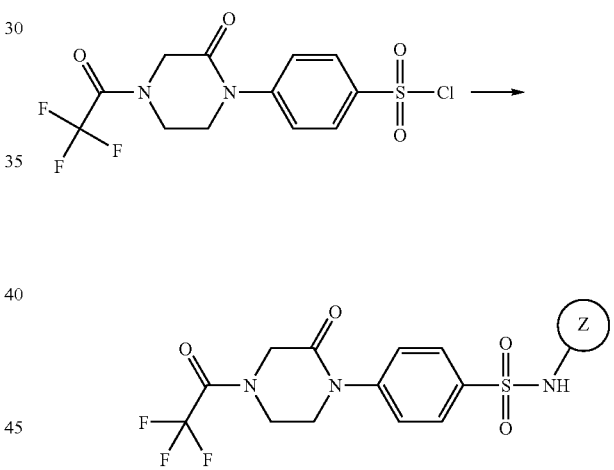

Under an N$_2$ atmosphere, a mixture of the sulfonyl chloride (1 mmol) and aminoheterocycle (1 mmol), and DABCO (1 mmol) in acetonitrile (5.0 mL) was stirred at RT for 19 h. The crude product was purified via silica gel chromatography using MeOH in CH$_2$Cl$_2$.

4-(2-Oxo-4-(2,2,2-trifluoroacetyl)piperazin-1-yl)-N-(thiazol-2-yl)benzenesulfonamide

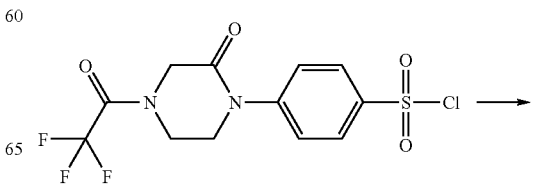

-continued

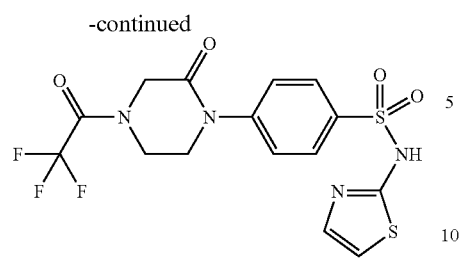

Synthesized according to general procedure 12, method A. The reaction was set up with 2-aminothiazole (2.4 g, 24.2 mmol), anhydrous pyridine (10 mL), and 4-(2-oxo-4-(2,2,2-trifluoroacetyl)piperazin-1-yl)benzene-1-sulfonyl chloride (9.0 g, 24.2 mmol). The dark oil was purified via silica gel chromatography using 5% MeOH in $CH_2Cl_2$ followed by a second purification on silica gel using 80% EtOAc in hexanes to obtain the desired sulfonamide as a white solid (5.1 g, 11.7 mmol, 48% yield). LC/MS (10%/99% $CH_3CN$ (0.035% TFA)/$H_2O$ (0.05% TFA)), m/z: M+1 obs=435.2; $t_R$=2.35 min.

4-(2-Oxo-4-(2,2,2-trifluoroacetyl)piperazin-1-yl)-N-(1,2,4-thiadiazol-5-yl)benzenesulfonamide

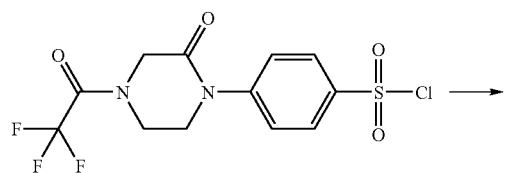

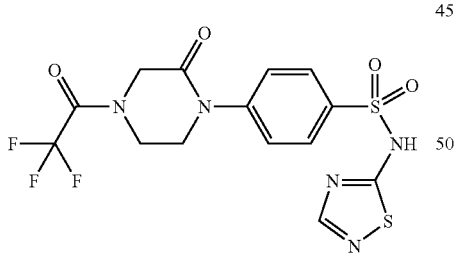

Synthesized according to general procedure 12, method A. The reaction was set up with 1,2,4-Thiadiazol-5-ylamine hydrochloride (0.56 g, 4.0 mmol), anhydrous pyridine (3.5 mL), and 4-(2-oxo-4-(2,2,2-trifluoroacetyl)piperazin-1-yl)benzene-1-sulfonyl chloride (1.5 g, 4.0 mmol). The dark oil was purified via silica gel chromatography using 5% MeOH in $CH_2Cl_2$ followed by a second purification on silica gel using 80% EtOAc in hexanes to obtain the desired sulfonamide as a white solid (0.73 g, 1.92 mmol, 48% yield). LC/MS (10%-99% $CH_3CN$ (0.035% TFA)/$H_2O$ (0.05% TFA)), m/z: M+1 obs=436.1; $t_R$=2.27 min.

4-(2-Oxo-4-(2,2,2-trifluoroacetyl)piperazin-1-yl)-N-(pyrimidin-4-yl)benzenesulfonamide

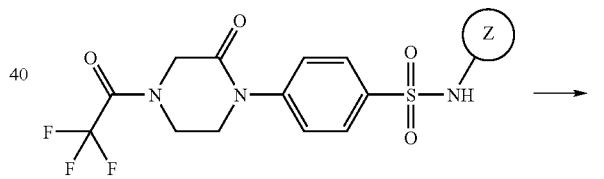

Synthesized according to general procedure 12, method B. The reaction was set up with 4-aminopyrimidine (0.26 g, 2.16 mmol), anhydrous acetonitrile (10 mL), DABCO (0.24 gm, 2.16 mmol) and 4-(2-oxo-4-(2,2,2-trifluoroacetyl)piperazin-1-yl)benzene-1-sulfonyl chloride (0.80 g, 2.16 mmol). The dark oil was purified via silica gel chromatography using 5% MeOH in $CH_2Cl_2$ followed by a second purification on silica gel using 80% methanol in dichloromethane to obtain the desired sulfonamide as a white solid (0.43 g, 0.93 mmol, 47% yield). LC/MS (10%-99% $CH_3CN$ (0.035% TFA)/$H_2O$ (0.05% TFA)), m/z: M+1 obs=439.3; $t_R$=2.3 min General Procedure 13

To a stirring solution of sodium hydroxide (10 equivalents, 10 mmol), and $H_2O$ (5.0 mL), at 0° C., was added the trifluoromethylacetyl amine (1 equivalent, 1 mmol) portionwise over 10 minutes. The mixture was stirred at ambient temperature for 30 minutes. The solution was cooled to 0° C. followed by the addition of 1.0 N HCl aqueous solution (10 equivalents, 10 mmol). The product was purified by azeotroping with MeOH or titration.

4-(2-Oxopiperazin-1-yl)-N-(thiazol-2-yl)benzenesulfonamide

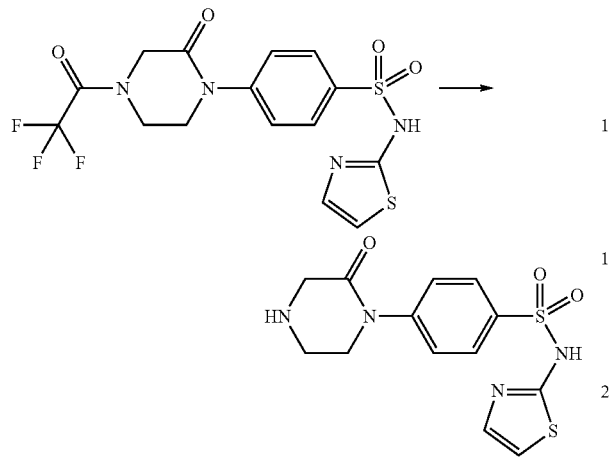

To a stirring solution of sodium hydroxide (1.38 g, 34.5 mmol), and H$_2$O (5.0 mL), at 0° C., was added 4-(2-oxo-4-(2,2,2-trifluoroacetyl)piperazin-1-yl)-N-(thiazol-2-yl)benzenesulfonamide (5.0 g, 11.5 mmol) portionwise over 10 minutes. The mixture was stirred at ambient temperature for 30 minutes. The solution was cooled to 0° C. followed by the addition of 1.0 N HCl aqueous solution (34.5 mL, 34.5 mmol). The light yellow solution was azeotroped with MeOH (4×100 mL) at <30° C. The obtained solid was suspended in 50% MeOH in CH$_2$Cl$_2$ (200 mL) and stirred for 5 minutes. The mixture was filtered and the filtrate was evaporated to give the desired amine as light yellow solid (2.5 g, 7.4 mmol, 64% yield). LC/MS (10%/99% CH$_3$CN (0.035% TFA)/H$_2$O (0.05% TFA)), m/z: M+1 obs=339.3; t$_R$=0.51 min.

4-(2-Oxopiperazin-1-yl)-N-(1,2,4-thiadiazol-5-yl)benzenesulfonamide

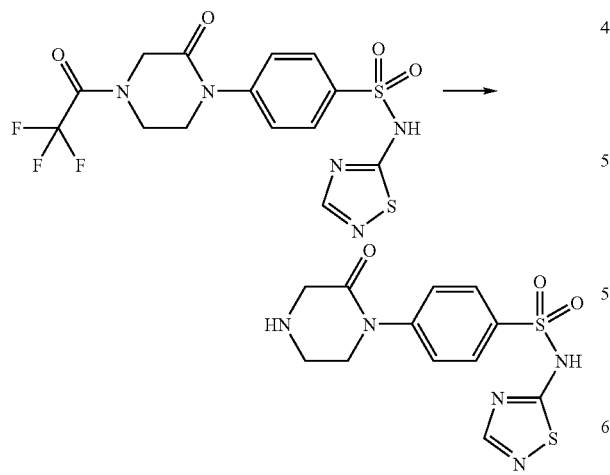

Prepared using general procedure 13. To a stirring solution of sodium hydroxide (0.67 g, 16.8 mmol), and H$_2$O (5.0 mL), at 0° C., was added 4-(2-oxo-4-(2,2,2-trifluoroacetyl)piperazin-1-yl)-N-(1,2,4-thiazol-2-yl)benzenesulfonamide (0.73 g, 1.68 mmol) portionwise over 10 minutes. The mixture was stirred at ambient temperature for 30 minutes. The solution was cooled to 0° C. followed by the addition of 1.0 N HCl aqueous solution (16.8 mL, 16.8 mmol). The light yellow solution was azeotroped with MeOH (4×100 mL) at <30° C. The obtained solid was suspended in 50% MeOH in CH$_2$Cl$_2$ (200 mL) and stirred for 5 minutes. The mixture was filtered and the filtrate was evaporated to give the desired amine as light yellow solid (1.15 g, 1.68 mmol, 100% yield). LC/MS (10%-99% CH$_3$CN (0.035% TFA)/H$_2$O (0.05% TFA)), m/z: M+1 obs=340.1; t$_R$=0.44 min.

4-(2-Oxopiperazin-1-yl)-N-(pyrimidin-4-yl)benzenesulfonamide

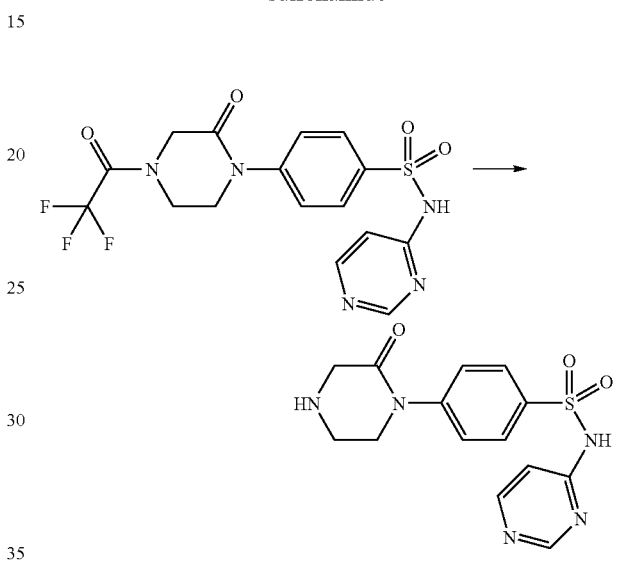

Prepared using general procedure 13. To a stirring solution of sodium hydroxide (1.0M in H$_2$O, 10 mL, 10 mmol), at 0° C., was added 4-(2-oxo-4-(2,2,2-trifluoroacetyl)piperazin-1-yl)-N-(pyrimidin-4-yl)benzenesulfonamide (0.45 g, 1.01 mmol) portionwise over 10 minutes. The mixture was stirred at ambient temperature for 30 minutes. The solution was cooled to 0° C. followed by the addition of 1.0 N HCl aqueous solution (10 mL, 10 mmol). The light yellow solution was azeotroped with MeOH (4×100 mL) at <30° C. The obtained solid was suspended in 50% MeOH in CH$_2$Cl$_2$ (200 mL) and stirred for 5 minutes. The mixture was filtered and the filtrate was evaporated to give the desired amine as light yellow solid (1.15 g, quantitative yield). LC/MS (10%-99% CH$_3$CN (0.035% TFA)/H$_2$O (0.05% TFA)), m/z: M+1 obs=334.1; t$_R$=0.44 min.

General Procedure 14, Method A

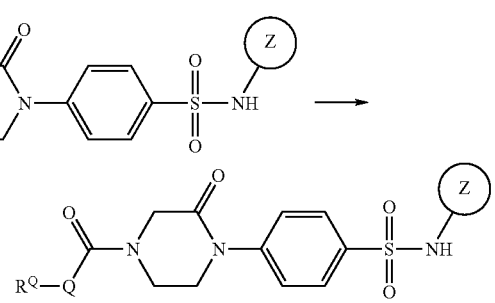

A mixture of piperazinone (1.0 equivalent), carboxylic acid (1.0 equivalent), HATU reagent (2.0 equivalent), sodium carbonate (3.0 equivalents), and DMF/CH₂Cl₂ (0.5-1.0 M in reference to piperazinone) was stirred at 25° C. for 19 h. Purification via silica gel chromatography using 5% MeOH in CH₂Cl₂ gave the desired product.

General Procedure 14, Method B

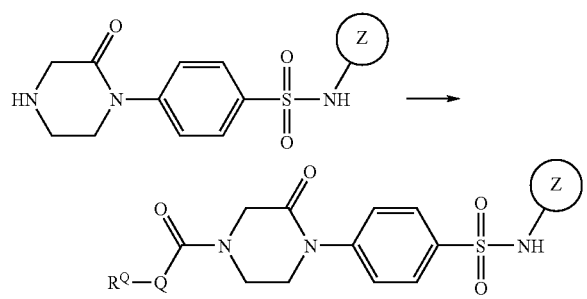

A mixture of piperazinone (1.5 equivalent), carboxylic acid (1.0 equivalent), HATU reagent (2.0 equivalent), sodium carbonate (2.0 equivalents), and DMF (1.3 M in reference to piperazinone) was stirred at 25° C. for 2-6 h. Purification via Gilson HPLC gave the desired product.

4-(2-Oxo-4-(2-(6-(trifluoromethyl)-1H-indol-1-yl) acetyl)piperazin-1-yl)-N-(thiazol-2-yl)benzene-sulfonamide

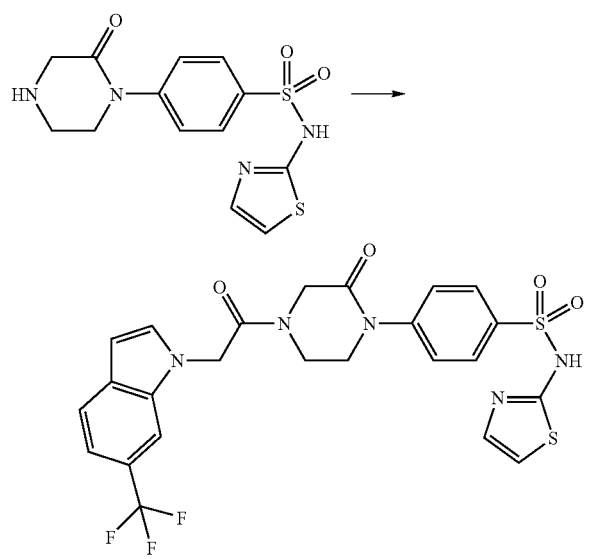

Synthesized according to general procedure 14, method A. The reaction was set up with 4-(2-oxopiperazin-1-yl)-N-(thiazol-2-yl)benzenesulfonamide (100 mg, 0.29 mmol), 2-(6-(trifluoromethyl)-1H-indol-1-yl)acetic acid (71 mg, 0.29 mmol), HATU reagent (220 mg, 0.58 mmol), sodium bicarbonate (74 mg, 0.87 mmol), and DMF/CH₂Cl₂-1/1 (0.50 mL) to obtain the desired amide as a white solid (55 mg, 0.10 mmol, 34% yield). $^1$H NMR (400 MHz, DMSO-d6) δ 12.78 (s, 1H), 7.91 (s, 1H), 7.85 (d, J=8.4 Hz, 2H), 7.75 (d, J=8.3 Hz, 1H), 7.58 (dd, J=5.1, 8.4 Hz, 2H), 7.52-7.48 (m, 1H), 7.32-7.27 (m, 2H), 6.85 (d, J=4.6 Hz, 1H), 6.61 (d, J=2.9 Hz, 1H), 5.40 (d, J=9.8 Hz, 2H), 4.49 (s, 1H), 4.22 (s, 1H), 4.01 (s, 2H), 3.81 (s, 2H). LC/MS (10%-99% CH₃CN (0.035% TFA)/H₂O (0.05% TFA), m/z: M+1 obs=564.4; $t_R$=3.17 min.

1-Methyl 2-(4-fluoro-1H-indol-1-yl) propanoate

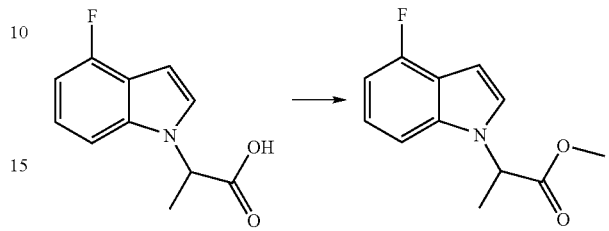

To a cooled (0-5° C.) solution of 2-(4-fluoro-1H-indol-1-yl)propanoic acid (19.0 g, 92 mmol) in methanol (250 mL) was added, dropwise, thionyl chloride (15 mL, 207 mmol). The resulting solution was stirred overnight at room temperature. The mixture was evaporated to dryness and the residue was dissolved in ethyl acetate (0.5 L). This solution was washed with water (2×200 mL), brine (200 mL), dried over sodium sulfate, filtered, and evaporated to dryness to give the desired methyl ester as brownish oil (26.0 g, 92 mmol, 100% yield). $^1$H-NMR (300 MHz, CDCl₃) δ 7.24-7.23 (m, 1H), 7.18-7.04 (m, 2H), 6.82-6.78 (m, 1H), 6.65-6.63 (m, 1H), 5.17 (q, J=7.3 Hz, 1H), 3.72 (s, 3H), 1.82 (d, J=7.3 Hz, 3H).

Methyl 2-(4-fluoro-1H-indol-1-yl)-2-methylpropanoate

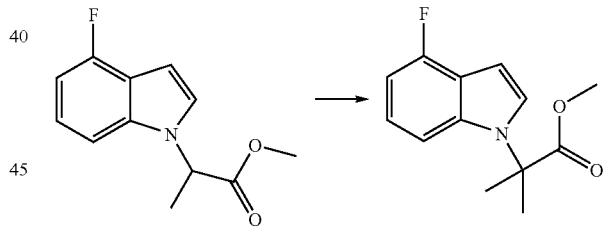

1-Methyl 2-(4-fluoro-1H-indol-1-yl) propanoate (20.6 g, 93 mmol) was dissolved in anhydrous THF (100 mL) under a nitrogen atmosphere. This solution was cooled to −78° C. and a solution of 1.8 M lithium diisopropylamide in THF/hexanes/ethylbenzene (commercial grade, 60 mL, 108 mmol) was slowly added via syringe. During the addition, the internal temperature was kept below −60° C. The mixture was stirred at −78° C. for 1 h. Methyl iodide (11 mL, 177 mmol) was added via syringe. After 15 minutes at −78° C. the dry ice/acetone bath was removed and the reaction mixture was left warming up to room temperature. Ethyl acetate (0.5 L) was added and the solution was washed with water (3×200 mL), 1N aq. HCl (2×200 mL), water (2×200 mL), brine (3×100 mL), and dried over sodium sulfate. The solution was evaporated to dryness at 50° C. under reduced pressure to yield the desired ester (21.3 g, 90 mmol, 97% yield).

$^1$H-NMR (300 MHz, CDCl$_3$): δ7.10-7.04 (m, 1H), 6.95-6.93 (m, 2H), 6.82-6.75 (m, 1H), 6.62-6.60 (m, 1H), 3.68 (s, 3H), 1.89 (s, 6H).

2-(4-Fluoro-1H-indol-1-yl)-2-methylpropanoic acid

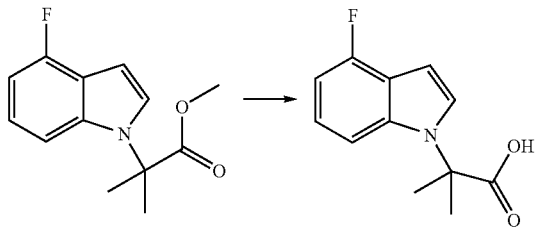

A mixture of 1-Methyl 2-(4-fluoro-1H-indol-1-yl)propanoate (21.3 g, 91 mmol), 1 N aq. NaOH (150 mL), and methanol (150 mL) was heated to 75° C. overnight. The volatiles were removed by evaporation under reduced pressure at 50° C. and ethyl acetate (250 mL) and water (200 mL) were added to the residue. The layers were separated and the aqueous layer was acidified with concentrated HCl to pH<1. The acidified layer was extracted with ethyl acetate (1×200 mL, 1×50 mL) and the combined extracts were washed with brine (100 mL), dried over sodium sulfate, filtered, and evaporated to dryness under reduced pressure at 50° C. to obtain the desired acid as a yellow oil (16.8 g, 76 mmol, 84% yield). $^1$H-NMR (300 MHz, CDCl$_3$): δ 7.12-6.99 (m, 2H), 6.83-6.77 (m, 2H), 6.63-6.62 (m 1H), 1.92 (s, 6H).

Methyl 2-(6-trifluoromethyl-1H-indol-1-yl) propanoate

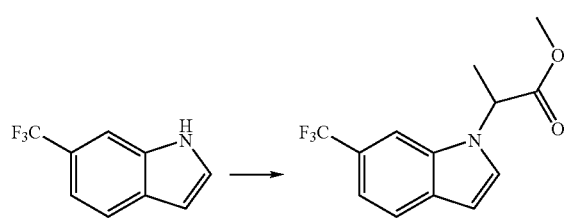

To a solution of 6-trifluoromethyl indole (1.33 g, 7.18 mmol) in DMSO (7 mL) was added portionwise potassium hydroxide (0.75 mL, 13.37 mmol). The resulting solution was stirred at room temperature for 15 minutes. To this was added methyl-2-bromo propionate (3.6 mL, 32.29 mmol) in a single portion. The reaction mixture was stirred at room temperature for 16 hrs. The solution was cooled to 0° C. and quenched with water (20 mL). The mixture was extracted with CH$_2$Cl$_2$ (50 mL). This solution was washed with a saturated solution of ammonium chloride (2×20 mL), brine (200 mL), dried over sodium sulfate, filtered, and concentrated. Purification via silica gel chromatography using 15-40% CH$_2$Cl$_2$ in hexanes gave the methyl ester as a clear oil (0.89 g, 3.23 mmol, 45% yield). LC/MS (10%/99% CH$_3$CN (0.035% TFA)/H$_2$O (0.05% TFA), m/z: M+1 obs=272.0; t$_R$=3.56 min. $^1$H NMR (400 MHz, CDCl$_3$) δ 7.73 (d, J=8.3 Hz, 1H), 7.62 (s, 1H), 7.45 (d, J=3.3 Hz, 1H), 7.39 (d, J=8.4 Hz, 1H), 6.67 (d, J=3.2 Hz, 1H), 5.26-5.20 (m, 1H), 3.76 (s, 3H), 1.88 (d, J=7.3 Hz, 3H).

Methyl 2-(6-trifluoromethyl-1H-indol-1-yl)-2-methylpropanoate

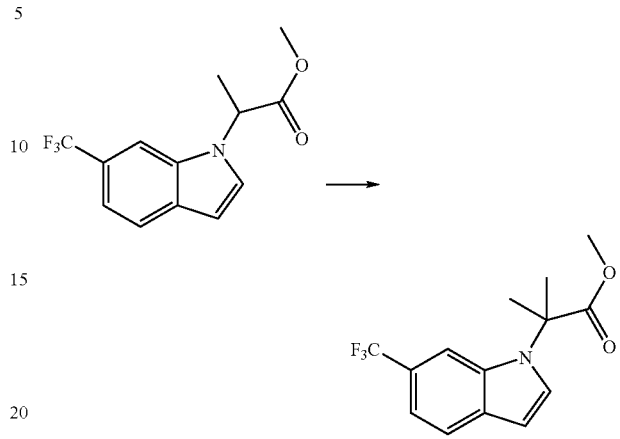

Methyl 2-(6-trifluoromethyl-1H-indol-1-yl) propanoate (0.89 g, 3.28 mmol) was dissolved in anhydrous THF (7 mL) under a nitrogen atmosphere. This solution was cooled to −78° C. and a solution of 2M lithium diisopropylamide in THF/heptane/ethylbenzene (1.97 mL, 3.94 mmol) was slowly added via syringe. During the addition, the internal temperature was kept below −60° C. The mixture was stirred at −78° C. for 1 h. Methyl iodide (0.39 mL, 6.23 mmol) was added via syringe. After 15 minutes at −78° C. the dry ice/acetone bath was removed and the reaction mixture was left to warm up to room temperature. Ethyl acetate (0.5 L) was added and the solution was washed with water (3×20 mL), 1N aq. HCl (2×20 mL), water (2×20 mL), brine (3×10 mL), and dried over sodium sulfate. The solution was evaporated to dryness at 50° C. under reduced pressure to give the desired ester (0.84 g, 2.95 mmol, 90% yield). $^1$H NMR (400 MHz, CDCl$_3$) δ 7.73 (d, J=8.3 Hz, 1H), 7.62 (s, 1H), 7.45 (d, J=3.3 Hz, 1H), 7.39 (d, J=8.4 Hz, 1H), 6.67 (d, J=3.2 Hz, 1H), 3.76 (s, 3H), 1.88 (s, 6H).

2-(6-Trifluoromethyl-1H-indol-1-yl)-2-methylpropanoic acid

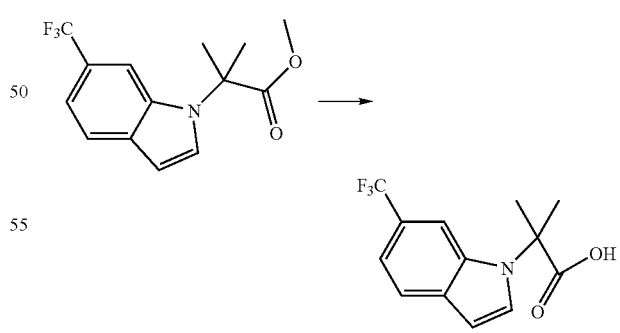

A mixture of methyl 2-(6-trifluoromethyl-1H-indol-1-yl)-2-methylpropanoate (1.48 g, 5.18 mmol), 1 N aq. NaOH (9 mL), and methanol:THF (1:1, 18 mL) was heated to 75° C. overnight. The volatiles were removed by evaporation under reduced pressure at 50° C. and to the residue was added ethyl acetate (50 mL) and water (15 mL). The layers were separated and the aqueous layer was acidified with concentrated HCl to pH<1. The acidified layer was extracted with ethyl acetate (3×20 mL), and the combined extracts were washed with brine (20 mL), and dried over sodium sulfate. The solution was concentrated and the residue was purified via silica gel chromatography using 0-5% methanol in CH$_2$Cl$_2$ to obtain the desired acid as a clear oil (0.58 g, 2.12 mmol, 41% yield). $^1$H NMR (400 MHz, CDCl$_3$) δ 7.65 (d, 1H), 7.42 (s, 1H), 7.35 (s, 1H), 7.29 (d, J=19.0 Hz, 1H), 6.51 (s, 1H), 1.92 (d, J=39.0 Hz, 6H). LC/MS (10%-99% CH$_3$CN (0.035% TFA)/H$_2$O (0.05% TFA), m/z: M+1 obs=272.2; t$_R$=3.61 min.

2-(5-Chloro-2-methyl-1H-indol-1-yl)propanoic acid

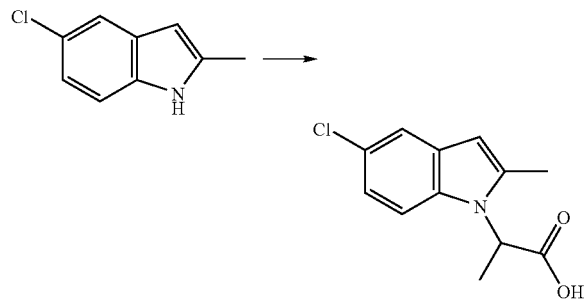

To a 0° C. solution of 5-chloro-2-methyl-indole (0.100 g, 0.6 mmol) in DMSO (6 mL) was added portionwise potassium hydroxide (0.33 g, 6 mmol). The resulting solution was stirred at room temperature for 15 minutes. To this was added methyl-2-bromo propionate (0.1 mL, 0.9 mmol) in a single portion. The reaction mixture was stirred at room temperature for 16 h. The solution was cooled to 0° C. and quenched with water (20 mL). The mixture was extracted with CH$_2$Cl$_2$ (50 mL). This solution was washed with a saturated solution of ammonium chloride (2×20 mL), brine (200 mL), and dried over sodium sulfate. The solution was concentrated and the residue was purified via silica gel chromatography using 15-40% CH$_2$Cl$_2$ in hexanes to obtain the methyl ester as a clear oil (0.05 g, 0.21 mmol, 35% yield). LC/MS (10%-99% CH$_3$CN (0.035% TFA)/H$_2$O (0.05% TFA), m/z: M+1 obs=238; t$_R$=3.03 min.

(R)-Methyl 2-hydroxy-3-methylbutanoate

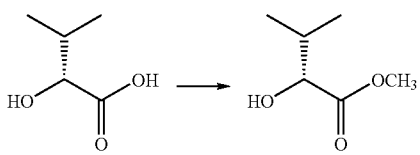

To a solution of (R)-2-hydroxy-3-methylbutanoic acid (5.0 gm, 42.2 mmol) in methanol was added a solution of TMS CH$_2$N$_2$ (2M) in hexane (65 mL), at 0° C., over 20 min. The reaction mixture was stirred at 0° C. for 1 h. The reaction was concentrated with a bath temperature of 20° C. and vacuum greater than 50 mm Hg. Purification via silica gel chromatography using 2-100% EtOAc in hexanes gave the ester as a yellow oil (438 mg, 12.7 mmol, 30% yield). $^1$H NMR (400 MHz, DMSO-d6) δ 5.30 (d, J=5.1 Hz, 1H), 3.81 (t, J=0.8 Hz, 1H), 3.63H), 1.94-1.86 (m, 1H), 0.88-0.82 (m, 6H).

(R)-1-(Methoxycarbonyl)-2-methylpropyl-trifluoromethane sulfonate

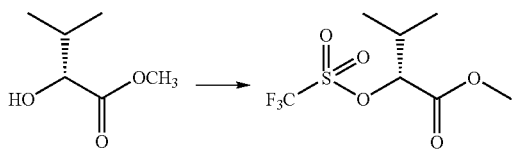

Triflic anhydride (0.58 mL, 3.31 mmol) was slowly added to a stirring solution of (R)-methyl 2-hydroxy-3-methylbutanoate (0.43 g, 3.31 mmol) in CH$_2$Cl$_2$ (5 mL), under N$_2$, at −30° C. The reaction mixture was stirred for 10 minutes followed by the addition of 2,6-lutidine (0.38 mL, 3.31 mmol). The reaction was stirred at room temperature for 16 hours. The reaction mixture was filtered over a small silica pad and washed with ethyl acetate and hexane (1:1, 10 mL). Concentration with a bath temperature of 20° C. and vacuum greater than 50 mm Hg gave the desired triflate as a yellow oil (0.78 g, 2.98 mmol, 90% yield). $^1$H NMR (400 MHz, DMSO-d6) δ 5.13 (s, 1H), 3.81 (s, 3H), 2.35-2.20 (m, 1H), 1.05-0.84 (m, 6H).

(S)-Ethyl 2-(6-chloro-3,4-dihydroquinolin-1(2H)-yl)-3-methylbutanoate

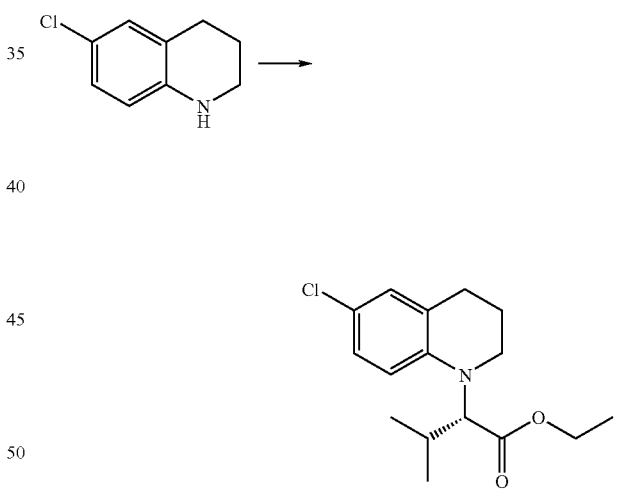

(R)-1-(Methoxycarbonyl)-2-methylpropyl-trifluoromethane sulfonate (200 mg, 0.75 mmol) in 1,2-dichloroethane (1 mL), was slowly added to a stirring solution of 6-chloro-1,2,3,4-tetrahydroquinoline (100 mg, 0.60 mmol), 2,6-lutidine (0.105 mL, 9.09 mmol), and 1,2-dichloroethane (5 mL), under N$_2$, at 25° C. The reaction was heated at 70° C. for 19 hours. The mixture was washed with H$_2$O and extracted twice with CH$_2$Cl$_2$. The organic layer was dried over MgSO$_4$, filtered, and concentrated. Purification via silica gel chromatography using 0-20% EtOAc in hexanes gave the desired ester as a yellow oil (30 mg, 0.11 mmol, 15% yield). LC/MS (10%-99% CH$_3$CN (0.035% TFA)/H$_2$O (0.05% TFA), m/z: M+1 obs=282.2; t$_R$=4.04 min.

547
(S)-2-(6-Chloro-3,4-dihydroquinolin-1(2H)-yl)-3-methylbutanoic acid

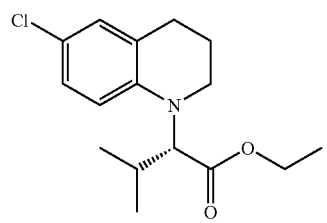

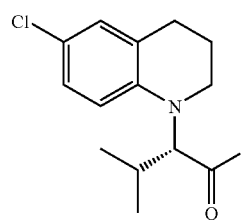

At 0° C., an aqueous 2.0 M KOH solution (14 mL, 28 mmol) was added to a stirring solution of (S)-2-(6-chloro-3,4-dihydroquinolin-1(2H)-yl)-3-methylbutanoic acid (80 mg, 0.28 mmol) in MeOH (2 mL). The reaction was allowed to warm up to RT and left stirring overnight. Due to the instability of the final product as a solid, the solution containing (S)-2-(6-chloro-3,4-dihydroquinolin-1(2H)-yl)-3-methylbutanoic acid was used for the next step without further work up. LC/MS (10%-99% $CH_3CN$ (0.035% TFA)/$H_2O$ (0.05% TFA), m/z: M+1 obs=268.4; $t_R$=3.57 min.

(S)-Methyl 2-hydroxy-4-methylpentanoate

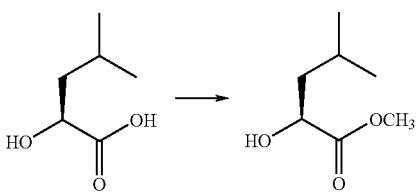

To a solution of (S)-2-hydroxy-4-methylpentanoic acid (3.0 g, 22.7 mmol) in methanol was added TMS $CH_2N_2$ (2M in hexanes, 34 mL, 17 mmol) dropwise, at 0° C., over 20 min The reaction mixture was stirred at 0° C. for 1 h. The solution was concentrated using a bath temperature of 20° C. and vacuum greater than 50 mm Hg. Purification via silica gel chromatography using 2-100% EtOAc in hexanes gave the ester as a yellow oil (2.14 g, 14.5 mmol, 64% yield). $^1$H NMR (400 MHz, DMSO-d6) δ 5.13 (s, 1H), 4.1-4.0 (m, 1H), 3.81 (s, 3H), 1.6-1.5 (m, 1H), 2.35-2.20 (m, 2H), 1.05-0.84 (m, 6H).

548
(S)-1-(Methoxycarbonyl)-3-methylbutyl-trifluoromethane sulfonate

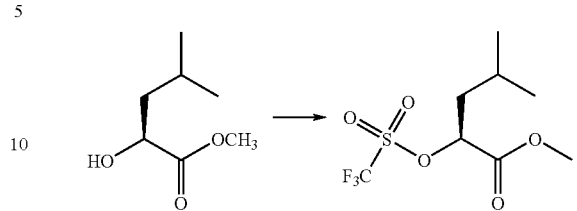

Under an $N_2$ atmosphere, at −30° C., triflic anhydride (2.69 mL, 16.0 mmol) was slowly added to a stirring solution of (R)-methyl 2-hydroxy-4-methylpentanoate (2.11 g, 14.5 mmol) in $CH_2Cl_2$ (33 mL). After stirring the reaction mixture for 10 minutes, 2,6-lutidine (1.94 mL, 16.7 mmol) was added. The reaction was stirred at room temperature for 16 h. The reaction mixture was filtered over a small silica pad and washed with ethyl acetate and haxane (1:4, 400 mL). The solution was concentrated using a bath temperature of 20° C. and vacuum greater than 50 mm Hg to obtain the desired triflate as a yellow oil (4.03 g, 16.7 mmol, 100% yield). $^1$H NMR (400 MHz, DMSO-d6) δ 4.08-4.01 (m, 1H), 3.82 (s, 3H), 2.52-2.50 (m, 2H), 1.99 (s, 1H), 1.19-0.90 (m, 6H).

(R)-Ethyl 2-(6-chloro-3,4-dihydroquinolin-1(2H)-yl)-4-methylpentanoate

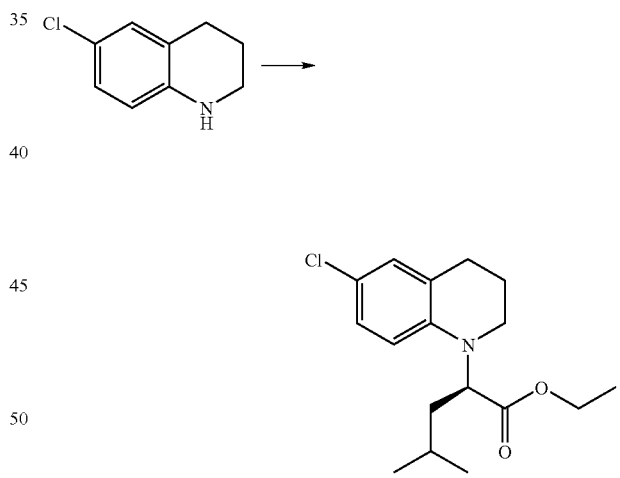

Under an $N_2$ atmosphere, at 25° C., (R)-1-(methoxycarbonyl)-2-methylpropyl-trifluoromethane sulfonate (300 mg, 1.08 mmol) in 1,2-dichloroethane (1 mL) was slowly added to a stirring solution of 6-chloro-1,2,3,4-tetrahydroquinoline (164 mg, 0.98 mmol) and 2,6-lutidine (0.132 mL, 1.13 mmol) in 1,2-dichloroethane (1.4 mL). The reaction was then heated at 70° C. for 19 hours. The mixture was washed with $H_2O$ and extracted twice with $CH_2Cl_2$. The organic layer was dried over $MgSO_4$, filtered, and concentrated. Purification via silica gel chromatography using 0-20% EtOAc in hexanes gave the ester as a yellow oil (295 mg, 0.98 mmol, 100% yield). LC/MS (10%-99% $CH_3CN$ (0.035% TFA)/$H_2O$ (0.05% TFA), m/z: M+1 obs=296.5; $t_R$=4.25 min.

(R)-2-(6-Chloro-3,4-dihydroquinolin-1(2H)-yl)-4-methylpentanoic acid

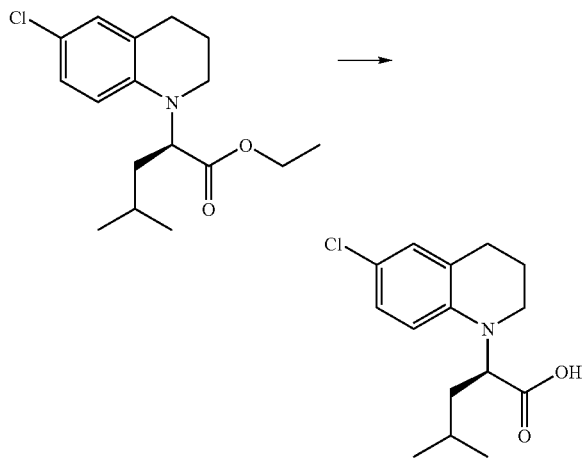

KOH (2.0 M in H$_2$O, 0.34 mL, 0.68 mmol) was added to a 0° C., stirring solution of (R)-ethyl 2-(6-chloro-3,4-dihydroquinolin-1(2H)-yl)-4-methylpentanoate (50 mg, 0.17 mmol) in MeOH (0.32 mL). The reaction was allowed to warm to RT and stirred overnight. Due to the instability of the final product as a solid, the solution containing (S)-2-(6-chloro-3,4-dihydroquinolin-1(2H)-yl)-3-methylbutanoic acid was used for the next step without further work up. LC/MS (10%/99% CH$_3$CN (0.035% TFA)/H$_2$O (0.05% TFA), m/z: M+1 obs=282.3; t$_R$=3.72 min.

4-(4-(2-(4-Fluoro-1H-indol-1-yl)-2-methylpropanoyl)-2-oxopiperazin-1-yl)-N-(thiazol-2-yl)benzenesulfonamide

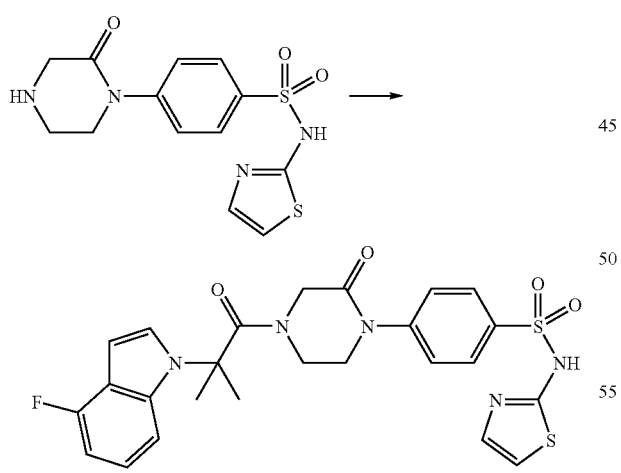

Synthesized according to general procedure 14, method A. The reaction was set up with 4-(2-oxopiperazin-1-yl)-N-(thiazol-2-yl)benzenesulfonamide (100 mg, 0.29 mmol), 2-(6-fluoro-1H-indol-1-yl)-2-methylpropanoic acid (66 mg, 0.29 mmol), HATU reagent (220 mg, 0.58 mmol), sodium bicarbonate (74 mg, 0.87 mmol), and DMF/CH$_2$Cl$_2$-1/1 (0.50 mL) to obtain the desired amide as a white solid (50 mg, 0.10 mmol, 32% yield). $^1$H NMR (400 MHz, DMSO-d6) δ 12.76 (s, 1H), 7.71 (d, J=8.5 Hz, 2H), 7.66 (s, 1H), 7.27-6.91 (m, 5H), 6.90-6.82 (m, 2H), 6.68 (d, J=3.0 Hz, 1H), 4.23 (s, 1H), 3.87 (bs, 1H), 3.57 (bs, 1H), 3.42-3.35 (m, 1H), 3.06 (s, 1H), 2.89 (s, 1H), 1.81 (d, J=8.3 Hz, 6H). LC/MS (10%-99% CH$_3$CN (0.035% TFA)/H$_2$O (0.05% TFA), m/z: M+1 obs=542.5; t$_R$=2.91 mm.

4-(4-(3-(5-Chloro-1H-indol-1-yl)propanoyl)-2-oxopiperazin-1-yl)-N-(thiazol-2-yl)benzenesulfonamide

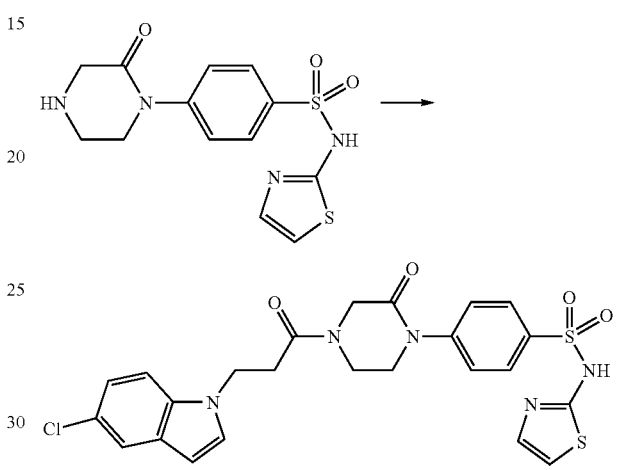

Synthesized according to general procedure 14, method A. The reaction was set up with 4-(2-oxopiperazin-1-yl)-N-(thiazol-2-yl)benzenesulfonamide (100 mg, 0.29 mmol), 3-(5-chloro-1H-indol-1-yl)propanoic acid (65 mg, 0.29 mmol), HATU reagent (220 mg, 0.58 mmol), sodium bicarbonate (74 mg, 0.87 mmol), and DMF/CH$_2$Cl$_2$-1/1 (0.50 mL) to obtain the desired amide as a white solid (50 mg, 0.10 mmol, 32% yield). $^1$H NMR (400 MHz, DMSO-d6) δ 12.77 (s, 1H), 7.81 (d, J=8.6 Hz, 2H), 7.58-7.53 (m, 2H), 7.49-7.44 (m, 3H), 7.26 (d, J=4.6 Hz, 1H), 7.13 (dd, J=2.1, 8.7 Hz, 1H), 6.84 (d, J=4.6 Hz, 1H), 6.42-6.41 (m, 1H), 4.47-4.40 (m, 2H), 4.18 (s, 1H), 4.15 (s, 1H), 3.77-3.74 (m, 4H), 2.94-2.90 (m, 2H). LC/MS (10%-99% CH$_3$CN (0.035% TFA)/H$_2$O (0.05% TFA), m/z: M+1 obs=544.2; t$_R$=3.00 min.

4-(4-(3-(5-Chloro-1H-indol-1-yl)propanoyl)-2-oxopiperazin-1-yl)-N-(thiazol-2-yl)benzenesulfonamide

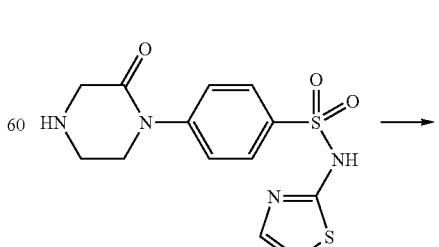

551

-continued

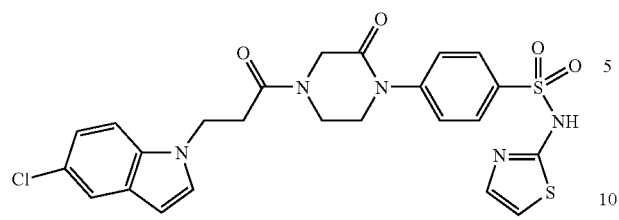

Synthesized according to general procedure 14, method B. The reaction was set up with 4-(2-oxopiperazin-1-yl)-N-(thiazol-2-yl)benzenesulfonamide (50 mg, 0.15 mmol), 3-(5-chloro-1H-indol-1-yl)propanoic acid (22 mg, 0.10 mmol), HATU reagent (76 mg, 0.20 mmol), sodium bicarbonate (17 mg, 0.20 mmol), and DMF (0.20 mL) to obtain the desired amide as a white solid (50 mg, 0.10 mmol, 32% yield). LC/MS (10%-99% $CH_3CN$ (0.035% TFA)/$H_2O$ (0.05% TFA), m/z: M+1 obs=574.0; $t_R$=3.23 min.

4-(4-(2-(5-Chloro-2-methyl-1H-indol-1-yl)propanoyl)-2-oxopiperazin-1-yl)-N-(thiazol-2-yl)benzenesulfonamide

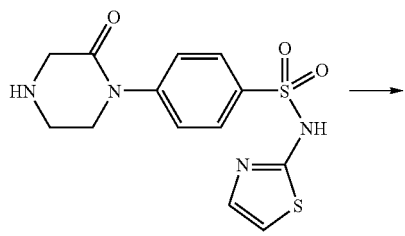

Synthesized according to general procedure 14, method B. The reaction was set up with 4-(2-oxopiperazin-1-yl)-N-(thiazol-2-yl)benzenesulfonamide (50 mg, 0.15 mmol), 2-(5-chloro-2-methyl-1H-indol-1-yl)propanoic acid (24 mg, 0.10 mmol), HATU reagent (76 mg, 0.20 mmol), sodium bicarbonate (17 mg, 0.20 mmol), and DMF (0.20 mL) to obtain the desired amide as a white solid (50 mg, 0.10 mmol, 32% yield). LC/MS (10%-99% $CH_3CN$ (0.035% TFA)/$H_2O$ (0.05% TFA), m/z: M+1 obs=558.0; $t_R$=3.02 min.

552

(S)-4-(4-(2-(6-Chloro-3,4-dihydroquinolin-1(2H)-yl)-3-methylbutanoyl)-2-oxopiperazin-1-yl)-N-(thiazol-2-yl)benzenesulfonamide

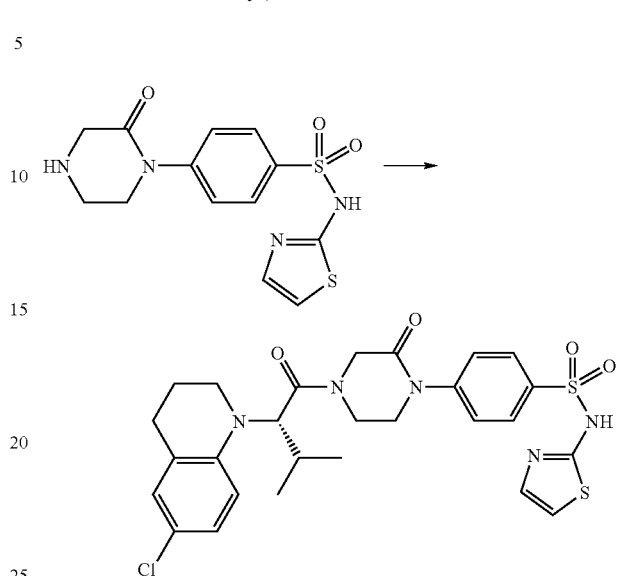

Synthesized according to general procedure 14, method B. The reaction was set up with 4-(2-oxopiperazin-1-yl)-N-(thiazol-2-yl)benzenesulfonamide (50 mg, 0.15 mmol), (S)-2-(6-chloro-3,4-dihydroquinolin-1(2H)-yl)-3-methylbutanoic acid (27 mg, 0.10 mmol), HATU reagent (76 mg, 0.20 mmol), sodium bicarbonate (17 mg, 0.20 mmol), and DMF (0.20 mL) to obtain the desired amide as a white solid (50 mg, 0.10 mmol, 32% yield). LC/MS (10%-99% $CH_3CN$ (0.035% TFA)/$H_2O$ (0.05% TFA), m/z: M+1 obs=588.0; $t_R$=3.37 min.

4-(4-(2-Methyl-2-(6-(trifluoromethyl)-1H-indol-1-yl)propanoyl)-2-oxopiperazin-1-yl)-N-(thiazol-2-yl)benzenesulfonamide

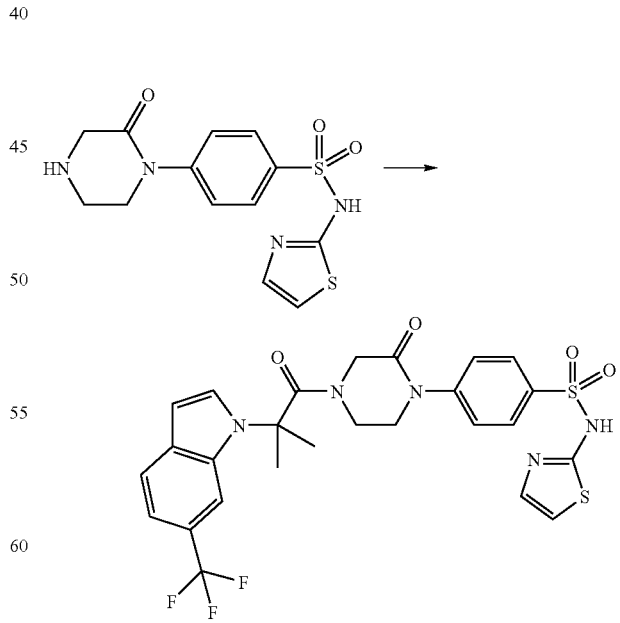

Synthesized according to general procedure 14, method B. The reaction was set up with 4-(2-oxopiperazin-1-yl)-N-(thiazol-2-yl)benzenesulfonamide (50 mg, 0.15 mmol), 2-methyl-2-(6-(trifluoromethyl)-1H-indol-1-yl)propanoic acid (27 mg, 0.10 mmol), HATU reagent (76 mg, 0.20 mmol), sodium bicarbonate (17 mg, 0.20 mmol), and DMF (0.20 mL) to obtain the desired amide as a white solid (50 mg, 0.10 mmol, 32% yield). LC/MS (10%-99% $CH_3CN$ (0.035% TFA)/$H_2O$ (0.05% TFA), m/z: M+1 obs=592.4; $t_R$=3.04 min.

(R)-4-(4-(2-(6-Chloro-3,4-dihydroquinolin-1(2H)-yl)-4-methylpentanoyl)-2-oxopiperazin-1-yl)-N-(thiazol-2-yl)benzenesulfonamide

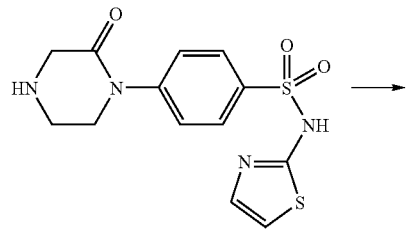

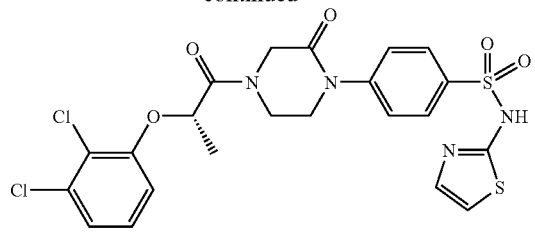

Synthesized according to general procedure 14, method B. The reaction was set up with 4-(2-oxopiperazin-1-yl)-N-(thiazol-2-yl)benzenesulfonamide (50 mg, 0.15 mmol), (S)-2-(2,3-dichlorophenoxy)propanoic acid (23 mg, 0.10 mmol), HATU reagent (76 mg, 0.20 mmol), sodium bicarbonate (17 mg, 0.20 mmol), and DMF (0.20 mL) to obtain the desired amide as a white solid (50 mg, 0.10 mmol, 32% yield). LC/MS (10%-99% $CH_3CN$ (0.035% TFA)/$H_2O$ (0.05% TFA), m/z: M+1 obs=555.3; $t_R$=2.85 min.

4-(2-Oxo-4-(2-(6-(trifluoromethyl)indolin-1-yl)acetyl)piperazin-1-yl)-N-(1,2,4-thiadiazol-5-yl)benzenesulfonamide

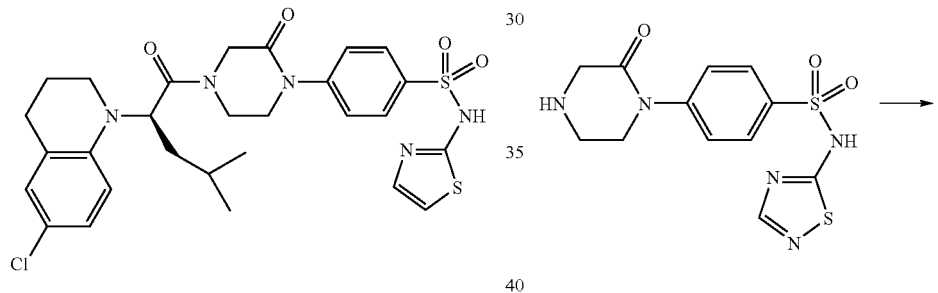

Synthesized according to general procedure 14, method B. The reaction was set up with 4-(2-oxopiperazin-1-yl)-N-(thiazol-2-yl)benzenesulfonamide (50 mg, 0.15 mmol), (R)-2-(6-chloro-3,4-dihydroquinolin-1(2H)-yl)-4-methylpentanoic acid (28 mg, 0.10 mmol), HATU reagent (76 mg, 0.20 mmol), sodium bicarbonate (17 mg, 0.20 mmol), and DMF (0.20 mL) to obtain the desired amide as a white solid (50 mg, 0.10 mmol, 32% yield). LC/MS (10%/99% $CH_3CN$ (0.035% TFA)/$H_2O$ (0.05% TFA), m/z: M+1 obs=602.0; $t_R$=3.50 min.

(S)-4-(4-(2-(2,3-Dichlorophenoxy)propanoyl)-2-oxopiperazin-1-yl)-N-(thiazol-2-yl)benzenesulfonamide

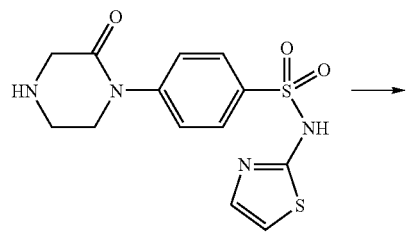

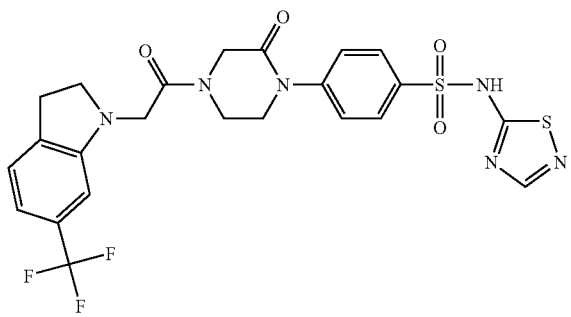

Synthesized according to general procedure 14, method B. The reaction was set up with 4-(2-oxopiperazin-1-yl)-N-(1,2,4-thiadiazol-5-yl)benzenesulfonamide (50 mg, 0.15 mmol), 2-(6-(trifluoromethyl)indolin-1-yl)acetic acid (25 mg, 0.10 mmol), HATU reagent (76 mg, 0.20 mmol), sodium bicarbonate (17 mg, 0.20 mmol), and DMF (0.20 mL) to obtain the desired amide as a white solid (50 mg, 0.10 mmol, 32% yield). LC/MS (10%-99% CH$_3$CN (0.035% TFA)/H$_2$O (0.05% TFA), m/z: M+1 obs=565.0; t$_R$=2.91 min.

Example 5

2,2,2-Trifluoro-1-(4-phenylpiperidin-1-yl)ethanone

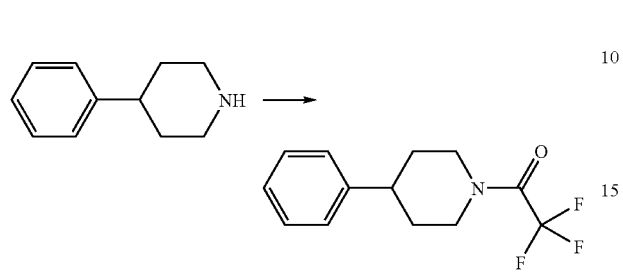

Under an N$_2$ atmosphere at −78° C., 2,2,2-trifluoroacetic anhydride (19.5 g, 12.9 mL, 93.0 mmol) was added to a solution of 4-phenylpiperidine (15.0 g, 93.0 mmol) and triethylamine (13 mL, 93.0 mmol) in CH$_2$Cl$_2$ (200 mL). The reaction was allowed to warm to RT over a period of 30 minutes. The mixture was partitioned between H$_2$O and CH$_2$Cl$_2$, and the organic layer was concentrated under reduced pressure. Purification via silica gel chromatography using 7/3 hexanes/EtOAc gave 2,2,2-trifluoro-1-(4-phenylpiperidin-1-yl)ethanone as a clear oil (21.0 g, 88%). $^1$H NMR (400 MHz, CDCl$_3$) δ 7.35-7.19 (m, 5H), 4.72-4.67 (m, 1H), 4.16-4.12 (m, 1H), 3.28-3.21 (m, 1H), 2.89-2.78 (m, 2H), 2.01-1.96 (m, 2H), 1.77-1.66 (m, 2H). LC/MS (10%-99% CH$_3$CN (0.035% TFA)/H$_2$O (0.05% TFA)), m/z: M+1 obs=258.1; t$_R$=3.27 min.

4-(1-(2,2,2-Trifluoroacetyl)piperidin-4-yl)benzene-1-sulfonyl chloride

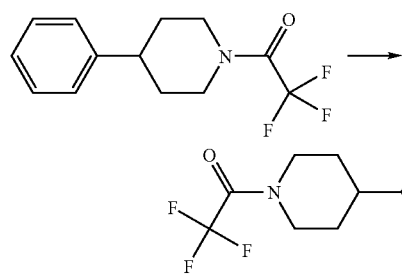

Chlorosulfonic acid (2 mL) was added to 2,2,2-trifluoro-1-(4-phenylpiperidin-1-yl)ethanone (1.0 g, 3.9 mmol) in a single portion, and the reaction was stirred for 20 minutes until gas evolution ceased (exothermic reaction). The solution was poured into a mixture of ice water (200 mL) and EtOAc (20 mL). The organic layer was concentrated and purified via silica gel chromatography using 8/2 hexanes/EtOAc to obtain 4-(1-(2,2,2-trifluoroacetyl)piperidin-4-yl)benzene-1-sulfonyl chloride as a clear oil (1.3 g, 94%). $^1$H NMR (400 MHz, CDCl$_3$) δ 8.02-8.00 (m, 2H), 7.48-7.45 (m, 2H), 4.78-4.73 (m, 1H), 4.19 (dd, J=14.0, 1.6 Hz, 1H), 3.32-3.25 (m, 1H), 3.02-2.86 (m, 2H), 2.03-2.02 (m, 2H), 1.81-1.70 (m, 2H).

General Procedure 15, Method A

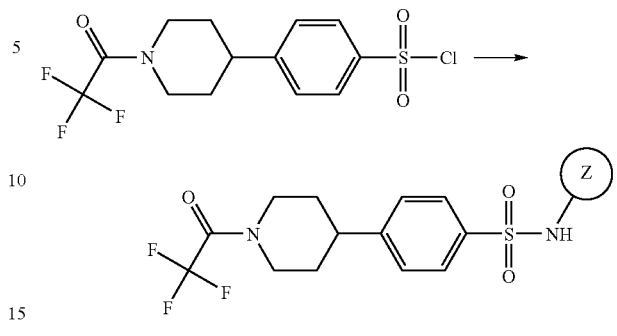

Under an N$_2$ atmosphere, a mixture of the sulfonyl chloride (1 mmol), the amine (1 mmol), and pyridine (0.3 mL) was stirred at RT for 19 h. The crude product was purified via silica gel chromatography to give the desired product.

General Procedure 15, Method B

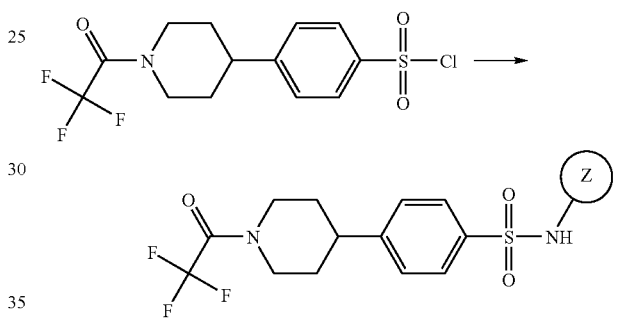

Under an N$_2$ atmosphere, a mixture of the sulfonyl chloride (1 mmol), the amine (1 mmol), and DABCO (5 equivalents, 5 mmol) in acetonitrile (1.8 mL) was heated to 40° C. until the reaction was complete. The crude product was purified via silica gel chromatography to give the desired product.

N-(1,2,4-Thiadiazol-5-yl)-4-(1-(2,2,2-trifluoroacetyl)piperidin-4-yl)benzenesulfonamide

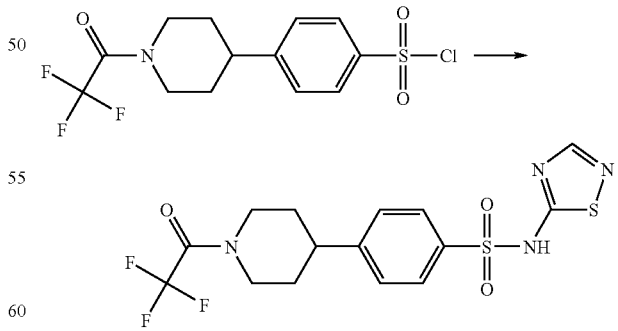

Prepared using general procedure 15, method A. Under an N$_2$ atmosphere, a mixture of 4-(1-(2,2,2-trifluoroacetyl)piperidin-4-yl)benzene-1-sulfonyl chloride (13.0 g, 36.5 mmol), 1,2,4-thiadiazol-5-amine hydrochloride (5.0 g, 36.5 mmol), and pyridine (10 mL) was stirred at RT for 19 h. The crude product was purified via silica gel chromatography using 5% MeOH in CH$_2$Cl$_2$ giving N-(1,2,4-thiadiazol-5-yl)-4-(1-(2,2,2-trifluoroacetyl)piperidin-4-yl)benzenesulfonamide as a clear oil (2.0 g). LC/MS (10%-99% CH$_3$CN (0.035% TFA)/H$_2$O (0.05% TFA)), m/z: M+1 obs=421.1; t$_R$=2.85 min.

N-(Pyrimidin-4-yl)-4-(1-(2,2,2-trifluoroacetyl)piperidin-4-yl)benzenesulfonamide

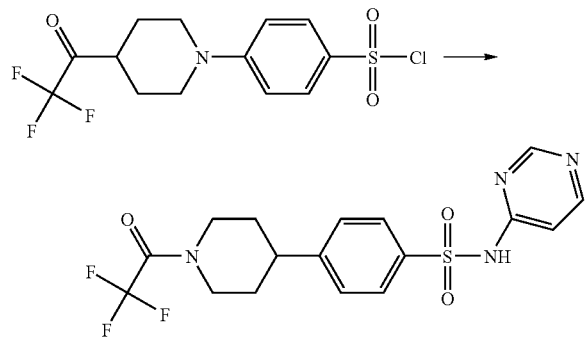

Prepared using general procedure 15, method B. Prepared using a mixture of 4-(1-(2,2,2-trifluoroacetyl)piperidin-4-yl)benzene-1-sulfonyl chloride (2.0 g, 5.6 mmol), 4-aminopyrimidine (535 mg, 5.6 mmol), DABCO (3.1 g, 28.0 mmol) and acetonitrile (10 mL). The reaction mixture was heated at 40° C. for 6 h. Purification via silica gel chromatography using 5% MeOH in CH$_2$Cl$_2$ gave N-(pyrimidin-4-yl)-4-(1-(2,2,2-trifluoroacetyl)piperidin-4-yl)benzenesulfonamide (850 mg, 36%). LC/MS (10%-99% CH$_3$CN (0.035% TFA)/H$_2$O (0.05% TFA)), m/z: M+1 obs=415.3; t$_R$=2.57 min.

N-(Thiazol-2-yl)-4-(1-(2,2,2-trifluoroacetyl)piperidin-4-yl)benzenesulfonamide

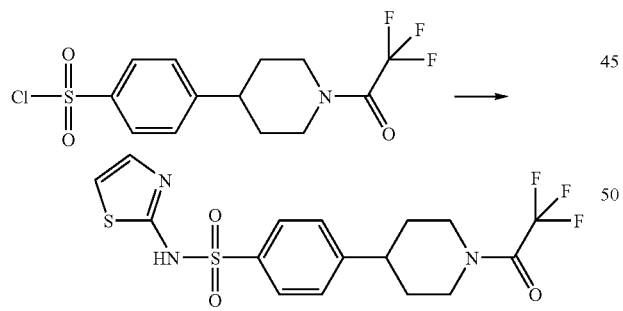

Prepared using general procedure 15, method A. A solution of 4-(1-(2,2,2-trifluoroacetyl)piperidin-4-yl)benzene-1-sulfonyl chloride (3 g, 8.43 mmol) and 2-aminothiazole (0.84 g, 8.43 mmol) in pyridine (2 ml) was stirred overnight at RT. The reaction was quenched with water, extracted with DCM, dried over Na$_2$SO$_4$, filtered and concentrated. Purification via silica gel chromatography using 0-5% methanol in DCM gave N-(thiazol-2-yl)-4-(1-(2,2,2-trifluoroacetyl)piperidin-4-yl)benzenesulfonamide (1.78 g, 50% yield). LC/MS: (10%-99% CH$_3$CN (0.035% TFA)/H$_2$O (0.05% TFA)), m/z M+1 obs=420.3; t$_R$=1.41 min.

General Procedure 16

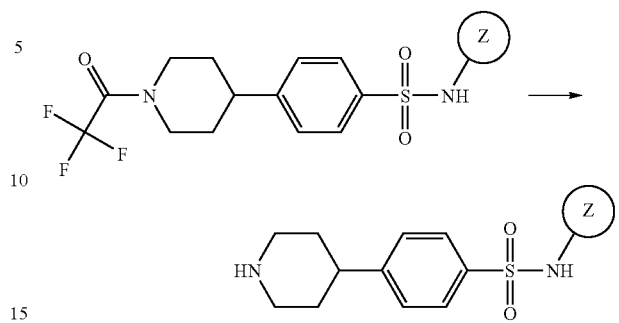

A solution of sulfonamide (1 equivalent), NaOH (10 equivalents), and H$_2$O (0.25 M) was stirred at RT for 1 h, then cooled to 0° C. Acetic acid (10 equivalents) was added, and the reaction was stirred at 0° C. for 20 min. The formed precipitate was filtered off and dried under vacuum to give the desired product.

4-(Piperidin-4-yl)-N-(1,2,4-thiadiazol-5-yl)benzenesulfonamide

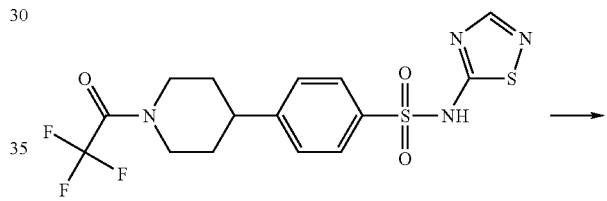

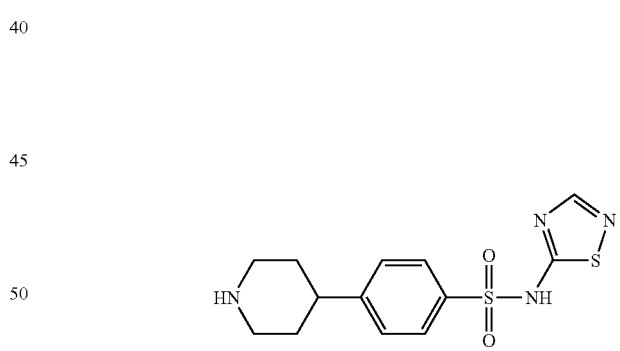

Prepared using general procedure 16. A mixture of N-(1,2,4-thiadiazol-5-yl)-4-(1-(2,2,2-trifluoroacetyl)piperidin-4-yl)benzenesulfonamide (2.0 g, 4.8 mmol), NaOH (1.92 g, 48.0 mmol), and H$_2$O (25 mL) was stirred at RT for 30 minutes. An aqueous 1.0 N HCl solution was added (48.0 mL, 48 mmol), and the mixture was azeotroped with MeOH (3×100 mL). A 9:1 solution of CH$_2$Cl$_2$ and MeOH (100 mL) was added, and the mixture was filtered to remove NaCl. The filtrate was concentrated under reduced pressure to give 4-(piperidin-4-yl)-N-(1,2,4-thiadiazol-5-yl)benzenesulfonamide as a clear oil which solidified upon standing (1.5 g, 96%). LC/MS (10%-99% CH$_3$CN (0.035% TFA)/H$_2$O (0.05% TFA)), m/z: M+1 obs=325.3; t$_R$=0.99 min.

4-(Piperidin-4-yl)-N-(pyrimidin-4-yl)benzenesulfonamide

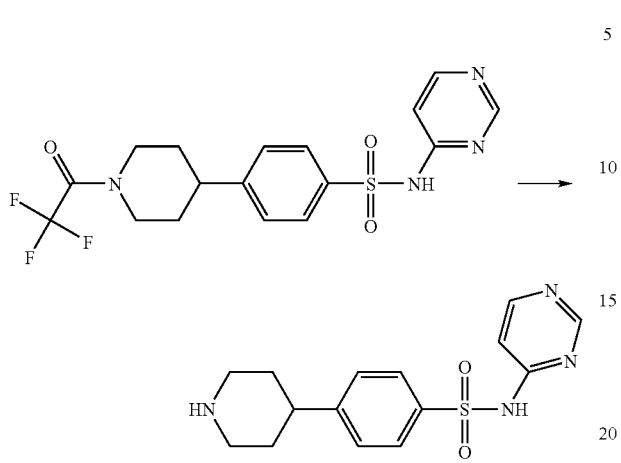

Prepared using general procedure 16. A mixture of N-(pyrimidin-4-yl)-4-(1-(2,2,2-trifluoroacetyl)piperidin-4-yl)benzenesulfonamide (850 mg, 2.1 mmol), NaOH (412 mg, 10.3 mmol), and $H_2O$ (3 mL) was stirred at RT for 30 minutes. A 1.0 N aqueous HCl solution was added (10.3 mL, 10.3 mmol), and the mixture was azeotroped with MeOH (3×50 mL). A 1:1 solution of $CH_2Cl_2$ and MeOH (10 mL) was added, and the mixture was filtered to remove NaCl. The filtrate was concentrated under reduced pressure to give 4-(piperidin-4-yl)-N-(pyrimidin-4-yl)benzenesulfonamide as a light yellow solid (710 mg). LC/MS (10%-99% $CH_3CN$ (0.035% TFA)/$H_2O$ (0.05% TFA)), m/z: M+1 obs=319.1; $t_R$=0.43 min.

4-(Piperidin-4-yl)-N-(thiazol-2-yl)benzenesulfonamide

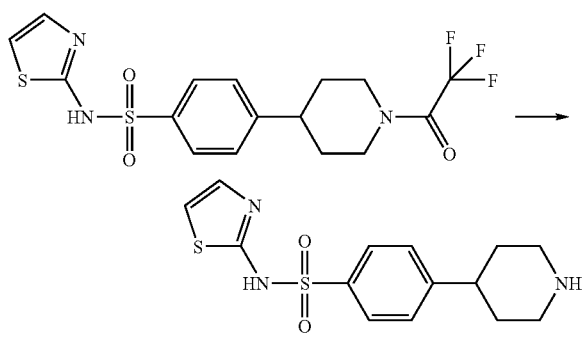

Prepared using general procedure 16. To N-(thiazol-2-yl)-4-(1-(2,2,2-trifluoroacetyl)piperidin-4-yl)benzenesulfonamide (1.5 g, 3.57 mmol) was added a solution of NaOH (1.43 g in 25 ml of $H_2O$). The reaction was stirred at RT for 30 minutes. The pH was adjusted to 10 with HOAc, and the product crashed out as a pink solid which was then filtered, azeotroped with acetonitrile and dried to give 4-(piperidin-4-yl)-N-(thiazol-2-yl)benzenesulfonamide (1 g, 87% yield). LC/MS (10%-99% $CH_3CN$ (0.035% TFA)/$H_2O$ (0.05% TFA)), m/z: M+1 obs=324.3; $t_R$=0.46 min.

General Procedure 17, Method A

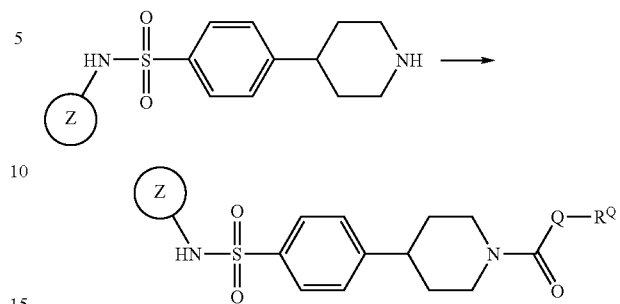

A mixture of the amine (0.15 mmol), carboxylic acid (0.15 mmol), BOP reagent (100 mg, 0.23 mmol), triethylamine (32 µL, 0.23 mmol), and DMF (0.3 mL) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

General Procedure 17, Method B

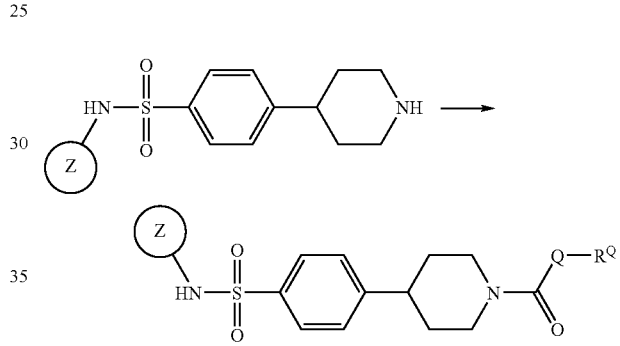

A mixture of the amine (0.15 mmol), carboxylic acid (0.15 mmol), HATU (0.15 mmol), triethylamine (0.15 mmol), and $CH_3CN$ (0.3 mL) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

General Procedure 17, Method C

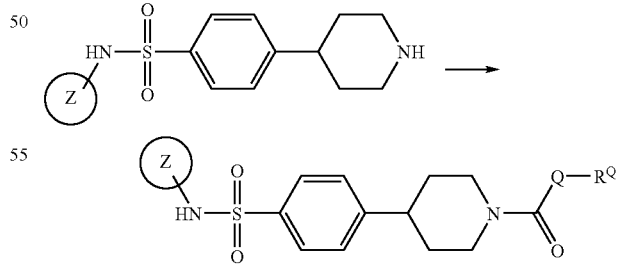

A mixture of the amine (0.15 mmol), carboxylic acid (0.15 mmol), HATU (0.19 mmol), DIEA (0.3 mmol), and THF (0.3 mL) or DMF (0.3 mL) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

561

4-(1-(3-(5-Chloro-1H-indol-1-yl)propanoyl)piperidin-4-yl)-N-(1,2,4-thiadiazol-5-yl)benzenesulfonamide

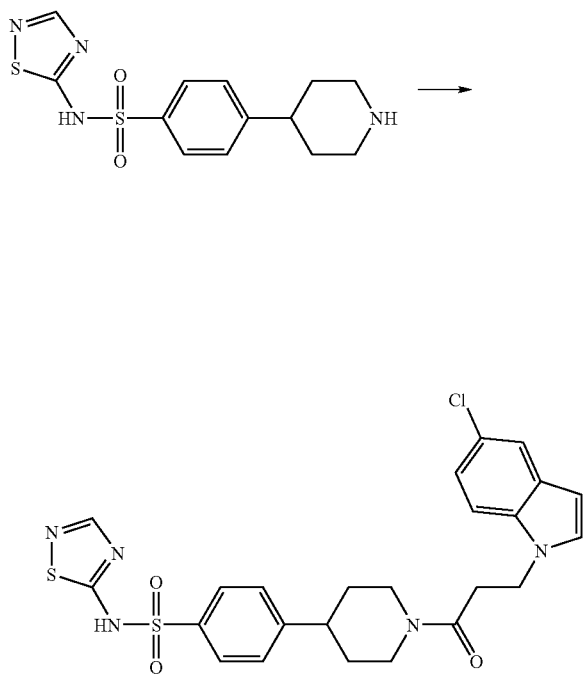

Synthesized according to general procedure 17, method A. Yield: 23%, ¹H NMR (400 MHz, DMSO-d6) δ 8.47 (s, 1H), 7.72 (d, J=8.4 Hz, 2H), 7.60 (s, 1H), 7.53 (d, J=4.0 Hz, 2H), 7.48 (s, 1H), 7.25 (d, J=8.4 Hz, 2H), 7.14 (d, J=8.7 Hz, 1H), 6.43 (s, 1H), 4.54-4.39 (m, 3H), 3.80 (d, J=13.7 Hz, 2H), 3.03-2.92 (m, 2H), 2.85-2.75 (m, 2H), 1.67 (d, J=12.5 Hz, 1H), 1.55 (d, J=12.4 Hz, 1H), 1.30-1.15 (m, 1H), 1.10-1.02 (m, 1H). LC/MS (10%-99% CH₃CN (0.035% TFA)/H₂O (0.05% TFA)), m/z: M+1 obs=530.1; $t_R$=3.18 min.

4-(1-(2-(3-Chloro-4-fluorophenoxy)acetyl)piperidin-4-yl)-N-(1,2,4-thiadiazol-5-yl)benzenesulfonamide

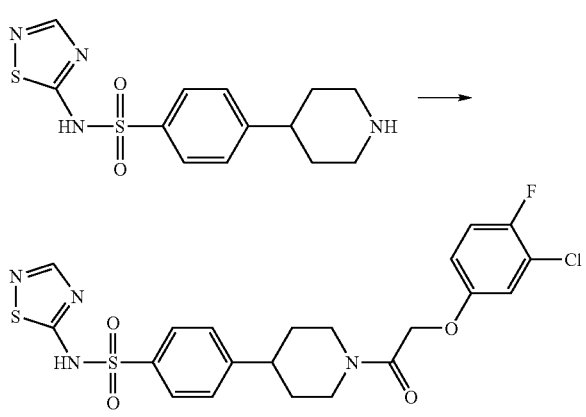

562

Synthesized according to general procedure 17, method A. LC/MS (10%-99% CH₃CN (0.035% TFA)/H₂O (0.05% TFA)), m/z: M+1 obs=511.2; $t_R$=3.15 min.

4-(1-(2-(6-Chloro-1H-indol-1-yl)acetyl)piperidin-4-yl)-N-(1,2,4-thiadiazol-5-yl)benzenesulfonamide

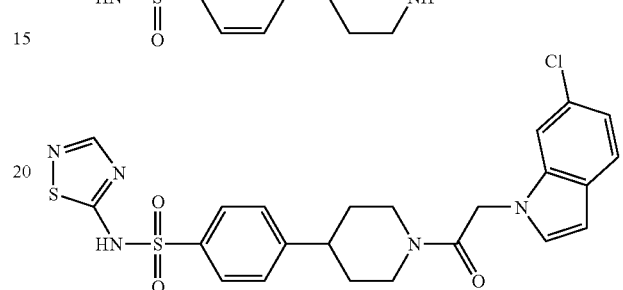

Synthesized according to general procedure 17, method B. Yield 42%. ¹H NMR (400 MHz, acetic acid-d4) δ 8.46 (s, 1H), 7.77 (d, J=8.3 Hz, 2H), 7.55 (d, J=8.1 Hz, 2H), 7.46 (d, J=8.3 Hz, 2H), 7.32 (s, 1H), 7.03 (d, J=10.2 Hz, 1H), 6.54 (d, 1H), 5.35-5.22 (m, 2H), 4.47 (d, J=13.2 Hz, 1H), 4.09 (d, J=12.7 Hz, 1H), 3.22 (t, J=12.2 Hz, 1H), 2.93 (t, J=10.3 Hz, 1H), 2.70 (t, J=11.9 Hz, 1H), 1.90-1.68 (m, 3H), 1.64-1.50 (m, 1H). LC/MS (10%-99% CH₃CN (0.035% TFA)/H₂O (0.05% TFA)), m/z: M+1 obs=516.2; $t_R$=3.06 min.

(R)-4-(4-(2-(4-Fluoro-1H-indol-1-yl)propanoyl)piperidin-4-yl)-N-(1,2,4-thiadiazol-5-yl)benzenesulfonamide

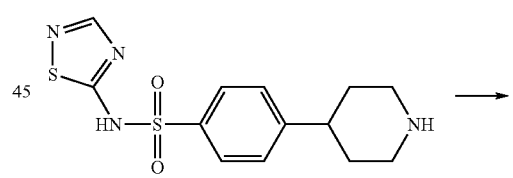

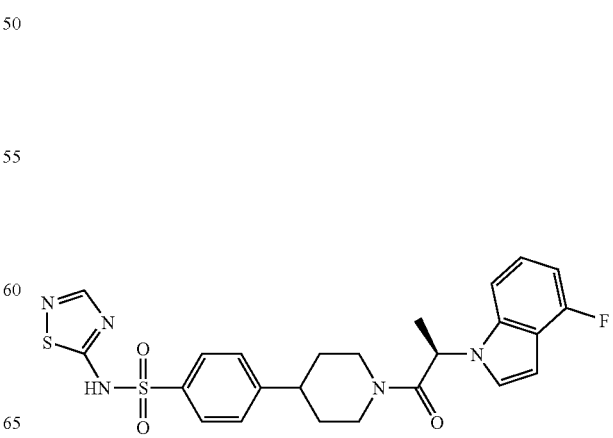

Synthesized according to general procedure 17, method A. Yield: 42%. LC/MS (10%-99% CH$_3$CN (0.035% TFA)/H$_2$O (0.05% TFA)), m/z: M+1 obs=514.3 t$_R$=3.10 min.

2-(5-Chloro-1H-pyrrolo[2,3-b]pyridin-1-yl)acetic acid

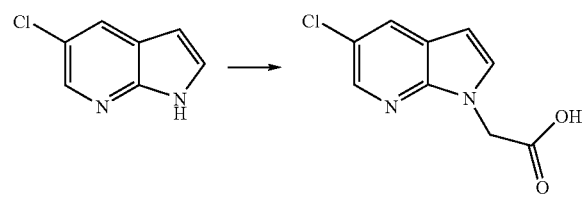

To a solution of NaOH (5.19 g, 129.8 mmol) in water (10 mL) was added tetrabutylammonium bromide (0.35 g, 1.08 mmol), 5-chloro-1H-pyrrolo[2,3-b]pyridine (1.5 g, 9.83 mmol), toluene (60 mL) and methyl 2-bromoacetate (9 g, 59 mmol). The reaction was heated overnight at 100° C. The reaction was quenched with water, the layers were separated and the aqueous layer was extracted with DCM. The combined organic layers were dried over Na$_2$SO$_4$, filtered and concentrated. 2-(5-chloro-1H-pyrrolo[2,3-b]pyridin-1-yl) acetate solution in THF was treated with NaOH and stirred at RT for 5 hours. The reaction mixture was then diluted with water and the pH was adjusted to 1 with 1N HCl to crash out the product. The reaction was then filtered, azeotroped with acetonitrile and dried to give 2-(5-chloro-1H-pyrrolo[2,3-b] pyridin-1-yl)acetic acid. (2 g, 97% yield). $^1$H NMR (400 MHz, DMSO-d6) δ 8.18 (d, J=2.3 Hz, 1H), 8.05 (d, J=2.3 Hz, 1H), 7.57 (d, J=3.5 Hz, 1H), 6.42 (d, J=3.5 Hz, 1H), 4.74 (s, 2H). LC/MS (10%-99% CH$_3$CN (0.035% TFA)/H$_2$O (0.05% TFA)), m/z: M+1 obs=211.1; t$_R$=1.10 min.

4-(1-(2-(5-chloro-1H-pyrrolo[2,3-b]pyridin-1-yl) acetyl)piperidin-4-yl)-N-(thiazol-2-yl)benzene-sulfonamide

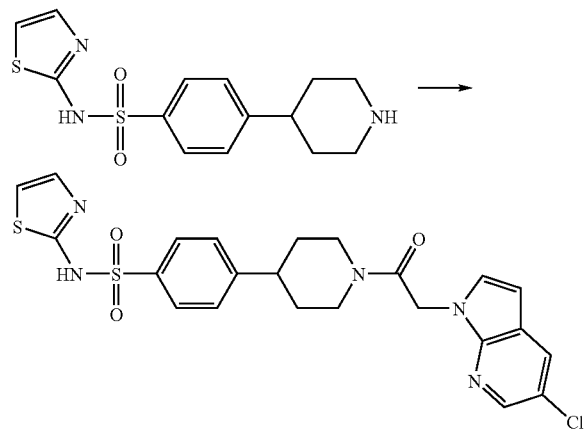

Synthesized according to general procedure 17, method C using THF as solvent. To a solution of 4-(piperidin-4-yl)-N-(thiazol-2-yl)benzenesulfonamide (0.35 g, 1.08 mmol) and 2-(5-chloro-1H-pyrrolo[2,3-b]pyridin-1-yl)acetic acid (0.25 g, 1.19 mmol) in THF (6 mL) was added HATU (0.533 g, 1.40 mmol) followed by the addition of DIEA (0.279 g, 2.16 mmol) at 0° C. under inert atmosphere. The reaction was quenched with water after 15 minutes, the layers were separated and the aqueous layer was extracted with DCM. The combined organic layers were dried over Na$_2$SO$_4$, filtered and concentrated. Purification via silica gel chromatography using 0-3% methanol in DCM gave 4-(1-(2-(5-chloro-1H-pyrrolo[2,3-b]pyridin-1-yl)acetyl)piperidin-4-yl)-N-(thiazol-2-yl)benzenesulfonamide (0.26 g, 46% yield). $^1$H NMR (400 MHz, DMSO-d6) δ 12.71 (s, 1H), 8.22 (d, J=2.3 Hz, 1H), 8.10 (d, J=2.3 Hz, 1H), 7.75 (d, J=8.4 Hz, 2H), 7.57 (d, J=3.5 Hz, 1H), 7.44 (d, J=8.4 Hz, 2H), 7.26 (d, J=4.6 Hz, 1H), 6.83 (d, J=4.6 Hz, 1H), 6.49 (d, J=3.5 Hz, 1H), 5.25 (d, J=2.6 Hz, 2H), 4.44 (d, J=12.9 Hz, 1H), 4.16 (d, J=12.8 Hz, 1H), 3.24 (t, J=11.7 Hz, 1H), 2.95-2.88 (m, 1H), 2.70 (t, J=11.7 Hz, 1H), 1.91-1.66 (m, 3H), 1.55-1.45 (m, 1H). LC/MS (10%-99% CH$_3$CN (0.035% TFA)/H$_2$O (0.05% TFA)), m/z: M+1 obs=516.5; t$_R$=1.57 min.

3-(5-Chloro-1H-pyrrolo[2,3-b]pyridin-1-yl)propanoic acid

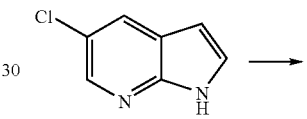

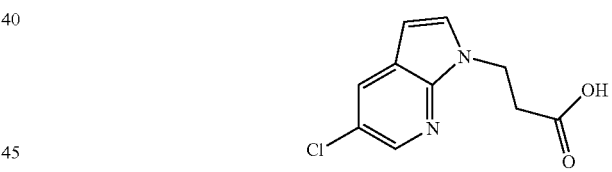

To a solution of NaOH (5.19 g, 129.8 mmol) in water (10 mL) was added tetrabutylammonium bromide (0.35 g, 1.08 mmol), 5-chloro-1H-pyrrolo[2,3-b]pyridine (1.5 g, 9.83 mmol), toluene (60 mL) and methyl 3-bromopropanoate (9.8 g, 59 mmol). The reaction mixture was heated overnight at 100° C. The reaction was quenched with water, the layers were separated and the aqueous layer was extracted with DCM. The combined organic layers were dried over Na$_2$SO$_4$, filtered and concentrated. 3-(5-chloro-1H-pyrrolo[2,3-b]pyridin-1-yl)propanoate solution in THF was treated with NaOH and stirred at RT for 5 hours. The reaction mixture was diluted with water and the pH was adjusted to 1 with 1N HCl to crash out the product. The reaction was then filtered, azeotroped with acetonitrile and dried to give 3-(5-chloro-1H-pyrrolo[2,3-b]pyridin-1-yl)propanoic acid. (1.97 g, 90% yield). $^1$H NMR (400 MHz, DMSO-d6) δ 8.25 (d, J=2.3 Hz, 1H), 8.09 (d, J=2.3 Hz, 1H), 7.64 (d, J=3.5 Hz, 1H), 6.46 (d, J=3.5 Hz, 1H), 4.46 (t, J=7.0 Hz, 2H), 2.82 (t, J=7.0 Hz, 3H). LC/MS (10%-99% CH$_3$CN (0.035% TFA)/H$_2$O (0.05% TFA)), m/z: M+1 obs=225.3; t$_R$=1.20 min.

4-(1-(3-(5-chloro-1H-pyrrolo[2,3-b]pyridin-1-yl)propanoyl)piperidin-4-yl)-N-(thiazol-2-yl)benzenesulfonamide

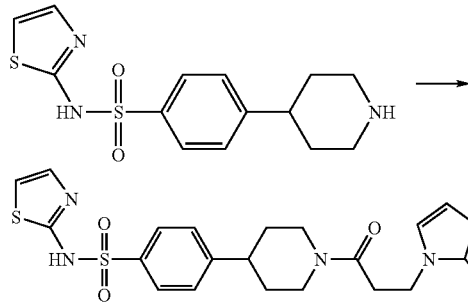

Synthesized according to general procedure 17, method C using THF as solvent. To a solution of 4-(piperidin-4-yl)-N-(thiazol-2-yl)benzenesulfonamide (0.1 g, 0.31 mmol) and 3-(5-chloro-1H-pyrrolo[2,3-b]pyridin-1-yl)propanoic acid (0.076 g, 0.34 mmol) in THF (2 mL) was added HATU (0.153 g, 0.40 mmol) followed by the addition of DIEA (0.08 g, 0.62 mmol) at 0° C. under inert atmosphere. The reaction was quenched with water after 15 minutes, the layers were separated and the aqueous layer was extracted with DCM. The combined organic layers were dried over $Na_2SO_4$, filtered and concentrated. Purification via silica gel chromatography using 0-3% methanol in DCM gave 4-(1-(3-(5-chloro-1H-pyrrolo[2,3-b]pyridin-1-yl)propanoyl)piperidin-4-yl)-N-(thiazol-2-yl)benzenesulfonamide (0.09 g, 55% yield). $^1$H NMR (400 MHz, DMSO-d6) δ 8.25 (d, J=2.3 Hz, 1H), 8.09 (d, J=2.3 Hz, 1H), 7.72 (d, J=8.4 Hz, 2H), 7.68 (d, J=3.5 Hz, 1H), 7.32 (d, J=8.4 Hz, 2H), 7.25 (d, J=4.6 Hz, 1H), 6.82 (d, J=4.6 Hz, 1H), 6.47 (d, J=3.5 Hz, 1H), 5.76 (s, 1H), 4.54-4.48 (m, 3H), 3.87 (d, J=13.7 Hz, 1H), 3.04-2.96 (m, 2H), 2.90-2.76 (m, 2H), 1.75-1.64 (m, 2H), 1.38-1.16 (m, 2H). LC/MS: m/z 530.06 (M+H)$^+$ at 1.55 min (10%-99% $CH_3CN$ (0.035% TFA)/$H_2O$ (0.05% TFA)).

4-(1-(2-(6-Chloro-1H-indol-1-yl)acetyl)piperidin-4-yl)-N-(1,2,4-thiadiazol-5-yl)benzenesulfonamide

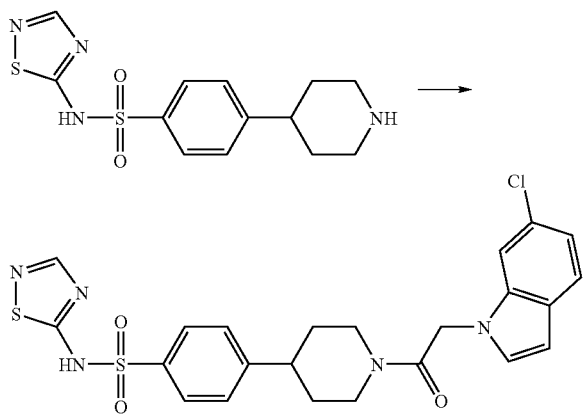

Synthesized according to general procedure 17, method C using DMF as solvent. LC/MS (10%-99% $CH_3CN$ (0.035% TFA)/$H_2O$ (0.05% TFA)), m/z: M+1 obs=515.5; $t_R$ 1.68 min.

(R)-4-(1-(2-(4-Fluoro-1H-indol-1-yl)propanoyl)piperidin-4-yl)-N-(pyrimidin-4-yl)benzenesulfonamide

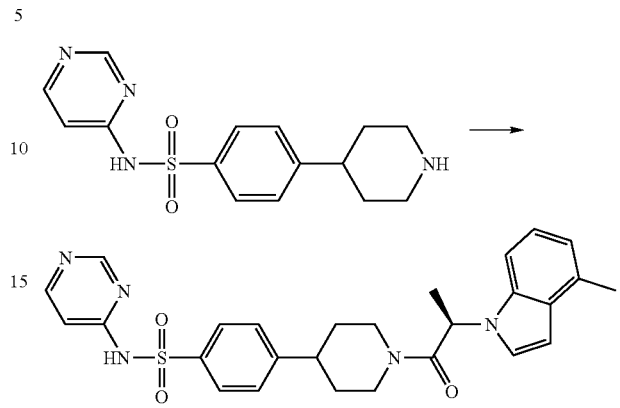

Synthesized according to general procedure 17, method A. LC/MS (10%-99% $CH_3CN$ (0.035% TFA)/$H_2O$ (0.05% TFA)), m/z: M+1 obs=508.5; $t_R$=2.91 min.

4-(1-(2-(6-Chloro-3,4-dihydroquinolin-1(2H)-yl)acetyl)piperidin-4-yl)-N-(pyrimidin-4-yl)benzenesulfonamide

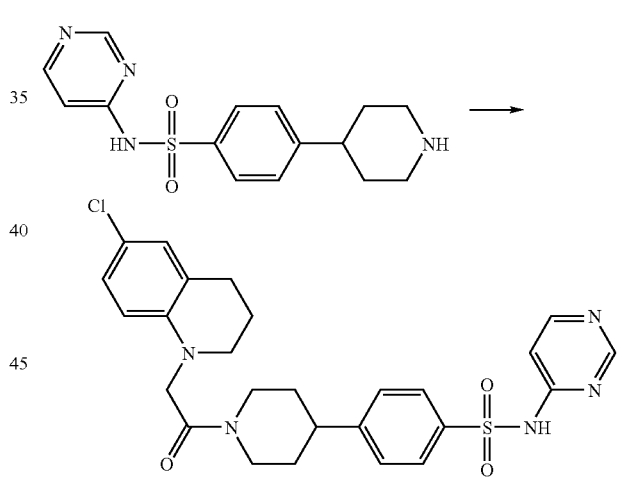

Synthesized according to general procedure 17, method A. LC/MS (10%-99% $CH_3CN$ (0.035% TFA)/$H_2O$ (0.05% TFA)), m/z: M+1 obs=526.3; $t_R$=2.93 min.

Example 6

General Procedure 18

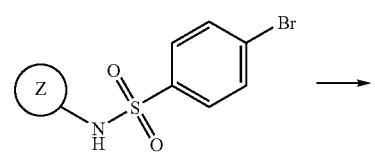

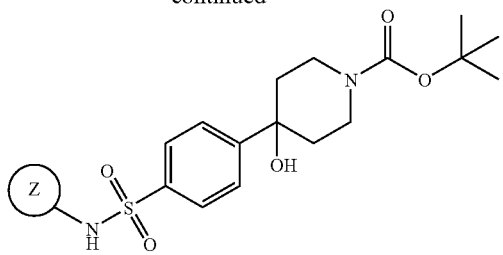

Bromide (1 equivalent, 1 mmol) was dissolved in dry THF (1 mmol) under a nitrogen atmosphere and cooled to <−90° C. n-BuLi (2.5 M in hexanes, 2 equivalents, 2 mmol) was added slowly via a syringe at such rate that the internal temperature did not exceed −85° C. The resulting dark suspension was left stirring at <−90° C. for half an hour. N—BOC-4-piperidone was added at once to the reaction mixture at −90° C. and the mixture was allowed to slowly warm to room temperature. At room temperature the reaction was quenched by addition of saturated aqueous ammonium chloride solution and evaporated to dryness. Ethyl acetate and aqueous ammonium chloride were added to the residue. The organic phase was washed with brine and silica was added to the organic phase before it was evaporated to dryness. The product was purified by column chromatography.

tert-Butyl-4-hydroxy-4-(4-(N-thiazol-2-ylsulfamoyl) phenyl)-piperidine-1-carboxylate

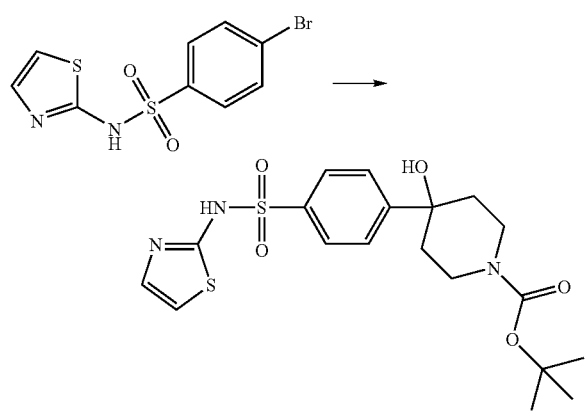

Prepared using general procedure 18. Bromide (5.7 g, 17.9 mmol) was dissolved in dry THF (3.7 g, 18.6 mmol) under a nitrogen atmosphere and cooled to <−90° C. n-BuLi (2.5 M in hexanes, 14.3 mL, 35.8 mmol) was added slowly via a syringe at such rate that the internal temperature did not exceed −85° C. The resulting dark suspension was left stirring at <−90° C. for half an hour. N—BOC-4-piperidone was added at once to the reaction mixture at −90° C. and the mixture was allowed to slowly warm to room temperature. At room temperature the reaction was quenched by the addition of 10 mL saturated aqueous ammonium chloride solution and evaporated to dryness. Ethyl acetate (200 mL) and half saturated aqueous ammonium chloride (300 mL) were added to the residue. The organic phase was washed with brine and 10 g of silica were added to the organic phase before it was evaporated to dryness. Purification via silica gel chromatography using 10-100% ethyl acetate in hexane gave tert-butyl-4-hydroxy-4-(4-(N-thiazol-2-ylsulfamoyl)phenyl)piperidine-1-carboxylate (4.7 g, 59%) as a pink solid. $^1$H-NMR (300 MHz, DMSO-$d_6$): δ 12.67 (s, 1H), 7.71 (d, J=8.5 Hz, 2H), 7.60 (d, J=8.5 Hz, 2H), 7.22 (d, J=4.5 Hz, 1H), 6.80 (d, J=4.5 Hz, 1H), 3.56-3.79 (m, 2H), 3.20-3.00 (m, 2H), 1.78-1.67 (m, 2H), 1.56-1.36 (m, 2H), 1.39 (s, 9H).

General Procedure 19

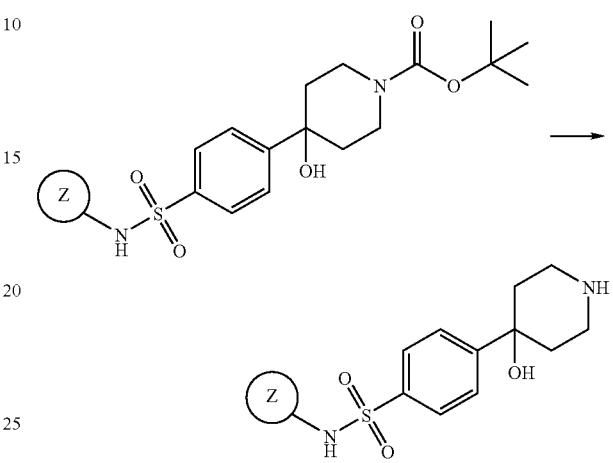

To a suspension of the Boc amine (1 equivalent, 1 mmol) in dichloromethane (45 mL) was added trifluoroacetic acid (2 mL) and the resulting clear solution was stirred at room temperature for one hour. The solution was evaporated to dryness under reduced pressure at 30° C. The residue was stirred with ethyl acetate and the solid was collected by filtration. The desired products were obtained by washing the filtrate with water and organic solvents.

4-(4-Hydroxypiperidin-4-yl)-N-(thiazol-2-yl)benzenesulfonamide

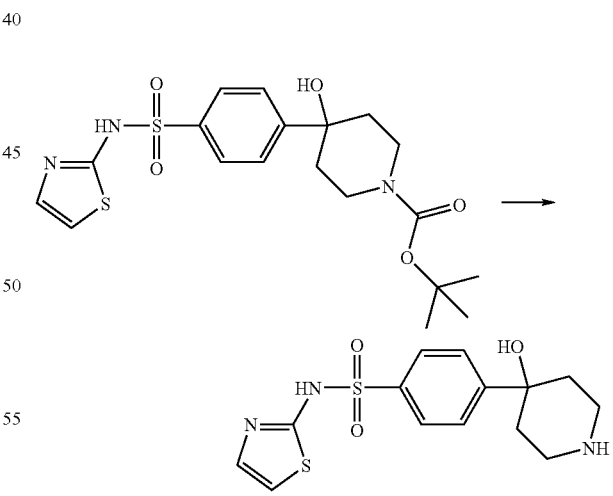

Prepared using general procedure 19. To a suspension of tert-Butyl-4-hydroxy-4-(4-(N-thiazol-2-ylsulfamoyl)phenyl)-piperidine-1-carboxylate (4.7 g, 11 mmol) in dichloromethane (500 mL) was added trifluoroacetic acid (23 mL) and the resulting clear solution was stirred at room temperature for one hour. The solution was evaporated to dryness under reduced pressure at 30° C. The residue was stirred with ethyl acetate (100 mL) and the solid was collected by filtration and washed with ethyl acetate (2×) to yield the trifluoroacetic acid salt. This solid was stirred with saturated aqueous sodium bicarbonate solution (25 mL) and the solid was collected by filtration, washed with water (2×), ethanol (2×), TBME (2×), and dried under vacuum at 50° C. to give 4-(4-hydroxypiperidin-4-yl)-N-(thiazol-2-yl)benzenesulfonamide (2.9 g, 79%) as a pink solid. $^1$H-NMR (300 MHz, DMSO-d$_6$): δ 7.69 (d, J=8.4 Hz, 2H), 7.37 (d, J=8.4 Hz, 2H), 6.99 (d, J=3.8 Hz, 1H), 6.53 (d, J=3.8 Hz, 1H), 3.28-3.13 (m, 4H), 2.11-2.00 (m, 2H), 1.72-1.40 (m, 2H).

General Procedure 20

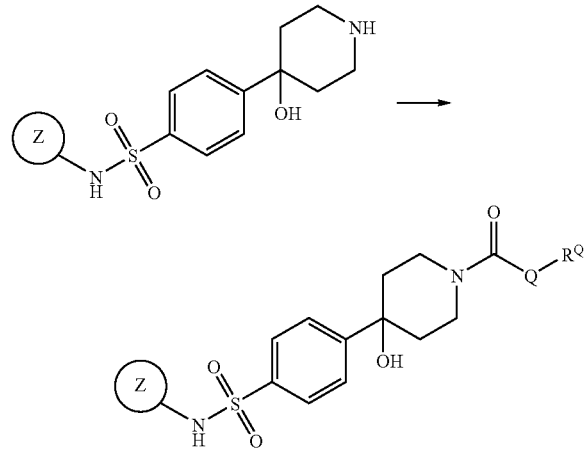

A solution of carboxylic acid (0.088 mmol, 1 equivalent) and HATU (0.088 mmol, 1 equivalent) in DMF (1 mL) was stirred under an N$_2$ atmosphere at 0° C. for 1 h. To this mixture, 4-(piperidin-4-ol)-N-(thiazol-2-yl)benzenesulfonamide (0.088 mmol, 1 equivalent) and NaHCO$_3$ (1-2 equivalents) were added under an N$_2$ atmosphere at RT, and the reaction was stirred for 16 h. The reaction mixture was filtered and purified by Gilson preparative HPLC (5-99% CH$_3$CN—H$_2$O) to isolate the desired product.

4-((S)-2-(2,3-Dichlorophenoxy)propanoyl)-piperidin-4-ol)-N-(thiazol-2-yl)benzenesulfonamide

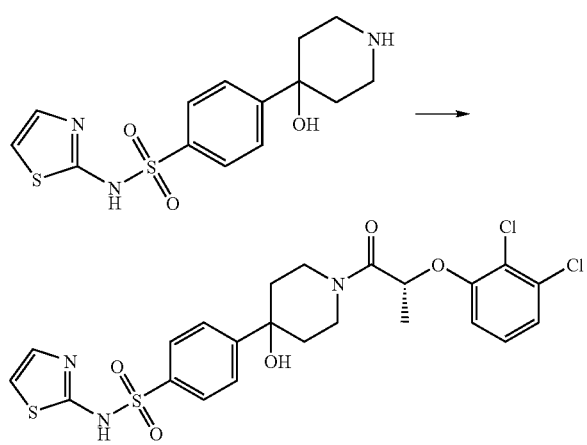

Prepared using general procedure 20. A solution of (S)-2-(2,3-dichlorophenoxy) propanoic acid (20 mg, 0.088 mmol) and HATU (33.5 mg, 0.088 mmol) in DMF (1 mL) was stirred under an N$_2$ atmosphere at 0° C. for 16 h. To this mixture, 4-(piperidin-4-ol)-N-(thiazol-2-yl)benzenesulfonamide (30 mg, 0.088 mmol) and NaHCO$_3$ (7 mg, 0.088 mmol) were added under an N$_2$ atmosphere at RT, and the reaction was stirred for 16 h. The reaction mixture was filtered and purified by Gilson preparative HPLC (5-99% CH$_3$CN—H$_2$O) to isolate 4-((S)-2-(2,3-dichlorophenoxy)propanoyl)-piperidin-4-ol)-N-(thiazol-2-yl)benzenesulfonamide (3 mg, 10%). LC/MS (10%-99% CH$_3$CN (0.035% TFA)/H$_2$O (0.05% TFA)), m/z: M+1 obs=556.2; t$_R$=2.95 min.

4-(1-(2-(6-Chloro-1H-indol-1-yl)acetyl)-4-hydroxypiperidin-4-yl)-N-(thiazol-2-yl)benzenesulfonamide

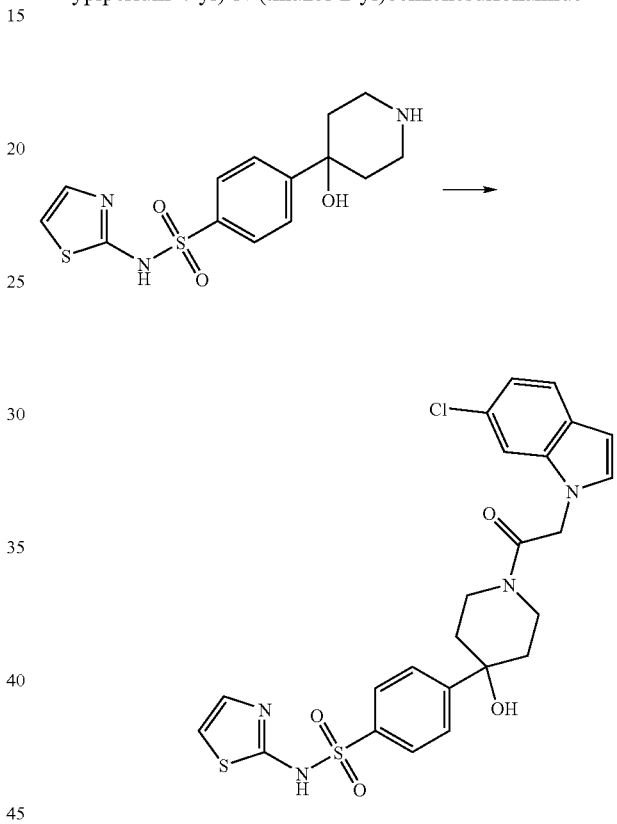

Prepared using general procedure 20. A solution of 2-(6-chloro-1H-indol-1-yl)acetic acid (184 mg, 0.88 mmol) and HATU (335 mg, 0.88 mmol) in DMF (3 mL) was stirred under an N$_2$ atmosphere at 0° C. for 1 h. To this mixture, 4-(4-hydroxypiperidin-4-yl)-N-(thiazol-2-yl)benzenesulfonamide (300 mg, 0.88 mmol) and NaHCO$_3$ (148 mg, 1.76 mmol) were added under an N$_2$ atmosphere at RT, and the reaction was stirred for 16 h. The reaction mixture was filtered and purified by Gilson preparative HPLC (5-99% CH$_3$CN—H$_2$O) to isolate 4-(1-(2-(6-chloro-1H-indol-1-yl)acetyl)-4-hydroxypiperidin-4-yl)-N-(thiazol-2-yl)benzenesulfonamide (246 mg, 52%). LC/MS (10%-99% CH$_3$CN (0.035% TFA)/H$_2$O (0.05% TFA)), m/z: M+1 obs=531.3; t$_R$=2.98 min. $^1$H NMR (400 MHz, DMSO-d6) 6, 7.78 (d, J=8.5 Hz, 2H), 7.63 (d, J=8.4 Hz, 2H), 7.55 (d, J=8.6 Hz, 2H), 7.29 (dd, J=28.5, 3.9 Hz, 2H), 7.03 (dd, J=9.3, 0.9 Hz, 1H), 6.83 (d, J=4.6 Hz, 1H), 6.47 (d, J=3.1 Hz, 1H), 5.23 (q, J=14.8 Hz, 2H), 4.27 (d, J=12.1 Hz, 1H), 3.87 (d, J=12.6 Hz, 1H), 3.51 (t, J=11.9 Hz, 1H), 3.02 (t, J=11.6 Hz, 1H), 2.04-1.97 (m, 1H), 1.81 (m, 1H), 1.67-1.61 (m, 2H).

Example 7

General Procedure 21

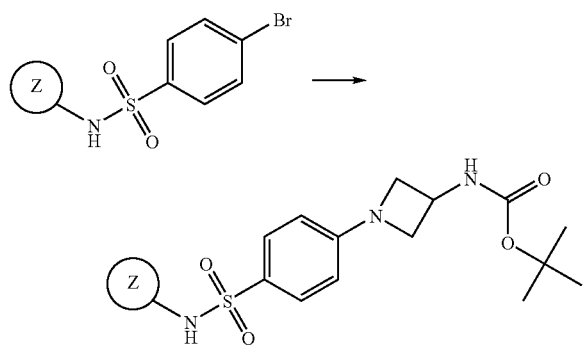

A solution of the bromide (1 equivalent, 1 mmol), tert-butyl azetidin-3-ylcarbamate acetate (1.1 equivalent, 1.1 mmol) sodium tert-butoxide (4.2 equivalents, 4.2 mmol), biphenyl-2-yl-di-tert-butylphosphine (0.12 equivalents, 0.12 mmol), and $Pd_2(dba)_3$ (0.03 equivalents, 0.03 mmol) in toluene (2.5 mL) was stirred at 75° C. for 16 h. The reaction mixture was poured into $H_2O$, and the pH was adjusted to 6. The aqueous layer was extracted with $CH_2Cl_2$, and the organics were combined, washed with saturated aqueous NaCl solution, dried over $MgSO_4$, and concentrated. Purification via silica gel chromatography gave the desired products.

tert-Butyl 1-(4-(N-thiazol-2-ylsulfamoyl)phenyl) azetidin-3-ylcarbamate

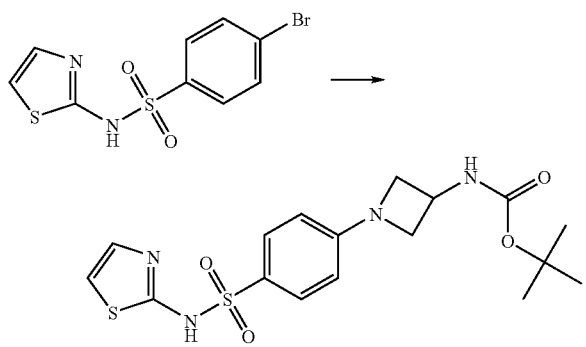

Prepared according to general procedure 21. A solution of 4-bromo-N-(thiazol-2-yl)benzenesulfonamide (2.0 g, 6.3 mmol), tert-butyl azetidin-3-ylcarbamate acetate (1.61 g, 6.9 mmol) sodium tert-butoxide (2.55 g, 26.5 mmol), biphenyl-2-yl-di-tert-butylphosphine (224 mg, 0.76 mmol), and $Pd_2(dba)_3$ (172 mg, 0.19 mmol) in toluene (16 mL) was stirred at 75° C. for 16 h. The reaction mixture was poured into $H_2O$, and the pH was adjusted to 6. The aqueous layer was extracted 4 times with $CH_2Cl_2$, and the organics were combined, washed with saturated aqueous NaCl solution, dried over $MgSO_4$, and concentrated. Purification via silica gel chromatography using 50-70% EtOAc in hexanes gave tert-butyl 1-(4-(N-thiazol-2-ylsulfamoyl)phenyl)azetidin-3-ylcarbamate (0.86 g, 33%). LC/MS (10%-99% $CH_3CN$ (0.035% TFA)/ $H_2O$ (0.05% TFA)), m/z: M+1 obs=411.0; $t_R$=2.54 min.

General Procedure 22

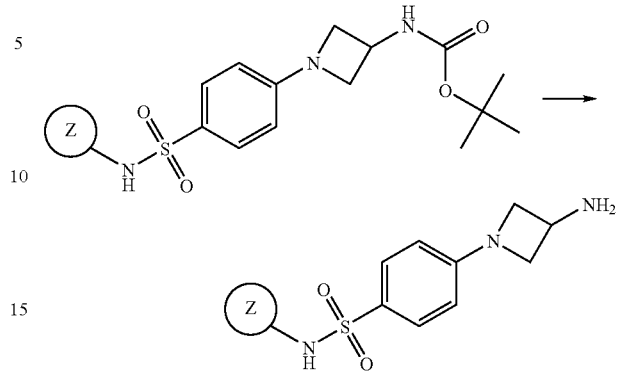

TFA (1.4 mL) was added dropwise to a solution of tert-butyl azetidinylcarbamate (1 equivalent, 1 mmol) in $CH_2Cl_2$ (10 mL), and the reaction was stirred at RT for 2 h. After evaporation of the solvents under reduced pressure, the residue was co-evaporated with EtOH. Trituration with $Et_2O$:$CH_2Cl_2$ gave desired products as TFA salts.

4-(3-Aminoazetidin-1-yl)-N-(thiazol-2-yl)benzenesulfonamide

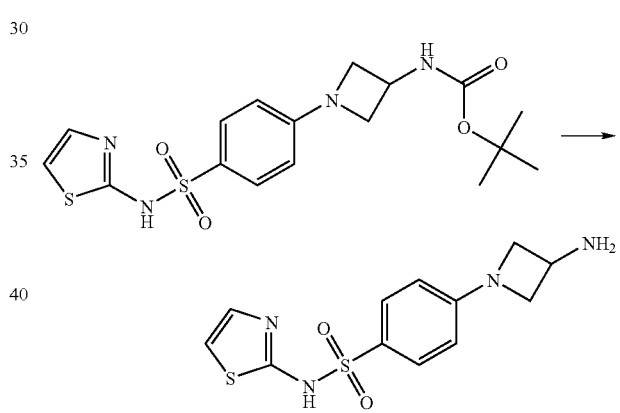

Prepared according to general procedure 22. TFA (3.0 mL) was added dropwise to a solution of tert-butyl 1-(4-(N-thiazol-2-ylsulfamoyl)phenyl)azetidin-3-ylcarbamate (0.86 g, 2.1 mmol) in $CH_2Cl_2$ (20 mL), and the reaction was stirred at RT for 2 h. After evaporation of the solvents under reduced pressure, the residue was co-evaporated with EtOH. Trituration using a 9:1 mixture of $Et_2O$:$CH_2Cl_2$ gave a tan solid which was identified as 4-(3-aminoazetidin-1-yl)-N-(thiazol-2-yl)benzenesulfonamide as a TFA salt (0.83 g, 93%). LC/MS (10%-99% $CH_3CN$ (0.035% TFA)/$H_2O$ (0.05% TFA)), m/z: M+1 obs=311.0; $t_R$=0.48 min.

General Procedure 23

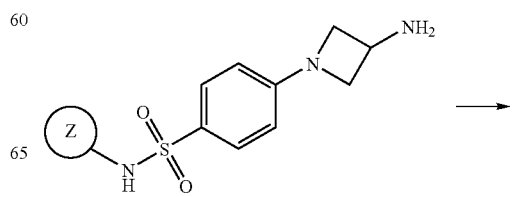

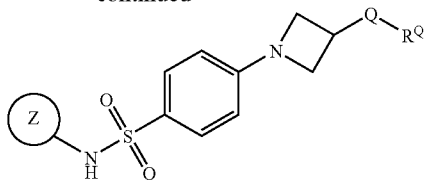

N,N-Diisopropylethylamine (78 µL, 0.45 mmol) was added to a solution of the amine (64 mg, 0.15 mmol), the acid (0.22 mmol) and HATU (91 mg, 0.24 mmol) in acetonitrile (0.4 mL), and the reaction was stirred at RT for 16 h. Purification via reverse phase HPLC (10%-99% CH₃CN (0.035% TFA)/H₂O (0.05% TFA) gave the desired product.

2-(6-Chloro-3,4-dihydroquinolin-1(2H)-yl)-N-(1-(4-(N-thiazol-2-ylsulfamoyl)phenyl)azetidin-3-yl)propanamide

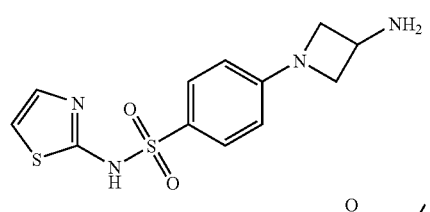

Synthesized according to general procedure 23. LC/MS (10%-99% CH₃CN (0.035% TFA)/H₂O (0.05% TFA)), m/z: M+1 obs=532.2; $t_R$=3.11 min.

1-(2,4-Dichlorophenyl)-N-(1-(4-(N-thiazol-2-ylsulfamoyl)phenyl)azetidin-3-yl)cyclopropanecarboxamide

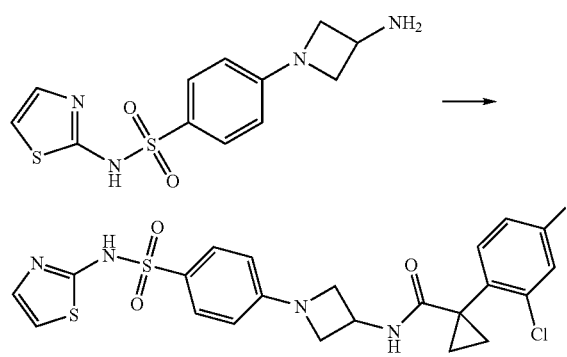

Synthesized according to general procedure 23. LC/MS (10-99% CH₃CN (0.035% TFA)/H₂O (0.05% TFA)), m/z: M+1 obs=523.2; $t_R$=3.04 min.

(S)-2-(1H-indol-1-yl)-N-(1-(4-(N-thiazol-2-ylsulfamoyl)phenyl)azetidin-3-yl)propanamide

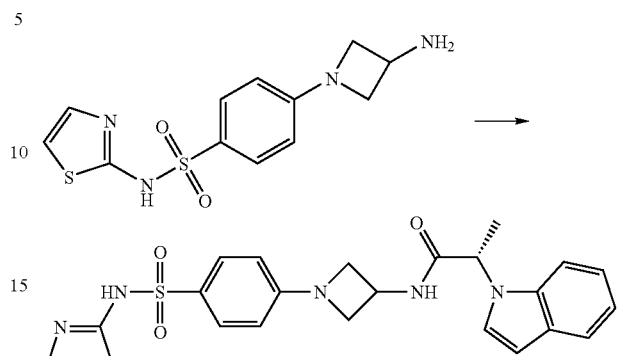

Synthesized according to general procedure 23. LC/MS (10%-99% CH₃CN (0.035% TFA)/H₂O (0.05% TFA)), m/z: M+1 obs=482.0; $t_R$=2.73 min.

3,4-Dichloro-N-{1-[4-(thiazol-2-ylsulfamoyl)-phenyl]-azetidin-3-yl}-benzamide

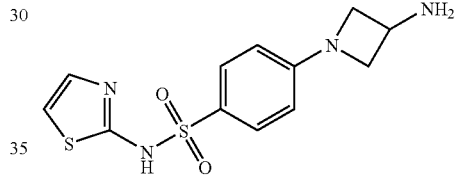

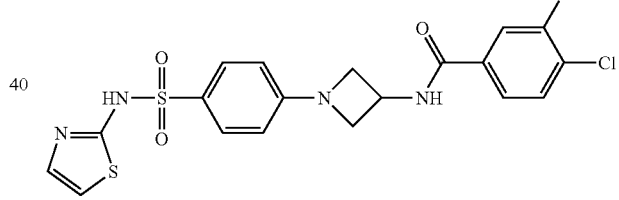

Synthesized according to general procedure 23. LC/MS (10%/99% CH₃CN (0.035% TFA)/H₂O (0.05% TFA)), m/z: M+1 obs=483.2; $t_R$=2.90.

General Procedure 24

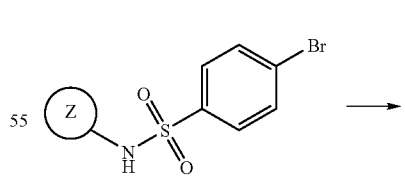

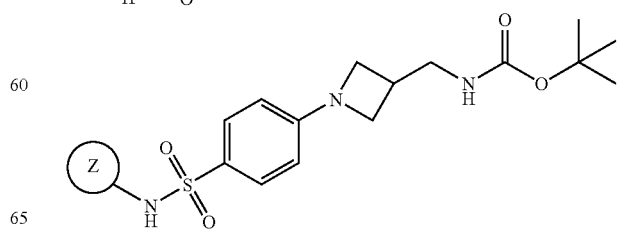

A solution of bromide (1 equivalent, 1 mmol), tert-butyl azetidin-3-ylmethylcarbamate acetate (1.1 equivalent g, 1.1 nmol) sodium tert-butoxide (4.2 equivalents, 4.2 mmol), biphenyl-2-yl-di-tert-butylphosphine (0.12 equivalents, 0.12 mmol), and $Pd_2(dba)_3$ (0.03 equivalents, 0.03 mmol) in toluene (2.5 mL) was stirred at 75° C. for 16 h. The reaction mixture was poured into $H_2O$, and the pH was adjusted to 6. The aqueous layer was extracted with $CH_2Cl_2$, and the organics were combined, washed with saturated aqueous NaCl solution, dried over $MgSO_4$, and concentrated. Purification via silica gel chromatography gave the desired products.

tert-Butyl-(1-(4-(N-thiazol-2-ylsulfamoyl)phenyl)azetidin-3-yl)methylcarbamate

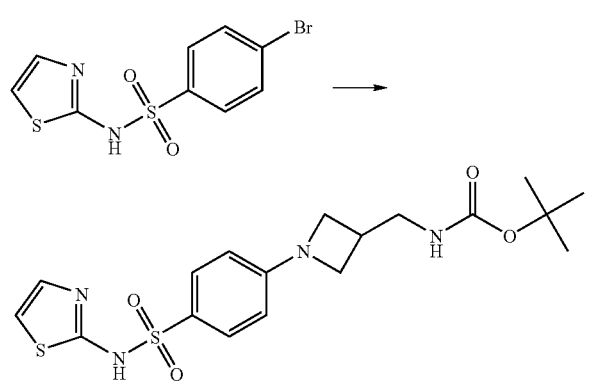

Prepared using general procedure 24. A solution of 4-bromo-N-(thiazol-2-yl)benzenesulfonamide (2.0 g, 6.3 mmol), tert-butyl azetidin-3-ylmethylcarbamate acetate (1.71 g, 6.93 mmol), sodium tert-butoxide (2.55 g, 26.5 mmol), biphenyl-2-yldi-tert-butylphosphine (224 mg, 0.76 mmol), and $Pd2(dba)_3$ (172 mg, 0.19 mmol) in toluene (16 mL) was stirred at 75° C. for 16 h. The reaction mixture was poured into $H_2O$, and the pH was adjusted to 6. The aqueous layer was extracted 4 times with $CH_2Cl_2$, and the organics were combined, washed with saturated aqueous NaCl solution, dried over MgSO4, and concentrated. Purification via silica gel chromatography using 50-90% EtOAc in hexanes gave tert-butyl-(1-(4-(N-thiazol-2-ylsulfamoyl)phenyl)azetidin-3-yl)methylcarbamate (0.58 g, 22%). LC/MS (10%-99% CH3CN (0.035% TFA)/$H_2O$ (0.05% TFA)), m/z: M+1 obs=425.0; $t_R$=2.59 min.

General Procedure 25

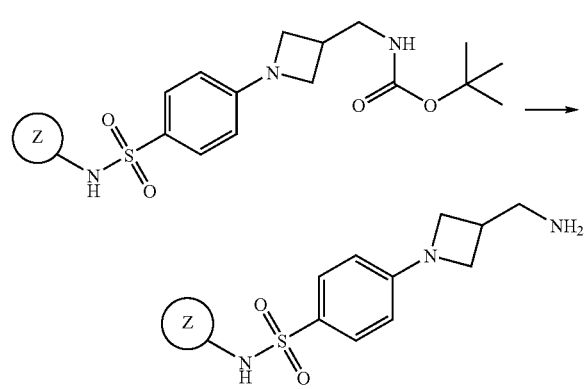

TFA (1.4 mL) was added dropwise to a solution of tert-butyl azetidinylcarbamate (1 equivalent, 1 mmol) in $CH_2Cl_2$ (10 mL), and the reaction was stirred at 0° C.-RT for 2 h. After evaporation of the solvents under reduced pressure, the residue was co-evaporated with EtOH. Trituration with $Et_2O$:$CH_2Cl_2$ gave desired products as TFA salts.

4-(3-(Aminomethyl)azetidin-1-yl)-N-(thiazol-2-yl)benzenesulfonamide

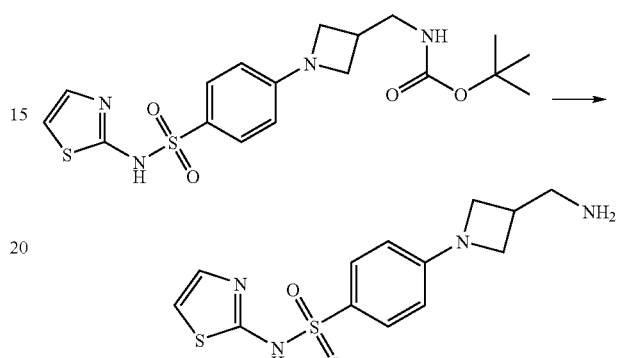

Prepared using general procedure 25. TFA (2.0 mL) was added to a solution of tert-butyl-(1-(4-(N-thiazol-2-ylsulfamoyl)phenyl)azetidin-3-yl)methylcarbamate (0.58 g, 1.2 mmol) in $CH_2Cl_2$ (15 mL), and the reaction was stirred from 0° C. to RT for 3 h. After evaporating the solvents under reduced pressure, the residue was co-evaporated with EtOH. Trituration using a 9:1 mixture of $Et_2O$:$CH_2Cl_2$ gave a white solid which was identified as 4-(3-(aminomethyl)azetidin-1-yl)-N-(thiazol-2-yl)benzenesulfonamide (0.65 g) as the TFA salt. LC/MS (10%-99% $CH_3CN$ (0.035% TFA)/$H_2O$ (0.05% TFA)), m/z: M+1 obs=325.2; $t_R$=0.59 min.

General Procedure 26

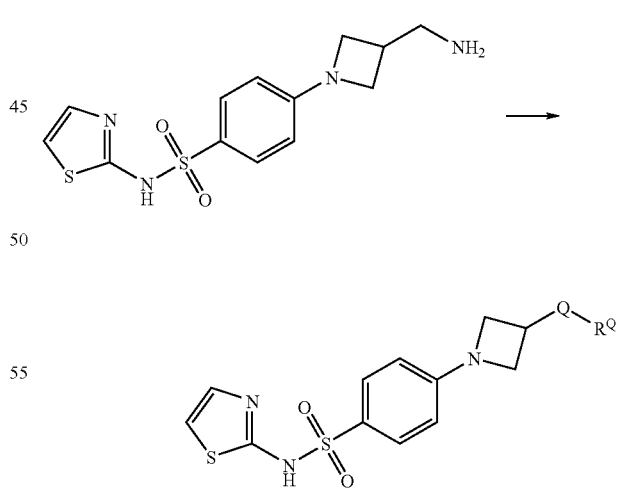

N,N-Diisopropylethylamine (78 μL, 0.45 mmol) was added to a solution of the amine (83 mg, 0.15 mmol), the acid (0.22 mmol) and HATU (91 mg, 0.24 mmol) in acetonitrile (0.4 mL), and the reaction was stirred at RT for 16 h. Purification via reverse phase HPLC (10%-99% $CH_3CN$ (0.035% TFA)/$H_2O$ (0.05% TFA) gave the desired products.

577

(S)-2-(4-Fluoro-1H-indol-1-yl)-N-((1-(4-(N-thiazol-2-ylsulfamoyl)phenyl)azetidin-3-yl)methyl)propanamide

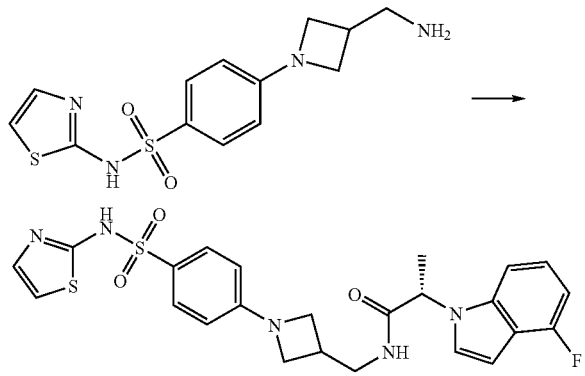

Synthesized according to general procedure 26. LC/MS (10%-99% CH$_3$CN (0.035% TFA)/H$_2$O (0.05% TFA)), m/z: M+1 obs=514.4; t$_R$=2.74 min.

2-(4-Chloro-3-fluorophenoxy)-N-((1-(4-(N-thiazol-2-ylsulfamoyl)phenyl)azetidin-3-yl)methyl)acetamide

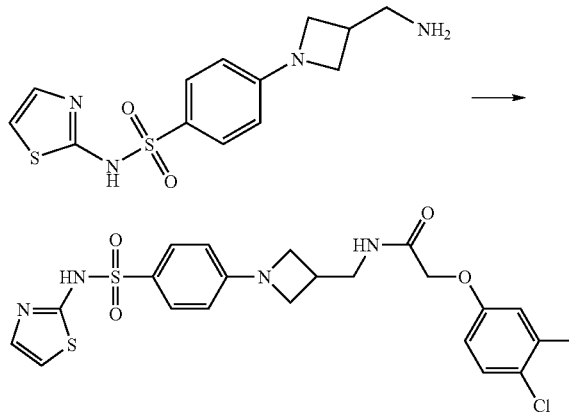

Synthesized according to general procedure 26. LC/MS (10%-99% CH$_3$CN (0.035% TFA)/H$_2$O (0.05% TFA)), m/z: M+1 obs=511.2; t$_R$=2.71 min.

Example 8

General Procedure 27

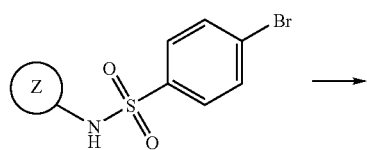

-continued

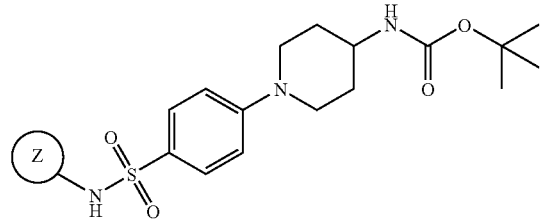

A mixture of 4-bromobenzenesulfonamide (1 equivalent), piperidine (1-10 equivalents), Pd$_2$(dba)$_3$ (0.02-0.075 equivalents), 2-(di-t-butylphosphino)biphenyl (0.08-0.2 equivalents), NaO-tBu (2-6 equivalents) and toluene (0.1-0.4 M of 4-bromobenzene sulfonamide) was heated at 70-80° C. for 2-6 h. Purification via silica gel chromatography using 10% MeOH in CH$_2$Cl$_2$ (with addition of 1-2% triethylamine) gave the desired product.

tert-Butyl 1-(4-(N-thiazol-2-ylsulfamoyl)phenyl)piperidin-4-ylcarbamate

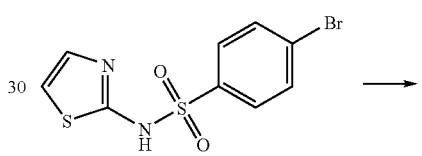

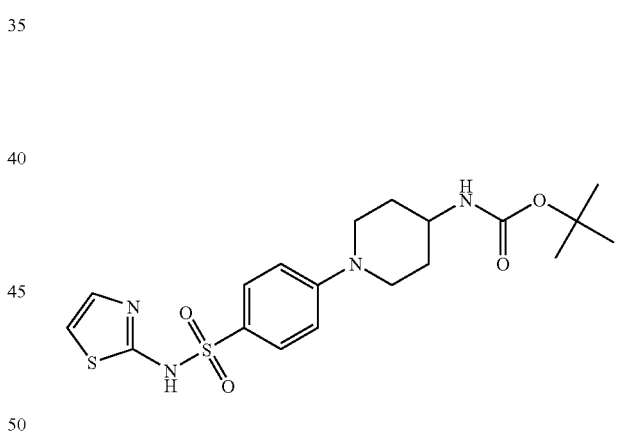

Prepared using general procedure 27. A mixture of 4-bromo-N-(thiazol-2-yl)benzenesulfonamide (500 mg, 1.57 mmol), tert-butyl piperidin-4-ylcarbamate (314 mg, 1.57 mmol), Pd$_2$(dba)$_3$ (43 mg, 0.05 mmol), 2-(di-t-butylphosphino)biphenyl (56 mg, 0.19 mmol), NaOtBu (423 mg, 4.4 mmol) and toluene (4 mL) was stirred at 70° C. for 3 h. After allowing the mixture to cool to RT, H$_2$O (50 mL) and EtOAc (50 mL) were added. After acidifying with a 1 M HCl solution to pH 4, the layers were separated, and the aqueous phase was extracted 3 times with CH$_2$Cl$_2$ (50 mL). The combined organic extracts were dried over MgSO$_4$ and absorbed onto Celite. Purification via silica gel chromatography using 10% MeOH in CH$_2$Cl$_2$ gave tert-butyl-1-(4-(N-thiazol-2-ylsulfamoyl)phenyl)piperidin-4-ylcarbamate as an off-white foam (520 mg, 76%). LC/MS (10%-99% CH$_3$CN (0.035% TFA)/H$_2$O (0.05% TFA)), m/z: M+1 obs=439.5; t$_R$=2.56 min.

tert-Butyl-1-(4-(N-1,2,4-thiadiazol-5-ylsulfamoyl)phenyl)piperidin-4-ylcarbamate

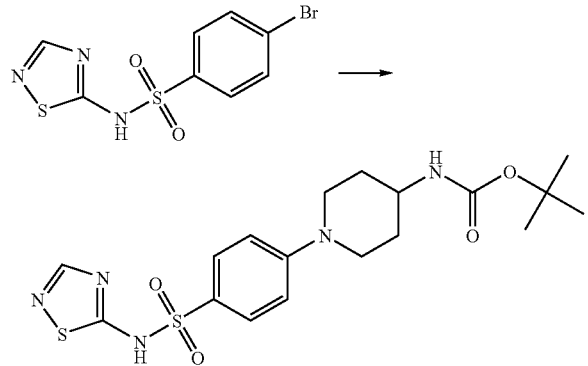

Prepared using general procedure 27. A mixture of 4-bromo-N-(1,2,4-thiadiazol-5-yl)benzenesulfonamide (3.7 g, 11.6 mmol), tert-butyl-piperidin-4-ylcarbamate (2.32 g, 11.6 mmol), Pd$_2$(dba)$_3$ (319 mg, 0.35 mmol), phosphine (415 mg, 1.39 mmol), NaOtBu (3.55 g, 34.8 mmol) and toluene (30 mL) was stirred at 70° C. for 3 h. After allowing the mixture to cool to RT, H$_2$O (50 mL) and EtOAc (50 mL) were added. After acidifying with a 1 M HCl solution to pH 4, the layers were separated, and the aqueous phase was extracted 3 times with CH$_2$Cl$_2$ (50 mL). The combined organic extracts were dried over MgSO$_4$ and absorbed onto Celite. Purification via silica gel chromatography using 10% MeOH in CH$_2$Cl$_2$ gave tert-Butyl 1-(4-(N-1,2,4-thiadiazol-5-ylsulfamoyl)phenyl)-piperidin-4-ylcarbamate as an off-white foam (357 mg, 70%). LC/MS (10%-99% CH$_3$CN (0.035% TFA)/H$_2$O (0.05% TFA)), m/z: M+1 obs=440.5; t$_R$=2.76 min.

General Procedure 28

Method A

TFA (1.4 mL) was added dropwise to a solution of tert-butyl carbamate (1 equivalent, 1 mmol) in CH$_2$Cl$_2$ (10 mL), and the reaction was stirred at RT for 2 h. The reaction was worked up or evaporated. Trituration or precipitation gave desired products.

Method B

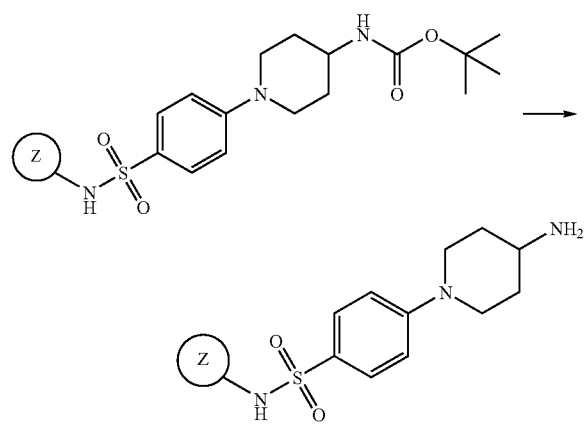

Under N$_2$ atmosphere, a solution of tert-butyl carbamate (1 equivalent, 3.74 mmol) in 4 M HCl/dioxane (60 mL) was stirred at RT for 16 hrs. The formed precipitate was filtered off and washed with dioxane (20 mL), to give the desired products.

4-(4-Aminopiperidin-1-yl)-N-(thiazol-2-yl)benzenesulfonamide

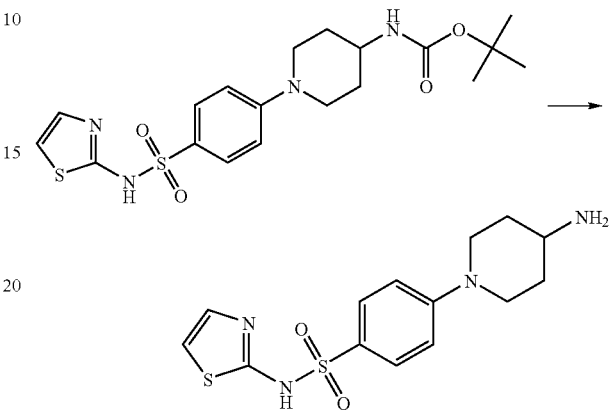

Prepared using general procedure 28, method A. A mixture of tert-butyl-1-(4-(N-thiazol-2-ylsulfamoyl)phenyl)piperidin-4-ylcarbamate (657 mg, 1.5 mmol), TFA (1.5 mL) and CH$_2$Cl$_2$ (10 mL) was stirred at RT under an N$_2$ atmosphere for 2.5 h. The reaction was poured into saturated NaHCO$_3$ solution (50 mL) and acidified to pH 3-4 with a 1 M HCl solution. The mixture was then extracted with CH$_2$Cl$_2$ (3×50 mL). Since LCMS analysis showed that the product was still in the aqueous layer, it was neutralized with saturated NaHCO$_3$ resulting in precipitation of a white solid which was filtered, washed with MeOH, and dried under vacuum to obtain 4-(4-aminopiperidin-1-yl)-N-(thiazol-2-yl)benzenesulfonamide (200 mg, 38% over 2 steps). $^1$H NMR (400 MHz, DMSO-d6) δ 7.57-7.45 (m, 4H), 6.94-6.89 (m, 3H), 6.44 (d, J=3.9 Hz, 1H), 3.83 (d, J=13.5 Hz, 2H), 3.20-3.14 (m, 1H), 2.83 (t, J=11.8 Hz, 2H), 1.84 (d, J=9.3 Hz, 2H), 1.51-1.41 (m, 2H).

4-(4-Aminopiperidin-1-yl)-N-(1,2,4-thiadiazol-5-yl)benzenesulfonamide

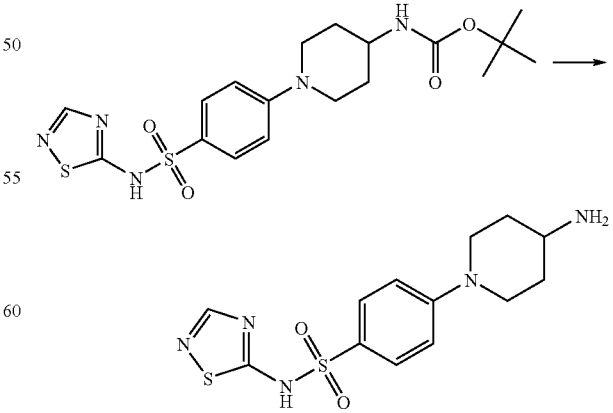

Prepared using general procedure 28, method B. Under N$_2$ atmosphere, a solution of tert-butyl-1-(4-(N-1,2,4-thiadiazol- 5-ylsulfamoyl)phenyl)piperidin-4-ylcarbamate (3 g, 7.02 mmol) in 4 M HCl/dioxane (100 mL) was stirred at RT for 16 h. The formed precipitate was filtered off and washed with dioxane (20 mL) to give 4-(4-aminopiperidin-1-yl)-N-(1,2,4-thiadiazol-5-yl)benzenesulfonamide (1.88 g, 81%). LC/MS (10%/99% CH$_3$CN (0.035% TFA)/H$_2$O (0.05% TFA)), m/z: M+1 obs=340; t$_R$=1.28 min.

General Procedure 29

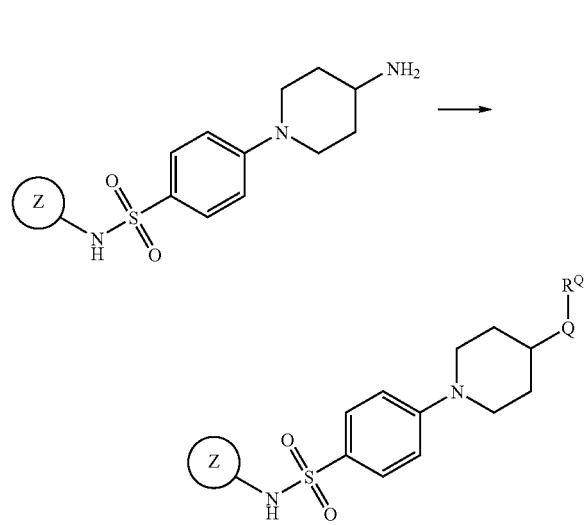

A solution of HATU (38 mg, 0.1 mmol) and triethylamine or DIEA (42 µL, 0.3 mmol) in acetonitrile or a 1:1 mixture of CH$_2$Cl$_2$ and DMF (1.0 mL) was added to the amine (34 mg, 0.1 mmol) and the acid (0.1 mmol). The reaction was stirred at RT overnight. After diluting the mixture with a 1:1 mixture of DMSO:MeOH (0.5 mL), the reaction was purified via reverse phase HPLC (5%-95% CH$_3$CN (0.035% TFA)/H$_2$O (0.05% TFA) to give the desired product.

2-(3-Chloro-4-fluorophenoxy)-N-(1-(4-(N-thiazol-2-ylsulfamoyl)phenyl)piperidin-4-yl)acetamide

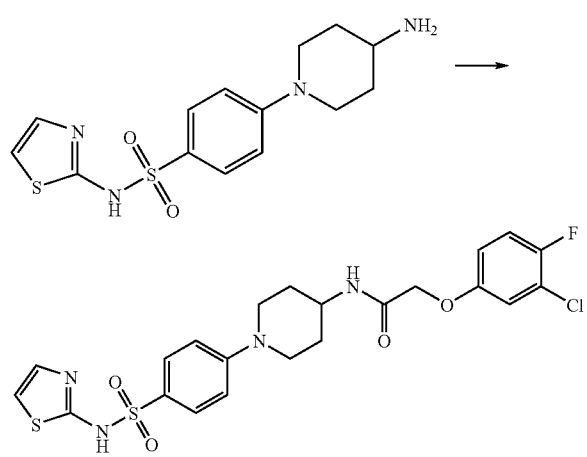

Synthesized according to general procedure 29. LC/MS (10%-99% CH$_3$CN (0.035% TFA)/H$_2$O (0.05% TFA)), m/z: M+1 obs=525.0; t$_R$=2.92 min.

3-(5-Chloro-1H-indol-1-yl)-N-(1-(4-(N-thiazol-2-ylsulfamoyl)phenyl)piperidin-4-yl)propanamide

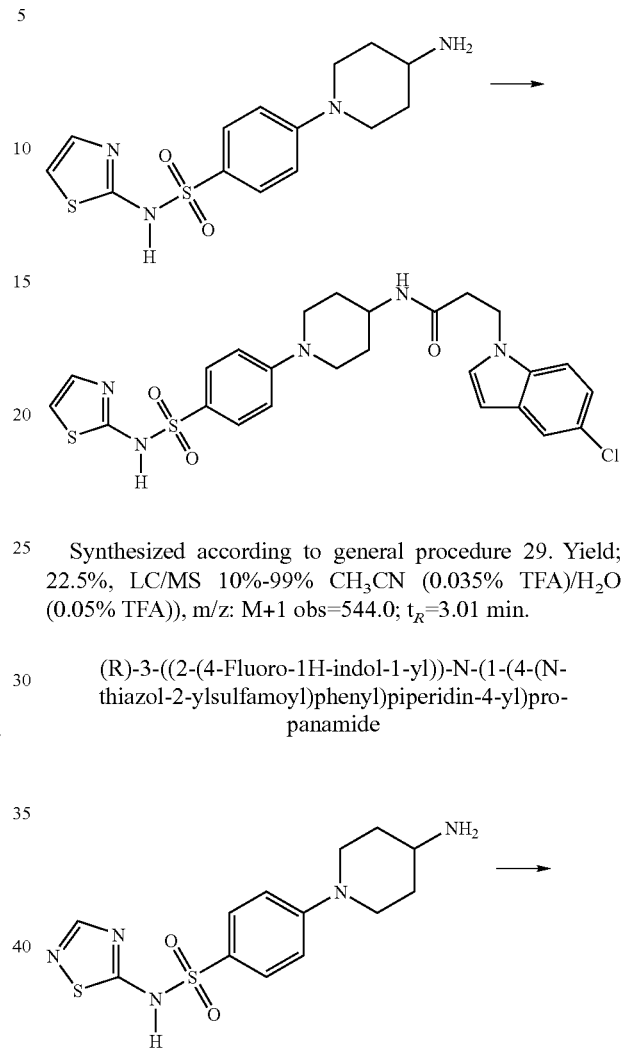

Synthesized according to general procedure 29. Yield; 22.5%, LC/MS 10%-99% CH$_3$CN (0.035% TFA)/H$_2$O (0.05% TFA)), m/z: M+1 obs=544.0; t$_R$=3.01 min.

(R)-3-((2-(4-Fluoro-1H-indol-1-yl))-N-(1-(4-(N-thiazol-2-ylsulfamoyl)phenyl)piperidin-4-yl)propanamide Synthesized according to general procedure 29. Yield; 35%, LC/MS 10%-99% CH$_3$CN (0.035% TFA)/H$_2$O (0.05% TFA)), m/z: M+1 obs=529.3; t$_R$=2.90 min. $^1$H NMR (400 MHz, DMSO-d4) 6, 8.41 (s, 1H), 8.29 (d, J=7.7 Hz, 1H), 7.57 (d, J=9.1 Hz, 2H), 7.53 (d, J=3.3 Hz, 1H), 7.30 (d, J=8.1 Hz, 1H), 7.13-7.08 (m, 1H), 7.01 (d, J=9.2 Hz, 2H), 6.81 (dd, J=10.6, 7.8 Hz, 1H), 6.51 (d, J=3.3 Hz, 1H), 5.12 (q, J=7.0 Hz, 1H), 3.85-3.76 (m, 3H), 3.04-2.93 (m, 2H), 1.74 (dd, J=48.6, 12.2 Hz, 1H), 1.64 (d, J=7.0 Hz, 4H), 1.50-1.31 (m, 2H).

3-(7-Chloro-1H-indol-1-yl)-N-(1-(4-(N-thiazol-2-ylsulfamoyl)phenyl)piperidin-4-yl)acetamide

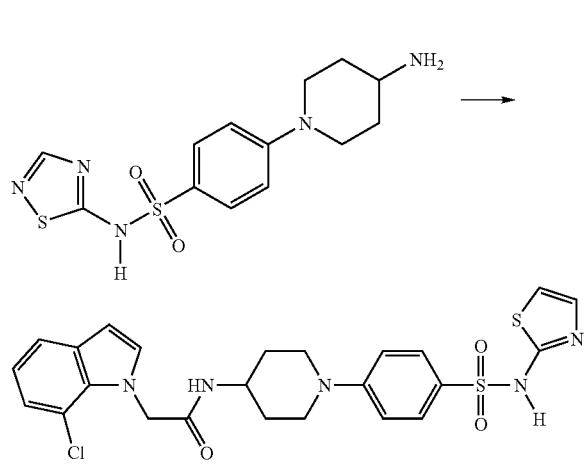

Synthesized according to general procedure 29. Yield; 31%, LC/MS 10%-99% CH$_3$CN (0.035% TFA)/H$_2$O (0.05% TFA)), m/z: M+1 obs=531.3; t$_R$=2.84 min. $^1$H NMR (400 MHz, DMSO-d6) δ 8.36 (s, 1H), 8.09 (d, J=7.8 Hz, 1H), 7.58 (d, J=9.1 Hz, 2H), 7.51 (d, J=8.8 Hz, 1H), 7.36 (s, 1H), 7.10 (d, J=7.6 Hz, 1H), 7.02-6.97 (m, 3H), 6.50 (d, J=3.2 Hz, 1H), 5.09 (s, 2H), 3.82 (d, J=13.4 Hz, 3H), 3.00 (t, J=11.2 Hz, 2H), 1.79 (d, J=9.4 Hz, 2H), 1.49-1.40 (m, 2H).

2,4-Dichloro-N-(1-(4-(N-thiazol-2-ylsulfamoyl)phenyl)piperidin-4-yl)benzamide

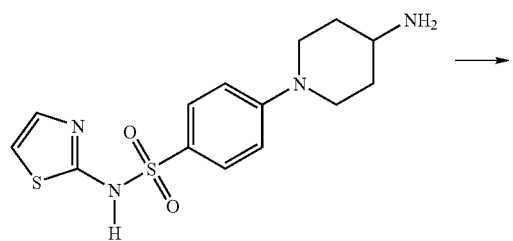

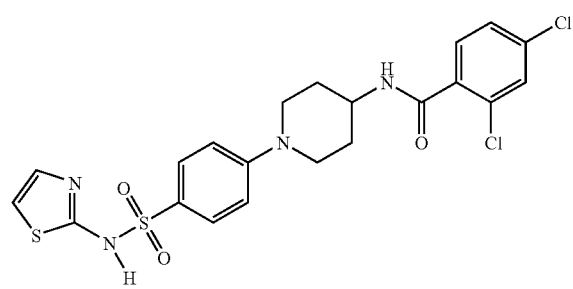

Synthesized according to general procedure 29. LC/MS (10%-99% CH$_3$CN (0.035% TFA)/H$_2$O (0.05% TFA)), m/z: M+1 obs=511.0; t$_R$=2.85 min.

General Procedure 30

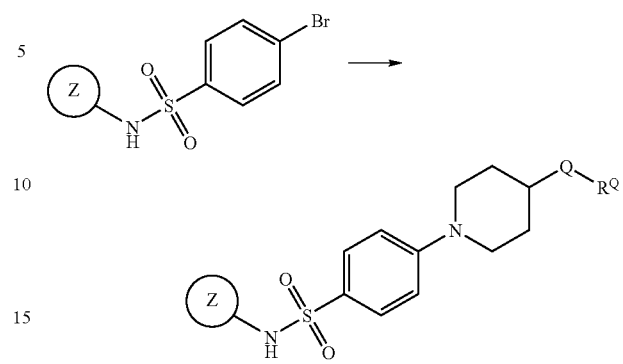

A mixture of 4-bromobenzenesulfonamide (1 equivalent), piperidine (1 equivalents), Pd$_2$(dba)$_3$ (0.02-0.075 equivalents), 4,5-bis(diphenyl)phosphino-9,9-dimethyl xanthene (0.08-0.3-0.8 equivalents) or 2-(di-t-butylphosphino)biphenyl (0.08-0.2 equivalents), NaO-tBu (2-6 equivalents) and 1,4-dioxane or toluene (0.1-0.4 M of 4-bromobenzenesulfonamide) was heated at 80° C. for 1-2 h. Purification via silica gel chromatography using 10% MeOH in CH$_2$Cl$_2$ (with addition of 1-2% triethylamine) gave the desired product.

4-(4-(6-Chloro-1,2,3,4-tetrahydroquinoline-1-carbonyl)piperidin-1-yl) N-(1,2,4-thiadiazol-5-yl)benzenesulfonamide

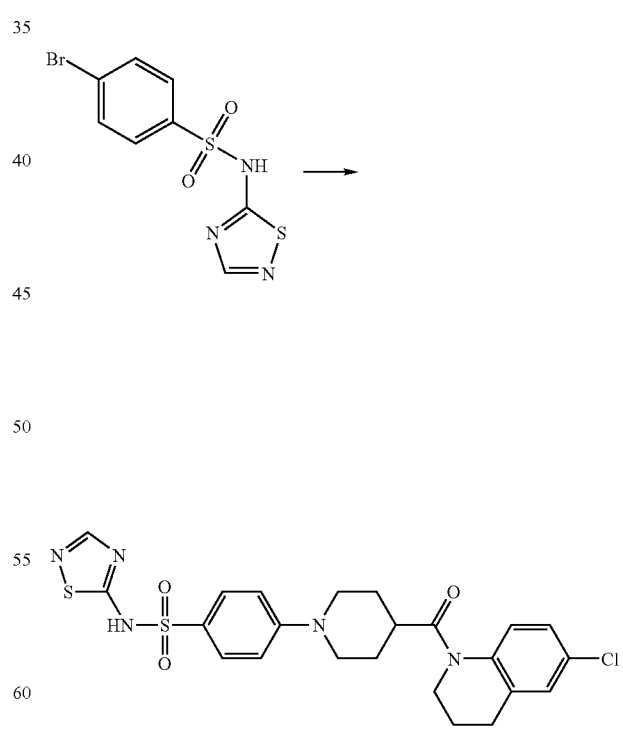

Synthesized according to general procedure 30 using xanthene ligand and dioxane. LC/MS (10%-99% CH$_3$CN (0.035% TFA)/H$_2$O (0.05% TFA)), m/z: M+1 obs=518.3; t$_R$=3.15 min.

4-(1,3-Dihydrospiro[indene-2,4'-piperidine]-1'-yl)-N-(thiazol-2-yl) benzenesulfonamide

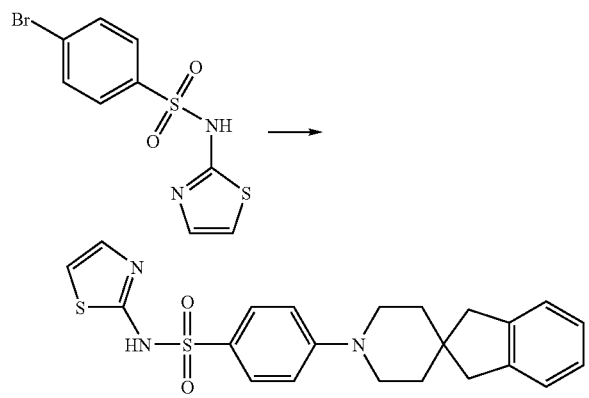

Synthesized according to general procedure 30 using 2-(di-t-butylphosphino) biphenyl and toluene. LC/MS (10%-99% CH$_3$CN (0.035% TFA)/H$_2$O (0.05% TFA)), m/z: M+1 obs=426.1; t$_R$=3.03 min.

Example 9

General Procedure 31

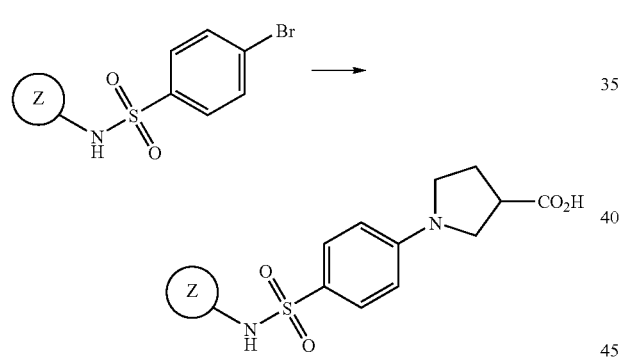

A mixture of 4-bromobenzenesulfonamide (1 equivalent), pyrrolidine-3-carboxylic acid (1-10 equivalents), Pd$_2$(dba)$_3$ (0.02-0.075 equivalents), 2-(dicyclohexylphosphino)-2',6'-dimethoxybiphenyl (0.08-0.2 equivalents), NaO-tBu (2-6 equivalents) and toluene (0.1-0.4 M of 4-bromobenzenesulfonamide) was heated at 80° C. for 2-6 h. Purification via silica gel chromatography using 10% MeOH in CH$_2$Cl$_2$ (with addition of 1-2% triethylamine) gave the desired product.

1-(4-(N-Thiazol-2-ylsulfamoyl)phenyl)pyrrolidine-3-carboxylic acid

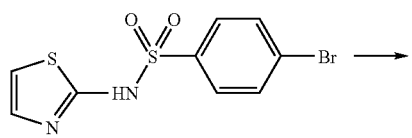

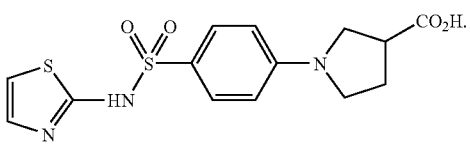

Prepared using general procedure 31. A mixture of 4-bromo-N-(thiazol-2-yl)benzenesulfonamide (4.70 g, 14.7 mmol), pyrrolidine-3-carboxylic acid (3.66 g, 22.1 mmol, 1.5 eq.), NaO-t-Bu (7.62 g, 79.3 mmol, 5.4 eq.), 2-(dicyclohexylphosphino)-2',6'-dimethoxybiphenyl (0.722 g, 1.76 mmol, 12 mol %) and tris(dibenzylideneacetone)-dipalladium (0.40 g, 3 mol %) in toluene (45 mL) was heated at 100° C. for 20 hours. The brown suspension was cooled to room temperature. Purification via silica gel chromatography using 1-10% MeOH in CH$_2$Cl$_2$ gave 1-(4-(N-thiazol-2-ylsulfamoyl)-phenyl)pyrrolidine-3-carboxylic acid (2.26 g, 43%). $^1$H NMR (300 MHz, DMSO-d$_6$): δ 7.55 (d, J=8 Hz, 2H); 7.17 (dd, J=4.7, 1.1 Hz, 1H); 6.73 (dd, J=4.7, 1.1 Hz, 1H); 6.55 (d, J=8 Hz, 2H); 3.50-3.23 (m, 4H, partly obscured by water from DMSO-d$_6$); 3.20-3.15 (m, 1H); 2.23-2.09 (m, 2H).

General Procedure 32

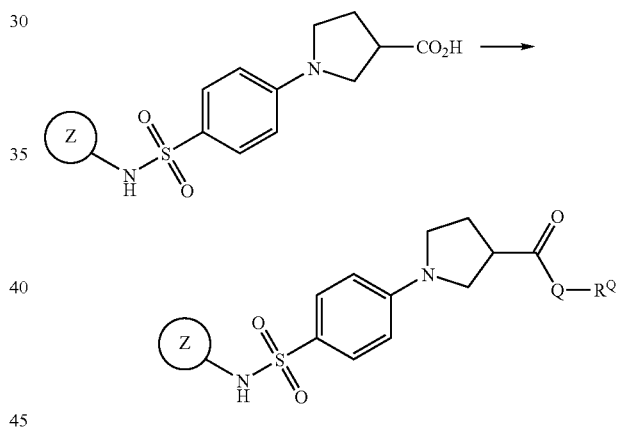

To the carboxylic acid (1.5 equivalent, 0.17 mmol) and NaHCO$_3$ (1.5 equivalent, 0.17 mmol) was added HATU (1.5 equivalent, 0.17 mmol) in DMF (0.15-0.25 M, 0.25 mL). A solution of amine (1 equivalent, 0.11 mmol) in DMF (0.15-0.25 M, 0.25 mL) was then added and the reaction mixture was stirred at RT for 19 h. Purification via reverse phase HPLC using 10%-99% CH$_3$CN (0.035% TFA)/H$_2$O (0.05% TFA) gave the desired product.

4-(3-(1,2,3,4-Tetrahydroquinoline-1-carbonyl)pyrrolidin-1-yl)-N-(thiazol-2-yl)benzenesulfonamide

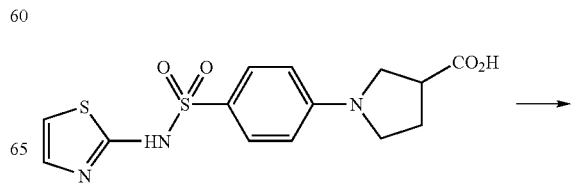

-continued

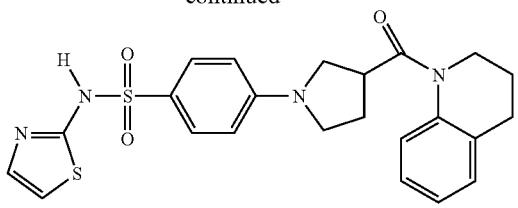

Synthesized according to general procedure 32. LC/MS (10%/99% CH₃CN (0.035% TFA)/H₂O (0.05% TFA)), m/z: M+1 obs=469; $t_R$=1.59 min.

4-(3-(6-Fluoro-1,2,3,4-tetrahydroquinoline-1-carbonyl)pyrrolidin-1-yl)-N-(thiazol-2-yl)benzenesulfonamide

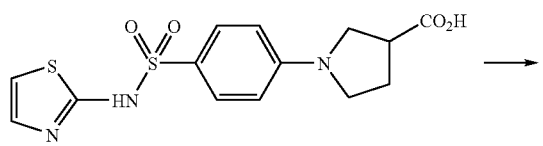

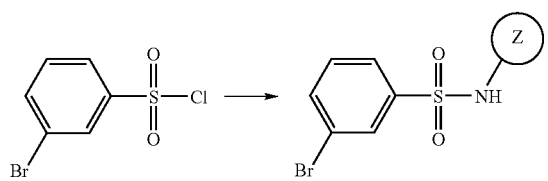

Synthesized according to general procedure 32. LC/MS (10%-99% CH₃CN (0.035% TFA)/H₂O (0.05% TFA)), m/z: M+1 obs=487; $t_R$=1.61 min.

Example 10

General Procedure 33

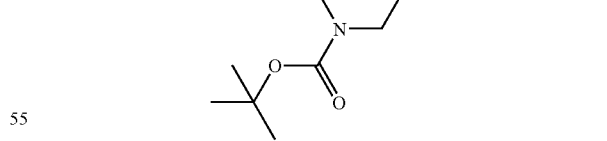

A mixture of 3-bromobenzene-1-sulfonyl chloride (17.61 mmol, 1 equivalent), amino heterocycle (17.61 mmol, 1 equivalent) and pyridine (2.2-4.4 M) was stirred under an N₂ atmosphere at RT for 19 h. Purification via silica gel chromatography using 5% MeOH in CH₂Cl₂ gave the desired product.

3-Bromo-N-(thiazol-2-yl)benzenesulfonamide

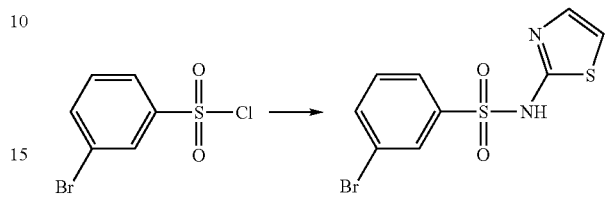

Synthesized according to general procedure 33. Yield: 55%. ¹H NMR (400 MHz, DMSO-d6) δ 7.89 (t, J=1.8 Hz, 1H), 7.83-7.79 (m, 1H), 7.52 (t, J=7.9 Hz, 2H), 7.10 (dd, J=168.4, 4.6 Hz, 2H). LC/MS (10%-99% CH₃CN (0.035% TFA)/H₂O (0.05% TFA)), m/z: M+1 obs=319.0; $t_R$=2.56 min.

General Procedure 34

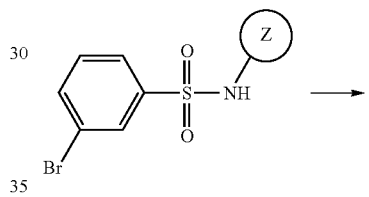

A mixture of 3-bromobenzenesulfonamide (3.14 mmol, 1 equivalent), tert-butyl piperazine-1-carboxylate (3.76 mmol, 1.2 equivalents), Pd₂(dba)₃ (0.23 mmol, 0.02-0.075 equivalents), 2-(di-t-butylphosphino)biphenyl (0.314 mmol, 0.08-0.2 equivalents), NaO-tBu (12.56 mmol, 2-6 equivalents) and toluene (0.1-0.4 M of 3-bromobenzenesulfonamide) was heated at 80° C. for 2-6 h. Purification via silica gel chromatography using 10% MeOH in CH₂Cl₂ (with addition of 1-2% triethylamine) gave the desired product.

589
tert-Butyl 4-(3-(N-thiazol-2-ylsulfamoyl)phenyl)piperazine-1-carboxylate

590
4-(piperazin-1-yl)-N-(thiazol-2-yl)benzenesulfonamide

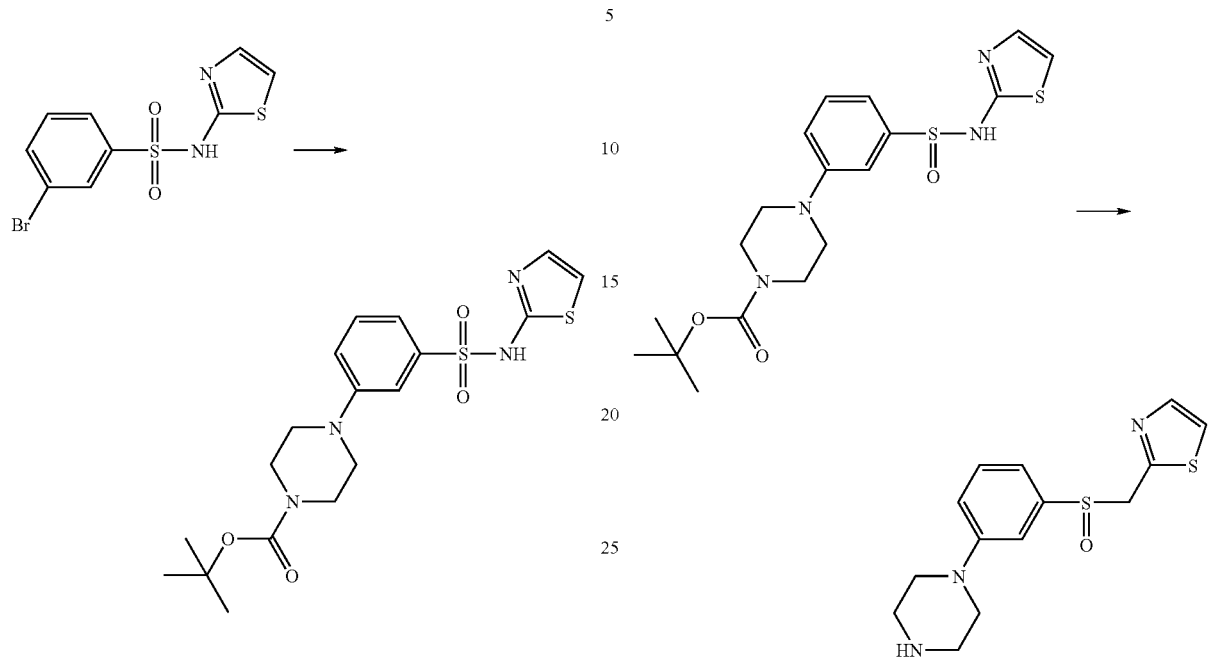

Synthesized according to general procedure 34. Yield: 82%. $^1$H NMR (400 MHz, DMSO-d6) δ 7.39-7.13 (m, 5H), 6.81 (d, J=4.6 Hz, 1H), 3.60-3.13 (m, 8H), 1.42 (s, 9H). LC/MS (10%/99% CH$_3$CN (0.035% TFA)/H$_2$O (0.05% TFA)), m/z: M+1 obs=425.2; t$_R$=3.24 min.

General Procedure 35

Prepared using general procedure 35. Under N$_2$ atmosphere, a solution of tert-butyl 4-(3-(N-thiazol-2-ylsulfamoyl)phenyl)piperizine-1-carboxylate (1 g, 2.35 mmol) in 4 M HCl/dioxane (117 mL) was stirred at RT for 16 hrs. The formed precipitate was filtered off and washed with dioxane (20 mL) to give 4-(piperazin-1-yl)-N-(thiazol-2-yl)benzenesulfonamide (0.405 g, 53%). LC/MS (10-99% CH$_3$CN (0.035% TFA)/H$_2$O (0.05% TFA)), m/z: M+1 obs=324; t$_R$=1.28 min.

General Procedure 36

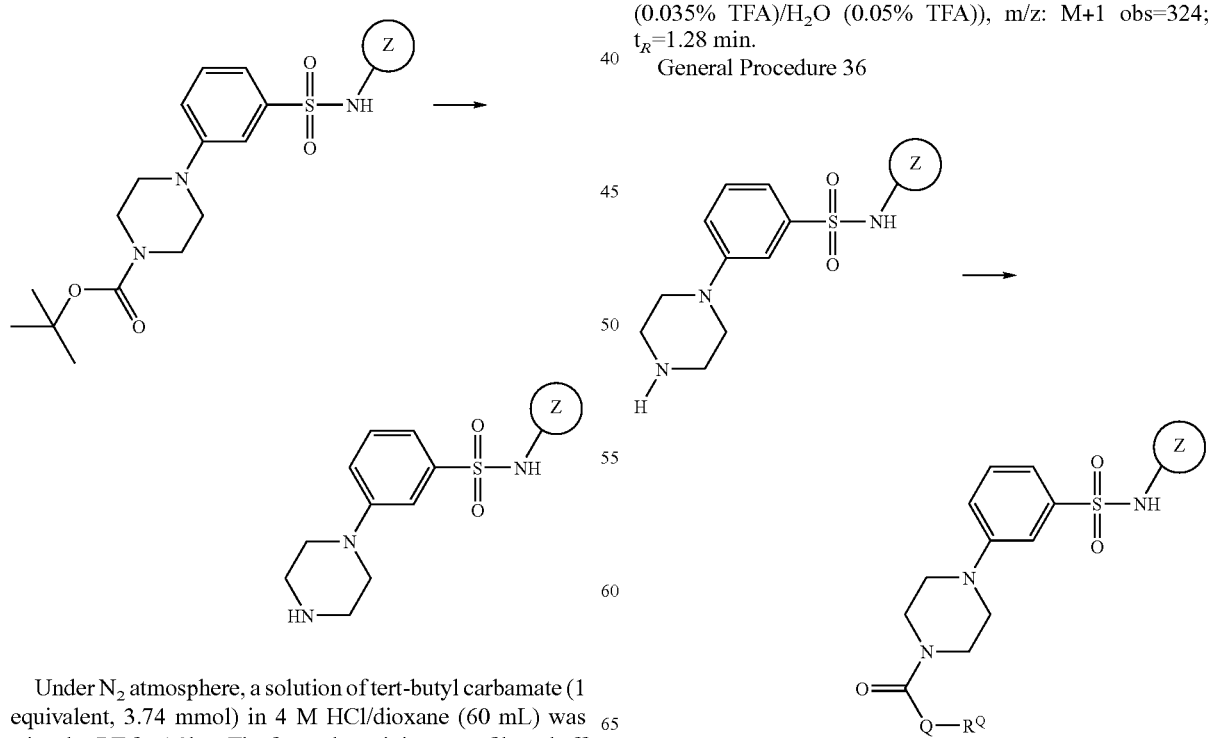

Under N$_2$ atmosphere, a solution of tert-butyl carbamate (1 equivalent, 3.74 mmol) in 4 M HCl/dioxane (60 mL) was stirred at RT for 16 hrs. The formed precipitate was filtered off and washed with dioxane (20 mL), gave desired products.

To the carboxylic acid (1.5 equivalent, 0.17 mmol) and NaHCO₃ (1.5 equivalent, 0.17 mmol) was added HATU (1.5 equivalent, 0.17 mmol) in DMF (0.15-0.25 M, 0.25 mL). A solution of the amine (1 equivalent, 0.11 mmol) in DMF (0.15-0.25 M, 0.25 mL) was then added and the reaction mixture was stirred at RT for 19 h. Purification via reverse phase HPLC using 10%-99% CH₃CN (0.035% TFA)/H₂O (0.05% TFA) gave the desired product.

(S)-3-(4-(2-(2,3-Dichlorophenoxy)propanoyl)piperazin-1-yl)-N-(thiazol-2-yl)benzenesulfonamide

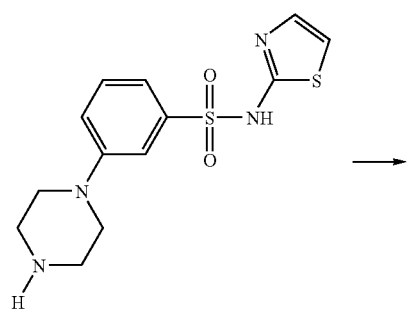

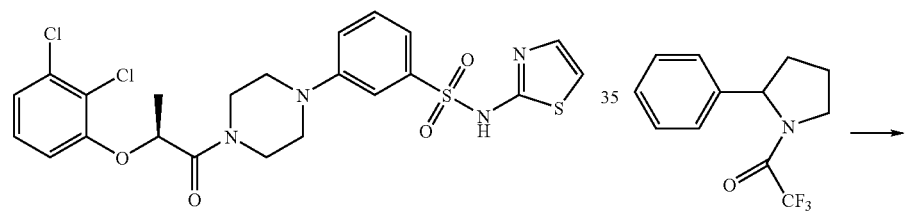

Synthesized according to general procedure 36. LC/MS (10%-99% CH₃CN (0.035% TFA)/H₂O (0.05% TFA)), m/z: M+1 obs=542; $t_R$=3.22 min.

(S)-3-(4-(2-(4-Fluoro-1H-indol-1-yl)propanoyl)piperazin-1-yl)-N-(thiazol-2-yl)benzenesulfonamide

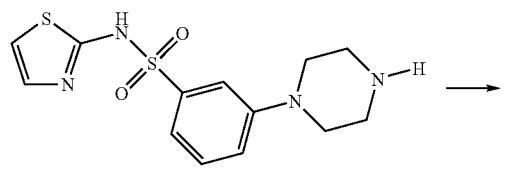

Synthesized according to general procedure 36. LC/MS (10%-99% CH₃CN (0.035% TFA)/H₂O (0.05% TFA)), m/z: M+1 obs=514; $t_R$=3.08 min.

Example 11

2,2,2-Trifluoro-1-(2-phenylpyrrolidin-1-yl)ethanone

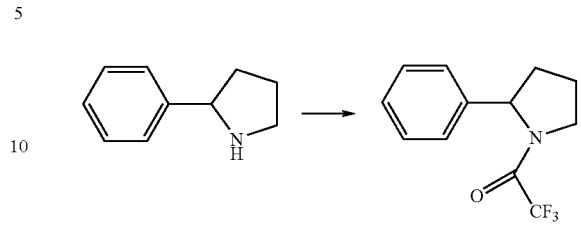

Under an N₂ atmosphere at −78° C., 2,2,2-trifluoroacetic anhydride (5.0 g, 33.9 mmol) was added dropwise to a solution of 2-phenylpyrrolidine (4.7 mL, 33.8 mmol), triethylamine (4.7 mL, 33.9 mmol), and CH₂Cl₂ (50 mL). The reaction was allowed to warm to RT over a period of 30 minutes. After evaporating the solvents under reduced pressure, purification via silica gel chromatography using 7/3 hexanes/EtOAc gave 2,2,2-trifluoro-1-(2-phenylpyrrolidin-1-yl)ethanone as a white solid (6.1 g, 62%). LC/MS (10%-99% CH₃CN (0.035% TFA)/H₂O (0.05% TFA)), m/z: M+1 obs=244.3; $t_R$=3.17 min.

4-(1-(2,2,2-Trifluoroacetyl)pyrrolidin-2-yl)benzene-1-sulfonyl chloride

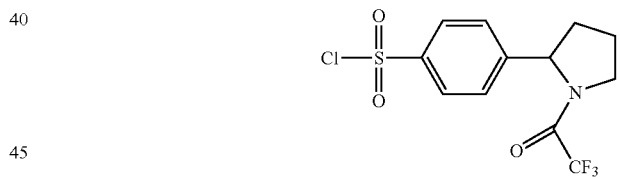

At 0° C., 2,2,2-trifluoro-1-(2-phenylpyrrolidin-1-yl)ethanone (2.0 g, 8.2 mmol) was added to chlorosulfonic acid (10 mL) and allowed to warm to 25° C. over 30 min. Then the mixture was poured into ice water and extracted with EtOAc. The organic layer was concentrated to obtain 4-(1-(2,2,2-trifluoroacetyl)pyrrolidin-2-yl)benzene-1-sulfonyl chloride as a clear oil which was used in the next reaction step without further purification.

General Procedure 37

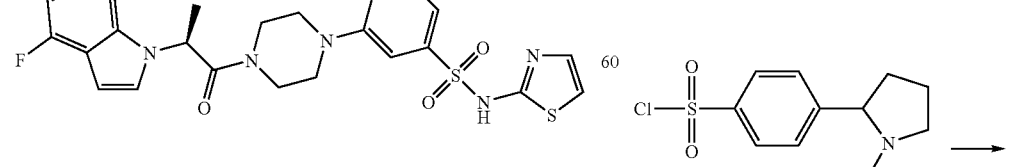

-continued

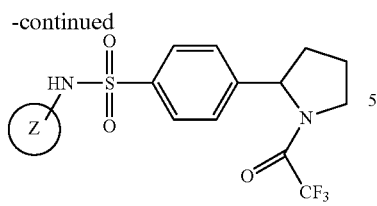

Under an $N_2$ atmosphere, a mixture of the 4-(1-(2,2,2-trifluoroacetyl)pyrrolidin-2-yl)benzene-1-sulfonyl chloride (1 equivalent, 1 mmol), the amino heterocycle (1 equivalent, 1 mmol), and pyridine (0.7 mL) was stirred at RT for 19 h. The crude product was purified via silica gel chromatography and tituration to give the desired products.

N-(Thiazol-2-yl)-4-(1-(2,2,2-trifluoroacetyl)pyrrolidin-2-yl)benzenesulfonamide

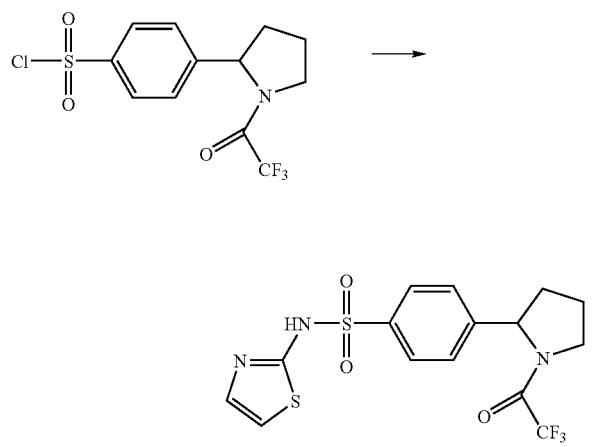

Prepared using general procedure 37. Under an $N_2$ atmosphere, a mixture of the 4-(1-(2,2,2-trifluoroacetyl)pyrrolidin-2-yl)benzene-1-sulfonyl chloride (1.1 g, 5.8 mmol), 2-aminothiazole (0.58 g, 5.8 mmol), and pyridine (4.0 mL) was stirred at RT for 19 h. The crude product was purified via silica gel chromatography using 3% MeOH in $CH_2Cl_2$. The resulting oil was taken up in a 2:1 mixture of $CH_2Cl_2$:$Et_2O$ (12 mL) and cooled to 0° C. for 20 minutes. The formed precipitate was filtered off and dried under vacuum to obtain N-(thiazol-2-yl)-4-(1-(2,2,2-trifluoroacetyl)pyrrolidin-2-yl)benzene-sulfonamide as a white solid (750 mg, 32%). LC/MS (10%-99% $CH_3CN$ (0.035% TFA)/$H_2O$ (0.05% TFA)), m/z: M+1 obs=405.1; $t_R$=2.68 min.

General Procedure 38

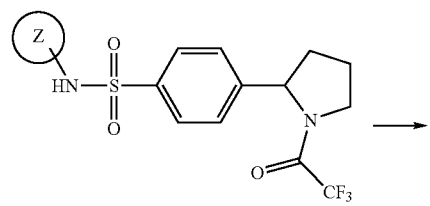

-continued

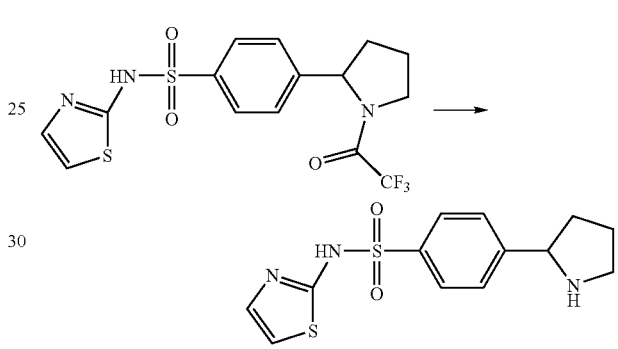

A solution of sulfonamide (1 equivalent), NaOH (10 equivalents), and $H_2O$ (0.25 M) was stirred at RT for 1 h, then cooled to 0° C. Acetic acid (10 equivalents) was added, and the reaction was stirred at 0° C. for 20 min. The formed precipitate was filtered off and dried under vacuum to give the desired product 4-(Pyrrolidin-2-yl)-N-(thiazol-2-yl)benzenesulfonamide Synthesized according to general procedure 38. A solution of N-(thiazol-2-yl)-4-(1-(2,2,2-trifluoroacetyl)pyrrolidin-2-yl)benzenesulfonamide (750 mg, 1.8 mmol), NaOH (221 mg, 5.5 mmol), and $H_2O$ (2.5 mL) was stirred at RT for 1 h, then cooled to 0° C. Hydrochloric acid (0.45 mL, 5.5 mmol) was added, and the reaction was stirred at 0° C. for 20 min. The formed precipitate was filtered off and dried under vacuum to give 4-(pyrrolidin-2-yl)-N-(thiazol-2-yl)benzenesulfonamide (300 mg, 53%). LC/MS (10%-99% $CH_3CN$ (0.035% TFA)/$H_2O$ (0.05% TFA)), m/z: M+1 obs=310.3; $t_R$=0.44 min.

General Procedure 39

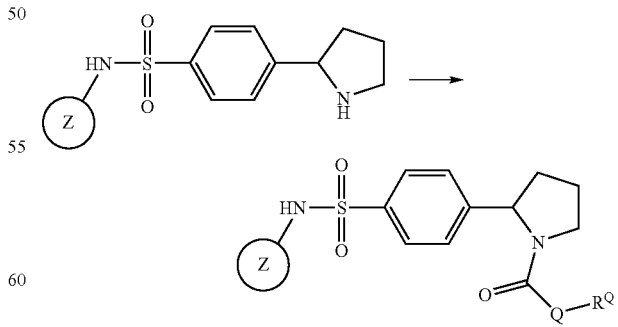

A solution of the sulfonamide (1 equivalent), BOP-reagent (1-1.5 equivalent), triethylamine (1-1.5 equivalent), and carboxylic acid (1-1.5 equivalent) in DMF (0.3-0.5 M) was stirred under an $N_2$ atmosphere at RT for 19 h. Purification via 4-(1-(2-(6-Chloro-1H-indol-1-yl)acetyl)pyrrolidin-2-yl)-N-(thiazol-2-yl)benzenesulfonamide

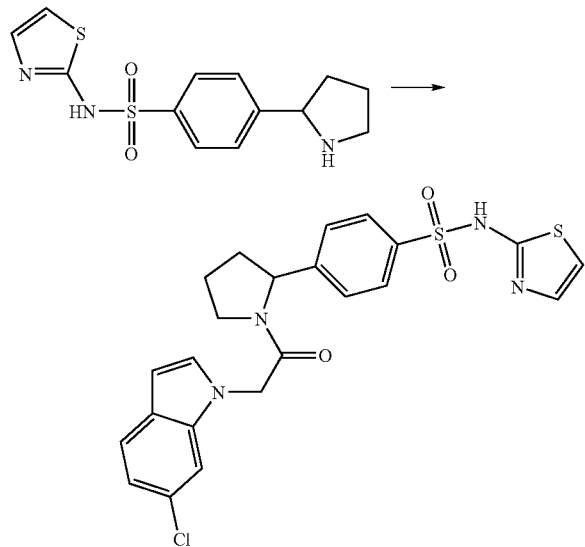

Synthesized according to general procedure 39. LC/MS (10%-99% CH$_3$CN (0.035% TFA)/H$_2$O (0.05% TFA)), m/z: M+1 obs=501.3; t$_R$=3.08 min.

4-(1-(3-(5-Chloro-1H-indol-1-yl)propanoyl)pyrrolidin-2-yl)-N-(thiazol-2-yl)benzenesulfonamide

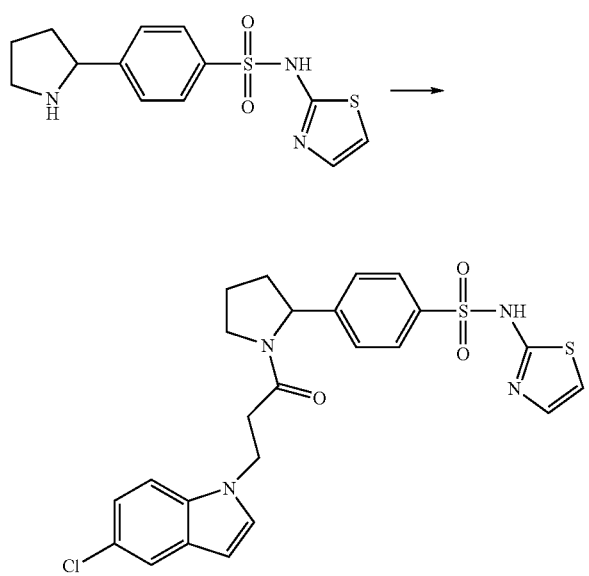

Synthesized according to general procedure 39. LC/MS (10%-99% CH$_3$CN (0.035% TFA)/H$_2$O (0.05% TFA)), m/z: M+1 obs=515.5; t$_R$=3.18 min.

Example 12

General Procedure 40

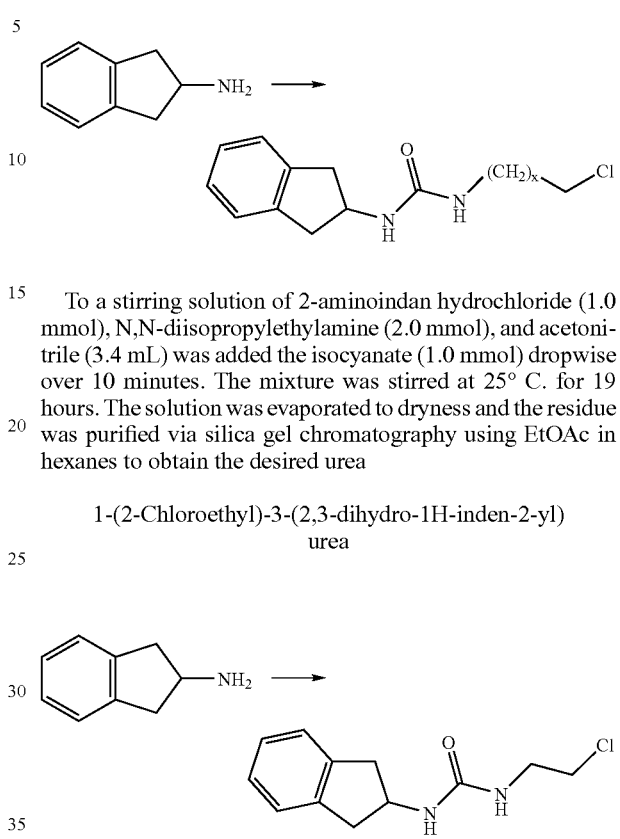

To a stirring solution of 2-aminoindan hydrochloride (1.0 mmol), N,N-diisopropylethylamine (2.0 mmol), and acetonitrile (3.4 mL) was added the isocyanate (1.0 mmol) dropwise over 10 minutes. The mixture was stirred at 25° C. for 19 hours. The solution was evaporated to dryness and the residue was purified via silica gel chromatography using EtOAc in hexanes to obtain the desired urea 1-(2-Chloroethyl)-3-(2,3-dihydro-1H-inden-2-yl)urea Synthesized according to general procedure 40. The reaction was set up with 2-aminoindan hydrochloride (5.0 g, 29.5 mmol), N,N-diisopropylethylamine (10.3 mL, 58.9 mmol), acetonitrile (100 mL), and 2-chloroethylisocyanate (2.52 mL, 29.5 mmol). Purification via silica gel chromatography using 50% EtOAc in hexanes gave the desired urea as a white solid (3.3 g, 13.8 mmol, 47% yield). $^1$H NMR (400 MHz, DMSO-d6) δ 7.23-7.18 (m, 2H), 7.15-7.11 (m, 2H), 6.38 (d, J=7.3 Hz, 1H), 6.03 (t, J=5.7 Hz, 1H), 4.36-4.28 (m, 1H), 3.57 (t, J=6.2 Hz, 2H), 3.38-3.29 (m, 2H), 3.12 (dd, J=7.1, 15.8 Hz, 2H), 2.68 (dd, J=5.5, 15.8 Hz, 2H).

1-(4-Chloropropyl)-3-(2,3-dihydro-1H-inden-2-yl)urea

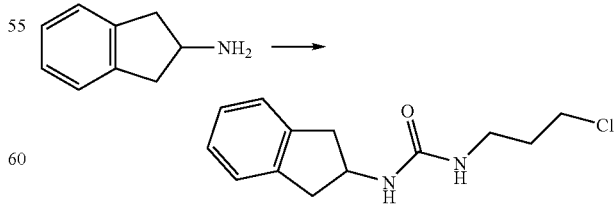

Synthesized according to general procedure 40. The reaction was set up with 2-aminoindan hydrochloride (2.0 g, 11.8 mmol), N,N-diisopropylethylamine (4.1 mL, 23.6 mmol), acetonitrile (20 mL), and 3-chloropropylisocyanate (1.2 mL, 11.8 mmol). Purification via silica gel chromatography using 80% EtOAc in hexanes gave the desired urea as a white solid (1.9 g, 7.5 mmol, 64% yield). $^1$H NMR (400 MHz, DMSO-d6) δ 7.23-7.19 (m, 2H), 7.15-7.11 (m, 2H), 6.13 (d, J=7.3 Hz, 1H), 5.86 (t, J=5.7 Hz, 1H), 4.35-4.27 (m, 1H), 3.62 (t, J=6.5 Hz, 2H), 3.14-3.08 (m, 4H), 2.68 (dd, J=5.6, 15.8 Hz, 2H), 1.84-1.78 (m, 2H).

General Procedure 41

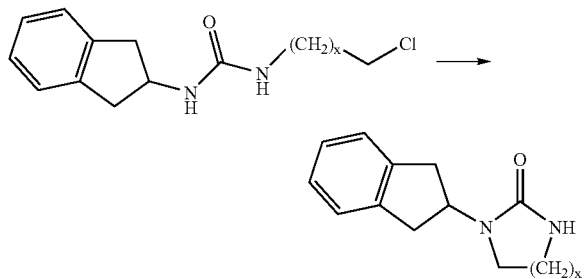

wherein x is 1-2;

To a stirring solution of urea (1.0 mmol) and DMF (3.8 mL) under $N_2$, at 0° C., was added sodium hydride (60% in mineral oil, 1.0 mmol) portionwise over 10 minutes. The mixture was stirred at ambient temperature for 3 hours. MeOH (1.0 mL) was added and the solution was evaporated to dryness under reduced pressure. The residue was purified via silica gel chromatography using EtOAc in hexanes to obtain the desired cyclic urea.

1-(2,3-Dihydro-1H-inden-2-yl)imidazolidin-2-one

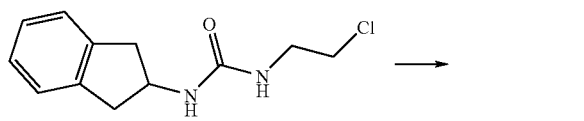

Synthesized according to general procedure 41. The reaction was set up with 1-(2-chloroethyl)-3-(2,3-dihydro-1H-inden-2-yl)urea (4.0 g, 16.8 mmol), DMF (15.0 mL), and sodium hydride (60% in mineral oil, 672 mg, 16.8 mmol). Purification via silica gel chromatography using 50% EtOAc in hexanes gave the desired cyclic urea as a white solid (1.1 g, 5.4 mmol, 30% yield). $^1$H NMR (400 MHz, DMSO-d6) δ 7.24-7.20 (m, 2H), 7.16-7.12 (m, 2H), 6.34 (s, 1H), 4.60-4.53 (m, 1H), 3.23-3.10 (m, 4H), 3.08-2.95 (m, H), 2.92-2.86 (m, 2H).

1-(2,3-Dihydro-1H-inden-2-yl)tetrahydropyrimidin-2 (1H)-one

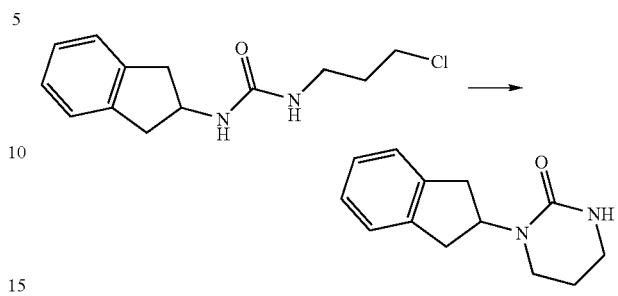

Synthesized according to general procedure 41. The reaction was set up with 1-(4-chlorobutyl)-3-(2,3-dihydro-1H-inden-2-yl)urea (1.0 g, 4.0 mmol), DMF, and sodium hydride (60% in mineral oil, 170 mg, 4.0 mmol). Purification via silica gel chromatography using 50% EtOAc in hexanes gave the desired cyclic urea as a white solid (250 mg, 1.2 mmol, 30% yield). $^1$H NMR (400 MHz, DMSO-d6) δ 7.22-7.18 (m, 2H), 7.14-7.10 (m, 2H), 6.26 (s, 1H), 5.22-5.11 (m, 1H), 3.09-2.87 (m, 8H), 1.76-1.60 (m, 2H).

General Procedure 42

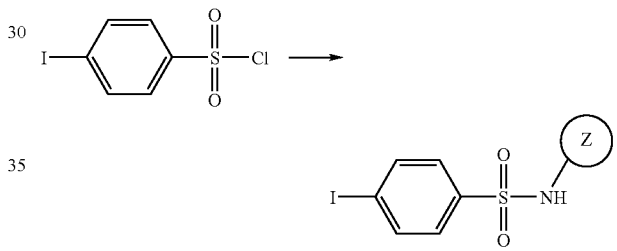

To a stirring solution of the aminoheterocycle (2.4 equivalents, 2.4 mmol) and pyridine (0.35 mL) under $N_2$, at 0° C., was added pipsyl chloride (1 equivalent, 1 mmol). The mixture was stirred at ambient temperature for 17 hours. $CH_2Cl_2$/MeOH-2/1 was added. The mixture was filtered and the filtrate was purified via silica gel chromatography using MeOH in $CH_2Cl_2$. The solid was triturated to give the desired products.

4-Iodo-N-(thiazol-2-yl)benzenesulfonamide

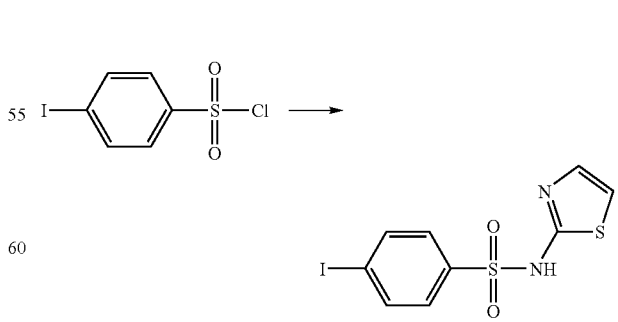

Prepared using general procedure 42. To a stirring solution of 2-aminothiazole (13.2 g, 132.2 mmol) and pyridine (20 mL) under $N_2$, at 0° C., was added pipsyl chloride (20.0 g, 55.1 mmol). The mixture was stirred at ambient temperature for 17 hours. CH$_2$Cl$_2$/MeOH-2/1 (100 mL) was added. The mixture was filtered and the filtrate was purified via silica gel chromatography using 5% MeOH in CH$_2$Cl$_2$. The solid was triturated with CH$_2$Cl$_2$ to obtain the desired sulfonamide as a white solid (8.4 g, 20.9 mmol, 38% yield). $^1$H NMR (400 MHz, DMSO-d6) δ 12.83 (s, 1H), 7.94-7.90 (m, 2H), 7.57-7.54 (m, 2H), 7.26 (d, J=4.6 Hz, 1H), 6.86 (d, J=4.6 Hz, 1H).

General Procedure 43

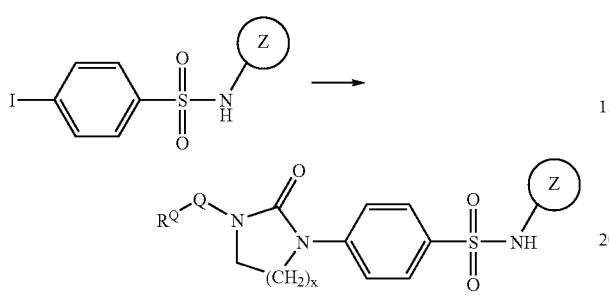

wherein x is 1-2;

Under an N$_2$ atmosphere, a mixture of the phenyl iodide (1 mmol), cyclic urea (1 mmol), copper(I) iodide (2 mmol), potassium carbonate (3 mmol), and NMP (3.0 mL) was stirred and heated at 220° C. in a sealed tube, via microwave, for 20 minutes. The crude product was purified via silica gel chromatography using MeOH in CH$_2$Cl$_2$.

4-(3-(2,3-Dihydro-1H-inden-2-yl)-2-oxoimidazolidin-1-yl)-N-(thiazol-2-yl)benzenesulfonamide

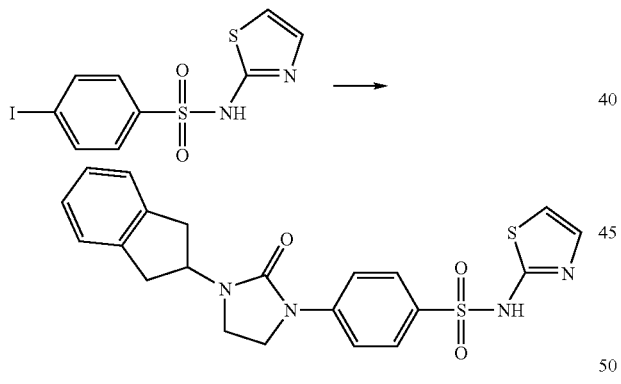

Synthesized according to general procedure 43. The reaction was set up with 4-iodo-N-(thiazol-2-yl)benzenesulfonamide (250 mg, 0.68 mmol), 1-(2,3-dihydro-1H-inden-2-yl)imidazolidin-2-one (138 mg, 0.68 mmol), copper(I) iodide (267 mg, 1.4 mmol), potassium carbonate (282 mg, 2.0 mmol), and NMP (1.7 mL). The dark mixture was purified via silica gel chromatography using 5% MeOH in CH$_2$Cl$_2$ followed by trituration with 50% Et$_2$O in CH$_2$Cl$_2$ to obtain the desired urea as a white solid (32 mg, 0.07 mmol, 10% yield). $^1$H NMR (400 MHz, DMSO-d6) δ 12.66 (s, 1H), 7.75-7.69 (m, 4H), 7.26-7.24 (m, 3H), 7.19-7.17 (m, 2H), 6.81 (d, J=4.5 Hz, 1H), 4.74 (dd, J=1.3, 14.2 Hz, 1H), 3.81-3.77 (m, 2H), 3.34-3.27 (m, 2H), 3.12 (dd, J=7.9, 16.1 Hz, 2H), 3.00 (dd, J=6.2, 16.1 Hz, 2H). LC/MS (10%-99% CH$_3$CN (0.035% TFA)/H$_2$O (0.05% TFA)), m/z: M+1 obs=441.2; t$_R$=1.45 min.

4-(3-(2,3-dihydro-1H-inden-2-yl)-2-oxotetrahydropyrimidin-1(2H)-yl)-N-(thiazol-2-yl)benzenesulfonamide

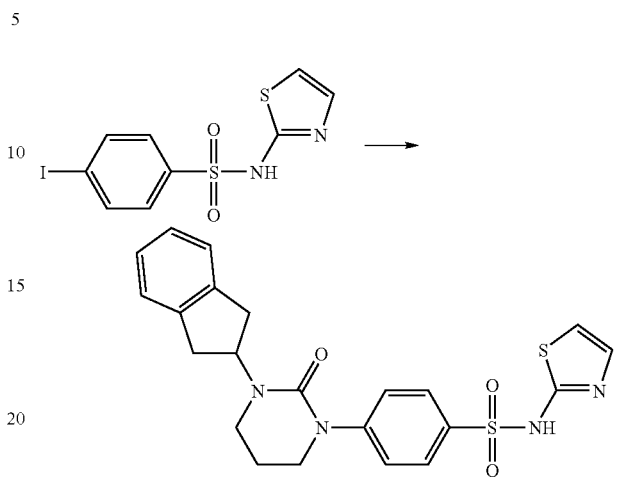

Synthesized according to general procedure 43. The reaction was set up with 4-iodo-N-(thiazol-2-yl)benzenesulfonamide (250 mg, 0.68 mmol), 1-(2,3-dihydro-1H-inden-2-yl)tetrahydropyrimidin-2(1H)-one (138 mg, 0.68 mmol), copper(I) iodide (267 mg, 1.4 mmol), potassium carbonate (282 mg, 2.0 mmol), and NMP (1.7 mL). The dark mixture was purified via silica gel chromatography using 10% MeOH in CH$_2$Cl$_2$ to obtain the desired urea as a white solid (45 mg, 0.10 mmol, 15% yield). $^1$H NMR (400 MHz, DMSO-d6) δ 12.71 (s, 1H), 7.71 (dd, J=1.9, 6.9 Hz, 2H), 7.45 (dd, J=1.9, 6.9 Hz, 2H), 7.26-7.21 (m, 3H), 7.23-7.11 (m, 2H), 6.83 (d, J=4.5 Hz, 1H), 5.25-5.19 (m, 1H), 3.68-3.65 (m, 2H), 3.20 (t, J=5.9 Hz, 2H), 3.09-2.98 (m, 4H), 2.01-1.91 (m, 2H). LC/MS (10%-99% CH$_3$CN (0.035% TFA)/H$_2$O (0.05% TFA)), m/z: M+1 obs=455.3; t$_R$=2.98 min.

Example 13

General Procedure 44

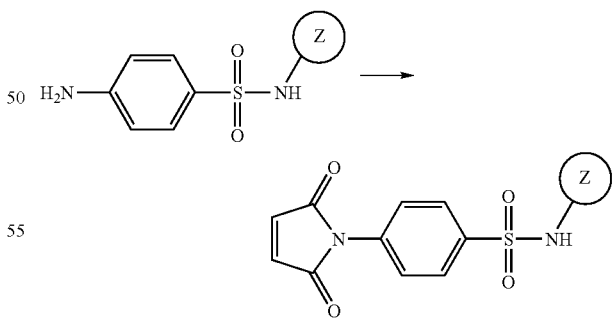

A mixture of sulfonamide (1 equivalent, 1 mmol) and maleic anhydride (1 equivalent, 1 mmol) was heated under refluxed for 16 hrs. The reaction was cooled to RT and then 0° C. externally using ice bath for 4 hrs. The formed precipitate was filtered off and washed with cold water. The crude solid was purified via silica gel chromatography using MeOH in CH$_2$Cl$_2$ to give the desired products.

601

(1H-Pyrrole-2,5-dione)-N-(thiazol-2-yl)benzene-sulfonamide

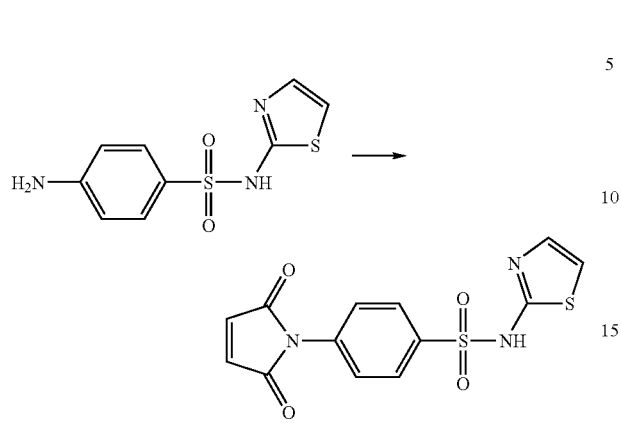

Prepared using general procedure 44. A mixture of sulfathiazole (5 gm, 19.5 mmol) and maleic anhydride (1.92 g, 19.5 mmol) was heated under refluxed for 16 hrs. The reaction was cooled to RT and then to 0° C. for 4 hrs. The formed precipitate was filtered off and washed with cold water. The crude solid was dissolved in $CH_2Cl_2$ and absorbed onto Celite. Purification via silica gel chromatography using 10% MeOH in $CH_2Cl_2$ gave (1H-pyrrole-2,5-dione)-N-(thiazol-2-yl)benzene sulfonamide (2 g, 30%). LC/MS (10%-99% $CH_3CN$ (0.035% TFA)/$H_2O$ (0.05% TFA)), m/z: M+1 obs=336.2; $t_R$=2.12 min.

General Procedure 45

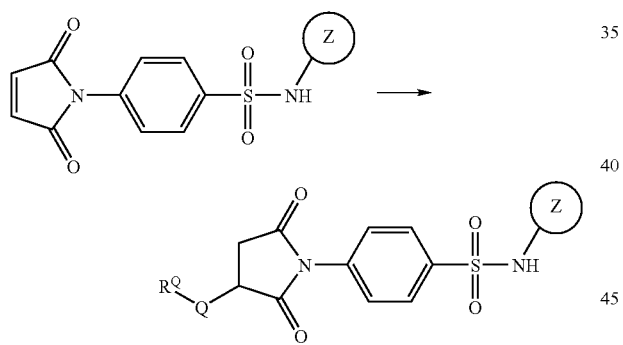

Prepared using general procedure 45. To a solution of (1H-pyrrole-2,5-dione)-sulfonamide (1 equivalent, 1 mmol) in acetic acid (17 mL) was added the amine (3 equivalents, 3 mmol). The reaction was microwaved at 110° C. for 4 hrs. The product was purified by chromatography.

4-(3-(6-Chloro-1,2,3,4-tetrahydroquinoline)-succinimide)-N-(thiazol-2-yl)benzenesulfonamide

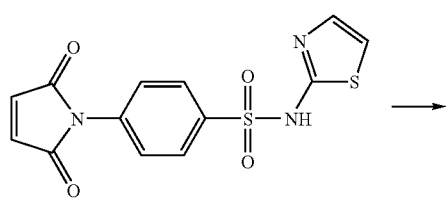

602

-continued

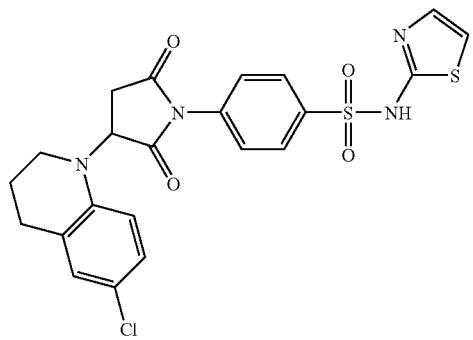

Prepared using general procedure 45. To a solution of (1H-pyrrole-2,5-dione)-N-(thiazol-2-yl)benzenesulfonamide (20 mg, 0.059 mmol) in acetic acid (1 mL) was added 6-chloro-1,2,3,4-tetrahydroquinoline (30 mg, 0.177 mmol). The reaction was microwaved at 110° C. for 4 hrs. The reaction mixture was filtered and purified by reverse phase preparative HPLC (5-99% $CH_3CN$—$H_2O$) to isolate 4-(3-(6-chloro-1,2,3,4-tetrahydroquinoline)-succinimide)-N-(thiazol-2-yl)benzenesulfonamide (3 mg, 10%). LC/MS (10-99% $CH_3CN$—$H_2O$). LC/MS (10%-99% $CH_3CN$ (0.035% TFA)/$H_2O$ (0.05% TFA)), m/z: M+1 obs=503.2; $t_R$=3.29 min.

Example 14

Route 1

(R)-5-(2-Hydroxyethyl)-2,2-dimethyl-1,3-dioxolan-4-one

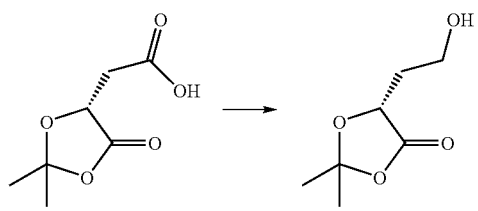

To a stirring solution of (R)-(−)-dimethyl-5-oxo-1,2-dioxolane-4-acetic acid (15.8 g, 91 mmol), and THF (90 mL), at 0° C., under $N_2$, was added borane-THF complex (1.0 M in THF, 100 mL, 100 mmol) dropwise over 60 minutes. The mixture was stirred at 0° C. for 2.5 hours and then allowed to warm to 25° C. The mixture was stirred at room temperature for 19 hours. The mixture was poured into MeOH (150 mL) and the solution was evaporated to dryness under reduced pressure at 25° C. The residue was purified via silica gel chromatography using 30% EtOAc in hexanes to obtain the desired alcohol as a clear oil (7.1 g, 44.6 mmol, 49% yield). $^1$H NMR (400 MHz, CDCl$_3$) δ 4.61-4.51 (m, 1H), 3.89-3.80 (m, 2H), 2.20-2.12 (m, 2H), 2.05-1.98 (m, 1H), 1.64 (s, 3H), 1.57 (s, 3H).

(R)-3-Hydroxydihydrofuran-2(3H)-one

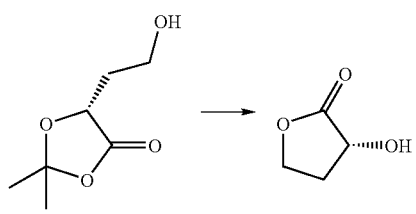

A solution of (R)-5-(2-hydroxyethyl)-2,2-dimethyl-1,3-dioxolan-4-one (33.0 g, 206 mmol), p-toluenesulfonic acid monohydrate (400 mg, 2.1 mmol), and benzene (300 mL) was stirred at 25° C. for 3 hours. The solution was evaporated to dryness under reduced pressure at 25° C. The residue was purified via silica gel chromatography using 50% EtOAc in hexanes to give the desired lactone as a clear oil (18.0 g, 176 mmol, 85% yield). $^1$H NMR (400 MHz, CDCl$_3$) δ 4.57-4.52 (m, 1H), 4.44 (td, J=9.0, 3.6 Hz, 1H), 4.28-4.21 (m, 1H), 3.72 (s, 1H), 2.66-2.58 (m, 1H), 2.35-2.24 (m, 1H).

(R)-3-(tert-butyldiphenylsilyloxy)dihydrofuran-2(3H)-one

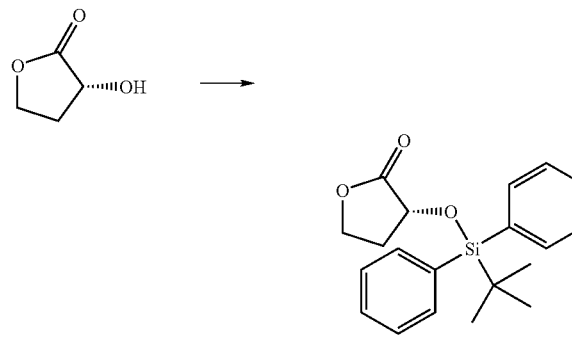

To a stirring solution of (R)-3-hydroxydihydrofuran-2(3H)-one (41.0 g, 401 mmol), imidazole (61.4 g, 920 mmol), and CH$_2$Cl$_2$ (175 mL) at 0° C., under N$_2$, was added t-butyl-diphenylsilyl chloride (129 mL, 138 g, 497 mmol) dropwise over 30 minutes. The mixture was stirred at room temperature for 19 hours. The mixture was partitioned between CH$_2$Cl$_2$ (700 mL) and H$_2$O (100 mL). The organic portion concentrated to dryness under reduced pressure. The residue was purified via silica gel chromatography using 50% EtOAc in hexane to give the desired lactone as a white solid (127 g, 373 mmol, 93% yield). $^1$H NMR (400 MHz, CDCl$_3$) δ 7.84-7.82 (m, 2H), 7.73-7.71 (m, 2H), 7.50-7.40 (m, 6H), 4.41-4.31 (m, 2H), 4.06-4.00 (m, 1H), 2.29-2.19 (m, 2H), 1.10 (s, 9H).

General Procedure 46

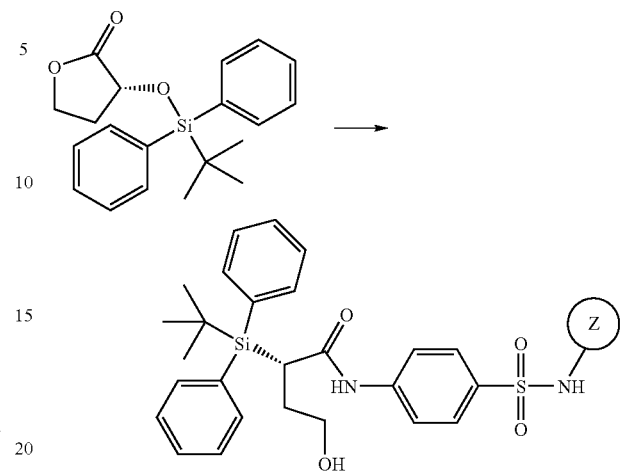

To a stirring suspension of the aniline (1.3 mmol) and CH$_2$Cl$_2$ (5.5 mL) under N$_2$, at 0° C., was added trimethylaluminum (1.3 mmol) dropwise over 20 minutes. The solution was stirred at ambient temperature for 30 minutes. The solution was cooled to 0° C. followed by the dropwise addition of (R)-3-(tert-butyldiphenylsilyloxy)dihydrofuran-2(3H)-one (1 mmol) in CH$_2$Cl$_2$ (1.0 mL) over 30 minutes. The solution was stirred at ambient temperature for 19 hours. The solution was cooled to 0° C. and aqueous 1.0 M HCl was added dropwise over 1.5 hours. The organic portion was washed with 1.0 N aqueous HCl (2×1.0 mL) and evaporated to dryness under reduced pressure. The residue was purified via silica gel using MeOH in CH$_2$Cl$_2$ to obtain the desired amide as a white solid.

(R)-2-(tert-Butyldiphenylsilyloxy)-4-hydroxy-N-(4-(N-thiazol-2-ylsulfamoyl)phenyl)butanamide

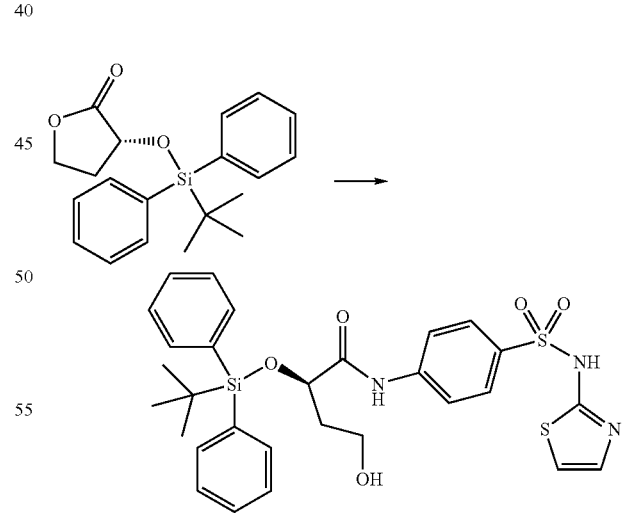

Synthesized according to general procedure 46. The reaction was set up with sulfathiazole (122 g, 477 mmol), CH$_2$Cl$_2$ (1.5 L), trimethylaluminum (2.0 M in hexanes, 239 mL, 477 mmol), and (R)-3-(tert-butyldiphenylsilyloxy)dihydrofuran-2(3H)-one (125 g, 367 mmol) in CH$_2$Cl$_2$ (250 mL). The reaction was purified via silica gel using 10% MeOH in CH$_2$Cl$_2$ to obtain the desired amide as a white solid (207 g, 348 mmol, 95% yield). $^1$H NMR (400 MHz, DMSO-d6) δ 8.73 (s, 1H), 7.76 (dd, J=1.8, 7.0 Hz, 1H), 7.74 (s, 1H), 7.59-7.53 (m, 4H), 7.44-7.28 (m, 8H), 7.09 (d, J=4.6 Hz, 1H), 6.46 (d, J=4.6 Hz, 1H), 4.34 (dd, J=4.1, 6.7 Hz, 1H), 3.64-3.59 (m, 1H), 3.54 (dd, J=6.1, 11.4 Hz, 1H), 1.99-1.91 (m, 1H), 1.81-1.70 (m, 1H), 1.10 (s, 9H). LC/MS (10%-99% CH$_3$CN (0.035% TFA)/H$_2$O (0.05% TFA)), m/z: M+1 obs=596.5; $t_R$=1.93 min.

General Procedure 47

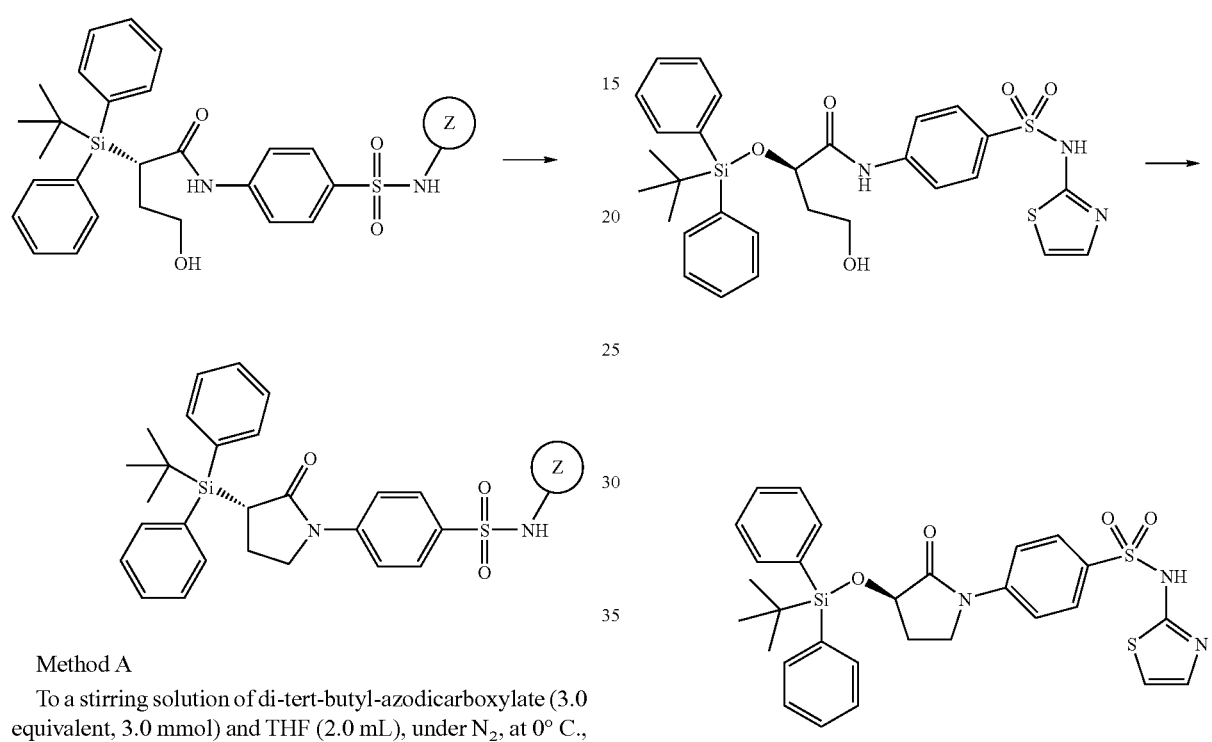

Method A

To a stirring solution of di-tert-butyl-azodicarboxylate (3.0 equivalent, 3.0 mmol) and THF (2.0 mL), under N$_2$, at 0° C., was added tributylphosphine (3.0 equivalent, 3.0 mmol), dropwise over 5 minutes. The colourless solution was stirred at 0° C. for 30 minutes. A solution of amidealcohol (1.0 equivalent, 1.0 mmol) in THF (0.60 mL) was added dropwise over 5 minutes. The solution was stirred at ambient temperature for 2 hours. To this solution was added H$_2$O (40 uL) and the solution was evaporated to dryness. The residue was purified via silica gel using EtOAc in hexanes to give the desired lactam.

Method B

The alcohol (1.0 equivalent, 1.0 mmol) in anhydrous DCM (4.0 mL) was stirred and cooled down to 0° C. To this, a solution of PPh$_3$ (1.5 equivalents, 1.5 mmol) in anhydrous DCM (0.90 mL) was slowly added followed by the slow addition of CBr$_4$ (1.5 equivalents, 1.5 mmol) in anhydrous DCM (0.90 mL). On completion of CBr$_4$ addition, the reaction was maintained at 0° C. for 5 min. The ice bath was removed and the reaction was stirred at room temperature for 4 h. The reaction was monitored by LCMS. The reaction was diluted with DCM and the organic layer was washed with saturated aqueous NaHCO$_3$ (X 2) and brine (X 1). The organic layer was dried over Na$_2$SO$_4$ and concentrated. The crude product was purified by column chromatography (gradient 0-100% EtOAc/Hexane) to provide the bromide as a pale yellow solid (9.0 g). To a solution of the bromide (1.0 equivalent, 1.0 mmol) in chloroform (3.5 mL; HPLC grade), DBU (equivalents, 2.0 mmol) was added and stirred at room temperature under N$_2$ atmosphere for ~1 h. The reaction was monitored by LCMS. The reaction was diluted with DCM and the organic layer was washed with aqueous 1 N HCl (X 3), saturated aqueous NaHCO$_3$ (X 2) and brine (X 1). The organic layer was dried over Na$_2$SO$_4$ and concentrated to provide the desired lactam as a yellow solid.

(R)-4-(3-(tert-Butyldiphenylsilyloxy)-2-oxopyrrolidin-1-yl)-N-(thiazol-2-yl)benzenesulfonamide Synthesized according to general procedure 47, method A. The reaction was set up with di-tert-butyl-azodicarboxylate (1.81 g, 7.88 mmol), THF (15 mL), tributylphosphine (1.59 g, 7.88 mmol), and (R)-2-(tert-butyldiphenylsilyloxy)-4-hydroxy-N-(4-(N-thiazol-2-ylsulfamoyl)phenyl)butanamide (1.56 g, 2.63 mmol). The residue was purified via silica gel using 40% EtOAc in hexanes to give the desired lactam as a white solid (1.3 g, 2.3 mmol, 86% yield). $^1$H NMR (400 MHz, DMSO-d6) δ 7.83-7.76 (m, 4H), 7.70 (dd, J=1.9, 7.0 Hz, 2H), 7.65 (dd, J=1.5, 8.0 Hz, 2H), 7.39-7.29 (m, 6H), 7.06 (d, J=4.6 Hz, 1H), 6.44 (d, J=4.6 Hz, 1H), 4.35 (dd, J=7.9, 9.2 Hz, 1H), 3.67-3.62 (m, 1H), 3.48-3.42 (m, 1H), 2.18-1.98 (m, 2H) 1.11 (s, 9H).

Synthesized according to general procedure 47, method B. The reaction was set up with (R)-2-(tert-Butyldiphenylsilyloxy)-4-hydroxy-N-(4-(N-thiazol-2-ylsulfamoyl)phenyl)butanamide (10.0 g, 16.78 mmol, 1.0 equiv.), DCM (70 mL), PPh$_3$ (6.6 g, 25.2 mmol, 1.5 equiv.), CBr$_4$ (8.35 g, 25.2 mmol, 1.5 equiv.), DBU (3.53 mL, 23.58 mmol, 2.0 equiv.) The organic layer was dried over Na$_2$SO$_4$ and concentrated to provide the lactam as a yellow solid (6.25 g, 92%). $^1$H NMR (400 MHz, DMSO-d6) δ 7.83-7.76 (m, 4H), 7.70 (dd, J=1.9, 7.0 Hz, 2H), 7.65 (dd, J=1.5, 8.0 Hz, 2H), 7.39-7.29 (m, 6H), 7.06 (d, J=4.6 Hz, 1H), 6.44 (d, J=4.6 Hz, 1H), 4.35 (dd, J=7.9, 9.2 Hz, 1H), 3.67-3.62 (m, 1H), 3.48-3.42 (m, 1H), 2.18-1.98 (m, 2H) 1.11 (s, 9H).

General Procedure 48

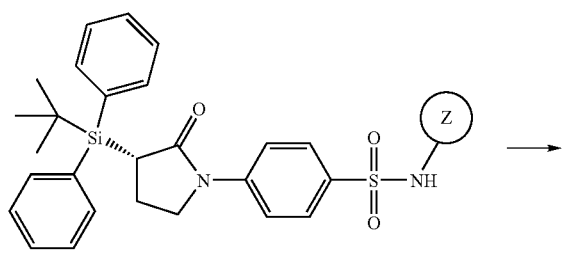

To a stirring suspension of benzenesulfonamide (1.0 mmol) in CH$_2$Cl$_2$ (2.3 mL), under N$_2$, at 0° C., was added N,N-diisopropylethylamine (2.0 mmol) followed by allylbromide (2.0 mmol). The mixture was stirred at ambient temperature for 19 hours. The mixture was evaporated to dryness under reduced pressure. The residue was purified via silica gel using EtOAc in hexanes to give the desired alkylsulfonamide.

(R)—N-Allyl-4-(3-(tert-butyldiphenylsilyloxy)-2-oxopyrrolidin-1-yl)-N-(thiazol-2-yl)benzenesulfonamide

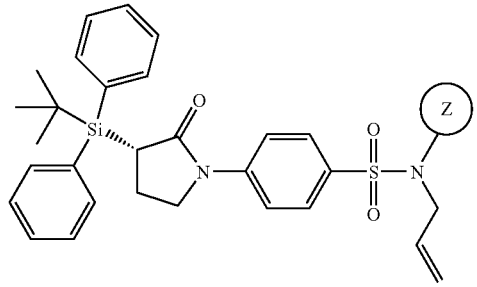

Prepared according to general procedure 48. The reaction was set up (R)-4-(3-(tert-butyldiphenylsilyloxy)-2-oxopyrrolidin-1-yl)-N-(thiazol-2-yl)benzenesulfonamide (50.0 g, 86.6 mmol), CH$_2$Cl$_2$ (200 mL), N,N-diisopropylethylamine (30.2 mL, 173.2 mmol), and allylbromide (15.0 mL, 173.2 mmol). The residue was purified via silica gel using 50% EtOAc in hexanes to give the desired sulfonamide as a white solid (45.0 g, 72.7 mmol, 84% yield). $^1$H NMR (400 MHz, DMSO-d6) δ. 7.85-7.79 (m, 6H), 7.70 (dd, J=1.6, 7.7 Hz, 2H), 7.49-7.40 (m, 6H), 7.36 (d, J=4.7 Hz, 1H), 6.93 (d, J=4.7 Hz, 1H), 5.90-5.82 (m, 1H), 5.16 (dd, J=1.3, 10.3 Hz, 1H), 4.97 (d, J=1.3 Hz, 1H), 4.56-4.52 (m, 3H), 3.76-3.72 (m, 1H), 3.56-3.48 (m, 1H), 2.28-2.25 (m, 1H), 2.19-1.98 (m, 1H), 1.11 (s, 9H).

(R)—N-Allyl-4-(3-hydroxy-2-oxopyrrolidin-1-yl)-N-(thiazol-2-yl)benzenesulfonamide

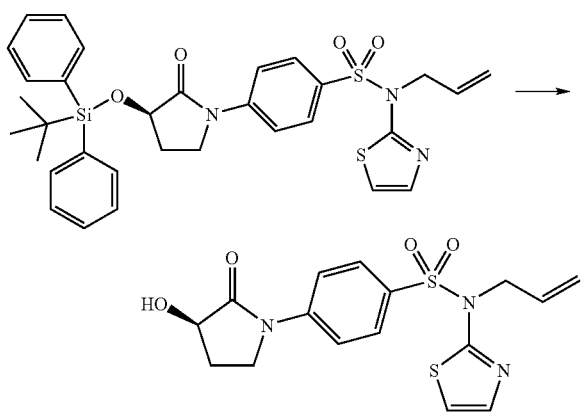

To a stirring solution of (R)—N-allyl-4-(3-(tert-butyldiphenylsilyloxy)-2-oxopyrrolidin-1-yl)-N-(thiazol-2-yl)benzenesulfonamide (78.7 g, 127 mmol) and THF (300 mL) under N$_2$, at 0° C., was added tetrabutylammonium fluoride (1.0 M in THF, 255 mL, 255 mmol) dropwise over 20 minutes. The mixture was stirred at ambient temperature for 2 hours. To this solution was added H$_2$O (5 mL) followed by evaporation to dryness. The residue was purified via silica gel using 30% EtOAc in hexanes to obtain the desired alcohol as a white solid (39.5 g, 104 mmol, 82% yield). $^1$H NMR (400 MHz, DMSO-d6) δ 7.86-7.80 (m, 4H), 7.37 (d, J=4.7 Hz, 1H), 6.93 (d, J=4.7 Hz, 1H), 5.92-5.83 (m, 2H), 5.17 (dd, J=1.3, 10.3 Hz, 1H), 4.98 (q, J=1.4 Hz, 1H), 4.55 (dt, J=5.3, 1.7 Hz, 2H), 4.36-4.30 (m, 1H), 3.81-3.76 (m, 1H), 3.70 (td, J=9.5, 5.4 Hz, 1H), 2.45-2.38 (m, 1H), 1.90-1.80 (m, 1H).

General Procedure 49

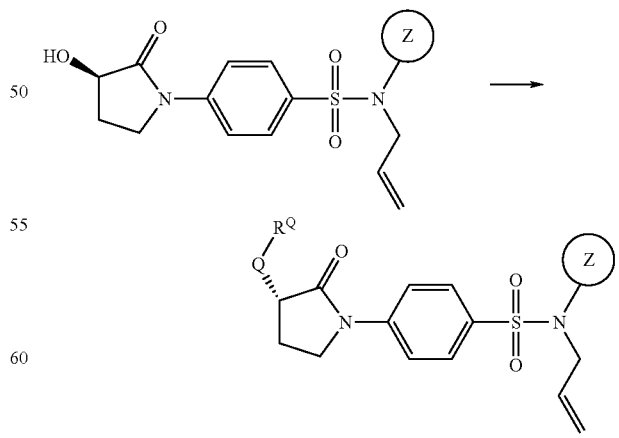

Method A

To a stirring solution of alcohol (1.0 mmol) and CH$_2$Cl$_2$ (3.0 mL) under N$_2$, at −40° C., was added N,N-diisopropylethylamine (2.0 mmol) followed by the dropwise addition of triflic anhydride (1.1 mmol) over 20 minutes. The mixture was stirred at −40° C. for 1 hour. To this solution was added amine (1.5 mmol) at −40° C. The solution was held at a specific temperature (−20° C. to 25° C.) for a specified time followed by quenching with $H_2O$ (5.5 mmol). The reaction was evaporated to dryness under reduced pressure. The residue was purified via silica gel using MeOH in $CH_2Cl_2$ to obtain the desired lactam.

Method B

Under an $N_2$ atmosphere at −30° C., N,N-diisopropylethylamine (2-4 equivalent) was added dropwise to a solution of alcohol (1 equivalent) in $CH_3CN$ (0.5 M). Trifluoromethanesulfonic anhydride (1.1-2.1 equivalent) was added drop wise to this solution maintaining the internal temperature of the reaction mixture below −30° C. To 0° C. solution of amine/phenol (1.5-3 equivalent) in $CH_3CN$ (0.5 mL) was added drop wise, NaH (0.9 equivalent to amine/phenol) in $CH_3CN$. Upon completion of addition, the mixture was stirred at 0° C. for 1 h. This amine reaction mixture was added to the above triflate mixture at −30° C. The reaction was allowed to warm up to 0° C. and was kept at this temperature for 24 h. The reaction mixture was washed with saturated aqueous sodium bicarbonate (2×), brine, dried over magnesium sulfate, and concentrated. Purification via silica gel chromatography using 0-40% ethyl acetate in hexane gave the desired product.

General Procedure 50

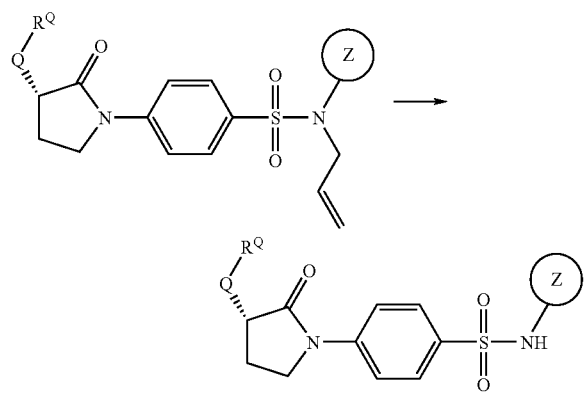

To a stirring suspension of allyl sulfonamide (1.0 mmol) and $CH_3CN$ (3.8 mL) was added $Pd(PPh_3)_4$ (0.2 mmol) and 1,3-dimethylbarbituric acid (10 mmol). The mixture was heated at 60° C. for 4 hours. The reaction was evaporated to dryness under reduced pressure. The residue was purified via silica gel using MeOH in $CH_2Cl_2$ to obtain the desired sulfonamide.

(S)—N-Allyl-4-(3-(4-chloro-5-fluoroindolin-1-yl)-2-oxopyrrolidin-1-yl)-N-(thiazol-2-yl)benzenesulfonamide

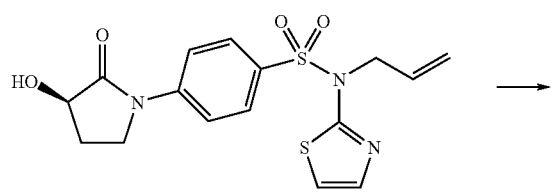

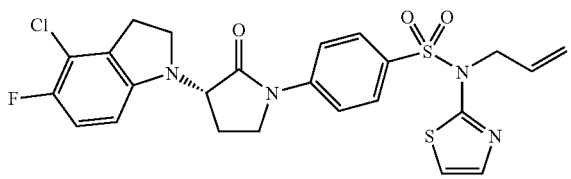

Synthesized according to general procedure 49, method A. The reaction was set up with (R)—N-allyl-4-(3-hydroxy-2-oxopyrrolidin-1-yl)-N-(thiazol-2-yl)benzene-sulfonamide (5.0 g, 13.2 mmol), triflic anhydride (2.43 mL, 14.5 mmol), diisopropylamine (4.6 mL, 26.4 mmol), $CH_2Cl_2$, and 4-$C_{1-5}$—F-indoline (3.4 g, 19.8 mmol). The reaction was held at −40° C. for 19 hours and quenched with $H_2O$ (0.10 mL). The residue was purified via silica gel using 10% MeOH in $CH_2Cl_2$ followed by trituration with $Et_2O/CH_2Cl_2$-9/1 (20 mL) to obtain the desired alcohol as a white solid (6.8 g, 12.8 mmol, 97% yield). $^1H$ NMR (400 MHz, DMSO-d6) δ 7.86-7.80 (m, 4H), 7.37 (d, J=4.7 Hz, 1H), 7.03-6.99 (m, 1H), 6.93 (d, J=4.7 Hz, 1H), 6.48 (dd, J=3.6, 8.7 Hz, 1H), 5.92-5.82 (m, 1H), 5.16 (dd, J=1.3, 10.3 Hz, 1H), 4.97 (d, J=1.3 Hz, 1H), 4.80 (dd, J=8.7, 10.9 Hz, 1H), 4.55 (dd, J=1.4, 4.0 Hz, 2H), 3.90-3.78 (m, 2H), 3.64-3.58 (m, 1H), 3.41-3.31 (m, 1H), 3.07-2.95 (m, 2H), 2.40-2.33 (m, 1H), 2.16-2.13 (m, 1H).

(S)-4-(3-(4-Chloro-5-fluoroindolin-1-yl)-2-oxopyrrolidin-1-yl)-N-(thiazol-2-yl)benzenesulfonamide

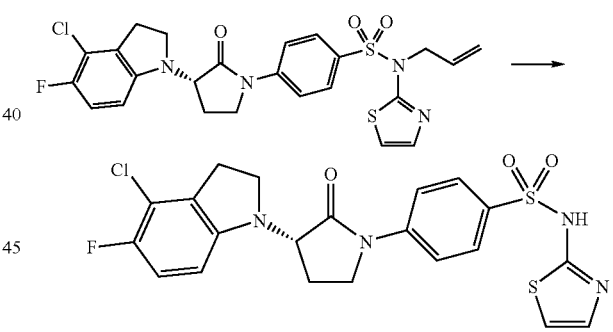

Synthesized according to general procedure 50. The reaction was set up with (S)—N-allyl-4-(3-(4-chloro-5-fluoroindolin-1-yl)-2-oxopyrrolidin-1-yl)-N-(thiazol-2-yl)benzene sulfonamide (17.5 g, 32.8 mmol), $CH_3CN$ (125 mL), $Pd(PPh_3)_4$ (7.6 g, 6.6 mmol) and 1,3-dimethylbarbituric acid (30.7 g, 196.8 mmol). The formed precipitate was filtered, washed with $CH_3CN/CH_2Cl_2$-1/1 (300 mL), and recrystallized from $MeOH/CH_2Cl_2$-1/9 to obtain the desired lactam as a white solid (11.0 g, 22.3 mmol, 68% yield). $^1H$ NMR (400 MHz, DMSO-d6) δ 7.87-7.80 (m, 4H), 7.26 (d, J=4.6 Hz, 1H), 7.03-6.99 (m, 1H), 6.83 (d, J=4.6 Hz, 1H), 6.48 (dd, J=3.6, 8.7 Hz, 1H), 4.80 (dd, J=8.8, 10.8 Hz, 1H), 3.90-3.78 (m, 2H), 3.64-3.55 (m, 1H), 3.41-3.32 (m, 1H), 3.08-2.93 (m, 2H), 2.40-2.33 (m, 1H), 2.16-2.10 (m, 1H). LC/MS (10%-99% $CH_3CN$ (0.035% TFA)/$H_2O$ (0.05% TFA)), m/z: M+1 obs=493.2; $t_R$=1.61 min.

611

(S)—N-Allyl-4-(3-(5,6-dichloro-1H-benzoimidazol-1-yl)-2-oxopyrrolidin-1-yl)-N-(thiazol-2-yl)benzenesulfonamide

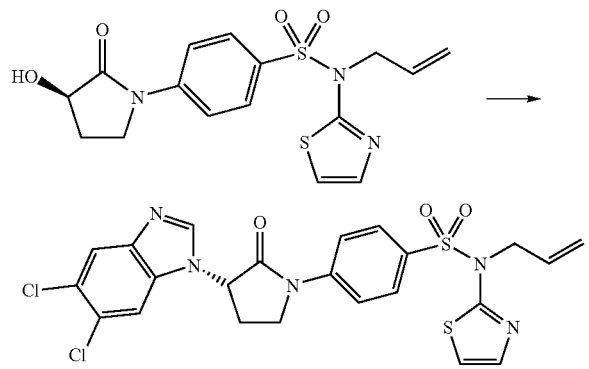

Synthesized according to general procedure 49, method B. LC/MS (10%-99% CH$_3$CN (0.035% TFA)/H$_2$O (0.05% TFA)), m/z: M+1 obs=548; t$_R$=1.33 min.

(S)-4-(3-(5,6-Dichloro-1H-benzoimidazol-1-yl)-2-oxopyrrolidin-1-yl)-N-(thiazol-2-yl)benzenesulfonamide

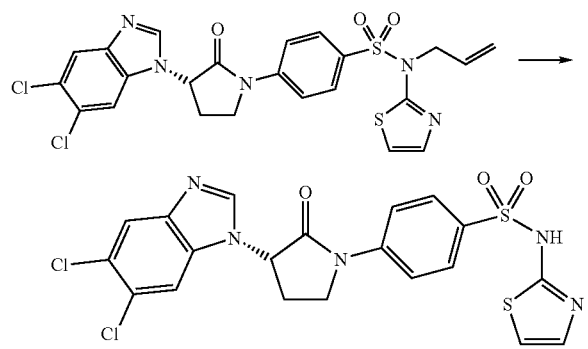

Synthesized according to general procedure 50. LC/MS (10%-99% CH$_3$CN (0.035% TFA)/H$_2$O (0.05% TFA)), m/z: M+1 obs=548; t$_R$=1.33 min.

(S)—N-Allyl-4-(3-(7-chloro-3,4-dihydroisoquinolin-2(1H)-yl)-2-oxopyrrolidin-1-yl)-N-(thiazol-2-yl)benzenesulfonamide

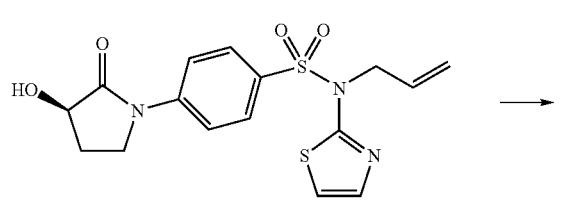

612

-continued

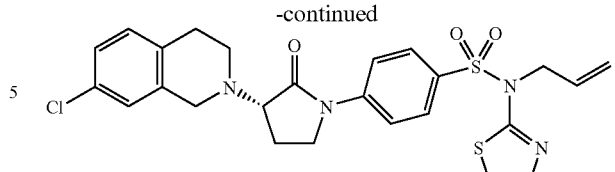

Synthesized according to general procedure 49, method A. LC/MS (10%-99% CH$_3$CN (0.035% TFA)/H$_2$O (0.05% TFA)), m/z: M+1 obs=528; t$_R$=1.71 min.

(S)-4-(3-(7-Chloro-3,4-dihydroisoquinolin-2(1H)-yl)-2-oxopyrrolidin-1-yl)-N-(thiazol-2-yl)benzenesulfonamide

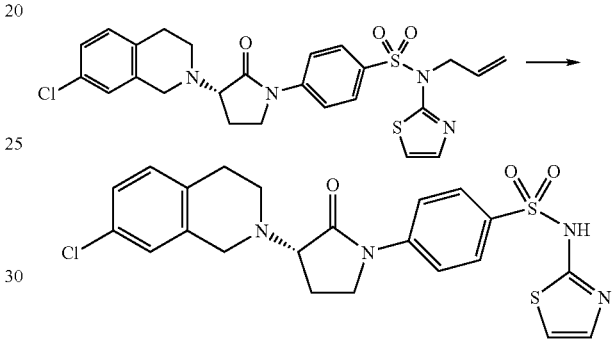

Synthesized according to general procedure 50. LC/MS (10%-99% CH$_3$CN (0.035% TFA)/H$_2$O (0.05% TFA)), m/z: M+1 obs=489.3; t$_R$=1.08 min (S)—Benzyl 5-fluoro-1-(2-oxo-1-(4-(N-thiazol-2-ylsulfamoyl)phenyl)pyrrolidin-3-yl)spiro[indoline-3,4-piperidine]-1'-carboxylate

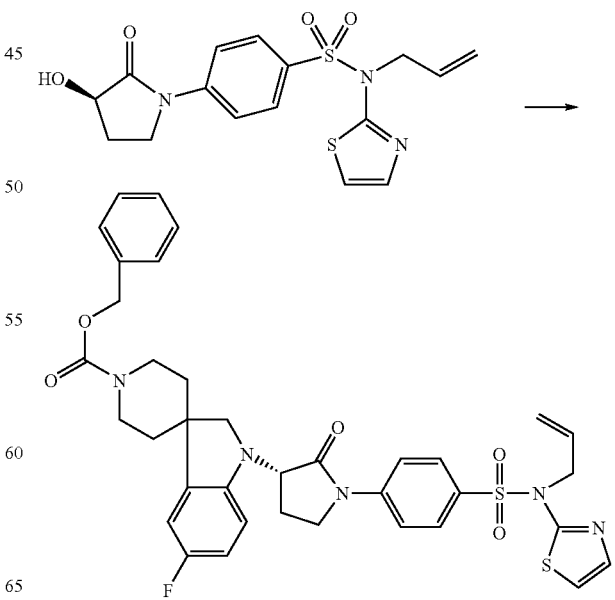

613

Synthesized according to general procedure 49, method A. LC/MS (10%-99% CH₃CN (0.035% TFA)/H₂O (0.05% TFA)), m/z: M+1 obs=702.5; t_R=2.7 min.

(S)—Benzyl 5-fluoro-1-(2-oxo-1-(4-(N-thiazol-2-ylsulfamoyl)phenyl)pyrrolidin-3-yl)spiro[indoline-3,4-piperidine]-1'-carboxylate

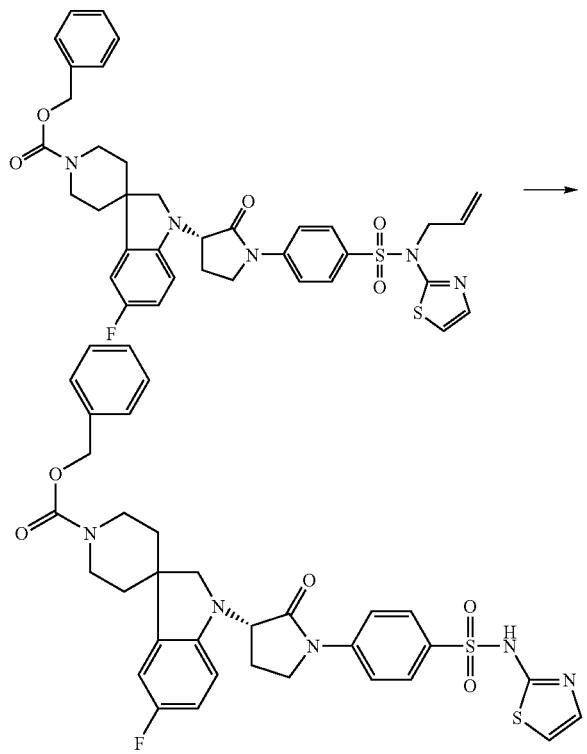

Synthesized according to general procedure 50. LC/MS (10%-99% CH₃CN (0.035% TFA)/H₂O (0.05% TFA)), m/z: M+1 obs=662.2; t_R=1.88 min.

Route 2

General Procedure 51

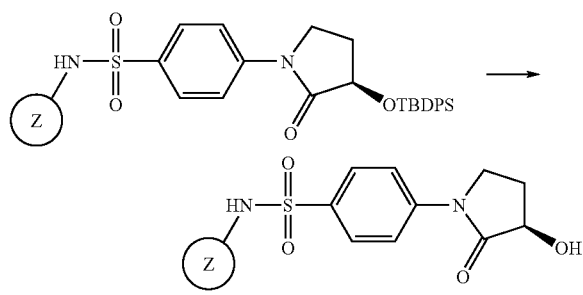

To a solution of protected TBDPS sulfonamide (1 equivalent) in THF (0.5-1 M) under N₂, was added a solution of tetra butyl ammonium fluoride in THF (1M, 4 equivalent). Upon completion of addition, the mixture was stirred at RT overnight. The reaction mixture was poured into water and extracted with CH₂Cl₂ (2×), dried over magnesium sulfate, and concentrated. Purification via silica gel chromatography using 2-10% MeOH in CH₂Cl₂ gave desired product.

614

(R)-4-(3-Hydroxy-2-oxopyrrolidin-1-yl-N-(thiazol-2-yl)benzenesulfonamide

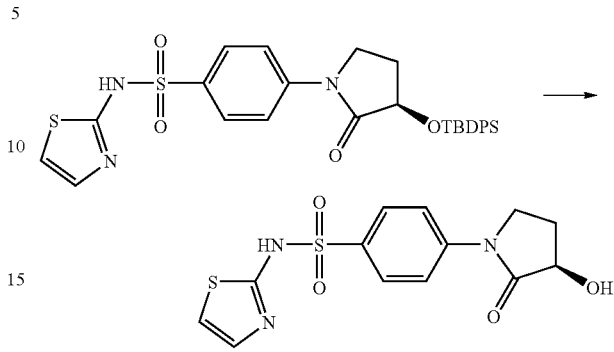

To a solution of (R)-4-(3-(tert-butyldiphenylsilyloxy)-2-oxopyrrolidin-1-yl-N-(thiazol-2-yl)benzenesulfonamide (5.5 gm, 9.53 mmol) in THF (40 mL) under N₂, was added a solution of tetrabutyl ammonium fluoride in THF (1 M, 40 mL, 38.12 mmol). Upon completion of addition, the mixture was stirred at RT overnight. The reaction mixture was poured into water and extracted with CH₂Cl₂ (2×50 mL), dried over magnesium sulfate, and concentrated. Purification via silica gel chromatography using 2-10% MeOH in CH₂Cl₂ gave (R)-4-(3-hydroxy-2-oxopyrrolidin-1-yl-N-(thiazol-2-yl)benzenesulfonamide (2.6 gm, 76%). LC/MS (10%-99% CH₃CN (0.035% TFA)/H₂O (0.05% TFA)), m/z: M+1 obs=340.0; t_R=0.54 min.

General Procedure 52

Method A

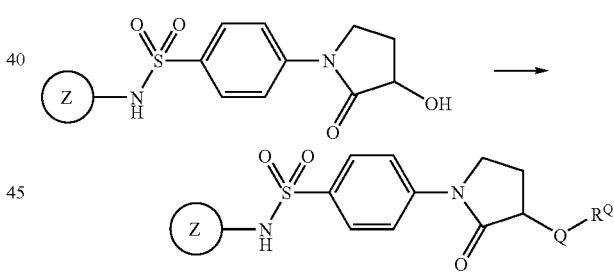

Under an N₂ atmosphere at −40° C., N,N-diisopropylethylamine (2-4 equivalent) was added drop wise to a solution of alcohol (1 equivalent) in CH₂Cl₂ (0.5 M). Trifluoromethanesulfonic anhydride (1.1-2.1 equivalent) was added dropwise to this solution maintaining the internal temperature of the reaction mixture below −40° C. Upon completion of addition, the mixture was stirred at −40° C. for 1 h. A solution of amine/phenol (1.5-3 equivalent) in CH₂Cl₂ (40 mL) was added drop wise to this solution maintaining the internal temperature of the reaction mixture below −40° C. The reaction was allowed to warm up to −20° C. and was kept at this temperature for 48 h. The reaction mixture was washed with saturated aqueous sodium bicarbonate (2×), brine, dried over magnesium sulfate, and concentrated. Purification via silica gel chromatography using 0-40% ethyl acetate in hexane gave desired product.

Method B

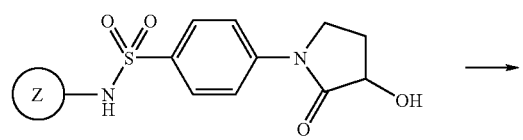

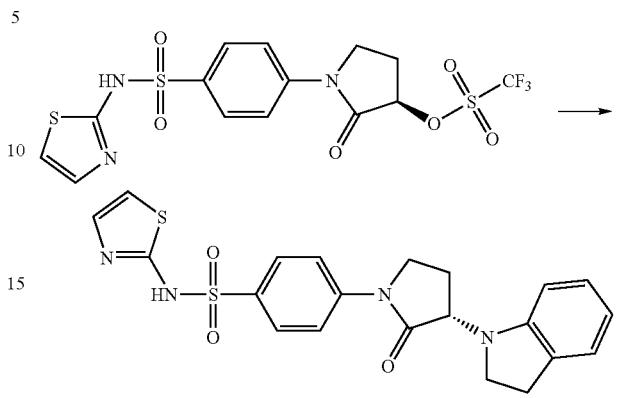

Under an N$_2$ atmosphere at −30° C., N,N-diisopropylethylamine (2-4 equivalent) was added drop wise to a solution of alcohol (1 equivalent) in CH$_3$CN (0.5 M). Trifluoromethanesulfonic anhydride (1.1-2.1 equivalent) was added dropwise to this solution maintaining the internal temperature of the reaction mixture below −30° C. To 0° C. solution of amine/phenol (1.5-3 equivalent) in CH$_3$CN (0.5 mL) was added drop wise, NaH (0.9 equivalent to amine/phenol) in CH$_3$CN. Upon completion of addition, the mixture was stirred at 0° C. for 1 h. This amine reaction mixture was added to above triflate mixture at −30° C. The reaction was allowed to warm up to 0° C. and was kept at this temperature for 24 h. The reaction mixture was washed with saturated aqueous sodium bicarbonate (2×), brine, dried over magnesium sulfate, and concentrated. Purification via silica gel chromatography using 0-40% ethyl acetate in hexane gave desired product.

(S)-4-(3-(4-(3,5-Dichlorophenyl)piperazin-1-yl)-2-oxopyrrolidin-1-yl)-N-(thiazol-2-yl)benzenesulfonamide

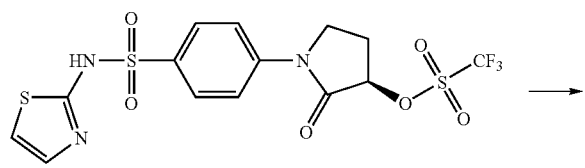

Synthesized according to general procedure 52, method B. LC/MS (10%-99% CH$_3$CN (0.035% TFA)/H$_2$O (0.05% TFA)), m/z: M+1 obs=484; t$_R$=1.66 min.

(S)-4-(3-(Indolin-1-yl)-2-oxopyrrolidin-1-yl)-N-(thiazol-2-yl)benzenesulfonamide Synthesized according to general procedure 52, method A. LC/MS (10%-99% CH$_3$CN (0.035% TFA)/H$_2$O (0.05% TFA)), m/z: M+1 obs=441.2; t$_R$=2.93 min.

General Procedure 53

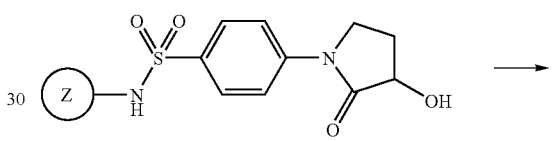

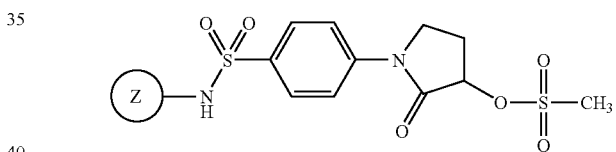

Under an N$_2$ atmosphere at 0° C., DMAP (1.5-3 equivalent) was added to a solution of alcohol (1 equivalent) in CH$_2$Cl$_2$ (0.5 M). To the reaction mixture was then added triethylamine (20 equivalent). Methanesulfonic anhydride (10 equivalent) was added dropwise to this solution at 0° C. Upon completion of addition, the mixture was stirred at RT overnight. The reaction mixture was poured into water and extracted with CH$_2$Cl$_2$ (2×), dried over magnesium sulfate, and concentrated. Purification via silica gel chromatography using 2-10% MeOH in CH$_2$Cl$_2$ gave mesylated alcohol. LC/MS (10%-99% CH$_3$CN (0.035% TFA)/H$_2$O (0.05% TFA)), m/z: M+1 obs=498.3; t$_R$=1.18 min.

General Procedure 54

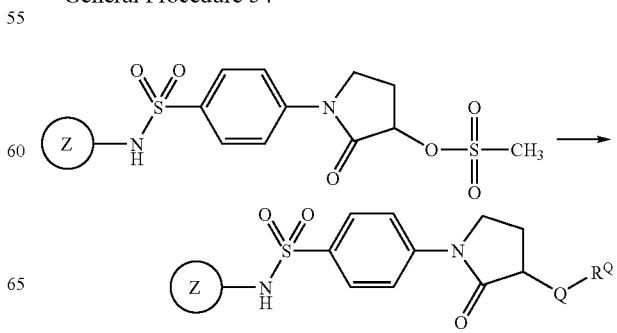

Method A

A solution of mesylate (1 equivalent), Cs$_2$CO$_3$ (10 equivalents), phenol (2-5 equivalents) in DMF (0.3-0.5 M) was stirred under an N$_2$ atmosphere at 80° C. for 19 h. Purification via reverse phase HPLC using 10%-99% CH$_3$CN (0.035% TFA)/H$_2$O (0.05% TFA) gave the desired product.

Method B

A solution of mesylate (1 equivalent), triethylamine (3 equivalents), amine (2-5 equivalents) in DMF (0.3-0.5 M) was stirred under an N$_2$ atmosphere at RT for 19 h. Purification via reverse phase HPLC using 10%-99% CH$_3$CN (0.035% TFA)/H$_2$O (0.05% TFA) gave the desired product.

Method C

A solution of mesylate (1 equivalent), potassium fluoride (1 equivalent), amine (2-5 equivalent) in acetonitrile (0.3-0.5 M) was microwaved at 150° C. for 10 min. Purification via reverse phase HPLC using 10%-99% CH$_3$CN (0.035% TFA)/H$_2$O (0.05% TFA) gave the desired product.

4-(3-(2-Chlorophenoxy)-2-oxopyrrolidin-1-yl)-N-(thiazol-2-yl)benzenesulfonamide

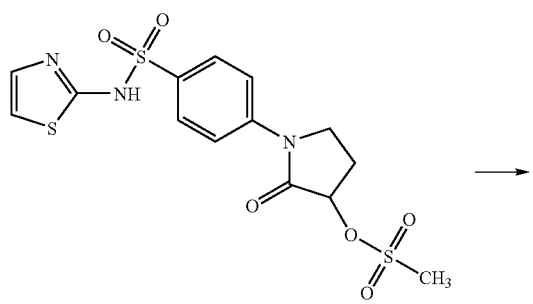

Synthesized according to general procedure 54, method A. LC/MS (10%-99% CH$_3$CN (0.035% TFA)/H$_2$O (0.05% TFA)), m/z: M+1 obs=450; t$_R$=1.58 min.

4-(3-(3-Chlorophenylamino)-2-oxopyrrolidin-1-yl)-N-(thiazol-2-yl)benzenesulfonamide

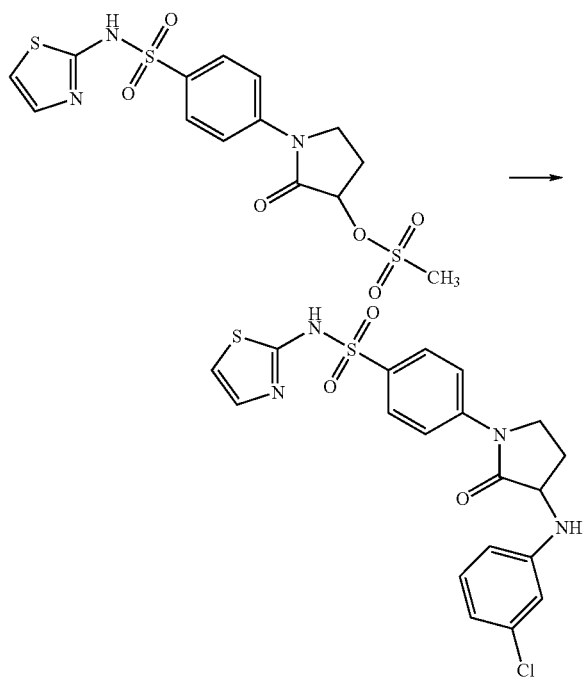

Synthesized according to general procedure 54, method C. LC/MS (10%-99% CH$_3$CN (0.035% TFA)/H$_2$O (0.05% TFA)), m/z: M+1 obs=449; t$_R$=1.51 min.

(S)-4-(3-(4-Methylpiperidin-1-yl)-2-oxopyrrolidin-1-yl)-N-(thiazol-2-yl)benzenesulfonamide

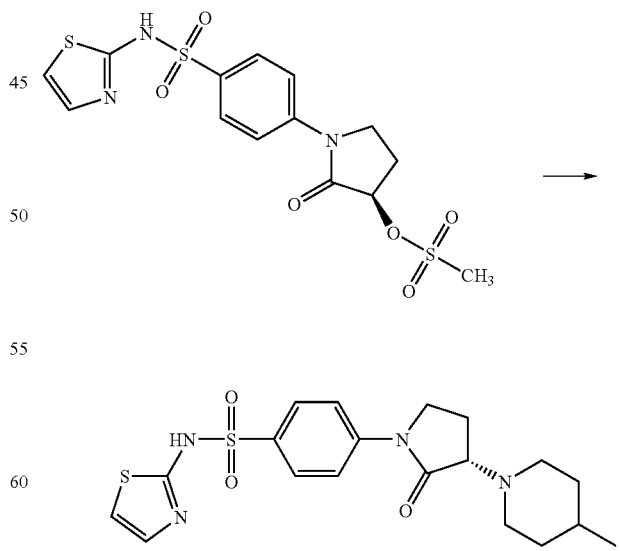

Synthesized according to general procedure 54, method B. LC/MS (10%-99% CH$_3$CN (0.035% TFA)/H$_2$O (0.05% TFA)), m/z: M+1 obs=421.8; t$_R$=0.88 min.

619
(S)-4-(3-(6-Chlorobenzo[d]thiazol-2-ylamino)-2-oxopyrrolidin-1-yl)-N-(thiazol-2-yl)benzenesulfonamide

620
4-(3-(2,6-Dichlorophenethylamino)-2-oxopyrrolidin-1-yl)-N-(thiazol-2-yl)benzenesulfonamide

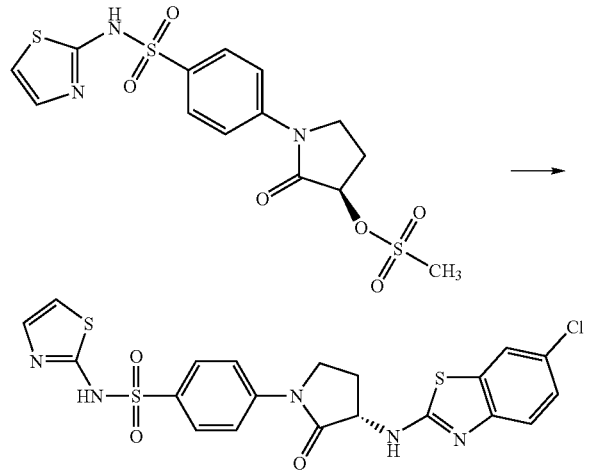

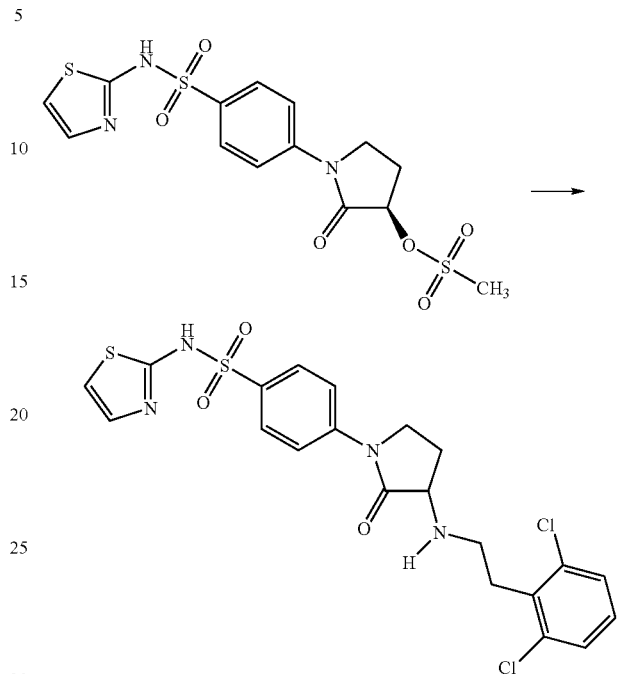

Synthesized according to general procedure 54, method A. LC/MS (10%-99% CH$_3$CN (0.035% TFA)/H$_2$O (0.05% TFA)), m/z: M+1 obs=506.2; t$_R$=1.56 min.

4-(3-(2-Chloro-6-methylbenzylamino)-2-oxopyrrolidin-1-yl)-N-(thiazol-2-yl)benzenesulfonamide

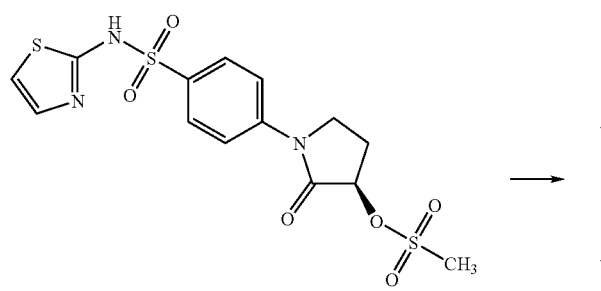

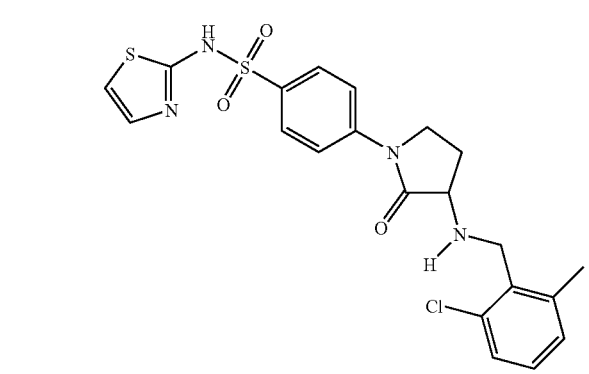

Synthesized according to general procedure 54, method B. LC/MS (10%-99% CH$_3$CN (0.035% TFA)/H$_2$O (0.05% TFA)), m/z: M+1 obs=477; t$_R$=1.04 min.

Synthesized according to general procedure 54, method B. LC/MS (10%-99% CH$_3$CN (0.035% TFA)/H$_2$O (0.05% TFA)), m/z: M+1 obs=511; t$_R$=1.12 min.

General Procedure 55

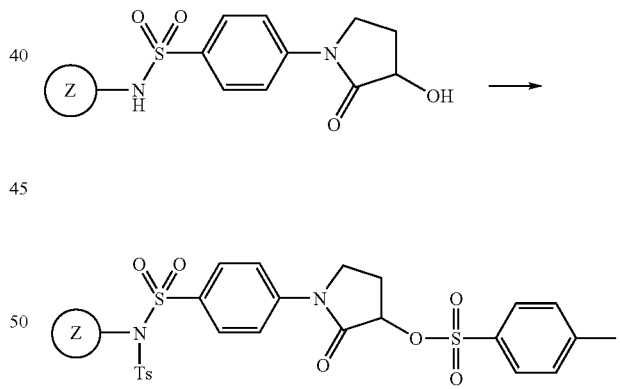

Under an N$_2$ atmosphere at −20° C., DMAP (1.5-3 equivalent) was added to a solution of alcohol (1 equivalent) in CH$_2$Cl$_2$ (0.5 M). To the reaction mixture then added triethylamine (3 equivalents). P-toluenesulfonic anhydride (3 equivalents) was added dropwise to this solution at −20° C. Upon completion of addition, the mixture was stirred at RT overnight. The reaction mixture was poured into water and extracted with CH$_2$Cl$_2$ (2×), dried over magnesium sulfate, and concentrated. Purification via silica gel chromatography using 2-10% MeOH in CH$_2$Cl$_2$ gave bis tosylated alcohol. LC/MS (10%-99% CH$_3$CN (0.035% TFA)/H$_2$O (0.05% TFA)), m/z: M+1 obs=648.5; t$_R$=1.92 min.

General Procedure 56

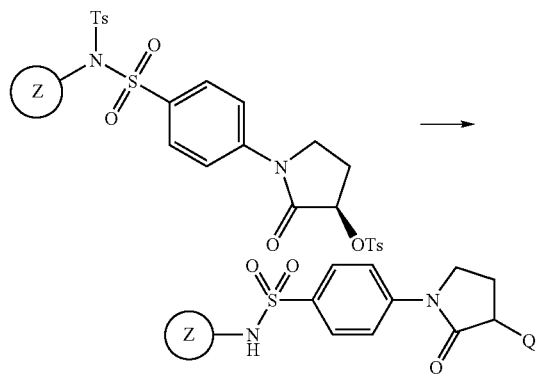

A solution of tosylated alcohol (1 equivalent), triethylamine (4 equivalents), amine (4 equivalents) in DMF (0.3-0.5 M) was stirred under $N_2$ atmosphere at 60° C. for 19 h. Purification via reverse phase HPLC using 10%-99% $CH_3CN$ (0.035% TFA)/$H_2O$ (0.05% TFA) gave the desired product.

(S)-4-(3-(4-(4-Chlorophenyl)piperidin-1-yl)-2-oxopyrrolidin-1-yl)-N-(thiazol-2-yl)benzenesulfonamide

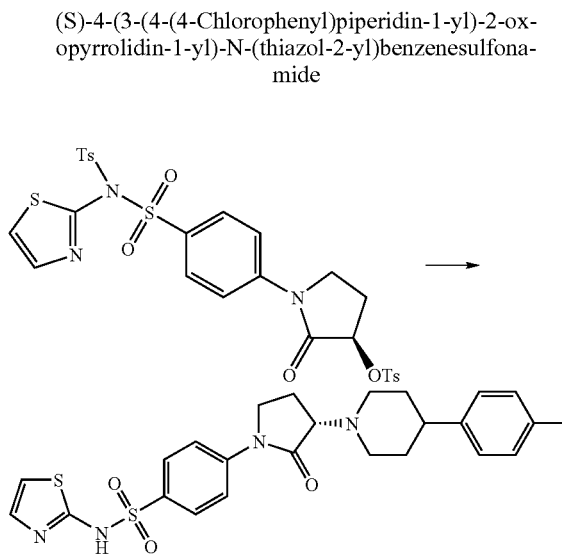

Synthesized according to general procedure 56. LC/MS (10%-99% $CH_3CN$ (0.035% TFA)/$H_2O$ (0.05% TFA)), m/z: M+1 obs=517.3; $t_R$=1.28 min.

(S)-4-(3-(4-(3,5-Dichlorophenyl)piperazin-1-yl)-2-oxopyrrolidin-1-yl)-N-(thiazol-2-yl)benzenesulfonamide

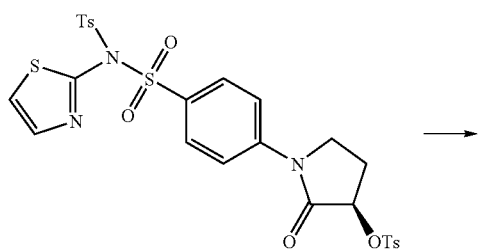

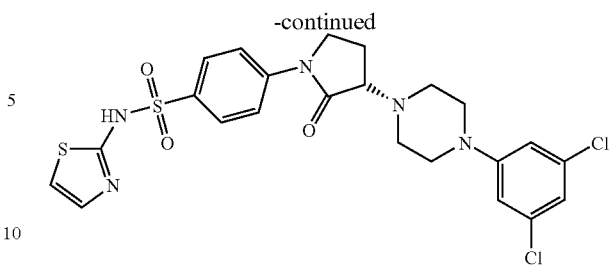

Synthesized according to general procedure 56. LC/MS (10%-99% $CH_3CN$ (0.035% TFA)/$H_2O$ (0.05% TFA)), m/z: M+1 obs=552; $t_R$=1.35 min.

4-((3S)-3-(3-((3,5-Dichlorophenyl)morpholino)-2-oxopyrrolidin-1-yl)-N-(thiazol-2-yl)benzenesulfonamide

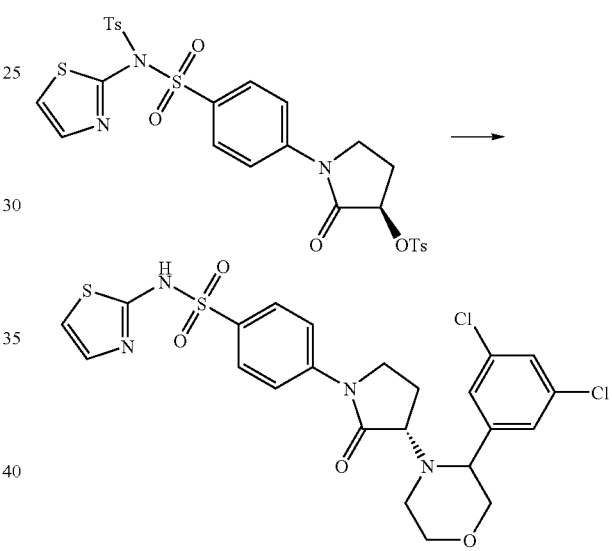

Synthesized according to general procedure 56. LC/MS (10%-99% $CH_3CN$ (0.035% TFA)/$H_2O$ (0.05% TFA)), m/z: M+1 obs=553; $t_R$=1.29 min.

Route 3

General Procedure 57

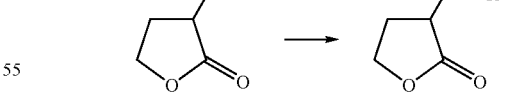

Under an $N_2$ atmosphere at −20° C., N,N-diisopropylethylamine (3 eq) was added dropwise to a solution of solution of (R)-(+)α-hydroxy-γ-butyrolactone (1 eq) in dichloromethane (0.5 mL). Then added trifluoromethanesulfonic anhydride (1-1.2 eq) dropwise by maintaining internal temperature of the reaction mixture <−20° C. Upon completion of addition, the mixture was stirred at −20° C. for 1 hour. Then added at −20° C., amine (1.5 eq) dropwise. The reaction was allowed to warm to RT over a period of 30 minutes and continued to stir at RT for 16 hrs. The reaction mixture was diluted with 200 mL of ethylacetate and washed with saturated sodium bicarbonate (3×). The organic layer was washed with a saturated aqueous NaCl solution (2×). The solution was dried over magnesium sulfate, filtered, and concentrated. Purification via silica gel chromatography using 10-30% ethyl acetate in hexane gave desired product.

General Procedure 58

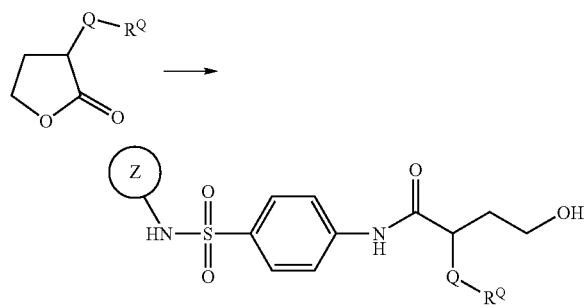

To a solution of sulfathiazole (1-1.2 eq.) in $CH_2Cl_2$ (0.5 M) under nitrogen at RT was added a solution of trimethylaluminum in hexane (2.0M, 1-1.2 eq.) over 5 min. After stirring at RT for 20 min, a solution of the lactone (1 eq.) in $CH_2Cl_2$ (0.4 M) was added over 10 min. Stirring was continued for 18-36 h at RT or reflux, then the reaction mixture was cooled to 0° C. and quenched by careful addition of aqueous 1 M HCl. Phases were separated, and the aqueous phase was extracted with $CH_2Cl_2$ (2×). The combined organic extracts were dried over $MgSO_4$ and concentrated. Purification via silica gel chromatography using 2-10% MeOH in $CH_2Cl_2$ gave the desired products.

General Procedure 59

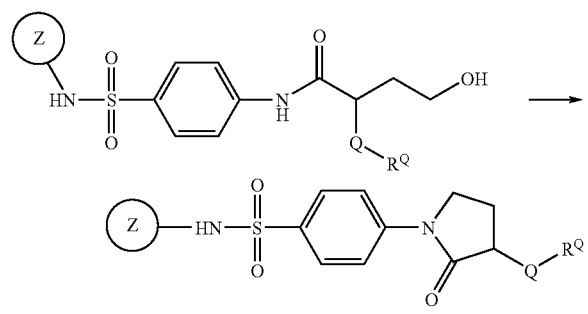

To a yellow solution of di-tert-butyl azo-dicarboxylate (2-4 eq.) in THF (0.4 M) at 0° C. under $N_2$ was slowly added tributylphosphine (2-4 eq.), The resulting colorless solution of the Mitsunobu reagent was stirred at RT for 10 min, and then added to a solution of the amido alcohol (1 eq.) in THF (0.3 M) at 0° C. under $N_2$. The reaction mixture was stirred for 10 min. at this temperature, and quenched by addition of a saturated aqueous $NaHCO_3$ solution. EtOAc was added, the phases were separated, and the aqueous layer was extracted with EtOAc (2×). The combined organic extracts were dried over $MgSO_4$ and concentrated. Purification via silica gel chromatography using EtOAc in hexane gave the desired products.

(S)-3-(4-Chloroindolin-1-yl)dihydrofuran-2(3H)-one

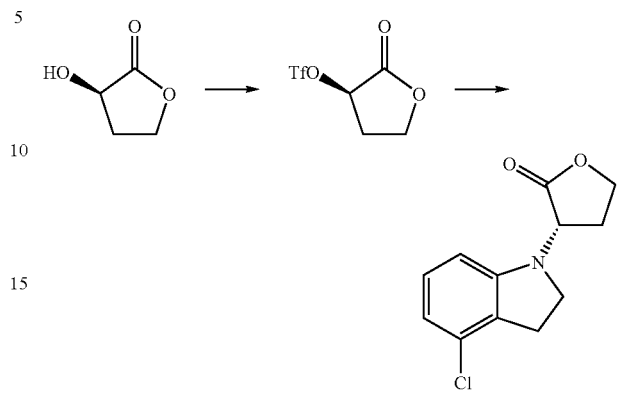

Prepared using general procedure 57. Under an $N_2$ atmosphere at –20° C., diisopropyl ethyl amine (7.59 g, 10.23 mL, 58.77 mmol) was added drop wise to a solution of solution of (R)-3-hydroxydihydrofuran-2(3H)-one (3 g, 29.38 mmol) in dichloromethane (50 mL). Then added trifluoromethanesulfonic anhydride (8.69 g, 5.18 mL, 30.81 mmol) drop wise by maintaining internal temperature of the reaction mixture <–20° C. Upon completion of addition, the mixture was stirred at –20° C. for 1 hour. Then added at –20° C., 4-chloroindoline (6.74 gm, 44.07 mmol) drop wise. The reaction was allowed to warm to RT over a period of 30 minutes and continued to stir at RT for 16 hrs. The reaction mixture was diluted with 200 mL of ethylacetate and washed with saturated sodium bicarbonate (3×50 mL). The organic layer was washed with a saturated aqueous NaCl solution (2×50 mL). The solution was dried over magnesium sulfate, filtered, and concentrated. Purification via silica gel chromatography using 10-30% ethyl acetate in hexane gave (S)-3-(4-chloroindolin-1-yl)dihydrofuran-2(3H)-one as a white solid (5.47 g, 80% yield). $^1$H NMR (400 MHz, DMSO-d6) δ 7.03 (t, J=8.0 Hz, 1H), 6.63 (dd, J=0.6, 8.0 Hz, 1H), 6.51 (d, J=7.9 Hz, 1H), 4.91 (dd, J=9.2, 11.2 Hz, 1H), 4.45-4.40 (m, 1H), 4.30-4.23 (m, 1H), 3.55-3.48 (m, 1H), 3.28 (dd, J=8.5, 18.0 Hz, 1H), 2.99-2.94 (m, 2H), 2.40-2.32 (m, 2H). LC/MS (10%-99% $CH_3CN$ (0.035% TFA)/$H_2O$ (0.05% TFA)), m/z: M+1 obs=237.9; $t_R$=1.51 min.

(S)-2-(4-Chloroindolin-1-yl)-4-hydroxy-N-(4-(N-thiazol-2-ylsulfamoyl)phenyl)butanamide

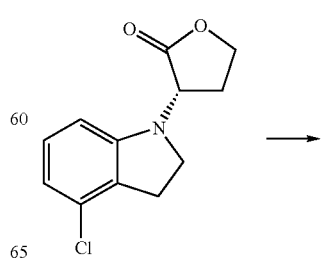

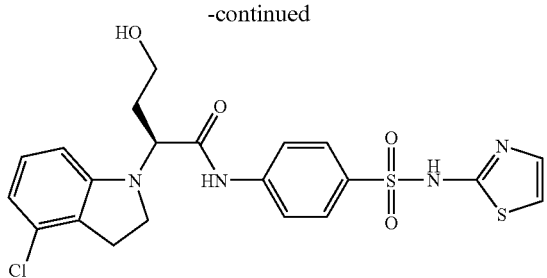

Prepared using general procedure 58. Under an N₂ atmosphere at RT, 2M-trimethyl aluminum in hexane (9.13 mL) was added dropwise to a stirring solution of sulfathiazole (4.6 g, 18.27 mmol) in dichloromethane (100 mL) in 30 minutes. Upon completion of addition, the mixture was stirred at RT for an hour. Added (s)-3-(4-chloroindolin-1-yl)dihydrofuran-2(3H)-one (3.56 g, 14.97 mmol) in dichloromethane (20 mL) to above solution over 30 minutes. The mixture was stirred for 16 hrs at RT. The reaction mixture was diluted with 500 mL of ethylacetate were added. The aqueous phase was acidified to pH 2 with an (1N) aqueous HCl solution. The ethyl acetate layer was washed with (1N) aqueous HCl (3×200 mL) till LCMS showed disappearance of sulfathiazole. The organic layer was dried over MgSO₄, filtered, concentrated. Purification via silica gel chromatography using 2-10% methanol in dichloromethane gave the amide as a white solid (5.9 g, 80% yield). LC/MS (10%-99% CH₃CN (0.035% TFA)/H₂O (0.05% TFA)), m/z: M+1 obs=493.2; $t_R$=1.46 min. ¹H NMR (400 MHz, DMSO) δ 12.69 (s, 1H), 7.74 (s, 4H), 7.24 (d, J=4.6 Hz, 1H), 6.98 (t, J=8.0 Hz, 1H), 6.81 (d, J=4.5 Hz, 1H), 6.56-6.54 (m, 2H), 4.71 (t, J=4.8 Hz, 1H), 4.43-4.39 (m, 1H), 3.79 (q, J=9.3 Hz, 1H), 3.64-3.58 (m, 2H), 3.51-3.48 (m, 1H), 3.17 (d, J=5.2 Hz, 1H), 3.00-2.89 (m, 1H), 1.93 (dd, J=6.0, 13.5 Hz, 1H), 1.88 (s, 1H).

(S)-4-(3-(4-Chloroindolin-1-yl)-2-oxopyrrolidin-1-yl)-N-(thiazol-2-yl)benzenesulfonamide

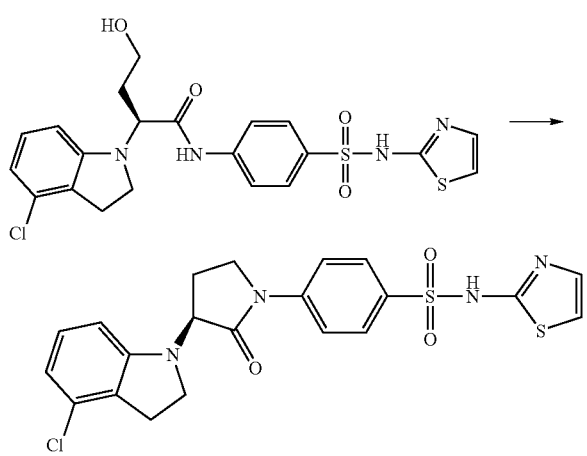

Prepared using general procedure 59. To a cooled (0° C.) solution of di-tert-butyl azo-dicarboxylate (3.73 g, 16.2 mmol) in THF (20 mL), was added drop wise tributyl phosphine (3.27 g, 4.0 mL, 16.2 mmol). Upon completion of addition, the mixture was stirred at 0° C. for 1 hour. To this solution was added (s)-4-(3-(4-chloroindolin-1-yl)-2-oxopyrrolidin-1-yl)-N-(thiazol-2-yl)benzenesulfonamide (2.0 g, 4.1 mmol) in dichloromethane (10 mL) dropwise over a 10 minute period at 0° C. Upon completion of addition, the mixture was stirred at 0° C. for 1 hour. The mixture was poured into cold water (35 mL), and extracted with EtOAc (3×100 mL). The organic portion was dried over magnesium sulfate, filtered, and concentrated. The residue was purified via silica gel chromatography using CH₂Cl₂ to gave the lactam as a white solid (700 mg, 35% yield). LC/MS (10%-99% CH₃CN (0.035% TFA)/H₂O (0.05% TFA)), m/z: M+1 obs=475.2; $t_R$=1.65 min, ¹H NMR (400 MHz, DMSO) δ 12.74 (s, 1H), 7.82 (m, 4H), 7.26 (d, J=4.6 Hz, 1H), 7.00 (t, J=8.0 Hz, 1H), 6.83 (d, J=4.6 Hz, 1H), 6.59 (d, J=7.9 Hz, 1H), 6.50 (d, J=7.9 Hz, 1H), 4.82 (dd, J=8.8, 10.8 Hz, 1H), 3.91-3.81 (m, 2H), 3.62-3.55 (m, 1H), 3.49-3.38 (m, 1H), 3.02-2.95 (m, 2H), 2.40-2.33 (m, 1H), 2.20-2.15 (m, 1H).

(S)-3-(6-Chloro-3,4-dihyroquinolin-1(2H)-yl)dihydrofuran-2(3H)-one

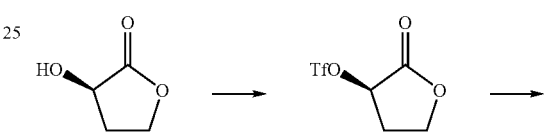

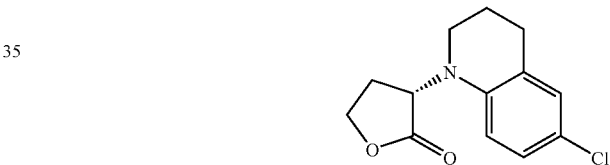

Prepared using general procedure 57. Under an N₂ atmosphere at −20° C., diisopropyl ethyl amine (15.9 mL, 91.4 mmol) was added drop wise to a solution of solution of (R)-3-Hydroxydihydrofuran-2(3H)-one (4.67 g, 45.7 mmol) in dichloromethane (70 mL). Then added trifluoromethanesulfonic anhydride (8.1 mL, 48.0 mmol) drop wise by maintaining internal temperature of the reaction mixture <−20° C. Upon completion of addition, the mixture was stirred at −20° C. for 1 hour. Then added at −20° C., 6-chloro-1,2,3,4-tetrahydroquinoline drop wise. The reaction was allowed to warm to RT over a period of 30 minutes and continued to stir at RT for 16 hrs. The reaction mixture was diluted with 200 mL of ethylacetate and washed with saturated sodium bicarbonate (3×50 mL). The organic layer was washed with a saturated aqueous NaCl solution (2×50 mL). The solution was dried over magnesium sulfate, filtered, and concentrated. Purification via silica gel chromatography using 5-50% ethyl acetate in hexane gave (S)-3-(6-chloro-3,4-dihydroquinolin-1(2H)-yl) dihydrofuran-2(3H)-one as a white solid (10.74 g, 93% yield). LC/MS (10%-99% CH₃CN (0.035% TFA)/H₂O (0.05% TFA)), m/z: M+1 obs=252.3; $t_R$=1.66 min. ¹H NMR (400 MHz, DMSO-d6) δ 7.03-6.98 (m, 2H), 6.74 (d, J=8.9 Hz, 1H), 5.07 (t, J=10.0 Hz, 1H), 4.42 (t, J=9.5 Hz, 1H), 4.30-4.23 (m, 1H), 3.16-3.02 (m, 2H), 2.68 (t, J=6.4 Hz, 2H), 2.44-2.27 (m, 2H), 1.87-1.77 (m, 2H).

(S)-2-(6-Chloro-3,4-dihydroquinolin-1(2H)-yl)-4-hydroxy-N-(4-(N-thiazol-2-ylsulfamoyl)phenyl)butanamide

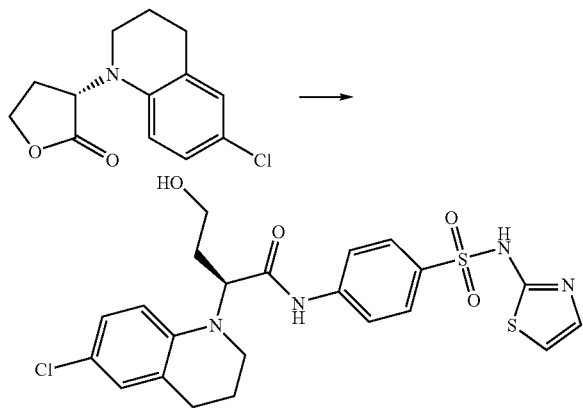

Prepared using general procedure 58. Under an N₂ atmosphere at RT, 2M-trimethylaluminium in hexane (19.2 mL, 38.4 mmol) was added drop wise to a stirring solution of sulfathiazole (9.81 g, 38.4 mmol) in dichloromethane (90 mL) in 30 minutes. Upon completion of addition, the mixture was stirred at RT for an hour. Added (S)-3-(6-chloro-3,4-dihydroquinolin-1-(2H)-yl)dihydrofuran-2-(3H)-one (10.7 g, 42.7 mol) in dichloromethane (90 mL) to above solution over 30 minutes. The mixture was stirred for 16 hrs at RT. The reaction mixture was diluted with 500 mL of ethylacetate were added. The aqueous phase was acidified to pH 2 with an (1N) aqueous HCl solution. The ethyl acetate layer was washed with (1N) aqueous HCl (3×200 mL) till LCMS showed disappearance of sulfathiazole. The organic layer was dried over MgSO₄, filtered, concentrated. Purification via silica gel chromatography using 2-10% methanol in dichloromethane gave the (S)-2-(6-chloro-3,4-dihydroquinolin-1(2H)-yl)-4-hydroxy-N-(4-(N-thiazol-2-ylsulfamoyl)phenyl)butanamide as a white solid (5.73 g, 30% yield). LC/MS (10%-99% CH₃CN (0.035% TFA)/H₂O (0.05% TFA)), m/z: M+1 obs=507.3; $t_R$=1.53 min. ¹H NMR (400 MHz, DMSO-d6) δ 10.38 (s, 1H), 7.78 (s, 4H), 7.24 (d, J=4.6 Hz, 1H), 7.01-6.96 (m, 2H), 6.82-6.76 (m, 2H), 4.68 (s, 1H), 4.59 (t, J=7.1 Hz, 1H), 4.03 (dd, J=14.2, 7.1 Hz, 1H), 3.47 (s, 2H), 3.35-3.21 (m, 2H), 2.69 (t, J=6.0 Hz, 2H), 2.14-2.06 (m, 1H), 1.93-1.78 (m, 2H).

(S)-4-(3-(6-Chloro-3,4-dihydroquinolin-(2H)1-yl)-2-oxopyrrolidin-1-yl)-N-(thiazol-2-yl)benzenesulfonamide

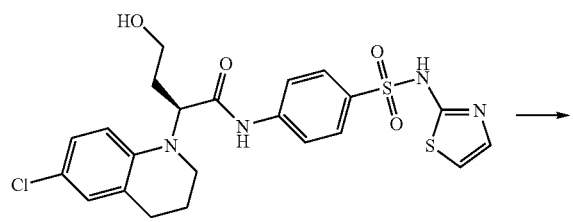

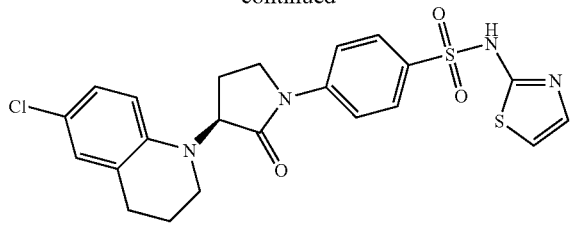

Prepared using general procedure 59. To a cooled (0° C.) solution of di-tert-butyl azodicarboxylate (0.937 g, 4.07 mmol) in THF (5 mL), was added drop wise tributyl phosphine (0.823 g, 1.01 mL, 4.07 mmol). Upon completion of addition, the mixture was stirred at 0° C. for 1 hour. To this solution was added (S)-2-(6-chloro-3,4-dihydroquinolin-1(2H)-yl)-4-hydroxy-N-(4-(N-thiazol-2-ylsulfamoyl)phenyl)butanamide (0.53 g, 1.01 mmol) in dichloromethane (10 mL) drop wise over a 10 minute period at 0° C. Upon completion of addition, the mixture was stirred at 0° C. for 1 hour. The mixture was poured into cold water (35 mL), and extracted with EtOAc (3×100 mL). The organic portion was dried over magnesium sulfate, filtered, and concentrated. The residue was purified via silica gel chromatography using CH₂Cl₂ to give (S)-4-(3-(6-chloro-3,4-dihydroquinolin-(2H) 1-yl)-2-oxopyrrolidin-1-yl)-N-(thiazol-2-yl)benzenesulfonamide as a white solid (222 mg, 45% yield). LC/MS (10%-99% CH₃CN (0.035% TFA)/H₂O (0.05% TFA)), m/z: M+1 obs=489.5; $t_R$=1.77 min. ¹H NMR (400 MHz, DMSO-d6) δ 12.74 (s, 1H), 7.85 (dd, J=23.1, 9.0 Hz, 4H), 7.26 (d, J=4.6 Hz, 1H), 7.00 (s, 1H), 6.98 (s, 1H), 6.83 (d, J=4.6 Hz, 1H), 6.75 (d, J=9.2 Hz, 1H), 5.00 (t, J=9.6 Hz, 1H), 3.90-3.79 (m, 2H), 3.16 (t, J=5.8 Hz, 2H), 2.70 (t, J=6.4 Hz, 2H), 2.43-2.36 (m, 2H), 2.18-2.08 (m, 2H).

Route 4

(S)-3-(4-Chloro-5-fluoroindolin-1-yl)-dihydrofuran-2(3H)-one

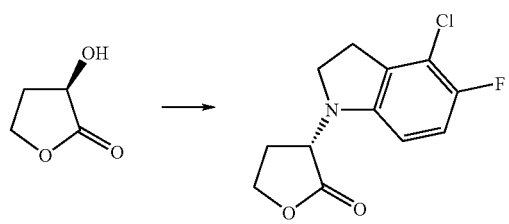

Prepared using general procedure 57. Under an N₂ atmosphere at −40° C., N,N-diisopropylethylamine (34.1 mL, 196 mmol) was added dropwise to a solution of solution of (R)-dihydro-3-hydroxyfuran-2(3H)-one (10.0 g, 98 mmol) in CH₂Cl₂ (100 mL). Trifluoromethanesulfonic anhydride (17.3 mL, 103 mmol) was added dropwise to this solution maintaining the internal temperature of the reaction mixture below −40° C. Upon completion of addition, the mixture was stirred at −40° C. for 1 h. A solution of 4-chloro-5-fluoroindoline (27.6, 147 mmol) in CH₂Cl₂ (40 mL) was added dropwise to this solution maintaining the internal temperature of the reaction mixture below −40° C. The reaction was allowed to warm up to −20° C. and was kept at this temperature for 48 h. The reaction mixture was washed with saturated aqueous sodium bicarbonate (2×), brine, dried over magnesium sulfate, and concentrated. Purification via silica gel chromatography using 0-40% ethyl acetate in hexane gave (S)-3-(4-chloro-5-fluoroindolin-1-yl)-dihydrofuran-2(3H)-one as a white solid (22.9 g, 90%). $^1$H NMR (400 MHz, DMSO-d6) δ 7.07-7.02 (m, 1H), 6.50 (dd, J=3.6, 8.6 Hz, 1H), 4.88 (dd, J=9.0, 11.4 Hz, 1H), 4.44-4.39 (m, 1H), 4.29-4.22 (m, 1H), 3.60-3.54 (m, 1H), 3.28 (dd, J=8.6, 17.8 Hz, 1H), 3.07-2.92 (m, 2H), 2.43-2.28 (m, 2H). LC/MS (10%-99% CH$_3$CN (0.035% TFA)/H$_2$O (0.05% TFA)), m/z: M+1 obs=256.1; $t_R$=1.54 min.

General Procedure 60

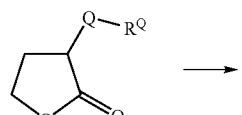

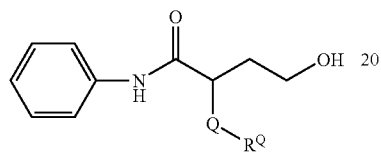

To a solution of aniline (1-1.2 eq.) in CH$_2$Cl$_2$ (0.5 M) under nitrogen at RT was added a solution of trimethylaluminum in hexane (2.0M, 1-1.2 eq.) over 5 min. After stirring at RT for 20 min, a solution of the lactone (1 eq.) in CH$_2$Cl$_2$ (0.4 M) was added over 10 min. Stirring was continued for 18-36 h at RT or reflux, then the reaction mixture was cooled to 0° C. and quenched by careful addition of aqueous 1 M HCl. Phases were separated, and the aqueous phase was extracted with CH$_2$Cl$_2$ (2×). The combined organic extracts were dried over MgSO$_4$ and concentrated. Purification via silica gel chromatography using 2-10% MeOH in CH$_2$Cl$_2$ gave the desired products.

(S)-2-(6-Chloro-3,4-dihydroquinolin-1(2H)-yl)-4-hydroxy-N-phenylbutanamide

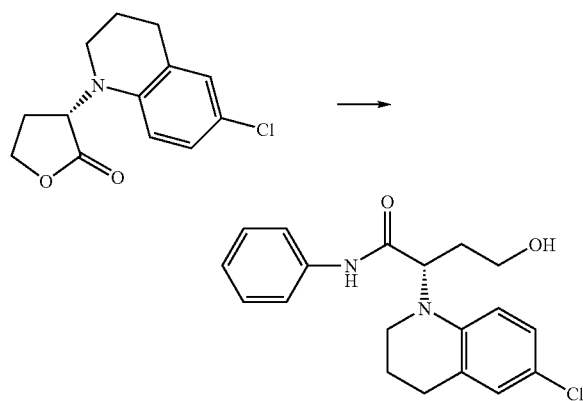

Prepared using general procedure 60: To a solution of aniline (1.0 mL, 11.1 mmol) in CH$_2$Cl$_2$ (25 mL) under nitrogen at RT was added a solution of trimethylaluminum in hexane (2.0 M, 5.5 mL, 11.0 mmol) over 5 min. After stirring at RT for 20 min, a solution of (S)-3-(6-chloro-3,4-dihydroquinolin-1(2H)-yl)-dihydrofuran-2(3H)-one (2.32 g, 9.2 mmol) in CH$_2$Cl$_2$ (25 mL) was added over 10 min. Stirring was continued for 18 h at RT, then the reaction mixture was cooled to 0° C. and quenched by careful addition of aqueous 1 M HCl (25 mL). Phases were separated, and the aqueous phase was extracted with CH$_2$Cl$_2$ (2×50 mL). The combined organic extracts were dried over MgSO$_4$ and concentrated. Purification via silica gel chromatography using 2-10% MeOH in CH$_2$Cl$_2$ gave (S)-2-(6-Chloro-3,4-dihydroquinolin-1(2H)-yl)-4-hydroxy-N-phenylbutanamide as a white solid (2.56 g, 81%). $^1$H NMR (400 MHz, DMSO-d6) δ 10.00 (s, 1H), 7.60 (dd, J=1.0, 8.5 Hz, 2H), 7.29 (dd, J=1.8, 14.1 Hz, 2H), 7.07-6.95 (m, 3H), 6.80 (d, J=9.0 Hz, 1H), 4.67 (t, J=4.9 Hz, 1H), 4.56 (t, J=7.2 Hz, 1H), 3.47 (dd, J=6.1, 11.2 Hz, 2H), 3.39-3.34 (m, 1H), 3.31-3.25 (m, 1H), 2.71-2.68 (m, 2H), 2.15-2.04 (m, 1H), 1.94-1.80 (m, 3H). LC/MS (10%-99% CH$_3$CN (0.035% TFA)/H$_2$O (0.05% TFA)), m/z: M+1 obs=345.3; $t_R$=3.44 min.

(S)-2-(4-Chloro-5-fluoroindolin-1-yl)-4-hydroxy-N-phenylbutanamide

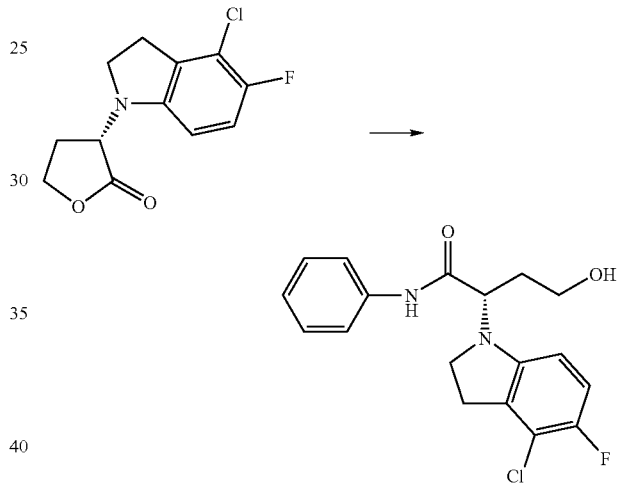

Prepared using general procedure 60: To a solution of aniline (1.4 mL, 15.6 mmol) in CH$_2$Cl$_2$ (37 mL) under nitrogen at RT was added a solution of trimethylaluminum in hexane (2.0 M, 7.8 mL, 15.6 mmol) over 5 min. After stirring at RT for 20 min, a solution of (S)-3-(4-chloro-5-fluoroindolin-1-yl)-dihydrofuran-2(3H)-one (4.0 g, 15.6 mmol) in CH$_2$Cl$_2$ (37 mL) was added over 10 min. Heated to reflux for 12 h, then the reaction mixture was cooled to 0° C. and quenched by careful addition of aqueous 1M HCl (70 mL). Phases were separated, and the aqueous phase was extracted with CH$_2$Cl$_2$ (2×75 L). The combined organic extracts were dried over MgSO$_4$ and concentrated. Purification via silica gel chromatography using 2-7.5% MeOH in CH$_2$Cl$_2$ gave (S)-2-(4-chloro-5-fluoroindolin-1-yl)-4-hydroxy-N-phenylbutanamide as a white solid (5.44 g, 100%). $^1$H NMR (400 MHz, DMSO-d6) δ 10.15 (s, 1H), 7.59 (d, J=7.6 Hz, 2H), 7.31-7.27 (m, 2H), 7.07-6.99 (m, 2H), 6.53 (dd, J=3.6, 8.6 Hz, 1H), 4.70 (t, J=4.9 Hz, 1H), 4.35 (t, J=7.4 Hz, 1H), 3.92-3.80 (m, 1H), 3.68-3.62 (m, 1H), 3.55-3.47 (m, 2H), 3.05-2.89 (m, 2H), 2.12-2.01 (m, 1H), 1.98-1.88 (m, 1H). LC/MS (10%-99% CH$_3$CN (0.035% TFA)/H$_2$O (0.05% TFA)), m/z: M+1 obs=349.1; $t_R$=1.69 min.

General Procedure 61

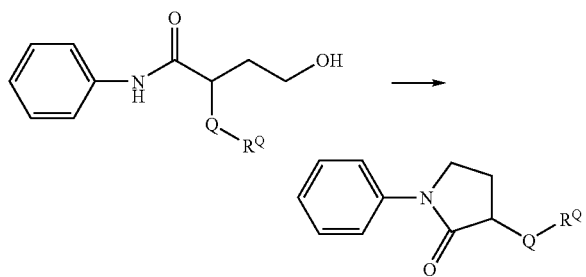

To a yellow solution of di-tert-butyl azo-dicarboxylate (2-4 eq.) in THF (0.4 M) at 0° C. under $N_2$ was slowly added tributylphosphine (2-4 eq.), The resulting colorless solution of the Mitsunobu reagent was stirred at RT for 10 min, and then added to a solution of the amido alcohol (1 eq.) in THF (0.3 M) at 0° C. under $N_2$. The reaction mixture was stirred for 10 min. at this temperature, and quenched by addition of a saturated aqueous $NaHCO_3$ solution. EtOAc was added, the phases were separated, and the aqueous layer was extracted with EtOAc (2×). The combined organic extracts were dried over $MgSO_4$ and concentrated. Purification via silica gel chromatography using EtOAc in hexane gave the desired products.

(S)-3-(6-Chloro-3,4-dihydroquinolin-1(2H)-yl)-1-phenylpyrrolidin-2-one

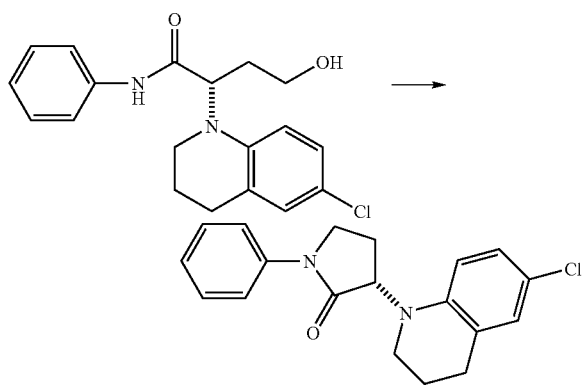

Prepared using general procedure 61: To a yellow solution of di-tert-butyl azo-dicarboxylate (2.23 g, 9.7 mmol) in THF (25 mL) at 0° C. under $N_2$ was slowly added tributylphosphine (2.4 mL, 9.7 mmol), The resulting colorless solution of the Mitsunobu reagent was stirred at RT for 10 min, and then added to a solution of (S)-2-(6-Chloro-3,4-dihydroquinolin-1(2H)-yl)-4-hydroxy-N-phenylbutanamide (2.56 g, 7.4 mmol) in THF (25 mL) at 0° C. under $N_2$. The reaction mixture was stirred for 10 min. at this temperature, and quenched by addition of a saturated aqueous $NaHCO_3$ solution. EtOAc was added, the phases were separated, and the aqueous layer was extracted with EtOAc (2×). The combined organic extracts were dried over $MgSO_4$ and concentrated. Purification via silica gel chromatography using 20-40 EtOAc in hexane gave (S)-3-(6-chloro-3,4-dihydroquinolin-1(2H)-yl)-1-phenylpyrrolidin-2-one as a white solid (2.43 g, 100%). LC/MS (10%-99% $CH_3CN$ (0.035% TFA)/$H_2O$ (0.05% TFA)), m/z: M+1 obs=327.5; $t_R$=1.50 min.

(S)-3-(4-Chloro-5-fluoroindolin-1-yl)-1-phenylpyrrolidin-2-one

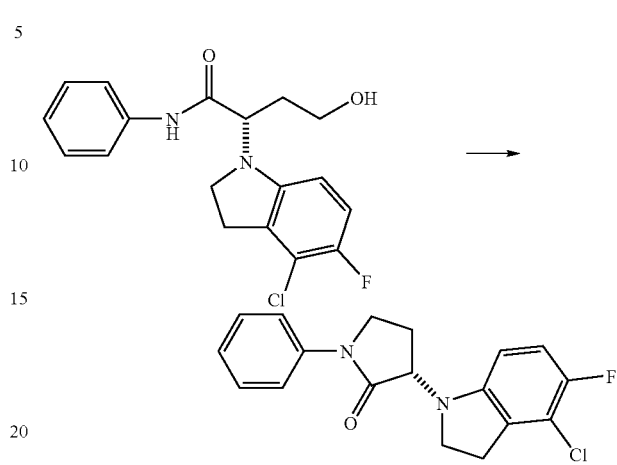

Prepared using general procedure 61: To a yellow solution of di-tert-butyl azo-dicarboxylate (2.72 g, 11.9 mmol) in THF (14 mL) at 0° C. under $N_2$ was slowly added tributylphosphine (3.0 mL, 11.9 mmol), The resulting colorless solution of the Mitsunobu reagent was stirred at RT for 10 min, and then added to a solution of (S)-2-(4-chloro-5-fluoroindolin-1-yl)-4-hydroxy-N-phenylbutanamide (1.03 g, 7.4 mmol) in THF (14 mL) at 0° C. under $N_2$. The reaction mixture was stirred for 10 min. at this temperature, and quenched by addition of a saturated aqueous $NaHCO_3$ solution. EtOAc was added, the phases were separated, and the aqueous layer was extracted with EtOAc (2×). The combined organic extracts were dried over $MgSO_4$ and concentrated. Purification via silica gel chromatography using 0-50 EtOAc in hexane gave (S)-3-(4-chloro-5-fluoroindolin-1-yl)-1-phenylpyrrolidin-2-one as a white solid (2.1 g, 82%). $^1H$ NMR (400 MHz, DMSO-d6) δ 7.71-7.68 (m, 2H), 7.42-7.38 (m, 2H), 7.17 (t, J=7.4 Hz, 1H), 7.04-6.99 (m, 1H), 6.49 (dd, J=3.6, 8.7 Hz, 1H), 4.77 (dd, J=8.8, 10.6 Hz, 1H), 3.85-3.81 (m, 2H), 3.62 (dd, J=2.7, 8.9 Hz, 1H), 3.40 (dd, J=8.6, 17.9 Hz, 1H), 3.05-2.95 (m, 2H), 2.40-2.31 (m, 1H), 2.21-2.10 (m, 1H). LC/MS (10%-99% $CH_3CN$ (0.035% TFA)/$H_2O$ (0.05% TFA)), m/z: M+1 obs=331.5; $t_R$=1.90 min.

General Procedure 62

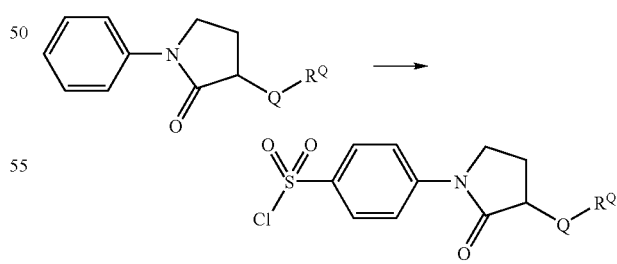

To chlorosulfonic acid (5-30 eq.) at 0° C. under $N_2$ was added the phenyl-pyrrolidin-2-one (1 eq.) in portions. The reaction mixture was heated to 50-60° C. for 15-20 min. and, after cooling to RT, carefully poured onto ice-water. EtOAc or $CH_2Cl_2$ were added, the phases were separated, and the aqueous layer was extracted with EtOAc or $CH_2Cl_2$ (2×). The combined organic extracts were dried over $MgSO_4$ and con-

4-((S)-3-(6-Chloro-3,4-dihydroquinolin-1(2H)-yl)-2-oxopyrrolidin-1-yl)benzene-1-sulfonyl chloride

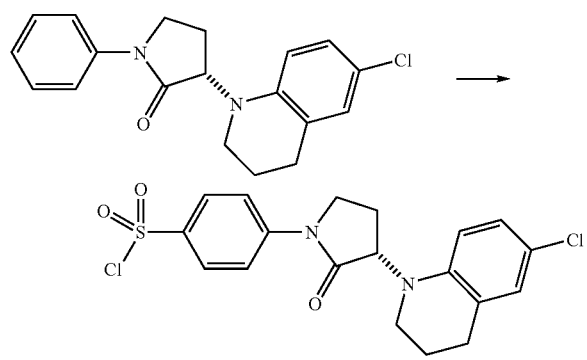

Prepared using general procedure 62: To chlorosulfonic acid (15 mL, 220 mmol) at 0° C. under $N_2$ was added (S)-3-(6-chloro-3,4-dihydroquinolin-1(2H)-yl)-1-phenylpyrrolidin-2-one (2.43 g, 7.4 mmol) in portions. The reaction mixture was heated to 50° C. for 15 min. and, after cooling to RT, carefully poured onto ice-water (500 mL). EtOAc (150 mL) was added, the phases were separated, and the aqueous layer was extracted with EtOAc (2×150 mL). The combined organic extracts were dried over $MgSO_4$ and concentrated. Purification via silica gel chromatography using 50-80% EtOAc in hexane gave 4-((S)-3-(6-Chloro-3,4-dihydroquinolin-1(2H)-yl)-2-oxopyrrolidin-1-yl)-benzene-1-sulfonyl chloride as an off-white solid (1.92 g, 61%). $^1$H NMR (400 MHz, DMSO-d6) δ 7.66 (dd, J=2.1, 6.8 Hz, 2H), 7.61 (dd, J=2.1, 6.8 Hz, 2H), 6.99 (d, J=9.0 Hz, 2H), 6.77 (d, J=8.7 Hz, 1H), 5.01-4.96 (m, 1H), 3.85-3.81 (m, 2H), 3.17 (t, J=5.6 Hz, 2H), 2.70 (t, J=6.4 Hz, 2H), 2.42-2.32 (m, 1H), 2.15-2.08 (m, 1H), 1.92-1.79 (m, 2H). LC/MS (10%-99% $CH_3CN$ (0.035% TFA)/$H_2O$ (0.05% TFA)), m/z: M+1 obs=425.1; $t_R$=4.03 min

4-((S)-3-(4-Chloro-5-fluoroindolin-1-yl)-2-oxopyrrolidin-1-yl)benzene-1-sulfonyl chloride

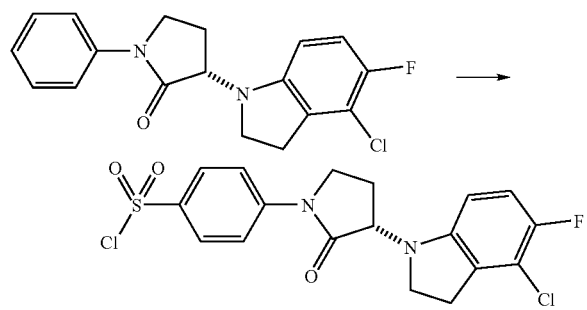

Prepared using general procedure 62: To chlorosulfonic acid (2.0 mL) at 0° C. under $N_2$ was added (S)-3-(4-chloro-5-fluoroindolin-1-yl)-1-phenylpyrrolidin-2-one (1.92 g, 5.8 mmol) in portions. The reaction mixture was heated to 60° C. for 20 min. and, after cooling to RT, carefully poured onto ice-water. EtOAc was added, the phases were separated, and the aqueous layer was extracted with EtOAc (2×). The combined organic extracts were dried over $MgSO_4$ and concentrated to give 4-((S)-3-(4-chloro-5-fluoroindolin-1-yl)-2-oxopyrrolidin-1-yl)benzene-1-sulfonyl chloride which was used without further purification. LC/MS (10%-99% $CH_3CN$ (0.035% TFA)/$H_2O$ (0.05% TFA)), m/z: M+1 obs=429.3; $t_R$=2.14 min.

General Procedure 63

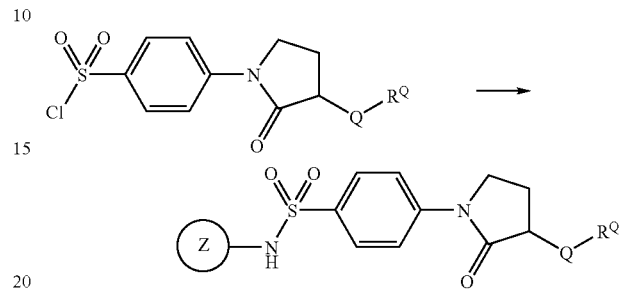

Method A

A solution of the sulfonyl chloride (1 eq.), 2-tert-butyl-1,1,3,3-tetramethylguanidine (5 eq.), and amine (1 eq.) in acetonitrile (0.3-0.5 M) was stirred under an $N_2$ atmosphere at RT for 19 h. Purification via reverse phase HPLC using 10%-99% $CH_3CN$ (0.035% TFA)/$H_2O$ (0.05% TFA) gave the desired products.

Method B:

A solution of the sulfonyl chloride (1 eq.), DABCO (5 eq.), and amine (1 eq.) in acetonitrile (0.3-0.5 M) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

Method C

A solution of the sulfonyl chloride (1 eq.), and amine (1 eq.) in pyridine (0.3-0.5 M) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

Method D

A solution of the sulfonyl chloride (1 eq.), phosphazene base P1-t-Bu-tris(tetramethylene) (5 eq.), and amine (1 eq.) in acetonitrile (0.3-0.5 M) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

4-((S)-3-(6-Chloro-3,4-dihydroquinolin-1(2H)-yl)-2-oxopyrrolidin-1-yl)-N-(1,2,4-thiadiazol-5-yl)benzenesulfonamide

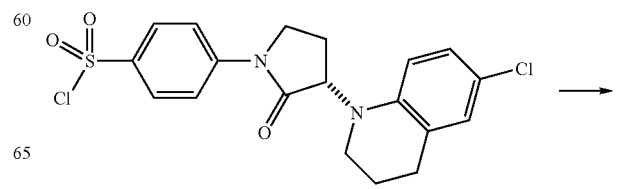

-continued

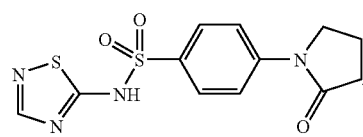

Synthesized according to general procedure 63, method A. LC/MS (10%-99% CH₃CN (0.035% TFA)/H₂O (0.05% TFA)), m/z: M+1 obs=490.3; $t_R$=3.47 min 4-((S)-3-(6-Chloro-3,4-dihydroquinolin-1(2H)-yl)-2-oxopyrrolidin-1-yl)-N-(pyrimidine-4-yl)benzenesulfonamide

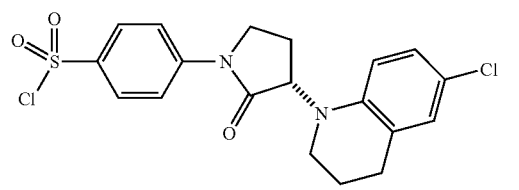

Synthesized according to general procedure 63, method B. LC/MS (10%-99% CH₃CN (0.035% TFA)/H₂O (0.05% TFA)), m/z: M+1 obs=484.5; $t_R$=3.11 min 4-((S)-3-(6-Chloro-3,4-dihydroquinolin-1(2H)-yl)-2-oxopyrrolidin-1-yl)-N-(thiazol-2-yl)benzenesulfonamide

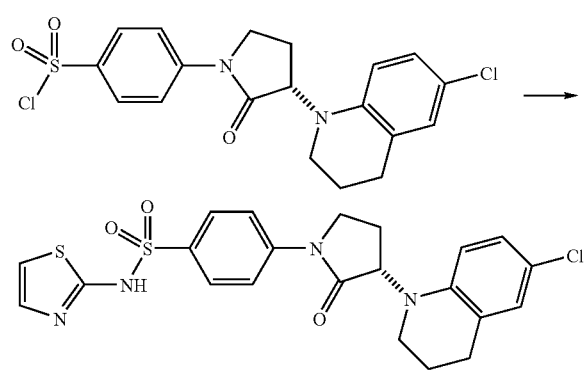

Synthesized according to general procedure 63, method C. LC/MS (10%-99% CH₃CN (0.035% TFA)/H₂O (0.05% TFA)), m/z: M+1 obs=489.3; $t_R$=3.36 min 4-((S)-3-(4-Chloro-5-fluoroindolin-1-yl)-2-oxopyrrolidin-1-yl)-N-(5-methyl-thiazol-2-yl)benzenesulfonamide

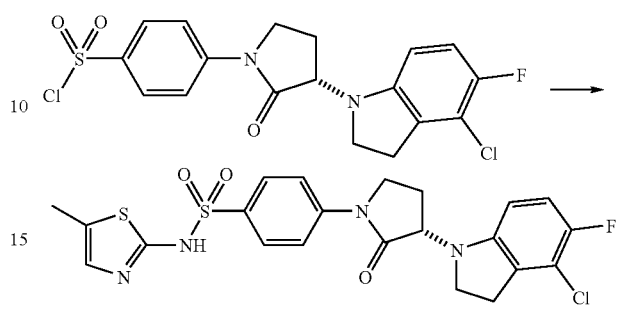

Synthesized according to general procedure 63, method A. LC/MS (10%-99% CH₃CN (0.035% TFA)/H₂O (0.05% TFA)), m/z: M+1 obs=507; $t_R$=1.75 min.

4-((S)-3-(4-Chloro-5-fluoroindolin-1-yl)-2-oxopyrrolidin-1-yl)-N-(1,3,4-thiadiazol-2-yl)benzenesulfonamide

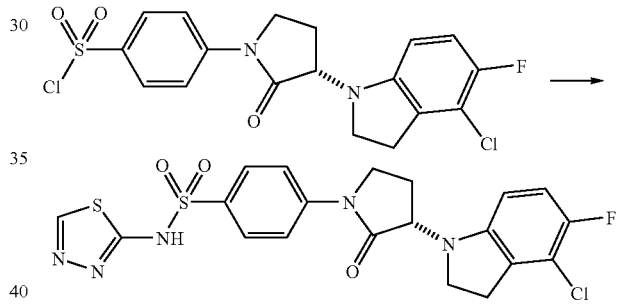

Synthesized according to general procedure 63, method A. LC/MS (10%-99% CH₃CN (0.035% TFA)/H₂O (0.05% TFA)), m/z: M+1 obs=494.3; $t_R$=1.68 min.

4-((S)-3-(4-Chloro-5-fluoroindolin-1-yl)-2-oxopyrrolidin-1-yl)-N-(6-chloropyradazin-2-yl)benzenesulfonamide

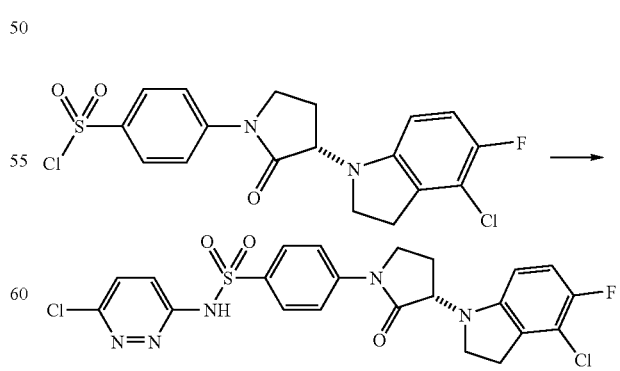

Synthesized according to general procedure 63, method D. LC/MS (10%-99% CH₃CN (0.035% TFA)/H₂O (0.05% TFA)), m/z: M+1 obs=522; $t_R$=1.83 min.

Route 5

(R)-3-(6-Chloro-3,4-dihydroquinolin-1(2H)-yl)pyrrolidin-2-one

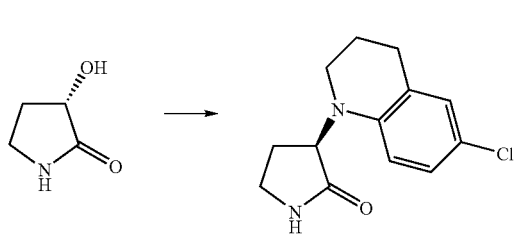

Prepared using general procedure 57. Under an N₂ atmosphere at −20° C., N,N-diisopropylethylamine (1.74 mL, 10.0 mmol) was added dropwise to a solution of (S)-3-hydroxypyrrolidin-2-one (500 mg, 5.0 mmol) in CH₂Cl₂ (8 mL). Trifluoromethanesulfonic anhydride (0.88 mL, 5.25 mmol) was added dropwise to this solution. Upon completion of addition, the mixture was stirred at −20° C. for 30 min. 6-Chloro-1,2,3,4-tetrahydroquinoline (1.26 g, 7.5 mmol) was added in one portion. The reaction was allowed to warm up to RT overnight. After 18 h, the reaction mixture was washed with saturated aqueous sodium bicarbonate (2×20 mL), brine (20 mL), dried over magnesium sulfate, and concentrated. Purification via silica gel chromatography using 0-30% ethyl acetate in hexane gave (R)-3-(6-chloro-3,4-dihydroquinolin-1(2H)-yl)pyrrolidin-2-one as a colorless oil (150 mg, 12%). LC/MS (10%-99% CH₃CN (0.035% TFA)/H₂O (0.05% TFA)), m/z: M+1 obs=251.3; $t_R$=2.77 min.

General Procedure 64

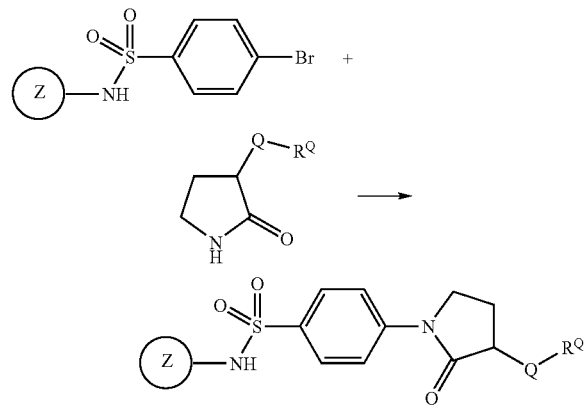

4-Bromo-benzenesulfonamide (1 eq.), pyrrolidin-2-one (1.2 eq.), copper (I) iodide (10 mol %), N,N'-dimethylethylenediamine (20 mol %), and K₂CO₃ (4 eq.) were combined in a microwave vial and set under nitrogen. NMP (0.4 M) was added, and the reaction mixture was heated to 200° C. for 30 min. using microwave irradiation. After cooling to RT, the reaction mixture was diluted with DMSO/MeOH (1:1) and purified via reverse phase HPLC using 10%-99% CH₃CN (0.035% TFA)/H₂O (0.05% TFA) to give the desired products.

(R)-4-(3-(6-Chloro-3,4-dihydroquinolin-1(2H)-yl)-2-oxopyrrolidin-1-yl)-N-(thiazol-2-yl)benzenesulfonamide

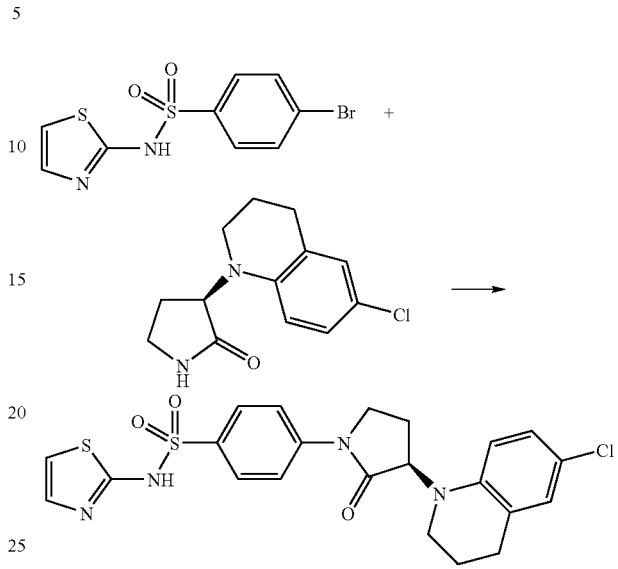

Prepared using general procedure 64. 4-Bromo-N-(thiazol-2-yl)benzenesulfonamide (54 mg, 0.17 mmol), (R)-3-(6-chloro-3,4-dihydroquinolin-1(2H)-yl)pyrrolidin-2-one (50 mg, 0.20 mmol), copper(I) iodide (3.8 mg, 10 mol %), N,N'-dimethylethylenediamine (4.2 µL, 20 mol %), and K₂CO₃ (94 mg, 0.68 mmol) were combined in a microwave vial and set under nitrogen. NMP (0.4 mL) was added, and the reaction mixture was heated to 200° C. for 30 min. using microwave irradiation. After cooling to RT, the reaction mixture was diluted with DMSO/MeOH (1:1, 0.6 mL) and purified via reverse phase HPLC using 10%-99% CH₃CN (0.035% TFA)/H₂O (0.05% TFA) to give (R)-4-(3-(6-chloro-3,4-dihydroquinolin-1(2H)-yl)-2-oxopyrrolidin-1-yl)-N-(thiazol-2-yl)benzenesulfonamide. LC/MS (10%-99% CH₃CN (0.035% TFA)/H₂O (0.05% TFA)), m/z: M+1 obs=489.3; $t_R$=3.27 min.

(S)-4-(3-(1H-Indol-1-yl)-2-oxopyrrolidin-1-yl)-N-(thiazol-2-yl)benzenesulfonamide A suspension of (S)-4-(3-(indolin-1-yl)-2-oxopyrrolidin-1-yl)-N-(thiazol-2-yl)-benzenesulfonamide (10 mg, 0.023 mmol) and activated MnO₂ (20 mg, 0.23 mmol) in CH₂Cl₂ (1.0 mL) was heated to 50° C. for 20 h. After cooling to RT, the reaction mixture was filtered through a syringe filter, concentrated and dissolved in DMSO/MeOH (1:1, 0.8 mL). Purification via reverse phase HPLC using 10%-99% CH₃CN (0.035% TFA)/H₂O (0.05% TFA) gave (S)-4-(3-(1H-Indol-1-yl)-2-oxopyrrolidin-1-yl)-N-(thiazol-2-yl)benzenesulfonamide. ¹H NMR (400 MHz, DMSO-d6) δ 7.84 (d, J=2.1 Hz, 2H), 7.82 (d, J=3.0 Hz, 2H), 7.47 (d, J=7.9 Hz, 1H), 7.29 (d, J=7.9 Hz, 1H), 7.19 (d, J=3.3 Hz, 1H), 7.08-7.03 (m, 1H), 7.01-6.94 (m, 2H), 6.62 (d, J=4.7 Hz, 1H), 6.44 (d, J=3.2 Hz, 1H), 5.51 (dd, J=8.9, 10.9 Hz, 1H), 4.02-3.98 (m, 2H), 2.72-2.68 (m, 1H), 2.49-2.40 (m, 1H). LC/MS (10%-99% CH₃CN (0.035% TFA)/H₂O (0.05% TFA)), m/z: M+1 obs=439.2; $t_R$=2.99 min.

(S)-4-(3-(5-chloro-1H-indol-1-yl)-2-oxopyrrolidin-1-yl)-N-(thiazol-2-yl)benzenesulfonamide

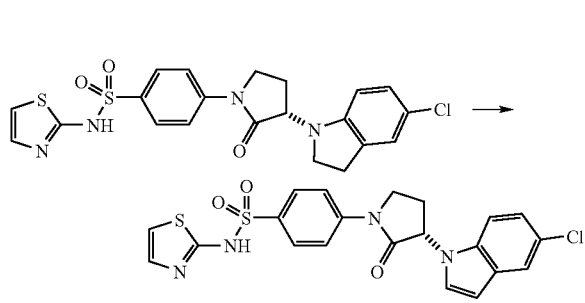

A suspension of (S)-4-(3-(5-chloroindolin-1-yl)-2-oxopyrrolidin-1-yl)-N-(thiazol-2-yl)benzenesulfonamide (11 mg, 0.023 mmol) and activated $MnO_2$ (20 mg, 0.23 mmol) in $CH_2Cl_2$ (1.0 mL) was heated to 50° C. for 20 h. After cooling to RT, the reaction mixture was filtered through a syringe filter, concentrated and dissolved in DMSO/MeOH (1:1, 0.8 mL). Purification via reverse phase HPLC using 10%-99% $CH_3CN$ (0.035% TFA)/$H_2O$ (0.05% TFA) gave (S)-4-(3-(5-chloro-1H-indol-1-yl)-2-oxopyrrolidin-1-yl)-N-(thiazol-2-yl)benzenesulfonamide. $^1H$ NMR (400 MHz, MeOD-d4) δ 7.83 (d, J=3.8 Hz, 2H), 7.81 (d, J=2.5 Hz, 2H), 7.46 (d, J=2.0 Hz, 1H), 7.29-7.26 (m, 2H), 7.04-6.99 (m, 2H), 6.62 (d, J=4.7 Hz, 1H), 6.43 (d, J=3.2 Hz, 1H), 5.51 (dd, J=8.9, 11.0 Hz, 1H), 3.99 (dd, J=6.1, 9.7 Hz, 2H), 2.75-2.67 (m, 1H), 2.48-2.38 (m, 1H). LC/MS (10%-99% $CH_3CN$ (0.035% TFA)/$H_2O$ (0.05% TFA)), m/z: M+1 obs=473.2; $t_R$=3.21 min.

Route 6

(R)—S-Ethyl 2-(2,2-dimethyl-5-oxo-1,3-dioxolan-4-yl)ethanethioate

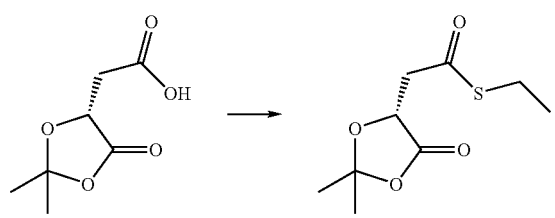

To a stirring suspension of (R)-(−)-dimethyl-5-oxo-1,2-dioxolane-4-acetic acid (3.5 g, 20 mmol), and $CH_2Cl_2$ (40 mL), at 0° C., under $N_2$, was added isovalerylchloroformate (2.9 mL, 22 mmol) dropwise over 5 minutes. The mixture was stirred at 0° C. for 10 minutes. Triethylamine (5.5 mL, 40 mmol) was added dropwise at 0° C. followed by the dropwise addition of ethanethiol (3.4 mL, 44 mmol). The pink mixture was stirred at 0° C. for 10 minutes. To the reaction was added $Et_2O$ (40 mL) and the mixture was filtered. The filtrate was washed with 1.0 N aqueous HCl (20 mL), 0.1 N aqueous NaOH (20 mL), $H_2O$ (20 mL) and brine (20 mL). The organic solution was evaporated to dryness under reduced pressure to obtain the desired thioester as a clear oil (3.4 g, 16 mmol, 82% yield). $^1H$ NMR (400 MHz, $CDCl_3$) δ 4.71-4.65 (m, 1H), 3.91-3.81 (m, 1H), 3.11-2.70 (m, 3H), 1.53 (s, 3H), 1.50 (s, 3H), 0.87-0.86 (m, 3H). LC/MS (10%-99% $CH_3CN$ (0.035% TFA)/$H_2O$ (0.05% TFA)), m/z: M+1 obs=219.4; $t_R$=1.33 min.

General Procedure 65

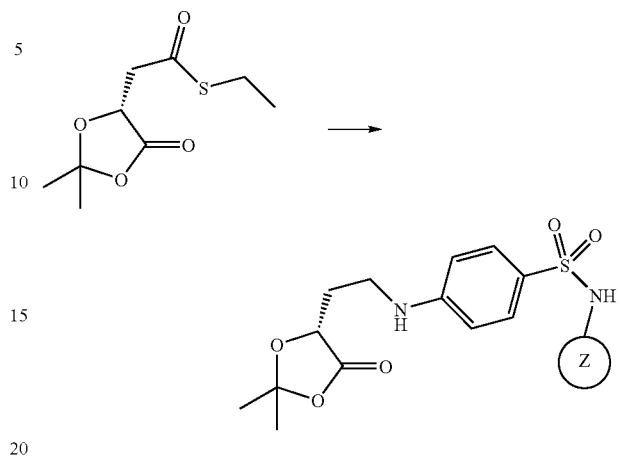

To a stirring mixture of (R)—S-ethyl 2-(2,2-dimethyl-5-oxo-1,3-dioxolan-4-yl)ethanethioate (1 equivalent), 10% palladium on carbon (470 mg), and $CH_2Cl_2$ (0.5-1 M) under $N_2$, at 25° C., was added triethylsilane (1.5 equivalent) dropwise over 10 minutes. The mixture was stirred at 25° C. for 1 hour. The mixture was filtered and the filtrate was evaporated to dryness under reduced pressure to give the desired aldehyde as clear oil. The aldehyde was added to a stirring mixture of sulfathiazole (0.5 equivalent), MeOH (1 M), and trifluoroacetic acid (0.1 M). To this solution was added sodium borohydride (2.5 equivalent) portionwise over 10 minutes. The mixture was stirred for 10 minutes and evaporated under reduced pressure. The residue was purified via silica gel chromatography using 5% MeOH in $CH_2Cl_2$ to obtain the desired amine.

(R)-4-(2-(2,2-Dimethyl-5-oxo-1,3-dioxolan-4-yl)ethylamino)-N-(thiazol-2-yl)benzenesulfonamide

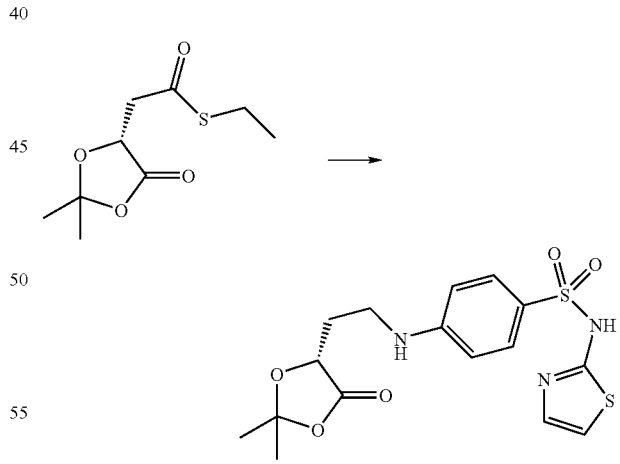

Synthesised according to general procedure 65. To a stirring mixture of (R)—S-ethyl 2-(2,2-dimethyl-5-oxo-1,3-dioxolan-4-yl)ethanethioate (1.9 g, 8.7 mmol), 10% palladium on carbon (470 mg), and $CH_2Cl_2$ (20 mL) under $N_2$, at 25° C., was added triethylsilane (2.08 mL, 13.0 mmol) dropwise over 10 minutes. The mixture was stirred at 25° C. for 1 hour. The mixture was filtered and the filtrate was evaporated to dryness under reduced pressure to give the desired aldehyde as a clear oil (1.2 g). The aldehyde was added to a stirring mixture of sulfathiazole (1.1 g, 4.3 mmol), MeOH (25 mL), and trifluoroacetic acid (2.5 mL). To this solution was added sodium borohydride (813 mg, 21.4 mmol) portionwise over 10 minutes. The mixture was stirred for 10 minutes and evaporated under reduced pressure. The residue was purified via silica gel chromatography using 5% MeOH in $CH_2Cl_2$ to obtain the desired amine as a white solid (1.5 g, 3.9 mmol, 45% yield). LC/MS (10%-99% $CH_3CN$ (0.035% TFA)/$H_2O$ (0.05% TFA)), m/z: M+1 obs=398.3; $t_R$=1.18 min.

General Procedure 66

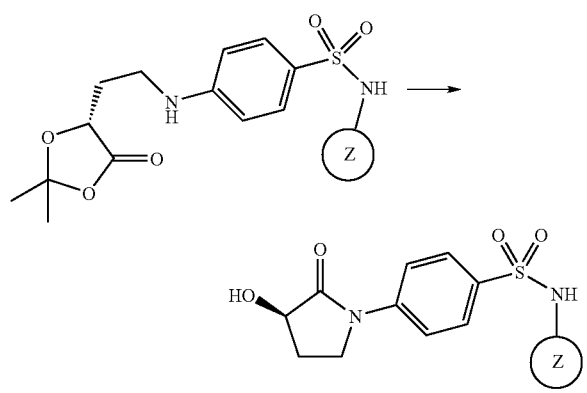

A stirring solution of benzenesulfonamide (1 equivalent), p-toluenesulfonic acid monohydrate (0.1 equivalent), and THF (0.5-1 M) was stirred at 80° C. for 3 hours. The mixture was concentrated to dryness under reduced pressure. The residue was purified via silica gel chromatography using 5% MeOH in $CH_2Cl_2$ to give the desired lactam.

(R)-4-(3-Hydroxy-2-oxopyrrolidin-1-yl)-N-(thiazol-2-yl)benzenesulfonamide

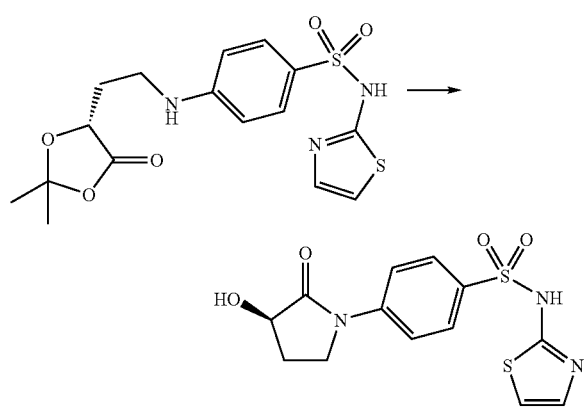

Synthesised according to general procedure 66. A stirring solution of (R)-4-(2-(2,2-dimethyl-5-oxo-1,3-dioxolan-4-yl)ethylamino)-N-(thiazol-2-yl)benzenesulfonamide (833 mg, 2.15 mmol), p-toluenesulfonic acid monohydrate (42 mg g, 0.22 mmol), and THF (10 mL) was stirred at 80° C. for 3 hours. The mixture was concentrated to dryness under reduced pressure. The residue was purified via silica gel chromatography using 5% MeOH in $CH_2Cl_2$ to give the desired lactam as a white solid (496 g, 1.4 mmol, 65% yield). $^1H$ NMR (400 MHz, DMSO-d6) δ 7.85 (dd, J=2.1, 6.9 Hz, 4H), 7.25 (d, J=4.6 Hz, 1H), 6.82 (d, J=4.6 Hz, 1H), 5.83 (d, J=5.9 Hz, 1H), 4.32 (d, J=5.3 Hz, 1H), 3.77 (dd, J=1.9, 9.0 Hz, 1H), 3.71-3.69 (m, 1H), 2.41-2.38 (m, 1H), 1.84 (dd, J=9.2, 12.3 Hz, 1H).). LC/MS (10%-99% $CH_3CN$ (0.035% TFA)/$H_2O$ (0.05% TFA)), m/z: M+1 obs=340.2; $t_R$=0.50 min.

General Procedure 67

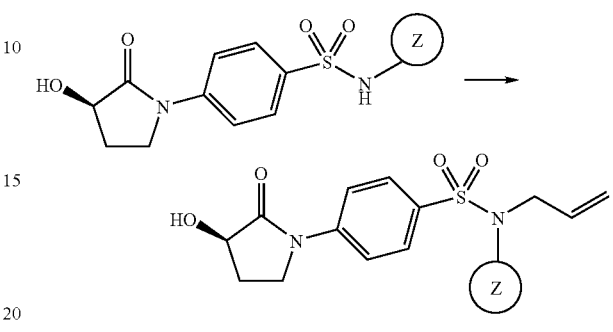

To a stirring suspension of N-benzenesulfonamide (1 equivalent) in $CH_2Cl_2$ (0.5-1 M), under $N_2$, at 0° C., was added N,N-diisopropylethylamine (1 equivalent) followed by allylbromide (1 equivalent). The mixture was stirred at ambient temperature for 19 hours. The mixture was evaporated to dryness under reduced pressure. The residue was purified via silica gel using 50% EtOAc in hexanes to give the desired sulfonamide.

(R)—N-Allyl-4-(3-hydroxy-2-oxopyrrolidin-1-yl)-N-(thiazol-2-yl)benzenesulfonamide

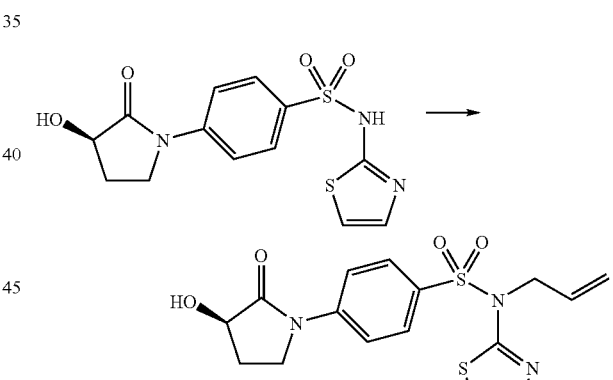

Synthesised according to general procedure 67. To a stirring suspension of (R)-4-(3-hydroxy-2-oxopyrrolidin-1-yl)-N-(thiazol-2-yl)benzenesulfonamide (200 mg, 0.59 mmol) in $CH_2Cl_2$ (0.50 mL), under $N_2$, at 0° C., was added N,N-diisopropylethylamine (0.10 mL, 0.59 mmol) followed by allylbromide (51 uL, 0.59 mmol). The mixture was stirred at ambient temperature for 19 hours. The mixture was evaporated to dryness under reduced pressure. The residue was purified via silica gel using 50% EtOAc in hexanes to give the desired sulfonamide as a white solid (220 mg, 0.57 mmol, 96% yield). $^1H$ NMR (400 MHz, DMSO-d6) δ 7.86-7.80 (m, 4H), 7.37 (d, J=4.7 Hz, 1H), 6.93 (d, J=4.7 Hz, 1H), 5.92-5.83 (m, 2H), 5.17 (dd, J=1.3, 10.3 Hz, 1H), 4.98 (q, J=1.4 Hz, 1H), 4.55 (dt, J=5.3, 1.7 Hz, 2H), 4.36-4.30 (m, 1H), 3.81-3.76 (m, 1H), 3.70 (td, J=9.5, 5.4 Hz, 1H), 2.45-2.38 (m, 1H), 1.90-1.80 (m, 1H).

(S)—N-Allyl-4-(3-(6-chloro-3,4-dihydroquinolin-1 (2H)-yl)-2-oxopyrrolidin-1-yl)-N-(thiazol-2-yl)benzenesulfonamide

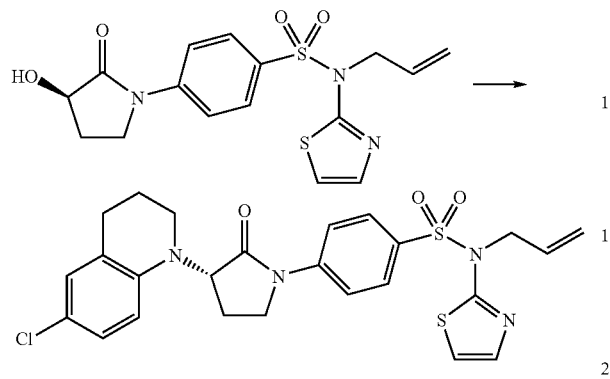

Synthesized according to general procedure 49. The reaction was set up with (R)—N-allyl-4-(3-hydroxy-2-oxopyrrolidin-1-yl)-N-(thiazol-2-yl)benzenesulfonamide (100 mg, 0.26 mmol) triflic anhydride (51 uL, 0.29 mmol), N,N-diisopropylethylamine (90 uL, 0.52 mmol), CH$_2$Cl$_2$, and 6-chloro-1,2,3,4-tetrahydroquinoline (65 mg, 0.39 mmol). The reaction was held at −25° C. for 19 hours and quenched with H$_2$O (30 uL). The residue was purified via silica gel using 10% MeOH in CH$_2$Cl$_2$ to obtain the desired lactam as a white solid (102 g, 0.19 mmol, 73% yield). $^1$H NMR (400 MHz, DMSO-d6) δ 7.87 (m, 4H), 7.37 (d, J=4.7 Hz, 1H), 7.99-7.95 (m, 3H), 6.93 (d, J=4.7 Hz, 1H), 6.75 (d, J=9.1 Hz, 1H), 5.92-5.82 (m, 1H), 5.17 (dd, J=1.3, 10.3 Hz, 1H), 5.01-4.97 (m, 2H), 4.56-4.55 (m, 2H), 3.89-3.79 (m, 2H), 3.42-3.23 (m, 1H), 3.20-3.11 (m, 2H), 2.70 (t, J=6.3 Hz, 2H), 2.42-2.33 (m, 1H), 2.17 (d, J=9.7 Hz, 1H), 1.93-1.76 (m, 2H).

(S)-4-(3-(6-Chloro-3,4-dihydroquinolin-1(2H)-yl)-2-oxopyrrolidin-1-yl)-N-(thiazol-2-yl)benzenesulfonamide

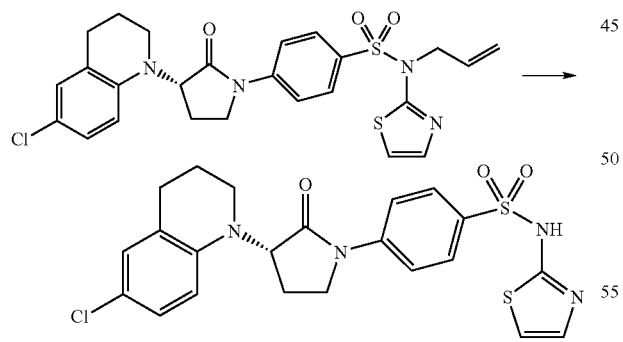

Synthesized according to general procedure 50. The reaction was set up with (S)—N-allyl-4-(3-(6-chloro-3,4-dihydroquinolin-1(2H)-yl)-2-oxopyrrolidin-1-yl)-N-(thiazol-2-yl)benzenesulfonamide (100 mg, 0.19 mmol), CH$_3$CN (1.5 mL), Pd(PPh$_3$)$_4$ (46 mg, 0.04 mmol) and 1,3-dimethylbarbituric acid (97 mg, 1.1 mmol). The reaction mixture was purified via silica gel chromatography using 5% MeOH in CH$_2$Cl$_2$ to obtain the desired lactam as a white solid (10 mg, 0.02 mmol, 11% yield). $^1$H NMR (400 MHz, DMSO-d6) δ 7.89-7.79 (m, 4H), 7.25 (d, J=4.6 Hz, 1H), 7.00-6.97 (m, 2H), 6.82 (d, J=4.6 Hz, 1H), 6.75 (d, J=8.7 Hz, 1H), 4.99 (dd, J=9.0, 10.2 Hz, 1H), 3.89-3.79 (m, 2H), 3.19-3.12 (m, 2H), 2.70 (t, J=6.3 Hz, 2H), 2.42-2.36 (m, 1H), 2.11-2.05 (m, 1H), 1.91-1.77 (m, 2H). LC/MS (10%-99% CH$_3$CN (0.035% TFA)/H$_2$O (0.05% TFA)), m/z: M+1 obs=489.3; t$_R$=1.73 min.

Example 15

General Procedure 68

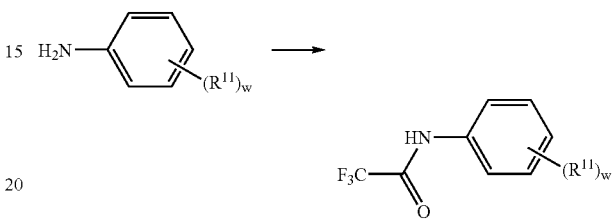

Under an N$_2$ atmosphere at −78° C., 2,2,2-trifluoroacetic anhydride (1 equivalent) was added drop wise to a solution of the aniline (1 equivalent), triethylamine (1 equivalent), and CH$_2$Cl$_2$ (0.6 M). The reaction was allowed to warm to RT over a period of 30 minutes. After evaporating the solvents under reduced pressure, purification via silica gel chromatography using 7/3 hexanes/EtOAc gave desired product.

General Procedure 69

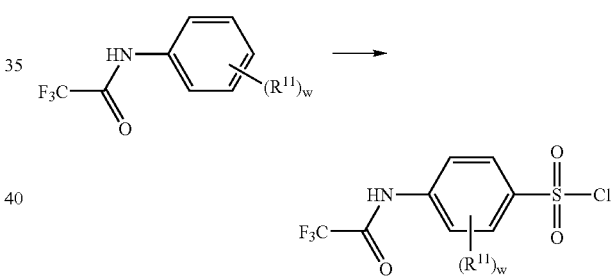

A mixture of acetamide (1 equivalent) and chlorosulfonic acid (5 equivalent) was heated at 155° C. for 15 min. After cooling to RT, the mixture was poured into ice water and extracted with EtOAc. The organic layer was concentrated and purified via silica gel chromatography using 7/3 hexanes/EtOAc gave desired product.

General Procedure 70

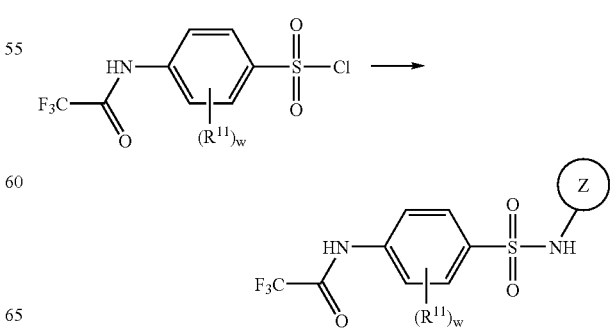

Under an N₂ atmosphere, a mixture of the sulfonyl chloride (1 mmol) and aminoheterocycle (1 mmol), and pyridine (1.0 mL) was stirred at RT for 19 h. The crude product was purified via silica gel chromatography using MeOH in CH₂Cl₂.

General Procedure 71

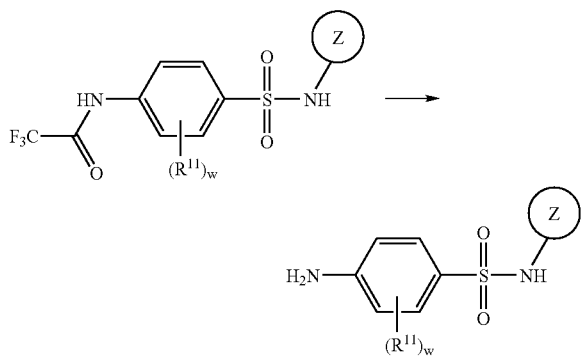

A solution of sulfonamide (1 equivalent), NaOH (10 equivalents), and H₂O (0.25 M) was stirred at RT for 1 h, then cooled to 0° C. Acetic acid (10 equivalents) was added, and the reaction was stirred at 0° C. for 20 min. The formed precipitate was filtered off and dried under vacuum to give the desired product.

General Procedure 72

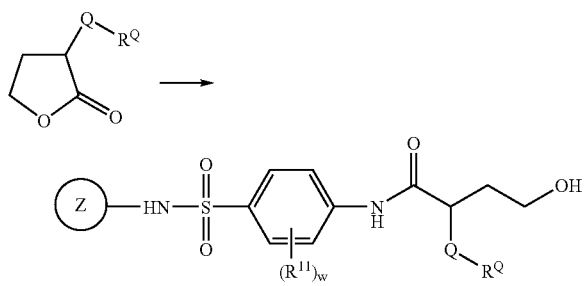

To a solution of sulfathiazole (1-1.2 eq.) in CH₂Cl₂ (0.5 M) under nitrogen at RT was added a solution of trimethylaluminum in hexane (2.0M, 1-1.2 eq.) over 5 min. After stirring at RT for 20 min, a solution of the lactone (1 eq.) in CH₂Cl₂ (0.4 M) was added over 10 min. Stirring was continued for 18-36 h at RT or reflux, then the reaction mixture was cooled to 0° C. and quenched by careful addition of aqueous 1 M HCl. Phases were separated, and the aqueous phase was extracted with CH₂Cl₂ (2×). The combined organic extracts were dried over MgSO₄ and concentrated. Purification via Gilson HPLC gave the desired product.

General Procedure 73

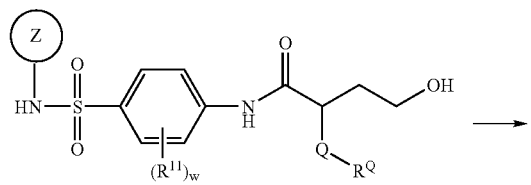

-continued

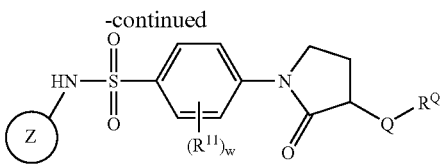

To a yellow solution of di-tert-butyl azo-dicarboxylate (2-4 eq.) in THF (0.4 M) at 0° C. under N₂ was slowly added tributylphosphine (2-4 eq.), The resulting colorless solution of the Mitsunobu reagent was stirred at RT for 10 min, and then added to a solution of the amido alcohol (1 eq.) in THF (0.3 M) at 0° C. under N₂. The reaction mixture was stirred for 10 min. at this temperature, and quenched by addition of a saturated aqueous NaHCO₃ solution. EtOAc was added, the phases were separated, and the aqueous layer was extracted with EtOAc (2×). The combined organic extracts were dried over MgSO₄ and concentrated. Purification via Gilson HPLC gave the desired product.

2,2,2-Trifluoro-N-o-tolylacetamide

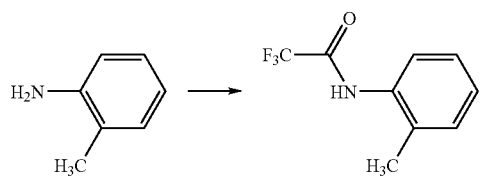

Synthesized according to general procedure 68. Under an N₂ atmosphere at −78° C., 2,2,2-trifluoroacetic anhydride (5.2 mL, 37.5 mmol) was added drop wise to a solution of o-toluidine (4.015 gm, 37.5 mmol), triethylamine (5.2 mL, 37.5 mmol), and CH₂Cl₂ (63 mL). The reaction was allowed to warm to RT over a period of 30 minutes. After evaporating the solvents under reduced pressure, purification via silica gel chromatography using 7/3 hexanes/EtOAc gave 2,2,2-trifluoro-N-o-tolylacetamide (6.69 g, 85%). LC/MS (10%-99% CH₃CN (0.035% TFA)/H₂O (0.05% TFA)), m/z: M+1 obs=204.3; t_R=1.25 min.

3-Methyl-4-(2,2,2-trifluoroacetamido)benzene-1-sulfonyl chloride

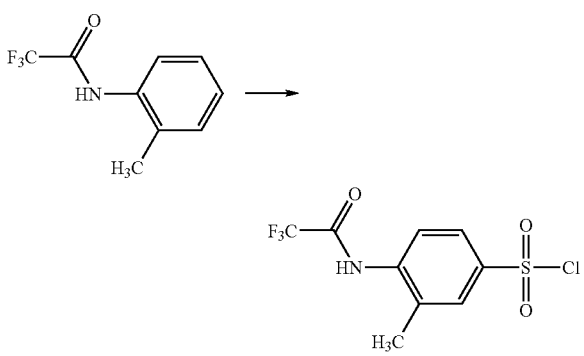

Synthesized according to general procedure 69. A mixture of 2,2,2-trifluoro-N-o-tolylacetamide (6.3 gm, 31 mmol) and chlorosulfonic acid (10.3 mL, 155 mmol) was heated at 155° C. for 15 min. After cooling to RT, the mixture was poured into ice water and extracted with EtOAc. The organic layer was concentrated and purified via silica gel chromatography using 0-25% EtOAc in hexanes gave 3-methyl-4-(2,2,2-trifluoroacetamido)benzene-1-sulfonyl chloride (7.8 g, 85%). $^1$H NMR (400 MHz, DMSO-d6) δ 11.01 (s, 1H), 7.53 (d, J=1.3 Hz, 1H), 7.46 (dd, J=8.1, 1.8 Hz, 1H), 7.21 (dd, J=8.1, 2.9 Hz, 1H), 2.18 (s, 3H).

2,2,2-Trifluoro-N-(2-methyl-4-(N-thiazol-2-ylsulfamoyl)phenyl)acetamide

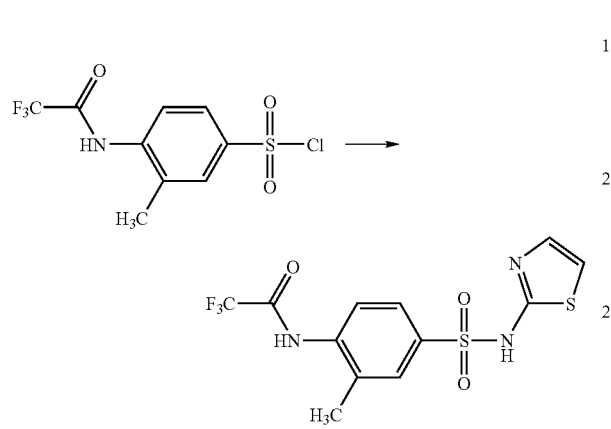

Synthesized according to general procedure 70. Under an N$_2$ atmosphere, a mixture of 3-methyl-4-(2,2,2-trifluoroacetamido)benzene-1-sulfonyl chloride (7.5 g, 24.9 mmol) and 2-aminothiazole (2.49 g, 24.9 mmol), and pyridine (15 mL) was stirred at RT for 19 h. Purification via silica gel chromatography using 0-10% MeOH in CH$_2$Cl$_2$ gave 2,2,2-trifluoro-N-(2-methyl-4-(N-thiazol-2-ylsulfamoyl)phenyl)acetamide (6.87 g, 76%). LC/MS (10%-99% CH$_3$CN (0.035% TFA)/H$_2$O (0.05% TFA)), m/z: M+1 obs=366.1; $t_R$=1.13 min.

4-Amino-3-methyl-N-(thiazol-2-yl)benzenesulfonamide

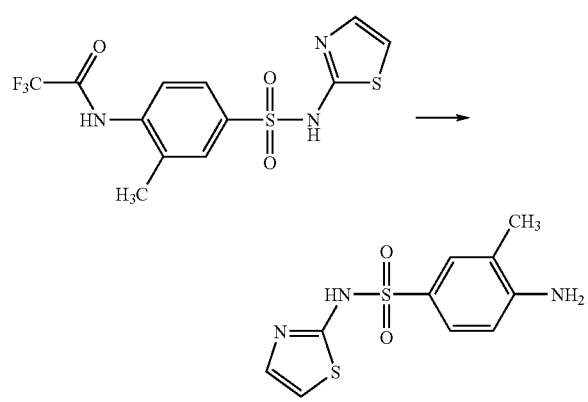

Synthesized according to general procedure 71. A solution of 2,2,2-trifluoro-N-(2-methyl-4-(N-thiazol-2-ylsulfamoyl)phenyl)acetamide (1 g, 2.74 mmol), NaOH (1.09 g, 27.4 mmol), and H$_2$O (5 mL) was stirred at RT for 1 h, then cooled to 0° C. 1 N hydrochloric acid (27.4 mL, 27.4 mmol) was added, and the reaction was stirred at 0° C. for 20 min. The formed precipitate was filtered off and dried under vacuum to give 4-amino-3-methyl-N-(thiazol-2-yl)benzenesulfonamide (232 mg, 31%).

(S)-2-(6-Chloro-3,4-dihydroquinolin-1(2H)-yl-4-hydroxy-N-(2-methyl-4-(N-thiazol-2-ylsulfamoyl)phenyl)butamide

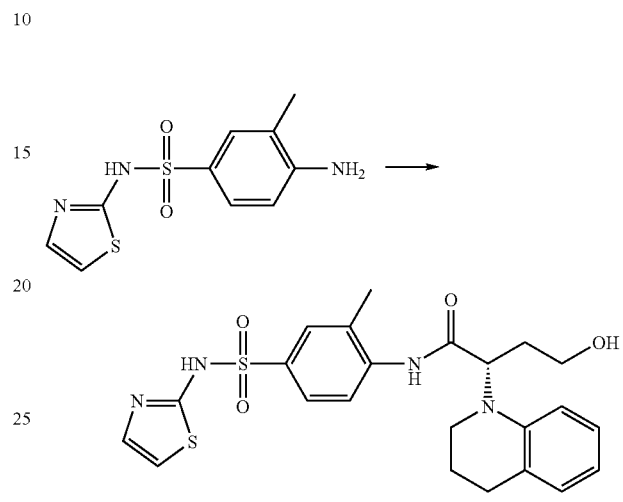

Synthesized according to general procedure 72. To a solution of 4-amino-3-methyl-N-(thiazol-2-yl)benzenesulfonamide (25 mg, 0.093 mmol) in CH$_2$Cl$_2$ (0.25 mL) under nitrogen at RT was added a solution of trimethylaluminum in hexane (2.0M, 0.046 mL, 0.093 mmol) over 5 min. After stirring at RT for 20 min, a solution of the (S)-3-(6-chloro-3,4-dihydroquinolin-1(2H)-yl)-dihydrofuran-2(3H)-one (78 mg, 0.278 mmol) in CH$_2$Cl$_2$ (0.25 mL) was added over 10 min. Stirring was continued for 18-36 h at RT or reflux, then the reaction mixture was cooled to 0° C. and quenched by careful addition of aqueous 1 M HCl. Phases were separated, and the aqueous phase was extracted with CH$_2$Cl$_2$ (2×). The combined organic extracts were dried over MgSO$_4$ and concentrated. Purification via silica gel chromatography using 2-10% MeOH in CH$_2$Cl$_2$ gave the (S)-2-(6-chloro-3,4-dihydroquinolin-1(2H)-yl-4-hydroxy-N-(2-methyl-4-(N-thiazol-2-ylsulfamoyl)phenyl)butamide (5 mg, 10%). LC/MS (10%-99% CH$_3$CN (0.035% TFA)/H$_2$O (0.05% TFA)), m/z: M+1 obs=521.3; $t_R$=1.53 min.

(S)-4-(3-(6-Chloro-3,4-dihydroquinolin-1(2H)-yl)-2-oxopyrrolidin-1-yl)-3-methyl-N-(thiazol-2-yl)benzenesulfonamide

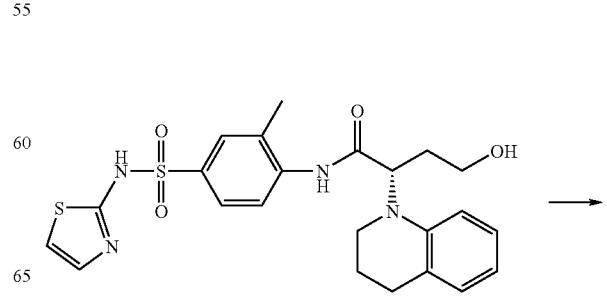

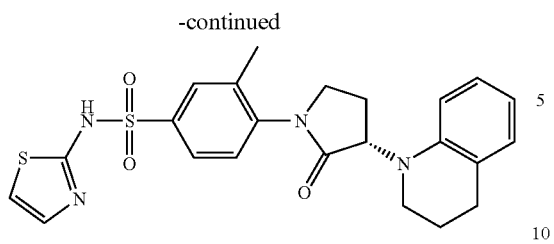

Synthesized according to general procedure 73. To a yellow solution of di-tert-butyl azo-dicarboxylate (81 mg, 0.35 mmol) in THF (0.2 mL) at 0° C. under $N_2$ was slowly added tributylphosphine (0.087 mL, 0.35 mmol), The resulting colorless solution of the Mitsunobu reagent was stirred at RT for 10 min, and then added to a solution of the amido alcohol (46 mg, 0.088 mmol) in THF (0.25 mL) at 0° C. under $N_2$. The reaction mixture was stirred for 10 min. at this temperature, and quenched by addition of a saturated aqueous $NaHCO_3$ solution. EtOAc was added, the phases were separated, and the aqueous layer was extracted with EtOAc (2×2 mL). The combined organic extracts were dried over $MgSO_4$ and concentrated. LC/MS (10%-99% $CH_3CN$ (0.035% TFA)/$H_2O$ (0.05% TFA)), m/z: M+1 obs=503.1; $t_R$=1.72 min.

2,2,2-Trifluoro-N-(2-fluorophenyl)acetamide

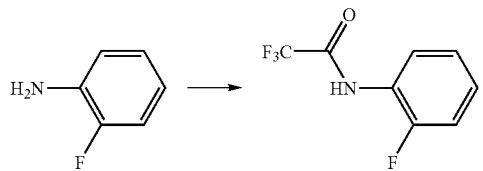

Synthesized according to general procedure 68. Under an $N_2$ atmosphere at −78° C., 2,2,2-trifluoroacetic anhydride (5.2 mL, 37.5 mmol) was added drop wise to a solution of 2-fluoroaniline (4.16 gm, 37.5 mmol), triethylamine (5.2 mL, 37.5 mmol), and $CH_2Cl_2$ (63 mL). The reaction was allowed to warm to RT over a period of 30 minutes. After evaporating the solvents under reduced pressure, purification via silica gel chromatography using 7/3 hexanes/EtOAc gave 2,2,2-trifluoro-N-(2-fluorophenyl)acetamide as a white solid (6.69 g, 88%). $^1$H NMR (400 MHz, DMSO-d6) δ 11.2 (s, 1H), 7.64-7.25 (m, 4H). LC/MS (10%/99% $CH_3CN$ (0.035% TFA)/$H_2O$ (0.05% TFA)), m/z: M+1 obs=208; $t_R$=1.18 min.

3-Fluoro-4-(2,2,2-trifluoroacetamido)benzene-1-sulfonyl chloride

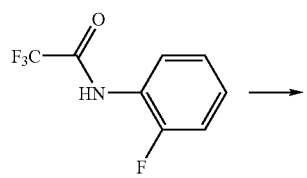

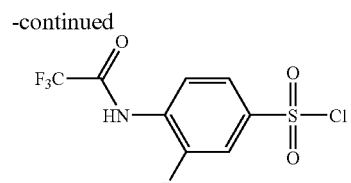

Synthesized according to general procedure 69. A mixture of 2,2,2-trifluoro-N-o-tolylacetamide (5.6 gm, 27.05 mmol) and chlorosulfonic acid (9 mL, 135 mmol) was heated at 155° C. for 15 min. After cooling to RT, the mixture was poured into ice water and extracted with EtOAc. The organic layer was concentrated and purified via silica gel chromatography using 0-25% EtOAc in hexanes gave 3-fluoro-4-(2,2,2-trifluoroacetamido)benzene-1-sulfonyl chloride (5.13 g, 62%). $^1$H NMR (400 MHz, DMSO-d6) δ 11.4 (s, 1H), 7.53 (d, J=1.3 Hz, 1H), 7.46 (dd, J=8.1, 1.8 Hz, 1H), 7.21 (dd, J=8.1, 2.9 Hz, 1H).

2,2,2-Trifluoro-N-(2-fluoro-4-(N-thiazol-2-ylsulfamoyl)phenyl)acetamide

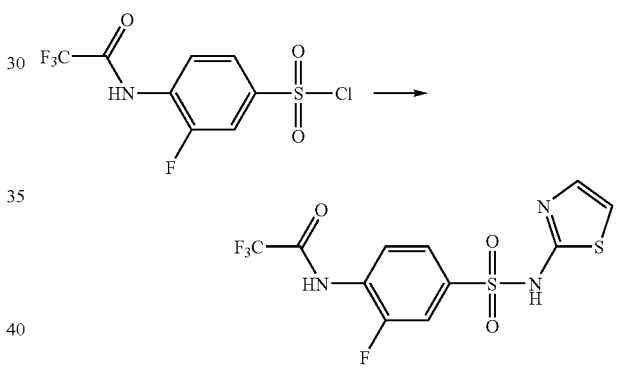

Synthesized according to general procedure 70. Under an $N_2$ atmosphere, a mixture of the 3-fluoro-4-(2,2,2-trifluoroacetamido)benzene-1-sulfonyl chloride (5.0 g, 16.4 mmol) and 2-aminothiazole (1.64 g, 16.4 mmol), and pyridine (9.6 mL) was stirred at RT for 19 h. Purification via silica gel chromatography using 0-10% MeOH in $CH_2Cl_2$ gave 2,2,2-trifluoro-N-(2-fluoro-4-(N-thiazol-2-ylsulfamoyl)phenyl) acetamide (3.28 g, 54%). LC/MS (10%-99% $CH_3CN$ (0.035% TFA)/$H_2O$ (0.05% TFA)), m/z: M+1 obs=370.1; $t_R$=1.07 min.

4-Amino-3-methyl-N-(thiazol-2-yl)benzenesulfonamide

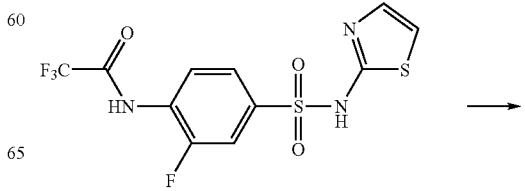

-continued

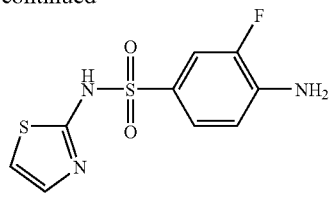

Synthesized according to general procedure 71. A solution of 2,2,2-trifluoro-N-(2-fluoro-4-(N-thiazol-2-ylsulfamoyl)phenyl)acetamide (2.0 g, 5.42 mmol), NaOH (2.17 g, 54.2 mmol), and $H_2O$ (9.7 mL) was stirred at RT for 1 h, then cooled to 0° C. 1 N hydrochloric acid (54.2 mL, 54.2 mmol) was added, and the reaction was stirred at 0° C. for 20 min. The formed precipitate was filtered off and dried under vacuum to give 4-amino-3-fluoro-N-(thiazol-2-yl)benzenesulfonamide (1.03 g, 70%). LC/MS (10%-99% $CH_3CN$ (0.035% TFA)/$H_2O$ (0.05% TFA)), m/z: M+1 obs=274.1; $t_R$=0.51 min (S)-2-(6-Chloro-3,4-dihydroquinolin-1(2H)-yl-4-hydroxy-N-(2-fluoro-4-(N-thiazol-2-ylsulfamoyl)phenyl)butamide

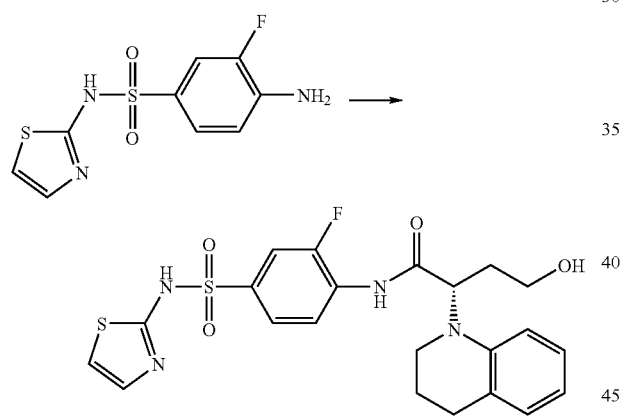

Synthesized according to general procedure 72. To a solution of 4-amino-3-fluoro-N-(thiazol-2-yl)benzenesulfonamide (0.5 g, 1.83 mmol) in $CH_2Cl_2$ (4.3 mL) under nitrogen at RT was added a solution of trimethylaluminum in hexane (2.0M, 0.91 mL, 1.83 mmol) over 5 min. After stirring at RT for 20 min, a solution of the (S)-3-(6-chloro-3,4-dihydroquinolin-1(2H)-yl)-dihydrofuran-2(3H)-one (0.46 g, 1.83 mmol) in $CH_2Cl_2$ (4.3 mL) was added over 10 min. Stirring was continued for 18-36 h at RT or reflux, then the reaction mixture was cooled to 0° C. and quenched by careful addition of aqueous 1 M HCl. Phases were separated, and the aqueous phase was extracted with $CH_2Cl_2$ (2×10 mL). The combined organic extracts were dried over $MgSO_4$ and concentrated. Purification via silica gel chromatography using 2-10% MeOH in $CH_2Cl_2$ gave the (S)-2-(6-chloro-3,4-dihydroquinolin-1(2H)-yl-4-hydroxy-N-(2-fluoro-4-(N-thiazol-2-ylsulfamoyl)phenyl)butamide (391 mg, 41%). LC/MS (10%-99% $CH_3CN$ (0.035% TFA)/$H_2O$ (0.05% TFA)), m/z: M+1 obs=525.1; $t_R$=1.56 min.

(S)-4-(3-(6-Chloro-3,4-dihydroquinolin-1(2H)-yl)-2-oxopyrrolidin-1-yl)-3-fluoro-N-(thiazol-2-yl)benzenesulfonamide

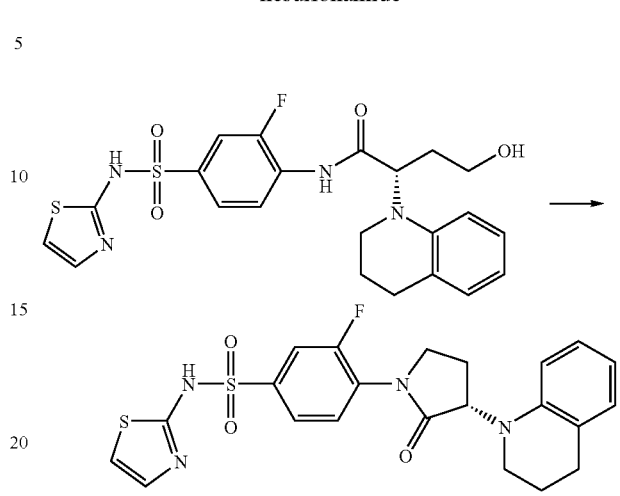

Synthesized according to general procedure 73. To a yellow solution of di-tert-butyl azo-dicarboxylate (138 mg, 0.6 mmol) in THF (0.75 mL) at 0° C. under $N_2$ was slowly added tributylphosphine (0.15 mL, 0.6 mmol), The resulting colorless solution of the Mitsunobu reagent was stirred at RT for 10 min, and then added to a solution of the amido alcohol (80 mg, 0.15 mmol) in THF (0.25 mL) at 0° C. under $N_2$. The reaction mixture was stirred for 10 min. at this temperature, and quenched by addition of a saturated aqueous $NaHCO_3$ solution. EtOAc was added, the phases were separated, and the aqueous layer was extracted with EtOAc (2×2 mL). The combined organic extracts were dried over $MgSO_4$ and concentrated. LC/MS (10%-99% $CH_3CN$ (0.035% TFA)/$H_2O$ (0.05% TFA)), m/z: M+1 obs=507.1; $t_R$=1.77 min.

Example 16

General Procedure 74

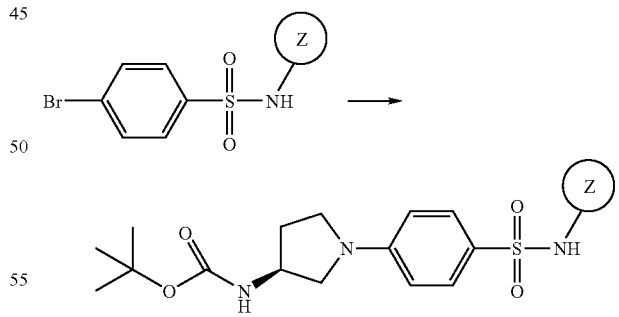

A mixture of bromide (1.0 equivalent, 1.0 mmol), pyrrolidine (1.0 equivalent, 1.0 mmol), $Pd_2(dba)_3$ (0.03 equivalents, 0.03 mmol), biphenyl-2-yldi-tert-butylphosphine (0.12 equivalents, 0.12 mmol), sodium tert-butoxide (2.8 equivalents, 2.8 mmol), and toluene (2.6 mL) was heated under $N_2$, at 70° C. for 1 hr. The reaction was cooled to RT and then neutralized to pH=7 with 1.0 N HCl aqueous solution. The crude solid was purified via silica gel chromatography using MeOH in $CH_2Cl_2$ to give the desired products.

653

(R)-tert-butyl1-(4-(N-1,2,4-thiadiazol-5-ylsulfamoyl)
phenyl)pyrrolidin-3-ylcarbamate

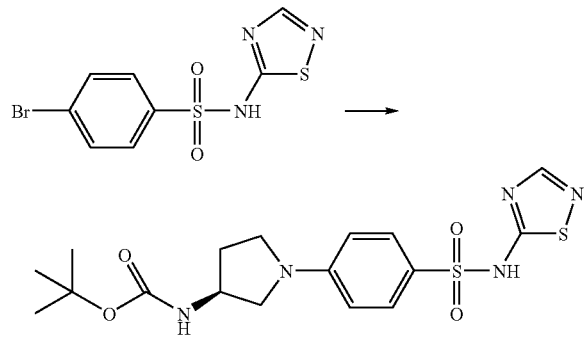

Prepared using general procedure 74. The reaction was set up with 4-bromo-N-(1,2,4-thiadiazol-5-yl)benzenesulfonamide (750 mg, 2.34 mmol), (R)-tert-butyl pyrrolidin-3-ylcarbamate (436 mg, 2.34 mmol), Pd$_2$(dba)$_3$ (64 mg, 0.07 mmol), biphenyl-2-yldi-tert-butylphosphine (84 mg, 0.28 mmol), sodium tert-butoxide (630 mg, 6.6 mmol), and toluene (6.0 mL). Purification via silica gel chromatography using 10% MeOH in CH$_2$Cl$_2$ gave the desired pyrrolidine as an orange solid (213 mg, 0.49 mmol, 21% yield). LC/MS (10%-99% CH$_3$CN (0.035% TFA)/H$_2$O (0.05% TFA)), m/z: M+1 obs=326.3; t$_R$=1.39 min.

General Procedure 75

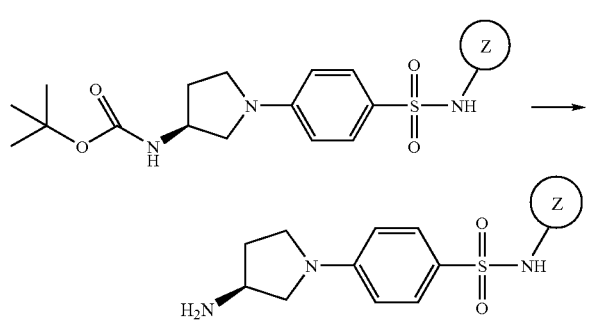

tert-Butyl pyrrolidin-3-ylcarbamate (1 equivalent, 1 mmol) was added to 4.0 N HCl in dioxane (43 equivalents, 43 mmol). The reaction was stirred at 25° C. for 5 minutes. The obtained precipitate was filtered off and dissolved in MeOH (10 mL). The organic solution was dried (MgSO$_4$) and evaporated to dryness to give the desired pyrrolidinamine.

(S)-4-(3-aminopyrrolidin-1-yl)-N-(1,2,4-thiadiazol-5-yl)benzenesulfonamide hydrochloride

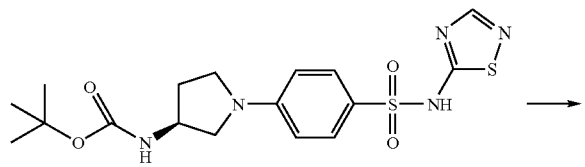

654

-continued

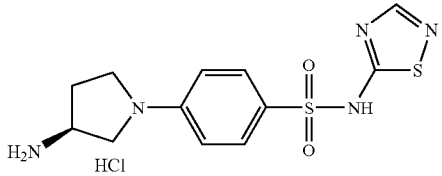

Prepared using general procedure 75. The reaction was set up with (S)-tert-butyl 1-(4-(N-1,2,4-thiadiazol-5-ylsulfamoyl)phenyl)pyrrolidin-3-ylcarbamate (995 mg, 2.34 mmol) and 4.0 N HCl in dioxane (25 mL, 100 mmol) to isolate the desired pyrrolidineamine as an orange solid (229 mg, 0.63 mmol, 27% yield). LC/MS (10%-99% CH$_3$CN (0.035% TFA)/H$_2$O (0.05% TFA)), m/z: M+1 obs=; t$_R$=min.

General Procedure 76

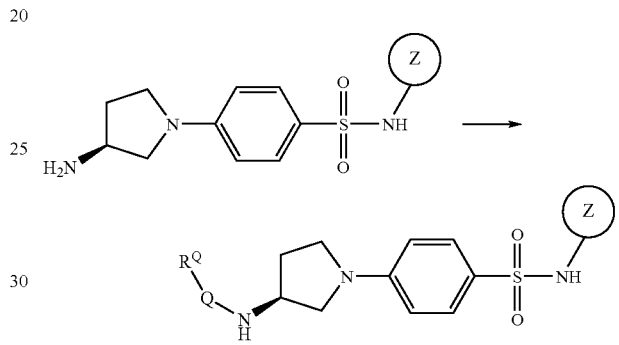

A solution of acid (1.1 equivalents, 1.1 mmol), HATU reagent (1.1 equivalent, 1.1 mmol), DMF (2.5 mL), and CH$_2$Cl$_2$ (2.5 mL) was stirred under N$_2$, at 0° C. for 30 minutes. To this solution was added the aminopyrrolidine (1 equivalent, 1 mmol) and diisopropylethylamine (2.2 equivalent, 2.2 mmol). The reaction was stirred at 25° C. for 19 hours. The obtained solution was purified via Gilson HPLC to give the desired pyrrolidinesulfonamide.

(S)—N-(1-(4-(N-1,2,4-thiadiazol-5-ylsulfamoyl)
phenyl)pyrrolidin-3-yl)-2-(6-chloro-1H-indol-1-yl)
acetamide

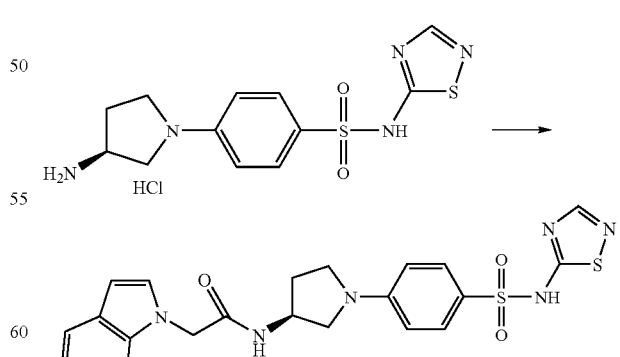

Prepared using general procedure 76. The reaction was set up with 2-(6-chloro-1H-indol-1-yl)acetic acid (32 mg, 0.10 mmol), HATU reagent (38 mg, 0.10 mmol), DMF (0.25 mL), and CH₂Cl₂ (0.25 mL), (S)-4-(3-aminopyrrolidin-1-yl)-N-(1,2,4-thiadiazol-5-yl)benzenesulfonamide hydrochloride (30 mg, 0.09 mmol) and diisopropylethylamine (35 mg, 0.20 mmol). The desired aminopyrrolidine was obtained as a white solid (14 mg, 0.03 mmol, 30% yield). ¹H NMR (400 MHz, DMSO-d6) δ 8.78-8.77 (m, 1H), 8.62 (d, J=6.7 Hz, 1H), 8.55 (d, J=7.0 Hz, 1H), 8.40 (s, 1H), 7.65-7.51 (m, 1H), 7.48 (d, J=1.8 Hz, 1H), 7.35 (d, J=3.2 Hz, 1H), 7.03 (dd, J=1.9, 8.4 Hz, 1H), 6.63 (d, J=9.0 Hz, 1H), 6.48 (s, 1H), 6.46 (dd, J=0.8, 3.2 Hz, 1H), 4.82 (s, 2H), 4.40 (d, J=5.9 Hz, 1H), 3.63-3.40 (m, 5H), 2.34-2.28 (m, 1H), 1.99-1.91 (m, 1H). LC/MS (10%-99% CH₃CN (0.035% TFA)/H₂O (0.05% TFA)), m/z: M+1 obs=517.3; $t_R$=2.95 min.

(R)—N—((R)-1-(4-(N-1,2,4-thiadiazol-5-ylsulfamoyl)phenyl)pyrrolidin-3-yl)-2-(4-fluoro-1H-indol-1-yl)propanamide

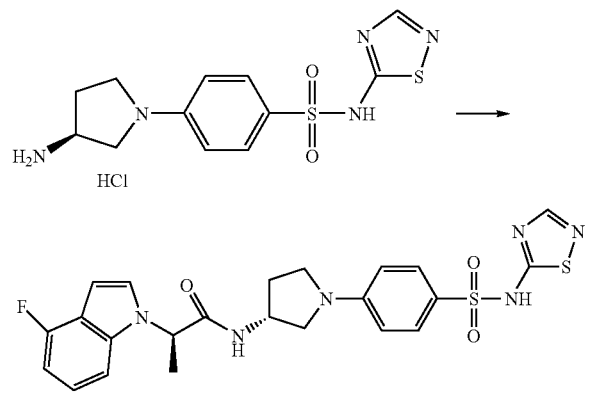

Prepared using general procedure 76. The reaction was set up with (R)-2-(4-fluoro-1H-indol-1-yl)propanoic acid (27 mg, 0.10 mmol), HATU reagent (38 mg, 0.10 mmol), DMF (0.25 mL), and CH₂Cl₂ (0.25 mL), (R)-4-(3-aminopyrrolidin-1-yl)-N-(1,2,4-thiadiazol-5-yl)benzenesulfonamide hydrochloride (30 mg, 0.09 mmol) and diisopropylethylamine (35 mg, 0.20 mmol). The desired aminopyrrolidine was obtained as a white solid (33 mg, 0.06 mmol, 72% yield). LC/MS (10%-99% CH₃CN (0.035% TFA)/H₂O (0.05% TFA)), m/z: M+1 obs=515.5; $t_R$=2.94 min.

(S)—N-(1-(4-(N-1,2,4-thiadiazol-5-ylsulfamoyl)phenyl)pyrrolidin-3-yl)-2-(6-chloro-1H-indol-1-yl)acetamide

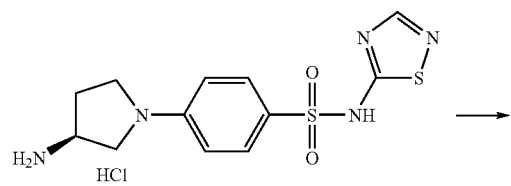

-continued

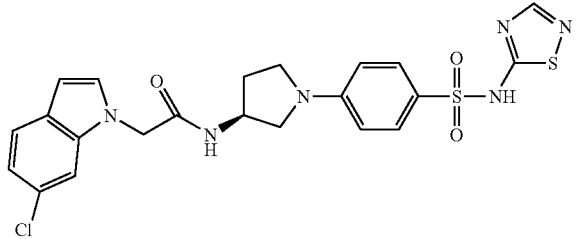

Prepared using general procedure 76. The reaction was set up with 2-(6-chloro-1H-1-indol-1-yl)acetic acid (20 mg, 0.10 mmol), HATU reagent (38 mg, 0.10 mmol), DMF (0.25 mL), and CH₂Cl₂ (0.25 mL), (R)-4-(3-aminopyrrolidin-1-yl)-N-(1,2,4-thiadiazol-5-yl)benzenesulfonamide hydrochloride (30 mg, 0.09 mmol) and diisopropylethylamine (35 mg, 0.20 mmol). The desired aminopyrrolidine was obtained as a white solid (33 mg, 0.06 mmol, 72% yield). ¹H NMR (400 MHz, DMSO-d6) δ 12.49 (s, 1H), 8.61 (d, J=6.7 Hz, 1H), 7.57=(dd, J=18.0, 8.6 Hz, 3H), 7.48 (s, 1H), 7.35 (d, J=3.2 Hz, 1H), 7.20 (d, J=4.6 Hz, 1H), 7.03 (dd, J=8.4, 1.8 Hz, 1H), 6.75 (d, J=4.6 Hz, 1H), 6.59 (d, J=8.9 Hz, 2H), 6.46 (d, J=3.2 Hz, 1H), 4.82 (s, 2H), 4.40 (d, J=5.3 Hz, 1H), 3.56-3.52 (m, 1H), 3.48-3.36 (m, 1H), 3.25-3.29 (m, 1H), 3.18 (dd, J=10.1, 3.4 Hz, 1H), 2.25-2.16 (m, 1H), 1.98-1.92 (m, 1H). LC/MS (10%-99% CH₃CN (0.035% TFA)/H₂O (0.05% TFA)), m/z: M+1 obs=516.5; $t_R$=3.09 min.

Table 3 below recites the analytical data for the compounds of Table 2 above.

| Cmpd No. | LC/MS M + 1 | LC/RT min |
|---|---|---|
| 1 | 530.1 | 3.18 |
| 2 | 447 | 1.46 |
| 3 | 544 | 3.28 |
| 4 | 478 | 2.55 |
| 5 | 558 | 3.4 |
| 6 | 527.3 | 2.78 |
| 7 | 547.3 | 3.19 |
| 8 | 489 | 1.72 |
| 9 | 493.3 | 2.65 |
| 10 | 484.2 | 3.24 |
| 11 | 494.3 | 2.71 |
| 12 | 461 | 0.99 |
| 13 | 552.3 | 2.68 |
| 14 | 525.3 | 2.84 |
| 15 | 511.2 | 3.15 |
| 16 | 492 | 2.95 |
| 17 | 466.3 | 1.44 |
| 18 | 503 | 1.06 |
| 19 | 510 | 2.98 |
| 20 | 430 | 1.58 |
| 21 | 439.5 | 2.49 |
| 22 | 517 | 2.84 |
| 23 | 411 | 0.37 |
| 24 | 526 | 2.84 |
| 25 | 472.2 | 1.88 |
| 26 | 501.3 | 3.08 |
| 27 | 542.4 | 2.76 |
| 28 | 493.3 | 2.79 |
| 29 | 513.5 | 1.59 |
| 30 | 487.3 | 1.94 |
| 31 | 527 | 3.27 |
| 32 | 515.2 | 2.96 |
| 33 | 528 | 3.17 |
| 34 | 488 | 2.15 |
| 35 | 555.1 | 2.84 |
| 36 | 473.3 | 2.44 |
| 37 | 525.3 | 3 |

-continued

| Cmpd No. | LC/MS M + 1 | LC/RT min |
|---|---|---|
| 38 | 504.3 | 1.82 |
| 39 | 546.3 | 2.85 |
| 40 | 491.3 | 2.5 |
| 41 | 457 | 1.09 |
| 42 | 512.2 | 3.08 |
| 43 | 463 | 2.05 |
| 44 | 489.3 | 1.73 |
| 45 | 528 | 2.87 |
| 46 | 535.5 | 2.64 |
| 47 | 554.3 | 2.68 |
| 48 | 557 | 2.94 |
| 49 | 499.6 | 2.88 |
| 50 | 530.1 | 1.01 |
| 51 | 443 | 0.98 |
| 52 | 508.5 | 2.95 |
| 53 | 544.2 | 3.02 |
| 54 | 576.3 | 3.11 |
| 55 | 551.2 | 2.91 |
| 56 | 512.5 | 2.55 |
| 57 | 593 | 2.83 |
| 58 | 547 | 3.19 |
| 59 | 528.3 | 0.98 |
| 60 | 544 | 3.01 |
| 61 | 485.2 | 2.31 |
| 62 | 410.2 | 1.61 |
| 63 | 529 | 2.73 |
| 64 | 476 | 2.12 |
| 65 | 503 | 1.76 |
| 66 | 535 | 2.97 |
| 67 | 467 | 1.85 |
| 68 | 545.3 | 1.82 |
| 69 | 555.5 | 2.91 |
| 70 | 518 | 1.81 |
| 71 | 535.3 | 2.59 |
| 72 | 531 | 2.8 |
| 73 | 493 | 1.69 |
| 74 | 463.2 | 2.59 |
| 75 | 434 | 1.47 |
| 76 | 523.2 | 3.04 |
| 77 | 494.5 | 2.83 |
| 78 | 450 | 1.57 |
| 79 | 530.2 | 3.11 |
| 80 | 480.1 | 1.58 |
| 81 | 523.3 | 2.85 |
| 82 | 503 | 1.71 |
| 83 | 539.5 | 2.48 |
| 84 | 544 | 2.9 |
| 85 | 441.2 | 1.99 |
| 86 | 525.2 | 3.03 |
| 87 | 489.2 | 1.36 |
| 88 | 555 | 1.1 |
| 89 | 478 | 2.6 |
| 90 | 493 | 1.96 |
| 91 | 435.2 | 1.49 |
| 92 | 559.3 | 3.1 |
| 93 | 528 | 3.16 |
| 94 | 544 | 3.29 |
| 95 | 455.5 | 1.59 |
| 96 | 532.2 | 3.11 |
| 97 | 544.3 | 2.4 |
| 98 | 524.2 | 2.95 |
| 99 | 495.5 | 2.59 |
| 100 | 483.2 | 2.9 |
| 101 | 490.2 | 2.81 |
| 102 | 515.05 | 1.63 |
| 103 | 578.3 | 3.12 |
| 104 | 446.3 | 1.43 |
| 105 | 455.3 | 1.58 |
| 106 | 480.3 | 1.5 |
| 107 | 484.5 | 1.96 |
| 108 | 484.5 | 3.11 |
| 109 | 577.3 | 2.91 |
| 110 | 486 | 2.51 |
| 111 | 544.5 | 2.91 |
| 112 | 535.5 | 2.8 |
| 113 | 502 | 3.8 |
| 114 | 502.3 | 1.87 |

-continued

| Cmpd No. | LC/MS M + 1 | LC/RT min |
|---|---|---|
| 115 | 475 | 3.6 |
| 116 | 484 | 1.63 |
| 117 | 530.2 | 3.1 |
| 118 | 589.5 | 3.33 |
| 119 | 484 | 1.66 |
| 120 | 534.8 | 2.94 |
| 121 | 527.2 | 1.63 |
| 122 | 473 | 0.99 |
| 123 | 526 | 3.08 |
| 124 | 532.3 | 3.09 |
| 125 | 592.4 | 3.04 |
| 126 | 528 | 3.15 |
| 127 | 495 | 1.76 |
| 128 | 505 | 1.54 |
| 129 | 564.5 | 3.28 |
| 130 | 544.3 | 2.91 |
| 131 | 558.3 | 3.4 |
| 132 | 381.3 | 0.41 |
| 133 | 502.3 | 1.08 |
| 134 | 472 | 2.08 |
| 135 | 447 | 0.92 |
| 136 | 415.2 | 2.33 |
| 137 | 526 | 2.78 |
| 138 | 421.1 | 2.68 |
| 139 | 521.5 | 2.84 |
| 140 | 547 | 3.09 |
| 141 | 460 | 1.66 |
| 142 | 508.3 | 1.05 |
| 143 | 545.5 | 3.08 |
| 144 | 463 | 1.01 |
| 145 | 470.3 | 2.43 |
| 146 | 516.5 | 2.18 |
| 147 | 508 | 2.58 |
| 148 | 555.1 | 2.85 |
| 149 | 514.4 | 2.74 |
| 150 | 518.3 | 1.92 |
| 151 | 530.2 | 2.91 |
| 152 | 525.3 | 2.89 |
| 153 | 531.3 | 3.01 |
| 154 | 576.3 | 3.21 |
| 155 | 525.3 | 2.95 |
| 156 | 468 | 1.65 |
| 157 | 443 | 1 |
| 158 | 555.3 | 2.85 |
| 159 | 510.4 | 3.08 |
| 160 | 527 | 1.64 |
| 161 | 511.2 | 2.71 |
| 162 | 367.3 | 0.34 |
| 163 | 447 | 1.5 |
| 164 | 505.3 | 2.88 |
| 165 | 548.3 | 1.05 |
| 166 | 458 | 1.75 |
| 167 | 444.4 | 1.57 |
| 168 | 528 | 2.85 |
| 169 | 528.2 | 3.06 |
| 170 | 558.3 | 3.14 |
| 171 | 484 | 1.71 |
| 172 | 526 | 2.67 |
| 173 | 544 | 3.3 |
| 174 | 531 | 3.25 |
| 175 | 496 | 2.66 |
| 176 | 560.3 | 3.39 |
| 177 | 541.2 | 3.12 |
| 178 | 459.4 | 2.96 |
| 179 | 488.5 | 2.16 |
| 180 | 570.3 | 2.8 |
| 181 | 452 | 1.54 |
| 182 | 471 | 1.19 |
| 183 | 487.3 | 1.93 |
| 184 | 545 | 2.9 |
| 185 | 575.5 | 3.31 |
| 186 | 497.3 | 2.93 |
| 187 | 535 | 2.94 |
| 188 | 548.3 | 1.36 |
| 189 | 521.4 | 2.58 |
| 190 | 523.5 | 2.92 |
| 191 | 458.4 | 1.78 |

| Cmpd No. | LC/MS M + 1 | LC/RT min |
|---|---|---|
| 192 | 552 | 1.92 |
| 193 | 530 | 2.9 |
| 194 | 530 | 2.9 |
| 195 | 469 | 1.7 |
| 196 | 492.4 | 2.53 |
| 197 | 450.2 | 2.05 |
| 198 | 464 | 1.69 |
| 199 | 561 | 3.01 |
| 200 | 516.3 | 2.7 |
| 201 | 496 | 2.26 |
| 202 | 464 | 1.74 |
| 203 | 517 | 2.95 |
| 204 | 524.4 | 1.13 |
| 205 | 542 | 3.22 |
| 206 | 588 | 3.37 |
| 207 | 455.3 | 2.98 |
| 208 | 608.4 | 3.47 |
| 209 | 508 | 3.16 |
| 210 | 501 | 2.64 |
| 211 | 516.5 | 1.57 |
| 212 | 434 | 1.48 |
| 213 | 518.1 | 1.77 |
| 214 | 444 | 1.71 |
| 215 | 484 | 1.72 |
| 216 | 516.3 | 2.76 |
| 217 | 506 | 2.89 |
| 218 | 493.2 | 1.55 |
| 219 | 489 | 1.72 |
| 220 | 466.3 | 2.51 |
| 221 | 505.3 | 2.55 |
| 222 | 443.5 | 1 |
| 223 | 574 | 2.9 |
| 224 | 515.3 | 3.1 |
| 225 | 545 | 3.33 |
| 226 | 564.5 | 3.26 |
| 227 | 526.3 | 2.89 |
| 228 | 555 | 3.22 |
| 229 | 513.5 | 1.62 |
| 230 | 509.5 | 1.79 |
| 231 | 507 | 1.77 |
| 232 | 496.2 | 3.16 |
| 233 | 475.2 | 3.21 |
| 234 | 491.3 | 2.42 |
| 235 | 528.2 | 2.85 |
| 236 | 514 | 2.73 |
| 237 | 499 | 2.79 |
| 238 | 514.2 | 3.23 |
| 239 | 509 | 2.62 |
| 240 | 529 | 3.18 |
| 241 | 444.4 | 1.58 |
| 242 | 497.2 | 2.97 |
| 243 | 514 | 2.76 |
| 244 | 500.3 | 1.74 |
| 245 | 576.5 | 3.18 |
| 246 | 575.2 | 3.45 |
| 247 | 530 | 3.17 |
| 248 | 468.3 | 2.31 |
| 249 | 525.2 | 3.23 |
| 250 | 536.5 | 2.63 |
| 251 | 531 | 2.94 |
| 252 | 514.1 | 2.83 |
| 253 | 536.3 | 2.68 |
| 254 | 536.5 | 1.25 |
| 255 | 529 | 2.72 |
| 256 | 490 | 2.08 |
| 257 | 544 | 2.83 |
| 258 | 509.5 | 2.87 |
| 259 | 531 | 3.25 |
| 260 | 490.3 | 2.4 |
| 261 | 441.2 | 2.92 |
| 262 | 531 | 2.81 |
| 263 | 444 | 1.7 |
| 264 | 512.3 | 3.03 |
| 265 | 495 | 1.06 |
| 266 | 547.2 | 3.38 |
| 267 | 480.2 | 1.54 |
| 268 | 528 | 3.15 |
| 269 | 575.5 | 3.05 |
| 270 | 546.3 | 2.91 |
| 271 | 497.5 | 3.09 |
| 272 | 533.3 | 1.29 |
| 273 | 609.3 | 3.32 |
| 274 | 545 | 3.3 |
| 275 | 530.2 | 3.28 |
| 276 | 490.3 | 2.13 |
| 277 | 540 | 2.72 |
| 278 | 544.3 | 2.78 |
| 279 | 458.2 | 1.31 |
| 280 | 509.5 | 2.87 |
| 281 | 536.3 | 2.73 |
| 282 | 460.3 | 1.4 |
| 283 | 512 | 2.12 |
| 284 | 552.3 | 1.33 |
| 285 | 472 | 1.63 |
| 286 | 495.5 | 1.57 |
| 287 | 421.3 | 0.88 |
| 288 | 521.4 | 2.62 |
| 289 | 493.3 | 1.63 |
| 290 | 471.3 | 1.37 |
| 291 | 463 | 0.96 |
| 292 | 544 | 3.15 |
| 293 | 455.5 | 1.53 |
| 294 | 514 | 3.09 |
| 295 | 566.5 | 2.92 |
| 296 | 510 | 2.81 |
| 297 | 592.3 | 3.35 |
| 298 | 546.4 | 3.22 |
| 299 | 527.2 | 1.62 |
| 300 | 571.5 | 3.18 |
| 301 | 533.3 | 3.28 |
| 302 | 493.2 | 1.46 |
| 303 | 528 | 3.16 |
| 304 | 497 | 2.86 |
| 305 | 526.3 | 2.93 |
| 306 | 526.3 | 2.94 |
| 307 | 441.4 | 2.98 |
| 308 | 429.4 | 1.87 |
| 309 | 449.3 | 1.51 |
| 310 | 560.3 | 3.04 |
| 311 | 474 | 2.34 |
| 312 | 571.5 | 3.5 |
| 313 | 574.1 | 3.46 |
| 314 | 517 | 2.54 |
| 315 | 547.2 | 3.38 |
| 316 | 558.3 | 3.1 |
| 317 | 484 | 1.73 |
| 318 | 551.5 | 2.59 |
| 319 | 458 | 2.52 |
| 320 | 486 | 2.41 |
| 321 | 542 | 2.91 |
| 322 | 486.3 | 2.58 |
| 323 | 477.2 | 2.31 |
| 324 | 493.3 | 1.98 |
| 325 | 510.2 | 3.08 |
| 326 | 500 | 2.74 |
| 327 | 476.2 | 1.46 |
| 328 | 455.3 | 1.61 |
| 329 | 564 | 3.17 |
| 330 | 463 | 1.03 |
| 331 | 509 | 2.62 |
| 332 | 546 | 3.3 |
| 333 | 525.3 | 2.72 |
| 334 | 483 | 0.29 |
| 335 | 493 | 1.65 |
| 336 | 497 | 3.04 |
| 337 | 515.3 | 3.1 |
| 338 | 514.5 | 3.03 |
| 339 | 429.5 | 2.03 |
| 340 | 558.3 | 2.9 |
| 341 | 544 | 3.26 |
| 342 | 514.3 | 2.81 |
| 343 | 490.3 | 1.77 |
| 344 | 536.3 | 2.7 |
| 345 | 520.5 | 1.15 |

| Cmpd No. | LC/MS M + 1 | LC/RT min |
|---|---|---|
| 346 | 480 | 2.67 |
| 347 | 503 | 1.06 |
| 348 | 457.5 | 1.13 |
| 349 | 505.3 | 2.89 |
| 350 | 450.5 | 1.53 |
| 351 | 482.5 | 1.05 |
| 352 | 557.3 | 2.11 |
| 353 | 545 | 3.27 |
| 354 | 531.3 | 3.24 |
| 355 | 450.3 | 1.64 |
| 356 | 514.5 | 3.03 |
| 357 | 484 | 2.9 |
| 358 | 457.2 | 2.5 |
| 359 | 459.5 | 2.37 |
| 360 | 464.3 | 2.48 |
| 361 | 475 | 1.71 |
| 362 | 560.3 | 3.12 |
| 363 | 477.5 | 2.24 |
| 364 | 493 | 1.86 |
| 365 | 484 | 1.77 |
| 366 | 518 | 3.2 |
| 367 | 444.4 | 1.64 |
| 368 | 455.3 | 1.59 |
| 369 | 489 | 1.08 |
| 370 | 516.4 | 3.02 |
| 371 | 505.3 | 2.68 |
| 372 | 502 | 1.76 |
| 373 | 472 | 1.96 |
| 374 | 434 | 1.5 |
| 375 | 429 | 0.89 |
| 376 | 560.5 | 2.99 |
| 377 | 516.3 | 2.41 |
| 378 | 497.97 | 2.72 |
| 379 | 529.9 | 3.1 |
| 380 | 498.3 | 2.01 |
| 381 | 530.3 | 1.55 |
| 382 | 461.2 | 2.74 |
| 383 | 593.3 | 3.32 |
| 384 | 540.3 | 2.67 |
| 385 | 541.5 | 2.99 |
| 386 | 440.3 | 1.9 |
| 387 | 588 | 3.37 |
| 388 | 459.2 | 1.35 |
| 389 | 446 | 1.4 |
| 390 | 542.5 | 3.02 |
| 391 | 511.2 | 2.94 |
| 392 | 501 | 2.81 |
| 393 | 541.2 | 3.07 |
| 394 | 496 | 2.76 |
| 395 | 444.4 | 1.59 |
| 396 | 564 | 3.27 |
| 397 | 514 | 2.78 |
| 398 | 560 | 2.98 |
| 399 | 473 | 1.03 |
| 400 | 514.5 | 3.02 |
| 401 | 552.3 | 1.37 |
| 402 | 473 | 2.67 |
| 403 | 524.2 | 3.16 |
| 404 | 515.3 | 3.1 |
| 405 | 530 | 3.27 |
| 406 | 531 | 2.9 |
| 407 | 505.3 | 2.92 |
| 408 | 524.5 | 2.74 |
| 409 | 579.3 | 2.74 |
| 410 | 495.2 | 2.16 |
| 411 | 544.3 | 2.85 |
| 412 | 514.5 | 1.08 |
| 413 | 472.3 | 2.29 |
| 414 | 532.3 | 2.98 |
| 415 | 511.5 | 1.24 |
| 416 | 507.3 | 2.81 |
| 417 | 550.3 | 2.73 |
| 418 | 515.3 | 3.06 |
| 419 | 514.2 | 2.7 |
| 420 | 546.2 | 3.2 |
| 421 | 473.2 | 3.15 |
| 422 | 519.5 | 3 |
| 423 | 454.2 | 2.58 |
| 424 | 555.3 | 3.18 |
| 425 | 525.2 | 2.87 |
| 426 | 556 | 2.83 |
| 427 | 540.2 | 3.06 |
| 428 | 511 | 2.9 |
| 429 | 473 | 1.46 |
| 430 | 539.5 | 2.89 |
| 431 | 531.3 | 3.24 |
| 432 | 487 | 1.61 |
| 433 | 494.5 | 2.51 |
| 434 | 493.3 | 2.38 |
| 435 | 461.5 | 0.99 |
| 436 | 529 | 2.9 |
| 437 | 497 | 2.8 |
| 438 | 544.2 | 2.98 |
| 439 | 528.3 | 3.09313 |
| 440 | 528.1 | 2.85 |
| 441 | 473.1 | 3.41 |
| 442 | 482.5 | 2.55 |
| 443 | 469 | 1.59 |
| 444 | 561.1 | 2.8 |
| 445 | 511 | 2.85 |
| 446 | 546.3 | 3.09 |
| 447 | 475.1 | 2.43 |
| 448 | 457.5 | 1.57 |
| 449 | 473.3 | 1.67 |
| 450 | 468.1 | 2.01 |
| 451 | 516.2 | 3.23 |
| 452 | 477 | 1.14 |
| 453 | 560.5 | 2.94 |
| 454 | 532.2 | 2.82 |
| 455 | 489.2 | 1.32 |
| 456 | 444.4 | 1.57 |
| 457 | 468.3 | 2.13 |
| 458 | 531.3 | 3.09 |
| 459 | 531 | 2.94 |
| 460 | 624 | 1.99 |
| 461 | 537 | 2.76 |
| 462 | 509.2 | 3.06 |
| 463 | 472 | 3.7 |
| 464 | 514.5 | 3.07 |
| 465 | 515.5 | 1.68 |
| 466 | 600.3 | 3.24 |
| 467 | 441.3 | 2.67 |
| 468 | 512.2 | 2.97 |
| 469 | 507.3 | 2.18 |
| 470 | 517.4 | 2.31 |
| 471 | 447 | 1.41 |
| 472 | 495.3 | 2.58 |
| 473 | 529.9 | 3.09 |
| 474 | 545.5 | 3.1 |
| 475 | 481 | 1.01 |
| 476 | 511 | 1.12 |
| 477 | 514 | 3.08 |
| 478 | 459.2 | 3.06 |
| 479 | 472 | 2.45 |
| 480 | 457.5 | 1.6 |
| 481 | 543.3 | 2.85 |
| 482 | 489.3 | 3.27 |
| 483 | 452.3 | 2.36 |
| 484 | 516.2 | 2.79 |
| 485 | 512.3 | 0.97 |
| 486 | 504.3 | 2.83 |
| 487 | 482.3 | 2.38 |
| 488 | 609.3 | 3.3 |
| 489 | 511 | 2.9 |
| 490 | 490.3 | 3.47 |
| 491 | 511 | 2.84 |
| 492 | 475 | 3.55 |
| 493 | 490.3 | 2.85 |
| 494 | 546.5 | 2.82 |
| 495 | 668.5 | 3.99 |
| 496 | 511.5 | 1.21 |
| 497 | 510.4 | 2.46 |
| 498 | 510.5 | 1.58 |
| 499 | 556 | 3.14 |

-continued

| Cmpd No. | LC/MS M + 1 | LC/RT min |
|---|---|---|
| 500 | 488 | 2.44 |
| 501 | 469.5 | 1.69 |
| 502 | 539.5 | 2.88 |
| 503 | 398.2 | 2.09 |
| 504 | 461.2 | 2.03 |
| 505 | 469.5 | 1.7 |
| 506 | 472.2 | 1.88 |
| 507 | 455.3 | 2.09 |
| 508 | 514.5 | 3.05 |
| 509 | 453 | 3.11 |
| 510 | 528.1 | 2.74 |
| 511 | 535.2 | 2.97 |
| 512 | 482 | 2.29 |
| 513 | 535 | 2.94 |
| 514 | 484 | 1.62 |
| 515 | 516.5 | 2.23 |
| 516 | 544.5 | 3.27 |
| 517 | 471.3 | 2.65 |
| 518 | 530.5 | 1 |
| 519 | 509.4 | 3.31 |
| 520 | 482.3 | 0.99 |
| 521 | 444.4 | 1.52 |
| 522 | 514.5 | 3.03 |
| 523 | 489.3 | 3.36 |
| 524 | 498 | 2.97 |
| 525 | 372.1 | 3.03 |
| 526 | 531.3 | 3.05 |
| 527 | 524.2 | 2.85 |
| 528 | 561.3 | 3.44 |
| 529 | 528.2 | 3.15 |
| 530 | 506 | 1.56 |
| 531 | 544.3 | 2.88 |
| 532 | 593.5 | 3.22 |
| 533 | 472.2 | 1.86 |
| 534 | 489 | 1.78 |
| 535 | 480.3 | 2.66 |
| 536 | 379.3 | 0.39 |
| 537 | 530 | 3.27 |
| 538 | 525.3 | 2.8 |
| 539 | 559.3 | 3.19 |
| 540 | 465 | 0.97 |
| 541 | 603.3 | 3 |
| 542 | 511.5 | 1.29 |
| 543 | 461 | 1.03 |
| 544 | 455.3 | 1.53 |
| 545 | 525.3 | 3.01 |
| 546 | 450.3 | 1.58 |
| 547 | 615.3 | 3.64 |
| 548 | 518.3 | 1.19 |
| 549 | 574 | 3.23 |
| 550 | 510 | 3.1 |
| 551 | 580.3 | 3.12 |
| 552 | 458.4 | 1.78 |
| 553 | 489 | 1.74 |
| 554 | 531.3 | 3.07 |
| 555 | 430 | 1.53 |
| 556 | 540.2 | 3.01 |
| 557 | 530 | 2.96 |
| 558 | 493.3 | 1.64 |
| 559 | 514.2 | 3.23 |
| 560 | 529 | 2.9 |
| 561 | 450.3 | 1.63 |
| 562 | 515 | 2.94 |
| 563 | 546.3 | 2.95 |
| 564 | 492.2 | 1.96 |
| 565 | 472 | 2.65 |
| 566 | 472 | 1.91 |
| 567 | 516.4 | 2.92 |
| 568 | 502 | 2.55 |
| 569 | 514.2 | 2.98 |
| 570 | 459.5 | 1.53 |
| 571 | 455 | 1.6 |
| 572 | 539.5 | 3.08 |
| 573 | 564.5 | 3.28 |
| 574 | 508 | 1.33 |
| 575 | 531.2 | 3.21 |
| 576 | 510.3 | 2.76 |

-continued

| Cmpd No. | LC/MS M + 1 | LC/RT min |
|---|---|---|
| 577 | 578.2 | 2.83 |
| 578 | 558.3 | 1.95 |
| 579 | 519.2 | 1.72 |
| 580 | 461 | 1.03 |
| 581 | 501.3 | 1.13 |
| 582 | 494.5 | 0.8 |
| 583 | 455.3 | 2.79 |
| 584 | 528.3 | 1.03 |
| 585 | 529 | 2.74 |
| 586 | 475 | 1.69 |
| 587 | 538.5 | 1.98 |
| 588 | 531 | 2.94 |
| 589 | 510.4 | 3.07 |
| 590 | 571.3 | 2.96 |
| 591 | 490.3 | 1.72 |
| 592 | 558.3 | 2.11 |
| 593 | 442.3 | 0.74 |
| 594 | 536.5 | 1.04 |
| 595 | 509.5 | 2.84 |
| 596 | 525 | 2.77 |
| 597 | 574.3 | 3.21 |
| 598 | 555 | 3.24 |
| 599 | 543.3 | 1.83 |
| 600 | 508.5 | 2.95 |
| 601 | 579.3 | 2.82 |
| 602 | 525.3 | 2.99 |
| 603 | 570 | 2.61 |
| 604 | 527.2 | 2.96 |
| 605 | 463.3 | 1.98 |
| 606 | 571.3 | 3 |
| 607 | 535.2 | 2.98 |
| 608 | 515.5 | 3.14 |
| 609 | 475 | 1.43 |
| 610 | 514.5 | 3.05 |
| 611 | 501 | 2.74 |
| 612 | 500 | 2.73 |
| 613 | 506.2 | 2.96 |
| 614 | 542 | 2.83 |
| 615 | 544.3 | 2.76 |
| 616 | 516 | 2.63 |
| 617 | 503.2 | 2.68 |
| 618 | 489 | 1.72 |
| 619 | 599.5 | 3.32 |
| 620 | 484.5 | 1.03 |
| 621 | 509.2 | 2.86 |
| 622 | 528.3 | 3.13 |
| 623 | 528 | 3.15 |
| 624 | 525.2 | 2.9 |
| 625 | 519.5 | 2.99 |
| 626 | 530.2 | 3.04 |
| 627 | 468 | 2.26203 |
| 628 | 488 | 2.09 |
| 629 | 558 | 3.02 |
| 630 | 472 | 1.85 |
| 631 | 562.3 | 2.99 |
| 632 | 503 | 3.29 |
| 633 | 536.3 | 1.21 |
| 634 | 514 | 3.08 |
| 635 | 551 | 0.54 |
| 636 | 502.3 | 1.11 |
| 637 | 460 | 1.53 |
| 638 | 552.3 | 2.7 |
| 639 | 545.5 | 3.26 |
| 640 | 497.5 | 3.08 |
| 641 | 489 | 1.74 |
| 642 | 545 | 2.9 |
| 643 | 512 | 1.25 |
| 644 | 441.2 | 1.25 |
| 645 | 441.3 | 1.43 |
| 646 | 530.3 | 2.94 |
| 647 | 442.3 | 3.06 |
| 648 | 491 | 3 |
| 649 | 541.1 | 3.11 |
| 650 | 556 | 3.14 |
| 651 | 511.4 | 3.13 |
| 652 | 484.3 | 1.71 |
| 653 | 578.5 | 3.11 |

-continued

| Cmpd No. | LC/MS M + 1 | LC/RT min |
|---|---|---|
| 654 | 531.1 | 3.27 |
| 655 | 521.5 | 2.73 |
| 656 | 518.3 | 1.21 |
| 657 | 530.2 | 3.15 |
| 658 | 561 | 3.19 |
| 659 | 530.2 | 3.16 |
| 660 | 443 | 1.01 |
| 661 | 496.3 | 2.78 |
| 662 | 529 | 3.15 |
| 663 | 509.4 | 2.84 |
| 664 | 508.5 | 2.91 |
| 665 | 500.3 | 1.73 |
| 666 | 526 | 2.68 |
| 667 | 511.5 | 1.74 |
| 668 | 498.5 | 1.16 |
| 669 | 545.5 | 3.11 |
| 670 | 531.3 | 1.19 |
| 671 | 521.4 | 2.62 |
| 672 | 477.2 | 1.43 |
| 673 | 518.3 | 1.21 |
| 674 | 511 | 1.13 |
| 675 | 531.3 | 3.24 |
| 676 | 505.3 | 2.92 |
| 677 | 569 | 1.97 |
| 678 | 471.3 | 1.45 |
| 679 | 508.5 | 2.8 |
| 680 | 542.2 | 3.22 |
| 681 | 419 | 2.82 |
| 682 | 513.3 | 1.98 |
| 683 | 439.5 | 2.32 |
| 863 | 525.3 | 2.98 |
| 685 | 448 | 1.61 |
| 686 | 515 | 2.89 |
| 687 | 559.1 | 3.08 |
| 688 | 560 | 3.31 |
| 689 | 578.3 | 2.73 |
| 690 | 458 | 1.81 |
| 691 | 552.5 | 1.27 |
| 692 | 489.5 | 2.79 |
| 693 | 510.2 | 3.09 |
| 694 | 544.3 | 2.81 |
| 695 | 522.3 | 2.61 |
| 696 | 492.3 | 1.68 |
| 697 | 457 | 1.07 |
| 698 | 547.5 | 3.41 |
| 699 | 529 | 3.21 |
| 700 | 544 | 3.32 |
| 701 | 516.3 | 3.17 |
| 702 | 558.4 | 2.94 |
| 703 | 544.9 | 3.3 |
| 704 | 554 | 3.17 |
| 705 | 447 | 0.93 |
| 706 | 419.3 | 2.95 |
| 707 | 459.3 | 1.35 |
| 708 | 535.3 | 1.62 |
| 709 | 529 | 2.84 |
| 710 | 443 | 1.07 |
| 711 | 524.5 | 2.66 |
| 712 | 540.3 | 3.01 |
| 713 | 452 | 1.49 |
| 714 | 477 | 1.13 |
| 715 | 426.1 | 3.08 |
| 716 | 495 | 2.29 |
| 717 | 511 | 2.98 |
| 718 | 530.3 | 2.98 |
| 719 | 464.3 | 1.68 |
| 720 | 498.3 | 1.08 |
| 721 | 528.1 | 2.84 |
| 722 | 528 | 3.15 |
| 723 | 485.2 | 2.61 |
| 724 | 429 | 0.88 |
| 725 | 450.3 | 2.33 |
| 726 | 545 | 3.29 |
| 727 | 544 | 3.08 |
| 728 | 510.5 | 2.75 |
| 729 | 614.3 | 3.54 |
| 730 | 515.5 | 3.18 |
| 731 | 461 | 1.02 |
| 732 | 547 | 3.12 |
| 733 | 529 | 3.21 |
| 734 | 535.2 | 2.88 |
| 735 | 528 | 3.15 |
| 736 | 457 | 1.1 |
| 737 | 522.3 | 2.66 |
| 738 | 545 | 3.25 |
| 739 | 508.4 | 2.78 |
| 740 | 531.1 | 3.15 |
| 741 | 544 | 3.27 |
| 742 | 541.5 | 2.96 |
| 743 | 521.5 | 2.74 |
| 744 | 521.3 | 2.9 |
| 745 | 554.9 | 3.03 |
| 746 | 510.5 | 2.99 |
| 747 | 471.3 | 2.43 |
| 748 | 478.3 | 2.06 |
| 749 | 510.5 | 2.9 |
| 750 | 476.3 | 3.06 |
| 751 | 499.3 | 3.11 |
| 752 | 401.3 | 2.71 |
| 753 | 552.3 | 1.3 |
| 754 | 608.4 | 3.52 |
| 755 | 662 | 1.86 |
| 756 | 555.3 | 2.49 |
| 757 | 529 | 2.84 |
| 758 | 538.5 | 1.04 |
| 759 | 527 | 2.86 |
| 760 | 539.5 | 2.88 |
| 761 | 500.3 | 2.39 |
| 762 | 561.3 | 3.09 |
| 763 | 493.2 | 1.55 |
| 764 | 529 | 3.17 |
| 765 | 477.3 | 2.46 |
| 766 | 477 | 1.08 |
| 767 | 490.3 | 2.35 |
| 768 | 477 | 1.04 |
| 769 | 528 | 3.15 |
| 770 | 475.3 | 1.64 |
| 771 | 510.5 | 3.05 |
| 772 | 555.3 | 2.57 |
| 773 | 528.2 | 3.13 |
| 774 | 525 | 3 |
| 775 | 477 | 1.12 |
| 776 | 444.4 | 1.68 |
| 777 | 509.5 | 2.87 |
| 778 | 539.5 | 2.42 |
| 779 | 546 | 2.94 |
| 780 | 459.3 | 1.57 |
| 781 | 554 | 3.37 |
| 782 | 516 | 3.9 |
| 783 | 544 | 2.9 |
| 784 | 475.2 | 3.19 |
| 785 | 447 | 0.92 |
| 786 | 525.1 | 2.81 |
| 787 | 493 | 2.78 |
| 788 | 530.3 | 2.98 |
| 789 | 481.1 | 2.88 |
| 790 | 525 | 2.92 |
| 791 | 441.4 | 1.25 |
| 792 | 504.5 | 1.83 |
| 793 | 490 | 2.27 |
| 794 | 500.59 | 2.83 |
| 795 | 539.3 | 2.93 |
| 796 | 511.4 | 2.89 |
| 797 | 515.3 | 3.09 |
| 798 | 495.5 | 1.57 |
| 799 | 519.5 | 3 |
| 800 | 546 | 3.37 |
| 801 | 482 | 2.73 |
| 802 | 521.3 | 2.87 |
| 803 | 589.3 | 3.32 |
| 804 | 542.4 | 2.8 |
| 805 | 564.3 | 3.2 |
| 806 | 502 | 2.65 |
| 807 | 565 | 2.91 |

-continued

| Cmpd No. | LC/MS M + 1 | LC/RT min |
|---|---|---|
| 808 | 496.2 | 3.16 |
| 809 | 529.3 | 1.59 |
| 810 | 623.2 | 3.47 |
| 811 | 515.3 | 3.1 |
| 812 | 496 | 2.69 |
| 813 | 558.3 | 3.1 |
| 814 | 507 | 1.73 |
| 815 | 493.3 | 2.28 |
| 816 | 519 | 2.77 |
| 817 | 528 | 3.14 |
| 818 | 528.1 | 2.96 |
| 819 | 460 | 1.56 |
| 820 | 440.2 | 1.85 |
| 821 | 535.3 | 2.63 |
| 822 | 538.3 | 2.66 |
| 823 | 545.5 | 3.11 |
| 824 | 497.2 | 2.04 |
| 825 | 511.3 | 2.95 |
| 826 | 455 | 1.32 |
| 827 | 517 | 2.83 |
| 828 | 524.5 | 2.81 |
| 829 | 533.2 | 2.81 |
| 830 | 516.2 | 3.28 |
| 831 | 536.5 | 1.01 |
| 832 | 479.3 | 2.62 |
| 833 | 553 | 1.29 |
| 834 | 545 | 3.33 |
| 835 | 466.3 | 2.41 |
| 836 | 501 | 2.78 |
| 837 | 602 | 3.5 |
| 838 | 498.1 | 3.04 |
| 839 | 515.3 | 3.1 |
| 840 | 459.3 | 2.02 |
| 841 | 516.3 | 2.7 |
| 842 | 551.2 | 2.97 |
| 843 | 469 | 3.07 |
| 844 | 538 | 2.96 |
| 845 | 483 | 1.7 |
| 846 | 509.2 | 2.16 |
| 847 | 536.3 | 2.71 |
| 848 | 560.3 | 2.94 |
| 849 | 490.3 | 2.41 |
| 850 | 596.5 | 3.26 |
| 851 | 536.5 | 2.66 |
| 852 | 560.3 | 3.09 |
| 853 | 452 | 1.65 |
| 854 | 471.2 | 2.45 |
| 855 | 528 | 3.05 |
| 856 | 531 | 3.21 |
| 857 | 560.3 | 3.1 |
| 858 | 516 | 2.82 |
| 859 | 529.3 | 1.68 |
| 860 | 553 | 1.29 |
| 861 | 512.3 | 0.97 |
| 862 | 530.5 | 1 |
| 863 | 524.4 | 1.13 |
| 864 | 508.5 | 1.03 |
| 865 | 522 | 1.83 |
| 866 | 528.3 | 0.98 |
| 867 | 508 | 1.75 |
| 868 | 530.1 | 1.01 |
| 869 | 562 | 2.03 |
| 870 | 562 | 1.92 |
| 871 | 379.3 | 0.39 |
| 872 | 528 | 1.1 |
| 873 | 507.2 | 1.71 |
| 874 | 518 | 1.89 |
| 875 | 488 | 1.52 |
| 876 | 494 | 1.73 |
| 877 | 367.3 | 0.34 |
| 878 | 528.3 | 1.03 |
| 879 | 525.3 | 0.99 |
| 880 | 520.3 | 1.15 |
| 881 | 548.3 | 1.17 |
| 882 | 381.3 | 0.41 |
| 883 | 507 | 1.75 |
| 884 | 548.3 | 1.05 |

-continued

| Cmpd No. | LC/MS M + 1 | LC/RT min |
|---|---|---|
| 885 | 536.5 | 1.01 |
| 886 | 520.3 | 1.11 |
| 887 | 508.3 | 1.05 |
| 888 | 508 | 1.33 |
| 889 | 520.3 | 1.12 |
| 890 | 566.3 | 1.41 |
| 891 | 569 | 1.97 |
| 892 | 457.5 | 1.13 |
| 893 | 520.1 | 1.16 |
| 894 | 508 | 1.77 |
| 895 | 533.3 | 1.29 |
| 896 | 507 | 1.8 |
| 897 | 517.3 | 1.28 |
| 898 | 536.3 | 1.22 |
| 899 | 536.5 | 1.04 |
| 900 | 488 | 1.68 |
| 901 | 536.3 | 1.22 |
| 902 | 494 | 1.68 |
| 903 | 488 | 1.6 |

Assays for Detecting and Measuring NaV Inhibition Properties of Compound

Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 μL of Bath Solution #2 (BS#2).
2) A 15 uM CC2-DMPE solution is prepared by mixing 5 mM coumarin stock solution with 10% Pluronic 127 1:1 and then dissolving the mix in the appropriate volume of BS#2.

3) After bath solution is removed from the 96-well plates, the cells are loaded with 80 µL of the CC2-DMPE solution. Plates are incubated in the dark for 30 minutes at room temperature.
4) While the cells are being stained with coumarin, a 15 µL oxonol solution in BS#2 is prepared. In addition to DiSBAC$_2$(3), this solution should contain 0.75 mM ABSC1 and 30 µL veratridine (prepared from 10 mM EtOH stock, Sigma #V-5754).
5) After 30 minutes, CC2-DMPE is removed and the cells are washed twice with 225 µL of BS#2. As before, the residual volume should be 40 µL.
6) Upon removing the bath, the cells are loaded with 80 µL of the DiSBAC$_2$(3) solution, after which test compound, dissolved in DMSO, is added to achieve the desired test concentration to each well from the drug addition plate and mixed thoroughly. The volume in the well should be roughly 121 µL. The cells are then incubated for 20-30 minutes.
7) Once the incubation is complete, the cells are ready to be assayed on VIPR® with a sodium add back protocol. 120 µL of Bath solution #1 is added to stimulate the NaV dependent depolarization. 200 µL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460nm} - background_{460nm})}{(intensity_{580nm} - background_{580nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound

Solutions [mM]

Bath Solution #1: NaCl 160, KCl 4.5, CaCl$_2$ 2, MgCl$_2$ 1, HEPES 10, pH 7.4 with NaOH Bath Solution #2 TMA-Cl 160, CaCl$_2$ 0.1, MgCl$_2$ 1, HEPES 10, pH 7.4 with KOH (final K concentration ~5 mM)

CC2-DMPE: prepared as a 5 mM stock solution in DMSO and stored at −20° C.

DiSBAC$_2$(3): prepared as a 12 mM stock in DMSO and stored at −20° C.

ABSC1: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

VIPR® Optical Membrane Potential Assay Method with Electrical Stimulation

The following is an example of how NaV1.3 inhibition activity is measured using the optical membrane potential method #2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC$_2$(3) as follows.

Reagents 100 mg/mL Pluronic F-127 (Sigma #P2443), in dry DMSO
10 mM DiSBAC$_2$(3) (Aurora #00-100-010) in dry DMSO
10 mM CC2-DMPE (Aurora #00-100-008) in dry DMSO
200 mM ABSC1 in H$_2$O
Hank's Balanced Salt Solution (Hyclone #SH30268.02) supplemented with 10 mM HEPES (Gibco #15630-080)

Loading Protocol

2×CC2-DMPE=20 µM CC2-DMPE: 10 mM CC2-DMPE is vortexed with an equivalent volume of 10% pluronic, followed by vortexing in required amounts of HBSS containing 10 mM HEPES. Each cell plate will require 5 mL of 2×CC2-DMPE. 50 µL of 2×CC2-DMPE is to wells containing washed cells, resulting in a 10 µM final staining concentration. The cells are stained for 30 minutes in the dark at RT.

2× DISBAC$_2$(3) with ABSC1=6 µM DISBAC$_2$(3) and 1 mM ABSC1: The required amount of 10 mM DISBAC$_2$(3) is added to a 50 ml conical tube and mixed with 1 µL 10% pluronic for each mL of solution to be made and vortexed together. Then HBSS/HEPES is added to make up 2× solution. Finally, the ABSC1 is added.

The 2× DiSBAC$_2$(3) solution can be used to solvate compound plates. Note that compound plates are made at 2× drug concentration. Wash stained plate again, leaving residual volume of 50 µL. Add 50 uL/well of the 2× DiSBAC$_2$(3) w/ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay buffer #1
140 mM NaCl, 4.5 mM KCl, 2 mM CaCl$_2$, 1 mM MgCl$_2$, 10 mM HEPES, 10 mM glucose, pH 7.40, 330 mOsm Pluronic stock (1000×): 100 mg/mL pluronic 127 in dry DMSO Oxonol stock (3333×): 10 mM DiSBAC$_2$(3) in dry DMSO Coumarin stock (1000×): 10 mM CC2-DMPE in dry DMSO ABSC1 stock (400×): 200 mM ABSC1 in water Assay Protocol Insert or use electrodes into each well to be assayed.

Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460nm} - background_{460nm})}{(intensity_{580nm} - background_{580nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

Voltage-Clamp Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), MgCl$_2$ (1), EGTA (1.5), CaCl$_2$ (0.1), HEPES (10), glucose (2), pH=7.42, 290 mOsm.

Extracellular solution (in mM): NaCl (138), CaCl$_2$ (1.26), KCl (5.33), KH2PO4 (0.44), MgCl2 (0.5), MgSO4 (0.41), NaHCO3 (4), Na2HPO4 (0.3), glucose (5.6), HEPES (10), CdCl2 (0.4), NiCl2 (0.1), TTX (0.25×10$^{-3}$).

Current-Clamp Assay for NaV Channel Inhibition Activity of Compounds

Cells were current-clamped in whole-cell configuration with a Multiplamp 700A amplifier (Axon Inst). Borosilicate pipettes (4-5 Mohm) were filled with (in mM):150 K-gluconate, 10 NaCl, 0.1 EGTA, 10 Hepes, 2 MgCl$_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

The exemplified compounds of Table 2 herein are active against one or more sodium channels as measured using the assays described hereinabove.

Many modifications and variations of the embodiments described herein may be made without departing from the scope, as is apparent to those skilled in the art. The specific embodiments described herein are offered by way of example only.

The invention claimed is:
1. A compound of formula I:

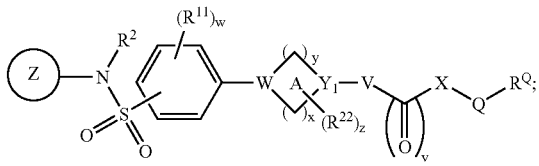

or a pharmaceutically acceptable salt thereof;
wherein:
ring Z is a 5-7 membered unsaturated or aromatic ring having 1-4 ring heteroatoms selected from O, S, or N, wherein Z is optionally substituted with up to q occurrences of $R^Z$ substitutents, wherein each $R^Z$ is independently selected from $R^1$, $R^2$, $R^3$, $R^4$, or $R^5$; and q is 0-4;
W is N and $Y_1$ is CH;
x and y each is independently 0-3; provided that x+y is 3;
w is 0-4;
v is 0;
z is 0-4;
V and X each is a bond;
Q is a bond;
$R^Q$ is a 3-7 membered monocyclic heterocyclic ring or an 8-12 membered bicyclic heterocyclic ring;
wherein $R^Q$ is optionally substituted with up to 4 substituents independently selected from $R^1$, $R^2$, $R^3$, $R^4$, or $R^5$;
$R^{11}$ is $R^2$ or Y;
$R^{22}$ is $R^1$, $R^2$, or $R^4$;
$R^1$ is oxo, $=NN(R^6)_2$, $=NN(R^7)_2$, $=NN(R^6R^7)$, $=N-OR^6$, $=N-OR^7$, $R^6$ or $(CH_2)_n-Y$; or two $R^1$ on adjacent ring atoms, taken together, form 1,2-methylenedioxy or 1,2-ethylenedioxy;
n is 0, 1 or 2;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;
$R^2$ is hydrogen or C1-C6 aliphatic, wherein each $R^2$ is optionally substituted with up to 2 substituents independently selected from $R^1$, $R^4$, or $R^5$;
$R^3$ is a C3-C8 cycloaliphatic, C6-C10 aryl, C3-C8 heterocyclic, or C5-C10 heteroaryl ring, wherein each $R^3$ is optionally substituted with up to 3 substituents independently selected from $R^1$, $R^2$, $R^4$ or $R^5$;
$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $OP(O)(OR^6)_2$, $OP(O)(OR^5)_2$, $OP(O)(OR^6)(OR^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6C(S)N(R^6)_2$, $NR^6C(S)NR^5R^6$, $NR^6C(S)N(R^5)_2$, $NR^5C(S)N(R^6)_2$, $NR^5C(S)NR^5R^6$, $NR^5C(S)N(R^5)_2$, $NR^6SO_2R^6$, $NR^6SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, $N(OR^5)R^6$, $P(O)(OR^6)N(R^6)_2$, $P(O)(OR^5)N(R^5R^6)$, $P(O)(OR^6)N(R^5)_2$, $P(O)(OR^5)N(R^5R^6)$, $P(O)(OR^5)N(R^6)_2$, $P(O)(OR^5)N(R^5)_2$, $P(O)(OR^6)_2$, $P(O)(OR^5)_2$, or $P(O)(OR^6)(OR^5)$;
$R^5$ is a C3-C8 cycloaliphatic, C6-C10 aryl, C3-C8 heterocyclic, or C5-C10 heteroaryl ring, wherein each $R^5$ optionally substituted with up to 3 $R^1$ substituents;
$R^6$ is H or C1-C6 aliphatic, wherein $R^6$ is optionally substituted with a $R^7$ substituent;
$R^7$ is a C3-C8 cycloaliphatic, C6-C10 aryl, C3-C8 heterocyclic, or C5-C10 heteroaryl ring, and each $R^7$ is optionally substituted with up to 2 substituents independently selected from C1-C6 aliphatic, or $(CH_2)_m$-Z' wherein m is 0-2;
Z' is selected from halo, CN, $NO_2$, $C(halo)_3$, $CH(halo)_2$, $CH_2(halo)$, $-OC(halo)_3$, $-OCH(halo)_2$, $-OCH_2(halo)$, OH, $S-(C1-C6)$ aliphatic, $S(O)-(C1-C6)$ aliphatic, $SO_2-(C1-C6)$aliphatic, $NH_2$, $NH-(C1-C6)$ aliphatic, $N((C1-C6)aliphatic)_2$, $N((C1-C6)aliphatic)R^8$, COOH, $C(O)O-(C1-C6)aliphatic$, or $O-(C1-C6)aliphatic$; and
$R^8$ is $CH_3C(O)-$, C6-C10 aryl sulfonyl-, or C1-C6 alkyl sulfonyl-.

2. The compound according to claim 1, wherein w is 0.

3. The compound according to claim 1, wherein Z is selected from:

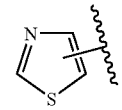

i

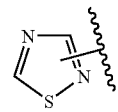

ii

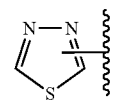

iii

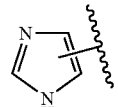

iv

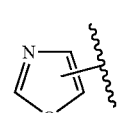

v

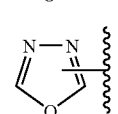

vi

vii

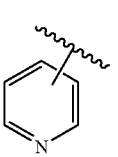

viii

-continued ix 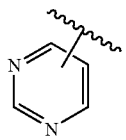

x 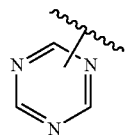

xi 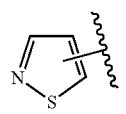

xii 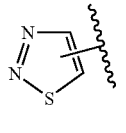

xiii 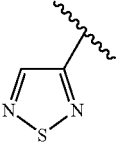

xiv 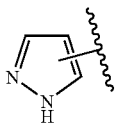

xv 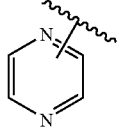

xvi 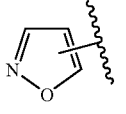

xvii 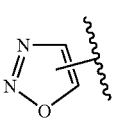

xviii 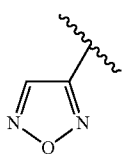

xix 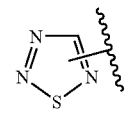

-continued xx 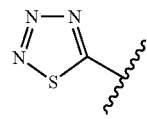

xxi 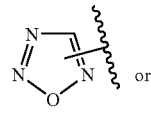 or xxii 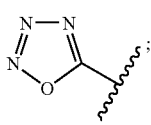 ;

wherein Z has up to two $R^Z$ substituents independently selected from $R^1$, $R^2$, or $R^5$.

4. The compound according to claim 3, wherein Z is an optionally substituted ring having formula i, formula II, formula viii, formula ix or formula x.

5. The compound according to claim 1, wherein $R^Q$ is an 8-12 membered saturated, or partially unsaturated bicyclic ring system having 1-5 heteroatoms independently selected from O, S, N, or NH, wherein $R^Q$ is optionally substituted with up to 4 substituents independently selected from $R^1$, $R^2$, $R^3$, $R^4$, or $R^5$.

6. The compound according to claim 5, wherein $R^Q$ is an optionally substituted ring selected from:

b-iv 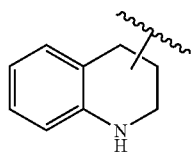

b-v 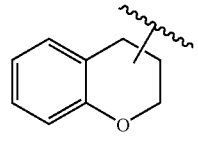

b-vi 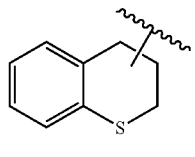

b-x 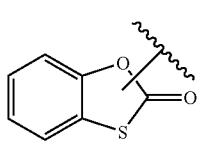

b-xi 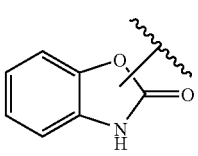

-continued

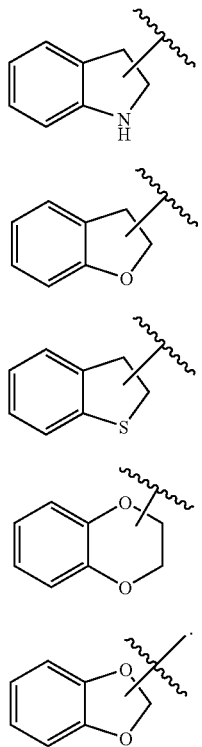

b-xiv b-xv b-xvi b-xx b-xxi

7. The compound according to claim 1, wherein said compound has formula VIA or formula VIB:

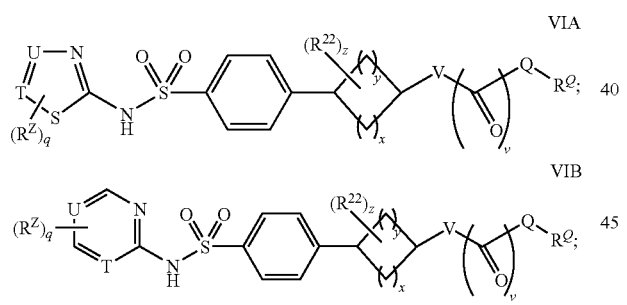

VIA

VIB wherein
U and T each is independently CH or N; provided that both U and T are not simultaneously N;
$R^{22}$ is $R^1$ or $R^2$;
$R^Z$ is selected from $R^1$, $R^2$, or $R^5$;
q is 0-2;
and
$R^Q$ is a 3-8-membered saturated, or partially unsaturated monocyclic heterocyclic ring having 1-3 heteroatoms independently selected from O, S, N, or NH, or an 8-12 membered saturated, or partially unsaturated bicyclic heterocyclic ring system having 1-5 heteroatoms independently selected from O, S, N, or NH; wherein $R^Q$ is optionally substituted with up to 4 substituents independently selected from $R^1$, $R^2$, $R^3$, $R^4$, or $R^5$.

8. The compound according to claim 7, wherein said compound has formula VIA-i:

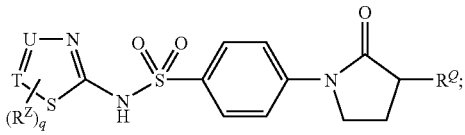

VIA-i wherein:
$R^Q$ is

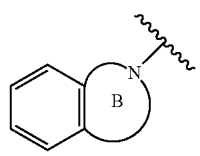

wherein ring B is a 5-6 membered heterocyclic ring having a single nitrogen heteroatom; wherein $R^Q$ is optionally substituted with up to 4 substituents independently selected from $R^1$, $R^2$, or $R^3$.

9. The compound according to claim 8, wherein U and T, both are CH.

10. The compound according to claim 8, wherein $R^Q$ is selected from:

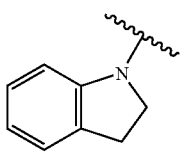
a

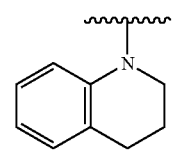
b

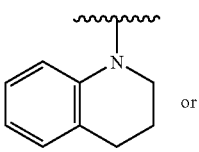
c or

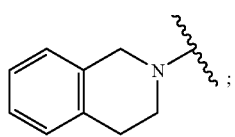
d wherein $R^Q$ is optionally substituted with up to 4 substituents independently selected from $R^1$, $R^2$, or $R^3$.

11. The compound according to claim 8, wherein $R^Q$ is selected from:
| $R^Q$ |
|---|
| 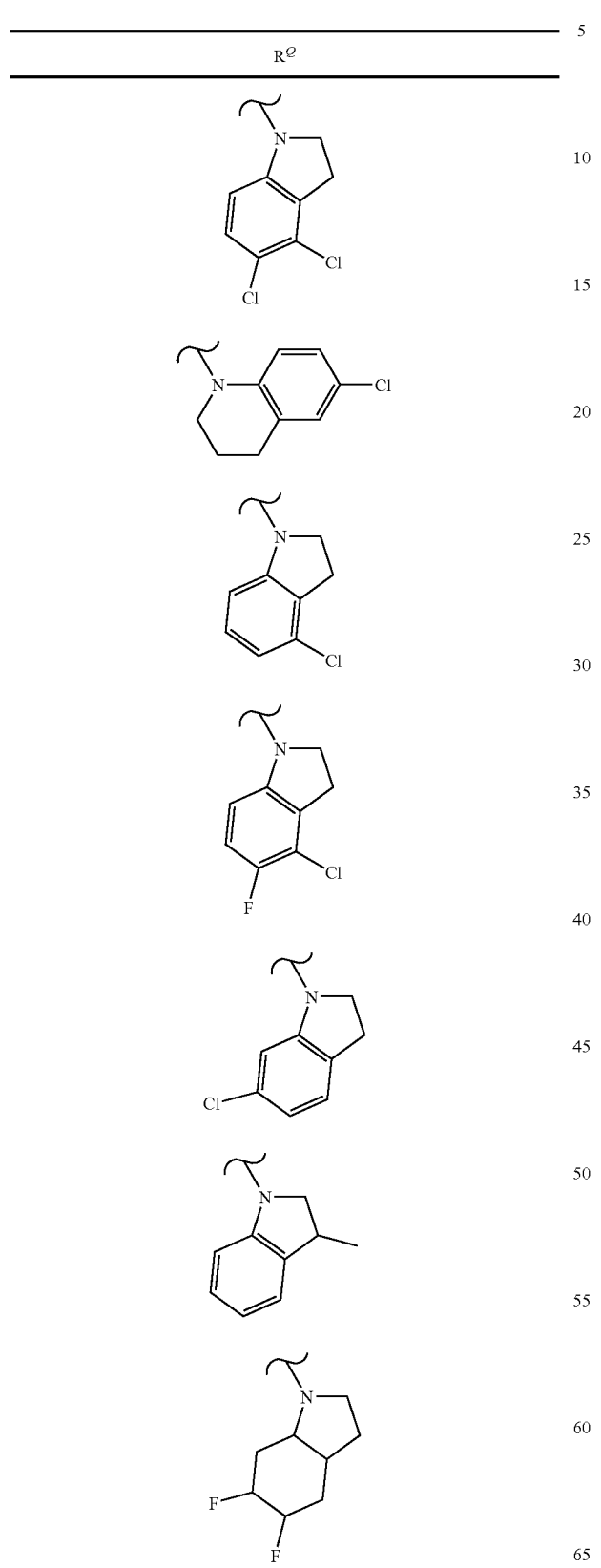 |
-continued
| $R^Q$ |
|---|
| 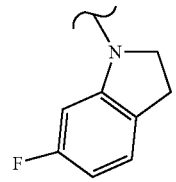 |
| 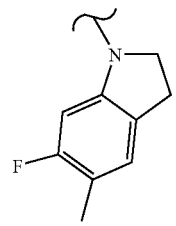 |
| 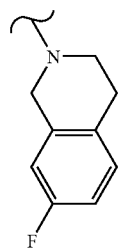 |
| 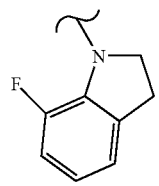 |
| 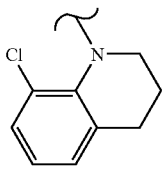 |
| 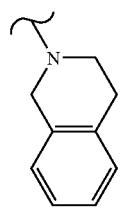 |
| 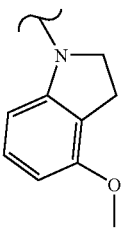 |

| 681 | 682 |
|---|---|
| -continued | -continued |
| R^Q | R^Q |
| 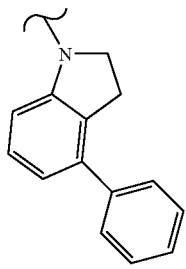 | 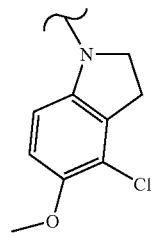 |
| 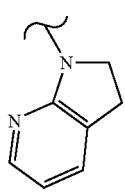 | 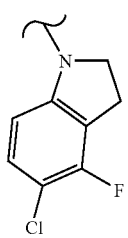 |
| 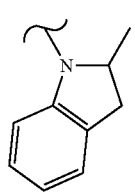 | 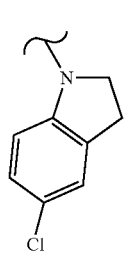 |
| 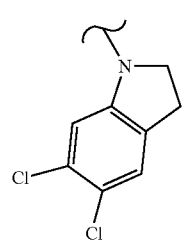 | 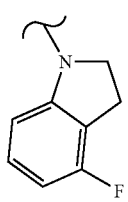 |
| 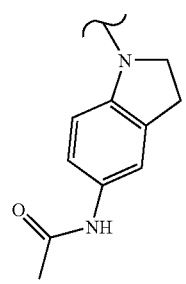 | 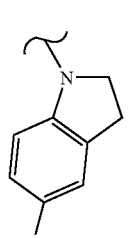 |
| 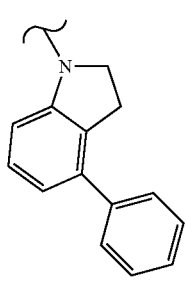 | 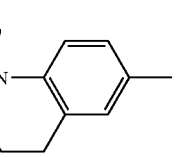 |
|  | 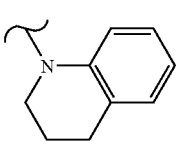 |

| 683 | 684 |
|---|---|
| -continued | -continued |
| R<sup>Q</sup> | R<sup>Q</sup> |
| | |
|---|---|
| 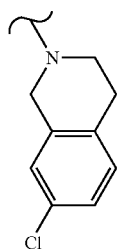 | 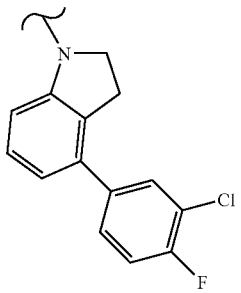 |
| 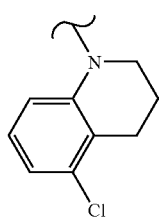 | 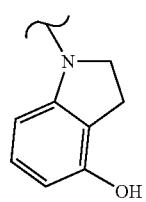 |
| 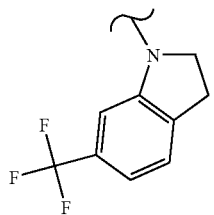 | 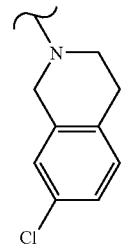 |
| 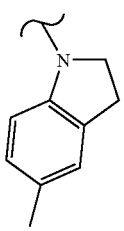 | 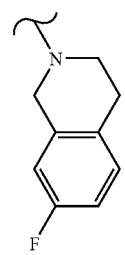 |
| 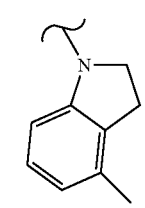 | 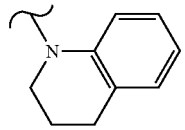 |
| 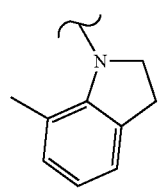 | 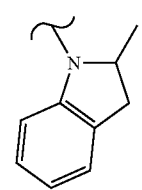 |

-continued
| $R^Q$ | $R^Q$ |
|---|---|
| 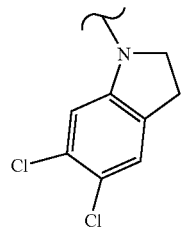 | 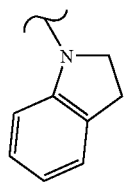 |
| 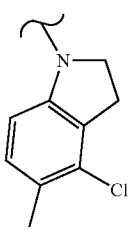 | 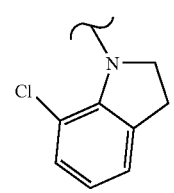 |
| 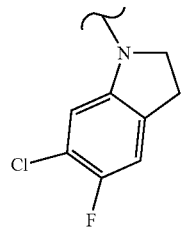 | 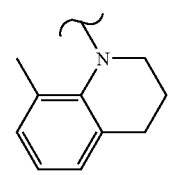 |
| 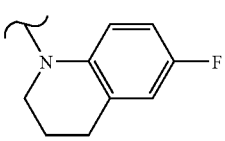 | |
| 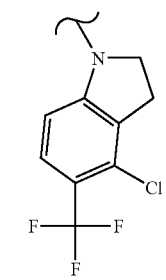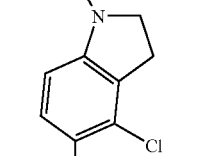 | 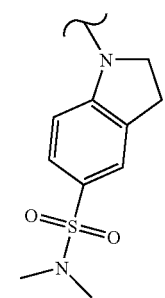 |
| 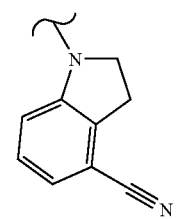 | 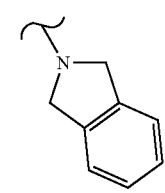 |
| 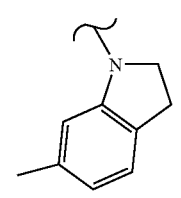 | 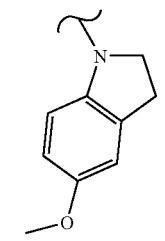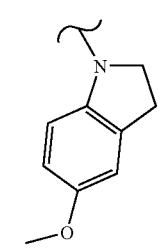 |

-continued

12. The compound according to claim 7, wherein said compound has formula VIA-iii:

VIA-iii wherein $R^Q$ is and wherein $R^Q$ is optionally substituted with up to 4 substituents independently selected from $R^1$, $R^2$, or $R^3$.

13. The compound according to claim 12, wherein the phenyl ring attached to the piperazine in said $R^Q$ is selected from:

-continued
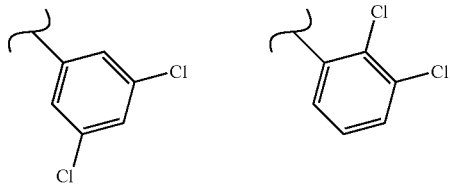
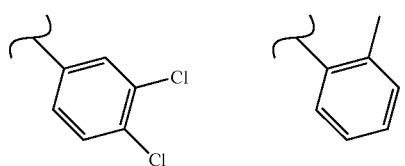
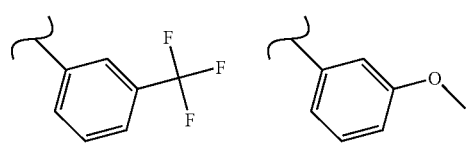
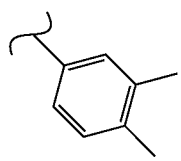
14. A compound selected from
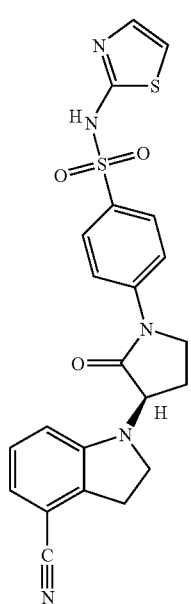
-continued
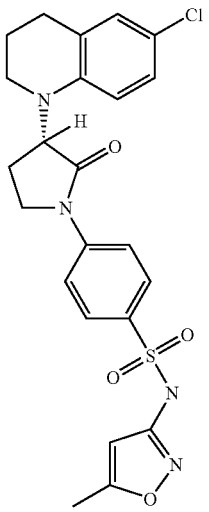
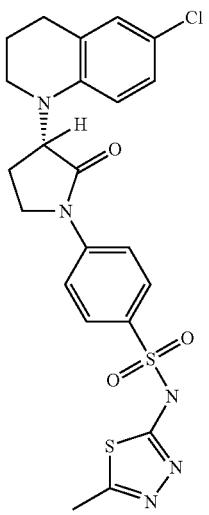
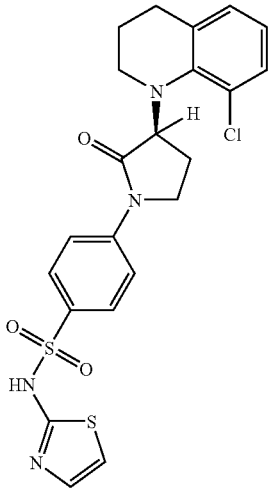

-continued
691
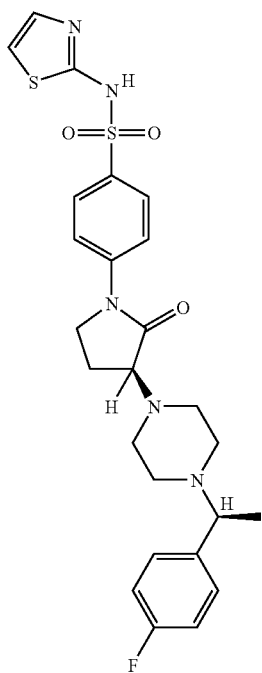
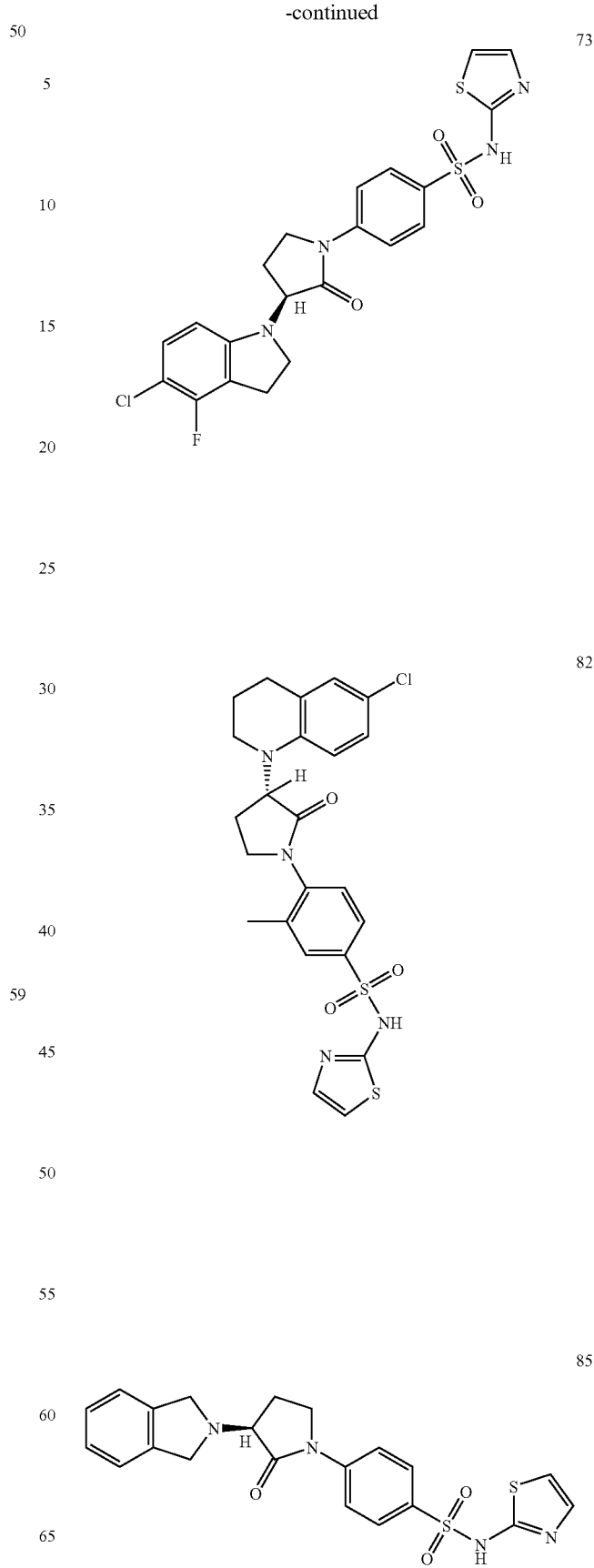

-continued
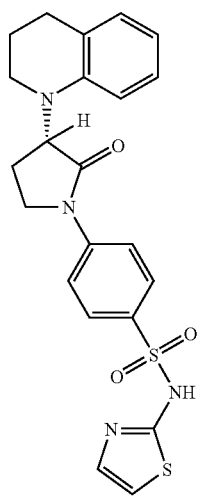
95
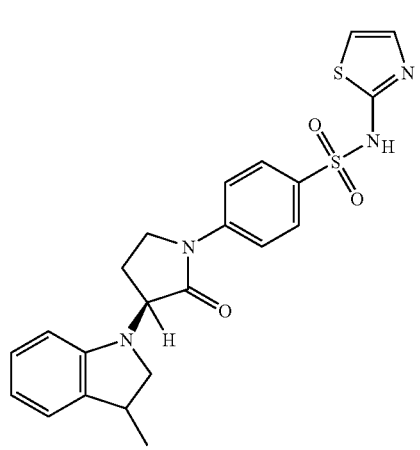
105
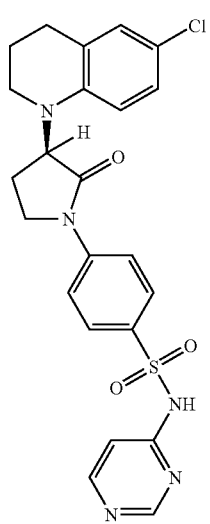
108
-continued
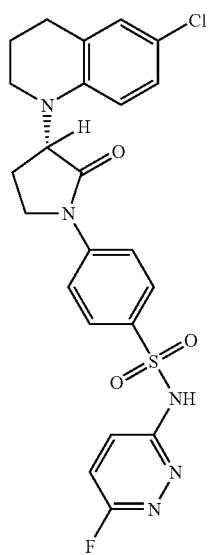
114
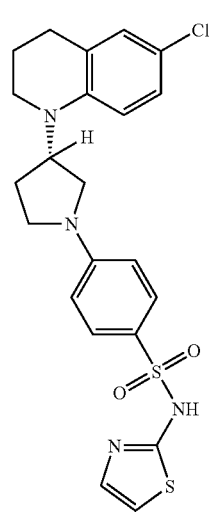
115
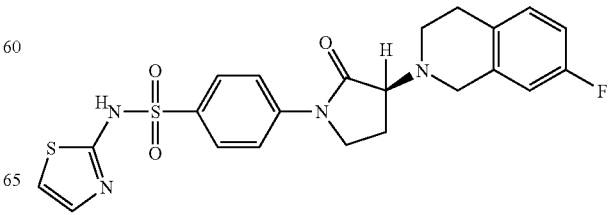
122

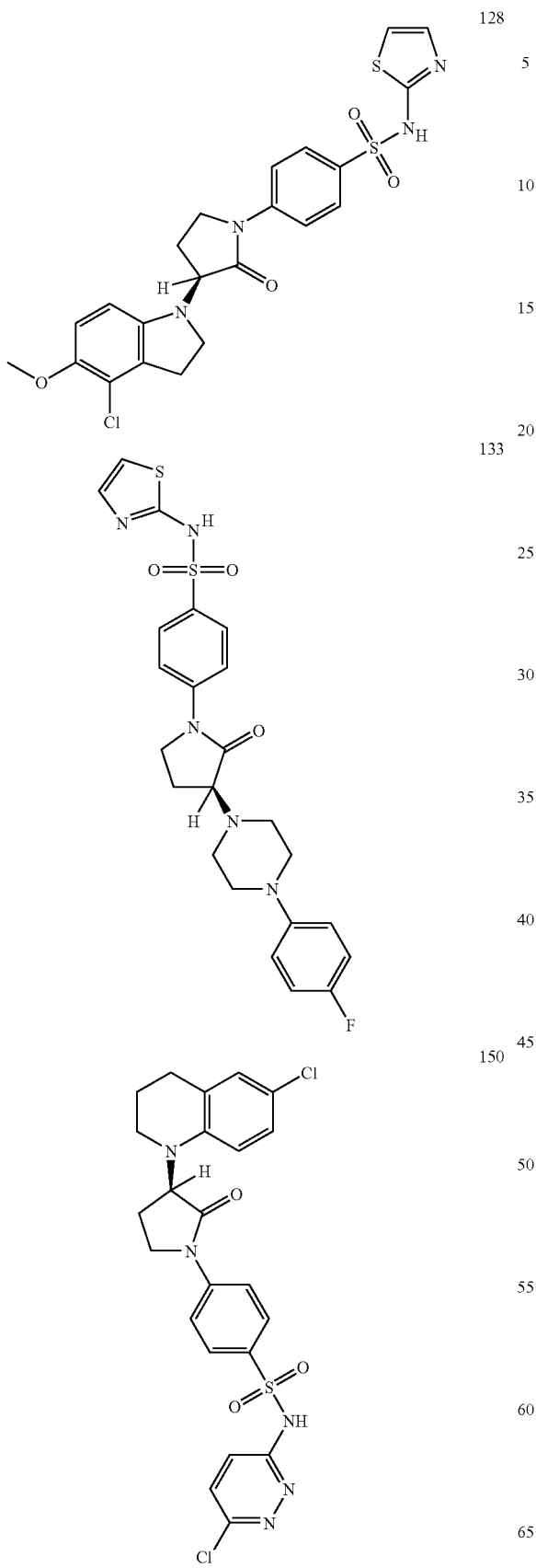

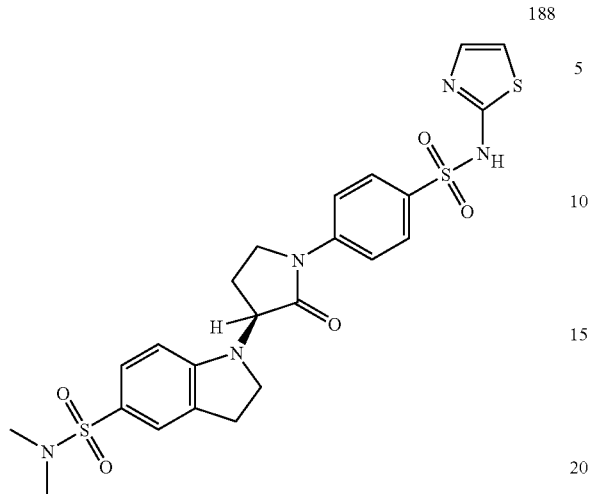
188
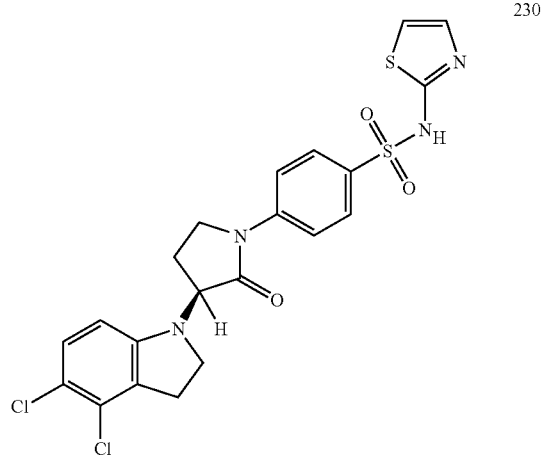
230
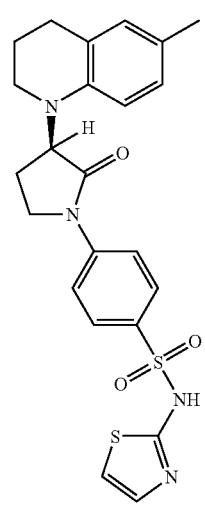
195
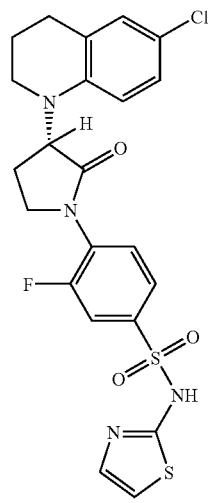
231
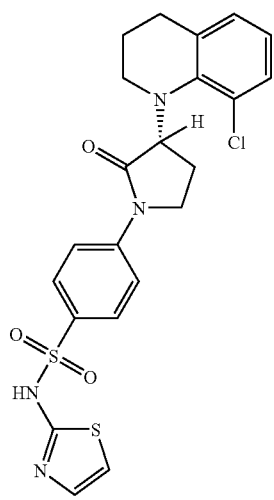
219
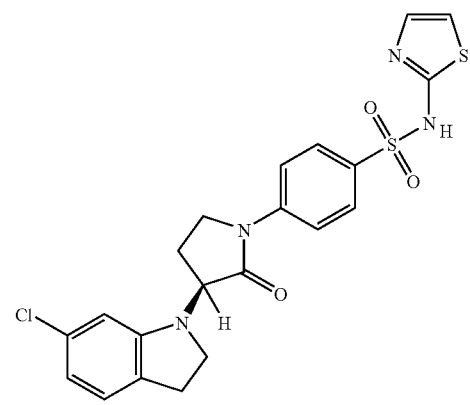
233

-continued
254
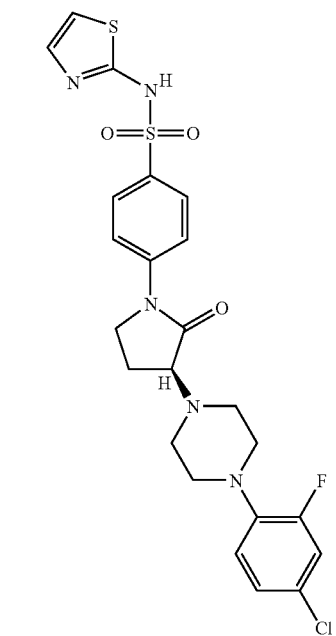
261
272
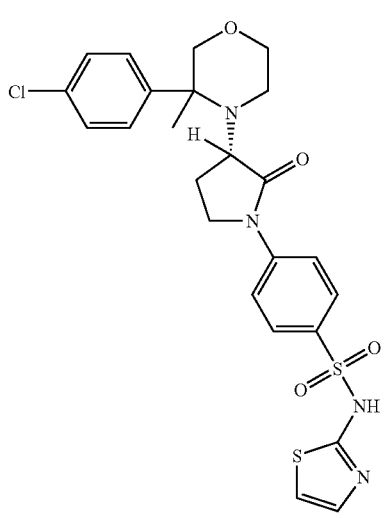
-continued
284
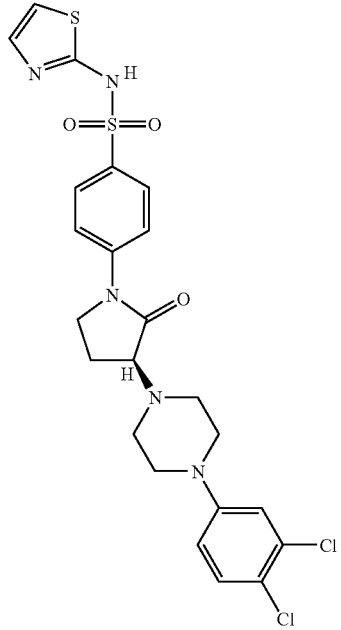
285
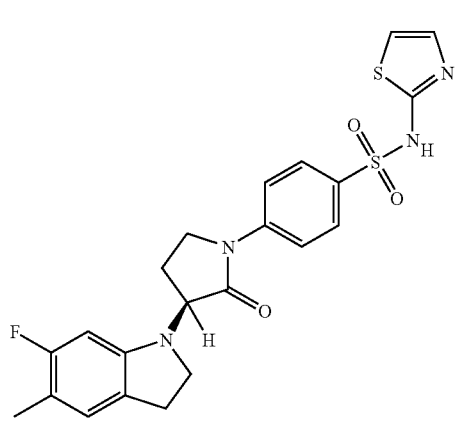
287

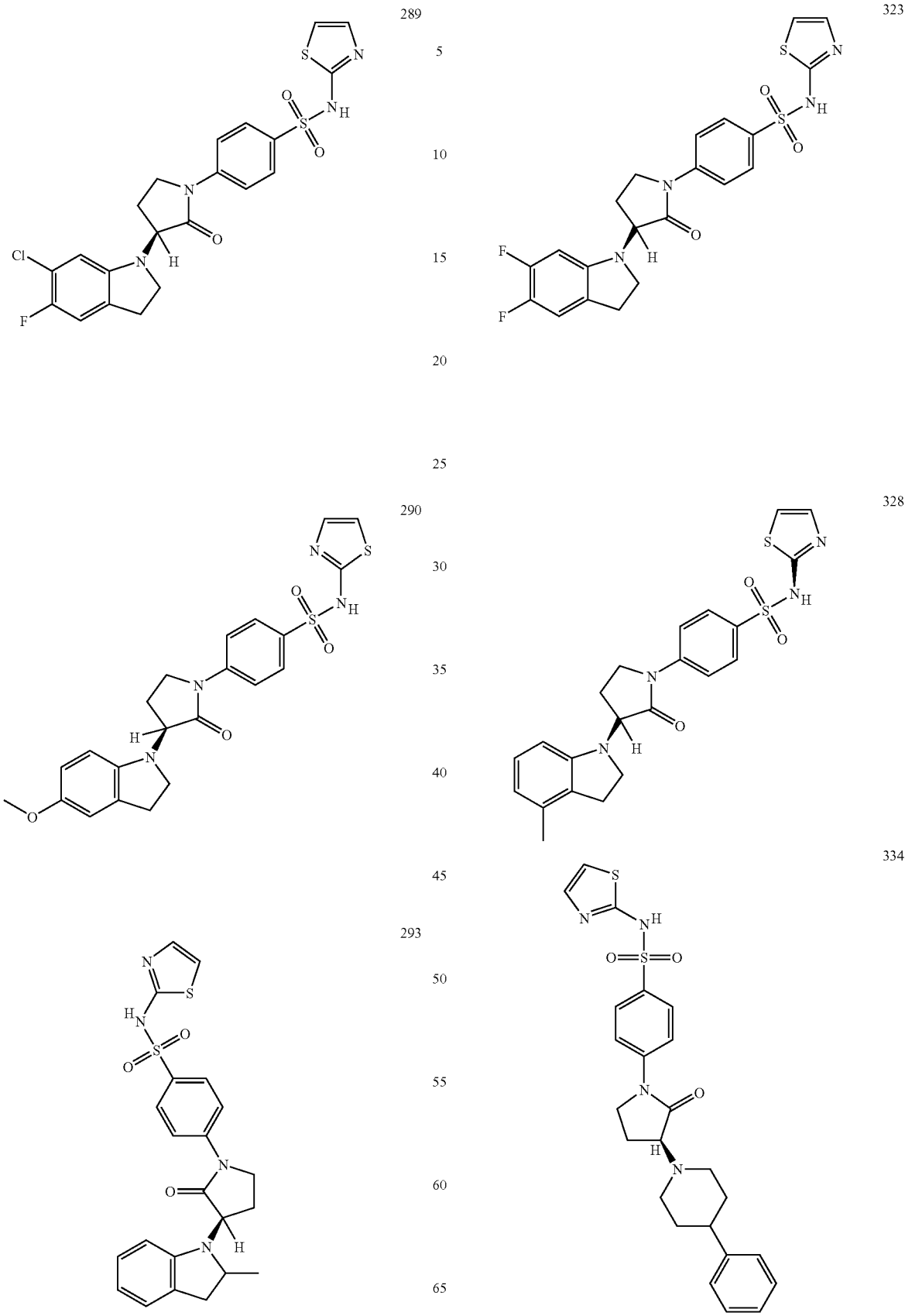

703
-continued
704
-continued
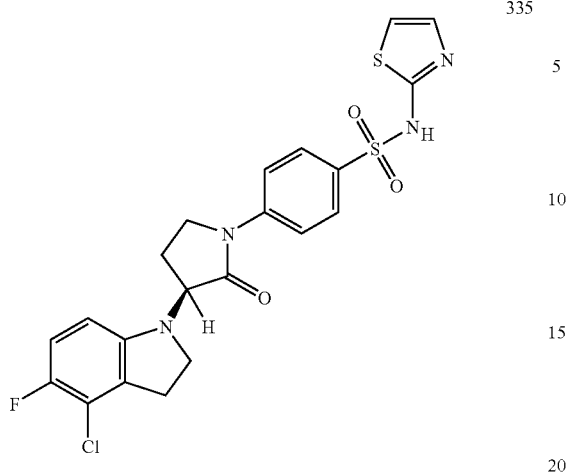
335
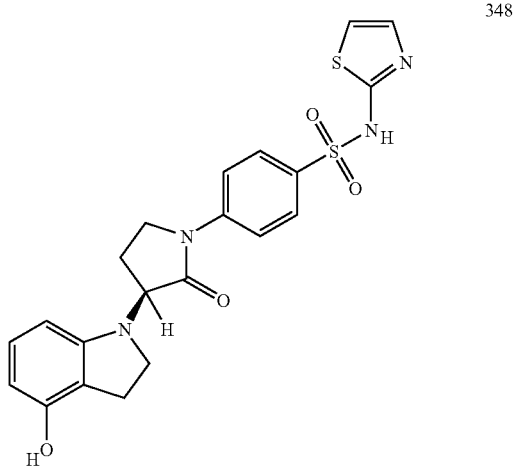
348
343
352
345
361
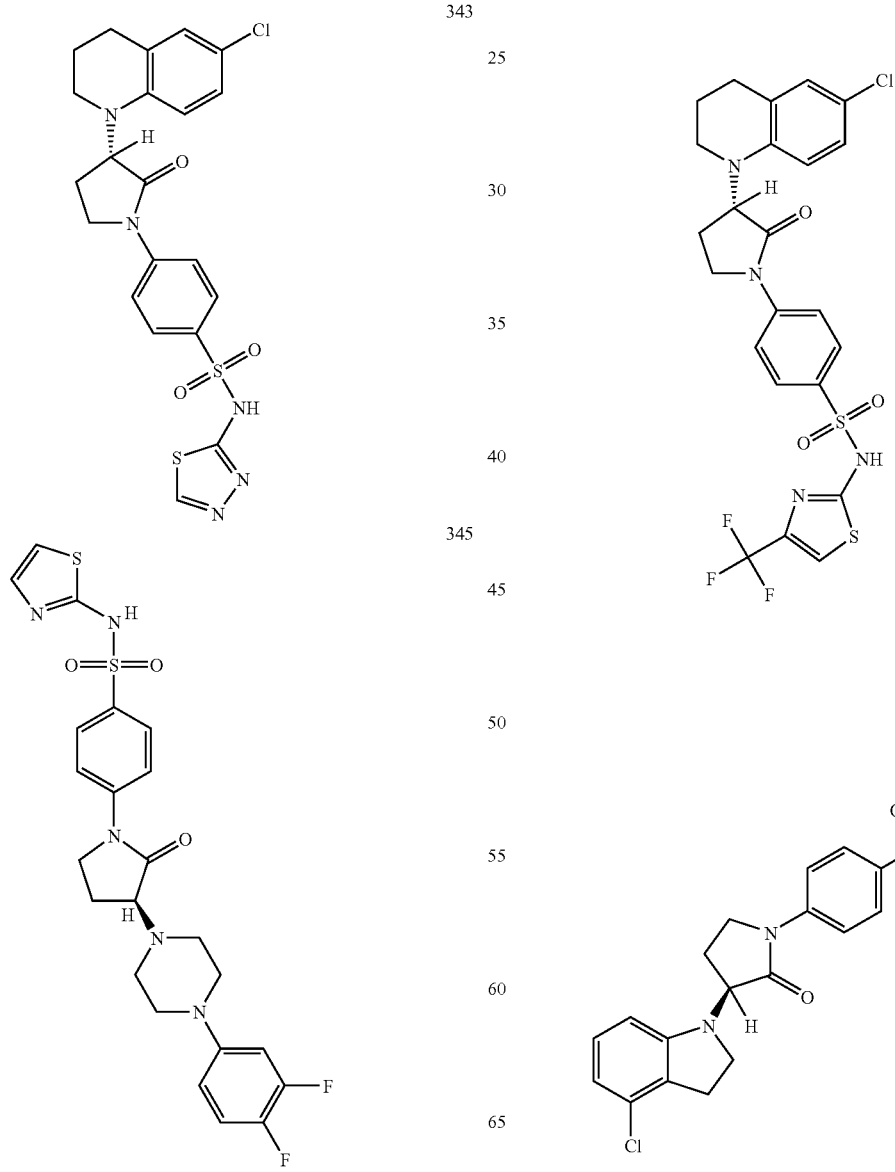

368
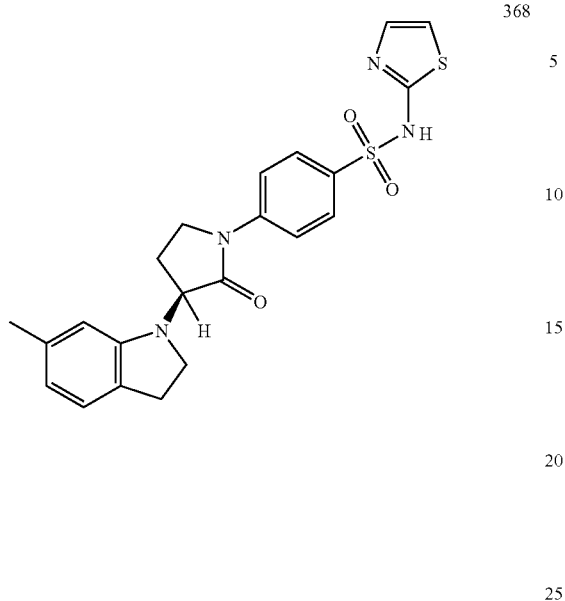
369
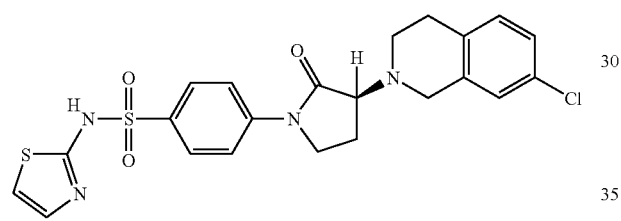
401
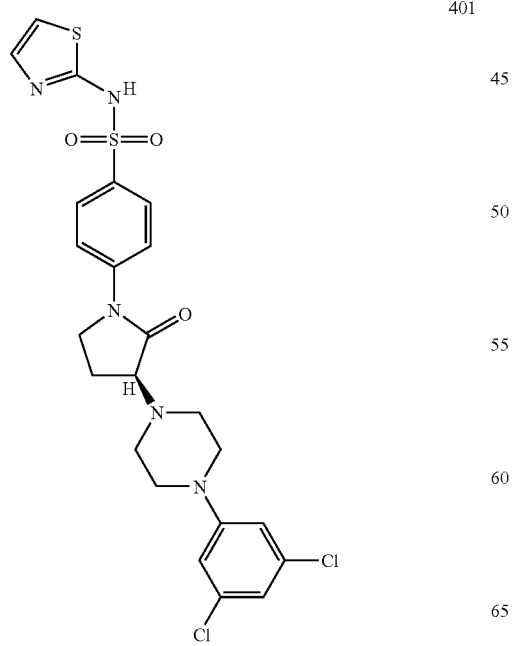
412
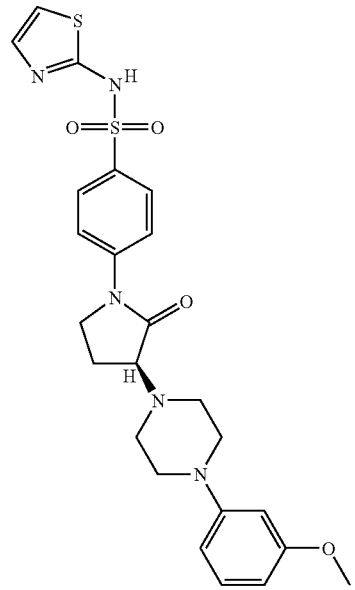
421
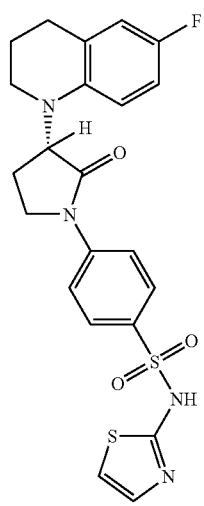
447
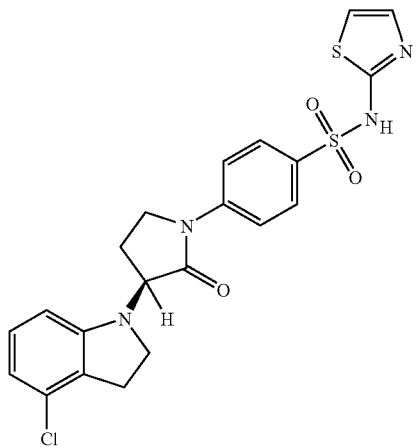

707
-continued
470
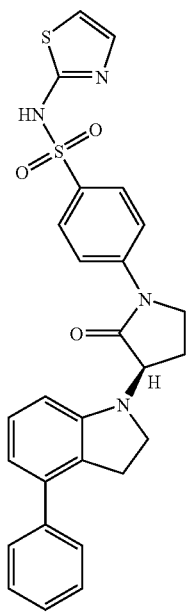
478
482
485
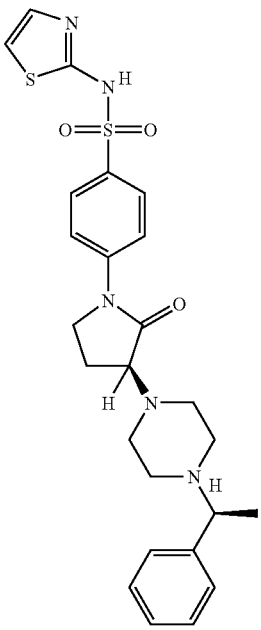
490
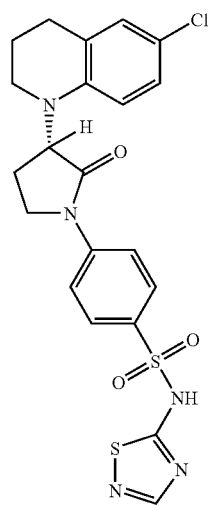
492
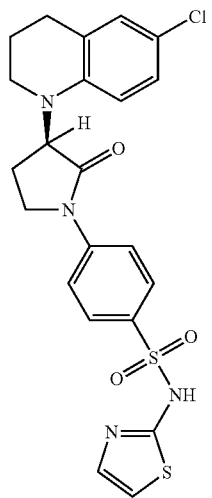

-continued
501 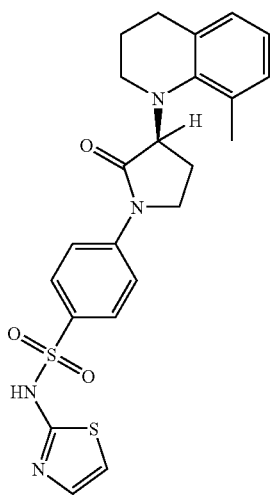
505 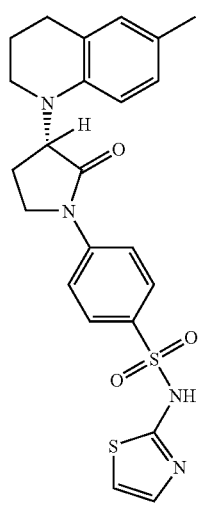
507 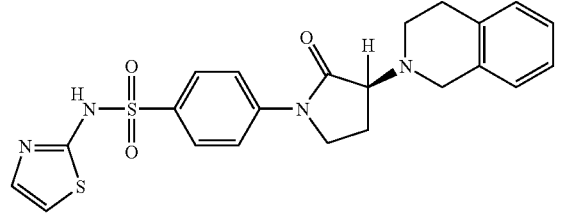
-continued
518 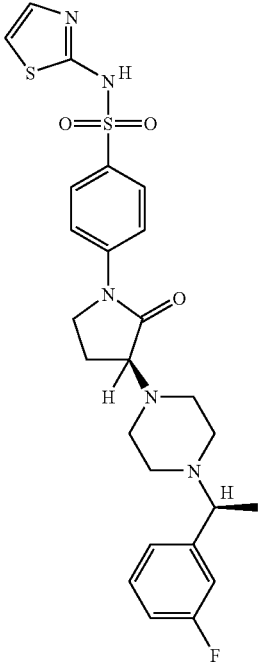
519 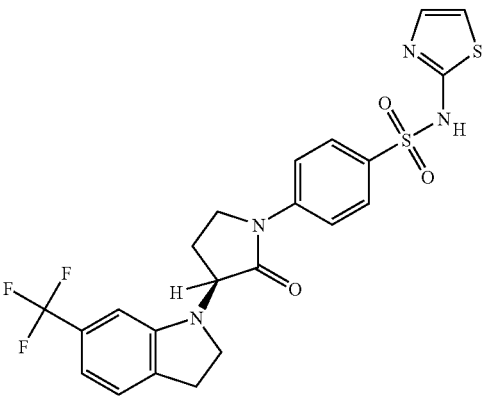
523 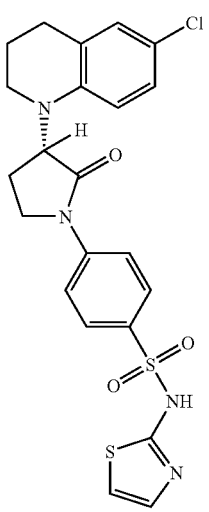

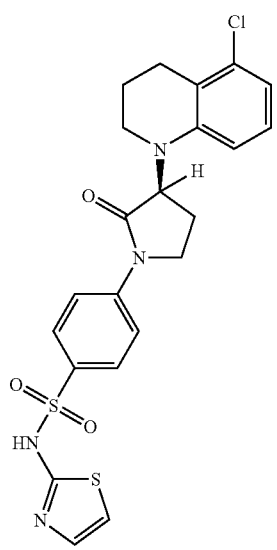
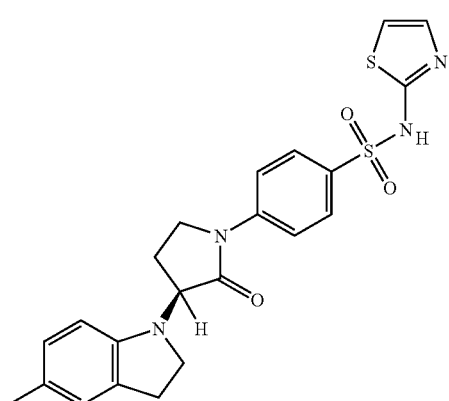

713
-continued
571 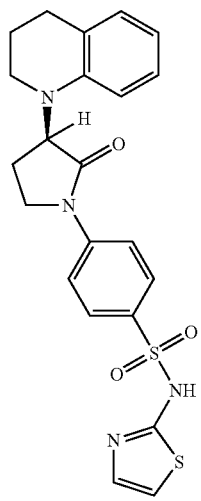
578 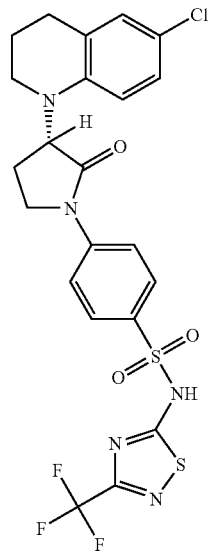
579 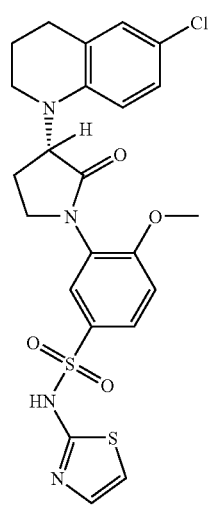
714
-continued
582 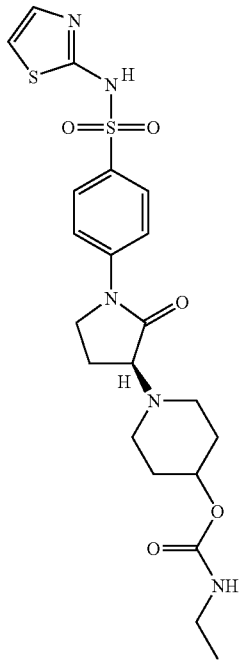
584 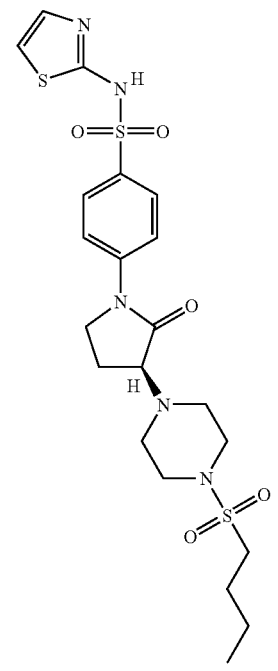

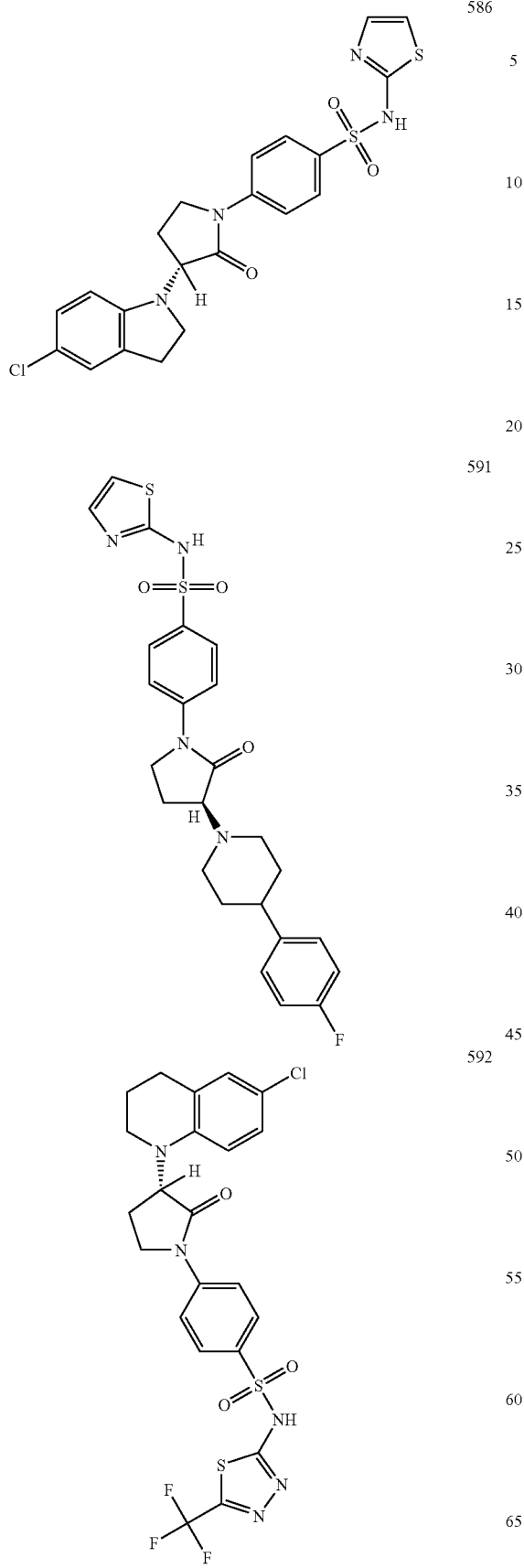
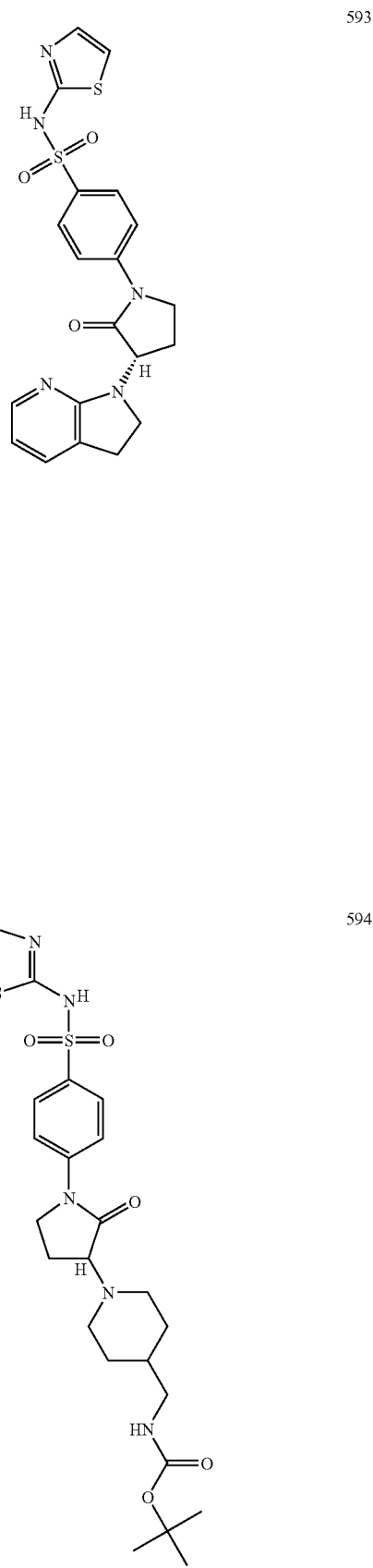

717 | 718
-continued | -continued
599
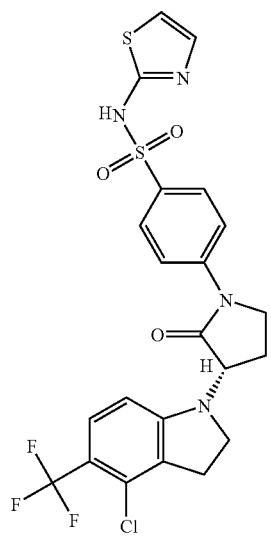
620
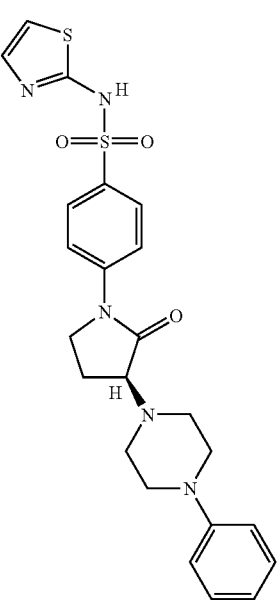
632
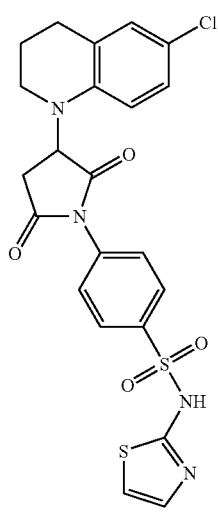
633
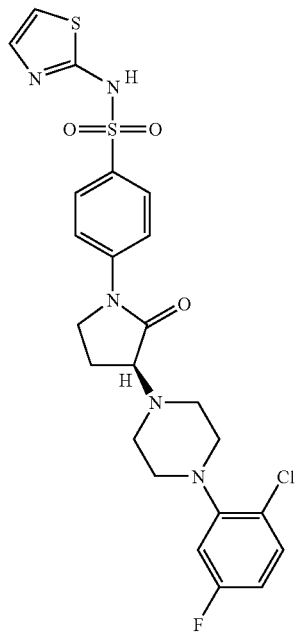
635
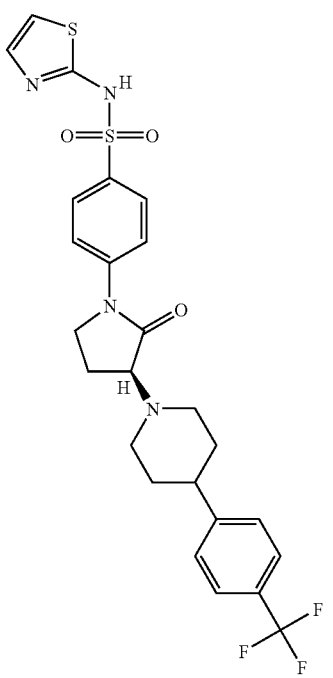

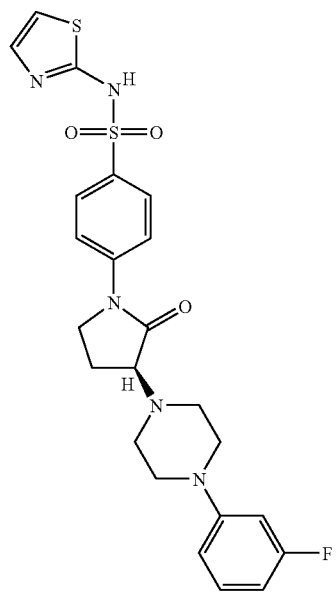
636
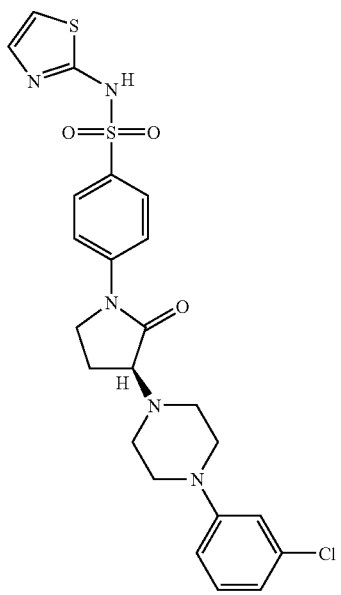
656
643
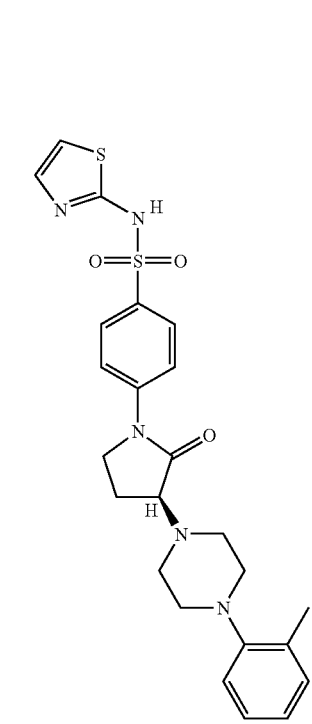
668

721
-continued
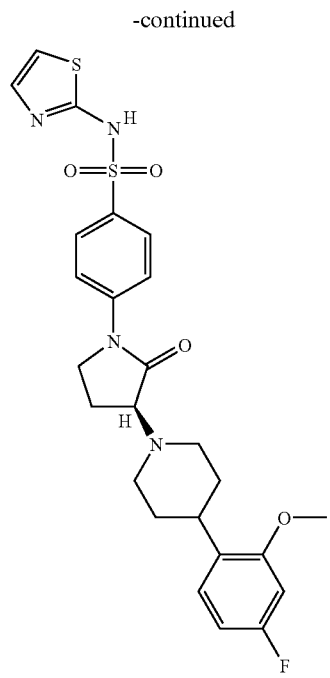
670
673
722
-continued
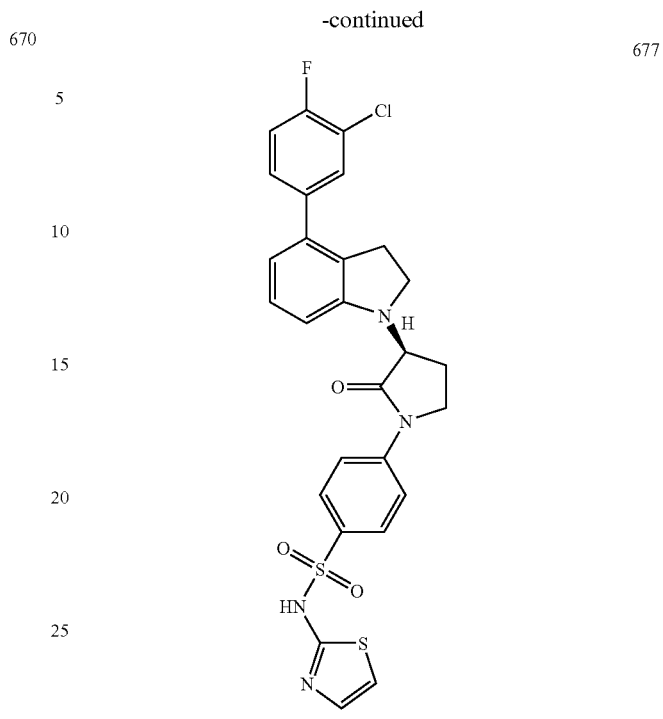
677
678
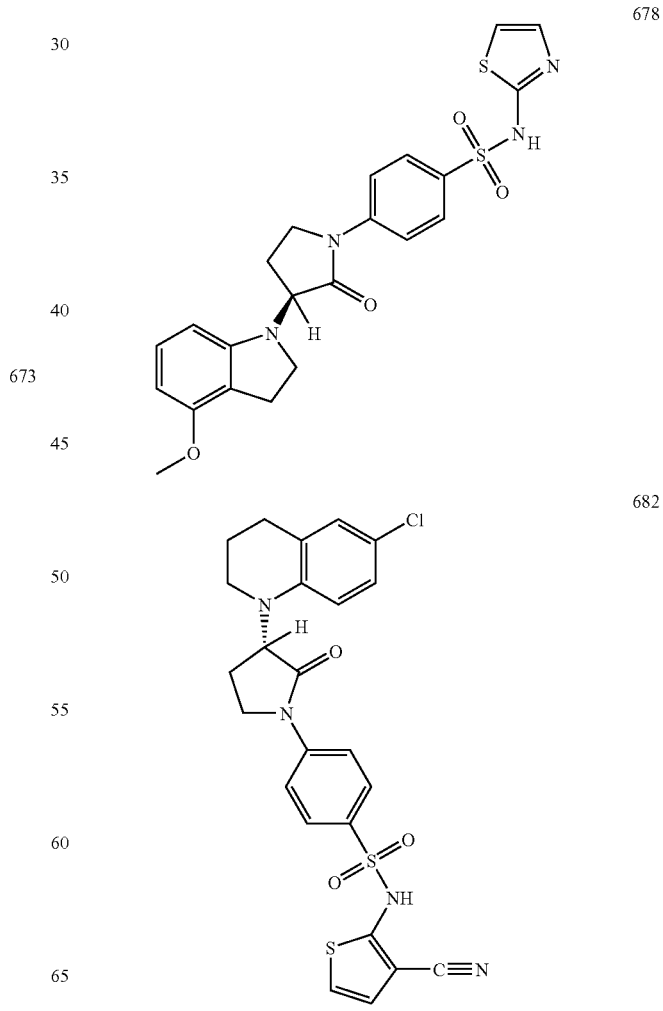
682

723
-continued
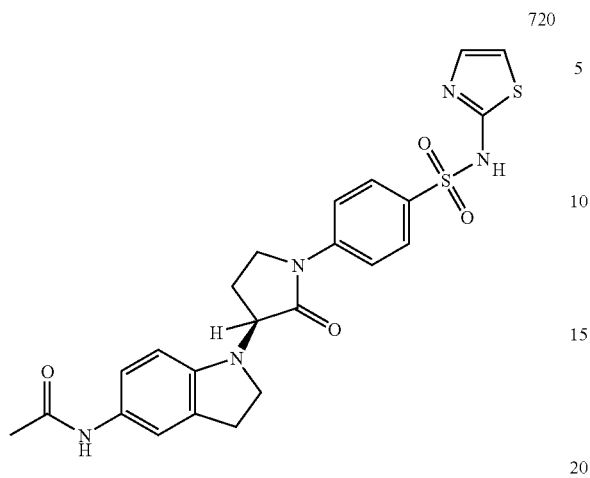
720
753
770
724
-continued
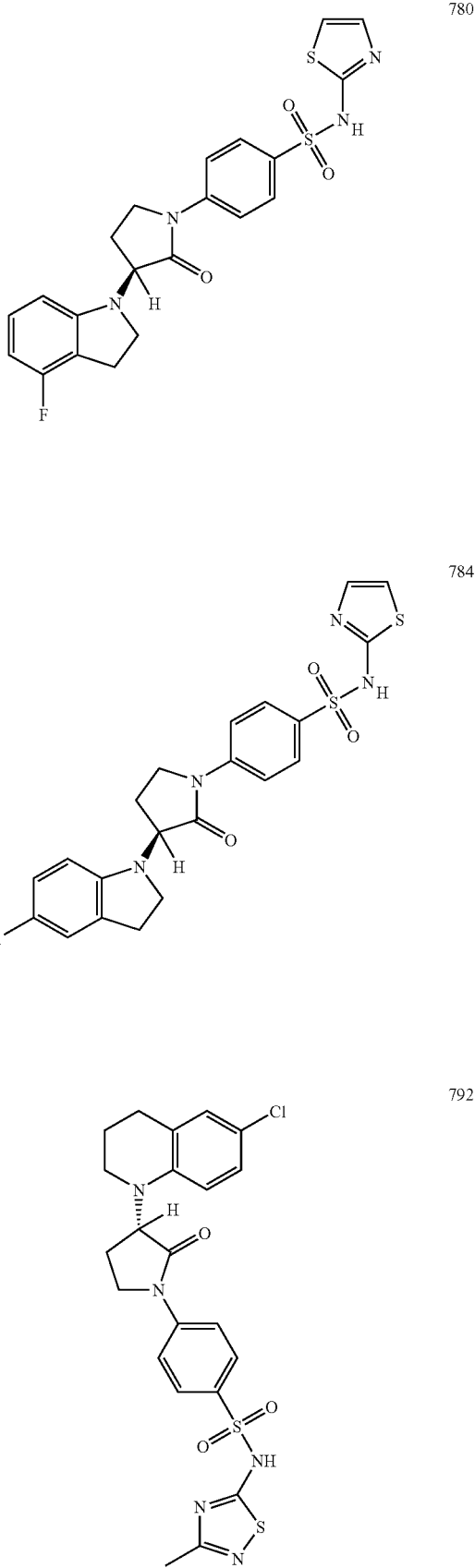
780
784
792

-continued
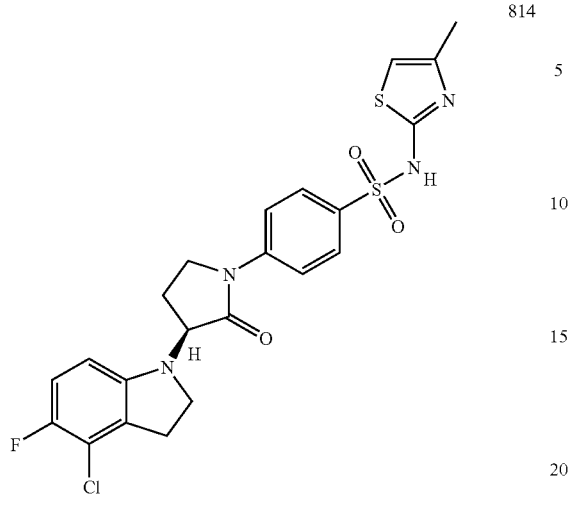
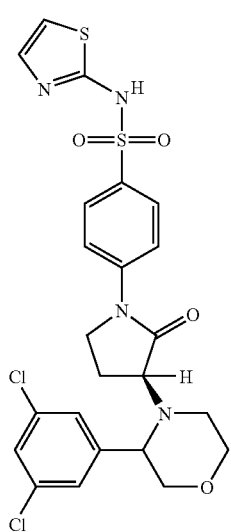

850
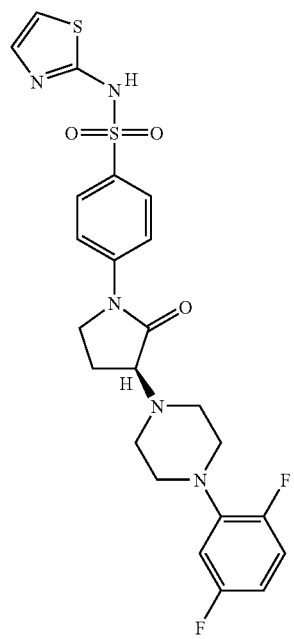
861
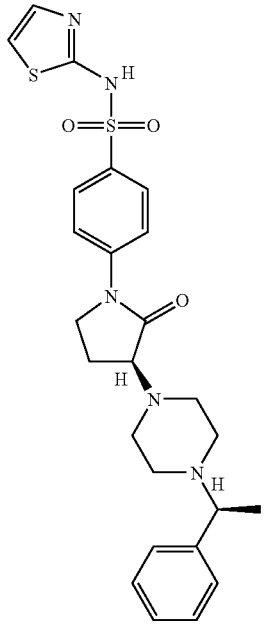
860
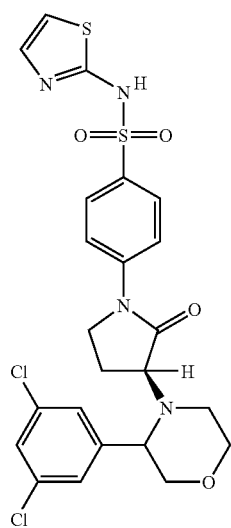
862
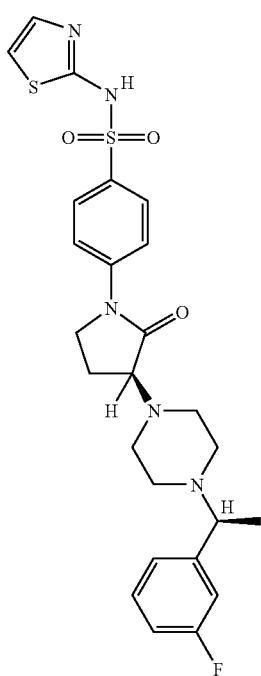

| 729 | 730 |
|---|---|
| 864 | 866 |
| 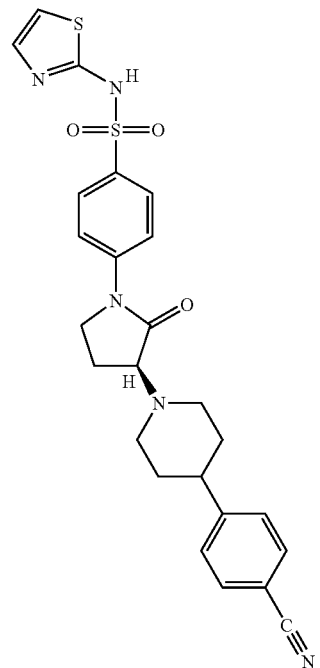 | 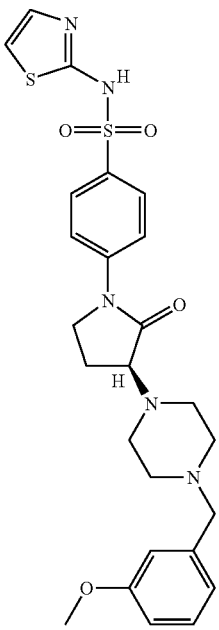 |
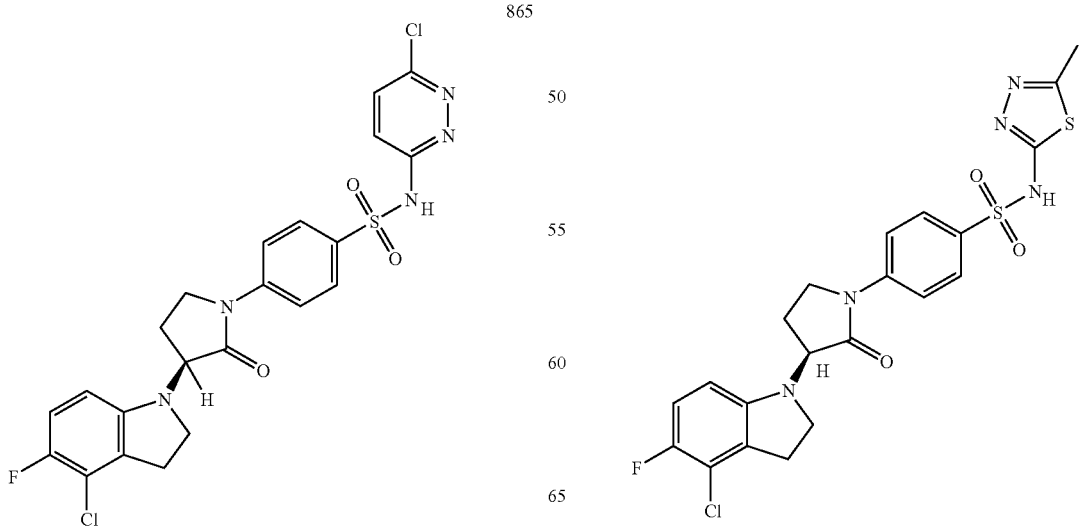

731
-continued
868
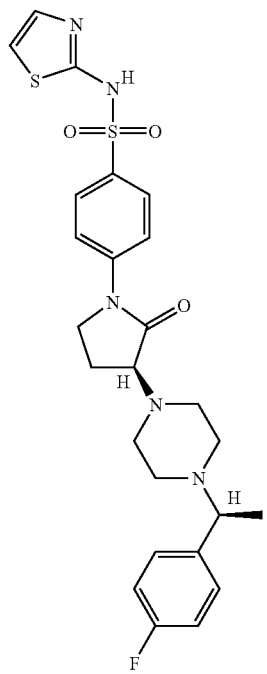
869
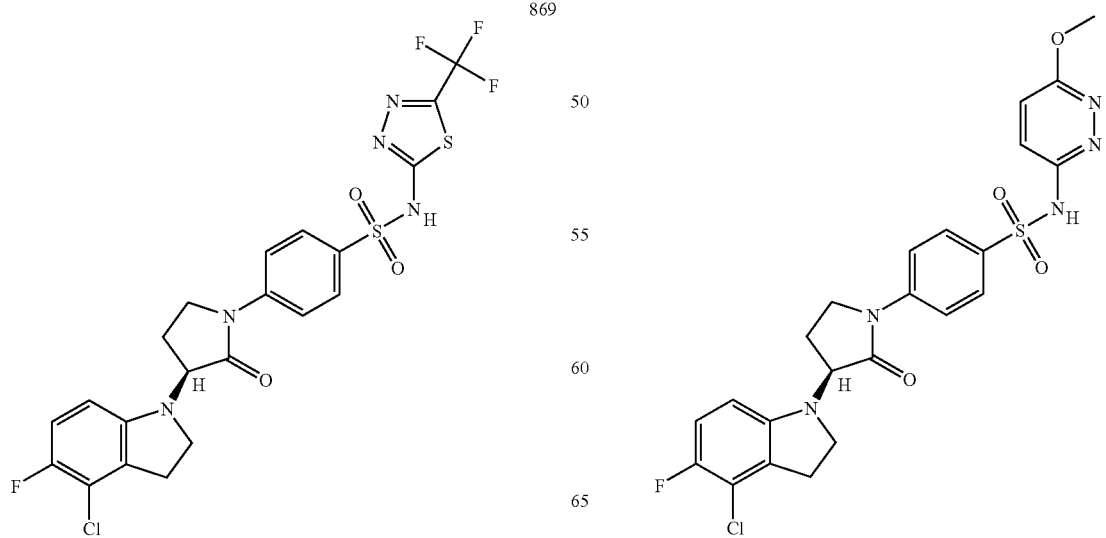
732
-continued
870
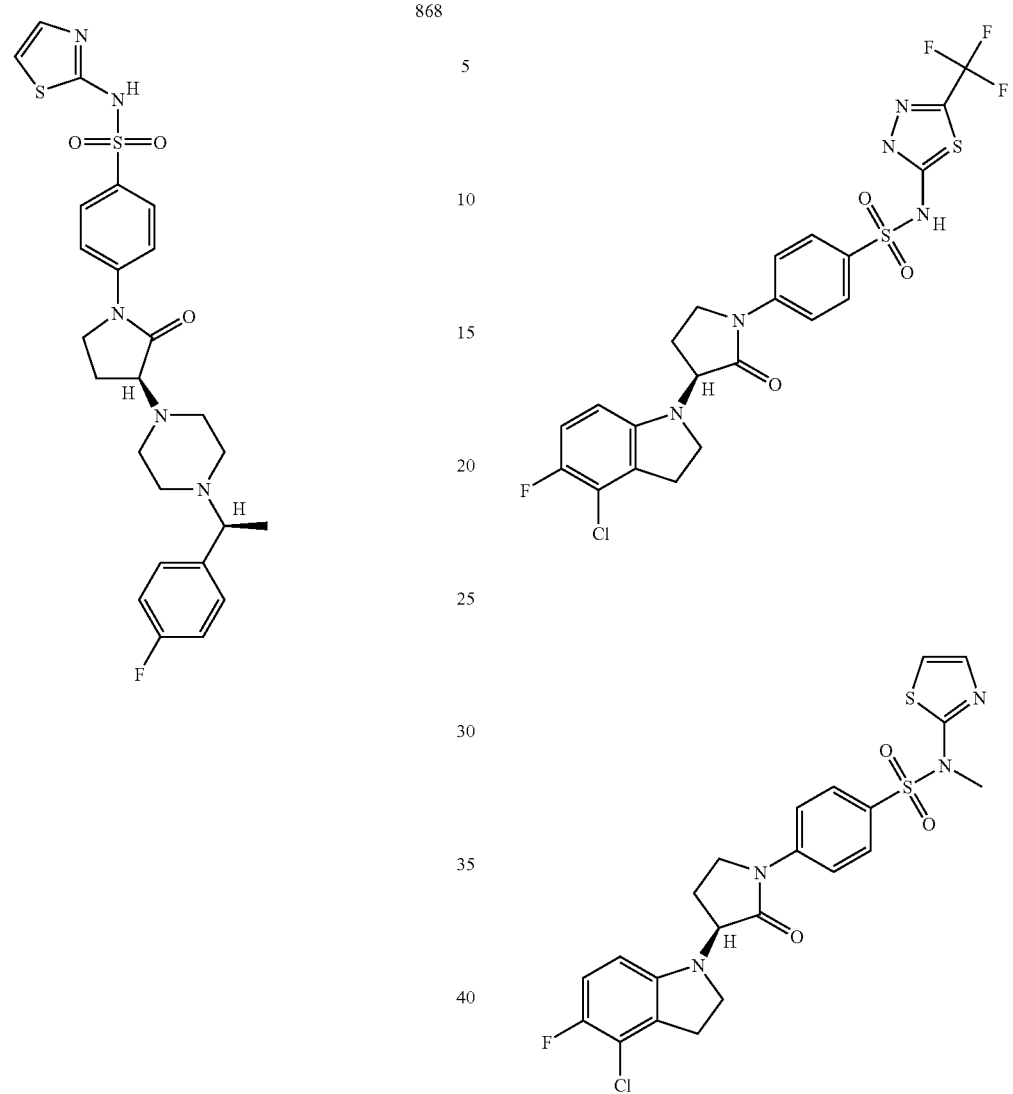
873
874

733
-continued
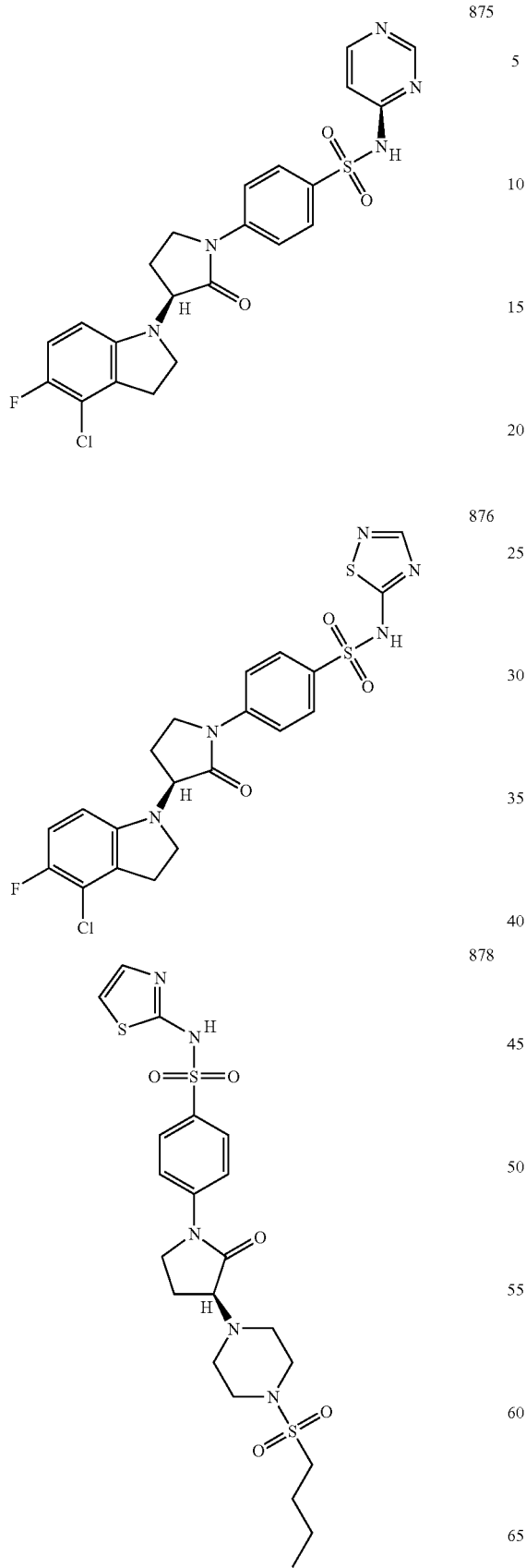
734
-continued

735
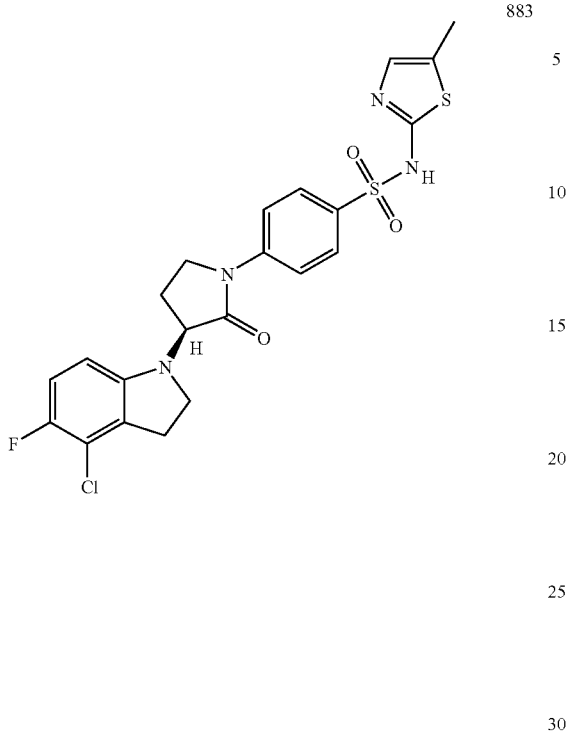
883
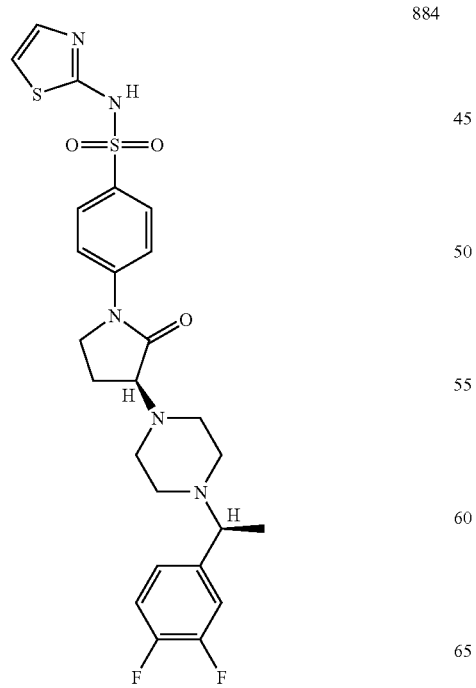
884
736
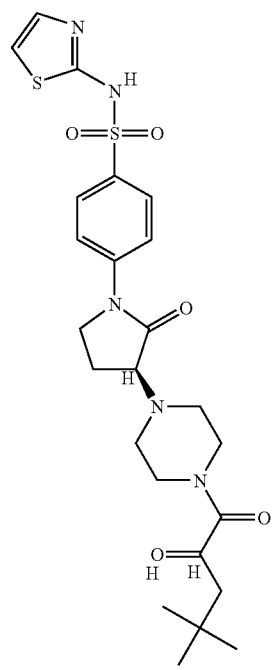
885
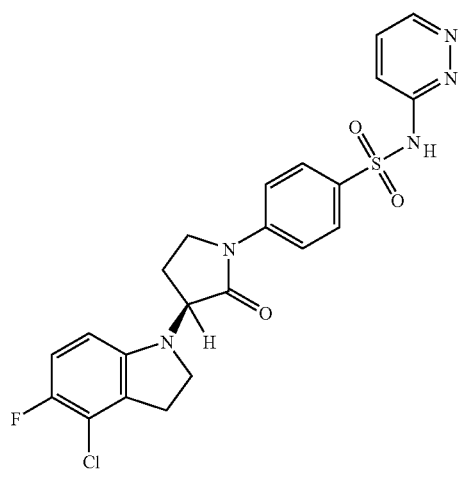
886

737
-continued
887
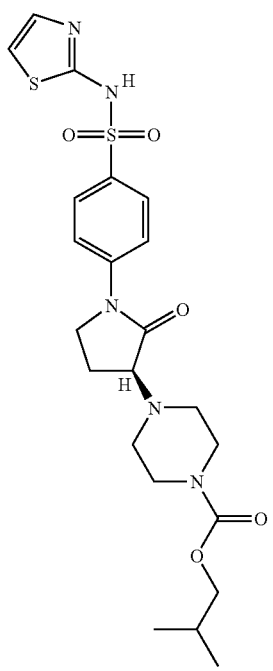
888
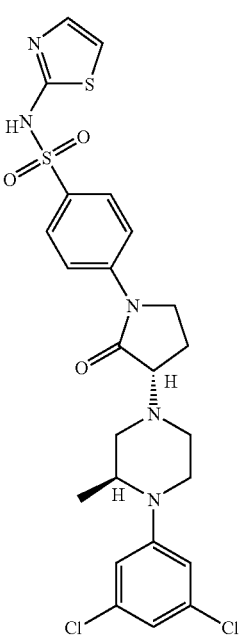
889
890
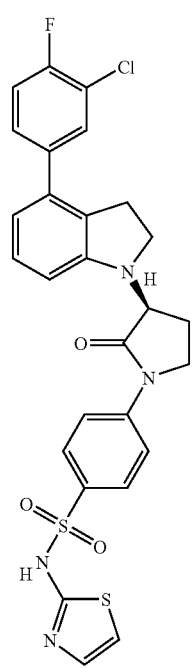
891

-continued
892 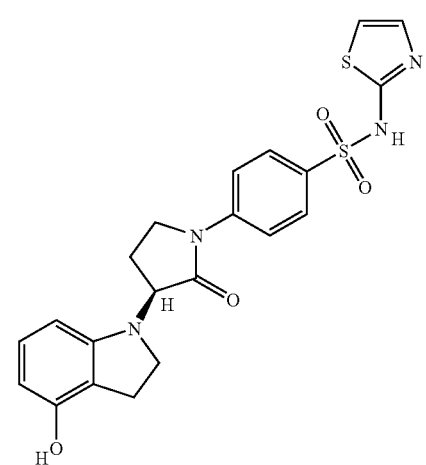
893 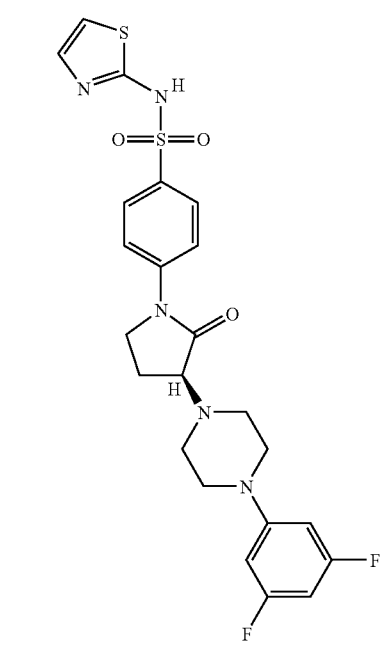
894 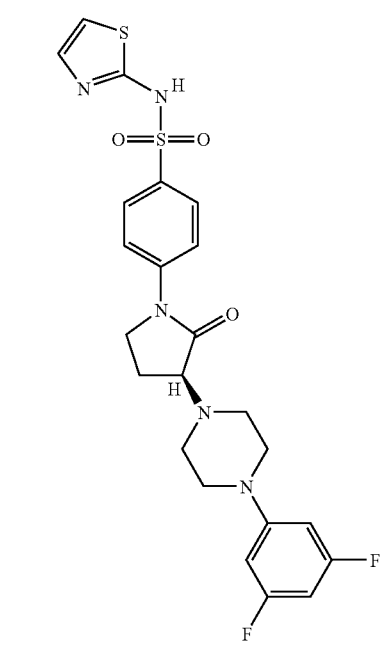
-continued
895 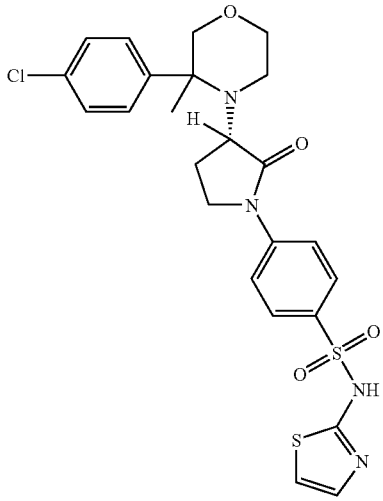
897 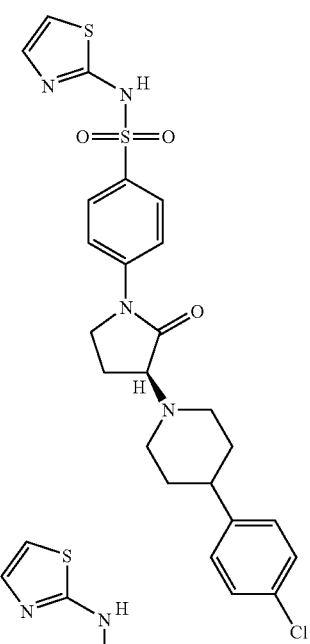
898 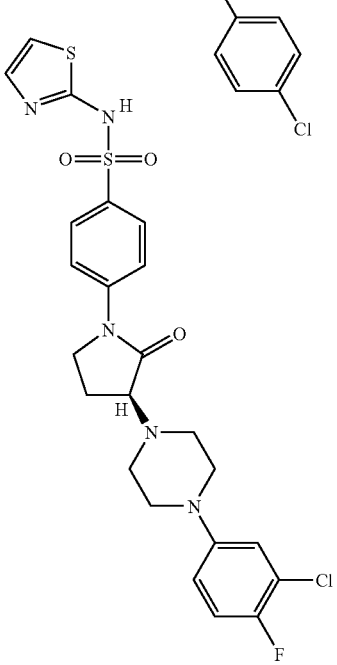

-continued
899
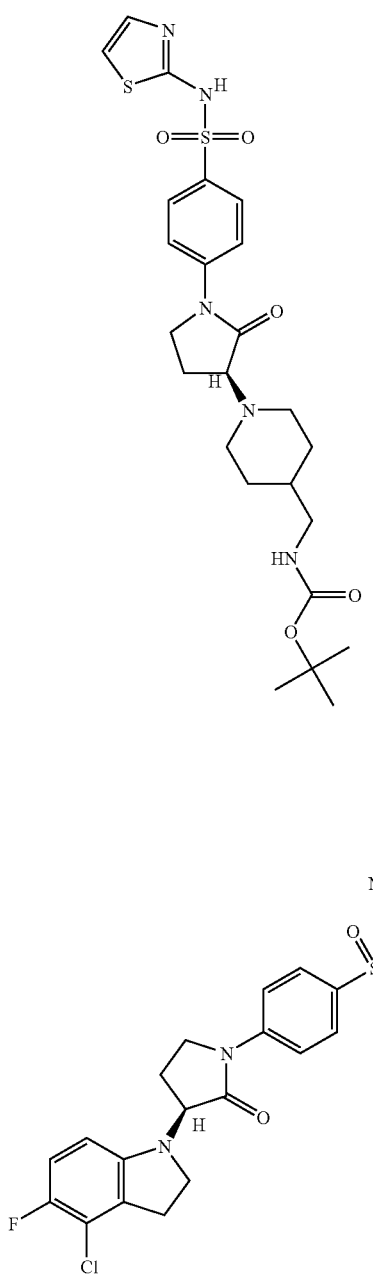
900
-continued
901
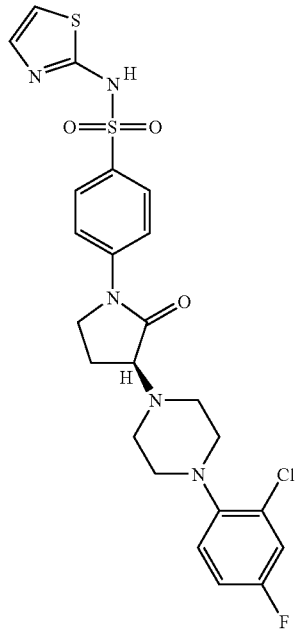
902
15. A pharmaceutical composition comprising a compound according to any one of claims 1-4, 5, 6, 7, 8, 9, 10, 11, and 12-14, and a pharmaceutically acceptable carrier, adjuvant, or a vehicle.
* * * * *